United States Patent
Konst et al.

(10) Patent No.: US 11,667,613 B2
(45) Date of Patent: Jun. 6, 2023

(54) ANTIVIRAL PYRAZOLOPYRIDINONE COMPOUNDS

(71) Applicants: Novartis AG, Basel (CH); Gilead Sciences, Inc., Foster City, CA (US)

(72) Inventors: Zef Konst, San Francisco, CA (US); Yipin Lu, Emeryville, CA (US); Robert Joseph Moreau, Emeryville, CA (US); Naomi Samadara Rajapaksa, South San Francisco, CA (US); Galen Shearn-Nance, San Francisco, CA (US); David Charles Tully, Emeryville, CA (US); Michael Robert Turner, Emeryville, CA (US); Joseph Michael Young, Emeryville, CA (US); Qian Zhao, Louisville, CO (US); Britton K. Corkey, Foster City, CA (US); Samuel E. Metobo, Foster City, CA (US)

(73) Assignees: Novartis AG, Basel (CH); Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/030,540

(22) Filed: Sep. 24, 2020

(65) Prior Publication Data

US 2021/0130302 A1 May 6, 2021

Related U.S. Application Data

(60) Provisional application No. 62/906,664, filed on Sep. 26, 2019.

(51) Int. Cl.
| | | |
|---|---|---|
| *C07D 471/04* | (2006.01) | |
| *C07D 471/14* | (2006.01) | |
| *A61K 31/4162* | (2006.01) | |
| *A61K 31/437* | (2006.01) | |
| *A61P 31/22* | (2006.01) | |
| *C07D 243/10* | (2006.01) | |

(52) U.S. Cl.
CPC .................................. *C07D 243/10* (2013.01)

(58) Field of Classification Search
CPC  C07D 471/04; C07D 471/14; A61K 31/4162; A61K 31/437; A61P 31/22
See application file for complete search history.

(56) References Cited

U.S. PATENT DOCUMENTS

| | | |
|---|---|---|
| 4,661,493 A | 4/1987 | Gibbs |
| 5,149,778 A | 9/1992 | Adams et al. |
| 5,484,771 A | 1/1996 | Beaulieu et al. |
| 5,502,036 A | 3/1996 | Adams et al. |
| 5,552,384 A | 9/1996 | Deziel |
| 5,830,864 A | 11/1998 | Deziel et al. |
| 6,111,090 A | 8/2000 | Gorman et al. |
| 6,284,798 B1 | 9/2001 | Amtmann et al. |
| 7,025,962 B1 | 4/2006 | Gorman et al. |
| 7,618,632 B2 | 11/2009 | Collins et al. |
| 7,812,135 B2 | 10/2010 | Smith et al. |
| 7,943,743 B2 | 5/2011 | Korman et al. |
| 8,008,449 B2 | 8/2011 | Korman et al. |
| 8,354,509 B2 | 1/2013 | Carven et al. |
| 8,388,967 B2 | 3/2013 | Smith et al. |
| 8,586,023 B2 | 11/2013 | Shiku et al. |
| 8,591,886 B2 | 11/2013 | Ponath et al. |
| 8,609,089 B2 | 12/2013 | Langermann et al. |
| 2007/0191387 A1 | 8/2007 | Wunberg et al. |
| 2010/0028330 A1 | 2/2010 | Collins et al. |
| 2011/0150892 A1 | 6/2011 | Thudium et al. |
| 2012/0039906 A1 | 2/2012 | Olive |
| 2012/0114649 A1 | 5/2012 | Langermann et al. |
| 2020/0079772 A1 | 3/2020 | Becker et al. |

FOREIGN PATENT DOCUMENTS

| | | |
|---|---|---|
| CN | 107936016 | 4/2018 |
| CN | 108178757 A | 6/2018 |
| EP | 0090505 B1 | 8/1990 |
| EP | 0408973 B1 | 10/1996 |
| EP | 1866339 B1 | 5/2013 |
| EP | 1947183 B1 | 7/2013 |
| EP | 2161336 B2 | 3/2017 |
| WO | 9318056 A1 | 9/1993 |

(Continued)

OTHER PUBLICATIONS

International Search Report, issued in PCT/US2020/052375, dated Feb. 1, 2021.
Trapani et al., "Synthesis and Benzodiazepine Receptor Binding of 5H-Pyrido[2,1-C][1,4]Benzothiazines," II Farmaco, vol. 45, No. 6, (1990), pp. 589-602.
Van Delden, C. et al. (2020) "Burden and Timeline of Infectious Diseases in the First Year After Solid Organ Transplantation in the Swiss Transplant Cohort Study" Clinical Infectious Diseases, 1-11.
Van Delden, C. et al. (2020) Supplement for "Burden and timeline of infectious diseases in the first year after solid organ transplantation in the Swiss Transplant Cohort study".

(Continued)

*Primary Examiner* — Brenda L Coleman
(74) *Attorney, Agent, or Firm* — McNeill Baur PLLC

(57) ABSTRACT

The invention provides compounds of Formula (I)

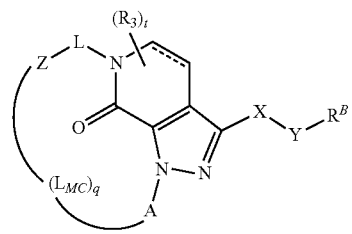

as described herein, along with pharmaceutically acceptable salts, pharmaceutical compositions containing such compounds, and methods to use these compounds, salts and compositions for treating viral infections, particularly infections caused by herpesviruses.

38 Claims, No Drawings

Specification includes a Sequence Listing.

(56) References Cited

FOREIGN PATENT DOCUMENTS

| | | |
|---|---|---|
| WO | 9724343 A1 | 7/1997 |
| WO | 9745401 A1 | 12/1997 |
| WO | 9811073 A1 | 3/1998 |
| WO | 9835685 A1 | 8/1998 |
| WO | 9845259 A2 | 10/1998 |
| WO | 9852948 A1 | 11/1998 |
| WO | 9918071 A1 | 4/1999 |
| WO | 9918072 A1 | 4/1999 |
| WO | 9918073 A1 | 4/1999 |
| WO | 99020758 A1 | 4/1999 |
| WO | 9932450 A1 | 7/1999 |
| WO | 9932477 A1 | 7/1999 |
| WO | 99040196 A1 | 8/1999 |
| WO | 9947507 A2 | 9/1999 |
| WO | 0039131 A1 | 7/2000 |
| WO | 00040561 A1 | 7/2000 |
| WO | 00040563 A1 | 7/2000 |
| WO | 0053610 A2 | 9/2000 |
| WO | 0058270 A2 | 10/2000 |
| WO | 01003720 A1 | 1/2001 |
| WO | 0125239 A2 | 4/2001 |
| WO | 0170706 A2 | 9/2001 |
| WO | 0170742 A1 | 9/2001 |
| WO | 0172728 A2 | 10/2001 |
| WO | 0174816 A1 | 10/2001 |
| WO | 0181318 A1 | 11/2001 |
| WO | 0198275 A2 | 12/2001 |
| WO | 0202558 A1 | 1/2002 |
| WO | 0204422 A2 | 1/2002 |
| WO | 0204444 A2 | 1/2002 |
| WO | 0204445 A1 | 1/2002 |
| WO | 0204462 A1 | 1/2002 |
| WO | 0206513 A2 | 1/2002 |
| WO | 02053543 A1 | 7/2002 |
| WO | 02064145 A1 | 8/2002 |
| WO | 02070487 A1 | 9/2002 |
| WO | 03020728 A1 | 3/2003 |
| WO | 03020729 A1 | 3/2003 |
| WO | 03026652 A1 | 4/2003 |
| WO | 03053971 A1 | 7/2003 |
| WO | 03053972 A1 | 7/2003 |
| WO | 03059878 A2 | 7/2003 |
| WO | 03059911 A2 | 7/2003 |
| WO | 03059912 A1 | 7/2003 |
| WO | 03099276 A1 | 12/2003 |
| WO | 04022566 A1 | 3/2004 |
| WO | 04022567 A1 | 3/2004 |
| WO | 04022568 A1 | 3/2004 |
| WO | 04065367 A1 | 8/2004 |
| WO | 04078163 A2 | 9/2004 |
| WO | 04083177 A2 | 9/2004 |
| WO | 2004082577 A2 | 9/2004 |
| WO | 04087140 A1 | 10/2004 |
| WO | 04087169 A1 | 10/2004 |
| WO | 04106345 A2 | 12/2004 |
| WO | 04111037 A1 | 12/2004 |
| WO | 05007190 A1 | 1/2005 |
| WO | 05012545 A2 | 2/2005 |
| WO | 05016927 A1 | 2/2005 |
| WO | 05018557 A2 | 3/2005 |
| WO | 05055808 A2 | 6/2005 |
| WO | 05072361 A2 | 8/2005 |
| WO | 05115451 A2 | 12/2005 |
| WO | 06083289 A2 | 8/2006 |
| WO | 06121168 A1 | 11/2006 |
| WO | 07005874 A2 | 1/2007 |
| WO | 07024922 A1 | 3/2007 |
| WO | 07092435 A2 | 8/2007 |
| WO | 07133822 A1 | 11/2007 |
| WO | 08137779 A2 | 11/2008 |
| WO | 09019553 A2 | 2/2009 |
| WO | 09101611 A1 | 8/2009 |
| WO | 09114335 A2 | 9/2009 |
| WO | 09137493 A1 | 11/2009 |
| WO | 10003118 A1 | 1/2010 |
| WO | 10019570 A2 | 2/2010 |
| WO | 10026029 A1 | 3/2010 |
| WO | 10027827 A2 | 3/2010 |
| WO | 10077634 A1 | 7/2010 |
| WO | 11028683 A1 | 3/2011 |
| WO | 11051726 A2 | 5/2011 |
| WO | 11066342 A2 | 6/2011 |
| WO | 11090754 A1 | 7/2011 |
| WO | 12115256 A1 | 8/2012 |
| WO | 12151195 A1 | 11/2012 |
| WO | 13039954 A1 | 3/2013 |
| WO | 13079174 A1 | 6/2013 |
| WO | 13085890 A1 | 6/2013 |
| WO | 13152063 A1 | 10/2013 |
| WO | 13152065 A2 | 10/2013 |
| WO | 2013171712 A1 | 11/2013 |
| WO | 14008218 A1 | 1/2014 |
| WO | 14070976 A1 | 5/2014 |
| WO | 14070978 A1 | 5/2014 |
| WO | 14070979 A1 | 5/2014 |
| WO | 15069844 A1 | 5/2015 |
| WO | 15153683 A1 | 10/2015 |
| WO | 15154820 A1 | 10/2015 |
| WO | 2015150957 A1 | 10/2015 |
| WO | 17193030 A1 | 11/2017 |
| WO | 20053654 A1 | 3/2020 |

OTHER PUBLICATIONS

Woo et al., "Immune inhibitory molecules LAG-3 and PD-1 synergistically regulate T cell function to promote tumoral immune escape", Cancer Res., (Feb. 2012) 72(4): pp. 917-927.

Yahav, D. et al. (2009) "Antiviral prophylaxis in haematological patients: Systematic review and meta-analysis" European Journal of Cancer, 45:3131-3148.

Zhou, X. et al. (2019) "First-Onset Herpesviral Infection and Lung Injury in Allogeneic Hematopoietic Cell Transplantation" American Journal of Respiratory and Critical Care Medicine 200(1):63-74.

Zhou, X. et al. (2019) Supplement to "First onset herpesviral infection and lung injury in allogeneic hematopoietic cell transplantation".

(2017) "Letermovir Assessment Report" European Medicines Agency, Committee for Medicinal Products for Human Use (CHMP), 1-124.

Abad, C. L. et al. (2016) "Treatment of alpha and beta herpesvirus infections in solid organ transplant recipients" Expert Review of Anti-infective Therapy, 15(2):93-110.

Bennett et al., "Program Death-1 Engagement Upon TCR Activation Has Distinct Effects on Costimulation and Cytokine-Driven Proliferation: Attenuation of ICOS, IL-4, and IL-21, but Not CD28, IL-7, and IL-15 Responses", J. Immunol. (Feb. 2003) 170: pp. 711-718.

Blank, Christian, Gajewski, Thomas F., Mackensen, Andreas, "Interaction of PD—LI on tumor cells with PD-1 on tumor-specific T cells as a mechanism of immune evasion: implications for tumor immunotherapy", Cancer Immunol. Immunother (2005), 54, pp. 307-314.

Blank, Christian, Mackensen, Andreas., "Contribution of the PD—LI/PD-1 pathway to T-cell exhaustion: an update on implications for chronic infections and tumor evasion", (2007) Cancer Immunol. Immunother. 56: pp. 739-745.

Boeckh, M. et al. (2006) "Long-term acyclovir for prevention of varicella zoster virus disease after allogeneic hematopoietic cell transplantation—a randomized double-blind placebo-controlled study" Blood, 107(5):1800-1805.

Brown et al., "Blockade of Programmed Death-1 Ligands on Dendritic Cells Enhances T Cell Activation and Cytokine Production", J. Immunol. (2003), 170: pp. 1257-1266.

Chen, S. et al. (2019) "Antiviral Agents as Therapeutic Strategies Against Cytomegalovirus Infections" Viruses, 12(21):1-11.

Danve-Szatanek, C. et al. (2004) "Surveillance Network for Herpes Simplex Virus Resistance to Antiviral Drugs: 3-Year Follow-Up" Journal of Clinical Microbiology, 42(1):242-249.

(56) References Cited

OTHER PUBLICATIONS

Deleenheer, B. et al. (2018) "Pharmacokinetic drug evaluation of letermovir prophylaxis for cytomegalovirus in hematopoietic stem cell transplantation" Expert Opinion on Drug Metabolism & Toxicology, 14(12):1197-1207.
Dong, Haidong, Chen, Lieping, "B7-HI pathway and its role in the evasion of tumor immunity", J. Mol. Med., (2003), 81: pp. 281-287.
Dunn, Walter, et al. "Functional profiling of a human cytomegalovirus genome", PNAS (Nov. 2003), vol. 100, No. 24., pp. 14223-14228.
Grantham, J. et al. (2019) "Development of a Sequencing Based Assay for Dectection of Resistance Mutations to Letermovir in UL56" Viracor, Eurofins Clinical Diagnostics, Poster.
Gugliesi, F. et al. (2020) "Where do we Stand after Decades of Studying Human Cytomegalovirus?" Microorganisms 8(685):1-30.
Hakki, M. et al. (2020) "Moving Past Ganciclovir and Foscarnet: Advances in CMV Therapy" Current Hematologic Malignancy Reports, 1-13.
Hamid, Omid. et al., "Safety and Tumor Responses with Lambrolizumab (Anti-PD-1) in Melanoma", New England Journal of Medicine, (2013), 369 (2): pp. 134-144.
Hill, J. et al. (2019) "Human Herpesvirus 6B and Lower Respiratory Tract Disease After Hematopoietic Cell Transplantation" Journal of Clinical Oncology 37: 1-13.
Hill, J. et al. (2019) Supplement to "Human Herpesvirus 6B and Lower Respiratory Tract Disease After Hematopoietic Cell Transplantation".
Hussein, I. et al. (2020) "The discovery and development of filociclovir for the prevention and treatment of human cytomegalovirus-related disease" Antiviral Research, 1-5.
International Search Report, issued in PCT/IB2019/001008, dated Feb. 24, 2020.
Ishida, Yasumasa, Agata, Yasutoshi, Shibahara, Keiichi, and Honjo, Tasuku, "Induced expression of PD-1, a novel member of the immunoglobulin gene superfamily, upon programmed cell death", EMBO Journal, (1992), vol. 11, No. 11: pp. 3887-3895.
Itell, H., et al. (2017) "Rhesus Monkeys for a Nonhuman Primate Model of Cytomegalovirus Infections" Curr Opin Virol. 25:126-133.
Konishi et al., "B7-HI Expression on Non-Small Cell Lung Cancer Cells and Its Relationship with Tumor-Infiltrating Lymphocytes and Their PD-1 Expression", Clin. Cancer Res., (Aug. 2004), 10: pp. 5094-5100.
Lau, C. et al. (2020) "LBA16—Letermovir Cytomegalovirus (CMV) Prophylaxis in Adult Seropositive Cord Blood Transplant (CBT) Recipients Is Highly Efficacious and Likely Cost-Effective" [ downloaded from https://tct.confex.com/tct/2020/meetingapp.cgi/Paper/15827] Poster No. LBA16, Transplantation & Cellular Therapy Meetings, World Center Marriott, Orlando, Florida, Feb. 22, 2020.
Letermovir Clinical Pharmacology and Biopharmaceutics Review(s) for 209939 and 209940, Aug. 8, 2017.
Lin, A. et al. (2019) "Letermovir for primary and secondary cytomegalovirus prevention in allogeneic hematopoietic cell transplant recipients: Real-world experience" Transpl Infect Dis 21:1-6.
Lischka, P. et al. (2010) "In Vitro and In Vivo Activities of the Novel Anticytomegalovirus Compound AIC246" Anitmicrobial Agents and Chemotherapy 54(3):1290-1297.
Ljungman, P. et al. (2019) "A Mortality Analysis of Letermovir Prophylaxis for Cytomegalovirus (CMV) in CMV-seropositive Recipients of Allogeneic Hematopoietic Cell Transplantation" Clinical Infectious Diseases, 1-9.
Iwai et al., "Involvement of PD—LI on tumor cells in the escape from host immune system and tumor immunotherapy by PD—LI blockade", Proc. Nat'/. Acad. Sci. (Sep. 2002), vol. 99, No. 19, pp. 12293-12297.
Ma et.al., "Real-time monitoring of DNA polymerase activity using molecular beacon", Analytical Biochemistry, (2006), 353 (1): pp. 141-143.
Marschall, M. et al. (2011) "In Vitro Evaluation of the Activities of the Novel Anticytomegalovirus Compound AlC246 (Letermovir) against Herpesviruses and Other Human Pathogenic Viruses" Antimicrobial Agents and Chemotherapy, 1135-1137.
Marty, F. et al. (2017) "Letermovir Prophylaxis for Cytomegalovirus in Hematopoietic-Cell Transplantation" N Engl J Med 377:2433-2444.
Marty, F. et al. (2018) "A Randomized, Double-Blind, Placebo-Controlled Phase 3 Trial of Oral Brincidofovirfor Cytomegalovirus Prophylaxis in Allogeneic Hematopoietic Cell Transplantation" Biol Blood Marrow Transplant 25:369-381.
Marty, F. et al. (2019) "Outcomes of patients with detectable CMV DNA at randomization in the phase III trial of letermovir for the prevention of CMV infection in allogeneic hematopoietic cell transplantation" The American Society of Transplantation and the American Society of Transplant Surgeons [https://doi.org/10.1111/ajt.15764].
Morfin, F., et al. (2004) "HSV excretion after bone marrow transplantation: a 4-year survey" Journal of Clinical Virology, 30:341-345.
Northrup, Alan B. et al., "Discovery of 1-[3-(1-Methyl-1H-pyrazol-4-yl)-5-oxo-5H-benzo[4,5]cycloheptal[l,2-b]pyridine-7-yl]-N-(pyridine-2-ylmethyl)methanesulfonamide (MK-8033): A Specific c-Met/Ron Dual Kinase Inhibitor with Preferential Affinity for Activated State of c-Met", J. Med. Chem., (2013), 56, 2294-2310.
Oien, N. et al. (2002) "Broad-Spectrum Antiherpes Activities of 4-Hydroxyquinoline Carboxamides, a Novel Class of Herpesvirus Polymerase Inhibitors" Anitmicrobial Agents Chemotherapy 46(3):724-730.
Okazaki, Taku, Iwai, Yoshiko, and Honjo, Tasuku, "New regulatory co-receptors: inducible co-stimulator and PD-1", (2002) Current Opinion in Immunology 14: 779-782.
Powers, C. et al. (2008) "Rhesus CMV: an emerging animal model for human CMV" Med Microbiol Immunol 197:109-115.
Qiao, J. et al. (2009) "Highly efficacious factor Xa inhibitors containing a-substituted phenylcycloalkyl P4 moieties" Bioorganic & Medicinal Chemistry Letters 19:462-468.
Schnute, M. et al. (2005) "4-Oxo-4,7-dihydrothieno[2,3-b]pyridines as Non-Nucleoside Inhibitors of Human Cytomegalovirus and Related Herpesvirus Polymerases" J. Med. Chem. 48:5794-5804.
Seo, S. et al. (2015) "Idiopathic pneumonia syndrome after hematopoietic cell transplantation: evidence of occult infectious etiologies" Blood, 125(24):3789-3797.
Stoelben, S. et al. (2013) "Preemptive treatment of Cytomegalovirus infection in kidney transplant recipients with letermovir: results of a Phase 2a study" Transplant International, 27:77-86.
Stranska, R. et al. (2005) "Survey of acyclovir-resistant herpes simplex virus in the Netherlands: prevalence and characterization" Journal of Clinical Virology 32:7-18.

SEQUENCE LISTING

<160> NUMBER OF SEQ ID NOS: 16

<210> SEQ ID NO 1
<211> LENGTH: 17
<212> TYPE: DNA
<213> ORGANISM: Artificial Sequence
<220> FEATURE:
<223> OTHER INFORMATION: PCR primer or probe

<400> SEQUENCE: 1
tagtcggtgg gctgtgt         17

<210> SEQ ID NO 2
<211> LENGTH: 20
<212> TYPE: DNA
<213> ORGANISM: Artificial Sequence
<220> FEATURE:
<223> OTHER INFORMATION: PCR primer or probe

<400> SEQUENCE: 2
aactgggtcc atgtagggat                                           20

<210> SEQ ID NO 3
<211> LENGTH: 22
<212> TYPE: DNA
<213> ORGANISM: Artificial Sequence
<220> FEATURE:
<223> OTHER INFORMATION: PCR primer or probe

<400> SEQUENCE: 3
tgcttgagct cctgcgtcgt ac                                        22

<210> SEQ ID NO 4
<211> LENGTH: 20
<212> TYPE: DNA
<213> ORGANISM: Artificial Sequence
<220> FEATURE:
<223> OTHER INFORMATION: PCR primer or probe

<400> SEQUENCE: 4
cctccgtatc gggacttcaa                                           20

<210> SEQ ID NO 5
<211> LENGTH: 20
<212> TYPE: DNA
<213> ORGANISM: Artificial Sequence
<220> FEATURE:
<223> OTHER INFORMATION: PCR primer or probe

<400> SEQUENCE: 5
tgaccgtcct cgcatacgta                                           20

<210> SEQ ID NO 6
<211> LENGTH: 16
<212> TYPE: DNA
<213> ORGANISM: Artificial Sequence
<220> FEATURE:
<223> OTHER INFORMATION: PCR primer or probe

<400> SEQUENCE: 6
ttggcgaaga gctaac                                               16

<210> SEQ ID NO 7
<211> LENGTH: 22
<212> TYPE: DNA
<213> ORGANISM: Artificial Sequence
<220> FEATURE:
<223> OTHER INFORMATION: PCR primer or probe

<400> SEQUENCE: 7
acacccctta tccccatact ag                                        22

<210> SEQ ID NO 8
<211> LENGTH: 22
<212> TYPE: DNA
<213> ORGANISM: Artificial Sequence
<220> FEATURE:
<223> OTHER INFORMATION: PCR primer or probe

<400> SEQUENCE: 8
atggttgata ttgctagggt gg                                        22

<210> SEQ ID NO 9
<211> LENGTH: 23
<212> TYPE: DNA
<213> ORGANISM: Artificial Sequence

```
<220> FEATURE:
<223> OTHER INFORMATION: PCR primer or probe

<400> SEQUENCE: 9
accgctaaca ttactgcagg cca                                           23

<210> SEQ ID NO 10
<211> LENGTH: 20
<212> TYPE: DNA
<213> ORGANISM: Artificial Sequence
<220> FEATURE:
<223> OTHER INFORMATION: PCR primer or probe

<400> SEQUENCE: 10
cggccgtgat ggaggctatg                                               20

<210> SEQ ID NO 11
<211> LENGTH: 18
<212> TYPE: DNA
<213> ORGANISM: Artificial Sequence
<220> FEATURE:
<223> OTHER INFORMATION: PCR primer or probe

<400> SEQUENCE: 11
agacagaggc caccacgg                                                 18

<210> SEQ ID NO 12
<211> LENGTH: 23
<212> TYPE: DNA
<213> ORGANISM: Artificial Sequence
<220> FEATURE:
<223> OTHER INFORMATION: PCR primer or probe

<400> SEQUENCE: 12
tgacctttgg ctcggcctcc tgc                                           23

<210> SEQ ID NO 13
<211> LENGTH: 22
<212> TYPE: DNA
<213> ORGANISM: Artificial Sequence
<220> FEATURE:
<223> OTHER INFORMATION: PCR primer or probe

<400> SEQUENCE: 13
gctgtcatct cttgtgggct gt                                            22

<210> SEQ ID NO 14
<211> LENGTH: 22
<212> TYPE: DNA
<213> ORGANISM: Artificial Sequence
<220> FEATURE:
<223> OTHER INFORMATION: PCR primer or probe

<400> SEQUENCE: 14
aaactcatgg gagctgctgg tt                                            22

<210> SEQ ID NO 15
<211> LENGTH: 26
<212> TYPE: DNA
<213> ORGANISM: Artificial Sequence
<220> FEATURE:
<223> OTHER INFORMATION: PCR primer or probe

<400> SEQUENCE: 15
cctgtcatgc ccacacaaat ctctcc                                        26
```

```
<210> SEQ ID NO 16
<211> LENGTH: 33
<212> TYPE: DNA
<213> ORGANISM: Artificial Sequence
<220> FEATURE:
<223> OTHER INFORMATION: Molecular Beacon

<400> SEQUENCE: 16
cctctccgtg tcttgtactt cccgtcagag agg                          33
```

ANTIVIRAL PYRAZOLOPYRIDINONE COMPOUNDS

RELATED APPLICATIONS

This application claims priority to U.S. Provisional Application No. 62/906,664, filed Sep. 26, 2019, the contents of which are hereby incorporated herein by reference.

STATEMENT REGARDING SEQUENCE LISTING

The Sequence Listing associated with this application is provided in text format in lieu of paper copy, and is hereby incorporated by reference into the specification. The name of the text file containing the Sequence Listing is "58231_ST25." The text file is 3 KB, was created on Sep. 23, 2020, and is being submitted electronically via EFS-Web, concurrent with the filing of this specification.

FIELD OF THE INVENTION

The present invention relates to novel bicyclic pyrazolopyridione compounds that are inhibitors of herpesvirus replication, and are thus useful to treat herpesvirus infections. The compounds inhibit viral DNA polymerases of various herpesviruses, including cytomegalovirus (CMV), herpes simplex viruses, and others. The invention provides novel bicyclic pyrazolopyridione compounds as disclosed herein, pharmaceutical compositions containing such compounds, and methods of using these compounds and compositions in the treatment and prevention of herpesvirus disease.

BACKGROUND

Human CMV, also known as human herpesvirus 5 (HHV-5), is a β-herpesvirus that affects all populations, worldwide, including adults and children with normal or compromised immune systems. While often asymptomatic in healthy individuals, CMV can become life-threatening in immunocompromised individuals. CMV is also cause for concern during pregnancy, as it can be transmitted from mother to fetus and cause severe birth defects. No treatment is approved to prevent or treat congenital CMV infection. In the transplant setting, the current anti-CMV therapies include the nucleoside analogs Valganciclovir (valGCV), Ganciclovir (GCV) and Cidofovir (CDV), and a pyrophosphate analog, Foscarnet (FOS). Each of these therapeutic agents inhibits the CMV DNA polymerase, a protein encoded by the UL54 gene, which is an enzyme essential for viral replication (PNAS 2003, 100(24), 14223-14228; WO2013/152063; WO 2005/012545). In solid organ transplant recipients, the first line therapy consists of either prophylaxis or preemptive treatment with GCV, or the orally bioavailable prodrug valGCV. GCV significantly decreases the risk of disease, and can effectively treat active CMV infection. However, the drug is poorly tolerated. GCV and valGCV can cause severe bone marrow suppression which, in stem cell transplant recipients, puts the patient at risk for engraftment failure. Second line therapies such as CDV and FOS, are associated with severe nephrotoxicity. Moreover, resistance to current anti-CMV nucleoside analogs is a significant cause of treatment failure. Novel classes of CMV therapeutic agents are therefore needed, particularly non-nucleoside compounds, to provide safer CMV treatments and to combat herpesviruses that are resistant to known classes of antivirals.

In addition to CMV, herpesviruses that cause widespread human viral infections include Epstein-Barr virus (EBV), Varicella zoster virus (VZV), and herpes simplex viruses HSV-1 and HSV-2. Other herpesviruses that cause disease in humans include human herpesvirus 6, human herpesvirus 7, and Kaposi's sarcoma-associated herpesvirus Herpesvirus infections are not only widespread, they also persist lifelong in their host in latent stage. By one estimate, over 90% of adult humans are latently infected with at least one herpesvirus that may be reactivated years later. Zoster (Shingles), for example, results when the varicella zoster virus (VZV) is reactivated from latency, typically many years after the original infection (chicken pox) has been controlled. Zoster is a painful condition that affects primarily older adults and individuals with immune dysfunction. Complications include post-herpetic neuralgia, a potentially debilitating and chronic pain syndrome, against which anti-VZV inhibitors (nucleosides) only have a marginal impact.

Immunocompromised individuals such as transplant patients are at high risk for herpesvirus reactivation such as CMV, HSV or VZV. Thus a safe and potent viral inhibitor with broad herpesvirus activity would be extremely valuable. The current invention provides novel compounds that are active against several herpesviruses, including CMV, HSV, VZV and EBV.

SUMMARY OF THE INVENTION

The present invention provides novel non-nucleoside compounds that inhibit herpesvirus DNA polymerases, with potent antiviral activity in vitro. Compounds are active against several herpesviruses, including CMV, HSV, VZV and EBV. A potent non-nucleoside polymerase inhibitor has significant advantages over the current anti-CMV agents. First, unlike nucleoside analogs, the compounds are not incorporated by human polymerases and are thus expected to have a better safety profile than the current anti-CMV drugs. Second, the compounds described herein are active on GCV-resistant virus, thus having a potential for rescue therapy in patients with cross-resistance to nucleoside analogs. Finally, the compounds are active against several human herpesviruses providing opportunity for a broad clinical use. The invention also provides pharmaceutical compositions containing the novel compounds as well as methods to use the compounds and compositions to inhibit herpesvirus replication or reactivation, and to treat disease conditions associated with or caused by herpesviruses. Further objects of this invention are described in the following description and the examples.

In one aspect, the invention provides compounds of Formula (I):

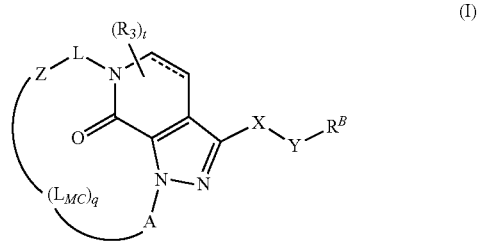

wherein:
X is

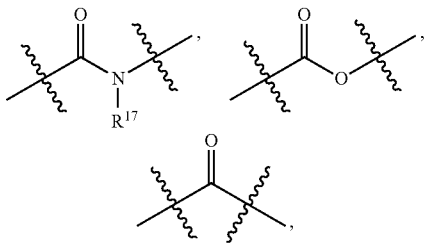

a 5-6 membered heteroaryl having 1 to 4 heteroatoms independently selected from N, O and S as ring members, a 5-6 membered heterocycloalkyl containing 1 to 4 ring members independently selected from N, NH, NR$^{17}$, O or S or a 5-6 membered heterocyclyl containing 1 to 4 ring members independently selected from N, NH, NR$^{17}$, O or S;

Y is a bond,

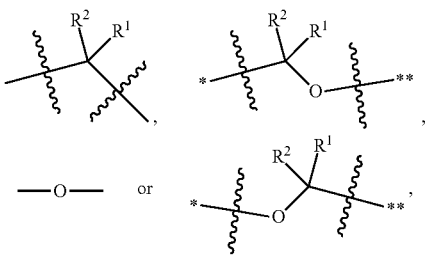

wherein the * of Y indicates the point of attachment to X and the ** of Y indicates the point of attachment to R$^B$;

q is 0 or 1;

when q is 1, then L$_{MC}$ is *—((CR$^{11}$R$^{12}$)$_n$O)$_m$(CR$^{11}$R$^{12}$)$_p$—**, *—C(=O)NR$^{15}$((CR$^{11}$R$^{12}$)$_n$O)$_m$(CR$^{11}$R$^{12}$)$_p$—**, *—(CR$^{11}$R$^{12}$)$_n$NR$^{15}$((CR$^{11}$R$^{12}$)$_n$O)$_m$(CR$^{11}$R$^{12}$)$_p$—**, *—(CR$^{11}$R$^{12}$)$_n$—**, *—((CR$^{11}$R$^{12}$)$_n$NR$^{15}$)$_m$(CR$^{11}$R$^{12}$)$_p$—**, *—(CR$^{11}$R$^{12}$)C(=O)NR$^{15}$(CR$^{11}$R$^{12}$)$_n$—**, *—C(=NR$^{15}$)(CR$^{11}$R$^{12}$)$_n$—**, *—O(CR$^{11}$R$^{12}$)$_n$—**, or *—NR$^{15}$(CR$^{11}$R$^{12}$)$_n$**,
wherein the * of L$_{MC}$ indicates the point of attachment to Z and the ** of L$_{MC}$ indicates the point of attachment to A;

when q is 1, then L$_{MC}$ is present, A is a bond and Z is

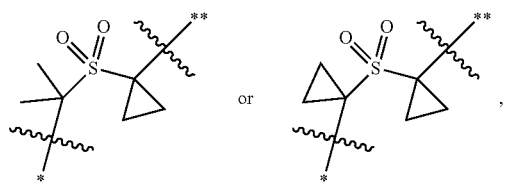

wherein the * of Z indicates the point of attachment to LMC and the ** of Z indicates the point of attachment to L;

m is 1, 2, 3, 4, 5, 6, 7, 8, 9 or 10;
each n is independently selected from 1, 2, 3, 4, 5, 7, 8, 9 and 10;

p is 1, 2, 3, 4, 5 or 6;
when q is 0, then L$_{MC}$ is absent, and Z is W, and A is R$^4$;
R$^B$ is H, C$_1$-C$_6$alkyl, phenyl, pyridinyl, thiophenyl, pyrimidinyl, or a 5-8 membered cycloalkyl, wherein R$^B$ is optionally substituted with 1 to 3 R$^5$ groups;
R$^1$ is selected from H, C$_1$-C$_3$alkyl and C$_1$-C$_3$alkyl substituted with 1 to 3 —OH groups;
R$^2$ is selected from H, C$_1$-C$_3$alkyl and C$_1$-C$_3$alkyl substituted with 1 to 3 —OH groups;
or R$^1$ and R$^2$ taken together with the carbon to which they are attached can form a 3-6 membered cycloalkyl ring;
t is 0, 1 or 2;
each R$^3$, when present, is a substituent on the ring to which -L-Z is directly attached, wherein each R$^3$ is independently selected from halo, CN, C$_1$-C$_3$alkoxy, C$_1$-C$_3$alkyl, C(=O)OR$^{10}$, and C(=O)NR$^{13}$R$^{14}$;
R$^4$ is H, C$_1$-C$_3$alkyl, C$_3$-C$_6$cycloalkyl, —(CH$_2$)$_2$O(CH$_2$)$_2$Br or a C$_1$-C$_3$alkyl substituted with 1 to 2 groups independently selected from —OH, —C(=O)R$^{15}$ and R$^{10}$;
each R$^5$ is independently selected from halo, —CN, hydroxy, —NR$^{13}$R$^{14}$, C$_3$-C$_6$cycloalkyl, C$_1$-C$_3$alkoxy, C$_1$-C$_3$haloalkyl, and C$_1$-C$_3$alkyl optionally substituted with 1 to 3 R$^6$ groups, wherein when R$^B$ is substituted with two R$^5$ and each R$^5$ is a C$_1$-C$_3$alkyl optionally substituted with 1 to 3 R$^6$ groups, when directly attached to the same carbon atom, may be taken together with the carbon to which both are directly attached to form a 3-5 membered cycloalkyl ring optionally substituted with 1 to 3 R$^6$ groups;
each R$^6$ is independently selected from halo, hydroxy, CN, C$_1$-C$_3$alkoxy, C$_1$-C$_3$alkyl, and C$_3$-C$_5$cycloalkyl,
or two R$^6$ groups, taken together with a carbon atom to which both are directly attached may form a 3-5 membered cycloalkyl ring or a 4-6 membered heterocyclic ring containing O, N or S as a ring member and optionally substituted with 1 to 2 groups independently selected from oxo and C$_1$-C$_3$alkyl;
L is a C$_1$-C$_4$ straight chain or branched alkylene linker, or L can be a C$_1$-C$_4$ straight chain or branched alkylene linker or a bond when W is an optionally substituted ring;
W is H, —OH, —OR$^{10}$, —C(=O)NR$^{13}$R$^{14}$, —C(=O)OR$^{13}$, —NR$^{13}$R$^{14}$, —NR$^{13}$C(=O)OR$^{10}$, —NR$^{13}$C(=O)R$^{10}$, —SO$_2$R$^{10}$, —SO$_2$NR$^{13}$R$^{14}$, —NR$^{13}$SO$_2$R$^{10}$, —P(=O)(OR$^{13}$)$_2$, —S(=O)R$^{10}$, —S(=O)(=NR$^{13}$)R$^{10}$, —CR$^{11}$R$^{12}$C(=O)NR$^{13}$R$^{14}$, —CR$^{11}$R$^{12}$C(=O)OR$^{13}$, —CR$^{11}$R$^{12}$NR$^{13}$R$^{14}$, —CR$^{11}$R$^{12}$NR$^{13}$C(=O)OR$^{10}$, —CR$^{11}$R$^{12}$NR$^{13}$C(=O)R$^{10}$, —CR$^{11}$R$^{12}$SO$_2$R$^{10}$, —CR$^{11}$R$^{12}$SO$_2$NR$^{13}$R$^{14}$, —CR$^{11}$R$^{12}$NR$^{13}$SO$_2$R$^{10}$, —CR$^{11}$R$^{12}$P(=O)(OR$^{13}$)$_2$, —CR$^{11}$R$^{12}$S(=O)R$^{10}$, —CR$^{11}$R$^{12}$S(=O)(=NR$^{13}$)R$^{10}$, a 3-6 membered cycloalkyl, phenyl, a 5-6-membered heterocycloalkyl containing one or two ring members independently selected from N, NH, NR$^{17}$, O or S, a 5-6-membered heterocyclyl containing one or two ring members independently selected from N, NH, NR$^{17}$, O or S, or a 5-membered heteroaryl having 1 to 4 heteroatoms selected from N, O and S as ring members that is optionally fused to phenyl,
wherein the 3-6 membered cycloalkyl, phenyl, 5-6-membered heterocycloalkyl, 5-6-membered heterocyclyl and 5-membered heteroaryl of W are each optionally substituted with 1 to 3 groups independently selected from C$_1$-C$_3$alkyl, oxo, halo, C$_1$-C$_3$haloalkyl, -L$^2$OH, -L$^2$OR$^{10}$, -L$^2$OC(=O)

$NR^{13}R^{14}$, -$L^2SO_2R^{10}$, -$L^2SO_2NR^{14}R^{10}$, -$L^2SO_2NR^{13}R^{14}$, -$L^2SO_2N=CR^{13}NR^{13}R^{14}$, -$L^2SO_2NR^{13}C(=O)R^{10}$, -$L^2C(=O)NR^{13}SO_2R^{10}$, -$L^2S(=O)R^{10}$, -$L^2S(=O)(=NR^{13})R^{10}$, -$L^2NR^{13}SO_2NR^{13}R^{14}$, -$L^2NR^{13}SO_2R^{10}$, -$L^2NR^{13}R^{14}$, -$L^2NR^{13}C(=O)R^{13}$, -$L^2NR^{13}C(=O)OR^{10}$, -$L^2C(=O)NR^{13}R^{14}$, and -$L^2C(=O)OR^{13}$;

$R^{10}$ is selected from $C_1$-$C_5$alkyl, $C_1$-$C_3$haloalkyl, 3-6 membered cycloalkyl, phenyl, 5-6 membered heteroaryl having 1 to 4 heteroatoms independently selected from N, O and S as ring members, 4-6 membered heterocycloalkyl containing one or two ring members independently selected from N, NH, $NR^{17}$, O or S and 4-6 membered heterocyclyl containing 1 to 2 ring members independently selected from N, NH, $NR^{17}$, O or S, wherein each $R^{10}$ is optionally substituted with 1 to 5 groups independently selected from $C_1$-$C_4$alkyl, deuterium, $C_1$-$C_4$haloalkoxy, -$L^3OH$, -$L^3CN$, -$L^3OC(=O)R^{14}$, -$L^3OR^{13}$, $C_1$-$C_3$haloalkyl, oxo, -$L^3$halo, -$L^3C_1$-$C_3$alkoxy, -$L^3OC(=O)NR^{13}R^{14}$, -$L^3SO_2R^{13}$, -$L^3SO_2NR^{13}R^{14}$, -$L^3SO_2NR^{13}C(=O)R^{13}$, -$L^3C(=O)NR^{13}SO_2R^{13}$, -$L^3S(=O)R^{13}$, -$L^3S(=O)(=NR^{14})R^{13}$, -$L^3NR^{13}SO_2NR^{13}R^{14}$, -$L^3NR^{13}SO_2R^{13}$, -$L^3NR^{13}R^{14}$, -$L^3NR^{14}C(=O)R^{13}$, -$L^3NR^{14}C(=O)OR^{13}$, -$L^3C(=O)NR^{13}R^{14}$, -$L^3C(=O)OR^{13}$, -$L^3$-(4-7-membered heterocycloalkyl containing 1 to 2 ring members independently selected from N, NH, $NR^{17}$, O or S), -$L^3$-(4-7-membered heterocyclyl containing 1 to 2 ring members independently selected from N, NH, $NR^{17}$, or S), -$L^3$-$C_3$-$C_5$cycloalkyl, and -$L^3$-(5-6 membered heteroaryl ring having 1 to 4 heteroatoms comprising 1-4 nitrogen atoms, 0 or 1 oxygen atoms, and 0 or 1 sulfur atoms as ring members), where the $C_1$-$C_4$alkyl, 4-7-membered heterocycloalkyl, 4-7-membered heterocyclyl, $C_3$-$C_5$cycloalkyl and 5-6 membered heteroaryl ring are each optionally further substituted with 1 to 3 groups independently selected from halo, $C_1$-$C_3$alkyl, $C_1$-$C_3$haloalkyl, -$L^4OR^{13}$, -$L^4CN$, and -$L^4NR^{13}R^{14}$;

$R^{11}$ and $R^{12}$ are each independently selected from H and $C_1$-$C_4$alkyl;

each $R^{13}$ is independently selected from H, $C_1$-$C_4$alkyl, a 4-7-membered heterocycloalkyl containing 1 to 2 ring members independently selected from N, NH, $NR^{17}$, O or S, a 4-7-membered heterocyclyl containing 1 to 2 ring members independently selected from N, NH, $NR^{17}$, O or S, and a $C_3$-$C_6$cycloalkyl, wherein the $C_1$-$C_4$alkyl, heterocycloalkyl, heterocyclyl and $C_3$-$C_6$cycloalkyl are optionally substituted with 1 to 3 groups independently selected from $C_1$-$C_4$alkyl, halo, —OH, —$NR^{15}R^{16}$, —C(=O)$OR^{15}$, $C_1$-$C_2$alkoxy and $C_1$-$C_4$alkyl substituted with 1 to 2 hydroxy groups;

$R^{14}$ is selected from H, $C_1$-$C_4$alkyl and $C_3$-$C_6$cycloalkyl, wherein the $C_1$-$C_4$alkyl and $C_3$-$C_6$cycloalkyl are optionally substituted with 1 to 3 groups independently selected from $C_1$-$C_4$alkyl, halo, —OH, —$NR^{15}R^{16}$, $C_1$-$C_2$alkoxy and $C_1$-$C_4$alkyl substituted with 1 to 2 hydroxy groups;

or $R^{13}$ and $R^{14}$, taken together with a nitrogen atom to which both are directly attached, can form a 4-6 membered ring optionally containing an additional N, O or S as a ring member and optionally substituted with one to three groups selected from $C_1$-$C_2$alkyl, $C_1$-$C_2$alkoxy, oxo, and hydroxy;

$R^{15}$ and $R^{16}$ are each independently selected from H and $C_1$-$C_4$alkyl;

each $R^{17}$ is independently selected from H, $C_1$-$C_4$alkyl and $C_3$-$C_8$cycloalkyl;

or $R^{17}$ is $C_1$-$C_4$alkyl which, together with a nitrogen atom to which it is directly attached and a nitrogen atom from the pyrazole ring, can form a 5-8 membered ring fused to the pyrazole ring;

each $L^2$ and $L^3$ and $L^4$ is independently a bond or a straight chain or branched $C_1$-$C_3$alkylene;

and

'---' represents a single or double bond.

Another aspect of the invention is a pharmaceutical composition comprising a compound of the invention, or a pharmaceutically acceptable salt thereof, and a pharmaceutically acceptable carrier. In an embodiment of this aspect the pharmaceutical composition according to this invention further comprises a therapeutically effective amount of at least one other antiviral agent.

Another aspect of the invention involves a method of treating or preventing a herpes virus disease and/or infection in a human being by administering to the human being an antivirally effective amount of a compound of the invention, a pharmaceutically acceptable salt thereof, or a composition as described above, alone or in combination with at least one other antiviral agent, administered together or separately.

Another aspect of the invention involves a method of treating or preventing a herpesvirus disease and/or infection in a human being by administering to the human being a compound of the invention, a pharmaceutically acceptable salt thereof, or a composition as described above, alone or in combination with at least one other antiviral agent, administered together or separately.

Still another aspect of this invention relates to a method of inhibiting the replication of CMV or another herpesvirus, comprising exposing the virus to an effective amount of a compound of the invention, or a pharmaceutically acceptable salt thereof, under conditions where replication of the virus is inhibited. This method can be practiced in vitro or in vivo.

Another aspect of the invention is the use of a compound of the invention, or a pharmaceutically acceptable salt thereof, in the manufacture of a medicament for the treatment or prevention of a herpesvirus disease and/or infection in a human being, including CMV.

Another embodiment of the invention provides a compound as described above, or a pharmaceutically acceptable salt thereof, as a medicament.

Another aspect of the invention is the use of a pharmaceutical composition as described hereinabove for the treatment of a CMV infection or other herpesvirus in a human being having or at risk of having the infection.

Another aspect of the invention is the use of a pharmaceutical composition as described hereinabove for the treatment of CMV disease or other herpesvirus infection in a human being having or at risk of having the disease.

Another aspect of the invention involves a method of treating viral disease and/or infection in a human being, the method comprising administering to the human being an antivirally effective amount of a compound of the invention, a pharmaceutically acceptable salt thereof, or a composition as described above, alone or in combination with at least one other antiviral agent, administered together or separately, wherein the viral disease or infection is selected from CMV infection in immunocompromised patients (e.g. transplant recipients), congenital CMV, genital herpes, oral herpes (cold sores), herpetic keratitis, neonatal herpes, herpes encephalitis, varicella (chickenpox), herpes zoster (shingles), infectious mononucleosis, post-transplant lymphoproliferative disease (PTLD), Castelman's disease and hemophagocytic lymphohistiocytosis.

Another aspect of the invention involves a method of treating a disorder that may be induced/exacerbated/accelerated by herpesvirus infections in a human being, the method comprising administering to the human being an effective amount of a compound of the invention, a pharmaceutically acceptable salt thereof, or a composition as described above, alone or in combination with at least one other antiviral agent, administered together or separately, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), celiac disease and type 1 diabetes.

Another aspect of the invention involves a method of treating a disorder that may be induced/exacerbated/accelerated by herpesvirus infections in a human being, the method comprising administering to the human being an effective amount of a compound of the invention, a pharmaceutically acceptable salt thereof, or a composition as described above, alone or in combination with at least one other antiviral agent, administered together or separately, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), atherosclerosis (AS), celiac disease and type 1 diabetes.

Another aspect of the invention is the use of a compound of the invention, or a pharmaceutically acceptable salt thereof, in the manufacture of a medicament for the treatment or prevention of a disorder that may be induced/exacerbated/accelerated by herpesvirus infections, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), celiac disease and type 1 diabetes.

Another aspect of the invention is the use of a compound of the invention, or a pharmaceutically acceptable salt thereof, in the manufacture of a medicament for the treatment or prevention of a disorder that may be induced/exacerbated/accelerated by herpesvirus infections, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), atherosclerosis (AS), celiac disease and type 1 diabetes.

Another aspect of the invention is the use of a pharmaceutical composition as described herein for the treatment of a viral disease and/or infection in a human being, wherein the viral disease or infection is selected from CMV infection in immunocompromised patients (e.g. transplant recipients), congenital CMV, genital herpes, oral herpes (cold sores), herpetic keratitis, neonatal herpes, herpes encephalitis, varicella (chickenpox), herpes zoster (shingles), infectious mononucleosis, post-transplant lymphoproliferative disease (PTLD), Castelman's disease and hemophagocytic lymphohistiocytosis.

Another aspect of the invention is the use of a pharmaceutical composition as described herein for the treatment of a disorder that may be induced/exacerbated/accelerated by herpesvirus infections, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), celiac disease and type 1 diabetes.

Another aspect of the invention is the use of a pharmaceutical composition as described herein for the treatment of a disorder that may be induced/exacerbated/accelerated by herpesvirus infections, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), atherosclerosis (AS), celiac disease and type 1 diabetes.

DETAILED DESCRIPTION

Various enumerated embodiments of the present invention are described herein. It will be recognized that features specified in each embodiment may be combined with other specified features to provide further embodiments of the present invention.

Definitions

For purposes of interpreting this specification, the following definitions will apply, and whenever appropriate, terms used in the singular will also include the plural. Terms used in the specification have the following meanings unless the context clearly indicates otherwise:

The term "alkyl," as used herein, refers to a fully saturated branched or straight chain hydrocarbon. In certain embodiments an alkyl group is a "$C_1$-$C_2$alkyl", "$C_1$-$C_3$alkyl" "$C_1$-$C_4$alkyl", "$C_1$-$C_5$alkyl", "$C_1$-$C_6$alkyl", "$C_1$-$C_7$alkyl", "$C_1$-$C_8$alkyl", "$C_1$-$C_9$alkyl" or "$C_1$-$C_{10}$alkyl", wherein the terms "$C_1$-$C_2$alkyl", "$C_1$-$C_3$alkyl", "$C_1$-$C_4$alkyl", "$C_1$-$C_5$alkyl", "$C_1$-$C_6$alkyl", "$C_1$-$C_7$alkyl", "$C_1$-$C_8$alkyl", "$C_1$-$C_9$alkyl" and "$C_1$-$C_{10}$alkyl", as used herein, refer to an alkyl group containing at least 1, and at most 2, 3, 4, 5, 6, 7, 8, 9 or 10 carbon atoms, respectively Non-limiting examples of alkyl groups include methyl, ethyl, n-propyl, isopropyl, n-butyl, isobutyl, sec-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl.

The term "alkoxy", as used herein, refers to —O-alkyl or -alkyl-O—, wherein the "alkyl" group is as defined herein. In certain embodiments an alkoxy group is a "$C_1$-$C_2$alkoxy", "$C_1$-$C_3$alkoxy", "$C_1$-$C_4$alkoxy", "$C_1$-$C_5$alkoxy", "$C_1$-$C_6$alkoxy", "$C_1$-$C_7$alkoxy", "$C_1$-$C_8$alkoxy", "$C_1$-$C_9$alkoxy" or "$C_1$-$C_{10}$alkoxy", wherein the terms "$C_1$-$C_2$alkoxy" "$C_1$-$C_3$alkoxy" "$C_1$-$C_4$alkoxy", "$C_1$-$C_5$alkoxy", "$C_1$-$C_6$alkoxy", "$C_1$-$C_7$alkoxy", "$C_1$-$C_8$alkoxy", "$C_1$-$C_9$alkoxy" and "$C_1$-$C_{10}$alkoxy", as used herein refer to —O—$C_1$-$C_2$alkyl, —O—$C_1$-$C_3$alkyl, —O—$C_1$-$C_4$alkyl, —O—$C_1$-$C_5$alkyl, —O—$C_1$-$C_6$alkyl, —O—$C_1$-$C_7$alkyl, —O—$C_1$-$C_8$alkyl, —O—$C_1$-$C_9$alkyl or —O—$C_1$-$C_{10}$alkyl, respectively. Non-limiting examples of "alkoxy" groups include methoxy, ethoxy, n-propoxy, isopropoxy, n-butoxy, isobutoxy, sec-butoxy, tert-butoxy, n-pentoxy, isopentoxy, hexoxy, heptoxy, octoxy, nonoxy, decoxy and the like.

The term "alkylene," as used herein, refers to a saturated branched or straight chain divalent hydrocarbon radical derived from an alkyl group as defined herein. In certain embodiments an alkylene group is a "$C_1$-$C_3$alkylene", "$C_1$-$C_4$alkylene" "$C_1$-$C_5$alkylene", "$C_1$-$C_6$alkylene", "$C_1$-$C_7$alkylene", "$C_1$-$C_8$alkylene", "$C_1$-$C_9$alkylene" or "$C_1$-$C_{10}$alkylene", wherein the terms "$C_1$-$C_3$alkylene", "$C_1$-

$C_4$alkylene", "$C_1$-$C_5$alkylene", "$C_1$-$C_6$alkylene", "$C_1$-$C_7$alkylene" and "$C_1$-$C_8$alkylene", as used herein, refer to an alkylene group containing at least 1, and at most 3, 4, 5, 6, 7, 8, 9 or 10 carbon atoms respectively. Non-limiting examples of alkylene groups as used herein include, methylene, ethylene, n-propylene, isopropylene, n-butylene, isobutylene, sec-butylene, t-butylene, n-pentylene, isopentylene, hexylene, heptylene, octylene, nonylene, decylene and the like.

In certain embodiments, an alkylene group is a "$C_1$-$C_2$alkylene", referring to an alkylene group containing at least 1, and at most 2, carbon atoms respectively.

The term "$C_3$-$C_8$cycloalkyl" as used herein, refers to a fully saturated, monocyclic hydrocarbon ring system having 3 to 8 carbon atoms as ring members. Non-limiting examples of such "$C_3$-$C_8$cycloalkyl" groups include cyclopropyl, cyclobutyl, cyclopentyl, cyclohexyl, cycloheptyl and cyclooctyl groups.

The term "$C_3$-$C_6$cycloalkyl" as used herein, refers to a fully saturated, monocyclic hydrocarbon ring system having 3 to 6 carbon atoms as ring members. Non-limiting examples of such "$C_3$-$C_8$cycloalkyl" groups include cyclopropyl, cyclobutyl, cyclopentyl and cyclohexyl groups.

The term "$C_5$-$C_8$cycloalkyl" as used herein, refers to a fully saturated, monocyclic hydrocarbon ring system having 5 to 8 carbon atoms as ring members. Non-limiting examples of such "$C_5$-$C_8$cycloalkyl" groups include cyclopentyl, cyclohexyl, cycloheptyl and cyclooctyl groups.

The term "haloalkyl" as used herein, refers to an alkyl as defined herein, wherein at least one of the hydrogen atoms of the alkyl is replaced by a halo group as defined herein. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Dihaloalkyl can have two and polyhaloalkyl groups can have two or more of the same halo atoms or a combination of different halo groups within the alkyl. Typically the polyhaloalkyl contains up to 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms, e.g., trifluoromethyl. Representative haloalkyl groups, unless specified otherwise, include methyl, ethyl, propyl, isopropyl, butyl, isobutyl, sec-butyl and tert-butyl that have at least one hydrogen substituted with halogen, such as where the halogen is fluorine: $CF_3CF_2-$, $(CF_3)_2CH-$, $CH_3-CF_2-$, $CF_3CF_2-$, $CF_3$, $CF_2H-$, $CF_3CF_2CH(CF_3)-$ or $CF_3CF_2CF_2CF_2-$.

The term "$C_1$-$C_3$haloalkyl" as used herein, refers to the respective "$C_1$-$C_3$alkyl", as defined herein, wherein at least one of the hydrogen atoms of the "$C_1$-$C_3$alkyl" is replaced by a halo atom. The $C_1$-$C_3$haloalkyl groups can be mono$C_1$-$C_3$haloalkyl, wherein such $C_1$-$C_3$haloalkyl groups have one iodo, one bromo, one chloro or one fluoro. Additionally, the $C_1$-$C_3$haloalkyl groups can be di$C_1$-$C_3$haloalkyl wherein such $C_1$-$C_3$haloalkyl groups can have two halo atoms independently selected from iodo, bromo, chloro or fluoro. Furthermore, the $C_1$-$C_3$haloalkyl groups can be poly$C_1$-$C_3$haloalkyl wherein such $C_1$-$C_3$haloalkyl groups can have two or more of the same halo atoms or a combination of two or more different halo atoms. Such poly$C_1$-$C_3$haloalkyl can be perhalo$C_1$-$C_3$haloalkyl where all the hydrogen atoms of the respective $C_1$-$C_3$alkyl have been replaced with halo atoms and the halo atoms can be the same or a combination of different halo atoms. Non-limiting examples of "$C_1$-$C_3$haloalkyl" groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, fluoroethyl, difluoroethyl, trifluoroethyl, difluoropropyl, dichloroethyl and dichloropropyl.

The term "haloalkoxy" as used herein, refers to the group —O-alkyl, wherein the "alkyl" group is as defined herein and wherein at least one of the hydrogen atoms of the alkyl group is replaced by a halo group as defined herein for "haloalkyl". The haloalkoxy can be monohaloalkoxy, dihaloalkoxy, trihaloalkoxy, or polyhaloalkoxy including perhaloalkoxy. A monohaloalkoxy can have one iodo, bromo, chloro or fluoro within the alkyl group. Dihaloalkoxy can have two and polyhaloalkoxy groups can have two or more of the same halo atoms or a combination of different halo groups within the alkyl. Typically the polyhaloalkoxy contains up to 6, or 4, or 3, or 2 halo groups. Non-limiting examples of haloalkoxy include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, difluoroethoxy, difluoropropoxy, dichloroethoxy and dichloropropoxy. A perhalo-alkoxy refers to an alkoxy having all hydrogen atoms replaced with halo atoms, e.g., trifluoromethoxy. Representative haloalkoxy groups, unless specified otherwise, include monofluoro-, difluoro- and trifluoro-substituted methoxy and ethoxy groups, e.g. $-OCF_3$, $-OCHF_2$, $-OCH_2F$, $-OCH_2CHF_2$ and $-OCH_2CF_3$.

The term "$C_1$-$C_4$haloalkoxy" as used herein, refers to the group $-O-C_1$-$C_4$alkyl, wherein the "alkyl" group is as defined herein and wherein at least one of the hydrogen atoms of the "$C_1$-$C_4$alkyl" is replaced by a halo atom as defined herein for "haloalkyl". The $C_1$-$C_4$haloalkoxy groups can be mono$C_1$-$C_4$haloalkoxy, wherein such $C_1$-$C_4$haloalkoxy groups have one iodo, one bromo, one chloro or one fluoro. Additionally, the $C_1$-$C_4$haloalkoxy groups can be di$C_1$-$C_4$haloalkoxy wherein such $C_1$-$C_4$haloalkoxy groups can have two halo atoms independently selected from iodo, bromo, chloro or fluoro. Furthermore, the $C_1$-$C_4$haloalkoxy groups can be poly$C_1$-$C_4$haloalkoxy wherein such $C_1$-$C_4$haloalkoxy groups can have two or more of the same halo atoms or a combination of two or more different halo atoms. Such poly$C_1$-$C_4$haloalkoxy can be perhalo$C_1$-$C_4$haloalkoxy where all the hydrogen atoms of the respective $C_1$-$C_4$alkoxy have been replaced with halo atoms and the halo atoms can be the same or a combination of different halo atoms. Non-limiting examples of "$C_1$-$C_4$haloalkoxy" groups include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, fluoroethoxy, difluoroethoxy, trifluoroethoxy, difluoropropoxy, dichloroethoxy and dichloropropoxy.

The terms "halo" or "halogen" as used herein, refer to fluoro (F), chloro (Cl), bromo (Br) or iodo (I).

The term "heteroaryl," as used herein, refers to
i) a 5-6 membered heteroaryl having 1 to 4 heteroatoms independently selected from the heteroatoms N, O and S as ring members, which refers to an aromatic, 5-6 membered monocyclic ring system having 1 to 4 heteroatoms independently selected from the heteroatoms N, O and S as ring members, though often a heteroaryl ring contains no more than one divalent O or S in the ring, ii) a 5-6 membered heteroaryl having 1 to 3 heteroatoms independently selected from the heteroatoms N, O and S as ring members, which refers to an aromatic, 5-6 membered monocyclic ring system having 1 to 3 heteroatoms independently selected from the heteroatoms N, O and S as ring members, iii) a 5-6 membered heteroaryl having 1 to 2 heteroatoms independently selected from the heteroatoms N, O and S as ring members, which refers to an aromatic, 5-6 membered monocyclic ring system having 1 to 2 heteroatoms independently selected from the heteroatoms N, O and S as ring members, iv) a 5 membered heteroaryl having 1 to 4 heteroatoms independently selected from the heteroatoms N, O and S as ring members, which refers to an aromatic, 5 membered monocyclic ring system having 1 to 4 heteroatoms independently selected from the heteroatoms N, O and S as ring members, v) a 6 membered heteroaryl having 1 to 4 heteroatoms independently selected from the heteroatoms N, O and S as ring members, which refers to an aromatic, 6 membered monocyclic ring system having 1 to 4 heteroatoms independently selected from the heteroatoms N, O and S as ring members, vi) a 5-6 membered heteroaryl having 1 to 4 nitrogen atoms as ring members, which refers to an aromatic, 5-6 membered monocyclic ring system having 1 to 4 nitrogen atoms as ring members, vii) a 9-10 membered bicyclic heteroaryl having 1 to 2 heteroatoms independently selected from the heteroatoms N, O and S as ring members, which refers to an aromatic, 9-10 membered fused bicyclic ring system having 1 to 2 heteroatoms independently selected from the heteroatoms N, O and S as ring members, and viii) a 9-10 membered bicyclic heteroaryl having 1 to 3 heteroatoms independently selected from the heteroatoms N, O and S as ring members, which refers to an aromatic, 9-10 membered fused bicyclic ring system having 1 to 3 heteroatoms independently selected from the heteroatoms N, O and S as ring members.

Non-limiting examples of heteroaryl groups, as used herein, include benzofuranyl, benzo[c]thiophenyl, benzothiophenyl, benzoxazolyl, benzthiazolyl, benzimidazolyl, cinnolinyl, furazanyl, furyl, imidazolyl, indolyl, indolizinyl, indazolyl, isoindolyl, isoquinolinyl, isoxazolyl, isothiazolyl, oxazolyl, oxaindolyl, oxadiazolyl, pyrazolyl, pyrrolyl, phthalazinyl, pyridyl, pyridazinyl, pyrazinyl, pyrimidinyl, quinoxalinyl, quinolinyl, quinazolinyl, tetrazolyl, thiazolyl, thiadiazolyl, thienyl, triazinyl, and triazolyl.

The term "heteroatoms" or "hetero atoms", as used herein, refers to nitrogen (N), oxygen (O) or sulfur (S) atoms.

The term "heterocycloalkyl," as used herein refers to a cycloalkyl group as defined herein having one to two carbon atoms in the ring structure being replaced with one to two groups independently selected from N, NH, $NR^{17}$, O or —S—, wherein $R^{17}$ is H, $C_1$-$C_6$alkyl or $C_3$-$C_8$cycloalkyl. In particular a heterocycloalkyl can be, i) a 4 to 6 membered heterocycloalkyl containing one to two ring members independently selected from N, NH, $NR^{17}$, O or —S—, which refers to a 4 to 6 ring membered heterocycloalkyl which is a fully saturated, monocyclic hydrocarbon ring structure having 4 to 6 ring members, wherein one to two of the ring members are independently selected from N, NH, $NR^{17}$, O or —S—, wherein $R^{17}$ is H, $C_1$-$C_6$alkyl or $C_3$-$C_8$cycloalkyl, ii) a 5 to 6 membered heterocycloalkyl containing one to two ring members independently selected from N, NH, $NR^{17}$, O or —S—, which refers to a 5 to 6 ring membered heterocycloalkyl which is a fully saturated, monocyclic hydrocarbon ring structure having 5 to 6 ring members, wherein one to two of the ring members are independently selected from N, NH, $NR^{17}$, O or —S—, wherein $R^{17}$ is H, $C_1$-$C_6$alkyl or $C_3$-$C_8$cycloalkyl, and iii) a 8 to 10 membered heterocycloalkyl containing one to two ring members independently selected from N, NH, $NR^{17}$, O or —S—, which refers to an 8 to 10 membered heterocycloalkyl which is a fully saturated, fused bicyclic ring structure having 8 to 10 ring members, wherein one to two of the ring members are independently selected from N, NH, $NR^{17}$, O or —S—, wherein $R^{17}$ is $C_1$-$C_6$alkyl or $C_3$-$C_8$cycloalkyl.

Non-limiting examples of heterocycloalkyl groups, as used herein, include azetadinyl, azetadin-1-yl, azetadin-2-yl, azetadin-3-yl, oxetanyl, oxetan-2-yl, oxetan-3-yl, oxetan-4-yl, thietanyl, thietan-2-yl, thietan-3-yl, thietan-4-yl, pyrrolidinyl, pyrrolidin-1-yl, pyrrolidin-2-yl, pyrrolidin-3-yl, pyrrolidin-4-yl, pyrrolidin-5-yl, tetrahydrofuranyl, tetrahydrofuran-2-yl, tetrahydrofuran-3-yl, tetrahydrofuran-4-yl, tetrahydrofuran-5-yl, tetrahydrothienyl, tetrahydrothien-2-yl, tetrahydrothien-3-yl, tetrahydrothien-4-yl, tetrahydrothien-5-yl, piperidinyl, piperidin-1-yl, piperidin-2-yl, piperidin-3-yl, piperidin-4-yl, piperidin-5-yl, piperidin-6-yl, tetrahydropyranyl, tetrahydropyran-2-yl, tetrahydropyran-3-yl, tetrahydropyran-4-yl, tetrahydropyran-5-yl, tetrahydropyran-6-yl, tetrahydrothiopyranyl, tetrahydrothiopyran-2-yl, tetrahydrothiopyran-3-yl, tetrahydrothiopyran-4-yl, tetrahydrothiopyran-5-yl, tetrahydrothiopyran-6-yl, piperazinyl, piperazin-1-yl, piperazin-2-yl, piperazin-3-yl, piperazin-4-yl, piperazin-5-yl, piperazin-6-yl, morpholinyl, morpholin-2-yl, morpholin-3-yl, morpholin-4-yl, morpholin-5-yl, morpholin-6-yl, thiomorpholinyl, thiomorpholin-2-yl, thiomorpholin-3-yl, thiomorpholin-4-yl, thiomorpholin-5-yl, thiomorpholin-6-yl, oxathianyl, oxathian-2-yl, oxathian-3-yl, oxathian-5-yl, oxathian-6-yl, dithianyl, dithian-2-yl, dithian-3-yl, dithian-5-yl, dithian-6-yl, dioxolanyl, dioxolan-2-yl, dioxolan-4-yl, dioxolan-5-yl, thioxanyl, thioxan-2-yl, thioxan-3-yl, thioxan-4-yl, thioxan-5-yl, dithiolanyl, dithiolan-2-yl, dithiolan-4-yl, dithiolan-5-yl, pyrazolidinyl, pyrazolidin-1-yl, pyrazolidin-2-yl, pyrazolidin-3-yl, pyrazolidin-4-yl, pyrazolidin-5-yl, 2-azabicyclo[4.2.0]octanyl, octahydro-1H-cyclopenta[b]pyridine and decahydroquinoline.

The term "hydroxy" or "hydroxyl" refers to the group —OH.

The term "oxo", as used herein refers to a "=O" group.

The term "heterocyclyl" as used herein refers to a 4 to 14 membered, saturated or partially saturated hydrocarbon ring structure having 1 to 7, 1 to 5, 1 to 3 or 1 to 2 ring members independently selected from N, NH, $NR^{36}$, O or S, wherein $R^{36}$ is $C_1$-$C_6$alkyl or $C_3$-$C_8$cycloalkyl. The term "heterocyclyl" includes single ring groups, bicyclic ring groups, fused ring groups, spiro ring groups, and bridged ring groups. The heterocyclic group can be attached to another group at a nitrogen or a carbon atom. In particular a heterocyclyl can be i) a 4-6 membered heterocyclyl containing 1 to 2 ring members independently selected from N, NH, $NR^{17}$, O or S, where $R^{17}$ is H, $C_1$-$C_6$alkyl or $C_3$-$C_8$cycloalkyl,
ii) a 4-7 membered heterocyclyl containing 1 to 2 ring members independently selected from N, NH, $NR^{17}$, O or S, where $R^{17}$ is H, $C_1$-$C_6$alkyl or $C_3$-$C_8$cycloalkyl,
iii) a 5-6 membered heterocyclyl containing 1 to 4 ring members independently selected from N, NH, $NR^{17}$, O or S, where $R^{17}$ is H, $C_1$-$C_6$alkyl or $C_3$-$C_8$cycloalkyl,
iv) a 5-6 membered heterocyclyl containing 1 to 2 ring members independently selected from N, NH, $NR^{17}$, O or S, where $R^{17}$ is H, $C_1$-$C_6$alkyl or $C_3$-$C_8$cycloalkyl,
v) a 8-10 membered fused bicyclic heterocyclyl containing 1 to 3 ring members independently selected from N, NH, $NR^{17}$, O or S, where $R^{17}$ is H, $C_1$-$C_6$alkyl or $C_3$-$C_8$cycloalkyl,
and
vi) a 8-10 membered fused tricyclic heterocyclyl containing 1 to 4 ring members independently selected from N, NH, $NR^{17}$, O or S, where $R^{17}$ is H, $C_1$-$C_6$alkyl or $C_3$-$C_8$cycloalkyl.

Non-limiting examples of heterocycloalkyl groups, as used herein, include dihydrobenzofuranyl, dihydrobenzo[c]thiophenyl, dihydrobenzothiophenyl, dihydrobenzoxazolyl, dihydrobenzthiazolyl, dihydrobenzimidazolyl, dihydrocinnolinyl, dihydrofurazanyl, dihydrofuryl, dihydroimidazolyl, dihydroindolyl, dihydroindolizinyl, dihydroindazolyl, dihydroisoindolyl, dihydroisoquinolinyl, dihydroisoxazolyl, dihydroisothiazolyl, dihydrooxazolyl, dihydrooxaindolyl, dihydrooxadiazolyl, dihydropyrazolyl, dihydropyrrolyl, dihydrophthalazinyl, dihydropyridyl, dihydropyridazinyl, dihydropyrazinyl, dihydropyrimidinyl, dihydroquinoxalinyl, dihydroquinolinyl, dihydroquinazolinyl, dihydrotetrazolyl, dihydrothiazolyl, dihydrothiadiazolyl, dihydrothienyl, dihydrotriazinyl, dihydrotriazolyl, tetrahydrobenzofuranyl, tetrahydrobenzo[c]thiophenyl, tetrahydrobenzothiophenyl, tetrahydrobenzoxazolyl, tetrahydrobenzthiazoly, tetrahydrobenzimidazolyl, tetrahydrocinnolinyl, tetrahydroindolyl, tetrahydroindolizinyl, tetrahydroindazolyl, tetrahydroisoindolyl, tetrahydroisoquinolinyl, tetrahydrooxaindolyl, tetrahydrophthalazinyl, tetrahydropyridyl, tetrahydropyridazinyl, tetrahydropyrazinyl, tetrahydropyrimidinyl, tetrahydroquinoxalinyl, tetrahydroquinolinyl, tetrahydroquinazolinyl, tetrahydrotriazinyl, hexahydrobenzofuranyl, hexahydrobenzo[c]thiophenyl, hexahydrobenzothiophenyl, hexahydrobenzoxazolyl, hexahydrobenzthiazolyl, hexahydrobenzimidazolyl, hexahydrocinnolinyl, hexahydroindolyl, hexahydroindolizinyl, hexahydroindazolyl, hexahydroisoindolyl, hexahydroisoquinolinyl, hexahydrooxaindolyl, hexahydrophthalazinyl, hexahydroquinoxalinyl, hexahydroquinolinyl, hexahydroquinazolinyl, octahydrocinnolinyl, octahydroisoquinolinyl, octahydrophthalazinyl, octahydroquinoxalinyl, octahydroquinolinyl and octahydroquinazolinyl.

As used herein, the term "subject" refers to an animal. In certain aspects, the animal is a mammal. A subject also refers to for example, primates (e.g., humans), cows, sheep, goats, horses, dogs, cats, rabbits, rats, mice, fish, birds and the like. In certain embodiments, the subject is a human. A "patient" as used herein refers to a human subject.

As used herein, the term "linker" refers to a bivalent chemical moiety that is capable of covalently linking together two spaced chemical moieties.

As used herein, the term "inhibition" or "inhibiting" refers to the reduction or suppression of a given condition, symptom, or disorder, or disease, or a decrease in the baseline activity of a biological activity or process.

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound, "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

The compound names provided herein were obtained using ChemDraw Ultra version 12.0 (CambridgeSoft®) or JChem version 5.3.1 (ChemAxon).

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

"Optionally substituted" means the group referred to can be substituted at one or more positions by any one or any combination of the radicals listed thereafter. The number, placement and selection of substituents is understood to encompass only those substitutions that a skilled chemist would expect to be reasonably stable; thus 'oxo' would not be a substituent on an aryl or heteroaryl ring, for example, and a single carbon atom would not have three hydroxy or amino substituents.

Groups may be substituted at the same position that they join the remainder of the defined molecule. For instance, a group may be substituted with a cyclopropyl, and the cyclopropyl may, in turn, be substituted with another group, at the same carbon by which it is joined to the rest of the molecule.

Unless specified otherwise, the term "compounds of the present invention", "compounds of the invention" or "compounds provided herein" refers to compounds of Formula (I), Formula (II), Formula (IIa), Formula (Ib), Formula (IIIa), Formula (IIIb), Formula (IIIc), Formula (IVa), Formula (IVb), Formula (IVc), Formula (IVd), Formula (Va), Formula (Vb), Formula (Vc), Formula (VI), Formula (VII), and Formula (VIII), and pharmaceutically acceptable salts, stereoisomers (including diastereoisomers and enantiomers), rotamers, tautomers and isotopically labeled compounds (including deuterium substitutions), as well as inherently formed moieties.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the Invention

The invention provides compounds having the structure of Formula (I), or pharmaceutically acceptable salt thereof:

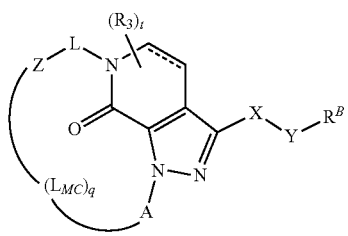

(I)

wherein:

X is

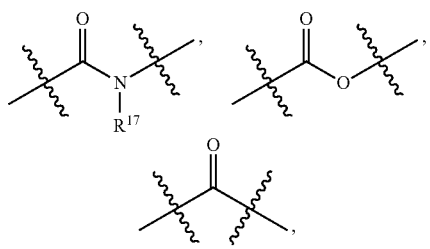

a 5-6 membered heteroaryl having 1 to 4 heteroatoms independently selected from N, O and S as ring members, a 5-6 membered heterocycloalkyl containing 1 to 4 ring members independently selected from N, NH, NR$^{17}$, O or S or a 5-6 membered heterocyclyl containing 1 to 4 ring members independently selected from N, NH, NR$^{17}$, O or S;

Y is a bond,

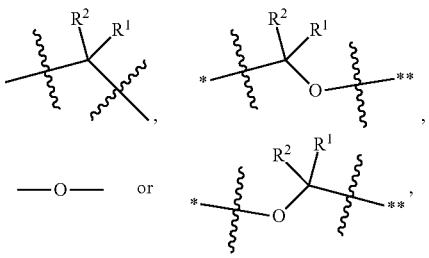

wherein the * of Y indicates the point of attachment to X and the ** of Y indicates the point of attachment to R$^B$;

q is 0 or 1;

when q is 1, then L$_{MC}$ is *—((CR$^{11}$R$^{12}$)$_n$O)$_m$(CR$^{11}$R$^{12}$)$_p$—**, *—C(=O)NR$^{15}$((CR$^{11}$R$^{12}$)$_n$O)$_m$(CR$^{11}$R$^{12}$)$^{**}$, *—(CR$^{11}$R$^{12}$)$_n$NR$^{15}$((CR$^{11}$R$^{12}$)$_n$O)$_m$(CR$^{11}$R$^{12}$)$_p$—**, *—(CR$^{11}$R$^{12}$)$_n$—**, *—((CR$^{11}$R$^{12}$)$_n$NR$^{15}$)$_m$(CR$^{11}$R$^{12}$)$_p$—**, *—(CR$^{11}$R$^{12}$)C(=O)NR$^{15}$(CR$^{11}$R$^{12}$)$_n$—**, *—C(=O)NR$^{15}$(CR$^{11}$R$^{12}$)$_n$—**, *—O(CR$^{11}$R$^{12}$)$_n$—**, or *—NR$^{15}$(CR$^{11}$R$^{12}$)$_n$—**, wherein the * of L$_{MC}$ indicates the point of attachment to Z and the ** of L$_{MC}$ indicates the point of attachment to A;

when q is 1, then LMC is present, A is a bond and Z is

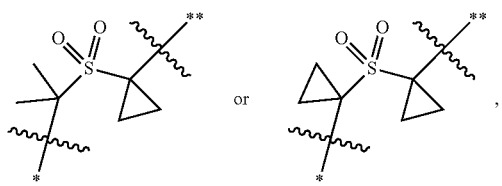

wherein the * of Z indicates the point of attachment to LMC and the ** of Z indicates the point of attachment to L;

m is 1, 2, 3, 4, 5, 6, 7, 8, 9 or 10;

each n is independently selected from 1, 2, 3, 4, 5, 7, 8, 9 and 10;

p is 1, 2, 3, 4, 5 or 6;

when q is 0, then LMC is absent, and Z is W, and A is R$^4$;

R$^B$ is H, C$_1$-C$_6$alkyl, phenyl, pyridinyl, thiophenyl, pyrimidinyl, or a 5-8 membered cycloalkyl, wherein R$^B$ is optionally substituted with 1 to 3 R$^5$ groups;

R$^1$ is selected from H, C$_1$-C$_3$alkyl and C$_1$-C$_3$alkyl substituted with 1 to 3 —OH groups;

R$^2$ is selected from H, C$_1$-C$_3$alkyl and C$_1$-C$_3$alkyl substituted with 1 to 3 —OH groups;

or R$^1$ and R$^2$ taken together with the carbon to which they are attached can form a 3-6 membered cycloalkyl ring;

t is 0, 1 or 2;

each R$^3$, when present, is a substituent on the ring to which -L-Z is directly attached, wherein each R$^3$ is independently selected from halo, CN, C$_1$-C$_3$alkoxy, C$_1$-C$_3$alkyl, C(=O)OR$^{10}$, and C(=O)NR$^{13}$R$^{14}$;

R$^4$ is H, C$_1$-C$_3$alkyl, C$_3$-C$_6$cycloalkyl, —(CH$_2$)$_2$O(CH$_2$)$_2$Br or a C$_1$-C$_3$alkyl substituted with 1 to 2 groups independently selected from —OH, —C(=O)R$^{15}$ and R$^{10}$;

each R$^5$ is independently selected from halo, —CN, hydroxy, —NR$^{13}$R$^{14}$, C$_3$-C$_6$cycloalkyl, C$_1$-C$_3$alkoxy, C$_1$-C$_3$haloalkyl, and C$_1$-C$_3$alkyl optionally substituted with 1 to 3 R$^6$ groups, wherein when R$^B$ is substituted with two $R^5$ and each $R^5$ is a $C_1$-$C_3$alkyl optionally substituted with 1 to 3 $R^6$ groups, when directly attached to the same carbon atom, may be taken together with the carbon to which both are directly attached to form a 3-5 membered cycloalkyl ring optionally substituted with 1 to 3 $R^6$ groups;

each $R^6$ is independently selected from halo, hydroxy, CN, $C_1$-$C_3$alkoxy, $C_1$-$C_3$alkyl, and $C_3$-$C_5$cycloalkyl, or two $R^6$ groups, taken together with a carbon atom to which both are directly attached can form a 3-5 membered cycloalkyl ring or a 4-6 membered heterocyclic ring containing O, N or S as a ring member and optionally substituted with 1 to 2 groups independently selected from oxo and $C_1$-$C_3$alkyl;

L is a $C_1$-$C_4$ straight chain or branched alkylene linker, or L can be a $C_1$-$C_4$ straight chain or branched alkylene linker or a bond when W is an optionally substituted ring;

W is H, —OH, —OR$^{10}$, —C(=O)NR$^{13}$R$^{14}$, —C(=O)OR$^{13}$, —NR$^{13}$R$^{14}$, —NR$^{13}$C(=O)OR$^{10}$, —NR$^{13}$C(=O)R$^{10}$, —SO$_2$R$^{10}$, —SO$_2$NR$^{13}$R$^{14}$, —NR$^{13}$SO$_2$R$^{10}$, —P(=O)(OR$^{13}$)$_2$, —S(=O)R$^{10}$, —S(=O)(=NR$^{13}$)R$^{10}$, —CR$^{11}$R$^{12}$C(=O)NR$^{13}$R$^{14}$, —CR$^{11}$R$^{12}$C(=O)OR$^{13}$, —CR$^{11}$R$^{12}$NR$^{13}$R$^{14}$, —CR$^{11}$R$^{12}$NR$^{13}$C(=O)OR$^{10}$, —CR$^{11}$R$^{12}$NR$^{13}$C(=O)R$^{10}$, —CR$^{11}$R$^{12}$SO$_2$R$^{10}$, —CR$^{11}$R$^{12}$SO$_2$NR$^{13}$R$^{14}$, —CR$^{11}$R$^{12}$NR$^{13}$SO$_2$R$^{10}$, —CR$^{11}$R$^{12}$P(=O)(OR$^{13}$)$_2$, —CR$^{11}$R$^{12}$S(=O)R$^{10}$, —CR$^{11}$R$^{12}$S(=O)(=NR$^{13}$)R$^{10}$, a 3-6 membered cycloalkyl, phenyl, a 5-6-membered heterocycloalkyl containing one or two ring members independently selected from N, NH, NR$^{17}$, O or S, a 5-6-membered heterocyclyl containing one or two ring members independently selected from N, NH, NR$^{17}$, O or S, or a 5-membered heteroaryl having 1 to 4 heteroatoms selected from N, O and S as ring members that is optionally fused to phenyl, wherein the 3-6 membered cycloalkyl, phenyl, 5-6-membered heterocycloalkyl, 5-6-membered heterocyclyl and 5-membered heteroaryl of W are each optionally substituted with 1 to 3 groups independently selected from $C_1$-$C_3$alkyl, oxo, halo, $C_1$-$C_3$haloalkyl, -L$^2$OH, -L$^2$OR$^{10}$, -L$^2$OC(=O)NR$^{13}$R$^{14}$, -L$^2$SO$_2$R$^{10}$, -L$^2$SO$_2$NR$^{13}$R$^{14}$, -L$^2$SO$_2$NR$^{13}$R$^{14}$, -L$^2$SO$_2$N=CR$^{13}$NR$^{13}$R$^{14}$, -L$^2$SO$_2$NR$^{13}$C(=O)R$^{10}$, -L$^2$C(=O)NR$^{13}$SO$_2$R$^{10}$, -L$^2$S(=O)R$^{10}$, -L$^2$S(=O)(=NR$^{13}$)R$^{10}$, -L$^2$NR$^{13}$SO$_2$NR$^{13}$R$^{14}$, -L$^2$NR$^{13}$SO$_2$R$^{10}$, -L$^2$NR$^{13}$R$^{14}$, -L$^2$NR$^{13}$C(=O)R$^{13}$, -L$^2$NR$^{13}$C(=O)OR$^{10}$, -L$^2$C(=O)NR$^{13}$R$^{14}$, and -L$^2$C(=O)OR$^{13}$;

$R^{10}$ is selected from $C_1$-$C_5$alkyl, $C_1$-$C_3$haloalkyl, 3-6 membered cycloalkyl, phenyl, 5-6 membered heteroaryl having 1 to 4 heteroatoms independently selected from N, O and S as ring members, 4-6 membered heterocycloalkyl containing one or two ring members independently selected from N, NH, NR$^{17}$, O or S and 4-6 membered heterocyclyl containing 1 to 2 ring members independently selected from N, NH, NR$^{17}$, O or S, wherein each $R^{10}$ is optionally substituted with 1 to 5 groups independently selected from $C_1$-$C_4$alkyl, deuterium, $C_1$-$C_4$haloalkoxy, -L$^3$OH, -L$^3$CN, -L$^3$OC(=O)R$^{14}$, -L$^3$OR$^{13}$, $C_1$-$C_2$haloalkoxy, oxo, -L$^3$halo, -L$^3$C$_1$-$C_3$alkoxy, -L$^3$OC(=O)NR$^{13}$R$^{14}$, -L$^3$SO$_2$R$^{13}$, -L$^3$SO$_2$NR$^{13}$R$^{14}$, -L$^3$SO$_2$NR$^{13}$C(=O)OR$^{13}$, -L$^3$C(=O)NR$^{13}$SO$_2$R$^{13}$, -L$^3$S(=O)R$^{13}$, -L$^3$S(=O)(=NR$^{14}$)R$^{13}$, -L$^3$NR$^{13}$SO$_2$NR$^{13}$R$^{14}$, -L$^3$NR$^{13}$SO$_2$R$^{13}$, -L$^3$NR$^{13}$R$^{14}$, -L$^3$NR$^{14}$C(=O)R$^{13}$, -L$^3$NR$^{14}$C(=O)OR$^{13}$, -L$^3$C(=O)NR$^{13}$R$^{14}$, -L$^3$C(=O)OR$^{13}$, -L$^3$-(4-7-membered heterocycloalkyl containing 1 to 2 ring members independently selected from N, NH, NR$^{17}$, O or S), -L$^3$-(4-7-membered heterocyclyl containing 1 to 2 ring members independently selected from N, NH, NR$^{17}$, or S)), -L$^3$-$C_3$-$C_5$cycloalkyl, and -L$^3$-(5-6 membered heteroaryl ring having 1 to 4 heteroatoms comprising 1-4 nitrogen atoms, 0 or 1 oxygen atoms, and 0 or 1 sulfur atoms as ring members), where the $C_1$-$C_4$alkyl, 4-7-membered heterocycloalkyl, 4-7-membered heterocyclyl, $C_3$-$C_5$cycloalkyl and 5-6 membered heteroaryl ring are each optionally further substituted with 1 to 3 groups independently selected from halo, $C_1$-$C_3$alkyl, $C_1$-$C_3$haloalkyl, -L$^4$OR$^{13}$, -L$^4$CN, and -L$^4$NR$^{13}$R$^{14}$;

$R^{11}$ and $R^{12}$ are each independently selected from H and $C_1$-$C_4$alkyl;

each $R^{13}$ is independently selected from H, $C_1$-$C_4$alkyl, a 4-7-membered heterocycloalkyl containing 1 to 2 ring members independently selected from N, NH, NR$^{17}$, O or S, a 4-7-membered heterocyclyl containing 1 to 2 ring members independently selected from N, NH, NR$^{17}$, O or S, and a $C_3$-$C_6$cycloalkyl, wherein the $C_1$-$C_4$alkyl, heterocycloalkyl, heterocyclyl and $C_3$-$C_6$cycloalkyl are optionally substituted with 1 to 3 groups independently selected from $C_1$-$C_4$alkyl, halo, —OH, —NR$^{15}$R$^{16}$, —C(=O)OR$^{15}$, $C_1$-$C_2$alkoxy and $C_1$-$C_4$alkyl substituted with 1 to 2 hydroxy groups;

$R^{14}$ is selected from H, $C_1$-$C_4$alkyl and $C_3$-$C_6$cycloalkyl, wherein the $C_1$-$C_4$alkyl and $C_3$-$C_6$cycloalkyl are optionally substituted with 1 to 3 groups independently selected from $C_1$-$C_4$alkyl, halo, —OH, —NR$^{15}$R$^{16}$, $C_1$-$C_2$alkoxy and $C_1$-$C_4$alkyl substituted with 1 to 2 hydroxy groups;

or $R^{13}$ and $R^{14}$, taken together with a nitrogen atom to which both are directly attached, can form a 4-6 membered ring optionally containing an additional N, O or S as a ring member and optionally substituted with one to three groups selected from $C_1$-$C_2$alkyl, $C_1$-$C_2$alkoxy, oxo, and hydroxy;

$R^{15}$ and $R^{16}$ are each independently selected from H and $C_1$-$C_4$alkyl;

each $L^2$ and $L^3$ and $L^4$ is independently a bond or a straight chain or branched $C_1$-$C_3$alkylene;

and

'$\text{---}$' represents a single or double bond.

Various embodiments of the compounds of the invention are described herein. It will be recognized that features specified in each embodiment may be combined with other specified features to provide further embodiments. The following enumerated embodiments are representative of the compounds of Formula (I) of the invention:

Embodiment 1. The compound of Formula (I), or a pharmaceutically acceptable salt thereof, wherein X is

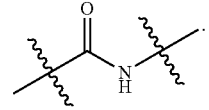 [SMILES: *NC(*)=O]

Embodiment 2. The compound of Formula (I), or a pharmaceutically acceptable salt thereof, wherein X is

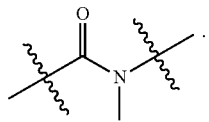 [SMILES: *C(=O)N(*)C]

Embodiment 3. The compound of Formula (I), or a pharmaceutically acceptable salt thereof, wherein X is

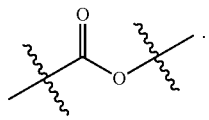 [SMILES: *OC(*)=O]

Embodiment 4. The compound of Formula (I), or a pharmaceutically acceptable salt thereof, wherein X is

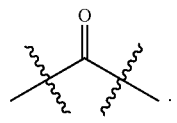 [SMILES: *C(*)=O]

Embodiment 5. The compound of Formula (I), or a pharmaceutically acceptable salt thereof, wherein X is a 5-6 membered heteroaryl having 1 to 4 heteroatoms independently selected from N, O and S as ring members.

Embodiment 6. The compound of Formula (I), or a pharmaceutically acceptable salt thereof, wherein X is a 5-6 membered heterocycloalkyl containing 1 to 4 ring members independently selected from N, NH, $NR^{17}$, O or S.

Embodiment 7. The compound of Formula (I), or a pharmaceutically acceptable salt thereof, wherein X is a 5-6 membered heterocyclyl containing 1 to 4 ring members independently selected from N, NH, $NR^{17}$, O or S Embodiment 8. The compound of Formula (I), or any one of Embodiments 1 to 7, or a pharmaceutically acceptable salt thereof, wherein Y is

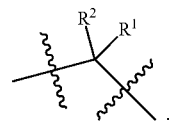

Embodiment 9. The compound of Formula (I), or any one of Embodiments 1 to 7, or a pharmaceutically acceptable salt thereof, wherein Y is

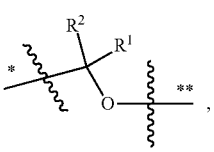

wherein the * of Y indicates the point of attachment to X and the ** of Y indicates the point of attachment to $R^B$.

Embodiment 10. The compound of Formula (I), or any one of Embodiments 1 to 7, or a pharmaceutically acceptable salt, thereof wherein Y is —O—.

Embodiment 11. The compound of Formula (I), or any one of Embodiments 1 to 7, or a pharmaceutically acceptable salt thereof, wherein Y is

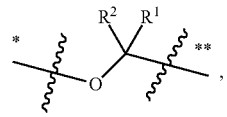

wherein the * of Y indicates the point of attachment to X and the ** of Y indicates the point of attachment to $R^B$.

Embodiment 12. The compound of Formula (I), or any one of Embodiments 1 to 7, or a pharmaceutically acceptable salt thereof, wherein Y is a bond.

Embodiment 13. The compound of Formula (I), or any one of Embodiments 1 to 12, or a pharmaceutically acceptable salt thereof, wherein q is 1, $L_{MC}$ is present and A is a bond.

Embodiment 14. The compound of Formula (I), or any one of Embodiments 1 to 13, or a pharmaceutically acceptable salt thereof, wherein q is 1, A is a bond and $L_{MC}$ is *—$((CR^{11}R^{12})_nO)_m(CR^{11}R^{12})_p$—**, *—C(=O)$NR^{15}$ $((CR^{11}R^{12})_nO)_m(CR^{11}R^{12})_p$—**, or *—$(CR^{11}R^{12})_nNR^{15}$ $((CR^{11}R^{12})_nO)_m(CR^{11}R^{12})_p$—**, wherein the * of $L_{MC}$ indicates the point of attachment to Z and the ** of $L_{MC}$ indicates the point of attachment to A.

Embodiment 15. The compound of Formula (I), or any one of Embodiments 1 to 14, or a pharmaceutically acceptable salt thereof, wherein q is 1, A is a bond and $L_{MC}$ is

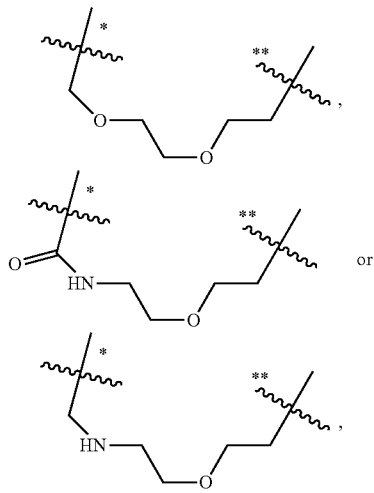

wherein the * of $L_{MC}$ indicates the point of attachment to Z and the ** of $L_{MC}$ indicates the point of attachment to A.

Embodiment 16. The compound of Formula (I), or any one of Embodiments 1 to 14, or a pharmaceutically acceptable salt thereof, wherein q is 1, A is a bond and $L_{MC}$ is

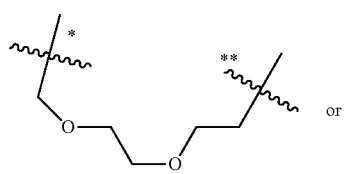

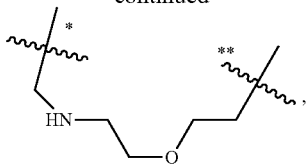

wherein the * of $L_{MC}$ indicates the point of attachment to Z and the ** of $L_{MC}$ indicates the point of attachment to A.

Embodiment 17. The compound of Formula (I), or any one of Embodiments 1 to 14, or a pharmaceutically acceptable salt thereof, wherein q is 1, A is a bond and $L_{MC}$ is

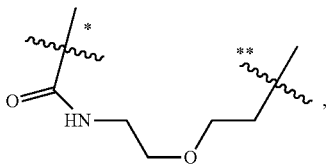 [SMILES: *CCOCCNC(*)=O]

wherein the * of $L_{MC}$ indicates the point of attachment to Z and the ** of $L_{MC}$ indicates the point of attachment to A.

Embodiment 18. The compound of Formula (I), or any one of Embodiments 1 to 17, or a pharmaceutically acceptable salt thereof, wherein q is 1 and Z is

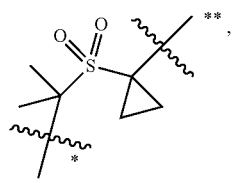 [SMILES: *C(C)(C)S(=O)(=O)C1(*)CC1]

wherein the * of Z indicates the point of attachment to $L_{MC}$ and the ** of Z indicates the point of attachment to L.

Embodiment 19. The compound of Formula (I), or any one of Embodiments 1 to 17, or a pharmaceutically acceptable salt thereof, wherein q is 1 and Z is

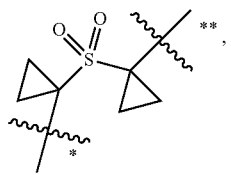 [SMILES: *C1(S(=O)(=O)C2(*)CC2)CC1]

wherein the * of Z indicates the point of attachment to $L_{MC}$ and the ** of Z indicates the point of attachment to L.

Embodiment 20. The compound of Formula (I), or any one of Embodiments 1 to 12, or a pharmaceutically acceptable salt thereof, wherein q is 0, $L_{MC}$ is absent and Z is W.

Embodiment 21. The compound of Formula (I) having the structure of Formula (II), or a pharmaceutically acceptable salt thereof,

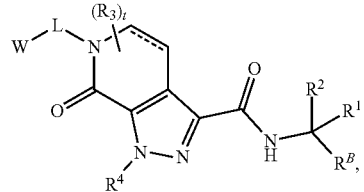

wherein W, L, t, $R^1$, $R^2$, $R^3$, $R^4$ and $R^B$ are as defined for Formula (I).

Embodiment 22. The compound of Formula (II) of any one of Embodiments 1 to 21, or a pharmaceutically acceptable salt thereof, wherein:

$R^B$ is phenyl, pyridinyl, thiophenyl, pyrimidinyl, or a 5-8 membered cycloalkyl, wherein $R^B$ is optionally substituted with 1 to 3 $R^5$ groups;

$R^1$ is selected from H, $C_1$-$C_3$alkyl and $C_1$-$C_3$alkyl substituted with 1 to 3 —OH groups;

$R^2$ is selected from H, $C_1$-$C_3$alkyl and $C_1$-$C_3$alkyl substituted with 1 to 3 —OH groups; or $R^1$ and $R^2$ taken together with the carbon to which they are attached can form a 3-6 membered cycloalkyl ring;

t is 0, 1 or 2;

each $R^3$, when present, is a substituent on the ring to which -L-W is directly attached, wherein each $R^3$ is independently selected from halo, CN, $C_1$-$C_3$alkoxy, $C_1$-$C_3$alkyl, C(=O)$OR^{10}$, and C(=O)$NR^{13}R^{14}$;

$R^4$ is H, $C_1$-$C_3$alkyl, $C_3$-$C_6$cycloalkyl, —(CH$_2$)$_2$O(CH$_2$)$_2$Br or a $C_1$-$C_3$alkyl substituted with 1 to 2 groups independently selected from —OH, —C(=O)$R^{15}$ and $R^{10}$;

each $R^5$ is independently selected from halo, —CN, hydroxy, —$NR^{13}R^{14}$, $C_3$-$C_6$cycloalkyl, $C_1$-$C_3$alkoxy, $C_1$-$C_3$haloalkyl, and $C_1$-$C_3$alkyl optionally substituted with 1 to 3 $R^6$ groups, wherein when $R^B$ is substituted with two $R^5$ and each $R^5$ is a $C_1$-$C_3$alkyl optionally substituted with 1 to 3 $R^6$ groups, when directly attached to the same carbon atom, may be taken together with the carbon to which both are directly attached to form a 3-5 membered cycloalkyl ring optionally substituted with 1 to 3 $R^6$ groups;

each $R^6$ is independently selected at each occurrence from halo, hydroxy, CN, $C_1$-$C_3$alkoxy, $C_1$-$C_3$alkyl, and $C_3$-$C_5$cycloalkyl, or two $R^6$ groups, taken together with a carbon atom to which both are directly attached may form a 3-5 membered cycloalkyl ring or a 4-6 membered heterocyclic ring containing O, N or S as a ring member and optionally substituted with 1 to 2 groups independently selected from oxo and $C_1$-$C_3$alkyl;

L is a $C_1$-$C_4$ straight chain or branched alkylene linker, or L can be a $C_1$-$C_4$ straight chain or branched alkylene linker or a bond when W is an optionally substituted ring;

W is H, —OH, —$OR^{10}$, —C(=O)$NR^{13}R^{14}$, —C(=O)O$R^{13}$, —$NR^{13}R^{14}$, —$NR^{13}$C(=O)$OR^{10}$, —$NR^{13}$C(=O)$R^{10}$, —SO$_2R^{10}$, —SO$_2NR^{13}R^{14}$, —$NR^{13}SO_2R^{10}$, —P(=O)($OR^{13}$)$_2$, —S(=O)$R^{10}$, —S(=O)(=$NR^{13}$)$R^{10}$, —$CR^{11}R^{12}$C(=O)$NR^{13}R^{14}$, —$CR^{11}R^{12}$C(=O)$OR^{13}$, —$CR^{11}R^{12}NR^{13}R^{14}$, —$CR^{11}R^{12}NR^{13}$C(=O)$OR^{10}$, —$CR^{11}R^{12}NR^{13}$C(=O)$R^{10}$, —$CR^{11}R^{12}SO_2R^{10}$, —$CR^{11}R^{12}SO_2NR^{13}R^{14}$, —$CR^{11}R^{12}NR^{13}SO_2R^{10}$, —$CR^{11}R^{12}P(=O)(OR^{13})_2$,

—$CR^{11}R^{12}S(=O)R^{10}$, —$CR^{11}R^{12}S(=O)(=NR^{13})R^{10}$, a 3-6 membered cycloalkyl, phenyl, a 5-6-membered heterocycloalkyl containing one or two ring members independently selected from N, NH, $NR^{17}$, O or S, a 5-6-membered heterocyclyl containing one or two ring members independently selected from N, NH, $NR^{17}$, O or S, or a 5-membered heteroaryl having 1 to 4 heteroatoms selected from N, O and S as ring members that is optionally fused to phenyl,
  wherein the 3-6 membered cycloalkyl, phenyl, 5-6-membered heterocycloalkyl, 5-6-membered heterocyclyl and 5-membered heteroaryl of W are each optionally substituted with 1 to 3 groups independently selected from $C_1$-$C_3$alkyl, oxo, halo, $C_1$-$C_3$haloalkyl, —OH, —$OR^{10}$, —OC(=O)$NR^{13}R^{14}$, —$SO_2R^{10}$, —$SO_2NR^{13}R^{14}$, —$SO_2NR^{13}R^{14}$, —$SO_2N=CR^{13}NR^{13}R^{14}$, —$SO_2NR^{13}C(=O)R^{10}$, —C(=O)$NR^{13}SO_2R^{10}$, —S(=O)$R^{10}$, —S(=O)(=$NR^{13}$)$R^{10}$, —$NR^{13}SO_2NR^{13}R^{14}$, —$NR^{13}SO_2R^{10}$, —$NR^{13}R^{14}$, —$NR^{13}C(=O)R^{13}$, —$NR^{13}C(=O)OR^{10}$, —C(=O)$NR^{13}R^{14}$, and —C(=O)$OR^{13}$;
$R^{10}$ is selected from $C_1$-$C_5$alkyl, $C_1$-$C_3$haloalkyl, 3-6 membered cycloalkyl, phenyl, 5-6 membered heteroaryl having 1 to 4 heteroatoms independently selected from N, O and S as ring members, 4-6 membered heterocycloalkyl containing one or two ring members independently selected from N, NH, $NR^{17}$, O or S and 4-6 membered heterocyclyl containing 1 to 2 ring members independently selected from N, NH, $NR^{17}$, O or S,
  wherein each $R^{10}$ is optionally substituted with 1 to 5 groups independently selected from $C_1$-$C_4$alkyl, deuterium, $C_1$-$C_4$haloalkoxy, —OH, —CN, —OC(=O)$R^{14}$, -$L^3OR^{13}$, $C_1$-$C_2$haloalkyl, oxo, -halo, —$C_1$-$C_3$alkoxy, —OC(=O)$NR^{13}R^{14}$, —$SO_2R^{13}$, —$SO_2NR^{13}R^{14}$, —$SO_2NR^{13}C(=O)R^{13}$, —C(=O)$NR^{13}SO_2R^{13}$, —S(=O)$R^{13}$, —S(=O)(=$NR^{14}$)$R^{13}$, —$NR^{13}SO_2NR^{13}R^{14}$, —$NR^{13}SO_2R^{13}$, —$NR^{13}R^{14}$, —$NR^{14}C(=O)R^{13}$, —$NR^{14}C(=O)OR^{13}$, —C(=O)$NR^{13}R^{14}$, —C(=O)$OR^{13}$, -(4-7-membered heterocycloalkyl containing 1 to 2 ring members independently selected from N, NH, $NR^{17}$, O or S), -(4-7-membered heterocyclyl containing 1 to 2 ring members independently selected from N, NH, $NR^{17}$, O or S), —$C_3$-$C_5$cycloalkyl, and -(5-6 membered heteroaryl ring having 1 to 4 heteroatoms comprising 1-4 nitrogen atoms, 0 or 1 oxygen atoms, and 0 or 1 sulfur atoms as ring members), where the $C_1$-$C_4$alkyl, 4-7-membered heterocycloalkyl, 4-7-membered heterocyclyl, $C_3$-$C_5$cycloalkyl and 5-6 membered heteroaryl ring are each optionally further substituted with 1 to 3 groups independently selected from halo, $C_1$-$C_3$alkyl, $C_1$-$C_3$haloalkyl, —$OR^{13}$, —CN, and —$NR^{13}R^{14}$;
$R^{11}$ and $R^{12}$ are each independently selected from H and $C_1$-$C_4$alkyl;
each $R^{13}$ is independently selected from H, $C_1$-$C_4$alkyl, a 4-7-membered heterocycloalkyl containing 1 to 2 ring members independently selected from N, NH, $NR^{17}$, O or S, a 4-7-membered heterocyclyl containing 1 to 2 ring members independently selected from N, NH, $NR^{17}$, O or S, and a $C_3$-$C_6$cycloalkyl, wherein the $C_1$-$C_4$alkyl, heterocyclyl and $C_3$-$C_6$cycloalkyl are optionally substituted with 1 to 3 groups selected from $C_1$-$C_4$alkyl, halo, —OH, —$NR^{15}R^{16}$, —C(=O)$OR^{15}$, $C_1$-$C_2$alkoxy and $C_1$-$C_4$alkyl substituted with 1 to 2 hydroxy groups;
$R^{14}$ is selected from H, $C_1$-$C_4$alkyl and $C_3$-$C_6$cycloalkyl, wherein the $C_1$-$C_4$alkyl and $C_3$-$C_6$cycloalkyl are optionally substituted with 1 to 3 groups independently selected from $C_1$-$C_4$alkyl, halo, —OH, —$NR^{15}R^{16}$, $C_1$-$C_2$alkoxy and $C_1$-$C_4$alkyl substituted with 1 to 2 hydroxy groups;
or $R^{13}$ and $R^{14}$, taken together with a nitrogen atom to which both are directly attached, can form a 4-6 membered ring optionally containing an additional N, O or S as a ring member and optionally substituted with one to three groups selected from $C_1$-$C_2$alkyl, $C_1$-$C_2$alkoxy, oxo, and hydroxy;
$R^{15}$ and $R^{16}$ are each independently selected from H and $C_1$-$C_4$alkyl;
$L^3$ is a bond or a straight chain or branched $C_1$-$C_3$alkylene;
and
'$=\!=\!=$' represents a single or double bond.

Embodiment 23. The compound of Formula (II) of any one of Embodiment 1 to 22, or a pharmaceutically acceptable salt thereof, wherein:
$R^B$ is phenyl, pyridinyl, thiophenyl or a 5-8 membered cycloalkyl, wherein $R^B$ is optionally substituted with 1 to 3 $R^5$ groups;
$R^1$ is selected from H, $C_1$-$C_3$alkyl and $C_1$-$C_3$alkyl substituted with 1 to 3 —OH groups;
$R^2$ is H;
t is 0, 1 or 2;
each $R^3$, when present, is a substituent on the ring to which -L-W is directly attached, wherein each $R^3$ is independently selected from $C_1$-$C_3$alkyl;
$R^4$ is H, $C_1$-$C_3$alkyl, $C_3$-$C_6$cycloalkyl, —$(CH_2)_2O(CH_2)_2$Br or a $C_1$-$C_3$alkyl substituted with 1 to 2 groups independently selected from —OH, —C(=O)$R^{15}$ and $R^{10}$;
each $R^5$ is independently selected from halo, —CN, $C_1$-$C_3$alkoxy and $C_1$-$C_3$alkyl;
L is a $C_1$-$C_4$ straight chain or branched alkylene linker, or L can be a $C_1$-$C_4$ straight chain or branched alkylene linker or a bond when W is an optionally substituted ring;
W is a 3-6 membered cycloalkyl, wherein the 3-6 membered cycloalkyl is substituted with 1 to 3 groups independently selected from —$SO_2R^{10}$, —$SO_2NR^{14}R^{10}$, —$SO_2NR^{13}R^{14}$, and —$SO_2N=CR^{13}NR^{13}R^{14}$;
$R^{10}$ is selected from $C_1$-$C_5$alkyl, $C_1$-$C_3$haloalkyl, 3-6 membered cycloalkyl, phenyl, 5-6 membered heteroaryl having 1 to 4 heteroatoms independently selected from N, O and S as ring members, 4-6 membered heterocycloalkyl containing one or two ring members independently selected from N, NH, $NR^{17}$, O or S and 4-6 membered heterocyclyl containing 1 to 2 ring members independently selected from N, NH, $NR^{17}$, O or S,
  wherein each $R^{10}$ is optionally substituted with 1 to 5 groups independently selected from $C_1$-$C_4$alkyl, deuterium, $C_1$-$C_4$haloalkoxy, —OH, —CN, —OC(=O)$R^{14}$, -$L^3OR^{13}$, —$NR^{13}R^{14}$, —$NR^{14}C(=O)R^{13}$, —$NR^{14}C(=O)OR^{13}$, —C(=O)$NR^{13}R^{14}$, —C(=O)$OR^{13}$, (4-7-membered heterocycloalkyl containing 1 to 2 ring members independently selected from N, NH, $NR^{17}$, O or S), (4-7-membered heterocyclyl containing 1 to 2 ring members independently selected from N, NH, $NR^{17}$, O or S), and —C₃-C₅cycloalkyl, where the C₁-C₄alkyl, 4-7-membered heterocycloalkyl, 4-7-membered heterocyclyl, and C₃-C₅cycloalkyl are each optionally further substituted with 1 to 3 groups independently selected from halo, —OR¹³, and —NR¹³R¹⁴;

R¹¹ and R¹² are each independently selected from H and C₁-C₄alkyl;

each R¹³ is independently selected from H, C₁-C₄alkyl, a 4-7-membered heterocycloalkyl containing 1 to 2 ring members independently selected from N, NH, NR¹⁷, O or S, a 4-7-membered heterocyclyl containing 1 to 2 ring members independently selected from N, NH, NR¹⁷, O or S, and a C₃-C₆cycloalkyl, wherein the C₁-C₄alkyl, heterocyclyl and C₃-C₆cycloalkyl are optionally substituted with 1 to 3 groups independently selected from C₁-C₄alkyl, halo, —OH, —NR¹⁵R¹⁶, —C(=O)OR¹⁵, and C₁-C₄alkyl substituted with 1 to 2 hydroxy groups;

R¹⁴ is selected from H and C₁-C₄alkyl;

R¹⁵ and R¹⁶ are each independently selected from H and C₁-C₄alkyl;

L³ is a bond or a straight chain or branched C₁-C₃alkylene;

and

'---' represents a single or double bond.

Embodiment 24. The compound of Formula (I) or Formula (II) having the structure of Formula (IIa), Formula (IIIb) or Formula (IIIc), or a pharmaceutically acceptable salt thereof:

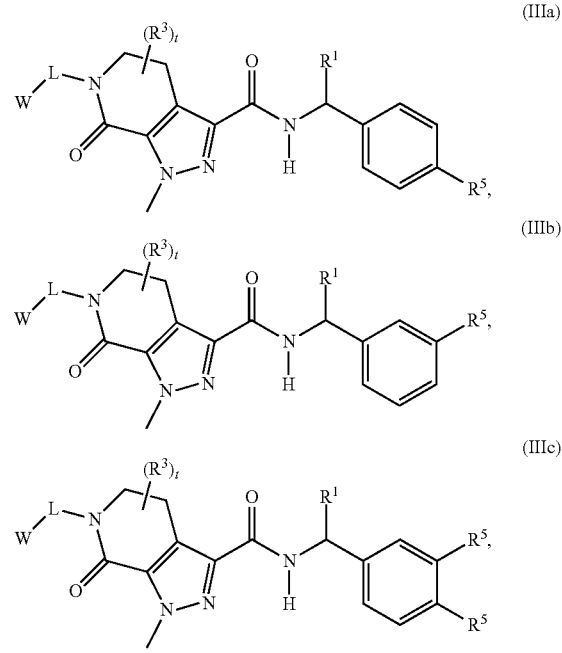

wherein:
W, L, t, R¹, R³ and R⁵ are as defined for Formula (I);
or W, L, t, R¹, R³ and R⁵ are as defined in Embodiment 22,
or W, L, t, R¹, R³ and R⁵ are as defined in Embodiment 23.

Embodiment 25. The compound of Formula (I) or Formula (II) having the structure of Formula (IIa), or a pharmaceutically acceptable salt thereof:

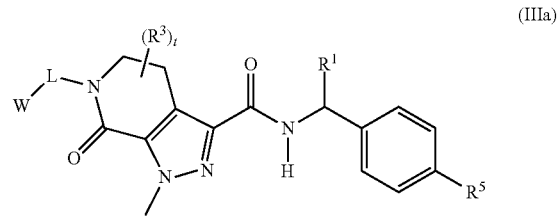

wherein:
W, L, t, R¹, R³ and R⁵ are as defined for Formula (I);
or W, L, t, R¹, R³ and R⁵ are as defined in Embodiment 22,
or W, L, t, R¹, R³ and R⁵ are as defined in Embodiment 23.

Embodiment 26. The compound of any one of Embodiment 1 to 25, or a pharmaceutically acceptable salt thereof, wherein:

R¹ is selected from H, C₁-C₃alkyl and C₁-C₃alkyl substituted with one —OH group;

t is 0, 1 or 2;

each R³, when present, is a substituent on the ring to which -L-W is directly attached, wherein each R³ is independently selected from halo, CN, C₁-C₃alkoxy, C₁-C₃alkyl, C(=O)OR¹⁰, and C(=O)NR¹³R¹⁴;

each R⁵ is independently selected from halo, CN, C₁-C₃alkyl and C₁-C₃alkoxy;

L is a C₁-C₄ straight chain or branched alkylene linker;

W is —SO₂R¹⁰, —SO₂NR¹³R¹⁴, —NR¹⁴SO₂R¹⁰, —CR¹¹R¹²SO₂R¹⁰, —CR¹¹R¹²SO₂NR¹³R¹⁴, —CR¹¹R¹²NR¹⁴SO₂R¹⁰, or an optionally substituted 3-6 membered cycloalkyl; wherein the optional substituents for said optionally substituted cycloalkyl are 1 to 3 groups independently selected from C₁-C₃alkyl, oxo, halo, —OH, —SO₂R¹⁰, —SO₂NR¹³R¹⁴, —SO₂NR¹⁴R¹⁰, —NR¹³SO₂NR¹³R¹⁴, —NR¹³SO₂R¹⁰, —NR¹³R¹⁴, —OR¹⁰, —NR¹³C(=O)OR¹⁰, —C(=O)NR¹³R¹⁴, and C(=O)OR¹³, R¹⁰ is selected from C₁-C₅alkyl, 3-6 membered cycloalkyl, phenyl, 5-6 membered heteroaryl having 1 to 4 heteroatoms independently selected from N, O and S as ring members, 4-6 membered heterocycloalkyl containing one or two ring members independently selected from N, NH, NR¹⁷, O or S and 4-6 membered heterocyclyl containing 1 to 2 ring members independently selected from N, NH, NR¹⁷, O or S, wherein each R¹⁰ is optionally substituted with 1 to 4 groups selected from C₁-C₃alkyl, oxo, CN, halo, C₁-C₃alkoxy, OH, and C₃-C₅cycloalkyl;

R¹¹ and R¹² are each independently selected from H and C₁-C₄alkyl;

each R¹³ is independently selected from H and C₁-C₄alkyl optionally substituted with halo, —OH or C₁-C₂alkoxy;

R¹⁴ is selected from H and C₁-C₄alkyl;

or R¹³ and R¹⁴, taken together with a nitrogen atom to which both are directly attached, can form a 4-6 membered ring optionally containing an additional N, O or S as a ring member and optionally substituted with one to two groups selected from C₁-C₂alkyl, C₁-C₂alkoxy, oxo, and hydroxyl.

Embodiment 27. The compound of any one of Embodiment 1 to 25, or a pharmaceutically acceptable salt thereof, wherein:

R¹ is H, methyl or methyl substituted with one —OH group;

t is 0, 1 or 2;

each R³, when present, is a substituent on the ring to which -L-W is directly attached, wherein each R³ is independently selected from methyl;

each R⁵ is independently selected from C, F, —CN, methyl, and —OCH₃;

L is —CH₂— or —CH₂CH₂—;

W is cyclopropyl substituted with —S₂R¹⁰, —SO₂NR¹³R¹⁴ or —SO₂NR¹⁴R¹⁰;

R¹⁰ is selected from methyl, ethyl, propyl, isopropyl, butyl, isobutyl, pentyl, cyclopropyl, cyclobutyl, pyridinyl, pyrazolyl, isoxazolyl, oxetanyl, tetrahydrofuranyl, tetrahydropyranyl, morpholinyl, piperidinyl, piperazinyl, pyrrolidinyl and azetidinyl, wherein each R¹⁰ is optionally substituted with 1 to 4 groups independently selected from methyl, ethyl, deuterium, —OCH₃, —OH, —OCHF₂, —CN, —NH₂, —NHCH₃, —N(CH₃)₂, —NHR¹³, —NHCH(=O), —NHC(=O)CH₃, —NHC(=O)OCH₃, —NHC(=O)CH₂NH₂, —NHC(=O)CH₂N(CH₃)₂, —NHC(=O)CH(CH₃)NH₂, —NHC(=O)C(CH₃)₂NH₂, —OCH₂CH₂OH, —OCH₂CH(CH₃)OH, —OCH₂CH(CH₃)₂OH, —OCH(F)CH₂OH, —OCF₂CH₂OH, —OCH₂CH₂NH₂, —OCH₂CH(CH₃)NH₂, —OCH₂C(CH₃)₂NH₂, —OCH₂CH₂NHCH₃, —OCH₂CH₂N(CH₃)₂, —OCH(F)CH₂NH₂, —OCF₂CH₂NH₂, —CH₂OCH₂CH₂NH₂, —CH₂CH₂OH, —CH₂OH, —CH₂NH₂, —O-azetidinyl, —C(=O)NH₂, —C(=O)NHCH₃, —OC(=O)CH₃, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl, where the methyl, ethyl, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl are each optionally further substituted with 1 to 3 groups independently selected from F, —OH, —OCH₃, —NH₂ and methyl;

R¹³ is selected from H, methyl, ethyl, isopropyl, propyl, butyl, isobutyl, pentyl a 4-7-membered heterocyclyl containing 1 to 2 two heteroatoms independently selected from N, O or S as ring members, and a C₃-C₆cycloalkyl, wherein the methyl, ethyl, isopropyl, propyl, butyl, isobutyl, pentyl heterocyclyl and C₃-C₆cycloalkyl are optionally substituted with 1 to 3 groups independently selected from methyl, ethyl, propyl, isopropyl, F, —OH, —NH₂, —N(CH₃)₂, —C(=O)OH, C₁-C₂alkoxy and C₁-C₄alkyl substituted with 1 to 2 hydroxy groups, and R¹⁴ is selected from H and methyl.

Embodiment 28. The compound of Formula (I) or Formula (II) having the structure of Formula (IVa), Formula (IVb) or Formula (IVc), or a pharmaceutically acceptable salt thereof:

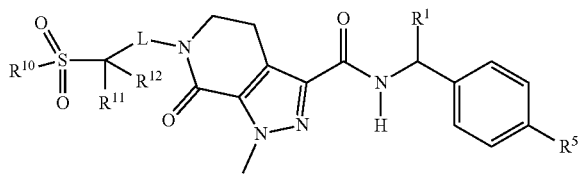

(IVa)

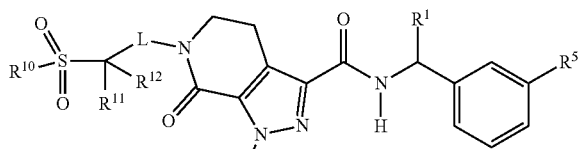

(IVb)

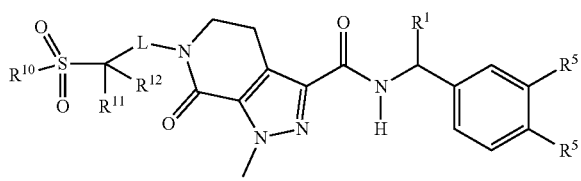

(IVc)

wherein:

L, R¹, R⁵, R¹⁰, R¹¹ and R¹² are as defined for Formula (I);

or L, R¹, R⁵, R¹⁰, R¹¹ and R¹² are as defined in Embodiment 22;

or L, R¹, R⁵, R¹⁰, R¹¹ and R¹² are as defined in Embodiment 23;

or L, R¹, R⁵, R¹⁰, R¹¹ and R¹² are as defined in Embodiment 26, or L, R¹, R⁵, R¹⁰, R¹¹ and R¹² are as defined in Embodiment 27.

Embodiment 29. The compound of Formula (I) or Formula (II) having the structure of Formula (IVa), or a pharmaceutically acceptable salt thereof:

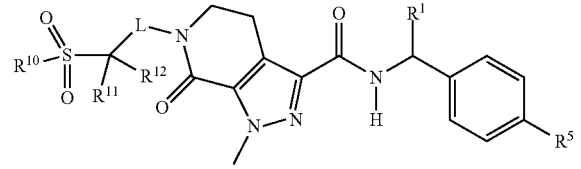

(IVa)

wherein:

L, R¹, R⁵, R¹⁰, R¹¹ and R¹² are as defined for Formula (I);

or L, R¹, R⁵, R¹⁰, R¹¹ and R¹² are as defined in Embodiment 22;

or L, R¹, R⁵, R¹⁰, R¹¹ and R¹² are as defined in Embodiment 23;

or L, R¹, R⁵, R¹⁰, R¹¹ and R¹² are as defined in Embodiment 26, or L, R¹, R⁵, R¹⁰, R¹¹ and R¹² are as defined in Embodiment 27.

Embodiment 30. The compound of Formula (I) or Formula (II) having the structure of Formula (Va), Formula (Vb) or Formula (Vc), or a pharmaceutically acceptable salt thereof:

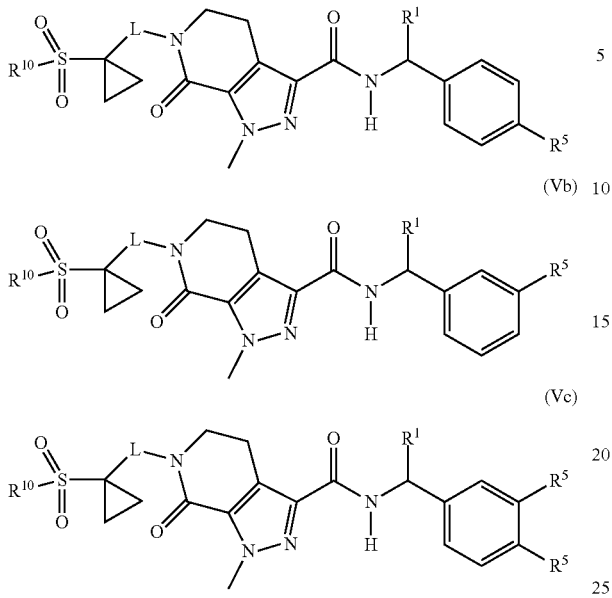

wherein:
L, $R^1$, $R^5$, and $R^{10}$ are as defined for Formula (I);
or L, $R^1$, $R^5$, and $R^{10}$ are as defined in Embodiment 22;
or L, $R^1$, $R^5$, and $R^{10}$ are as defined in Embodiment 23;
or L, $R^1$, $R^5$, and $R^{10}$ are as defined in Embodiment 26,
or L, $R^1$, $R^5$, and $R^{10}$ are as defined in Embodiment 27.

Embodiment 31. The compound of Formula (I) or Formula (II) having the structure of Formula (Va), or a pharmaceutically acceptable salt thereof:

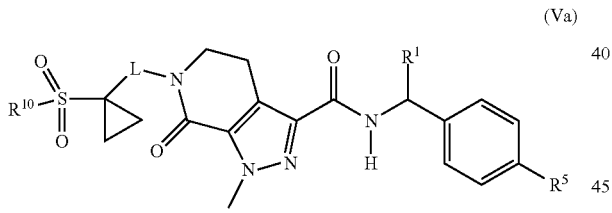

wherein:
L, $R^1$, $R^5$, and $R^{10}$ are as defined for Formula (I);
or L, $R^1$, $R^5$, and $R^{10}$ are as defined in Embodiment 22;
or L, $R^1$, $R^5$, and $R^{10}$ are as defined in Embodiment 23;
or L, $R^1$, $R^5$, and $R^{10}$ are as defined in Embodiment 26,
or L, $R^1$, $R^5$, and $R^{10}$ are as defined in Embodiment 27.

Embodiment 32. The compound of any one of Embodiment 1 to 31, or a pharmaceutically acceptable salt thereof, wherein:
$R^1$ is H, methyl or methyl substituted with one —OH group;
each $R^5$ is independently selected from Cl, F, and —CN;
L is a bond or $CH_2$ or $CH_2CH_2$;
$R^{10}$ is selected from methyl, ethyl, propyl, isopropyl, butyl, isobutyl, pentyl, cyclopropyl, cyclobutyl, pyridinyl, pyrazolyl, isoxazolyl, oxetanyl, tetrahydrofuranyl, tetrahydropyranyl, morpholinyl, piperidinyl, piperazinyl, pyrrolidinyl and azetidinyl,
wherein each $R^{10}$ is optionally substituted with 1 to 4 groups independently selected from methyl, ethyl, deuterium, —$OCH_3$, —OH, —$OCHF_2$, —CN, —$NH_2$, —$NHCH_3$, —$N(CH_3)_2$, —$NHR^{13}$, —NHCH(=O), —NHC(=O)$CH_3$, —NHC(=O)$OCH_3$, —NHC(=O)$CH_2NH_2$, —NHC(=O)$CH_2N(CH_3)_2$, —NHC(=O)$CH(CH_3)NH_2$, —NHC(=O)$C(CH_3)_2NH_2$, —$OCH_2CH_2OH$, —$OCH_2CH(CH_3)OH$, —$OCH_2CH(CH_3)_2OH$, —$OCH(F)CH_2OH$, —$OCF_2CH_2OH$, —$OCH_2CH_2NH_2$, —$OCH_2CH(CH_3)NH_2$, —$OCH_2C(CH_3)_2NH_2$, —$OCH_2CH_2NHCH_3$, —$OCH_2CH_2N(CH_3)_2$, —$OCH(F)CH_2NH_2$, —$OCF_2CH_2NH_2$, —$CH_2OCH_2CH_2NH_2$, —$CH_2CH_2OH$, —$CH_2OH$, —$CH_2NH_2$, —O-azetidinyl, —C(=O)$NH_2$, —C(=O)$NHCH_3$, —OC(=O)$CH_3$, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl,
where the methyl, ethyl, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl are each optionally further substituted with 1 to 3 groups independently selected from F, —OH, —$OCH_3$, —$NH_2$ and
and
$R^{11}$ and $R^{12}$ each independently represent H or methyl.

Embodiment 33. The compound of any one of Embodiment 1 to 32, or a pharmaceutically acceptable salt thereof, wherein:
$R^1$ is H, methyl or methyl substituted with one —OH group;
each $R^5$ is independently selected from Cl, F, and —CN;
L is a bond or $CH_2$ or $CH_2CH_2$;
and
$R^{10}$ is selected from methyl, ethyl, propyl, isopropyl, butyl, isobutyl, pentyl, cyclopropyl, cyclobutyl, pyridinyl, pyrazolyl, isoxazolyl, oxetanyl, tetrahydrofuranyl, tetrahydropyranyl, morpholinyl, piperidinyl, piperazinyl, pyrrolidinyl and azetidinyl,
wherein each $R^{10}$ is optionally substituted with 1 to 4 groups independently selected from methyl, ethyl, deuterium, —$OCH_3$, —OH, —$OCHF_2$, —CN, —$NH_2$, —$NHCH_3$, —$N(CH_3)_2$, —$NHR^{13}$, —NHCH(=O), —NHC(=O)$CH_3$, —NHC(=O)$OCH_3$, —NHC(=O)$CH_2NH_2$, —NHC(=O)$CH_2N(CH_3)_2$, —NHC(=O)$CH(CH_3)NH_2$, —NHC(=O)$C(CH_3)_2NH_2$, —$OCH_2CH_2OH$, —$OCH_2CH(CH_3)OH$, —$OCH_2CH(CH_3)_2OH$, —$OCH(F)CH_2OH$, —$OCF_2CH_2OH$, —$OCH_2CH_2NH_2$, —$OCH_2CH(CH_3)NH_2$, —$OCH_2C(CH_3)_2NH_2$, —$OCH_2CH_2NHCH_3$, —$OCH_2CH_2N(CH_3)_2$, —$OCH(F)CH_2NH_2$, —$OCF_2CH_2NH_2$, —$CH_2OCH_2CH_2NH_2$, —$CH_2CH_2OH$, —$CH_2OH$, —$CH_2NH_2$, —O-azetidinyl, —C(=O)$NH_2$, —C(=O)$NHCH_3$, —OC(=O)$CH_3$, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl,
where the methyl, ethyl, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl are each optionally further substituted with 1 to 3 groups independently selected from F, —OH, —$OCH_3$, —$NH_2$.

Embodiment 34. The compound of Formula (I) having the structure of Formula (VI), or a pharmaceutically acceptable salt thereof,

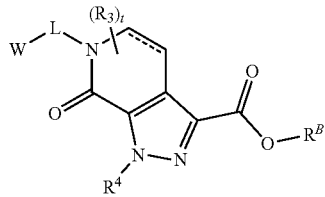

(VI)

wherein:
W, L, t, $R^3$, $R^4$, and $R^B$ are as defined for Formula (I).

Embodiment 35. A compound of Formula (VII), or a pharmaceutically acceptable salt thereof,

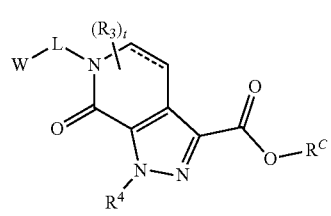

(VII)

wherein:
$R^C$ is H or $C_1$-$C_6$ alkyl optionally substituted with 1 to 3 $R^6$ groups;
t is 0, 1 or 2;
each $R^3$, when present, is a substituent on the ring to which -L-W is directly attached, wherein each $R^3$ is independently selected from halo, CN, $C_1$-$C_3$alkoxy, $C_1$-$C_3$alkyl, C(=O)$OR^{10}$, and C(=O)$NR^{13}R^{14}$;
$R^4$ is H, halo, or $C_{1-3}$ alkyl;
L is a $C_1$-$C_4$ straight chain or branched alkylene linker or a bond;
W is H, —OH, —$OR^{10}$, —C(=O)$NR^{13}R^{14}$, —C(=O)O $R^{13}$, —$NR^{13}R^{14}$, —$NR^{13}$C(=O)$OR^{10}$, —$NR^{13}$C(=O)$R^{10}$, —$SO_2R^{10}$, —$SO_2NR^{13}R^{14}$, —$NR^{13}SO_2R^{10}$, —P(=O)$(OR^{13})_2$, —S(=O)$R^{10}$, —S(=O)(=$NR^{13}$)$R^{10}$, —$CR^{11}R^{12}$C(=O)$NR^{13}R^{14}$, —$CR^{11}R^{12}$C(=O)$OR^{13}$, —$CR^{11}R^{12}NR^{13}R^{14}$, —$CR^{11}R^{12}NR^{13}$C(=O)$OR^{10}$, —$CR^{11}R^{12}NR^{13}$C(=O)$R^0$, —$CR^{11}R^{12}SO_2R^{10}$, —$CR^{11}R^{12}SO_2NR^{13}R^{14}$, —$CR^{11}R^{12}NR^{13}SO_2R^{10}$, —$CR^{11}R^{12}P(=O)(OR^{13})_2$, —$CR^{11}R^{12}S(=O)R^{10}$, —$CR^{11}R^{12}S(=O)(=NR^{13})R^{10}$, a 3-6 membered cycloalkyl, phenyl, a 5-6-membered heterocycloalkyl containing one or two ring members independently selected from N, NH, $NR^{17}$, O or S, a 5-6-membered heterocyclyl containing one or two ring members independently selected from N, NH, $NR^{17}$, O or S, or a 5-membered heteroaryl having 1 to 4 heteroatoms selected from N, O and S as ring members that is optionally fused to phenyl,
wherein the 3-6 membered cycloalkyl, phenyl, 5-6-membered heterocycloalkyl, 5-6-membered heterocyclyl and 5-membered heteroaryl of W are each optionally substituted with 1 to 3 groups independently selected from $C_1$-$C_3$alkyl, oxo, halo, $C_1$-$C_3$haloalkyl, —OH, —$OR^{10}$, —OC(=O)$NR^{13}R^{14}$, —$SO_2R^{10}$, —$SO_2NR^{14}R^{10}$, —$SO_2NR^{13}R^{14}$, —$SO_2N$=$CR^{13}NR^{13}R^{14}$, —$SO_2NR^{13}$C(=O)$R^{10}$, —C(=O)$NR^{13}SO_2R^{10}$, —S(=O)$R^{10}$, —S(=O)(=$NR^{13}$)$R^{10}$, —$NR^{13}SO_2NR^{13}R^{14}$, —$NR^{13}SO_2R^{10}$, —$NR^{13}R^{14}$, —$NR^{13}$C(=O)$R^{13}$, —$NR^{13}$C(=O)$OR^{10}$, —C(=O)$NR^{13}R^{14}$, and —C(=O)$OR^{13}$;

$R^{10}$ is selected from $C_1$-$C_5$alkyl, $C_1$-$C_3$haloalkyl, 3-6 membered cycloalkyl, phenyl, 5-6 membered heteroaryl having 1 to 4 heteroatoms independently selected from N, O and S as ring members, 4-6 membered heterocycloalkyl containing one or two ring members independently selected from N, NH, $NR^{17}$, O or S and 4-6 membered heterocyclyl containing 1 to 2 ring members independently selected from N, NH, $NR^{17}$, O or S,
wherein each $R^{10}$ is optionally substituted with 1 to 5 groups independently selected from $C_1$-$C_4$alkyl, deuterium, $C_1$-$C_4$haloalkoxy, —OH, —CN, —OC(=O)$R^{14}$, -$L^3OR^{13}$, $C_1$-$C_2$haloalkyl, oxo, -halo, —$C_1$-$C_3$alkoxy, —OC(=O)$NR^{13}R^{14}$, —$SO_2R^{13}$, —$SO_2NR^{13}R^{14}$, —$SO_2NR^{13}$C(=O)$R^{13}$, —C(=O)$NR^{13}SO_2R^{13}$, —S(=O)$R^{13}$, —S(=O)(=$NR^{14}$)$R^{13}$, —$NR^{13}SO_2NR^{13}R^{14}$, —$NR^{13}SO_2R^{13}$, —$NR^{13}R^{14}$, —$NR^{14}$C(=O)$R^{13}$, —$NR^{14}$C(=O)$OR^{13}$, —C(=O)$NR^{13}R^{14}$, —C(=O)$OR^{13}$, (4-7-membered heterocycloalkyl containing 1 to 2 ring members independently selected from N, NH, $NR^{17}$, O or S), (4-7-membered heterocyclyl containing 1 to 2 ring members independently selected from N, NH, $NR^{17}$, O or S), —$C_3$-$C_5$cycloalkyl, and -(5-6 membered heteroaryl ring having 1 to 4 heteroatoms comprising 1-4 nitrogen atoms, 0 or 1 oxygen atoms, and 0 or 1 sulfur atoms as ring members), where the $C_1$-$C_4$alkyl, 4-7-membered heterocycloalkyl, 4-7-membered heterocyclyl, $C_3$-$C_5$cycloalkyl and 5-6 membered heteroaryl ring are each optionally further substituted with 1 to 3 groups independently selected from halo, $C_1$-$C_3$alkyl, $C_1$-$C_3$haloalkyl, —$OR^{13}$, —CN, and —$NR^{13}R^{14}$;

$R^{11}$ and $R^{12}$ are each independently selected from H and $C_1$-$C_4$alkyl;
each $R^{13}$ is independently selected from H, $C_{1-4}$ alkyl optionally substituted with halo, —OH, amino, or $C_{1-2}$ alkoxy, and $C_{3-6}$ alkyl optionally substituted with halo, —OH, amino, or $C_{1-2}$ alkoxy;
$R^{14}$ is independently selected from H, $C_{1-4}$ alkyl optionally substituted with halo, —OH, amino, or $C_{1-2}$ alkoxy, and $C_{3-6}$ alkyl optionally substituted with halo, —OH, amino, or $C_{1-2}$ alkoxy
or $R^{13}$ and $R^{14}$, taken together with a nitrogen atom to which both are directly attached, can form a 4-6 membered ring optionally containing an additional N, O or S as a ring member and optionally substituted with one to three groups selected from $C_{1-2}$ alkyl, $C_{1-2}$ alkoxy, oxo, and hydroxy;
$L^3$ is a bond or a straight chain or branched $C_{1-3}$ alkylene;
each $R^6$ is independently selected at each occurrence from halo, hydroxy, CN, $C_1$-$C_3$alkoxy, $C_1$-$C_3$alkyl, and $C_3CO_5$cycloalkyl,
or
two $R^6$ groups, taken together with a carbon atom to which both are directly attached can form a 3-5 membered cycloalkyl ring or a 4-6 membered heterocyclic ring containing O, N or S as a ring member and optionally substituted with 1 to 2 groups independently selected from oxo and $C_1$-$C_3$alkyl.

Embodiment 36. The compound of Formula (VII) of Embodiment 35, or a pharmaceutically acceptable salt thereof, wherein Re is H, methyl, ethyl, propyl, isopropyl, t-butyl or n-butyl.

Embodiment 37. The compound of any one of Embodiments 34 to 36, or a pharmaceutically acceptable salt thereof, wherein:

L is a $C_1$-$C_4$ straight chain or branched alkylene linker;
W is —$SO_2R^{10}$, —$SO_2NR^{13}R^{14}$, —$NR^4SO_2R^{10}$, —$CR^{11}R^{12}SO_2R^{10}$, —$CR^{11}R^{12}SO_2NR^{13}R^{14}$, —$CR^{11}R^{12}NR^{14}SO_2R^{10}$, or an optionally substituted $C_1$-$C_3$ alkyl, or an optionally substituted 3-6 membered cycloalkyl;
  wherein the optional substituents for said optionally substituted $C_1$-$C_3$ alkyl and optionally substituted cycloalkyl are 1 to 3 groups independently selected from $C_1$-$C_3$alkyl, oxo, halo, —OH, —$SO_2R^{10}$, —$SO_2NR^{13}R^{14}$, —$SO_2NR^{14}R^{10}$, —$NR^{13}SO_2NR^{13}R^{14}$, —$NR^{13}SO_2R^{10}$, —$NR^{13}R^{14}$, —$OR^{10}$, —$NR^{13}C(=O)OR^{10}$, —$C(=O)NR^{13}R^{14}$, and $C(=O)OR^{13}$;
$R^{10}$ is selected from $C_1$-$C_5$alkyl, 3-6 membered cycloalkyl, phenyl, 5-6 membered heteroaryl having 1 to 4 heteroatoms independently selected from N, O and S as ring members, 4-6 membered heterocycloalkyl containing one or two ring members independently selected from N, NH, $NR^{17}$, O or S and 4-6 membered heterocyclyl containing 1 to 2 ring members independently selected from N, NH, $NR^{17}$, O or S,
  wherein each $R^{10}$ is optionally substituted with 1 to 4 groups selected from $C_1$-$C_3$alkyl, oxo, CN, halo, $C_1$-$C_3$alkoxy, OH, and $C_3$-$C_5$cycloalkyl;
$R^{11}$ and $R^{12}$ are each independently selected from H and $C_1$-$C_4$alkyl;
each $R^{13}$ is independently selected from H and $C_1$-$C_4$alkyl optionally substituted with halo, —OH or $C_1$-$C_2$alkoxy;
$R^{14}$ is selected from H and $C_1$-$C_4$alkyl;
or $R^{13}$ and $R^{14}$, taken together with a nitrogen atom to which both are directly attached, can form a 4-6 membered ring optionally containing an additional N, O or S as a ring member and optionally substituted with one to two groups selected from $C_1$-$C_2$alkyl, $C_1$-$C_2$alkoxy, oxo, and hydroxyl.

Embodiment 38. The compound of Formula (I), or according to any one of Embodiments 1 to 34, or a pharmaceutically acceptable salt thereof, wherein $R^B$ is selected from phenyl, pyridinyl, thiophenyl and cyclohexyl, each of which is optionally substituted with 1 to 3 $R^5$ groups.

Embodiment 39. The compound of Formula (I), or according to any one of Embodiments 1 to 34, or a pharmaceutically acceptable salt thereof, wherein $R^B$ is pyridinyl optionally substituted with 1 to 3 $R^5$ groups.

Embodiment 40. The compound of Formula (I), or according to any one of Embodiments 1 to 34, or a pharmaceutically acceptable salt thereof, wherein $R^B$ is pyridine-3-yl optionally substituted with 1 to 3 $R^5$ groups.

Embodiment 41. The compound of Formula (I), or according to any one of Embodiments 1 to 34, or a pharmaceutically acceptable salt thereof, wherein $R^B$ is pyridine-2-yl optionally substituted with 1 to 3 $R^5$ groups.

Embodiment 42. The compound of Formula (I), or according to any one of Embodiments 1 to 34, or a pharmaceutically acceptable salt thereof, wherein $R^B$ is thiophenyl optionally substituted with 1 to 3 $R^5$ groups.

Embodiment 43. The compound of Formula (I), or according to any one of Embodiments 1 to 34, or a pharmaceutically acceptable salt thereof, wherein $R^B$ is thiophen-2-yl optionally substituted with 1 to 3 $R^5$ groups.

Embodiment 44. The compound of Formula (I), or according to any one of Embodiments 1 to 34, or a pharmaceutically acceptable salt thereof, wherein $R^B$ is cyclohexyl optionally substituted with 1 to 3 $R^5$ groups.

Embodiment 45. The compound of Formula (I), or according to any one of Embodiments 1 to 34, or a pharmaceutically acceptable salt thereof, wherein $R^B$ is phenyl optionally substituted with 1 to 3 $R^5$ groups.

Embodiment 46. The compound of Formula (I), or according to any one of Embodiments 1 to 34, or a pharmaceutically acceptable salt thereof, wherein $R^B$ is selected from phenyl, pyridinyl, thiophenyl and cyclohexyl, each of which is optionally substituted with 1 to 3 $R^5$ groups independently selected from halo, $C_1$-$C_3$alkoxy, $C_1$-$C_3$alkyl and —CN.

Embodiment 47. The compound of Formula (I), or according to any one of Embodiments 1 to 34, or a pharmaceutically acceptable salt thereof, wherein $R^B$ is pyridine-3-yl optionally substituted with 1 to 3 $R^5$ groups.

Embodiment 48. The compound of Formula (I), or according to any one of Embodiments 1 to 34, or a pharmaceutically acceptable salt thereof, wherein $R^B$ is pyridine-2-yl optionally substituted with 1 to 3 $R^5$ groups independently selected from halo, $C_1$-$C_3$alkoxy, $C_1$-$C_3$alkyl and —CN.

Embodiment 49. The compound of Formula (I), or according to any one of Embodiments 1 to 34, or a pharmaceutically acceptable salt thereof, wherein $R^B$ is thiophenyl optionally substituted with 1 to 3 $R^5$ groups independently selected from halo, $C_1$-$C_3$alkoxy, $C_1$-$C_3$alkyl and —CN.

Embodiment 50. The compound of Formula (I), or according to any one of Embodiments 1 to 34, or a pharmaceutically acceptable salt thereof, wherein $R^B$ is thiophen-2-yl optionally substituted with 1 to 3 $R^5$ groups independently selected from halo, $C_1$-$C_3$alkoxy, $C_1$-$C_3$alkyl and —CN.

Embodiment 51. The compound of Formula (I), or according to any one of Embodiments 1 to 34, or a pharmaceutically acceptable salt thereof, wherein $R^B$ is cyclohexyl optionally substituted with 1 to 3 $R^5$ groups independently selected from halo, $C_1$-$C_3$alkoxy, $C_1$-$C_3$alkyl and —CN.

Embodiment 52. The compound of Formula (I), or according to any one of Embodiments 1 to 34, or a pharmaceutically acceptable salt thereof, wherein $R^B$ is phenyl optionally substituted with 1 to 3 $R^5$ groups independently selected from halo, $C_1$-$C_3$alkoxy, $C_1$-$C_3$alkyl and —CN.

Embodiment 53. The compound of Formula (I), or according to any one of Embodiments 1 to 34, or a pharmaceutically acceptable salt thereof, wherein $R^B$ is selected from phenyl, pyridinyl, thiophenyl and cyclohexyl, each of which is optionally substituted with 1 to 3 $R^5$ groups independently selected from Cl, F, —$OCH_3$, methyl and —CN.

Embodiment 54. The compound of Formula (I), or according to any one of Embodiments 1 to 34, or a pharmaceutically acceptable salt thereof, wherein $R^B$ is pyridine-2-yl optionally substituted with 1 to 3 $R^5$ groups independently selected from Cl, F, —$OCH_3$, methyl and —CN.

Embodiment 55. The compound of Formula (I), or according to any one of Embodiments 1 to 34, or a pharmaceutically acceptable salt thereof, wherein $R^B$ is thiophenyl optionally substituted with 1 to 3 $R^5$ groups independently selected from Cl, F, —$OCH_3$, methyl and —CN.

Embodiment 56. The compound of Formula (I), or according to any one of Embodiments 1 to 34, or a pharmaceutically acceptable salt thereof, wherein $R^B$ is thiophen-2-yl optionally substituted with 1 to 3 $R^5$ groups independently selected from Cl, F, —OCH$_3$, methyl and —CN.

Embodiment 57. The compound of Formula (I), or according to any one of Embodiments 1 to 34, or a pharmaceutically acceptable salt thereof, wherein $R^B$ is cyclohexyl optionally substituted with 1 to 3 $R^5$ groups independently selected from C, F, —OCH$_3$, methyl and —CN.

Embodiment 58. The compound of Formula (I), or according to any one of Embodiments 1 to 34, or a pharmaceutically acceptable salt thereof, wherein $R^B$ is phenyl optionally substituted with 1 to 3 $R^5$ groups independently selected from C, F, —OCH$_3$, methyl and —CN.

Embodiment 59. The compound of Formula (I), or according to any one of Embodiments 1 to 34, or a pharmaceutically acceptable salt thereof, wherein $R^B$ is selected from phenyl, pyridinyl, thiophenyl and cyclohexyl, each of which is optionally substituted with 1 to 2 $R^5$ groups independently selected from halo, $C_1$-$C_3$alkoxy, $C_1$-$C_3$alkyl and —CN.

Embodiment 60. The compound of Formula (I), or according to any one of Embodiments 1 to 34, or a pharmaceutically acceptable salt thereof, wherein $R^B$ is pyridine-3-yl optionally substituted with 1 to 2 $R^5$ groups.

Embodiment 61. The compound of Formula (I), or according to any one of Embodiments 1 to 34, or a pharmaceutically acceptable salt thereof, wherein $R^B$ is pyridine-2-yl optionally substituted with 1 to 2 $R^5$ groups independently selected from halo, $C_1$-$C_3$alkoxy, $C_1$-$C_3$alkyl and —CN.

Embodiment 62. The compound of Formula (I), or according to any one of Embodiments 1 to 34, or a pharmaceutically acceptable salt thereof, wherein $R^B$ is thiophenyl optionally substituted with 1 to 2 $R^5$ groups independently selected from halo, $C_1$-$C_3$alkoxy, $C_1$-$C_3$alkyl and —CN.

Embodiment 63. The compound of Formula (I), or according to any one of Embodiments 1 to 34, or a pharmaceutically acceptable salt thereof, wherein $R^B$ is thiophen-2-yl optionally substituted with 1 to 2 $R^5$ groups independently selected from halo, $C_1$-$C_3$alkoxy, $C_1$-$C_3$alkyl and —CN.

Embodiment 64. The compound of Formula (I), or according to any one of Embodiments 1 to 34, or a pharmaceutically acceptable salt thereof, wherein $R^B$ is cyclohexyl optionally substituted with 1 to 2 $R^5$ groups independently selected from halo, $C_1$-$C_3$alkoxy, $C_1$-$C_3$alkyl and —CN.

Embodiment 65. The compound of Formula (I), or according to any one of Embodiments 1 to 34, or a pharmaceutically acceptable salt thereof, wherein $R^B$ is phenyl optionally substituted with 1 to 2 $R^5$ groups independently selected from halo, $C_1$-$C_3$alkoxy, $C_1$-$C_3$alkyl and —CN.

Embodiment 66. The compound of Formula (I), or according to any one of Embodiments 1 to 34, or a pharmaceutically acceptable salt thereof, wherein $R^B$ is pyridine-2-yl optionally substituted with 1 to 2 $R^5$ groups independently selected from C, F, —OCH$_3$, methyl and —CN.

Embodiment 67. The compound of Formula (I), or according to any one of Embodiments 1 to 34, or a pharmaceutically acceptable salt thereof, wherein $R^B$ is thiophenyl optionally substituted with 1 to 2 $R^5$ groups independently selected from C, F, —OCH$_3$, methyl and —CN.

Embodiment 68. The compound of Formula (I), or according to any one of Embodiments 1 to 34, or a pharmaceutically acceptable salt thereof, wherein $R^B$ is thiophen-2-yl optionally substituted with 1 to 2 $R^5$ groups independently selected from C, F, —OCH$_3$, methyl and —CN.

Embodiment 69. The compound of Formula (I), or according to any one of Embodiments 1 to 34, or a pharmaceutically acceptable salt thereof, wherein $R^B$ is cyclohexyl optionally substituted with 1 to 2 $R^5$ groups independently selected from Cl, F, —OCH$_3$, methyl and —CN.

Embodiment 70. The compound of Formula (I), or according to any one of Embodiments 1 to 34, or a pharmaceutically acceptable salt thereof, wherein $R^B$ is phenyl optionally substituted with 1 to 2 $R^5$ groups independently selected from Cl, F, —OCH$_3$, methyl and —CN.

Embodiment 71. The compound of any one of Embodiments 38, 45, 46, 52, 53, 58, 59, 65 or 70, or a pharmaceutically acceptable salt thereof, wherein the substituents on the phenyl ring $R^B$ are at the meta and/or para positions of the phenyl ring.

Embodiment 72. The compound of any one of Embodiments 1-34, 38, 45, 46, 52, 53, 58, 59, 65 or 70, or a pharmaceutically acceptable salt thereof, wherein $R^B$ is selected from:

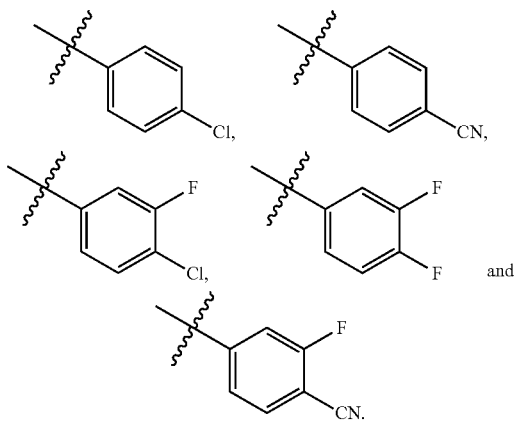

Embodiment 73. The compound of any one of Embodiments 1-34, 38, 45, 46, 52, 53, 58, 59, 65 or 70, or a pharmaceutically acceptable salt thereof, wherein $R^B$ is selected from:

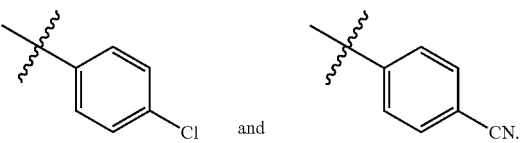 [SMILES: *c1ccc(Cl)cc1 ; *c1ccc(C#N)cc1]

Embodiment 74. The compound of Formula (I), or according to any one of Embodiments 1 to 73, or a pharmaceutically acceptable salt thereof, wherein $R^1$ is H.

Embodiment 75. The compound of Formula (I), or according to any one of Embodiments 1 to 73, or a pharmaceutically acceptable salt thereof, wherein $R^1$ is $C_1$-$C_3$alkyl.

Embodiment 76. The compound of Formula (I), or according to any one of Embodiments 1 to 73, or a pharmaceutically acceptable salt thereof, wherein $R^1$ is methyl.

Embodiment 77. The compound of Formula (I), or according to any one of Embodiments 1 to 73, or a pharmaceutically acceptable salt thereof, wherein $R^1$ is $C_1$-$C_3$alkyl substituted with 1 to 3 —OH groups.

Embodiment 78. The compound of Formula (I), or according to any one of Embodiments 1 to 73, or a pharmaceutically acceptable salt thereof, wherein $R^1$ is —CH$_2$OH.

Embodiment 79. The compound of Formula (I) or according to any one of Embodiments 1 to 78, or a pharmaceutically acceptable salt thereof, wherein $R^2$ is H.

Embodiment 80. The compound of Formula (I), or according to any one of Embodiments 1 to 78, or a pharmaceutically acceptable salt thereof, wherein $R^2$ is $C_1$-$C_3$alkyl.

Embodiment 81. The compound of Formula (I), or according to any one of Embodiments 1 to 78, or a pharmaceutically acceptable salt thereof, wherein $R^2$ is methyl.

Embodiment 82. The compound of Formula (I), or according to any one of Embodiments 1 to 78, or a pharmaceutically acceptable salt thereof, wherein $R^2$ is $C_1$-$C_3$alkyl substituted with 1 to 3 —OH groups.

Embodiment 83. The compound of Formula (I), or according to any one of Embodiments 1 to 78, or a pharmaceutically acceptable salt thereof, wherein $R^2$ is —CH$_2$OH.

Embodiment 84. The compound of Formula (I), or according to any one of Embodiments 1 to 83, or a pharmaceutically acceptable salt thereof, wherein each $R^3$ is independently selected from halo, CN, $C_1$-$C_3$alkoxy, $C_1$-$C_3$alkyl, C(=O)OR$^{10}$, and C(=O)NR$^{13}$R$^{14}$.

Embodiment 85. The compound of Formula (I), or according to any one of Embodiments 1 to 83, or a pharmaceutically acceptable salt thereof, wherein each $R^3$ is independently selected from halo, CN, $C_1$-$C_3$alkoxy and $C_1$-$C_3$alkyl.

Embodiment 86. The compound of Formula (I), or according to any one of Embodiments 1 to 83, or a pharmaceutically acceptable salt thereof, wherein each $R^3$ is independently selected from Cl, F, CN, —OCH$_3$ and methyl.

Embodiment 87. The compound of Formula (I), or according to any one of Embodiments 1 to 83, or a pharmaceutically acceptable salt thereof, wherein $R^3$ is methyl.

Embodiment 88. The compound of Formula (I), or according to any one of Embodiments 1 to 83, or a pharmaceutically acceptable salt thereof, wherein $R^3$ is absent.

Embodiment 89. The compound of Formula (I), or according to any one of Embodiments 1 to 88, or a pharmaceutically acceptable salt thereof, wherein $R^4$ is H, $C_1$-$C_3$alkyl, $C_3$-$C_6$cycloalkyl or a $C_1$-$C_3$alkyl substituted with 1 to 2 groups independently selected from —OH, —C(=O)R$^{15}$ and R$^{10}$.

Embodiment 90. The compound of Formula (I), or according to any one of Embodiments 1 to 88, or a pharmaceutically acceptable salt thereof, wherein $R^4$ is H, methyl, cyclopropyl,

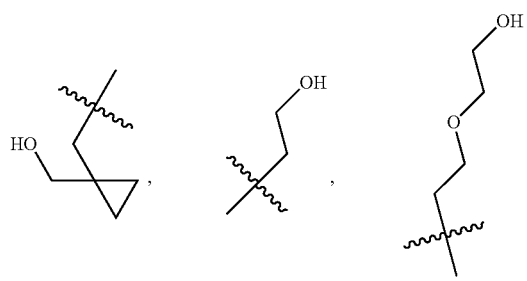

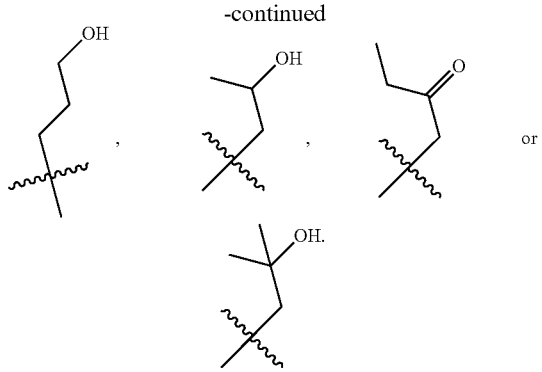

Embodiment 91. The compound of Formula (I), or according to any one of Embodiments 1 to 88, or a pharmaceutically acceptable salt thereof, wherein $R^4$ is H or $C_1$-$C_3$alkyl.

Embodiment 92. The compound of Formula (I), or according to any one of Embodiments 1 to 88, or a pharmaceutically acceptable salt thereof, wherein $R^4$ is H or methyl Embodiment 93. The compound of Formula (I) or according to any one of Embodiments 1 to 88, or a pharmaceutically acceptable salt thereof, wherein $R^4$ is H.

Embodiment 94. The compound of Formula (I) or according to any one of Embodiments 1 to 88, or a pharmaceutically acceptable salt thereof, wherein $R^4$ is methyl.

Embodiment 95. The compound of Formula (I), or according to any one of Embodiments 1 to 88, or a pharmaceutically acceptable salt thereof, wherein $R^4$ is a $C_1$-$C_3$alkyl substituted with 1 to 2 groups independently selected from —OH, —C(=O)R$^{15}$ and R$^{10}$.

Embodiment 96. The compound of Formula (I), or according to any one of Embodiments 1 to 88, or a pharmaceutically acceptable salt thereof, wherein $R^4$ is

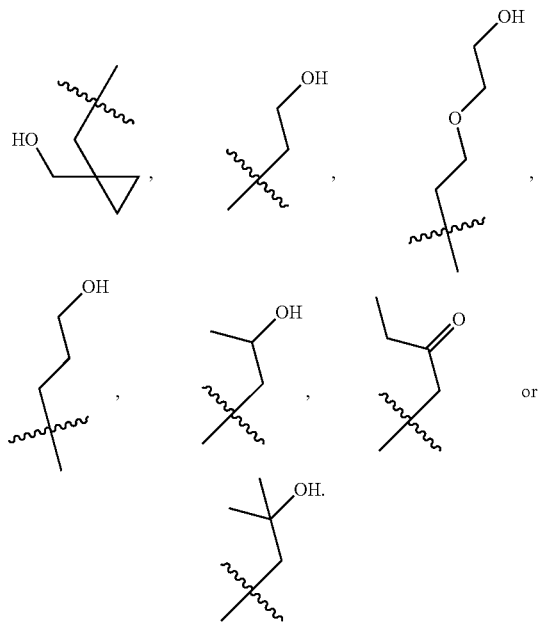

Embodiment 97. The compound of Formula (I), or according to any one of Embodiments 1 to 88, or a pharmaceutically acceptable salt thereof, wherein $R^4$ is $C_3$-$C_6$cycloalkyl.

Embodiment 98. The compound of Formula (I), or according to any one of Embodiments 1 to 87, or a pharmaceutically acceptable salt thereof, wherein $R^4$ is cyclopropyl.

Embodiment 99. The compound of Formula (I), or according to any one of Embodiments 1 to 98, or a pharmaceutically acceptable salt thereof, wherein each $R^5$ is independently selected from halo, —CN, hydroxy, —$NR^{13}R^{14}$, $C_3$-$C_6$cycloalkyl, $C_1$-$C_3$alkoxy, $C_1$-$C_3$ haloalkyl, and $C_1$-$C_3$alkyl optionally substituted with 1 to 3 $R^6$ groups, wherein two of said $C_1$-$C_3$alkyl optionally substituted with 1 to 3 $R^6$ groups, when directly attached to the same carbon atom, can be taken together with the carbon to which both are attached to form a 3-5 membered cycloalkyl ring optionally substituted with 1 to 3 $R^6$ groups.

Embodiment 100. The compound of Formula (I), or according to any one of Embodiments 1 to 98, or a pharmaceutically acceptable salt thereof, wherein each $R^5$ is independently selected from halo, —CN, $C_1$-$C_3$alkoxy, and $C_1$-$C_3$alkyl.

Embodiment 101. The compound of Formula (I), or according to any one of Embodiments 1 to 98, or a pharmaceutically acceptable salt thereof, wherein each $R^5$ is independently selected from Cl, F, —CN, —$OCH_3$ and methyl.

Embodiment 102. The compound of Formula (I), or according to any one of Embodiments 1 to 98, or a pharmaceutically acceptable salt thereof, wherein each $R^5$ is independently selected from $C_1$ and —CN.

Embodiment 103. The compound of Formula (I), or according to any one of Embodiments 1 to 102, or a pharmaceutically acceptable salt thereof, wherein each $R^6$ is independently selected at each occurrence from halo, hydroxy, CN, $C_1$-$C_3$alkoxy, $C_1$-$C_3$alkyl, and $C_3$-$C_5$cycloalkyl.

Embodiment 104. The compound of Formula (I), or according to any one of Embodiments 1 to 102, or a pharmaceutically acceptable salt thereof, wherein each $R^6$ is hydroxy.

Embodiment 105. The compound of Formula (I) or according to any one of Embodiments 1 to 104, or a pharmaceutically acceptable salt thereof, wherein
W is H, —OH, —OR, —C(=O)$NR^{13}R^{14}$, —C(=O)$OR^{13}$, —$NR^{13}R^{14}$, —$NR^{13}C$(=O)$OR^{10}$, —$NR^{13}C$(=O)$R^{10}$, —$SO_2R^{10}$, —$SO_2NR^{13}R^{14}$, —$NR^{13}SO_2R^{10}$, —P(=O)($OR^{13}$)$_2$, —S(=O)$R^{10}$, —S(=O)(=$NR^{13}$)$R^{10}$, —$CR^{11}R^{12}C$(=O)$NR^{13}R^{14}$, —$CR^{11}R^{12}C$(=O)$OR^{13}$, —$CR^{11}R^{12}NR^{13}R^{14}$, —$CR^{11}R^{12}NR^{13}C$(=O)$OR^{10}$, —$CR^{11}R^{12}NR^{13}C$(=O)$R^{10}$, —$CR^{11}R^{12}SO_2R^{10}$, —$CR^{11}R^{12}SO_2NR^{13}R^{14}$, —$CR^{11}R^{12}NR^{13}SO_2R^{10}$, —$CR^{11}R^{12}P$(=O)($OR^{13}$)$_2$, —$CR^{11}R^{12}S$(=O)$R^{10}$, —$CR^{11}R^{12}S$(=O)(=$NR^{13}$)$R^{10}$, a 3-6 membered cycloalkyl, phenyl, a 5-6-membered heterocycloalkyl containing one or two ring members independently selected from N, NH, $NR^{17}$, O or S, a 5-6-membered heterocyclyl containing one or two ring members independently selected from N, NH, $NR^{17}$, O or S, or a 5-membered heteroaryl having 1 to 4 heteroatoms selected from N, O and S as ring members that is optionally fused to phenyl,
wherein the 3-6 membered cycloalkyl, phenyl, 5-6-membered heterocycloalkyl, 5-6-membered heterocyclyl and 5-membered heteroaryl of W are each optionally substituted with 1 to 3 groups independently selected from $C_1$-$C_3$alkyl, oxo, halo, $C_1$-$C_3$haloalkyl, -$L^2$OH, -$L^2OR^{10}$, -$L^2OC$(=O)$NR^{13}R^{14}$, -$L^2SO_2R^{10}$, -$L^2SO_2NR^{13}R^{14}$, -$L^2SO_2NR^{13}R^{14}$, -$L^2SO_2N$=$CR^{13}NR^{13}R^{14}$, -$L^2SO_2NR^{13}C$(=O)$R^{10}$, -$L^2C$(=O)$NR^{13}SO_2R^{10}$, -$L^2S$(=O)$R^{10}$, -$L^2S$(=O)(=$NR^{13}$)$R^{10}$, -$L^2NR^{13}SO_2NR^{13}R^{14}$, -$L^2NR^{13}SO_2R^{10}$, -$L^2NR^{13}R^{14}$, -$L^2NR^{13}C$(=O)$R^{13}$, -$L^2NR^{13}C$(=O)$OR^{10}$, -$L^2C$(=O)$NR^{13}R^{14}$, and -$L^2C$(=O)$OR^{13}$ Embodiment 106. The compound of Formula (I) or according to any one of Embodiments 1 to 104, or a pharmaceutically acceptable salt thereof, wherein
W is H, —OH, —OR, —C(=O)$NR^{13}R^{14}$, —C(=O)$OR^{13}$, —$NR^{13}R^{14}$, —$NR^{13}C$(=O)$OR^{10}$, —$NR^{13}C$(=O)$R^{10}$, —$SO_2R^{10}$, —$SO_2NR^{13}R^{14}$, —$NR^{13}SO_2R^{10}$, —P(=O)($OR^{13}$)$_2$, —S(=O)$R^{10}$, —S(=O)(=$NR^{13}$)$R^{10}$, —$CR^{11}R^{12}C$(=O)$NR^{13}R^{14}$, —$CR^{11}R^{12}C$(=O)$OR^{13}$, —$CR^{11}R^{12}NR^{13}R^{14}$, —$CR^{11}R^{12}NR^{13}C$(=O)$OR^{10}$, —$CR^{11}R^{12}NR^{13}C$(=O)$R^{10}$, —$CR^{11}R^{12}SO_2R^{10}$, —$CR^{11}R^{12}SO_2NR^{13}R^{14}$, —$CR^{11}R^{12}NR^{13}SO_2R^{10}$, —$CR^{11}R^{12}P$(=O)($OR^{13}$)$_2$, —$CR^{11}R^{12}S$(=O)$R^{10}$ or —$CR^{11}R^{12}S$(=O)(=$NR^{13}$)$R^{10}$.

Embodiment 107. The compound of Formula (I) or according to any one of Embodiments 1 to 104, or a pharmaceutically acceptable salt thereof, wherein
W is a 3-6 membered cycloalkyl, phenyl, a 5-6-membered heterocycloalkyl containing one or two ring members independently selected from N, NH, $NR^{17}$, O or S, a 5-6-membered heterocyclyl containing one or two ring members independently selected from N, NH, $NR^{17}$, O or S, or a 5-membered heteroaryl having 1 to 4 heteroatoms selected from N, O and S as ring members that is optionally fused to phenyl,
wherein the 3-6 membered cycloalkyl, phenyl, 5-6-membered heterocycloalkyl, 5-6-membered heterocyclyl and 5-membered heteroaryl of W are each optionally substituted with 1 to 3 groups independently selected from $C_1$-$C_3$alkyl, oxo, halo, $C_1$-$C_3$haloalkyl, -$L^2$OH, -$L^2OR^{10}$, -$L^2OC$(=O)$NR^{13}R^{14}$, -$L^2SO_2R^{10}$, -$L^2SO_2NR^{13}R^{14}$, -$L^2SO_2N$=$CR^{13}NR^{13}R^{14}$, -$L^2SO_2NR^{13}C$(=O)$R^{10}$, -$L^2C$(=O)$NR^{13}SO_2R^{10}$, -$L^2S$(=O)$R^{10}$, -$L^2S$(=O)(=$NR^{13}$)$R^{10}$, -$L^2NR^{13}SO_2NR^{13}R^{14}$, -$L^2NR^{13}SO_2R^{10}$, -$L^2NR^{13}R^{14}$, -$L^2NR^{13}C$(=O)$R^{13}$, -$L^2NR^{13}C$(=O)$OR^{10}$, -$L^2C$(=O)$NR^{13}R^{14}$, and -$L^2C$(=O)$OR^{13}$ Embodiment 108. The compound of Formula (I) or according to any one of Embodiments 1 to 104, or a pharmaceutically acceptable salt thereof, wherein
W is a 3-6 membered cycloalkyl optionally substituted with 1 to 3 groups independently selected from $C_1$-$C_3$alkyl, oxo, halo, $C_1$-$C_3$haloalkyl, -$L^2$OH, -$L^2OR^{10}$, -$L^2OC$(=O)$NR^{13}R^{14}$, -$L^2SO_2R^{10}$, -$L^2SO_2NR^{13}R^{14}$, -$L^2SO_2NR^{13}R^{14}$, -$L^2SO_2N$=$CR^{13}NR^{13}R^{14}$, -$L^2SO_2NR^{13}C$(=O)$R^{10}$, -$L^2C$(=O)$NR^{13}SO_2R^{10}$, -$L^2S$(=O)$R^{10}$, -$L^2S$(=O)(=$NR^{13}$)$R^{10}$, -$L^2NR^{13}SO_2NR^{13}R^{14}$, -$L^2NR^{13}SO_2R^{10}$, -$L^2NR^{13}R^{14}$, -$L^2NR^{13}C$(=O)$R^{13}$, -$L^2NR^{13}C$(=O)$OR^{10}$, -$L^2C$(=O)$NR^{13}R^{14}$, and -$L^2C$(=O)$OR^{13}$ Embodiment 109. The compound of Formula (I) or according to any one of Embodiments 1 to 104, or a pharmaceutically acceptable salt thereof, wherein
W is cyclopropyl substituted with —$O_2R^{10}$, —$SO_2NR^{14}R^{10}$, —$SO_2NR^{13}R^{14}$, or —$SO_2N$=$CR^{13}NR^{13}R^{14}$, —$SO_2NR^{13}C$(=O)$R^{10}$, —C(=O)$NR^{13}SO_2R^{10}$, —S(=O)$R^{10}$, —S(=O)(=$NR^{13}$)$R^{10}$, —$NR^{13}SO_2NR^{13}R^{14}$, —$NR^{13}SO_2R^{10}$, —NR$^{13}$R$^{14}$, —NR$^{13}$C(=O)R$^{13}$, —NR$^{13}$C(=O)OR$^{10}$, —C(=O)NR$^{13}$R$^{14}$, and —C(=O)OR$^{13}$.

Embodiment 110. The compound of Formula (I) or according to any one of Embodiments 1 to 104, or a pharmaceutically acceptable salt thereof, wherein W is cyclopropyl substituted with —SO$_2$R$^{10}$, —SO$_2$NR$^{14}$R$^{10}$, —SO$_2$NR$^{13}$R$^{14}$, or —SO$_2$N=CR$^{13}$NR$^{13}$R$^{14}$.

Embodiment 111. The compound of Formula (I) or according to any one of Embodiments 1 to 104, or a pharmaceutically acceptable salt thereof, wherein the moiety W-L- is selected from:

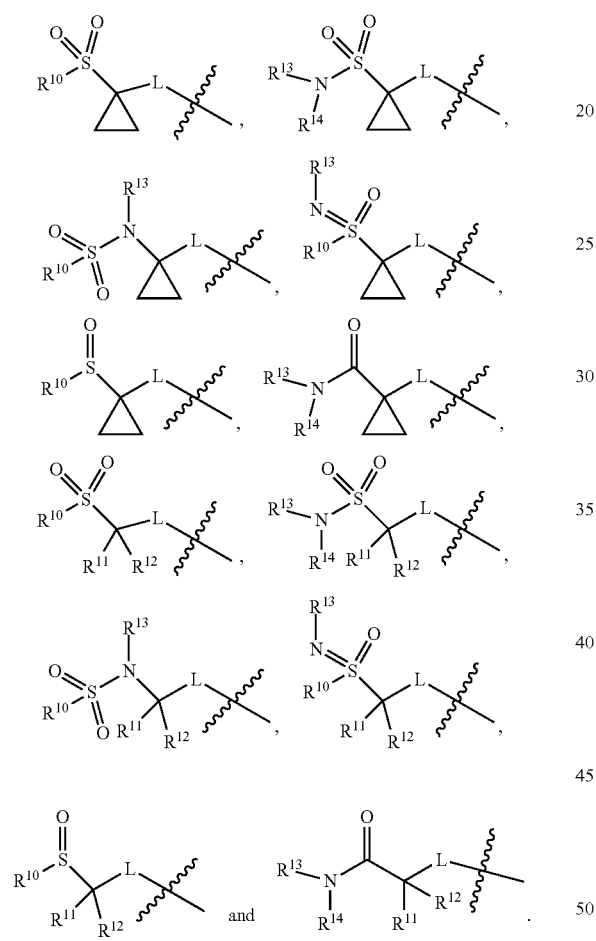

Embodiment 112. The compound of Formula (I) or according to any one of Embodiments 1 to 104, or a pharmaceutically acceptable salt thereof, wherein W is selected from

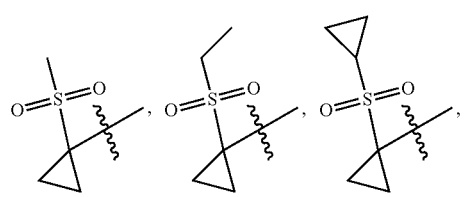

-continued

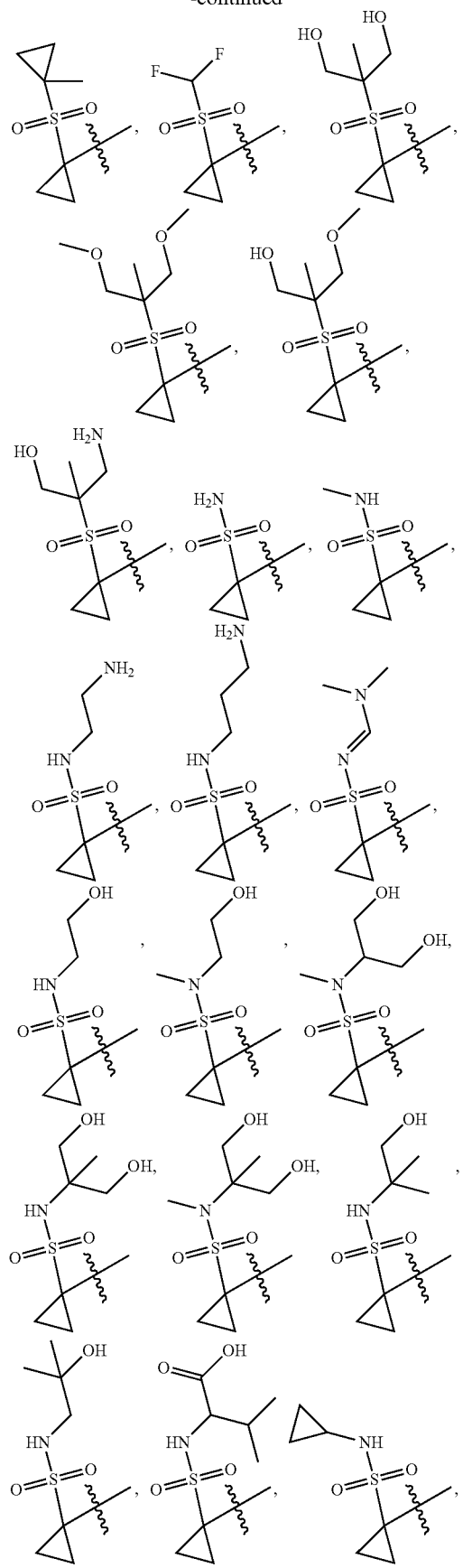

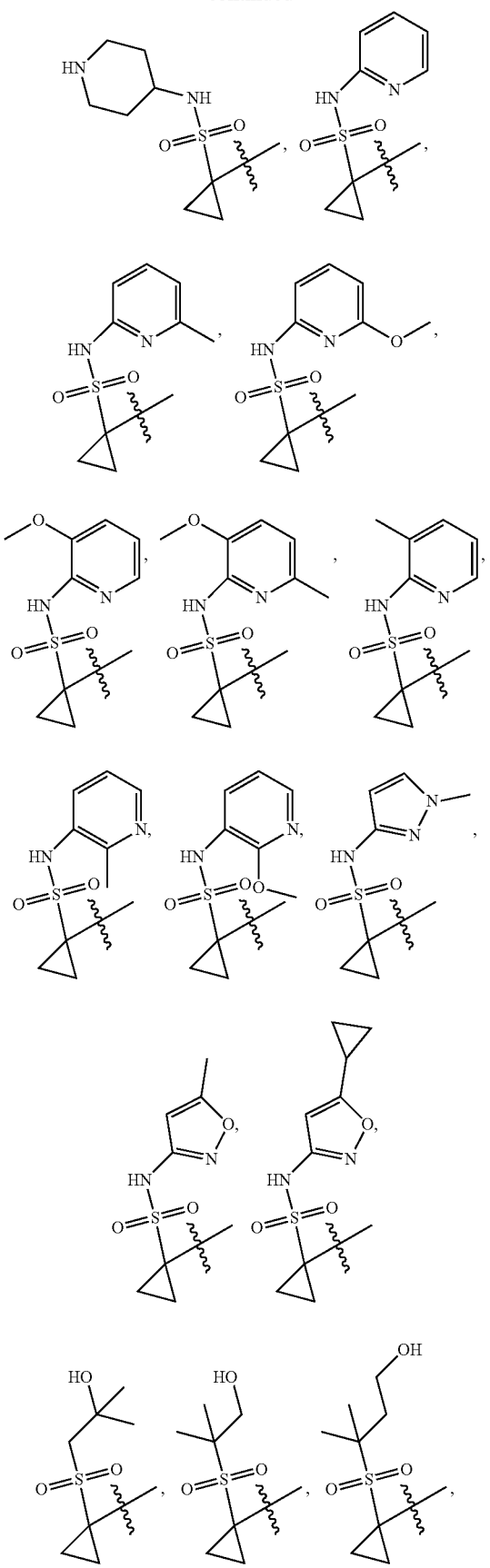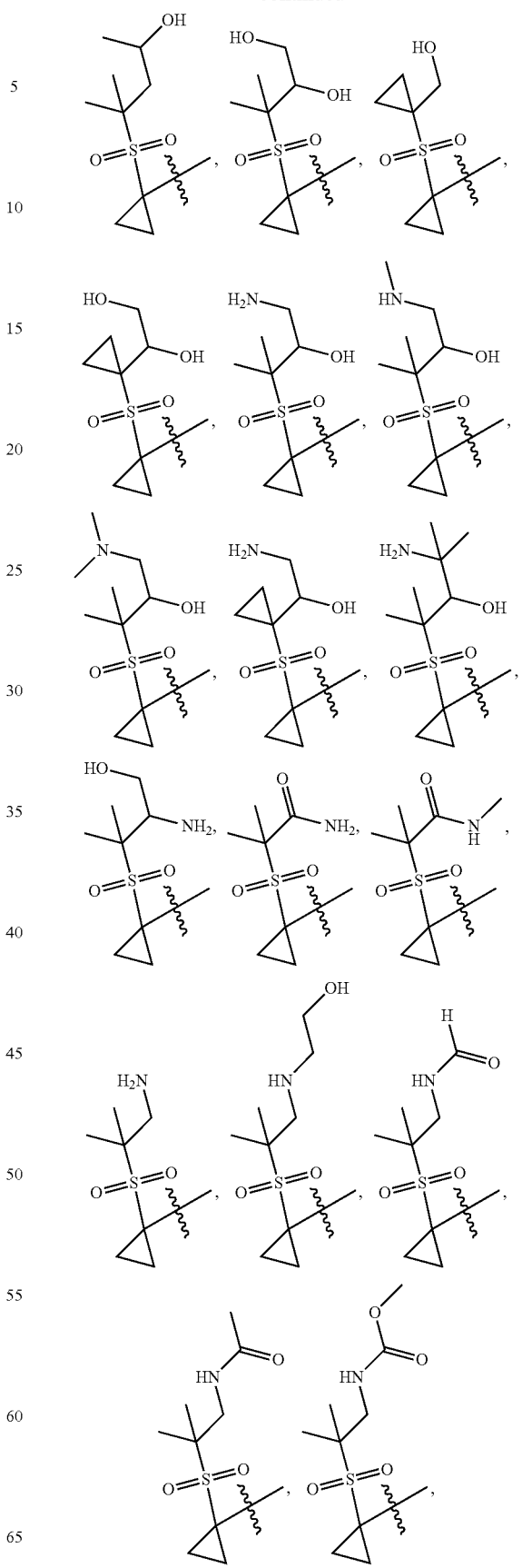

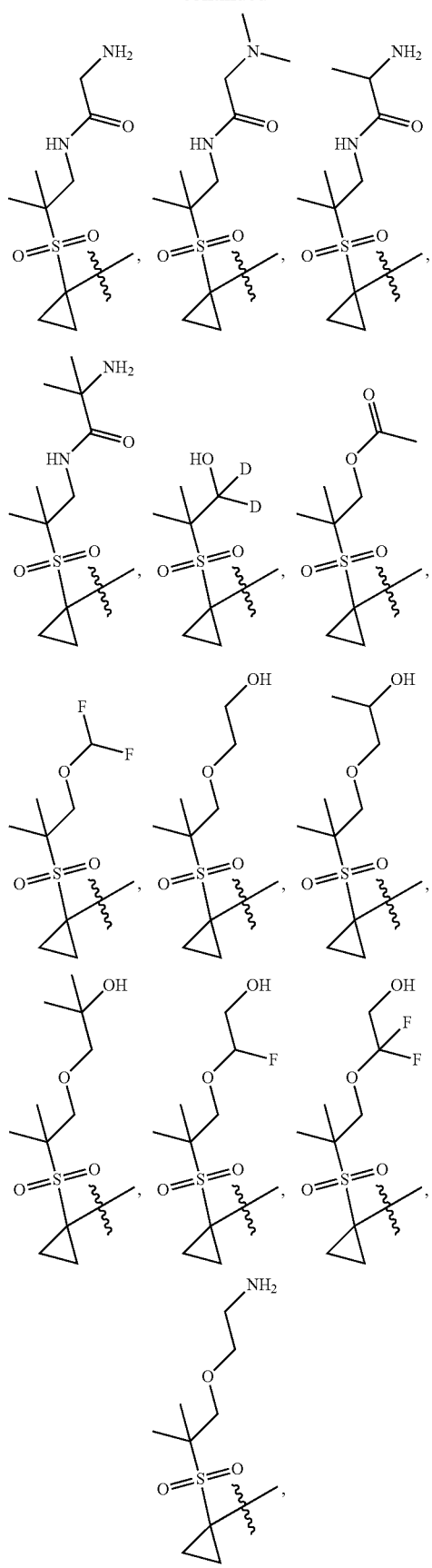
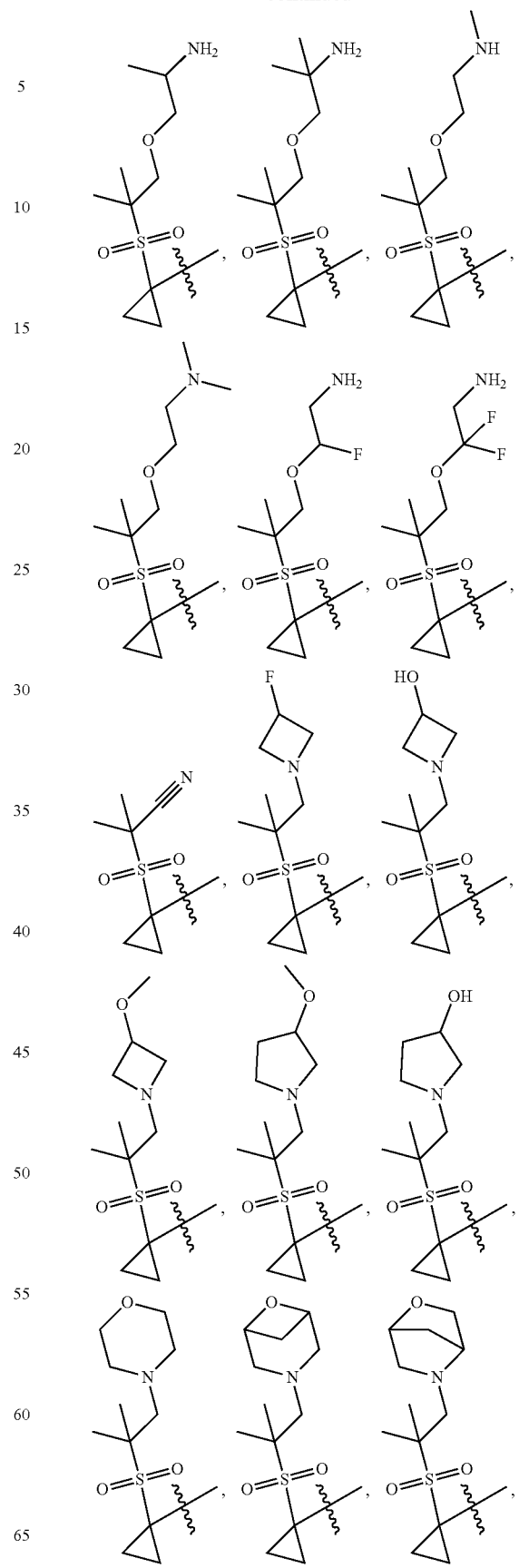

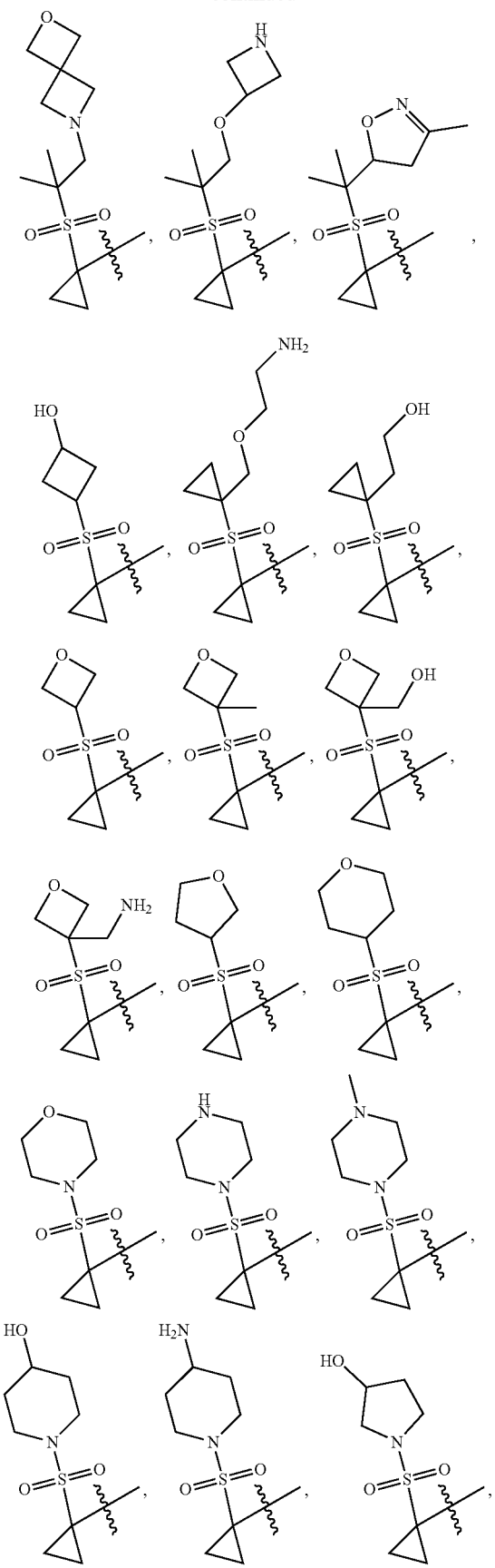

Embodiment 113. The compound of Formula (I), or according to any one of Embodiments 1 to 112, or a pharmaceutically acceptable salt thereof, wherein $R^{10}$ is selected from $C_1$-$C_4$alkyl, $C_1$-$C_3$haloalkyl, 3-6 membered cycloalkyl, phenyl, 5-6 membered heteroaryl having 1 to 4 heteroatoms independently selected from N, O and S as ring members, 4-6 membered heterocycloalkyl containing one or two ring members independently selected from N, NH, $NR^{17}$, O or S and 4-6 membered heterocyclyl containing 1 to 2 ring members independently selected from N, NH, $NR^{17}$, O or S, wherein each $R^{10}$ is optionally substituted with 1 to 5 groups independently selected from $C_1$-$C_4$alkyl, deuterium, $C_1$-$C_4$haloalkoxy, —OH, —CN, —OC(=O)$R^{14}$, -$L^3OR^{13}$, $C_1$-$C_2$haloalkyl, oxo, -halo, —$C_1$-$C_3$alkoxy, —OC(=O)$NR^{13}R^{14}$, —$SO_2R^{13}$, —$SO_2NR^{13}R^{14}$, —$SO_2NR^{13}$C(=O)$R^{13}$, —C(=O)$NR^{13}SO_2R^{13}$, —S(=O)$R^{13}$, —S(=O)(=$NR^{14}$)$R^{13}$, —$NR^{13}SO_2NR^{13}R^{14}$, —$NR^{13}SO_2R^{13}$, —$NR^{13}R^{14}$, —$NR^{14}$C(=O)$R^{13}$, —$NR^{14}$C(=O)$OR^{13}$, —C(=O)$NR^{13}R^{14}$, —C(=O)$OR^{13}$, -(4-7-membered heterocyclyl containing one to 2 two heteroatoms independently selected from N, O or S as ring members), —$C_3$-$C_5$cycloalkyl, and -(5-6 membered heteroaryl ring having 1 to 4 heteroatoms comprising 1-4 nitrogen atoms, 0 or 1 oxygen atoms, and 0 or 1 sulfur atoms as ring members), where the $C_1$-$C_4$alkyl, 4-7-membered heterocycloalkyl, 4-7-membered heterocyclyl, $C_3$-$C_5$cycloalkyl and 5-6 membered heteroaryl ring are each optionally further substituted with 1 to 3 groups independently selected from halo, $C_1$-$C_3$alkyl, $C_1$-$C_3$haloalkyl, -$L^4OR^{13}$, -$L^4CN$, and -$L^4NR^{13}R^{14}$.

Embodiment 114. The compound of Formula (I), or according to any one of Embodiments 1 to 112, or a pharmaceutically acceptable salt thereof, wherein $R^{10}$ is selected from $C_1$-$C_4$alkyl, $C_1$-$C_3$haloalkyl, 3-6 membered cycloalkyl, 5-6 membered heteroaryl having 1 to 4 heteroatoms independently selected from N, O and S as ring members, 4-6 membered heterocycloalkyl containing one or two ring members independently selected from N, NH, $NR^{17}$, O or S and 4-6 membered heterocyclyl containing 1 to 2 ring members independently selected from N, NH, $NR^{17}$, O or S, wherein each $R^{10}$ is optionally substituted with 1 to 5 groups independently selected from $C_1$-$C_4$alkyl, deuterium, $C_1$-$C_4$haloalkoxy, —OH, —CN, —OC(=O)$R^{14}$, -$L^3OR^{13}$, —$NR^{13}R^{14}$, —$NR^{14}C$(=O)$R^{13}$, —$NR^{14}C$(=O)$OR^{13}$, —C(=O)$NR^{13}R^{14}$, —C(=O)$OR^{13}$, (4-7-membered heterocycloalkyl containing 1 to 2 ring members independently selected from N, NH, $NR^{17}$, O or S), -(4-7-membered heterocyclyl containing 1 to 2 ring members independently selected from N, NH, $NR^{17}$, O or S), and —$C_3$-$C_5$cycloalkyl, where the $C_1$-$C_4$alkyl, 4-7-membered heterocycloalkyl, 4-7-membered heterocyclyl and $C_3$-$C_5$cycloalkyl are each optionally further substituted with 1 to 3 groups independently selected from halo, —$OR^{13}$, —CN, and —$NR^{13}R^{14}$.

Embodiment 115. The compound of Formula (I), or according to any one of Embodiments 1 to 110, or a pharmaceutically acceptable salt thereof, wherein $R^{10}$ is selected from methyl, ethyl, propyl, isopropyl, butyl, isobutyl, pentyl, cyclopropyl, cyclobutyl, pyridinyl, pyrazolyl, isoxazolyl, oxetanyl, tetrahydrofuranyl, tetrahydropyranyl, morpholinyl, piperidinyl, piperazinyl, pyrrolidinyl and azetidinyl, wherein each $R^{10}$ is optionally substituted with 1 to 4 groups independently selected from methyl, ethyl, deuterium, —$OCH_3$, —OH, —$OCHF_2$, —CN, —$NH_2$, —$NHCH_3$, —$N(CH_3)_2$, —$NHR^{13}$, —NHCH(=O), —NHC(=O)$CH_3$, —NHC(=O)$OCH_3$, —NHC(=O)$CH_2NH_2$, —NHC(=O)$CH_2N(CH_3)_2$, —NHC(=O)CH($CH_3$)$NH_2$, —NHC(=O)C($CH_3$)$_2NH_2$, —$OCH_2CH_2OH$, —$OCH_2CH(CH_3)$OH, —$OCH_2CH(CH_3)_2$OH, —OCH(F)$CH_2$OH, —$OCF_2CH_2$OH, —$OCH_2CH_2NH_2$, —$OCH_2$CH($CH_3$)$NH_2$, —$OCH_2C(CH_3)_2NH_2$, —$OCH_2CH_2$$NHCH_3$, —$OCH_2CH_2N(CH_3)_2$, —OCH(F)$CH_2NH_2$, —$OCF_2CH_2NH_2$, —$CH_2OCH_2CH_2NH_2$, —$CH_2CH_2OH$, —$CH_2OH$, —$CH_2NH_2$, —O-azetidinyl, —C(=O)$NH_2$, —C(=O)$NHCH_3$, —OC(=O)$CH_3$, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl, where the methyl, ethyl, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl are each optionally further substituted with 1 to 3 groups independently selected from F, —OH, —$OCH_3$, —$NH_2$ and methyl.

Embodiment 116. The compound of Formula (I), or according to any one of Embodiments 1 to 112, or a pharmaceutically acceptable salt thereof, wherein $R^{10}$ is selected from methyl, ethyl, propyl, isopropyl, butyl, isobutyl and pentyl, wherein each $R^{10}$ is optionally substituted with 1 to 4 groups independently selected from methyl, ethyl, deuterium, —$OCH_3$, —OH, —$OCHF_2$, —CN, —$NH_2$, —$NHCH_3$, —$N(CH_3)_2$, —$NHR^{13}$, —NHCH(=O), —NHC(=O)$CH_3$, —NHC(=O)$OCH_3$, —NHC(=O)$CH_2NH_2$, —NHC(=O)$CH_2N(CH_3)_2$, —NHC(=O)CH($CH_3$)$NH_2$, —NHC(=O)C($CH_3$)$_2NH_2$, —$OCH_2CH_2OH$, —$OCH_2CH(CH_3)$OH, —$OCH_2CH(CH_3)_2$OH, —OCH(F)$CH_2$OH, —$OCF_2CH_2$OH, —$OCH_2CH_2NH_2$, —$OCH_2CH(CH_3)NH_2$, —$OCH_2C(CH_3)_2NH_2$, —$OCH_2CH_2NHCH_3$, —$OCH_2CH_2N(CH_3)_2$, —OCH(F)$CH_2NH_2$, —$OCF_2CH_2NH_2$, —$CH_2OCH_2CH_2NH_2$, —$CH_2CH_2OH$, —$CH_2OH$, —$CH_2NH_2$, —O-azetidinyl, —C(=O)$NH_2$, —C(=O)$NHCH_3$, —OC(=O)$CH_3$, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl, where the methyl, ethyl, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl are each optionally further substituted with 1 to 3 groups independently selected from F, —OH, —$OCH_3$, —$NH_2$ and methyl.

Embodiment 117. The compound of Formula (I), or according to any one of Embodiments 1 to 112, or a pharmaceutically acceptable salt thereof, wherein $R^{10}$ is selected from cyclopropyl and cyclobutyl, wherein each $R^{10}$ is optionally substituted with 1 to 4 groups independently selected from methyl, ethyl, deuterium, —$OCH_3$, —OH, —$OCHF_2$, —CN, —$NH_2$, —$NHCH_3$, —$N(CH_3)_2$, —$NHR^{13}$, —NHCH(=O), —NHC(=O)$CH_3$, —NHC(=O)$OCH_3$, —NHC(=O)$CH_2NH_2$, —NHC(=O)$CH_2N(CH_3)_2$, —NHC(=O)CH($CH_3$)$NH_2$, —NHC(=O)C($CH_3$)$_2NH_2$, —$OCH_2CH_2OH$, —$OCH_2CH(CH_3)$OH, —$OCH_2CH(CH_3)_2$OH, —OCH(F)$CH_2$OH, —$OCF_2CH_2$OH, —$OCH_2CH_2NH_2$, —$OCH_2$CH($CH_3$)$NH_2$, —$OCH_2C(CH_3)_2NH_2$, —$OCH_2CH_2$$NHCH_3$, —$OCH_2CH_2N(CH_3)_2$, —OCH(F)$CH_2NH_2$, —$OCF_2CH_2NH_2$, —$CH_2OCH_2CH_2NH_2$, —$CH_2CH_2OH$, —$CH_2OH$, —$CH_2NH_2$, —O-azetidinyl, —C(=O)$NH_2$, —C(=O)$NHCH_3$, —OC(=O)$CH_3$, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl, where the methyl, ethyl, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl are each optionally further substituted with 1 to 3 groups independently selected from F, —OH, —$OCH_3$, —$NH_2$ and methyl.

Embodiment 118. The compound of Formula (I), or according to any one of Embodiments 1 to 112, or a pharmaceutically acceptable salt thereof, wherein $R^{10}$ is selected from pyridinyl, pyrazolyl and isoxazolyl, wherein each $R^{10}$ is optionally substituted with 1 to 4 groups independently selected from methyl, ethyl, deuterium, —$OCH_3$, —OH, —$OCHF_2$, —CN, —$NH_2$, —$NHCH_3$, —$N(CH_3)_2$, —$NHR^{13}$, —NHCH(=O), —NHC(=O)$CH_3$, —NHC(=O)$OCH_3$, —NHC(=O)$CH_2NH_2$, —NHC(=O)$CH_2N(CH_3)_2$, —NHC(=O)CH($CH_3$)$NH_2$, —NHC(=O)C($CH_3$)$_2NH_2$, —$OCH_2CH_2OH$, —$OCH_2CH(CH_3)$OH, —$OCH_2CH(CH_3)_2$OH, —OCH(F)$CH_2$OH, —$OCF_2CH_2$OH, —$OCH_2CH_2NH_2$, —$OCH_2$CH($CH_3$)$NH_2$, —$OCH_2C(CH_3)_2NH_2$, —$OCH_2CH_2$$NHCH_3$, —$OCH_2CH_2N(CH_3)_2$, —OCH(F)$CH_2NH_2$, —$OCF_2CH_2NH_2$, —$CH_2OCH_2CH_2NH_2$, —$CH_2CH_2OH$, —$CH_2OH$, —$CH_2NH_2$, —O-azetidinyl, —C(=O)$NH_2$, —C(=O)$NHCH_3$, —OC(=O)$CH_3$, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl, where the methyl, ethyl, cyclopropyl, azetidinyl, pyrrolidinyl, morpholinyl, 6-oxa-3-azabicyclo

[3.1.1]heptanyl, 2-oxa-5-azabicyclo[2.2.1]heptanyl, 2-oxa-6-azaspiro[3.3]heptanyl and 4,5-dihydroisoxazolyl are each optionally further substituted with 1 to 3 groups independently selected from F, —OH, —OCH₃, —NH₂ and methyl.

Embodiment 119. The compound of Formula (I), or according to any one of Embodiments 1 to 112, or a pharmaceutically acceptable salt thereof, wherein R¹⁰ is selected from oxetanyl, tetrahydrofuranyl, tetrahydropyranyl, morpholinyl, piperidinyl, piperazinyl, pyrrolidinyl and azetidinyl, wherein each R¹⁰ is optionally substituted with 1 to 4 groups independently selected from methyl, ethyl, deuterium, —OCH₃, —OH, —OCHF₂, —CN, —NH₂, —NHCH₃, —N(CH₃)₂, —NHR¹³, —NHCH(=O), —NHC(=O)CH₃, —NHC(=O)OCH₃, —NHC(=O)CH₂NH₂, —NHC(=O)CH₂N(CH₃)₂, —NHC(=O)CH(CH₃)NH₂, —NHC(=O)C(CH₃)₂NH₂, —OCH₂CH₂OH, —OCH₂CH(CH₃)OH, —OCH₂CH(CH₃)₂OH, —OCH(F)CH₂OH, —OCF₂CH₂OH, —OCH₂CH₂NH₂, —OCH₂CH(CH₃)NH₂, —OCH₂C(CH₃)₂NH₂, —OCH₂CH₂NHCH₃, —OCH₂CH₂N(CH₃)₂, —OCH(F)CH₂NH₂, —OCF₂CH₂NH₂, —CH₂OCH₂CH₂NH₂, —CH₂CH₂OH, —CH₂OH, —CH₂NH₂, —O-azetidinyl, —C(=O)NH₂, —C(=O)NHCH₃, —OC(=O)CH₃, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl, where the methyl, ethyl, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl are each optionally further substituted with 1 to 3 groups independently selected from F, —OH, —OCH₃, —NH₂ and methyl.

Embodiment 120. The compound of Formula (I), or according to any one of Embodiments 1 to 112, or a pharmaceutically acceptable salt thereof, wherein R¹⁰ is selected from

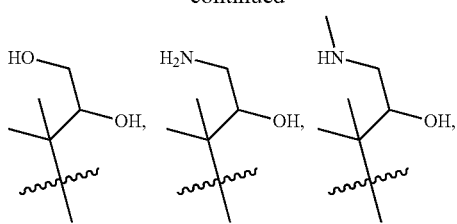

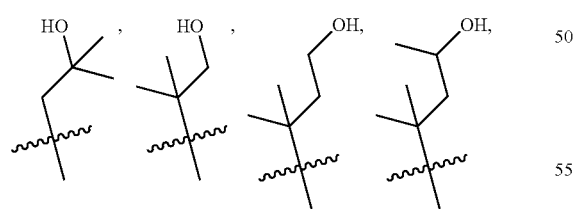

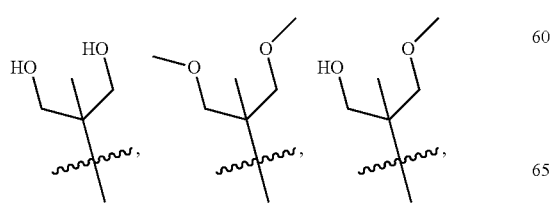

-continued

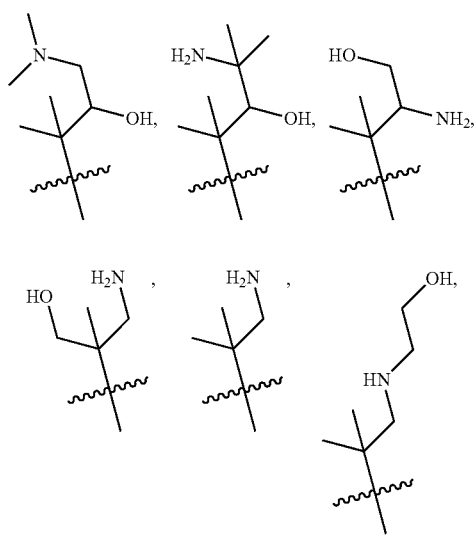

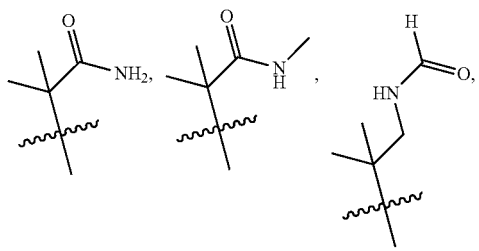

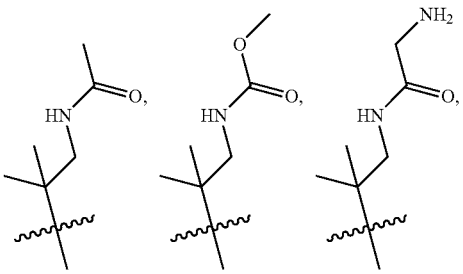

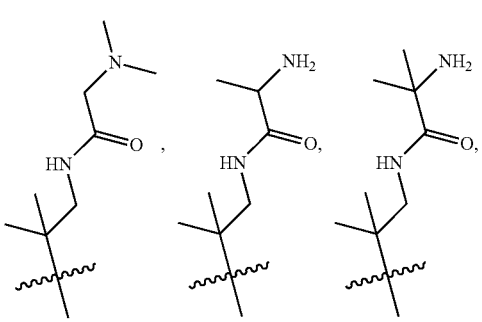

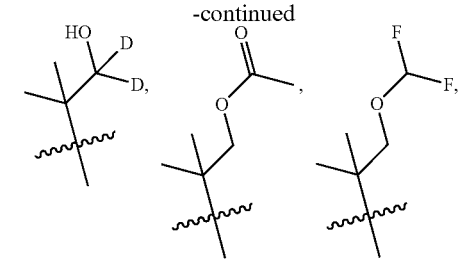
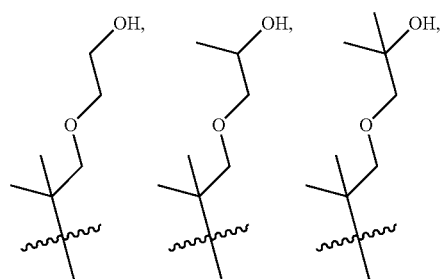
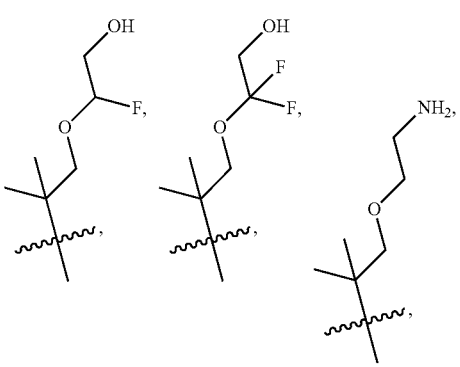
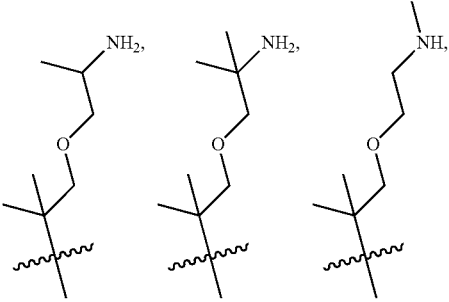
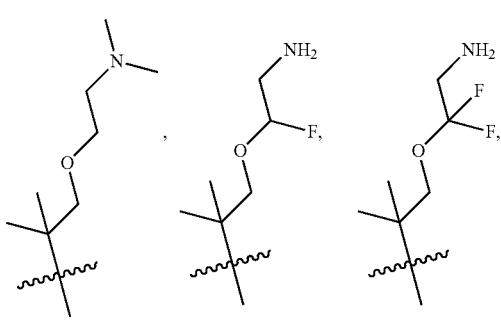
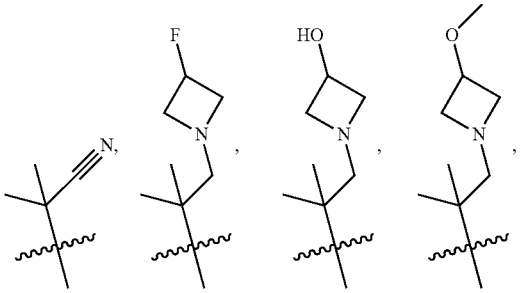
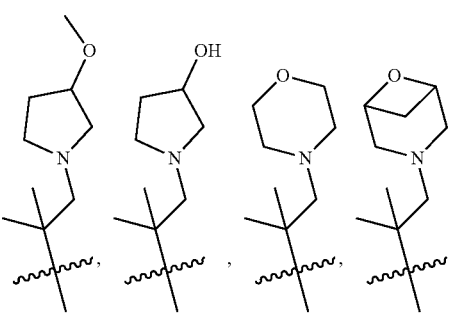
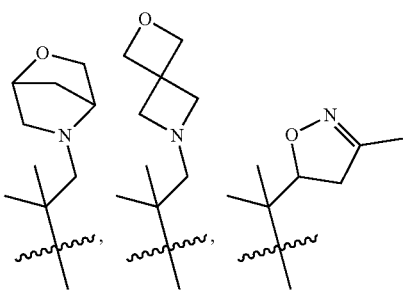
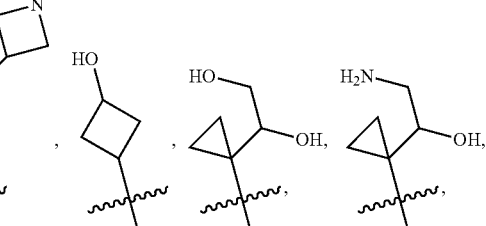
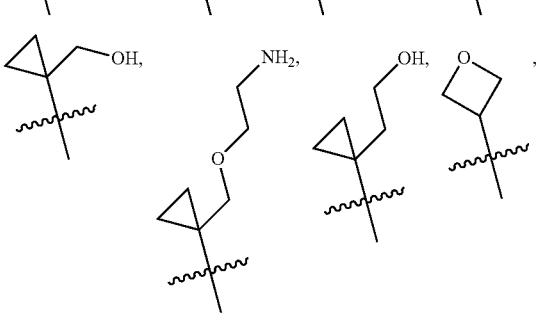
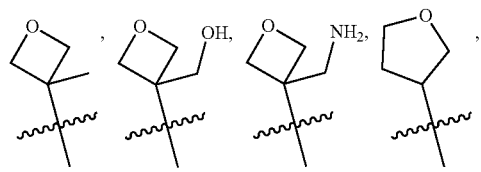

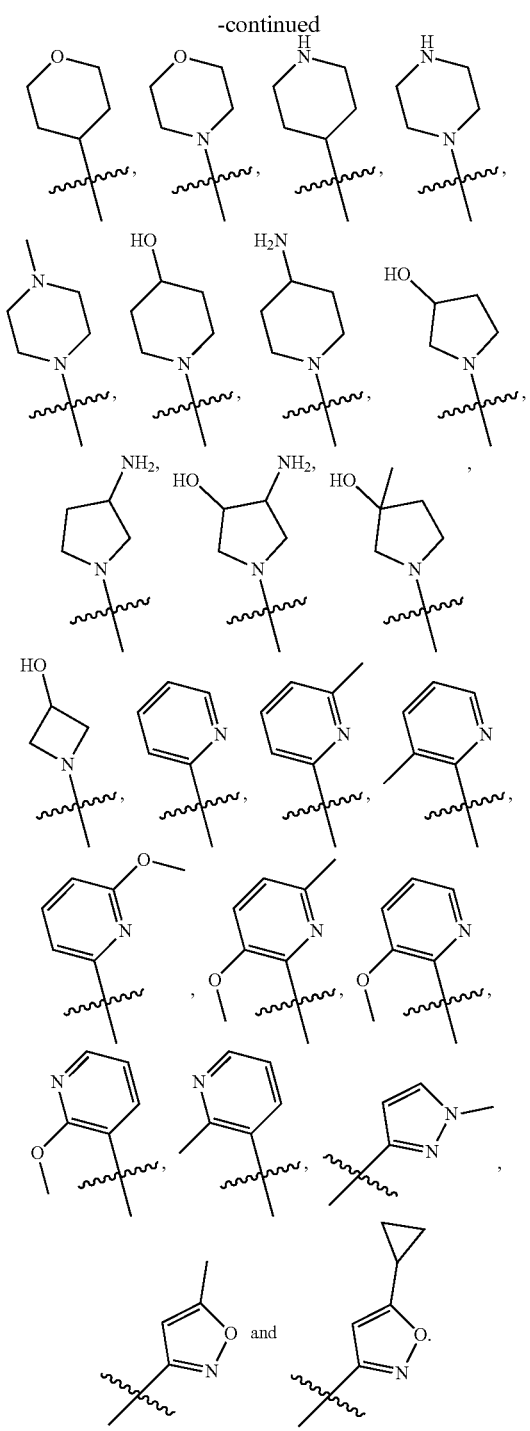

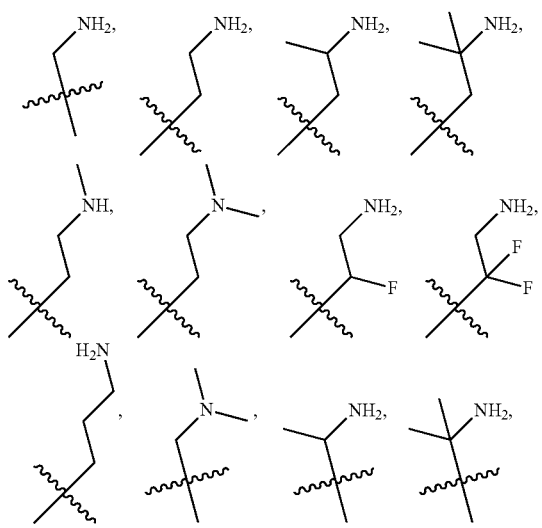

Embodiment 121. The compound of Formula (I), or according to any one of Embodiments 1 to 120, or a pharmaceutically acceptable salt thereof, wherein $R^{11}$ and $R^{12}$ are each independently selected from H and methyl.

Embodiment 122. The compound of Formula (I), or according to any one of Embodiments 1 to 121, or a pharmaceutically acceptable salt thereof, wherein each $R^{13}$ is independently selected from H, $C_1$-$C_4$alkyl, a 4-7-membered heterocycloalkyl containing 1 to 2 ring members independently selected from N, NH, $NR^{17}$, O or S, a 4-7-membered heterocyclyl containing 1 to 2 ring members independently selected from N, NH, $NR^{17}$, O or S, and a $C_3$-$C_6$cycloalkyl, wherein the $C_1$-$C_4$alkyl, heterocyclyl and $C_3$-$C_6$cycloalkyl are optionally substituted with 1 to 3 groups independently selected from $C_1$-$C_4$alkyl, halo, —OH, —$NR^{15}R^{16}$, —C(=O)$OR^{15}$, $C_1$-$C_2$alkoxy and $C_1$-$C_4$alkyl substituted with 1 to 2 hydroxy groups.

Embodiment 123. The compound of Formula (I), or according to any one of Embodiments 1 to 121, or a pharmaceutically acceptable salt thereof, wherein each $R^{13}$ is independently selected from H, $C_1$-$C_4$alkyl, a 4-7-membered heterocycloalkyl containing 1 to 2 ring members independently selected from N, NH, $NR^{17}$, O or S, a 4-7-membered heterocyclyl containing 1 to 2 ring members independently selected from N, NH, $NR^{17}$, O or S, and a $C_3$-$C_6$cycloalkyl, wherein the $C_1$-$C_4$alkyl, heterocyclyl and $C_3$-$C_6$cycloalkyl are optionally substituted with 1 to 3 groups independently selected from $C_1$-$C_4$alkyl, halo, —OH, —$NR^{15}R^{16}$, —C(=O)$OR^{15}$ and $C_1$-$C_4$alkyl substituted with 1 to 2 hydroxy groups.

Embodiment 124. The compound of Formula (I), or according to any one of Embodiments 1 to 121, or a pharmaceutically acceptable salt thereof, wherein each $R^{13}$ is independently selected from H or $C_1$-$C_4$alkyl, wherein the $C_1$-$C_4$alkyl, is optionally substituted with 1 to 3 groups independently selected from $C_1$-$C_4$alkyl, halo, —OH, —$NR^{15}R^{16}$, —C(=O)$OR^{15}$ and $C_1$-$C_4$alkyl substituted with 1 to 2 hydroxy groups.

Embodiment 125. The compound of Formula (I), or according to any one of Embodiments 1 to 121, or a pharmaceutically acceptable salt thereof, wherein each $R^{13}$ is independently selected from a 4-7-membered heterocycloalkyl containing 1 to 2 ring members independently selected from N, NH, $NR^{17}$, O or S, a 4-7-membered heterocyclyl containing 1 to 2 ring members independently selected from N, NH, $NR^{17}$, O or S, and a $C_3$-$C_6$cycloalkyl, wherein the heterocyclyl and $C_3$-$C_6$cycloalkyl are optionally substituted with 1 to 3 groups independently selected from $C_1$-$C_4$alkyl, halo, —OH, —$NR^{15}R^{16}$, —C(=O)$OR^{15}$ and $C_1$-$C_4$alkyl substituted with 1 to 2 hydroxy groups.

Embodiment 126. The compound of Formula (I), or according to any one of Embodiments 1 to 121, or a pharmaceutically acceptable salt thereof, wherein each $R^{13}$ is independently selected from H, methyl, —$CHF_2$, -continued

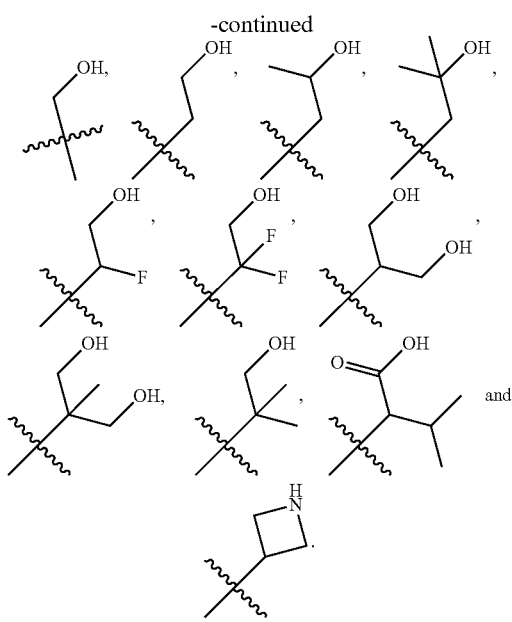

Embodiment 127. The compound of Formula (I), or according to any one of Embodiments 1 to 126, or a pharmaceutically acceptable salt thereof, wherein $R^{14}$ is selected from H, $C_1$-$C_4$alkyl and $C_3$-$C_6$cycloalkyl, wherein the $C_1$-$C_4$alkyl and $C_3$-$C_6$cycloalkyl are optionally substituted with 1 to 3 groups independently selected from $C_1$-$C_4$alkyl, halo, —OH, —$NR^{15}R^{16}$, $C_1$-$C_2$alkoxy and $C_1$-$C_4$alkyl substituted with 1 to 2 hydroxy groups.

Embodiment 128. The compound of Formula (I), or according to any one of Embodiments 1 to 126, or a pharmaceutically acceptable salt thereof, wherein $R^{14}$ is selected from H and $C_1$-$C_4$alkyl.

Embodiment 129. The compound of Formula (I), or according to any one of Embodiments 1 to 126, or a pharmaceutically acceptable salt thereof, wherein $R^{14}$ is H or methyl.

Embodiment 130. The compound of Formula (I), or according to any one of Embodiments 1 to 130, or a pharmaceutically acceptable salt thereof, wherein $R^{15}$ is selected from H and $C_1$-$C_4$alkyl.

Embodiment 131. The compound of Formula (I), or according to any one of Embodiments 1 to 130, or a pharmaceutically acceptable salt thereof, wherein $R^{15}$ is H or methyl.

Embodiment 132. The compound of Formula (I), or according to any one of Embodiments 1 to 131, or a pharmaceutically acceptable salt thereof, wherein $R^{16}$ is selected from H and $C_1$-$C_4$alkyl.

Embodiment 133. The compound of Formula (I), or according to any one of Embodiments 1 to 131, or a pharmaceutically acceptable salt thereof, wherein $R^{16}$ is H or methyl.

Embodiment 134. The compound of Formula (I), or according to any one of Embodiments 1 to 133, or a pharmaceutically acceptable salt thereof, wherein $L^2$ is a bond or a straight chain or branched $C_1$-$C_3$alkylene.

Embodiment 135. The compound of Formula (I), or according to any one of Embodiments 1 to 133, or a pharmaceutically acceptable salt thereof, wherein $L^2$ is a bond, —$CH_2$— or —$CH_2CH_2$—.

Embodiment 136. The compound of Formula (I), or according to any one of Embodiments 1 to 133, or a pharmaceutically acceptable salt thereof, wherein $L^2$ is a bond.

Embodiment 137. The compound of Formula (I), or according to any one of Embodiments 1 to 136, or a pharmaceutically acceptable salt thereof, wherein $L^3$ is a bond or a straight chain or branched $C_1$-$C_3$alkylene.

Embodiment 138. The compound of Formula (I), or according to any one of Embodiments 1 to 136, or a pharmaceutically acceptable salt thereof, wherein $L^3$ is a bond, —$CH_2$— or —$CH_2CH_2$—.

Embodiment 139. The compound of Formula (I), or according to any one of Embodiments 1 to 136, or a pharmaceutically acceptable salt thereof, wherein $L^3$ is a bond.

Embodiment 140. The compound of Formula (I), or according to any one of Embodiments 1 to 139, or a pharmaceutically acceptable salt thereof, wherein $L^4$ is a bond or a straight chain or branched $C_1$-$C_3$alkylene.

Embodiment 141. The compound of Formula (I), or according to any one of Embodiments 1 to 139, or a pharmaceutically acceptable salt thereof, wherein $L^4$ is a bond, —$CH_2$— or —$CH_2CH_2$—.

Embodiment 142. The compound of Formula (I), or according to any one of Embodiments 1 to 139, or a pharmaceutically acceptable salt thereof, wherein $L^4$ is a bond.

Embodiment 143. The compound of Formula (I), or according to any one of Embodiments 1 to 142, wherein L can be a $C_1$-$C_4$ straight chain or branched alkylene linker or a bond when W is an optionally substituted ring.

Embodiment 144. The compound of Formula (I), or according to any one of Embodiments 1 to 142, wherein L is a $C_1$-$C_4$ straight chain or branched alkylene linker.

Embodiment 145. The compound of Formula (I), or according to any one of Embodiments 1 to 142, wherein L is —$CH_2$— or —$CH_2CH_2$—.

Embodiment 146. The compound of Formula (I), or according to any one of Embodiments 1 to 142, wherein L is —$CH_2$—.

Embodiment 147. The compound of Formula (I), or according to any one of Embodiments 1 to 111, wherein L is a bond when W is an optionally substituted ring.

Embodiment 148. The compound of Formula (I) having the structure of Formula (II), or a pharmaceutically acceptable salt thereof,

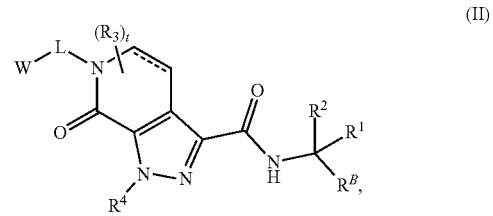

(II)

wherein

W is cyclopropyl substituted with —$SO_2R^{10}$, —$SO_2NR^{13}R^{14}$ or —$SO_2NR^{14}R^{10}$;

$R^{10}$ is selected from methyl, ethyl, propyl, isopropyl, butyl, isobutyl, cyclopropyl, and pyridinyl; wherein the $R^{10}$ is optionally substituted with 1 to 4 groups independently selected from methyl, ethyl, —OH, —$NH_2$, —$CH_2OH$, and —$CH_2NH_2$;

L is a $C_1$-$C_4$ straight chain or branched alkylene linker;

$R^1$ is selected from H and $C_1$-$C_3$alkyl;

$R^2$ is H;

t is 0 and $R^3$ is absent;

R[4] is H, $C_1$-$C_3$alkyl, or a $C_1$-$C_3$alkyl substituted with 1 to 2 groups independently selected from —OH and methyl;

each R[13] and R[14] is independently selected from H and $C_1$-$C_4$alkyl;

and R[B] is phenyl optionally substituted with 1 to 3 R[5] groups; and each R[5] is independently halo, —CN, $C_1$-$C_3$alkoxy or $C_1$-$C_3$alkyl.

Embodiment 149. The compound of Formula (I) having the structure of Formula (II), or a pharmaceutically acceptable salt thereof,

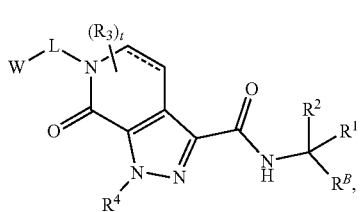

wherein

W is cyclopropyl substituted with —$SO_2R^{10}$ or —$SO_2NR^{14}R^{10}$;

R[10] is selected from methyl, ethyl, propyl, isopropyl, butyl, isobutyl, pentyl, cyclopropyl, and pyridinyl; wherein the R[10] is optionally substituted with 1 to 2 groups independently selected from methyl, —OH, —$NH_2$, —$CH_2OH$, and —$CH_2NH_2$;

L is —$CH_2$— or —$CH_2CH_2$;

R[1] is selected from H and $C_1$-$C_3$ alkyl;

R[2] is H;

t is 0 and R[3] is absent;

R[4] is H, $C_1$-$C_3$alkyl, or a $C_1$-$C_3$alkyl substituted with 1 to 2 groups independently selected from —OH and methyl;

R[14] is H;

and R[B] is phenyl optionally substituted with 1 R[5] group; and R[5] is halo or —CN.

Embodiment 150. The compound of Formula (I) having the structure of Formula (II), or a pharmaceutically acceptable salt thereof,

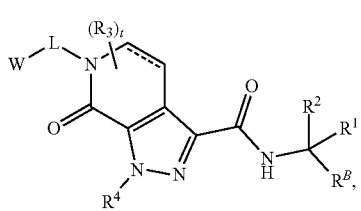

wherein

W is cyclopropyl substituted with —$SO_2R^{10}$ or —$SO_2NR^{14}R^{10}$;

R[10] is selected from methyl, ethyl, propyl, isopropyl, butyl, isobutyl, pentyl, cyclopropyl, and pyridinyl; wherein the R[10] is optionally substituted with 1 to 2 groups independently selected from methyl, —OH, —$NH_2$, —$CH_2OH$, and —$CH_2NH_2$;

L is —$CH_2$—;

R[1], R[2], and R[14] are each H;

t is 0 and R[3] is absent;

R[4] is H, $C_1$-$C_3$alkyl, or a $C_1$-$C_3$alkyl substituted with 1 to 2 groups independently selected from —OH and methyl;

and R[B] is phenyl optionally substituted with 1 R[5] group; and R[5] is halo or —CN.

Embodiment 151. The compound of Formula (I) selected from a compound of any of Examples 1-242, or a pharmaceutically acceptable salt thereof. This embodiment includes each of the Examples represented in the Table of Bioactivity Data provided herein.

Embodiment 152. A compound of Formula (I), or a pharmaceutically acceptable salt thereof, selected from:

N-(4-Cyanobenzyl)-6-((1-(cyclopropylsulfonyl)cyclopropyl)methyl)-1-methyl-7-oxo-6,7-dihydro-1H-pyrazolo[3,4-c]pyridine-3-carboxamide;

N-(4-cyanobenzyl)-1-methyl-6-((1-(methylsulfonyl)cyclopropyl)methyl)-7-oxo-6,7-dihydro-1H-pyrazolo[3,4-c]pyridine-3-carboxamide;

N-(4-cyanobenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

N-(4-Chlorobenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

6-((1-(Cyclopropylsulfonyl)cyclopropyl)methyl)-N-(4-fluorobenzyl)-1-methyl-7-oxo-4,5,6,7-tetrahydro-1H-pyrazolo[3,4-c]pyridine-3-carboxamide;

N-(4-Cyanobenzyl)-6-((1-(cyclopropylsulfonyl)cyclopropyl)methyl)-N, 1-dimethyl-7-oxo-4,5,6,7-tetrahydro-1H-pyrazolo[3,4-c]pyridine-3-carboxamide;

N-((6-Chloropyridin-3-yl)methyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

6-((1-(Cyclopropylsulfonyl)cyclopropyl)methyl)-1-methyl-N-(4-methylbenzyl)-7-oxo-4,5,6,7-tetrahydro-1H-pyrazolo[3,4-c]pyridine-3-carboxamide;

N-(4-Cyano-3-fluorobenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

N-((5-Chlorothiophen-2-yl)methyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

N-(4-Cyano-3-methylbenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

N-(4-Cyano-2-methylbenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

N-(4-Cyano-2-fluorobenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

N-((5-Cyanopyridin-2-yl)methyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

N-(4-Cyano-3-methoxybenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

(S)—N-(1-(4-Cyanophenyl)ethyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

(R)—N-(1-(4-Cyanophenyl)ethyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

(R)—N-(1-(4-Chlorophenyl)-2-hydroxyethyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

(S)—N-(1-(4-Chlorophenyl)-2-hydroxyethyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-(ethylsulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-1-methyl-6-((1-(methylsulfonyl)cyclopropyl)methyl)-7-oxo-4,5,6,7-tetrahydro-1H-pyrazolo[3,4-c]pyridine-3-carboxamide;

N-(4-Chlorobenzyl)-1-methyl-6-((1-(methylsulfonyl)cyclopropyl)methyl)-7-oxo-4,5,6,7-tetrahydro-1H-pyrazolo[3,4-c]pyridine-3-carboxamide;

N-(4-Cyano-3-fluorobenzyl)-1-methyl-6-((1-(methylsulfonyl)cyclopropyl)methyl)-7-oxo-4,5,6,7-tetrahydro-1H-pyrazolo[3,4-c]pyridine-3-carboxamide;

4-Cyanobenzyl 6-((1-(cyclopropylsulfonyl)cyclopropyl)methyl)-1-methyl-7-oxo-4,5,6,7-tetrahydro-1H-pyrazolo[3,4-c]pyridine-3-carboxylate;

4-(2-(6-((1-(cyclopropylsulfonyl)cyclopropyl)methyl)-1-methyl-7-oxo-4,5,6,7-tetrahydro-1H-pyrazolo[3,4-c]pyridin-3-yl)-2-oxoethoxy)benzonitrile;

4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,3,4-oxadiazol-2-yl)methyl)benzonitrile;

4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,2,4-oxadiazol-3-yl)methyl)benzonitrile;

4-((3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,2,4-oxadiazol-5-yl)methyl)benzonitrile;

4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-2H-tetrazol-2-yl)methyl)benzonitrile;

4-((5-(6-((1-(cyclopropylsulfonyl)cyclopropyl)methyl)-1-methyl-7-oxo-4,5,6,7-tetrahydro-1H-pyrazolo[3,4-c]pyridin-3-yl)-1H-tetrazol-1-yl)methyl)benzonitrile;

4-(3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile;

(R)-4-(3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile;

(S)-4-(3-(6-((1-(cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile;

4-((3-(6-((1-(Cyclopropylsulfonyl)cyclopropyl)methyl)-1-methyl-7-oxo-4,5,6,7-tetrahydro-1H-pyrazolo[3,4-c]pyridin-3-yl)isoxazol-5-yl)methyl)benzonitrile;

4-((4-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1H-1,2,3-triazol-1-yl)methyl)benzonitrile;

6-((1-(Cyclopropylsulfonyl)cyclopropyl)methyl)-3-(1-((4,4-difluorocyclohexyl)methyl)-1H-1,2,3-triazol-4-yl)-1-methyl-5,6-dihydro-1H-pyrazolo[3,4-c]pyridin-7(4H)-one;

N-(4-Chlorophenoxy)-1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxamide;

N-(4-Cyanobenzyl)-6-((1-((difluoromethyl)sulfonyl)cyclopropyl)methyl)-1-methyl-7-oxo-4,5,6,7-tetrahydro-1H-pyrazolo[3,4-c]pyridine-3-carboxamide;

N-(4-Chlorobenzyl)-6-((1-((difluoromethyl)sulfonyl)cyclopropyl)methyl)-1-methyl-7-oxo-4,5,6,7-tetrahydro-1H-pyrazolo[3,4-c]pyridine-3-carboxamide;

N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide;

(R)—N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide;

(S)—N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide;

N-(4-Cyanobenzyl)-1-cyclopropyl-6-((1-(cyclopropylsulfonyl)cyclopropyl)methyl)-7-oxo-4,5,6,7-tetrahydro-1H-pyrazolo[3,4-c]pyridine-3-carboxamide;

N-(4-Chlorobenzyl)-6-((1-(cyclopropylsulfonyl)cyclopropyl)methyl)-7-oxo-4,5,6,7-tetrahydro-1H-pyrazolo[3,4-c]pyridine-3-carboxamide;

N-(4-Cyanobenzyl)-6-((1-(cyclopropylsulfonyl)cyclopropyl)methyl)-7-oxo-4,5,6,7-tetrahydro-1H-pyrazolo[3,4-c]pyridine-3-carboxamide;

4-((8-((1-(Methylsulfonyl)cyclopropyl)methyl)-1,7-dioxo-3,4,7,8,9,10-hexahydropyrido[3',4':3,4]pyrazolo[1,5-a]pyrazin-2(1H)-yl)methyl)benzonitrile;

N-(4-Cyanobenzyl)-6-((1-(cyclopropylsulfonyl)cyclopropyl)methyl)-1-((1-(hydroxymethyl)cyclopropyl)methyl)-7-oxo-4,5,6,7-tetrahydro-1H-pyrazolo[3,4-c]pyridine-3-carboxamide;

N-(4-Cyanobenzyl)-1-((1-(hydroxymethyl)cyclopropyl)methyl)-6-((1-(methylsulfonyl)cyclopropyl)methyl)-7-oxo-4,5,6,7-tetrahydro-1H-pyrazolo[3,4-c]pyridine-3-carboxamide;

N-(4-Cyanobenzyl)-6-((1-((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide;

N-(4-chlorobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-((6-Chloropyridin-3-yl)methyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Fluorobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(1-(4-Cyanophenyl)ethyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(R)—N-(1-(4-Cyanophenyl)ethyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((1-hydroxy-2-methylpropan-2-yl-1,1-$d_2$)sulfonyl)cyclopropyl)methyl)-1-methyl-7-oxo-4,5,6,7-tetrahydro-1H-pyrazolo[3,4-c]pyridine-3-carboxamide;

2-((1-((3-((4-Cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropyl acetate;

N-(4-Cyanobenzyl)-6-((1-((1-(difluoromethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((2-cyanopropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((1-(3-fluoroazetidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-1-methyl-6-((1-((2-methyl-1-morpholinopropan-2-yl)sulfonyl)cyclopropyl)methyl)-7-oxo-4,5,6,7-tetrahydro-1H-pyrazolo[3,4-c]pyridine-3-carboxamide;

(R)—N-(4-cyanobenzyl)-6-((1-((1-(3-methoxypyrrolidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

6-((1-((1-(6-Oxa-3-azabicyclo[3.1.1]heptan-3-yl)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

6-((1-((1-(2-Oxa-5-azabicyclo[2.2.1]heptan-5-yl)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-Cyanobenzyl)-6-((1-((1-(3-hydroxyazetidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((1-(3-methoxyazetidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-1-methyl-6-((1-((2-methyl-1-(2-oxa-6-azaspiro[3.3]heptan-6-yl)propan-2-yl)sulfonyl)cyclopropyl)methyl)-7-oxo-4,5,6,7-tetrahydro-1H-pyrazolo[3,4-c]pyridine-3-carboxamide;

N-(4-Cyanobenzyl)-6-((1-((1-(3-hydroxypyrrolidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((1-((2-hydroxyethyl)amino)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

6-((1-((1-Amino-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-Cyanobenzyl)-6-((1-((1-formamido-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

6-((1-((1-Acetamido-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

Methyl (2-((1-((3-((4-cyanobenzyl)carbamoyl)-1-methyl-7-oxo-1,4,5,7-tetrahydro-6H-pyrazolo[3,4-c]pyridin-6-yl)methyl)cyclopropyl)sulfonyl)-2-methylpropyl)carbamate;

6-((1-((1-(2-Aminoacetamido)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(R)-6-((1-((1-(2-Aminopropanamido)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(S)-6-((1-((1-(2-Aminopropanamido)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

6-((1-((1-(2-Amino-2-methylpropanamido)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-Cyanobenzyl)-6-((1-((1-((2-(dimethylamino)acetamido)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(R)—N-(4-Cyanobenzyl)-6-((1-((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(4-Cyanobenzyl)-6-((1-((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(R)-6-((1-((1-(2-Amino-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(S)-6-((1-((1-(2-Amino-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-Cyanobenzyl)-6-((1-((1-(1,1-difluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

6-((1-((1-(2-amino-1,1-difluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-Cyanobenzyl)-6-((1-((1-(2-hydroxy-2-methylpropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((1-(2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Chlorobenzyl)-6-((1-((1-(2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(R)—N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

6-((1-((1-(2-Aminoethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

6-((1-((1-(2-Aminoethoxy)-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

6-((1-((1-(2-aminoethoxy)-2-methylpropan-2-yl)sulfonyl)cyclopropyl)methyl)-N-(4-fluorobenzyl)-1-methyl-7-oxo-4,5,6,7-tetrahydro-1H-pyrazolo[3,4-c]pyridine-3-carboxamide;

6-((1-((1-((2-Aminoethoxy)methyl)cyclopropyl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

6-((1-((1-((2-aminoethoxy)methyl)cyclopropyl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(R)-6-((1-((1-(2-Aminopropoxy)-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

(S)-6-((1-((1-(2-Aminopropoxy)-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

(R)-6-((1-((1-(2-Aminopropoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(S)-6-((1-((1-(2-Aminopropoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-Cyanobenzyl)-1-methyl-6-((1-((2-methyl-1-(2-(methylamino)ethoxy)propan-2-yl)sulfonyl)cyclopropyl)methyl)-7-oxo-4,5,6,7-tetrahydro-1H-pyrazolo[3,4-c]pyridine-3-carboxamide;

6-((1-(1-(Azetidin-3-yloxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

6-((1-((1-(2-Amino-2-methylpropoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-Cyanobenzyl)-6-((1-((1-(2-(dimethylamino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

4-((4-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-1H-1,2,3-triazol-1-yl)methyl)benzonitrile;

4-(3-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile;

(R)-4-(3-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile;

(S)-4-(3-(6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile;

6-((1-((1-Amino-2-methyl-1-oxopropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

N-(4-Chlorobenzyl)-1-methyl-6-((1-(((2-methyl-1-(methylamino)-1-oxopropan-2-yl)sulfonyl)cyclopropyl)methyl)-7-oxo-4,5,6,7-tetrahydro-1H-pyrazolo[3,4-c]pyridine-3-carboxamide;

(R)—N-(4-Cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide;

(S)—N-(4-Cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide;

N-(4-Cyanobenzyl)-6-((1-((4-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

N-(4-cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide;

(R)—N-(4-Cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(4-Cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-(((1-(2-hydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((2-hydroxy-2-methylpropyl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-(((1s,3s)-3-hydroxycyclobutyl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-(((1r,3r)-3-hydroxycyclobutyl)sulfonyl)cyclopropyl)methyl)-1-methyl-7-oxo-4,5,6,7-tetrahydro-1H-pyrazolo[3,4-c]pyridine-3-carboxamide;

N-(4-Chlorobenzyl)-1-methyl-7-oxo-6-((1-sulfamoylcyclopropyl)methyl)-4,5,6,7-tetrahydro-1H-pyrazolo[3,4-c]pyridine-3-carboxamide;

(E)-N-(4-Chlorobenzyl)-6-((1-(N-((dimethylamino)methylene)sulfamoyl)cyclopropyl)methyl)-1-methyl-7-oxo-4,5,6,7-tetrahydro-1H-pyrazolo[3,4-c]pyridine-3-carboxamide;

N-(4-Cyanobenzyl)-1-methyl-6-((1-(N-methylsulfamoyl)cyclopropyl)methyl)-7-oxo-4,5,6,7-tetrahydro-1H-pyrazolo[3,4-c]pyridine-3-carboxamide;

N-(4-Cyanobenzyl)-1-methyl-6-((1-(morpholinosulfonyl)cyclopropyl)methyl)-7-oxo-4,5,6,7-tetrahydro-1H-pyrazolo[3,4-c]pyridine-3-carboxamide;

N-(4-Cyanobenzyl)-6-((1-((4-hydroxypiperidin-1-yl)sulfonyl)cyclopropyl)methyl)-1-methyl-7-oxo-4,5,6,7-tetrahydro-1H-pyrazolo[3,4-c]pyridine-3-carboxamide;

(R)—N-(4-Cyanobenzyl)-6-((1-((3-hydroxypyrrolidin-1-yl)sulfonyl)cyclopropyl)methyl)-1-methyl-7-oxo-4,5,6,7-tetrahydro-1H-pyrazolo[3,4-c]pyridine-3-carboxamide;

(S)—N-(4-Cyanobenzyl)-6-((1-((3-hydroxypyrrolidin-1-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((3-hydroxyazetidin-1-yl)sulfonyl)cyclopropyl)methyl)-1-methyl-7-oxo-4,5,6,7-tetrahydro-1H-pyrazolo[3,4-c]pyridine-3-carboxamide;

N-(4-cyanobenzyl)-6-((1-(N-cyclopropylsulfamoyl)cyclopropyl)methyl)-1-methyl-7-oxo-4,5,6,7-tetrahydro-1H-pyrazolo[3,4-c]pyridine-3-carboxamide;

(S)—N-(4-Cyanobenzyl)-6-((1-((3-hydroxy-3-methylpyrrolidin-1-yl)sulfonyl)cyclopropyl)methyl)-1-methyl-7-oxo-4,5,6,7-tetrahydro-1H-pyrazolo[3,4-c]pyridine-3-carboxamide;

(R)—N-(4-Cyanobenzyl)-6-((1-((3-hydroxy-3-methylpyrrolidin-1-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-1-methyl-6-((1-(N-(oxetan-3-yl)sulfamoyl)cyclopropyl)methyl)-7-oxo-4,5,6,7-tetrahydro-1H-pyrazolo[3,4-c]pyridine-3-carboxamide;

N-(4-Cyanobenzyl)-1-methyl-7-oxo-6-((1-(piperazin-1-ylsulfonyl)cyclopropyl)methyl)-4,5,6,7-tetrahydro-1H-pyrazolo[3,4-c]pyridine-3-carboxamide;

6-((1-(N-(3-Aminopropyl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide;

6-((1-(N-(2-Aminoethyl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-Cyanobenzyl)-1-methyl-6-((1-((4-methylpiperazin-1-yl)sulfonyl)cyclopropyl)methyl)-7-oxo-4,5,6,7-tetrahydro-1H-pyrazolo[3,4-c]pyridine-3-carboxamide;

N-(4-Cyanobenzyl)-1-methyl-7-oxo-6-((1-(N-(piperidin-4-yl)sulfamoyl)cyclopropyl)methyl)-4,5,6,7-tetrahydro-1H-pyrazolo[3,4-c]pyridine-3-carboxamide;

6-((1-((4-Aminopiperidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

6-((1-(((3R,4R)-3-Amino-4-hydroxypyrrolidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

6-((1-(((3S,4S)-3-Amino-4-hydroxypyrrolidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(R)-6-((1-((3-Aminopyrrolidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(S)-6-((1-((3-Aminopyrrolidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-Chlorobenzyl)-6-((1-(N-(2-hydroxyethyl)sulfamoyl)cyclopropyl)methyl)-1-methyl-7-oxo-4,5,6,7-tetrahydro-1H-pyrazolo[3,4-c]pyridine-3-carboxamide;

N-(4-Chlorobenzyl)-6-((1-(N-(2-hydroxyethyl)-N-methylsulfamoyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-(N-(2-hydroxyethyl)sulfamoyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-(N-(2-hydroxyethyl)-N-methylsulfamoyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-(N-(1,3-dihydroxypropan-2-yl)-N-methylsulfamoyl)cyclopropyl)methyl)-1-methyl-7-oxo-4,5,6,7-tetrahydro-1H-pyrazolo[3,4-c]pyridine-3-carboxamide;

N-(4-Chlorobenzyl)-6-((1-(N-(1-hydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-(N-(1-hydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxamide;

N-(4-Chlorobenzyl)-6-((1-((3-hydroxyazetidin-1-yl)sulfonyl)cyclopropyl)methyl)-1-methyl-7-oxo-4,5,6,7-tetrahydro-1H-pyrazolo[3,4-c]pyridine-3-carboxamide;

N-(4-Chlorobenzyl)-1-methyl-6-((1-(N-methylsulfamoyl)cyclopropyl)methyl)-7-oxo-4,5,6,7-tetrahydro-1H-pyrazolo[3,4-c]pyridine-3-carboxamide;

N-(4-Chlorobenzyl)-6-((1-(N-(2-hydroxy-2-methylpropyl)sulfamoyl)cyclopropyl)methyl)-1-methyl-7-oxo-4,5,6,7-tetrahydro-1H-pyrazolo[3,4-c]pyridine-3-carboxamide;

N-(4-Chlorobenzyl)-6-((1-(N-(1,3-dihydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxamide;

N-(4-Chlorobenzyl)-6-((1-(N-(1,3-dihydroxy-2-methylpropan-2-yl)-N-methylsulfamoyl)cyclopropyl)methyl)-1-methyl-7-oxo-4,5,6,7-tetrahydro-1H-pyrazolo[3,4-c]pyridine-3-carboxamide;

N-(4-Cyanobenzyl)-1-methyl-7-oxo-6-((1-(N-(pyridin-2-yl)sulfamoyl)cyclopropyl)methyl)-4,5,6,7-tetrahydro-1H-pyrazolo[3,4-c]pyridine-3-carboxamide;

N-(4-Cyanobenzyl)-1-methyl-6-((1-(N-(1-methyl-1H-pyrazol-3-yl)sulfamoyl)cyclopropyl)methyl)-7-oxo-4,5,6,7-tetrahydro-1H-pyrazolo[3,4-c]pyridine-3-carboxamide;

N-(4-Cyanobenzyl)-1-methyl-6-((1-(N-(6-methylpyridin-2-yl)sulfamoyl)cyclopropyl)methyl)-7-oxo-4,5,6,7-tetrahydro-1H-pyrazolo[3,4-c]pyridine-3-carboxamide;

N-(4-Chlorobenzyl)-1-methyl-7-oxo-6-((1-(N-(pyridin-2-yl)sulfamoyl)cyclopropyl)methyl)-4,5,6,7-tetrahydro-1H-pyrazolo[3,4-c]pyridine-3-carboxamide;

N-(4-Cyanobenzyl)-6-((1-(N-(3-methoxypyridin-2-yl)sulfamoyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-(N-(3-methoxy-6-methylpyridin-2-yl)sulfamoyl)cyclopropyl)methyl)-1-methyl-7-oxo-4,5,6,7-tetrahydro-1H-pyrazolo[3,4-c]pyridine-3-carboxamide;

N-(4-Cyanobenzyl)-1-methyl-6-((1-(N-(2-methylpyridin-3-yl)sulfamoyl)cyclopropyl)methyl)-7-oxo-4,5,6,7-tetrahydro-1H-pyrazolo[3,4-c]pyridine-3-carboxamide;

N-(4-Cyanobenzyl)-6-((1-(N-(2-methoxypyridin-3-yl)sulfamoyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-(N-(6-methoxypyridin-2-yl)sulfamoyl)cyclopropyl)methyl)-1-methyl-7-oxo-4,5,6,7-tetrahydro-1H-pyrazolo[3,4-c]pyridine-3-carboxamide;

N-(4-Cyanobenzyl)-1-methyl-6-((1-(N-(3-methylpyridin-2-yl)sulfamoyl)cyclopropyl)methyl)-7-oxo-4,5,6,7-tetrahydro-1H-pyrazolo[3,4-c]pyridine-3-carboxamide;

N-(4-Cyanobenzyl)-1-methyl-6-((1-(N-(5-methylisoxazol-3-yl)sulfamoyl)cyclopropyl)methyl)-7-oxo-4,5,6,7-tetrahydro-1H-pyrazolo[3,4-c]pyridine-3-carboxamide;

N-(4-Chlorobenzyl)-1-methyl-6-((1-(N-(5-methylisoxazol-3-yl)sulfamoyl)cyclopropyl)methyl)-7-oxo-4,5,6,7-tetrahydro-1H-pyrazolo[3,4-c]pyridine-3-carboxamide;

N-(4-Cyanobenzyl)-6-((1-(N-(5-cyclopropylisoxazol-3-yl)sulfamoyl)cyclopropyl)methyl)-1-methyl-7-oxo-4,5,6,7-tetrahydro-1H-pyrazolo[3,4-c]pyridine-3-carboxamide;

N-(4-Cyanobenzyl)-1-methyl-6-((1-(oxetan-3-ylsulfonyl)cyclopropyl)methyl)-7-oxo-4,5,6,7-tetrahydro-1H-pyrazolo[3,4-c]pyridine-3-carboxamide;

N-(4-Cyanobenzyl)-1-methyl-7-oxo-6-((1-((tetrahydro-2H-pyran-4-yl)sulfonyl)cyclopropyl)methyl)-4,5,6,7-tetrahydro-1H-pyrazolo[3,4-c]pyridine-3-carboxamide;

(S)—N-(4-Cyanobenzyl)-1-methyl-7-oxo-6-((1-((tetrahydrofuran-3-yl)sulfonyl)cyclopropyl)methyl)-4,5,6,7-tetrahydro-1H-pyrazolo[3,4-c]pyridine-3-carboxamide;

(R)—N-(4-Cyanobenzyl)-1-methyl-7-oxo-6-((1-((tetrahydrofuran-3-yl)sulfonyl)cyclopropyl)methyl)-4,5,6,7-tetrahydro-1H-pyrazolo[3,4-c]pyridine-3-carboxamide;

N-(4-Cyanobenzyl)-1-methyl-6-((1-((3-methyloxetan-3-yl)sulfonyl)cyclopropyl)methyl)-7-oxo-4,5,6,7-tetrahydro-1H-pyrazolo[3,4-c]pyridine-3-carboxamide;

N-(4-Cyanobenzyl)-6-((1-((3-(hydroxymethyl)oxetan-3-yl)sulfonyl)cyclopropyl)methyl)-1-methyl-7-oxo-4,5,6,7-tetrahydro-1H-pyrazolo[3,4-c]pyridine-3-carboxamide;

6-((1-((3-(Aminomethyl)oxetan-3-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-chlorobenzyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-cyanobenzyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(1-(4-Chlorophenyl)ethyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(R)—N-(1-(4-Chlorophenyl)ethyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((1,3-dimethoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(R)—N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

6-((1-((1-Amino-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(S)-6-((1-((1-Amino-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(R)-6-((1-((1-Amino-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

6-((1-((1-Amino-3-hydroxy-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

(S)-6-((1-((1-Amino-3-hydroxy-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

(R)-6-((1-((1-Amino-3-hydroxy-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

N-(4-chlorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(4-Chlorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

(R)—N-(4-Chlorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(4-Cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

(R)—N-(4-Cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(4-Cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;

(R)—N-(4-Cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;

(S)—N-(4-Chlorobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;

(R)—N-(4-Chlorobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;

(R)-6-((1-((4-Amino-3-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(S)-6-((1-((4-Amino-3-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(S)-6-((1-((4-Amino-3-hydroxy-2-methylbutan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

(R)-6-((1-((4-Amino-3-hydroxy-2-methylbutan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

(R)—N-(4-Cyanobenzyl)-6-((1-((3-hydroxy-2-methyl-4-(methylamino)butan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(4-Cyanobenzyl)-6-((1-((3-hydroxy-2-methyl-4-(methylamino)butan-2-yl)sulfonyl)cyclopropyl)methyl)-1-methyl-7-oxo-4,5,6,7-tetrahydro-1H-pyrazolo[3,4-c]pyridine-3-carboxamide;

(R)—N-(4-Chlorobenzyl)-6-((1-((3-hydroxy-2-methyl-4-(methylamino)butan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(4-Chlorobenzyl)-6-((1-((3-hydroxy-2-methyl-4-(methylamino)butan-2-yl)sulfonyl)cyclopropyl)methyl)-1-methyl-7-oxo-4,5,6,7-tetrahydro-1H-pyrazolo[3,4-c]pyridine-3-carboxamide;

(R)—N-(4-Chlorobenzyl)-6-((1-((4-(dimethylamino)-3-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(4-Chlorobenzyl)-6-((1-((4-(dimethylamino)-3-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

6-((1-((1-(2-Amino-1-hydroxyethyl)cyclopropyl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

6-((1-((1-(2-Amino-1-hydroxyethyl)cyclopropyl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

6-((1-((4-amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(R)-6-((1-((4-Amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(S)-6-((1-((4-Amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(R)-6-((1-((3-amino-4-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(R)-6-((1-((3-Amino-4-hydroxy-2-methylbutan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide hydrochloride;

((1-((3-((4-Chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-D-valine;

N-(4-Cyanobenzyl)-6-((1-(cyclopropylsulfonyl)cyclopropyl)methyl)-1-(2-hydroxyethyl)-7-oxo-4,5,6,7-tetrahydro-1H-pyrazolo[3,4-c]pyridine-3-carboxamide;

N-(4-Cyanobenzyl)-1-(2-hydroxyethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide;

N-(4-Chlorobenzyl)-6-((1-(cyclopropylsulfonyl)cyclopropyl)methyl)-1-(2-hydroxyethyl)-7-oxo-4,5,6,7-tetrahydro-1H-pyrazolo[3,4-c]pyridine-3-carboxamide;

N-(4-Chlorobenzyl)-1-(2-hydroxyethyl)-6-((1-(methylsulfonyl)cyclopropyl)methyl)-7-oxo-4,5,6,7-tetrahydro-1H-pyrazolo[3,4-c]pyridine-3-carboxamide;

N-(4-Cyanobenzyl)-6-((1-((1-hydroxy-2-methylpropan-2-yl)sulfonyl)cyclopropyl)methyl)-1-(2-hydroxyethyl)-7-oxo-4,5,6,7-tetrahydro-1H-pyrazolo[3,4-c]pyridine-3-carboxamide;

N-(4-chlorobenzyl)-6-((1-((1-hydroxy-2-methylpropan-2-yl)sulfonyl)cyclopropyl)methyl)-1-(2-hydroxyethyl)-7-oxo-4,5,6,7-tetrahydro-1H-pyrazolo[3,4-c]pyridine-3-carboxamide;

N-(4-Chlorobenzyl)-1-(2-(2-hydroxyethoxy)ethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide;

1-(2-(2-aminoethoxy)ethyl)-N-(4-chlorobenzyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide;

N-(4-Cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide;

(S)—N-(4-Cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide;

(R)—N-(4-Cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide;

N-(4-Cyanobenzyl)-6-((1-(cyclopropylsulfonyl)cyclopropyl)methyl)-7-oxo-1-(2-oxobutyl)-4,5,6,7-tetrahydro-1H-pyrazolo[3,4-c]pyridine-3-carboxamide;

N-(4-Cyanobenzyl)-6-((1-(cyclopropylsulfonyl)cyclopropyl)methyl)-1-((1-hydroxycyclopropyl)methyl)-7-oxo-4,5,6,7-tetrahydro-1H-pyrazolo[3,4-c]pyridine-3-carboxamide;

N-(4-Chlorobenzyl)-6-((1-(cyclopropylsulfonyl)cyclopropyl)methyl)-1-(2-hydroxy-2-methylpropyl)-7-oxo-4,5,6,7-tetrahydro-1H-pyrazolo[3,4-c]pyridine-3-carboxamide;

N-(4-Cyanobenzyl)-6-((1-(cyclopropylsulfonyl)cyclopropyl)methyl)-1-(2-hydroxy-2-methylpropyl)-7-oxo-4,5,6,7-tetrahydro-1H-pyrazolo[3,4-c]pyridine-3-carboxamide;

N-(4-Chlorobenzyl)-1-(2-hydroxy-2-methylpropyl)-6-((1-(methylsulfonyl)cyclopropyl)methyl)-7-oxo-4,5,6,7-tetrahydro-1H-pyrazolo[3,4-c]pyridine-3-carboxamide;

N-(4-Cyanobenzyl)-1-(2-hydroxy-2-methylpropyl)-6-((1-(methylsulfonyl)cyclopropyl)methyl)-7-oxo-4,5,6,7-tetrahydro-1H-pyrazolo[3,4-c]pyridine-3-carboxamide;

N-(4-Cyanobenzyl)-6-((1-(ethylsulfonyl)cyclopropyl)methyl)-1-(2-hydroxy-2-methylpropyl)-7-oxo-4,5,6,7-tetrahydro-1H-pyrazolo[3,4-c]pyridine-3-carboxamide;

N-(4-Cyanobenzyl)-1-(2-hydroxy-2-methylpropyl)-6-((1-((1-(hydroxymethyl)cyclopropyl)sulfonyl)cyclopropyl)methyl)-7-oxo-4,5,6,7-tetrahydro-1H-pyrazolo[3,4-c]pyridine-3-carboxamide;

N-(4-Cyanobenzyl)-6-((1-((1-hydroxy-2-methylpropan-2-yl)sulfonyl)cyclopropyl)methyl)-1-(2-hydroxy-2-methylpropyl)-7-oxo-4,5,6,7-tetrahydro-1H-pyrazolo[3,4-c]pyridine-3-carboxamide;

N-(4-Cyanobenzyl)-6-((1-(cyclopropylsulfonyl)cyclopropyl)methyl)-1-(3-hydroxypropyl)-7-oxo-4,5,6,7-tetrahydro-1H-pyrazolo[3,4-c]pyridine-3-carboxamide;

N-(4-Cyanobenzyl)-1-(3-hydroxypropyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide;

Ethylene glycol macrocycle N-(4-cyanobenzyl)carboxamide;

Ethylene glycol macrocycle N-(4-chlorobenzyl)carboxamide;

Lactam macrocycle N-(4-cyanobenzyl)carboxamide, and

Amine macrocycle N-(4-cyanobenzyl)carboxamide.

Embodiment 153. A compound of Formula (I), or a pharmaceutically acceptable salt thereof, selected from:

N-(4-Chlorobenzyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

N-(4-Cyanobenzyl)-6-((1-(cyclopropylsulfonyl)cyclopropyl)methyl)-1-(2-hydroxyethyl)-7-oxo-4,5,6,7-tetrahydro-1H-pyrazolo[3,4-c]pyridine-3-carboxamide;

N-(4-Cyanobenzyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(R)-6-((1-((4-Amino-3-hydroxy-2-methylbutan-2-yl)sulfo-
nyl)cyclopropyl)methyl)-N-(4-cyanobenzyl)-1-methyl-7-
oxo-4,5,6,7-tetrahydro-1H-pyrazolo[3,4-c]pyridine-3-
carboxamide;

(S)-6-((1-((4-Amino-3-hydroxy-2-methylbutan-2-yl)sulfo-
nyl)cyclopropyl)methyl)-N-(4-cyanobenzyl)-1-methyl-7-
oxo-4,5,6,7-tetrahydro-1H-pyrazolo[3,4-c]pyridine-3-
carboxamide;

N-(4-Cyanobenzyl)-1-(2-hydroxyethyl)-6-((1-((1-methyl-
cyclopropyl)sulfonyl)cyclopropyl)methyl)-7-oxo-4,5,6,
7-tetrahydro-1H-pyrazolo[3,4-c]pyridine-3-carboxamide;

N-(4-Cyanobenzyl)-6-((1-(cyclopropylsulfonyl)cyclopro-
pyl)methyl)-1-(2-hydroxy-2-methylpropyl)-7-oxo-4,5,6,
7-tetrahydro-1H-pyrazolo[3,4-c]pyridine-3-carboxamide;

N-(4-Cyanobenzyl)-6-((1-((1-hydroxy-2-methylpropan-2-
yl)sulfonyl)cyclopropyl)methyl)-1-(2-hydroxy-2-methyl-
propyl)-7-oxo-4,5,6,7-tetrahydro-1H-pyrazolo[3,4-c]
pyridine-3-carboxamide;

N-(4-chlorobenzyl)-6-((1-((1-hydroxy-2-methylpropan-2-
yl)sulfonyl)cyclopropyl)methyl)-1-(2-hydroxyethyl)-7-
oxo-4,5,6,7-tetrahydro-1H-pyrazolo[3,4-c]pyridine-3-
carboxamide;

(R)—N-(4-Cyanobenzyl)-6-((1-((3,4-dihydroxy-2-meth-
ylbutan-2-yl)sulfonyl)cyclopropyl)methyl)-1-methyl-7-
oxo-4,5,6,7-tetrahydro-1H-pyrazolo[3,4-c]pyridine-3-
carboxamide;

N-(4-Cyanobenzyl)-1-(2-hydroxy-2-methylpropyl)-6-((1-
((1-(hydroxymethyl)cyclopropyl)sulfonyl)cyclopropyl)
methyl)-7-oxo-4,5,6,7-tetrahydro-1H-pyrazolo[3,4-c]
pyridine-3-carboxamide;

and

N-(4-Cyanobenzyl)-1-methyl-7-oxo-6-((1-(N-(pyridin-2-yl)
sulfamoyl)cyclopropyl)methyl)-4,5,6,7-tetrahydro-1H-
pyrazolo[3,4-c]pyridine-3-carboxamide Embodiment 154. A compound of Formula (II) of any one of Embodiments 21 to 23, having the structure of Formula (IIa), or a pharmaceutically acceptable salt thereof:

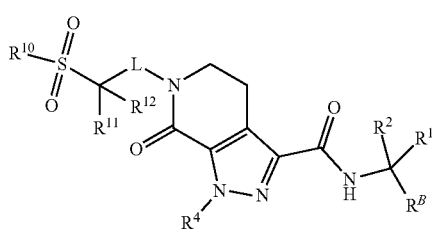

wherein L, $R^1$, $R^2$, $R^B$, $R^4$, $R^{10}$, $R^{11}$, and $R^{12}$ are as defined for Formula (I);
or L, $R^1$, $R^2$, $R^B$, $R^4$, $R^{10}$, $R^{11}$ and $R^{12}$ are as defined in Embodiment 21;
or L, $R^1$, $R^2$, $R^B$, $R^4$, $R^{10}$, $R^{11}$ and $R^{12}$ are as defined in Embodiment 22;
or L, $R^1$, $R^2$, $R^B$, $R^4$, $R^{10}$, $R^{11}$ and $R^{12}$ are as defined in Embodiment 23.

Embodiment 155. A compound of Formula (II) of any one of Embodiments 21 to 23, having the structure of Formula (IIb), or a pharmaceutically acceptable salt thereof:

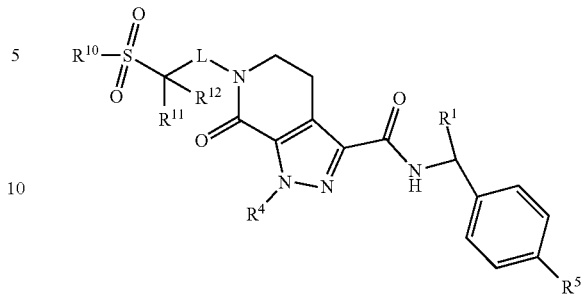

wherein L, $R^1$, $R^4$, $R^5$, $R^{10}$, $R^{11}$, and $R^{12}$ are as defined for Formula (I);
or L, $R^1$, $R^4$, $R^5$, $R^{10}$, $R^{11}$, and $R^{12}$ are as defined in Embodiment 21;
or L, $R^1$, $R^4$, $R^5$, $R^{10}$, $R^{11}$, and $R^{12}$ are as defined in Embodiment 22;
or L, $R^1$, $R^4$, $R^5$, $R^{10}$, $R^{11}$, and $R^{12}$ are as defined in Embodiment 23.

Embodiment 156. The compound of Embodiment 155, or pharmaceutically acceptable salt thereof, wherein $R^5$ is —CN or halo.

Embodiment 157. The compound of any one of Embodiments 154-156, or a pharmaceutically acceptable salt thereof, wherein $R^4$ is methyl.

Embodiment 158. A compound of Formula (IVa), having the structure of Formula (IVd)

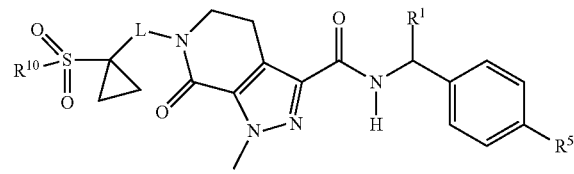

wherein L, $R^1$, $R^5$, and $R^{10}$ are as defined for Formula (I);
or L, $R^1$, $R^5$, and $R^{10}$ are as defined in Embodiment 22;
or L, $R^1$, $R^4$, $R^5$, $R^{10}$, $R^{11}$, and $R^{12}$ are as defined in Embodiment 23.

Embodiment 159. The compound of Embodiment 158, or pharmaceutically acceptable salt thereof, wherein $R^5$ is —CN or halo.

Embodiment 160. The compound of Formula (Vc) of Embodiment 30, or pharmaceutically acceptable salt thereof, wherein each $R^5$ is halo, and $R^{10}$ is $C_1$-$C_5$ alkyl substituted with two -$L^3$OH, wherein $L^3$ is as defined in Formula (I).

Embodiment 161. The compound of Formula (Va) of Embodiment 30, or pharmaceutically acceptable salt thereof, wherein $R^5$ is halo, and $R^{10}$ is $C_1$-$C_5$ alkyl substituted with two -$L^3$OH, wherein $L^3$ is as defined in Formula (I).

Embodiment 162. The compound of Formula (Va) of Embodiment 30, or pharmaceutically acceptable salt thereof, wherein $R^5$ is —CN, and $R^{10}$ is $C_1$-$C_5$ alkyl substituted with two -$L^3$OH, wherein $L^3$ is as defined in Formula (I).

Embodiment 163. A compound of Formula (I), having the structure of Formula (VIII), or a pharmaceutically acceptable salt thereof,

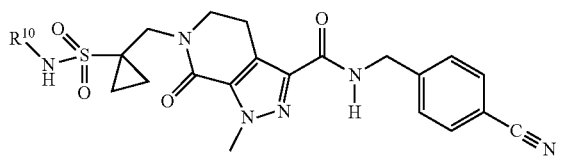

(VIII)

wherein $R^{10}$ is selected from:
- phenyl, unsubstituted or substituted with one —CN;
- 6-membered heteroaryl having 1-2 heteroatoms, each heteroatom being N, unsubstituted or substituted with one group selected from -$L^3$halo, -$L^3$OH, or -$L^3$NHC(=O)$R^{13}$, wherein $L^3$ is a bond or a straight chain or branched $C_1$-$C_3$ alkylene, and $R^{13}$ is $C_1$-$C_4$ alkyl; and
- $C_1$-$C_5$ alkyl substituted with one -$L^3$C(=O)NR13R14 or 2 or 3 -$L^3$OH, wherein $L^3$ is a bond or a straight chain or branched $C_1$-$C_3$ alkylene, $R^{13}$ is H or $C_1$-$C_4$ alkyl, and $R^{14}$ is H or $C_1$-$C_4$ alkyl.

Embodiment 164. The compound of Embodiment 163, or a pharmaceutically acceptable salt thereof, wherein $L^3$ is a bond.

Embodiment 165. The compound of Embodiment 163 or 164, or a pharmaceutically acceptable salt thereof, wherein $R^{10}$ is unsubstituted 6-membered heteroaryl having 1-2 heteroatoms, each heteroatom being N.

Embodiment 166. The compound of any one of Embodiments 163-165, or a pharmaceutically acceptable salt thereof, wherein the compound is selected from: N-(4-cyanobenzyl)-6-((1-(N-(6-(hydroxymethyl)pyridin-2-yl)sulfamoyl)cyclopropyl)methyl)-1-methyl-7-oxo-4,5,6,7-tetrahydro-1H-pyrazolo[3,4-c]pyridine-3-carboxamide;

6-((1-(N-(6-acetamidopyridin-2-yl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-cyanobenzyl)-1-methyl-7-oxo-6-((1-(N-(pyrazin-2-yl)sulfamoyl)cyclopropyl)methyl)-4,5,6,7-tetrahydro-1H-pyrazolo[3,4-c]pyridine-3-carboxamide;

N-(4-cyanobenzyl)-1-methyl-7-oxo-6-((1-(N-phenylsulfamoyl)cyclopropyl)methyl)-4,5,6,7-tetrahydro-1H-pyrazolo[3,4-c]pyridine-3-carboxamide;

N-(4-cyanobenzyl)-6-((1-(N-(3-fluoropyridin-2-yl)sulfamoyl)cyclopropyl)methyl)-1-methyl-7-oxo-4,5,6,7-tetrahydro-1H-pyrazolo[3,4-c]pyridine-3-carboxamide;

N-(4-cyanobenzyl)-6-((1-(N-(2-cyanophenyl)sulfamoyl)cyclopropyl)methyl)-1-methyl-7-oxo-4,5,6,7-tetrahydro-1H-pyrazolo[3,4-c]pyridine-3-carboxamide;

N-(4-chloro-3-fluorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

(R)—N-(4-chloro-3-fluorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

(S)—N-(4-chloro-3-fluorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

N-(4-cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

6-((1-(N-(4-amino-2-methyl-4-oxobutan-2-yl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-cyanobenzyl)-6-((1-(N-(3-(dimethylamino)-3-oxopropyl)sulfamoyl)cyclopropyl)methyl)-1-methyl-7-oxo-4,5,6,7-tetrahydro-1H-pyrazolo[3,4-c]pyridine-3-carboxamide;

N-(4-cyanobenzyl)-6-((1-(((3S,4S)-3,4-dihydroxypyrrolidin-1-yl)sulfonyl)cyclopropyl)methyl)-1-methyl-7-oxo-4,5,6,7-tetrahydro-1H-pyrazolo[3,4-c]pyridine-3-carboxamide;

N-(4-cyanobenzyl)-1-methyl-7-oxo-6-((1-(N-(1-(pyridazin-3-yl)cyclopropyl)sulfamoyl)cyclopropyl)methyl)-4,5,6,7-tetrahydro-1H-pyrazolo[3,4-c]pyridine-3-carboxamide;

N-(4-cyanobenzyl)-6-((1-(N-(1,3-dihydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxamide;

N-(4-cyanobenzyl)-1-methyl-7-oxo-6-((1-(N-(pyrimidin-2-ylmethyl)sulfamoyl)cyclopropyl)methyl)-4,5,6,7-tetrahydro-1H-pyrazolo[3,4-c]pyridine-3-carboxamide;

N-(4-cyanobenzyl)-1-methyl-7-oxo-6-((1-(N-(1-(pyrazin-2-yl)ethyl)sulfamoyl)cyclopropyl)methyl)-4,5,6,7-tetrahydro-1H-pyrazolo[3,4-c]pyridine-3-carboxamide;

N-(4-cyanobenzyl)-1-methyl-7-oxo-6-((1-(N-(pyrazin-2-ylmethyl)sulfamoyl)cyclopropyl)methyl)-4,5,6,7-tetrahydro-1H-pyrazolo[3,4-c]pyridine-3-carboxamide;

N-(4-cyanobenzyl)-6-((1-(N-(1,3-dihydroxy-2-(hydroxymethyl)propan-2-yl)sulfamoyl)cyclopropyl)methyl)-1-methyl-7-oxo-4,5,6,7-tetrahydro-1H-pyrazolo[3,4-c]pyridine-3-carboxamide; and N-(4-cyanobenzyl)-1-methyl-7-oxo-6-((1-sulfamoylcyclopropyl)methyl)-4,5,6,7-tetrahydro-1H-pyrazolo[3,4-c]pyridine-3-carboxamide.

Embodiment 167. The compound of any one of embodiments 1-150, or a pharmaceutically acceptable salt thereof, wherein $R^4$ is $C_2$-$C_3$ alkyl substituted with 1 to 2 groups independently selected from —OH and $R^{10}$.

Embodiment 168. The compound of any one of claims 1-150 and 167, or a pharmaceutically acceptable salt thereof, wherein $R^4$ is substituted with —OH, and optionally substituted with methyl.

Embodiment 169. The compound of any one of claims 1-150 and 167-168, or a pharmaceutically acceptable salt thereof, wherein W is $L^2SO_2R^{10}$.

Embodiment 170. The compound of any one of claims 1-150 and 167-169, or a pharmaceutically acceptable salt thereof, wherein $L^2$ is a bond and $R^{10}$ is $C_1$-$C_4$ alkyl substituted with 1-3 groups selected from $C_1$-$C_4$ alkyl and —OH.

Compounds of Formula (VII) are novel and useful as intermediates for preparation of the compounds of Formula (I)-(VI) described herein.

Compounds of Formula (VII) are novel and useful as intermediates for preparation of the compounds of Formula (VIII) described herein.

General Synthetic Procedures

The compounds of the invention can be produced by organic synthesis methods known to one of ordinary skill in the art with reference to the following reaction general synthetic schemes below and in more detail in the Examples.

All starting materials, building blocks, reagents, acids, bases, dehydrating agents, solvents, and catalysts utilized to synthesize the compounds of the invention are either commercially available or can be produced by organic synthesis methods known to one of ordinary skill in the art (Houben-Weyl 4th Ed. 1952, Methods of Organic Synthesis, Thieme, Volume 21).

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der Organischen Chemie" (Methods of Organic Chemistry), Houben Weyl, 4th edition, Volume 15/1, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

General methods for the synthesis of compounds of Formula (I) are provided below in Schemes I-VI. In particular Schemes I to III show general methods 1 to 14 for the synthesis of compounds of Formula (I) wherein Z is W and $L_{MC}$ is absent, and wherein $R^1$, $R^2$, $R^3$, $R^4$, $R^{15}$, $R^B$, t, L and W are as defined herein for compounds of Formula (I).

Scheme I

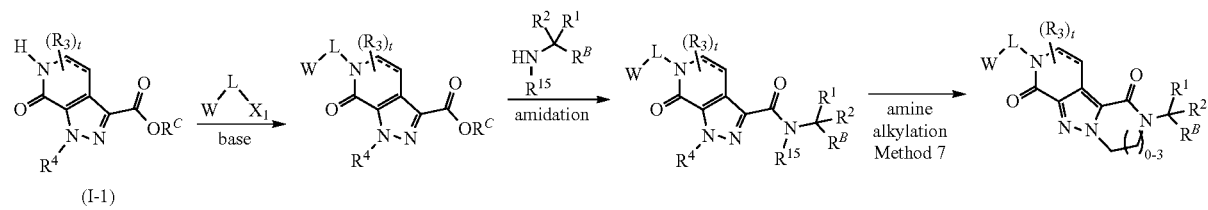

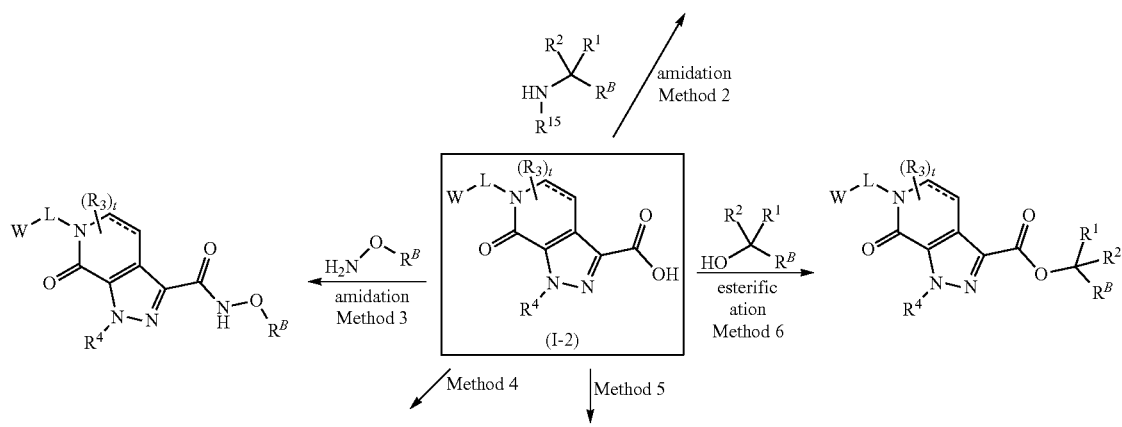

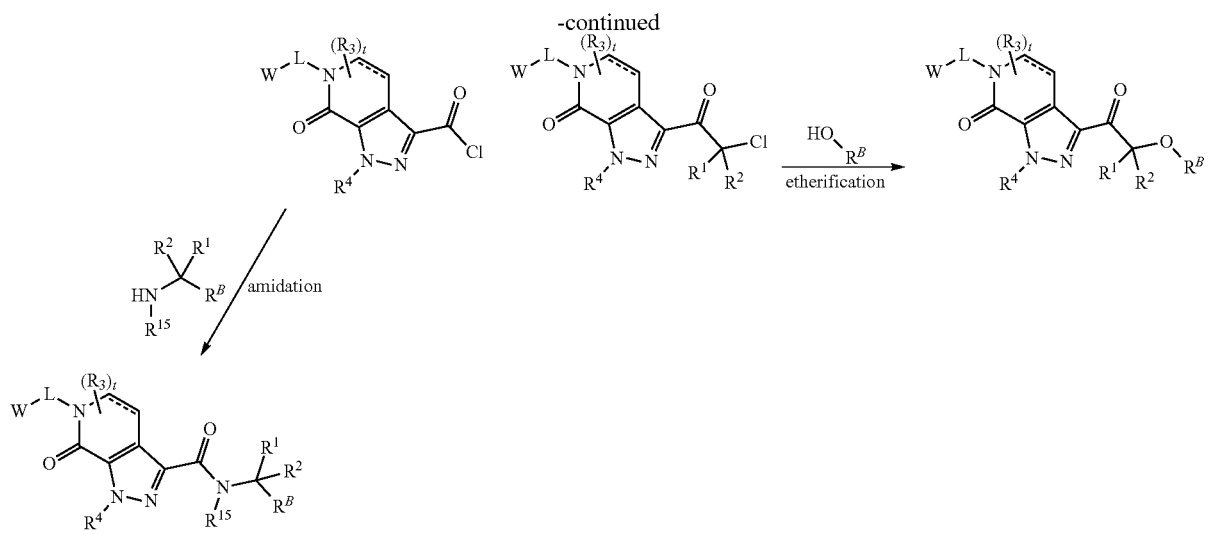

Scheme I shows general methods 1 to 7 for synthesizing compounds of Formula (I) wherein X is

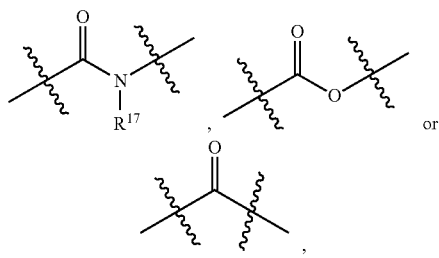

and Y is a bond

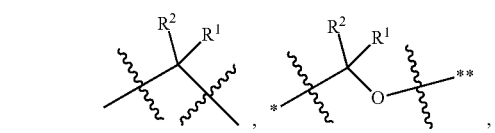

—O— or

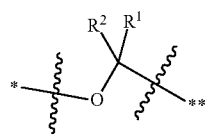

The bicyclic intermediate (e.g., Intermediate I-1) can be N-alkylated to attach the W-L- moiety of interest, for e.g. where L is attached through —CH$_2$—. W-L-X$_1$ represents a suitable alkylating agent for such reactions, where X$_1$ is a leaving group such as halo (e.g. Br or I) or a sulfonate leaving group such as mesylate, tosylate, or triflate. The W-L- moiety can of course contain functional groups that can be further modified in the product of Formula (I), such as hydroxyl groups or amine groups, e.g. in protected form, which can be deprotected and further derivatized.

R$^C$ can be a simple alkyl ester such as methyl, ethyl, propyl, isopropyl, t-butyl or n-butyl; and if W-L- contains an ester, R$^C$ can be a different ester such as benzyl that can be readily differentiated from the one in W-L-, so R$^C$ can be selectively hydrolyzed for the coupling reaction in Scheme I. In some of the examples, the R$^C$ is an ester that hydrolyzes under the alkylation reaction conditions, presumably due to the presence of adventitious moisture or hydroxide; in other examples, a separate hydrolysis step is used such as addition of lithium, sodium or potassium hydroxide and water. The resulting free carboxylate compound is then readily coupled to a suitable amine containing a desired R$^B$ group using standard amide bond formation conditions and suitable reagents. This can be a direct amidation of the carboxylate (method 1 and method 2), or it can be accomplished by converting the carboxylic acid into an activated intermediate (acyl chloride, acyl anhydride, etc.) (method 4) as known in the art and illustrated by the accompanying examples. Examples of amide coupling reagents used in methods 1, 2, 4 and 5 include, but are not limited to, EDCI, HATU, HBTU, TBTU and T3P. In addition, the carboxylic acid can be converted into an activated intermediate (method 5) which undergoes subsequent etherification. Typical etherification occurs using a alkyl halides (Cl, Br, I) in the presence of a base such as KCO$_3$ or KOH.

Alternatively the carboxylic acid undergoes esterification (method 6) using Lewis or Brønstedt acid-catalyzed esterification of the carboxylic acid with an alcohol, however examples of other esterification reagents include diethyl azodicarboxylate (DEAD) or diisopropyl azodicarboxylate (DIAD), di-tert-butyl azodicarboxylate (DTBAD), dicyclohexylcarbodiimide (DCC)/4-N,N-dimethylaminopyridine (DMAP) and 2,4,6-trichlorobenzoyl chloride/4-N,N-dimethylaminopyridine (DMAP).

Finally, for compounds of Formula (I) where in R$^4$ is H and R$^{15}$ comprises an alkylhalide moiety, the secondary amine on the pyrazolyl ring can be alkylated (method 7) thereby forming a third fused ring. Alternatively, hydroamination and amine alkylation with alcohols can be used when R$^{15}$ comprises the appropriate reactive group.

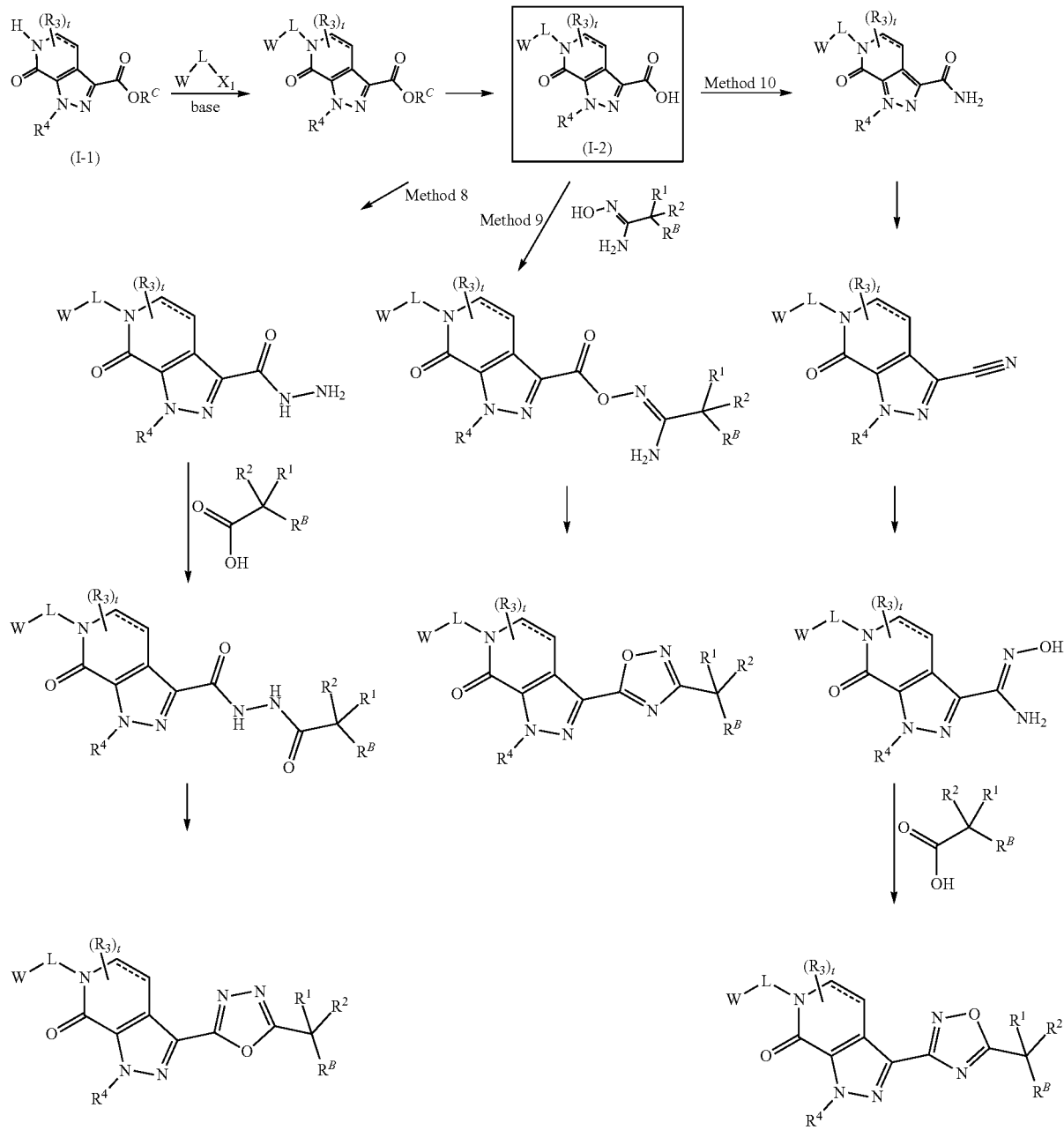

Scheme II shows general methods for synthesizing compounds of Formula (I), wherein X is a 5-6 membered heteroaryl, and Y is

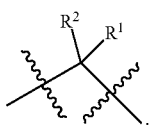

Utilizing the carboxylic acid intermediate described in Scheme (I), compounds of Formula (i) containing an oxadiazole are readily obtained. In method 8, oxadiazole synthesis occurs by the condensation with the carboxylic acid followed by dehydrative cyclization of the resulting diacyl hydrazide intermediate. Alternatively, in method 9, oxadiazole synthesis occurs by the condensation of carboxylic acid and amidoximes followed by cyclization. Finally, in method 10 the carboxylic acid intermediate is converted into the amide, followed by nitrile formation which is subsequently used to form the amidoxime intermediate. Oxadiazole formation then occurs by condensation of the carboxylic acid and amidoximes, followed by cyclization. Reagents used in such methods are known in the art and illustrated by the accompanying examples.

Scheme III

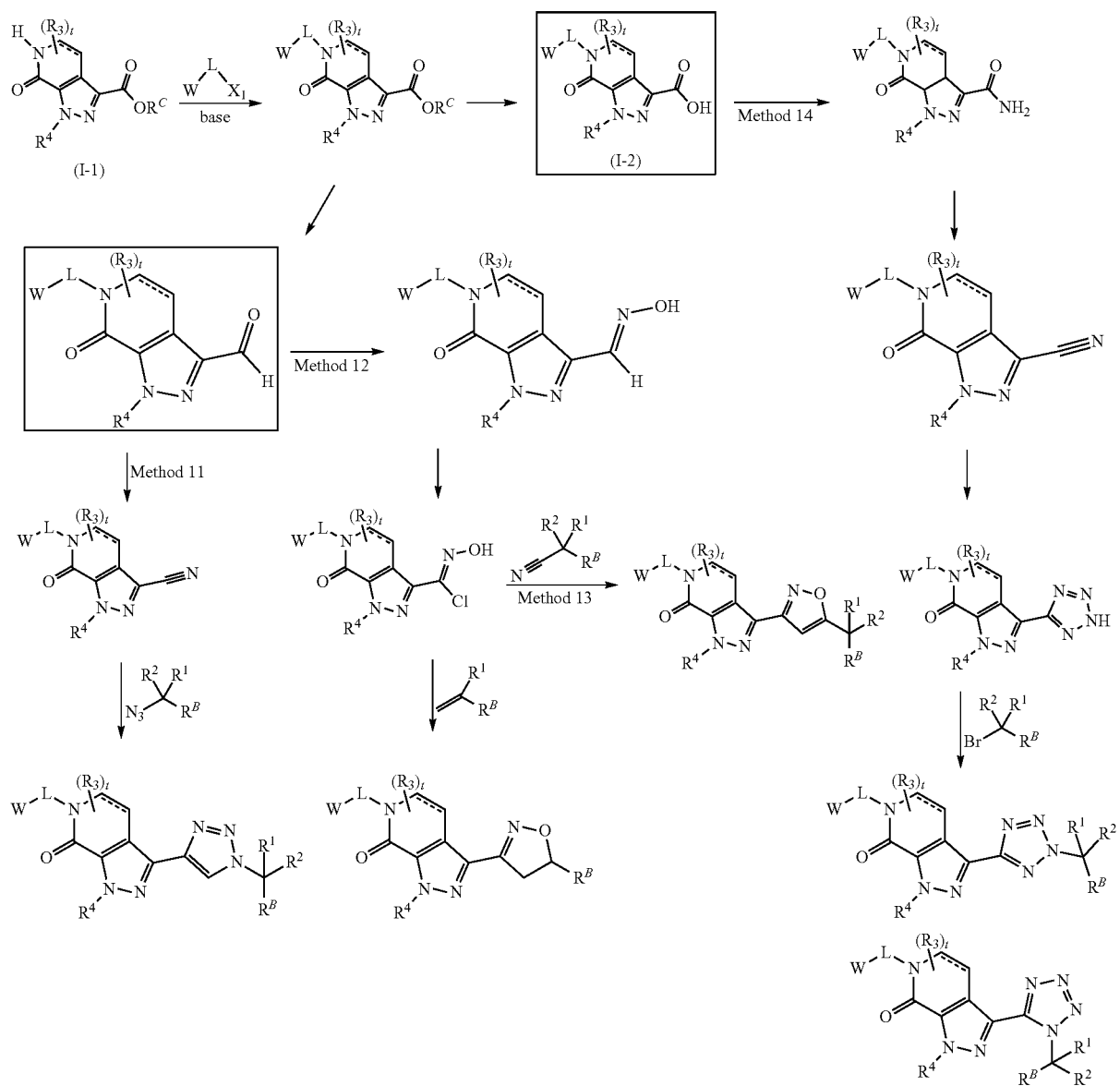

Scheme III shows general methods for synthesizing compounds of Formula (I), wherein X is a 5-6 membered heteroaryl or a 5-6 membered heterocyclyl, and Y is a bond or

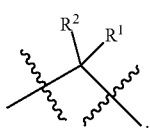

Utilizing the carboxylic acid intermediate or corresponding ester intermediate described in Scheme (I), compounds of Formula (I) containing a triazole, tetrazole, isoxazole or a dihydroisoxazole are obtained. In method 11, an aldehyde intermediate, formed from the ester, is used to form a nitrile intermediate. Subsequent copper catalyzed "click" chemistry with the nitrile intermediate and an azide intermediate results in triazole formation. In addition, in method 12, the aldehyde intermediate, formed from the ester, is used to form an oxime intermediate which is subsequently converted to the carbimidoyl chloride derivative. Reaction of the carbimidoyl chloride derivative with an alkene gives the dihydroisoxazole. Alternatively, reaction of the carbimidoyl chloride derivative with a nitrile intermediate (method 13) gives the isoxazole. Finally, in method 14 the carboxylic acid intermediate is converted into the amide, followed by nitrile formation and subsequent formation of a tetrazole intermediate, which is then N-alkylated using an alkyl halide.

Scheme IV shows a general method for the synthesis of compounds of Formula (I) wherein LMC is present, and wherein $R^1$, $R^2$, $R^3$, $R^4$, $R^{15}$, $R^B$, t and L are as defined herein for compounds of Formula (I).

Scheme IV

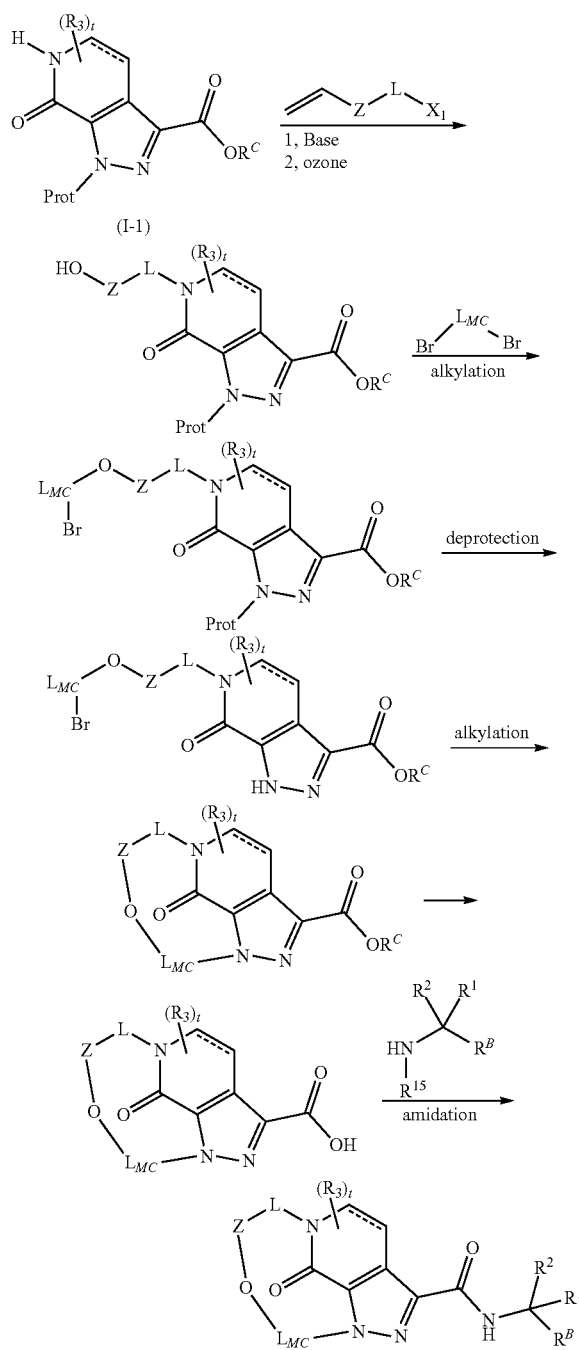

Scheme V

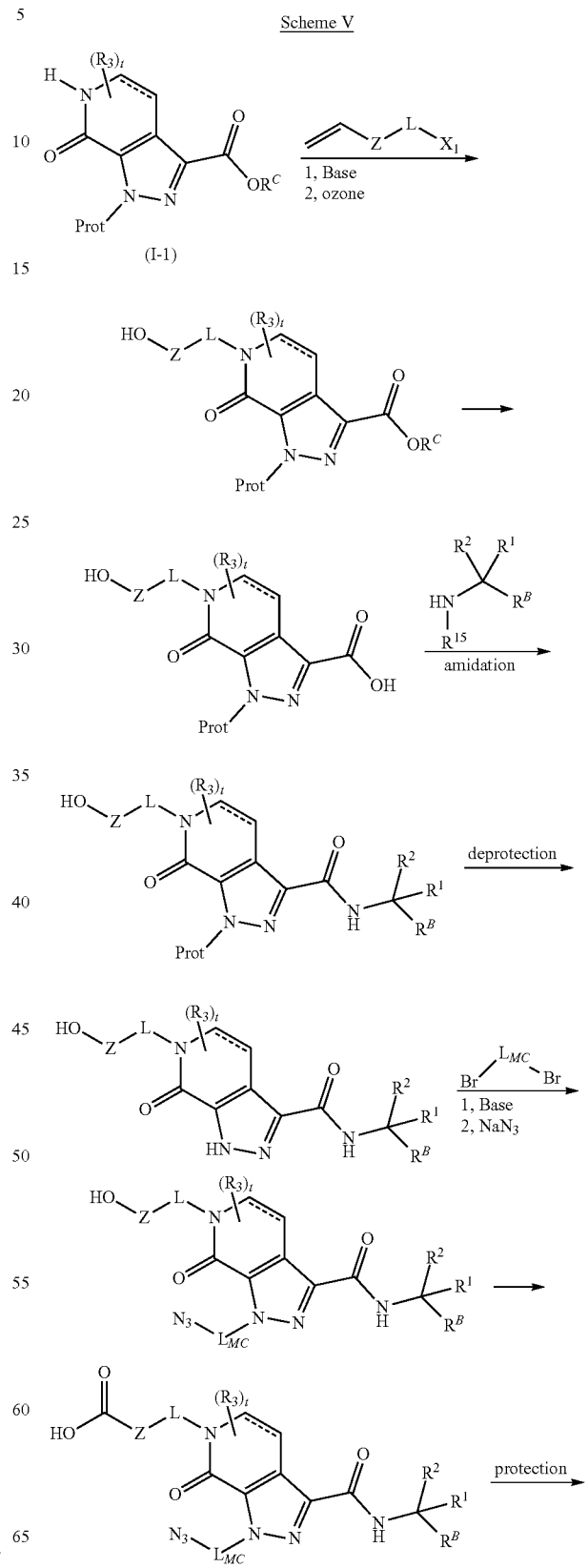

wherein $R^1$, $R^2$, $R^3$, $R^4$, $R^{15}$, $R^B$, t and L are as defined herein for compounds of Formula (I).

In Scheme (IV) the amine protected bicyclic intermediate (e.g., Intermediate I-1) described in Scheme (I), is utilized to obtain macrocyclic compounds of Formula (I). Here the bicyclic intermediate can be N-alkylated as described in Scheme I to attach the OH—Z-L- moiety of interest, e.g. where L is attached through —CH$_2$—. The hydroxyl of the OH—Z-L group is alkylated, thereby attaching a linker moiety which, after deprotection of the amine, is further attached by N-alkylation of the deprotected amine. The ester is converted to the corresponding carboxylic acid which is subsequently amidated with a desired amine intermediate.

Scheme V shows a general method for the synthesis of compounds of Formula (I) wherein LMC is present, and

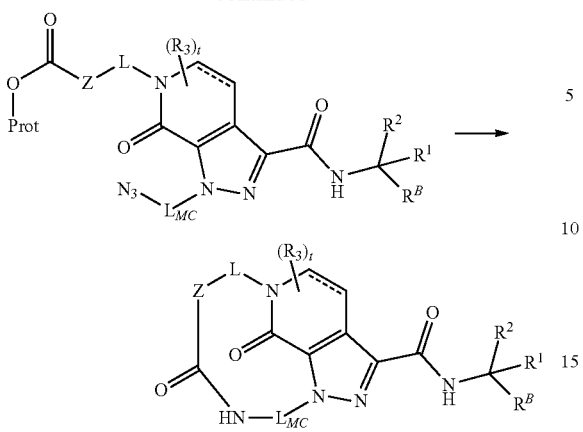

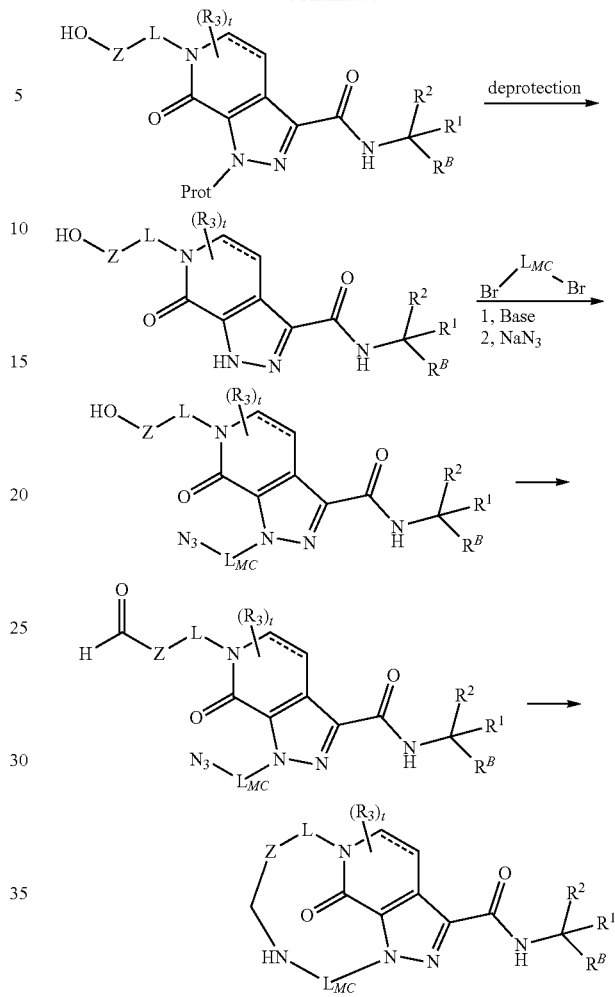

In Scheme (V) the amine protected bicyclic intermediate (e.g., Intermediate I-1) described in Scheme (I), is utilized to obtain macrocyclic compounds of Formula (I). Here the bicyclic intermediate can be N-alkylated as described in Scheme to attach the OH—Z-L- moiety of interest, especially where L is attached through —CH$_2$—. The ester is then converted to the corresponding carboxylic acid which is subsequently amidated with a desired amine intermediate. After deprotection, the amine is alkylated to attach a linker which is subsequently activated with an azide moiety. The hydroxyl of the OH—Z-L group is converted to a carboxylic acid which is then amidated via the azide moiety thereby attaching the linker and completing the macrocycle formation.

Scheme VI shows a general method for the synthesis of compounds of Formula (I) wherein LMC is present, and wherein $R^1$, $R^2$, $R^3$, $R^4$, $R^{15}$, $R^B$, t and L are as defined herein for compounds of Formula (I).

Scheme VI

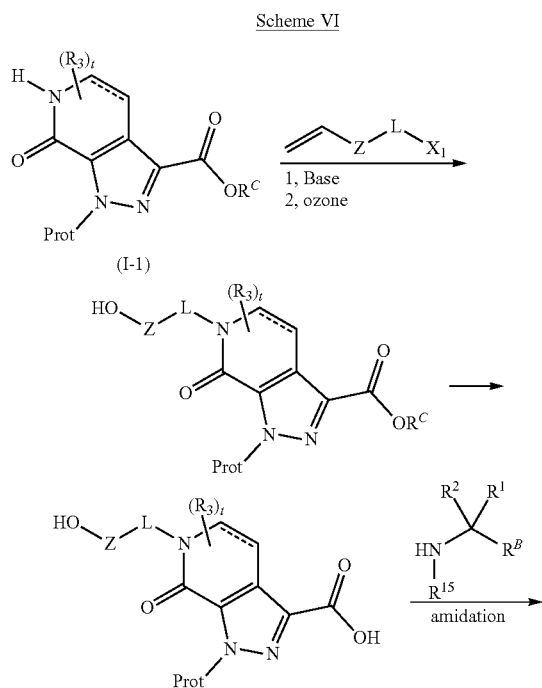

In Scheme (VI) the amine protected bicyclic intermediate (e.g. Intermediate I-1) described in Scheme (I), is utilized to obtain macrocyclic compounds of Formula (I). Here the bicyclic intermediate can be N-alkylated as described in Scheme I to attach the OH—Z-L- moiety of interest, e.g. where L is attached through —CH$_2$—. The ester is then converted to the corresponding carboxylic acid which is subsequently amidated with a desired amine intermediate. After deprotection, the amine is alkylated to attach a linker which is subsequently activated with an azide moiety. The hydroxyl of the OH—Z-L group is converted to an aldehyde which is then amidated via the azide moiety, thereby attaching the linker and completing the macrocycle formation.

Although Schemes IV-VI show general methods for synthesizing macrocyclic compounds of Formula (I) wherein X is

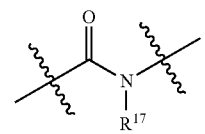

and Y is a bond,

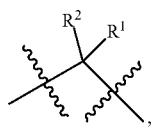

such methods can be used for embodiments where X is

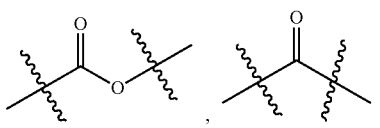

a 5-6 membered heteroaryl, a 5-6 membered heterocycloalkyl or a 5-6 membered heterocyclyl, and Y is a bond,

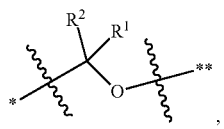

—O— or

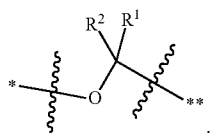

Using these method described above along with additional extensions, modifications and variations illustrated by the following Examples, a skilled person can readily prepare various compounds of Formula (I)-(VI).

Intermediates and final products can be worked up and/or purified according to suitable methods, e.g., using chromatographic methods, distribution methods, (re-) crystallization, and the like.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers or diastereomers, for example, by chromatography and/or fractional crystallization.

Mixtures of isomers obtainable according to the invention can be separated in a manner known per se into the individual isomers; diastereoisomers can be separated, for example, by partitioning between polyphasic solvent mixtures, recrystallization and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Many compounds of the invention contain one or more chiral centers. These compounds may be made and used as single isomers or as mixtures of isomers. Methods for separating the isomers, including diastereomers and enantiomers, are known in the art, and examples of suitable methods are described herein. In certain embodiments, the compounds of the invention are used as a single substantially pure isomer, meaning at least 90% of a sample of the compound is the specified isomer and less than 10% of the sample is any other isomer or mixture of isomers. E.g., at least 95% of the sample is a single isomer. In view of the present disclosure, selection of a suitable isomer is within the ordinary level of skill. For example, one isomer may be more active in the herpesvirus DNA polymerase in vitro assay described herein. Where in vitro activity differences between isomers are relatively small, e.g. less than about a factor of 4, a single isomer may be selected based on activity level against viral replication in cell culture, using methods such as those described herein: e.g. the isomer having a lower $IC_{50}$ or $EC_{50}$ may be selected.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethyl hexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent may be used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralization of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Any formula given herein is intended to represent unlabeled forms as well as isotopically labeled forms of the compounds of the present invention having up to three atoms with non-natural isotope distributions, e.g., sites that are enriched in deuterium or $^{13}C$ or $^{15}N$. Isotopically labeled compounds have structures depicted by the formulas given herein except that one or more atoms are replaced by an atom having a selected atomic mass or mass number other than the natural-abundance mass distribution. Examples of isotopes that can be usefully over-incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds of the present invention, for example those into which radioactive isotopes, such as $^3H$ and $^{14}C$, or those in which non-radioactive isotopes, such as $^2H$ and $^{13}C$ are present at levels substantially above normal isotope distribution. Such isotopically labelled compounds are useful in metabolic studies (with $^{14}C$, for example), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent typically employed. Labeled samples may be useful with quite low isotope incorporation, such as where a radiolabel is used to detect trace amounts of the compound.

Further, more extensive substitution with heavier isotopes, particularly deuterium (i.e., $^2H$ or D), may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention, and typically a sample of a compound having deuterium as a substituent has at least 50% deuterium incorporation at the labeled position(s). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The invention also provides methods of making compounds of Formula I as described herein and intermediates useful for preparation of compounds of Formula (I). The invention thus also includes a method to make a compound of Formula (I), which comprises: contacting a compound of Formula (A)

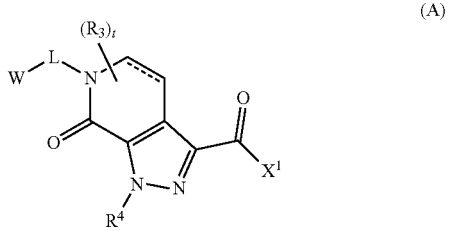

(A)

wherein:
$X_1$ represents —OH or a leaving group;
t is 0, 1 or 2;
each $R^3$, when present, is a substituent on the ring to which -L-W is directly attached, wherein each $R^3$ is independently selected from halo, CN, $C_1$-$C_3$alkoxy, $C_1$-$C_3$alkyl, C(=O)$OR^{10}$, and C(=O)$NR^{13}R^{14}$;
$R^4$ is H, $C_1$-$C_3$alkyl, $C_3$-$C_6$cycloalkyl or a $C_1$-$C_3$alkyl substituted with 1 to 2 groups independently selected from —OH, —C(=O)$R^{15}$ and $R^{10}$;

L is a $C_1$-$C_4$ straight chain or branched alkylene linker or a bond;
W is H, —OH, —$OR^{10}$, —C(=O)$NR^{13}R^{14}$, —C(=O)$OR^{13}$, —$NR^{13}R^{14}$, —$NR^{13}$C(=O)$OR^{10}$, —$NR^{13}$C(=O)$R^{10}$, —$SO_2R^{10}$, —$SO_2NR^{13}R^{14}$, —$NR^{13}SO_2R^{10}$, —P(=O)($OR^{13}$)$_2$, —S(=O)$R^{10}$, —S(=O)(=$NR^{13}$)$R^{10}$, —$CR^{11}R^{12}$C(=O)$NR^{13}R^{14}$, —$CR^{11}R^{12}$C(=O)$OR^{13}$, —$CR^{11}R^{12}NR^{13}R^{14}$, —$CR^{11}R^{12}NR^{13}$C(=O)$OR^{10}$, —$CR^{11}R^{12}NR^{13}$C(=O)$R^{10}$, —$CR^{11}R^{12}SO_2R^{10}$, —$CR^{11}R^{12}SO_2NR^{13}R^{14}$, —$CR^{11}R^{12}NR^{13}SO_2R^{10}$, —$CR^{11}R^{12}P$(=O)($OR^{13}$)$_2$, —$CR^{11}R^{12}S$(=O)$R^{10}$, —$CR^{11}R^{12}S$(=O)(=$NR^{13}$)$R^{10}$, a 3-6 membered cycloalkyl, phenyl, a 5-6-membered heterocycloalkyl containing one or two ring members independently selected from N, NH, $NR^{17}$, O or S, a 5-6-membered heterocyclyl containing one or two ring members independently selected from N, NH, $NR^{17}$, O or S, or a 5-membered heteroaryl having 1 to 4 heteroatoms selected from N, O and S as ring members that is optionally fused to phenyl,
wherein the 3-6 membered cycloalkyl, phenyl, 5-6-membered heterocycloalkyl, 5-6-membered heterocyclyl and 5-membered heteroaryl of W are each optionally substituted with 1 to 3 groups independently selected from $C_1$-$C_3$alkyl, oxo, halo, $C_1$-$C_3$haloalkyl, -$L^2$OH, -$L^2OR^{10}$, -$L^2$OC(=O)$NR^{13}R^{14}$, -$L^2SO_2R^{10}$, -$L^2SO_2NR^{14}R^{10}$, -$L^2SO_2NR^{13}R^{14}$, -$L^2SO_2N$=$CR^{13}NR^{13}R^{14}$, -$L^2SO_2NR^{13}C$(=O)$R^{10}$, -$L^2$C(=O)$NR^{13}SO_2R^{10}$, -$L^2$S(=O)$R^{10}$, -$L^2$S(=O)(=$NR^{13}$)$R^{10}$, -$L^2NR^{13}SO_2NR^{13}R^{14}$, -$L^2NR^{13}SO_2R^{10}$, -$L^2NR^{13}R^{14}$, -$L^2NR^{13}$C(=O)$R^{13}$, -$L^2NR^{13}$C(=O)$OR^{10}$, -$L^2$C(=O)$NR^{13}R^{14}$, and -$L^2$C(=O)$OR^{13}$;
$R^{10}$ at each occurrence is independently selected from $C_1$-$C_4$alkyl, $C_1$-$C_3$haloalkyl, 3-6 membered cycloalkyl, phenyl, 5-6 membered heteroaryl having 1 to 4 heteroatoms independently selected from N, O and S as ring members, 4-6 membered heterocycloalkyl containing one or two ring members independently selected from N, NH, $NR^{17}$, O or S and 4-6 membered heterocyclyl containing 1 to 2 ring members independently selected from N, NH, $NR^{17}$, O or S,
wherein each $R^{10}$ is optionally substituted with 1 to 5 groups independently selected from $C_1$-$C_4$alkyl, deuterium, $C_1$-$C_4$haloalkoxy, -$L^3$OH, -$L^3$CN, -$L^3$OC(=O)$R^{14}$, -$L^3OR^{13}$, $C_1$-$C_2$haloalkyl, oxo, -$L^3$halo, -$L^3C_1$-$C_3$alkoxy, -$L^3$OC(=O)$NR^{13}R^{14}$, -$L^3SO_2R^{13}$, -$L^3SO_2NR^{13}R^{14}$, -$L^3SO_2NR^{13}$C(=O)$R^{13}$, -$L^3$C(=O)$NR^{13}SO_2R^{13}$, -$L^3$S(=O)$R^{13}$, -$L^3$S(=O)(=$NR^{14}$)$R^{13}$, -$L^3NR^{13}SO_2NR^{13}R^{14}$, -$L^3NR^{13}SO_2R^{13}$, -$L^3NR^{13}R^{14}$, -$L^3NR^{14}$C(=O)$R^{13}$, -$L^3NR^{14}$C(=O)$OR^{13}$, -$L^3$C(=O)$NR^{13}R^{14}$, -$L^3$C(=O)$OR^{13}$, -$L^3$-(4-7-membered heterocycloalkyl containing 1 to 2 ring members independently selected from N, NH, $NR^{17}$, O or S), -$L^3$-(4-7-membered heterocyclyl containing 1 to 2 ring members independently selected from N, NH, $NR^{17}$, O or S), -$L^3$-$C_3$-$C_5$cycloalkyl, and -$L^3$-(5-6 membered heteroaryl ring having 1 to 4 heteroatoms comprising 1-4 nitrogen atoms, 0 or 1 oxygen atoms, and 0 or 1 sulfur atoms as ring members), where the $C_1$-$C_4$alkyl, 4-7-membered heterocycloalkyl, 4-7-membered heterocyclyl, $C_3$-$C_5$cycloalkyl and 5-6 membered heteroaryl ring are each optionally further substituted with 1 to 3 groups independently selected from halo, $C_1$-$C_3$alkyl, $C_1$-$C_3$haloalkyl, -$L^4OR^{13}$, -$L^4CN$, and -$L^4NR^{13}R^{14}$;

$R^{11}$ and $R^{12}$ are each independently selected from H and $C_1$-$C_4$alkyl;

each $R^{13}$ is independently selected from H, $C_1$-$C_4$alkyl, a 4-7-membered heterocycloalkyl containing 1 to 2 ring members independently selected from N, NH, $NR^{17}$, O or S, a 4-7-membered heterocyclyl containing 1 to 2 ring members independently selected from N, NH, $NR^{17}$, O or S, and a $C_3$-$C_6$cycloalkyl, wherein the $C_1$-$C_4$alkyl, heterocyclyl and $C_3$-$C_6$cycloalkyl are optionally substituted with 1 to 3 groups independently selected from $C_1$-$C_4$alkyl, halo, —OH, —$NR^{15}R^{16}$, —C(=O)$OR^{15}$, $C_1$-$C_2$alkoxy and $C_1$-$C_4$alkyl substituted with 1 to 2 hydroxy groups;

$R^{14}$ is selected from H, $C_1$-$C_4$alkyl and $C_3$-$C_6$cycloalkyl, wherein the $C_1$-$C_4$alkyl and $C_3$-$C_6$cycloalkyl are optionally substituted with 1 to 3 groups independently selected from $C_1$-$C_4$alkyl, halo, —OH, —$NR^{15}R^{16}$, $C_1$-$C_2$alkoxy and $C_1$-$C_4$alkyl substituted with 1 to 2 hydroxy groups;

or $R^{13}$ and $R^{14}$, taken together with a nitrogen atom to which both are directly attached, can form a 4-6 membered ring optionally containing an additional N, O or S as a ring member and optionally substituted with one to three groups selected from $C_1$-$C_2$alkyl, $C_1$-$C_2$alkoxy, oxo, and hydroxy;

each $L^2$ and $L^3$ and $L^4$ is independently a bond or a straight chain or branched $C_1$-$C_3$alkylene, and '---' represents a single or double bond;

with a compound of Formula (I-2):

(I-2)

wherein:

$R^B$ is phenyl, pyridinyl, thiophenyl, pyrimidinyl, or a 5-8 membered cycloalkyl, wherein $R^B$ is optionally substituted with 1 to 3 $R^5$ groups;

$R^1$ is selected from H, $C_1$-$C_3$alkyl and $C_1$-$C_3$alkyl substituted with 1 to 3 —OH groups;

$R^2$ is selected from H, $C_1$-$C_3$alkyl and $C_1$-$C_3$alkyl substituted with 1 to 3 —OH groups;

or $R^1$ and $R^2$ taken together with the carbon to which they are attached can form a 3-6 membered cycloalkyl ring;

each $R^5$ is independently selected from halo, —CN, hydroxy, —$NR^{13}R^{14}$, $C_3$-$C_6$cycloalkyl, $C_1$-$C_3$alkoxy, $C_1$-$C_3$haloalkyl, and $C_1$-$C_3$alkyl optionally substituted with 1 to 3 $R^6$ groups, wherein when $R^B$ is substituted with two $R^5$ and each $R^5$ is a $C_1$-$C_3$alkyl optionally substituted with 1 to 3 $R^6$ groups, when directly attached to the same carbon atom, may be taken together with the carbon to which both are directly attached to form a 3-5 membered cycloalkyl ring optionally substituted with 1 to 3 $R^6$ groups;

each $R^6$ is independently selected from halo, hydroxy, CN, $C_1$-$C_3$alkoxy, $C_1$-$C_3$alkyl, and $C_3$-$C_5$cycloalkyl, or two $R^6$ groups, taken together with a carbon atom to which both are directly attached may form a 3-5 membered cycloalkyl ring or a 4-6 membered heterocyclic ring containing O, N or S as a ring member and optionally substituted with 1 to 2 groups independently selected from oxo and $C_1$-$C_3$alkyl;

each $R^{13}$ is independently selected from H, $C_1$-$C_4$alkyl, a 4-7-membered heterocycloalkyl containing 1 to 2 ring members independently selected from N, NH, $NR^{17}$, O or S, a 4-7-membered heterocyclyl containing 1 to 2 ring members independently selected from N, NH, $NR^{17}$, O or S, and a $C_3$-$C_6$cycloalkyl, wherein the $C_1$-$C_4$alkyl, heterocyclyl and $C_3$-$C_6$cycloalkyl are optionally substituted with 1 to 3 groups independently selected from $C_1$-$C_4$alkyl, halo, —OH, —$NR^{15}R^{16}$, —C(=O)$OR^{15}$, $C_1$-$C_2$alkoxy and $C_1$-$C_4$alkyl substituted with 1 to 2 hydroxy groups;

$R^{14}$ is selected from H, $C_1$-$C_4$alkyl and $C_3$-$C_6$cycloalkyl, wherein the $C_1$-$C_4$alkyl and $C_3$-$C_6$cycloalkyl are optionally substituted with 1 to 3 groups independently selected from $C_1$-$C_4$alkyl, halo, —OH, —$NR^{15}R^{16}$, $C_1$-$C_2$alkoxy and $C_1$-$C_4$alkyl substituted with 1 to 2 hydroxy groups;

or $R^{13}$ and $R^{14}$, taken together with a nitrogen atom to which both are directly attached, can form a 4-6 membered ring optionally containing an additional N, O or S as a ring member and optionally substituted with one to three groups selected from $C_1$-$C_2$alkyl, $C_1$-$C_2$alkoxy, oxo, and hydroxy;

$R^{15}$ and $R^{16}$ are each independently selected from H and $C_1$-$C_4$alkyl, and each $R^{17}$ is independently selected from H, $C_1$-$C_4$alkyl and $C_3$-$C_8$cycloalkyl.

Typically, for these methods, the compounds of Formula (A) and Formula (I-2) are brought together or mixed in the presence of an inert solvent under conditions suitable for formation of an amide bond, including known methods used for peptide synthesis. For example, where X represents —OH, any of wide range of dehydrating agents suitable for formation of an amide bond from an amine and a carboxylic acid can be used. Some of these are illustrated by the Examples herein, and include carbodiimides (e.g., dicyclohexyl carbodiimide; diisopropyl carbodiimide; EDC; and the like). Optionally, reaction with a carbodiimide can be facilitated by the presence of an activating agent such as HOBt, HOAt, N-hydroxysuccinimide, or the like. Alternatively, the acid of Formula (A) or a salt thereof can be activated by reaction with an activating agent such as HATU, HBTU, BOP, PyBOP, PyBrOP, TBTU, COMU, or TFFH, optionally in the presence of a base such as triethylamine, DIPEA, DMAP, pyridine, and the like, prior to being contacted with the amine compound of Formula (I-2). Where X represents a leaving group, it can be halo (e.g. Cl), or an acyl group such as —OC(O)—O—R* where R* represents a $C_1$-$C_6$ alkyl, optionally substituted with up to three halo or $C_{1-3}$ alkoxy groups.

In certain embodiments, the compound of Formula (A) is a compound of Formula (VII):

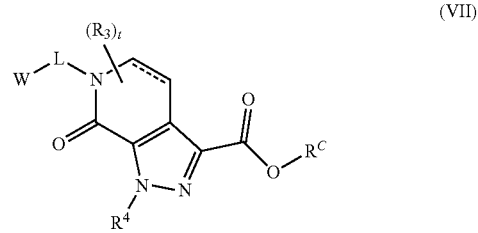

(VII)

where $R^C$ is H; L is —CH$_2$—; and W is cyclopropyl substituted with —SO$_2$R$^{10}$, —SO$_2$NR$^{14}$R$^{10}$, or —SO$_2$NR$^{13}$R$^{14}$, where t, R$^{10}$, R$^{13}$ and R$^{14}$ are as defined for Formula (A).

The compounds of Formula (A) and (I-2) as described above and methods of using them to make compounds of the invention are also aspects of the invention.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

Pharmaceutical Compositions and Routes of Administration

Included within the scope of this invention is a pharmaceutical composition comprising a compound of Formula (I), or a pharmaceutically acceptable salt thereof, and a pharmaceutically acceptable carrier.

According to a further aspect of this embodiment the pharmaceutical composition according to this invention further comprises a therapeutically effective amount of at least one other antiviral agent.

The compounds of the invention can be administered by known methods, including oral, parenteral, inhalation, and the like. In certain embodiments, the compound of the invention is administered orally, as a pill, lozenge, troche, capsule, solution, or suspension. In other embodiments, a compound of the invention is administered by injection or infusion. Infusion is typically performed intravenously, often over a period of time between about 15 minutes and 4 hours. In other embodiments, a compound of the invention is administered intranasally or by inhalation; inhalation methods are particularly useful for treatment of respiratory infections. Compounds of the present invention exhibit oral bioavailability, and can be administered by oral administration.

The language "pharmaceutical composition" includes preparations suitable for administration to mammals, e.g. humans. When the compounds of the present invention are administered as pharmaceuticals to mammals, e.g., humans, they can be given per se or as a pharmaceutical composition containing, for example, 0.1 to 99.5% (e.g., 0.5 to 90%) of at least one compound of Formula (I) or any subgenus thereof as active ingredient in combination with a pharmaceutically acceptable carrier, or optionally two or more pharmaceutically acceptable carriers.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Typically, pharmaceutically acceptable carriers are sterilized and/or substantially pyrogen-free.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, inhalation, topical, transdermal, buccal, sublingual, rectal, vaginal and/or parenteral administration. The formulations may conveniently be presented in unit dosage form and may be prepared by suitable methods. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, e.g. from about 5 percent to about 70 percent, or from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored base, for example, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration may comprise one or more compounds of the invention in combination with one or more pharmaceutically acceptable carriers such as sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, glycol ethers, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. In some embodiments, compounds of the invention are administered by Intravenous infusion. Infusion may be used to deliver a single daily dose or multiple doses. In some embodiments, a compound of the invention is administered by infusion over an interval between 15 minutes and 4 hours, typically between 0.5 and 3 hours. Such infusion may be used once per day, twice per day or up to three times per day.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors.

A physician or veterinarian having ordinary skill in the art can determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated effects, will range from about 0.0001 to about 100 mg per kilogram of body weight per day, more e.g. from about 0.01 to about 50 mg per kg per day, or from about 0.1 to about 20 mg per kg per day. An effective amount is that amount which prevents or treats a viral infection, such as CMV or another herpesvirus.

If desired, the effective daily dose of the active compound may be administered as a single dose per day, or as two, three, four, five, six or more sub-doses administered separately at appropriate intervals throughout the day, optionally, in unit dosage forms. Compounds delivered orally or by inhalation, are commonly administered in one to four doses per day. Compounds delivered by injection are typically administered once per day, or once every other day. Compounds delivered by infusion are typically administered in one to three doses per day. When multiple doses are administered within a day, the doses may be administered at intervals of about 4 hours, about 6 hours, about 8 hours or about 12 hours.

While it is possible for a compound of the present invention to be administered alone, they are generally administered as a pharmaceutical composition such as those described herein. Thus methods of using the compounds of the invention include administering the compound as a pharmaceutical composition, wherein at least one compound of the invention is admixed with a pharmaceutically acceptable carrier prior to administration.

Various embodiments of the pharmaceutical compositions of the invention are described herein. It will be recognized that features specified in each embodiment may be combined with other specified features to provide further embodiments. The following enumerated embodiments are representative of the pharmaceutical compositions of the invention.

Embodiment 171. A pharmaceutical composition, comprising a compound of Formula (I) or according to any one of Embodiments 1 to 153, or a pharmaceutically acceptable salt thereof, and at least one pharmaceutically acceptable carrier.

Embodiment 172. The pharmaceutical composition of Embodiment 154 further comprising a at least one other antiviral agent.

Embodiment 173. The pharmaceutical composition of Embodiment 155 wherein the at least one other antiviral agent is selected from a herpesvirus entry inhibitor; a herpesvirus early transcription event inhibitor; a herpesvirus helicase-primase inhibitor; a herpesvirus DNA polymerase inhibitor such as Ganciclovir (Cytovene®), Valganciclovir (Valcyte®; Cymeval®), Cidofovir (Vistide®), Foscarnet (Foscavir®), CMX001, cyclopropavir (MBX-400) and Valaciclovir (Valtrex®; Zelitrex®); an inhibitor of UL97 kinase such as Maribavir; a herpesvirus protease inhibitor; a herpesvirus terminase inhibitor such as AIC246 (Letermovir); a herpesvirus maturation inhibitor; other inhibitors such as Artesunate; a CMV vaccine such as TransVax and a herpesvirus biological agent such as Cytogam (Cytotect®).

Embodiment 174. A pharmaceutical composition, comprising a compound of Formula (I) or according to any one of Embodiments 154 to 170, or a pharmaceutically acceptable salt thereof, and at least one pharmaceutically acceptable carrier.

Embodiment 175. The pharmaceutical composition of Embodiment 174 further comprising a at least one other antiviral agent.

Embodiment 176. The pharmaceutical composition of Embodiment 175 wherein the at least one other antiviral agent is selected from a herpesvirus entry inhibitor; a herpesvirus early transcription event inhibitor; a herpesvirus helicase-primase inhibitor; a herpesvirus DNA polymerase inhibitor such as Ganciclovir (Cytovene®), Valganciclovir (Valcyte®; Cymeval®), Cidofovir (Vistide®), Foscarnet (Foscavir®), CMX001, cyclopropavir (MBX-400) and Valaciclovir (Valtrex®; Zelitrex®); an inhibitor of UL97 kinase such as Maribavir; a herpesvirus protease inhibitor; a herpesvirus terminase inhibitor such as AIC246 (Letermovir); a herpesvirus maturation inhibitor; other inhibitors such as Artesunate; a CMV vaccine such as TransVax and a herpesvirus biological agent such as Cytogam (Cytotect®).

Pharmacology and Utility

Another aspect of the invention involves a method of treating or preventing a herpesvirus disease and/or infection in a human being by administering to the human being an antivirally effective amount of a compound of the invention, a pharmaceutically acceptable salt thereof, or a composition as described above, alone or in combination with at least one other antiviral agent, administered together or separately.

Still another aspect of this invention relates to a method of inhibiting the replication of CMV or another herpesvirus, comprising exposing the virus to an effective amount of the compound of Formula (I), or a salt thereof, under conditions where replication of the virus is inhibited. This method can be practiced in vitro or in vivo.

Also within the scope of this invention is the use of a compound of Formula (I), or a pharmaceutically acceptable salt thereof, in the manufacture of a medicament for the treatment or prevention of a herpesvirus disease and/or infection in a human being, including CMV.

Another embodiment of the invention provides a compound as described above, or a pharmaceutically acceptable salt thereof, as a medicament.

The invention also provides the use of a pharmaceutical composition as described herein for the treatment of a CMV infection or other herpesvirus in a human being having or at risk of having the infection.

The invention also provides the use of a pharmaceutical composition as described herein for the treatment of CMV disease or other herpesvirus infection in a human being having or at risk of having the disease.

An additional aspect of this invention refers to an article of manufacture comprising a composition effective to treat a herpesvirus disease and/or infection; and packaging material comprising a label which indicates that the composition can be used to treat disease and/or infection by a herpesvirus such as CMV; wherein the composition comprises a compound of Formula (I) according to this invention or a pharmaceutically acceptable salt thereof.

Further included in the scope of the invention is the use of a compound of Formula (I), or a salt thereof, to inhibit the replication of CMV.

The dose range of the compounds of the invention applicable per day is usually from 0.01 to 100 mg/kg of body weight, e.g. from 0.1 to 50 mg/kg of body weight. Each dosage unit may conveniently contain from 5% to 95% active compound (w/w). For example, such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

An "effective amount" of a compound is that amount necessary or sufficient to treat or prevent a viral infection and/or a disease or condition described herein. In an example, an effective amount of a herpesvirus or CMV DNA polymerase inhibitor of Formula I is an amount sufficient to treat viral infection in a subject. In another example, an effective amount of the DNA polymerase inhibitor is an amount sufficient to treat a viral infection, such as, but not limited to CMV, VZV or EBV, in a subject in need of such treatment. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a viral infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. The invention provides methods of use of compounds of the present invention in the treatment of these diseases or for preparation of pharmaceutical compositions having compounds of the present invention for the treatment of these diseases.

Another aspect of the invention involves a method of treating viral disease and/or infection in a human being, the method comprising administering to the human being an antivirally effective amount of a compound of the invention, a pharmaceutically acceptable salt thereof, or a composition as described above, alone or in combination with at least one other antiviral agent, administered together or separately, wherein the viral disease or infection is selected from CMV infection in immunocompromised patients (e.g. transplant recipients), congenital CMV, genital herpes, oral herpes (cold sores), herpetic keratitis, neonatal herpes, herpes encephalitis, varicella (chickenpox), herpes zoster (shingles), infectious mononucleosis, post-transplant lymphoproliferative disease (PTLD), Castelman's disease and hemophagocytic lymphohistiocytosis.

Another aspect of the invention involves a method of treating a disorder that may be induced/exacerbated/accelerated by herpesvirus infections in a human being, the method comprising administering to the human being an effective amount of a compound of the invention, a pharmaceutically acceptable salt thereof, or a composition as described above, alone or in combination with at least one other antiviral agent, administered together or separately, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), celiac disease and type 1 diabetes.

Another aspect of the invention involves a method of treating a disorder that may be induced/exacerbated/accelerated by herpesvirus infections in a human being, the method comprising administering to the human being an effective amount of a compound of the invention, a pharmaceutically acceptable salt thereof, or a composition as described above, alone or in combination with at least one other antiviral agent, administered together or separately, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), atherosclerosis (AS), celiac disease and type 1 diabetes.

Another aspect of the invention is the use of a compound of the invention, or a pharmaceutically acceptable salt thereof, in the manufacture of a medicament for the treatment or prevention of a disorder that may be induced/exacerbated/accelerated by herpesvirus infections, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), celiac disease and type 1 diabetes.

Another aspect of the invention is the use of a compound of the invention, or a pharmaceutically acceptable salt thereof, in the manufacture of a medicament for the treatment or prevention of a disorder that may be induced/exacerbated/accelerated by herpesvirus infections, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), atherosclerosis (AS), celiac disease and type 1 diabetes.

Another aspect of the invention is the use of a pharmaceutical composition as described herein for the treatment of a viral disease and/or infection in a human being, wherein the viral disease or infection is selected from CMV infection in immunocompromised patients (e.g. transplant recipients), congenital CMV, genital herpes, oral herpes (cold sores), herpetic keratitis, neonatal herpes, herpes encephalitis, varicella (chickenpox), herpes zoster (shingles), infectious mononucleosis, post-transplant lymphoproliferative disease (PTLD), Castelman's disease and hemophagocytic lymphohistiocytosis.

Another aspect of the invention is the use of a pharmaceutical composition as described herein for the treatment of a disorder that may be induced/exacerbated/accelerated by herpesvirus infections, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), celiac disease and type 1 diabetes.

Another aspect of the invention is the use of a pharmaceutical composition as described herein for the treatment of a disorder that may be induced/exacerbated/accelerated by herpesvirus infections, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), atherosclerosis (AS), celiac disease and type 1 diabetes.

Various embodiments of the methods of treatment and use of the compounds of the invention are described herein. It will be recognized that features specified in each embodiment may be combined with other specified features to provide further embodiments. The following enumerated embodiments are representative of methods of treatment and use of the compounds of the invention.

Embodiment 177. A method to treat a herpesvirus infection, which comprises administering to a patient having a herpesvirus infection a compound of Formula (I) of any one of Embodiments 1-153 or a pharmaceutical composition comprising a compound of Formula (I) or any one of Embodiments 1-153.

Embodiment 178. The method of Embodiment 177, wherein the herpesvirus is selected from cytomegalovirus (CMV), Epstein-Barr virus (EBV), Varicella zoster virus (VZV), herpes simplex virus including HSV-1 and HSV-2, herpesvirus 6, human herpesvirus 7, and Kaposi's sarcoma-associated herpesvirus.

Embodiment 179. A method to treat a herpesvirus infection, which comprises administering to a patient having a herpesvirus infection a compound of Formula (I) of any one of Embodiments 154-170 or a pharmaceutical composition comprising a compound of Formula (I) or any one of Embodiments 154-170.

Embodiment 180. The method of Embodiment 179, wherein the herpesvirus is selected from cytomegalovirus (CMV), Epstein-Barr virus (EBV), Varicella zoster virus (VZV), herpes simplex virus including HSV-1 and HSV-2, herpesvirus 6, human herpesvirus 7, and Kaposi's sarcoma-associated herpesvirus.

Embodiment 181. Use of a compound of any one of Embodiments 1-170, of a pharmaceutically acceptable salt thereof, for the preparation of a medicament for the treatment of a viral infection.

Embodiment 182. A compound for use in the treatment of a viral infection in a patient in need thereof, comprising a compound of any one of Embodiments 1-170.

Embodiment 183. A compound as disclosed in Examples 1-262.

Embodiment 184. Use of a compound of any one of Embodiments 1-170 and 183 in the treatment of a viral infection.

Combination Treatment

In some embodiments, the compound of Formula (I) is co-administered with at least one additional agent selected from: a herpesvirus entry inhibitor, a herpesvirus early transcription event inhibitor, a herpesvirus helicase-primase inhibitor, another herpesvirus DNA polymerase inhibitor, an inhibitor of UL97 kinase, a herpesvirus protease inhibitor, a herpesvirus terminase inhibitor, a herpesvirus maturation inhibitor, an inhibitor of another target in the herpesvirus life cycle, a herpesvirus vaccine and a herpesvirus biological agent. In some embodiments, the herpesvirus is CMV.

These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of the invention, or a pharmaceutically acceptable salt thereof.

When the composition of this invention comprises a combination of a compound of the invention and one or more additional therapeutic or prophylactic agent, both the compound and the additional agent should be present at dosage levels of between about 10 to 100%, for example between about 10 and 80% of the dosage normally administered in a monotherapy regimen.

Antiviral agents contemplated for use in such combination therapy include agents (compounds or biologicals) that are effective to inhibit the formation and/or replication of a virus in a human being, including but not limited to agents that interfere with either host or viral mechanisms necessary for the formation and/or replication of a virus in a human being. Such agents can be selected from: a herpesvirus entry inhibitor; a herpesvirus early transcription event inhibitor; a herpesvirus helicase-primase inhibitor; a herpesvirus DNA polymerase inhibitor such as Ganciclovir (Cytovene®), Valganciclovir (Valcyte®; Cymeval®), Cidofovir (Vistide®), Foscarnet (Foscavir®), CMX001, cyclopropavir (MBX-400) and Valaciclovir (Valtrex®; Zelitrex®); an inhibitor of UL97 kinase such as Maribavir; a herpesvirus protease inhibitor; a herpesvirus terminase inhibitor such as AIC246 (Letermovir); a herpesvirus maturation inhibitor; other inhibitors such as Artesunate; a CMV vaccine such as TransVax and a herpesvirus biological agent such as Cytogam (Cytotect®).

A compound of the present invention may also be used in combination with other agents (combination partners), e.g., an additional antiviral agent that is or is not of the formula I, for treatment of a viral infection in a subject.

By the term "combination", is meant either a fixed combination in one dosage unit form, as separate dosage forms suitable for use together either simultaneously or sequentially, or as a kit of parts for the combined administration where a compound of the present invention and a combination partner may be administered independently at the same time or separately within time intervals that especially allow that the combination partners show a cooperative, e.g., synergistic, effect, or any combination thereof.

In certain embodiments of the present invention, a compound of the present invention is used in combination with a second antiviral agent, such as those named herein.

The second antiviral agent may be administered in combination with the compounds of the present inventions wherein the second antiviral agent is administered prior to, simultaneously, or after the compound or compounds of the present invention. When simultaneous administration of a compound of the invention with a second agent is desired and the route of administration is the same, then a compound of the invention may be formulated with a second agent into the same dosage form. An example of a dosage form containing a compound of the invention and a second agent is a tablet or a capsule.

In some embodiments, a combination of a compound of the invention and a second antiviral agent may provide synergistic activity. The compound of the invention and second antiviral agent may be administered together, separate but simultaneously, or sequentially.

Use of Compounds of the Invention in Combination with Immunomodulators

The compounds and compositions described herein can be used or administered in combination with one or more therapeutic agents that act as immunomodulators, e.g., an activator of a costimulatory molecule, or an inhibitor of an immune-inhibitory molecule, or a vaccine. The Programmed Death 1 (PD-1) protein is an inhibitory member of the extended CD28/CTLA4 family of T cell regulators (Okazaki et al. (2002) Curr Opin Immunol 14: 391779-82; Bennett et al. (2003) J. Immunol. 170:711-8). PD-1 is expressed on activated B cells, T cells, and monocytes. PD-1 is an immune-inhibitory protein that negatively regulates TCR signals (Ishida, Y. et al. (1992) EMBO J. 11:3887-3895; Blank, C. et al. (Epub 2006 Dec. 29) Immunol. Immunother. 56(5):739-745), and is up-regulated in chronic infections. The interaction between PD-1 and PD-L1 can act as an immune checkpoint, which can lead to, e.g., a decrease in infiltrating lymphocytes, a decrease in T-cell receptor mediated proliferation, and/or immune evasion by cancerous or infected cells (Dong et al. (2003) J. Mol. Med, 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66). Immunomodulation can be achieved by binding to either the immune-inhibitory protein (e.g., PD-1) or to binding proteins that modulate the inhibitory protein (e.g., PD-L1, PD-L2).

In one embodiment, the combination therapies of the invention include an immunomodulator that is an inhibitor or antagonist of an inhibitory molecule of an immune checkpoint molecule. In another embodiment the immunomodulator binds to a protein that naturally inhibits the immuno-inhibitory checkpoint molecule. When used in combination with antiviral compounds, these immunomodulators can enhance the antiviral response, and thus enhance efficacy relative to treatment with the antiviral compound alone.

The term "immune checkpoints" refers to a group of molecules on the cell surface of CD4 and CD8 T cells. These molecules can effectively serve as "brakes" to down-modulate or inhibit an adaptive immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells. Immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD160, 24 and/or TGFR beta. Inhibition of an inhibitory molecule can be performed by inhibition at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide, e.g., a soluble ligand, or an antibody or antigen-binding fragment thereof, that binds to the inhibitory molecule.

By "in combination with," it is not intended to imply that the therapy or the therapeutic agents must be administered at the same time and/or formulated for delivery together, although these methods of delivery are within the scope described herein. The immunomodulator can be administered concurrently with, prior to, or subsequent to, one or more compounds of the invention, and optionally one or more additional therapies or therapeutic agents. The therapeutic agents in the combination can be administered in any order. In general, each agent will be administered at a dose and/or on a time schedule determined for that agent. It will further be appreciated that the therapeutic agents utilized in this combination may be administered together in a single composition or administered separately in different compositions. In general, it is expected that each of the therapeutic agents utilized in combination be utilized at levels that do not exceed the levels at which they are utilized individually. In some embodiments, the levels utilized in combination will be lower than those utilized individually.

In certain embodiments, the antiviral compounds described herein are administered in combination with one or more immunomodulators that are inhibitors of PD-1, PD-L1 and/or PD-L2. Each such inhibitor may be an antibody, an antigen binding fragment thereof, an immunoadhesin, a fusion protein, or an oligopeptide. Examples of such immunomodulators are known in the art.

In some embodiments, the immunomodulator is an anti-PD-1 antibody chosen from MDX-1106, Merck 3475 or CT-011.

In some embodiments, the immunomodulator is an immunoadhesin (e.g., an immunoadhesin comprising an extracellular or PD-1 binding portion of PD-LI or PD-L2 fused to a constant region (e.g., an Fc region of an immunoglobulin sequence).

In some embodiments, the immunomodulator is a PD-1 inhibitor such as AMP-224.

In some embodiments, the immunomodulator is a PD-LI inhibitor such as anti-PD-LI antibody.

In some embodiments, the immunomodulator is an anti-PD-LI binding antagonist chosen from YW243.55.S70, MPDL3280A, MEDI-4736, MSB-0010718C, or MDX-1105. MDX-1105, also known as BMS-936559, is an anti-PD-LI antibody described in WO2007/005874. Antibody YW243.55.S70 is an anti-PD-LI described in WO 2010/077634.

In some embodiments, the immunomodulator is nivolumab (CAS Registry Number: 946414-94-4). Alternative names for nivolumab include MDX-1106, MDX-1106-04, ONO-4538, or BMS-936558. Nivolumab is a fully human IgG4 monoclonal antibody which specifically blocks PD-1. Nivolumab (clone $5C_4$) and other human monoclonal antibodies that specifically bind to PD-1 are disclosed in U.S. Pat. No. 8,008,449, EP2161336 and WO2006/121168.

In some embodiments, the immunomodulator is an anti-PD-1 antibody Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al (2013) New England Journal of Medicine 369 (2): 134-44, U.S. Pat. No. 8,354,509, WO2009/114335, and WO2013/079174.

In some embodiments, the immunomodulator is Pidilizumab (CT-011; Cure Tech), a humanized IgG1k monoclonal antibody that binds to PD1. Pidilizumab and other humanized anti-PD-1 monoclonal antibodies are disclosed in WO2009/101611.

Other anti-PD1 antibodies useful as immunomodulators for use in the methods disclosed herein include AMP 514 (Amplimmune), and anti-PD1 antibodies disclosed in U.S. Pat. No. 8,609,089, US 2010028330, and/or US 20120114649. In some embodiments, the anti-PD-L1 antibody is MSB0010718C. MSB0010718C (also referred to as A09-246-2; Merck Serono) is a monoclonal antibody that binds to PD-L1.

In some embodiments, the immunomodulator is MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents useful as immunomodulators for methods of the invention include YW243.55.570 (see WO2010/077634), MDX-1105 (also referred to as BMS-936559), and anti-PD-L1 binding agents disclosed in WO2007/005874.

In some embodiments, the immunomodulator is AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the immunomodulator is an anti-LAG-3 antibody such as BMS-986016. BMS-986016 (also referred to as BMS986016) is a monoclonal antibody that binds to LAG-3. BMS-986016 and other humanized anti-LAG-3 antibodies are disclosed in US 2011/0150892, WO2010/019570, and WO2014/008218

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CDT LIGHT, NKG2C, SLAMF7, NKp80, CD160, B7-H3 or CD83 ligand.

In another embodiment, the combination therapies disclosed herein include an immunomodulator that is a costimulatory molecule, e.g., an agonist associated with a positive signal that includes a costimulatory domain of CD28, CD27, ICOS and/or GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 09050581, U.S. Pat. No. 8,586,023, PCT Publication Nos.: WO 2010/003118 and 2011/090754, or an anti-GITR antibody described, e.g., in U.S. Pat. No. 7,025,962, European Patent No.: 194718381, U.S. Pat. Nos. 7,812,135, 8,388,967, 8,591,886, European Patent No.: EP 1866339, PCT Publication No.: WO 2011/028683, PCT Publication No. WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the immunomodulator used is a soluble ligand (e.g., a CTLA-4-Ig), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example. Exemplary anti-CTLA4 antibodies include Tremelimumab (IgG2 monoclonal antibody available from Pfizer, formerly known as ticilimumab, CP-675,206); and lpilimumab (CTLA-4 antibody, also known as MDX-010, CAS No. 477202-00-9).

In one embodiment, an anti-PD-1 antibody molecule is administered after treatment with a compound of the invention as described herein.

In another embodiment, an anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) Cancer Res. 72(4):917-27).

Exemplary immunomodulators that can be used in the combination therapies include, but are not limited to, e.g., afutuzumab (available from Roche®); pegfigrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

Exemplary doses of such immunomodulators that can be used in combination with the antiviral compounds of the invention include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Examples of embodiments of the methods of using the antiviral compounds of the invention in combination with an immunomodulator include these, which may be used along with a compound of Formula I or any subgenus or species thereof that is disclosed herein:

i. A method to treat a viral infection in a subject, comprising administering to the subject a compound of Formula (I) as described herein, and an immunomodulator.

ii. The method of embodiment i, wherein the immunomodulator is an activator of a costimulatory molecule or an inhibitor of an immune checkpoint molecule.

iii. The method of either of embodiments i and ii, wherein the activator of the costimulatory molecule is an agonist of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 and CD83 ligand.

iv. The method of any of embodiments i-iii above, wherein the inhibitor of the immune checkpoint molecule is chosen from PD-1, PD-L1, PD-L2, CTLA4, TIM3, LAG3, VISTA, BTLA, TIGIT, LAIR1, CD160, 2B4 and TGFR beta.

v. The method of any of any of embodiments i-iii, wherein the inhibitor of the immune checkpoint molecule is chosen from an inhibitor of PD-1, PD-L1, LAG-3, TIM-3 or CTLA4, or any combination thereof.

vi. The method of any of embodiments i-v, wherein the inhibitor of the immune checkpoint molecule is a soluble ligand or an antibody or antigen-binding fragment thereof, that binds to the immune checkpoint molecule.

vii. The method of any of embodiments i-vi, wherein the antibody or antigen-binding fragment thereof is from an IgG1 or IgG4 (e.g., human IgG1 or IgG4).

viii. The method of any of embodiments i-vii, wherein the antibody or antigen-binding fragment thereof is altered, e.g., mutated, to increase or decrease one or more of: Fc receptor binding, antibody glycosylation, the number of cysteine residues, effector cell function, or complement function.

ix. The method of any of embodiments i-viii, wherein the antibody molecule is a bispecific or multispecific antibody molecule that has a first binding specificity to PD-1 or PD-L1 and a second binding specificity to TIM-3, LAG-3, or PD-L2.

x. The method of any of embodiments i-ix, wherein the immunomodulator is an anti-PD-1 antibody chosen from Nivolumab, Pembrolizumab or Pidilizumab.

xi. The method of any of embodiments i-x, wherein the immunomodulator is an anti-PD-L1 antibody chosen from YW243.55.S70, MPDL3280A, MEDI-4736, MSB-0010718C, or MDX-1105.

xii. The method of any of embodiments i-x, wherein the immunomodulator is an anti-LAG-3 antibody molecule.

xiii. The method of embodiment xii, wherein the anti-LAG-3 antibody molecule is BMS-986016.

xiv. The method of any of embodiments i-x, wherein the immunomodulator is an anti-PD-1 antibody molecule administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg., e.g., once a week to once every 2, 3, or 4 weeks.

xv. The method of embodiment xiv, wherein the anti-PD-1 antibody molecule is administered at a dose from about 10 to 20 mg/kg every other week.

xvi. The method of embodiment xv, wherein the anti-PD-1 antibody molecule, e.g., nivolumab, is administered intravenously at a dose from about 1 mg/kg to 3 mg/kg, e.g., about 1 mg/kg, 2 mg/kg or 3 mg/kg, every two weeks.

xvii. The method of embodiment xv, wherein the anti-PD-1 antibody molecule, e.g., nivolumab, is administered intravenously at a dose of about 2 mg/kg at 3-week intervals.

EXAMPLES

The invention is further illustrated by the following examples, which should not be construed as limiting. The assays used throughout the Examples are well established in the art: demonstration of efficacy in these assays is generally regarded as predictive of efficacy in subjects.

LIST OF ABBREVIATIONS

| | |
|---|---|
| Ac | acetyl |
| ACN or MeCN | Acetonitrile |
| AcOEt/EtOAc | Ethyl acetate |
| AcOH | acetic acid |
| aq | aqueous |
| Bn | benzyl |
| Bu | butyl (nBu = n-butyl, tBu = tert-butyl) |
| CDI | Carbonyldiimidazole |
| $CH_3CN$ | Acetonitrile |
| DBU | 1,8-Diazabicyclo[5.4.0]-undec-7-ene |
| $Boc_2O$ | di-tert-butyl dicarbonate |
| DCE | 1,2-Dichloroethane |
| DCM | Dichloromethane |
| DIAD | Diisopropyl azodicarboxylate |
| DiBAI-H | Diisobutylaluminum Hydride |
| DIPEA or DIEA | N-Ethyldiisopropylamine |
| DMA | N,N-dimethylacetamide |
| DMAP | Dimethylaminopyridine |
| DMF | N,N-Dimethylformamide |
| DMSO | Dimethylsulfoxide |
| EDC | 1-Ethyl-3-(3-dimethylaminopropyl)carbodiimide |
| ESI | Electrospray ionisation |
| $Et_2O$ | Diethylether |
| $Et_3N$ | Triethylamine |
| Ether | Diethylether |
| EtOAc | Ethyl acetate |
| EtOH | Ethanol |
| FC | Flash Chromatography |
| h | hour(s) |
| HATU | O-(7-Azabenzotriazole-1-yl)-N,N,N'N'-tetramethyluronium hexafluorophosphate |
| HBTU | O-(Benzotriazol-1-yl)-N,N,N',N'-tetramethyluronium hexafluorophosphate |
| HCl | Hydrochloric acid |
| HMPA | Hexamethylphosphoramide |
| HOBt | 1-Hydroxybenzotriazole |
| HPLC | High Performance Liquid Chromatography |
| $H_2O$ | Water |
| IPA | isopropanol |
| L | liter(s) |
| LC-MS | Liquid Chromatography Mass Spectrometry |
| LiHMDS | Lithium bis(trimethylsilyl)amide |
| $MgSO_4$ | Magnesium Sulfate |
| Me | methyl |
| MeI | Iodomethane |
| MeOH | Methanol |
| mg | milligram |
| min | minute(s) |

-continued

LIST OF ABBREVIATIONS

| | |
|---|---|
| mL | milliliter |
| MS | Mass Spectrometry |
| MsCl | methanesulfonyl chloride |
| $NaHCO_3$ | Sodium Bicarbonate |
| $Na_2SO_4$ | Sodium Sulfate |
| NBS | N-bromosuccinimide |
| NCS | N-chlorosuccinimide |
| $NH_2OH$ | hydroxylamine |
| NMO | 4-methylmorpholine N-oxide |
| Pd/C | palladium on charcoal |
| $Pd(OH)_2$ | palladium hydroxide |
| PG | protecting group |
| Ph | phenyl |
| $Ph_3P$ | triphenyl phosphine |
| Prep | Preparative |
| Rf | ratio of fronts |
| RP | reverse phase |
| Rt | Retention time |
| RT | Room temperature |
| SFC | Supercritical Fluid Chromatography |
| $SiO_2$ | Silica gel |
| $SOCl_2$ | Thionyl Chloride |
| T3P ® | Propylphosphonic acid anhydride |
| TBAF | Tetrabutylammonium fluoride |
| TBDMS | t-Butyldimethylsilyl |
| TBDPS | t-Butyldiphenylsilyl |
| TBTU | O-(Benzotriazol-1-yl)-N,N,N',N'-tetramethyluronium tetrafluoroborate |
| TEA | Triethylamine |
| TFA | Trifluoroacetic acid |
| THF | Tetrahydrofuran |
| TIPS | Triisopropylsilyl |
| TLC | Thin Layer Chromatography |
| TPAP | tetrapropylammonium perruthenate |
| TsCl | toluene sulfonyl chloride |
| TsOH | toluene sulfonic acid |

Preparation of Key Intermediates

Intermediate 1

1-(bromomethyl)-1-(cyclopropylsulfonyl)cyclopropane (Int-1)

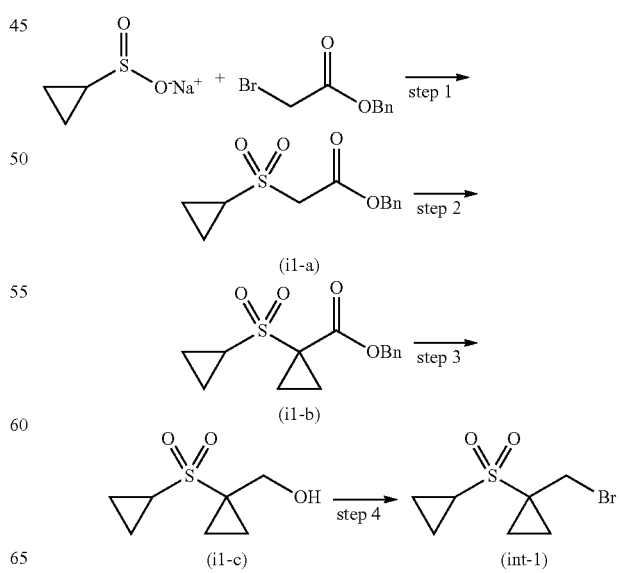

Step 1: To a slurry of sodium cyclopropanesulfinate (5.79 g, 45.2 mmol, 1.2 equiv) in DMF (30 mL) was added benzyl 2-bromoacetate (5.97 mL, 37.7 mmol, 1.0 equiv). The resulting mixture was stirred overnight at rt, then it was diluted with $H_2O$ and $Et_2O$. The layers were separated, then the aqueous layer was extracted with $Et_2O$. The combined organic extracts were washed with brine, dried with $Na_2SO_4$, filtered, and concentrated to afford benzyl 2-(cyclopropylsulfonyl)acetate (i1-a). $^1H$ NMR (400 MHz, $CDCl_3$) δ 7.44-7.34 (m, 5H), 5.26 (s, 2H), 4.09-4.03 (m, 2H), 2.76-2.67 (m, 1H), 1.31-1.24 (m, 2H), 1.09-1.02 (m, 2H).

Step 2: To a solution of benzyl 2-(cyclopropylsulfonyl)acetate (1-a) (937 g, 36.8 mmol, 2.0 equiv) in DMF (350 mL) was added $K_2CO_3$ (10.18 g, 73.7 mmol, 1.0 equiv) and 1,2-dibromoethane (3.81 mL, 44.2 mmol, 1.2 equiv). The resulting mixture was stirred at 60° C. for 12 h before it was cooled to rt and diluted with $Et_2O$. The solids were removed by filtration, the filtrate was washed with water, and the aqueous layer was extracted with $Et_2O$. The combined organic extracts were washed with brine, dried with $Na_2SO_4$, filtered, and concentrated. The oil was purified by column chromatography ($SiO_2$, 0-100% DCM/heptane) to afford benzyl 1-(cyclopropylsulfonyl)cyclopropanecarboxylate (i1-b). $^1H$ NMR (400 MHz, $CDCl_3$) δ 7.41-7.32 (m, 5H), 5.26-5.22 (m, 2H), 3.00 (tt, J=8.09, 4.90 Hz, 1H), 1.78-1.72 (m, 2H), 1.68-1.63 (m, 2H), 1.25-1.20 (m, 2H), 1.01-0.95 (m, 2H).

Step 3: To a solution of benzyl 1-(cyclopropylsulfonyl)cyclopropanecarboxylate (i1-b) (6.53 g, 23.29 mmol) in THF (50 mL) was added $LiBH_4$ (2.0 M in THF, 11.65 mL, 23.29 mmol). The resulting solution was stirred at rt overnight before the reaction mixture was added to a 2 M HCl/ice mixture. The biphasic mixture was extracted with DCM, then the combined organic extracts were dried with $Na_2SO_4$, filtered, and concentrated. The oil was purified by column chromatography ($SiO_2$, 0-100% EtOAc/heptane) to afford (1-(cyclopropylsulfonyl)cyclopropyl)methanol (i1-c). TLC $R_f$=0.2 (1:3 EtOAc/petroleum ether). $^1H$ NMR (400 MHz, $CDCl_3$) δ 3.92 (d, J=6.11 Hz, 2H), 2.59-2.50 (m, 2H), 1.52-1.47 (m, 2H), 1.29-1.23 (m, 2H), 1.10-1.01 (m, 4H). MS (ESI): m/z 177.1 $[M+H]^+$.

Step 4: A solution of (1-(cyclopropylsulfonyl)cyclopropyl)methanol (i1-c) (10.0 g, 56.7 mmol, 1.0 equiv) and DPPE (16.0 g, 39.7 mmol, 0.7 equiv) in THF (100 mL) was cooled 0° C. to before a solution of $CBr_4$ (38.0 g, 1135 mmol, 2.0 equiv) in THF (20 mL) was added over 0.5 h. After 90 min at 25° C., the solids were removed by filtration and the filtrate was concentrated. The residue was purified by column chromatography (SiO2, 10-25% EtOAc/petroleum ether) to give 1-(bromomethyl)-1-(cyclopropylsulfonyl)cyclopropane (int-1). TLC $R_f$=0.5 (25% EtOAc/petroleum ether). $^1H$ NMR (400 MHz, CDCl3) δ 3.89 (s, 2H), 2.66 (m, 1H), 1.78-1.69 (m, 2H), 1.33-1.26 (m, 2H), 1.23-1.18 (m, 2H), 1.16-1.09 (m, 2H).

Intermediate 2

1-(bromomethyl)-1-((1-methylcyclopropyl)sulfonyl)cyclopropane (Int-2)

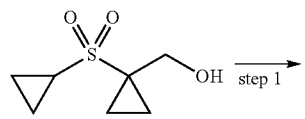

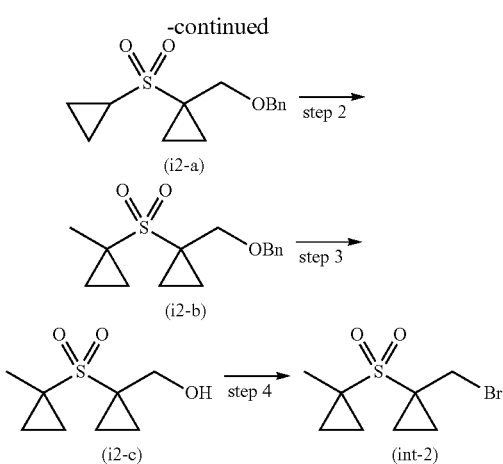

Step 1: A solution of (1-(cyclopropylsulfonyl)cyclopropyl)methanol (30 g, 170 mmol, 1.0 equiv) in DMF (300 mL) was cooled to 0° C. before NaH (60% in mineral oil, 13.6 g, 341 mmol, 2.0 equiv) was added portion wise (gas evolution). The reaction mixture was stirred at 0° C. for 0.5 h, then NaI (1.7 g, 17.0 mmol, 0.1 equiv) and BnBr (29 g, 170 mmol, 1.0 equiv) were added at 0° C. The reaction mixture was stirred at 0° C. for 3 h before it was poured into saturated $NH_4Cl$ (300 mL) and extracted with EtOAc (3×100 mL). The combined organic extracts were dried with $Na_2SO_4$, filtered and concentrated. The material was purified by trituration from EtOAc/petroleum ether to afford (((1-(cyclopropylsulfonyl)cyclopropyl)methoxy)methyl)benzene (i2-a). $^1H$ NMR (400 MHz, $CDCl_3$) δ 7.38-7.32 (m, 5H), 4.59 (s, 2H), 3.82 (s, 2H), 2.70 (m, 1H), 1.51-1.49 (m, 2H), 1.22-1.20 (m, 2H), 1.03-0.98 (m, 4H).

Step 2: n-BuLi (2.5 M in hexanes, 2.16 mL, 5.40 mmol, 1.2 equiv) was added dropwise to a solution of (((1-(cyclopropylsulfonyl)cyclopropyl)methoxy)methyl)benzene (i2-a) (1.2 g, 4.50 mmol, 1.0 equiv) in THF (20 mL) at −60° C. The reaction was stirred at 0° C. for 30 min, then MeI (0.84 mL, 13.5 mmol, 3.0 equiv) was added at 0° C. The reaction was stirred at 25° C. for 1 h before it was quenched with water (20 mL) and extracted with EtOAc (3×10 mL). The combined organic extracts were washed with brine (20 mL), dried over $Na_2SO_4$, filtered and concentrated. The residue was purified by RP-HPLC to give (((1-((1-methylcyclopropyl)sulfonyl)cyclopropyl)methoxy)methyl)benzene (i2-b). TLC $R_f$=0.4 (1:5 EtOAc/petroleum ether). MS (ESI): m/z 281.0 $[M+H]^+$.

Step 3: A mixture of (((1-((1-methylcyclopropyl)sulfonyl)cyclopropyl)methoxy)methyl)benzene (i2-b) (900 mg, 2.71 mmol, 1.0 equiv) and Pd/C (200 mg) in MeOH (10 mL) and AcOH (10 mL) was stirred under a hydrogen atmosphere at 20° C. for 12 h. The solids were removed by filtration and the filtrate was concentrated. The residue was diluted with water (10 mL), neutralized with saturated $Na_2CO_3$, and extracted with EtOAc (3×5 mL). The combined organic extracts were dried with $Na_2SO_4$, filtered and concentrated to provide (1-((1-methylcyclopropyl)sulfonyl) cyclopropyl)methanol (i2-c). TLC $R_f$=0.1 (1:5 EtOAc/petroleum ether). $^1H$ NMR (400 MHz, MeOH-$d_4$) δ 3.78 (s, 2H), 1.43 (s, 3H), 1.30-1.29 (m, 2H), 1.24-1.22 (m, 2H), 1.00-0.98 (m, 2H), 0.78-0.76 (m, 2H).

Step 4: A solution of (1-((1-methylcyclopropyl)sulfonyl)cyclopropyl)methanol) (i2-c) (220 mg, 1.16 mmol, 1.0 equiv) in THF (4 mL) was cooled to −40° C. before $Et_3N$ (234 mg, 2.32 mmol, 2.0 equiv) and MsCl (199 mg, 1.73 mmol, 1.5 equiv) were added. The mixture was stirred at −40° C. for 1 h, then it was placed in an ice bath and LiBr (502 mg, 5.78 mmol, 5.0 equiv) was added in one portion. The mixture was stirred at 25° C. for 1 h before it was diluted with water (20 mL) and extracted with EtOAc (3×20 mL). The combined organic extracts were washed with brine (20 mL), dried over Na$_2$SO$_4$, filtered and concentrated. The residue was purified by column chromatography (SiO$_2$, 10-25% EtOAc/petroleum ether) to afford 1-(bromomethyl)-1-((1-methylcyclopropyl)sulfonyl)cyclopropane (int-2). TLC R$_f$=0.8 (25% EtOAc/petroleum ether). $^1$H NMR (400 MHz, MeOH-d$_4$) δ 3.95 (s, 2H), 1.70-1.65 (m, 2H), 1.58 (s, 3H), 1.51-1.46 (m, 2H), 1.33-1.27 (m, 3H), 1.01-0.95 (m, 2H).

Intermediate 3

1-(bromomethyl)-1-(ethylsulfonyl)cyclopropane (Int-3)

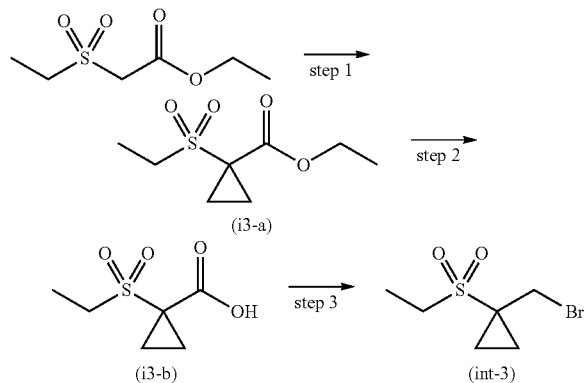

Step 1: Ethyl 1-(ethylsulfonyl)cyclopropanecarboxylate (i3-a) was obtained using the method described for the synthesis of intermediate (i1-b), except benzyl 2-(cyclopropylsulfonyl)acetate (1-a) was replaced with ethyl 2-(ethylsulfonyl)acetate. TLC R$_f$=0.5 (33% EtOAc/petroleum ether). $^1$H NMR (400 MHz, CDCl$_3$) δ 4.23 (q, J=7.2 Hz, 2H), 3.45 (q, J=7.5 Hz, 2H), 2.02 (s, 1H), 1.78-1.72 (m, 2H), 1.66-1.60 (m, 2H), 1.38 (t, J=7.5 Hz, 3H), 1.28 (t, J=7.2 Hz, 3H).

Step 2: A solution of ethyl 1-(ethylsulfonyl)cyclopropanecarboxylate (i3-a) (15 g, 72.7 mmol, 1.0 equiv) in THF (150 mL) was cooled to 0° C. before LiAlH$_4$ (3.3 g, 87.2 mmol, 1.2 equiv) was added portion wise. The mixture was allowed to warm to rt and stir at that temperature for 3 h, then it was quenched with a solution of sodium hydroxide (3.3 g) in water (10 mL). The solids were removed by filtration and the filtrate was concentrated under reduced pressure. The residue was purified by column chromatography (SiO$_2$, 15-50% EtOAc/petroleum ether) to give (1-(ethylsulfonyl)cyclopropyl)methanol (i3-b). TLC R$_f$=0.1 (33% EtOAc/petroleum ether). $^1$H NMR (400 MHz, CDCl$_3$) δ 3.82 (s, 2H), 3.15 (q, J=7.6 Hz, 2H), 2.56 (s, 1H), 1.44-1.40 (m, 2H), 1.34 (t, J=7.6 Hz, 3H), 0.97-0.93 (m, 2H).

Step 3: 1-(Bromomethyl)-1-(ethylsulfonyl)cyclopropane (int-3) was obtained using the method described in step 4 for the synthesis of intermediate (int-1), except (1-(cyclopropylsulfonyl)cyclopropyl)methanol (1-c) was replaced with (1-(ethylsulfonyl)cyclopropyl)methanol (i3-b). $^1$H NMR (400 MHz, CDCl$_3$) δ 3.79 (s, 2H), 3.28-3.16 (m, 2H), 1.74-1.66 (m, 2H), 1.36 (t, J=7.5 Hz, 3H), 1.16-1.08 (m, 2H).

Intermediate 4

1-(Bromomethyl)-1-(methylsulfonyl)cyclopropane (Int-4)

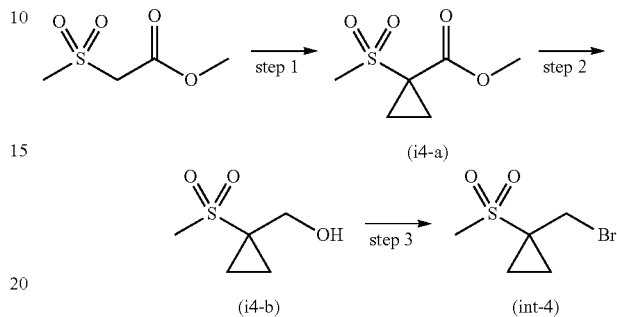

Step 1: Methyl 1-(methylsulfonyl)cyclopropanecarboxylate (i4-a) was obtained using the method described for the synthesis of intermediate (i1-b), except benzyl 2-(cyclopropylsulfonyl)acetate (1-a) was replaced with methyl 2-(methylsulfonyl)acetate. $^1$H NMR (400 MHz, CDCl$_3$) δ 3.81 (s, 3H), 3.20 (s, 3H), 1.84-1.79 (m, 2H), 1.70-1.65 (m, 2H).

Step 2: (1-(Methylsulfonyl)cyclopropyl)methanol (i4-b) was obtained using the method described for the synthesis of intermediate (i1-c), except benzyl 1-(cyclopropylsulfonyl)cyclopropanecarboxylate (1-b) was replaced with methyl 1-(methylsulfonyl)cyclopropanecarboxylate (i4-a). $^1$H NMR (400 MHz, CDCl$_3$) δ 3.92 (d, J=5.53 Hz, 2H), 3.04 (s, 3H), 2.48 (t, J=5.45 Hz, 1H), 1.54-1.48 (m, 2H), 1.08-1.01 (m, 2H).

Step 3: 1-(Bromomethyl)-1-(methylsulfonyl)cyclopropane (int-4) was obtained using the method described in step 4 for the synthesis of intermediate (int-1), except (1-(cyclopropylsulfonyl)cyclopropyl)methanol (1-c) was replaced with (1-(Methylsulfonyl)cyclopropyl)methanol (i4-b). $^1$H NMR (400 MHz, CDCl$_3$) δ 3.86 (s, 1H), 3.10 (s, 3H), 1.79-1.76 (m, 2H), 1.23-1.19 (m, 2H).

Intermediate 5 ethyl 1-methyl-1H-pyrazolo[3,4-c]pyridine-3-carboxylate (Int-5)

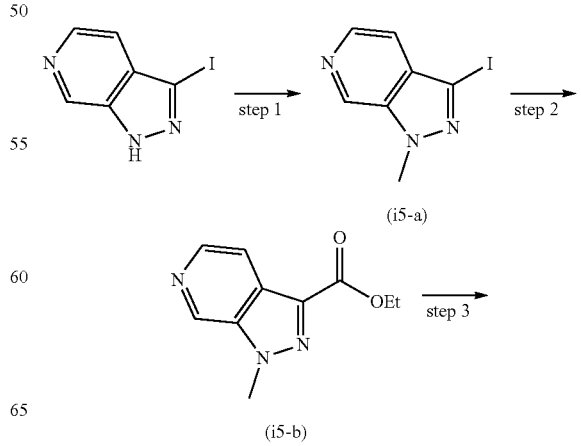

119
-continued

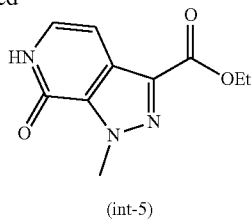

(int-5)

Step 1: To a solution of 3-iodo-1H-pyrazolo[3,4-c]pyridine (7.2 g, 29.4 mmol, 1.0 equiv) in DMF (160 mL) was added NaH (60% in mineral oil, 2.4 g, 58.8 mmol, 2.0 equiv) portion wise at 0° C. (gas evolution). The mixture was stirred for 30 min before CH$_3$I (8.7 g, 61.3 mmol, 2.1 equiv) was added at 0° C. After the reaction mixture was stirred at 0° C. for 30 min and at 15° C. for 1 h, the mixture was diluted with H$_2$O (300 mL) and neutralized to pH 7 with 1 M HCl. The aqueous layer was extracted with EtOAc (3×200 mL) and the combined organic extracts were dried with Na$_2$SO$_4$, filtered, and concentrated. The crude solid was purified by RP-HPLC to give 3-iodo-1-methyl-1H-pyrazolo[3,4-c]pyridine (5-a). $^1$H NMR (400 MHz, CDCl$_3$) b 8.86 (s, 1H), 8.31 (d, J=5.6 Hz, 1H), 7.30 (d, J=5.6 Hz, 1H), 4.15 (s, 3H). MS (ESI): m/z 260.1 [M+H]$^+$.

Step 2: To a solution of 3-iodo-1-methyl-1H-pyrazolo[3,4-c]pyridine (i5-a) (4.0 g, 15.4 mmol, 1.0 equiv) in EtOH (150 mL) was added Pd(dppf)Cl$_2$ (3.95 g, 5.41 mmol, 0.35 equiv) and Et$_3$N (6.44 mL, 46.3 mmol, 3.0 equiv). The mixture was stirred under a CO atmosphere (50 psi) at 40° C. for 24 h before it was concentrated. The residue was dry loaded onto silica gel and purified by column chromatography (SiO$_2$, 20-75% EtOAc/petroleum ether) to afford ethyl 1-methyl-1H-pyrazolo[3,4-c]pyridine-3-carboxylate (i5-b). $^1$H NMR (400 MHz, CDCl$_3$) δ 8.97 (d, J=1.0 Hz, 1H), 8.40 (d, J=5.6 Hz, 1H), 7.98 (dd, J=1.2, 5.6 Hz, 1H), 4.46 (q, J=7.2 Hz, 2H), 4.22 (s, 3H), 1.42 (t, J=7.2 Hz, 3H). MS (ESI): m/z 206.3 [M+H]$^+$.

Step 3: To a solution of N-oxide×(221 mg, 1.0 mmol, 1.0 equiv) in DMF (3 mL) was added TFAA (1.5 mL) dropwise at 20° C. The reaction mixture was stirred for 18 h before it was diluted with ice water (10 mL). The mixture was neutralized with 10% Na$_2$CO$_3$ and extracted with EtOAc (4×3 mL). The combined organic extracts were dried with Na$_2$SO$_4$, filtered, and concentrated. The residue was purified by column chromatography (SiO$_2$, 50% EtOAc/petroleum ether) to give ethyl 1-methyl-7-oxo-6,7-dihydro-1H-pyrazolo[3,4-c]pyridine-3-carboxylate (int-5). $^1$H NMR (400 MHz, MeOH-d$_4$) δ 7.08 (d, J=7.1 Hz, 1H), 6.95 (d, J=7.1 Hz, 1H), 4.45 (q, J=7.1 Hz, 2H), 4.41 (s, 3H), 1.45 (t, J=7.2 Hz, 3H). MS (ESI): m/z 222.1 [M+H]$^+$.

120
Intermediate 6 ethyl 6-((1-(cyclopropylsulfonyl)cyclopropyl)methyl)-1-methyl-7-oxo-6,7-dihydro-1H-pyrazolo[3,4-c]pyridine-3-carboxylate (Int-6)

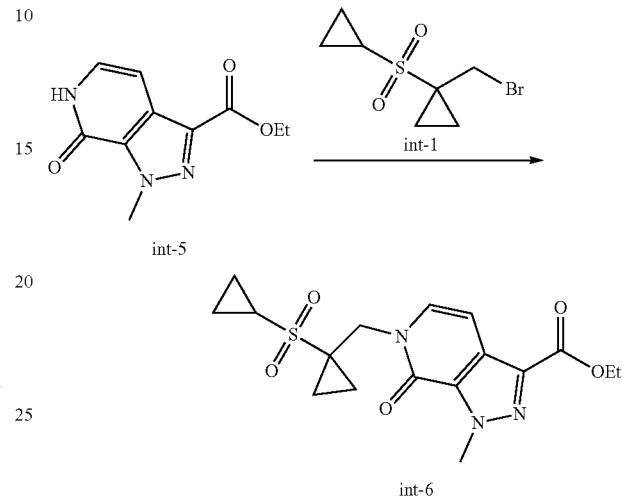

A mixture of ethyl 1-methyl-7-oxo-6,7-dihydro-1H-pyrazolo[3,4-c]pyridine-3-carboxylate (int-5) (80 mg, 0.37 mmol, 1.0 equiv), Cs$_2$CO$_3$ (620 mg, 1.9 mmol, 5.0 equiv) and 1-(bromomethyl)-1-(cyclopropylsulfonyl)cyclopropane (int-1) (177 mg, 0.74 mmol, 2.0 equiv) in DMF (2 mL) was stirred at 50° C. for 12 h before it was diluted with water (2 mL) and extracted with EtOAc (3×2 mL). The combined organic extracts were washed with water (4 mL) and brine (2×4 mL), dried over Na$_2$SO$_4$, filtered and concentrated. The residue was purified by prep-TLC (SiO$_2$, 67% EtOAc/petroleum ether) to give ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6). TLC R$_f$=0.4 (67% EtOAc/petroleum ether). $^1$H NMR (400 MHz, MeOH-d$_4$) δ 7.39 (br d, J=7.2 Hz, 1H), 6.93 (br d, J=7.3 Hz, 1H), 4.63 (s, 2H), 4.47-4.42 (m, 2H), 4.39 (s, 3H), 1.43-1.39 (m, 3H), 1.15-1.02 (m, 8H).

Intermediate 7 ethyl 1-methyl-6-((1-(methylsulfonyl)cyclopropyl)methyl)-7-oxo-6,7-dihydro-1H-pyrazolo[3,4-c]pyridine-3-carboxylate (Int-7)

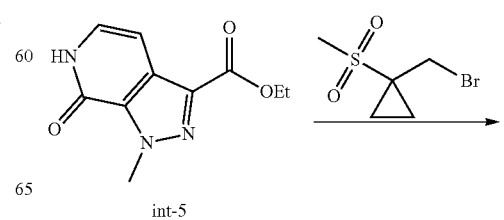

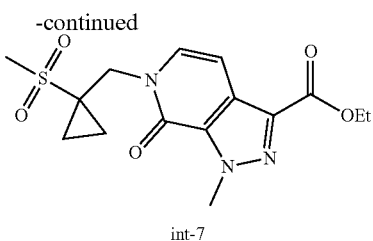

Ethyl 1-methyl-6-((1-(methylsulfonyl)cyclopropyl)methyl)-7-oxo-6,7-dihydro-1H-pyrazolo[3,4-c]pyridine-3-carboxylate (int-7) was obtained using the method described for the synthesis of intermediate (int-6), except 1-(bromomethyl)-1-(cyclopropylsulfonyl)cyclopropane (int-1) was replaced with 1-(bromomethyl)-1-(methylsulfonyl)cyclopropane (int-4). TLC $R_f$=0.2 (33% EtOAc/petroleum ether). $^1$H NMR (400 MHz, MeOH-d$_4$) δ 7.38 (d, J=7.4 Hz, 1H), 6.93 (d, J=7.3 Hz, 1H), 4.57 (s, 2H), 4.44 (q, J=7.2 Hz, 2H), 4.40 (s, 3H), 3.01 (s, 3H), 1.49-1.46 (m, 2H), 1.43 (t, J=7.2 Hz, 3H), 1.31-1.27 (m, 2H).

Intermediate 8

(Z)-Ethyl 2-chloro-2-(2-cyclopropylhydrazono)acetate (Int-8)

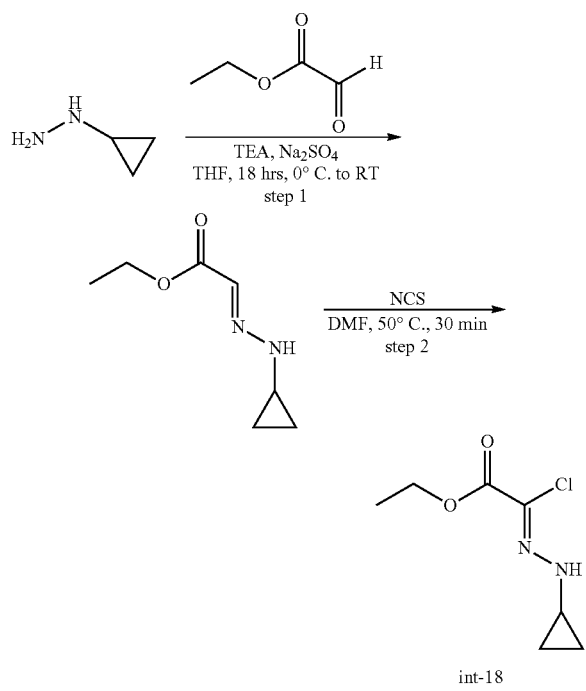

Step 1: To a solution of ethyl 2-oxoacetate (2.7 g, 13.2 mmol) in THF (20 mL) was added K$_2$CO$_3$ (6.1 g, 44.0 mmol) and cyclopropylhydrazine dihydrochloride (2.0 g, 13.8 mmol) at 0° C. The mixture was stirred at 25° C. for 12 h. The mixture was diluted with water (5 mL) and extracted with EtOAc (2×20 mL). The combined organic extracts were dried over Na$_2$SO$_4$, filtered and concentrated. The residue was purified by Prep-TLC (SiO$_2$, 50% EtOAc/petroleum ether) to afford (E)-ethyl 2-(2-cyclopropylhydrazono)acetate. TLC $R_f$=0.5 (50% EtOAc/petroleum ether). MS (ESI): m/z 157.1 [M+H]$^+$.

Step 2: To a solution of (E)-ethyl 2-(2-cyclopropylhydrazono)acetate (500 mg, 3.2 mmol) in DMF (5 mL) was added NCS (470 mg, 3.52 mmol) at 50° C. The reaction was stirred at 50° C. for 30 min before it was diluted with water and extracted with EtOAc (2×20 mL). The combined organic extracts were dried over Na$_2$SO$_4$, filtered and concentrated. The residue was purified by column chromatography (SiO$_2$, 0-50% EtOAc/petroleum ether) to afford (Z)-ethyl 2-chloro-2-(2-cyclopropylhydrazono)acetate (int-8). TLC $R_f$=0.5 (25% EtOAc/petroleum ether). MS (ESI): m/z 191.0 [M+H]$^+$.

Intermediate 9

Ethyl(Z)-2-bromo-2-(2-methylhydrazono)acetate (Int-9)

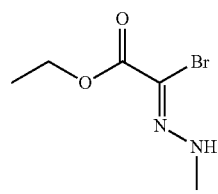

Ethyl (Z)-2-bromo-2-(2-methylhydrazono)acetate (int-9) was obtained using the procedure described for the synthesis of (Z)-Ethyl 2-chloro-2-(2-cyclopropylhydrazono)acetate (int-8), except in step 1 cyclopropylhydrazine dihydrochloride was replaced with methylhydrazine and in step 2 NCS was replaced with NBS. $^1$H NMR (500 MHz, CDCl$_3$) δ 6.50 (s, 1H), 4.34 (q, J=6.9 Hz, 2H), 3.30 (s, 3H), 1.35 (t, J=7.0 Hz, 3H). MS (ESI): m/z 209.1 [M+H]$^+$.

Intermediate 10 ethyl 1-methyl-7-oxo-4,5,6,7-tetrahydro-1H-pyrazolo[3,4-c]pyridine-3-carboxylate (Int-10)

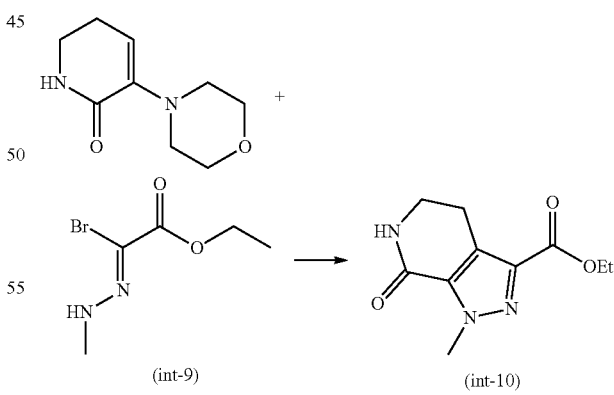

Ethyl (Z)-2-bromo-2-(2-methylhydrazono)acetate (int-9) (9.78 g, 30.2 mmol, 1.1 equiv, 93% pure) was dissolved in EtOAc (91 mL, 0.3 M), cooled to 0° C., and 3-morpholino-5,6-dihydropyridin-2(1H)-one (5.00 g, 27.4 mmol, 1.0 equiv) was added in one portion. Triethylamine (11.5 mL, 82 mmol 3.0 equiv) was added and the reaction vessel was removed from the ice bath and stirred for 20 min at room temperature. The reaction mixture was then heated at 77° C. for 5 h, during which time the solution became a beige suspension. The reaction vessel was cooled in an ice bath and 5 mL of 4 N HCl was added dropwise. After stirring for 45 min, the reaction mixture was removed from the ice bath and partitioned between $CH_2C_2$ (50 mL) and $H_2O$ (50 mL). The organic layer was collected and the aqueous layer was extracted with $CH_2C_2$ (2×50 mL), then the combined organic extracts were dried ($MgSO_4$), filtered, and concentrated until solids began to crash out of solution. The solids were collected via filtration (3.48 g) and the mother liquor was concentrated and purified by column chromatography ($SiO_2$, 50-100% EtOAc/heptane) to afford an additional 1.1 g of product. The solids were combined to give ethyl 1-methyl-7-oxo-4,5,6,7-tetrahydro-1H-pyrazolo[3,4-c]pyridine-3-carboxylate (int-10). $^1$H NMR (400 MHz, $CDCl_3$) δ 5.76 (br s, 1H), 4.42 (q, J=7.1 Hz, 2H), 4.26 (s, 3H), 3.60 (dt, J=2.7, 7.0 Hz, 2H), 3.12 (t, J=7.0 Hz, 2H), 1.42 (t, J=7.1 Hz, 3H). MS (ESI): m/z 288.0 $[M+H]^+$.

Intermediate 11

6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (Int-11)

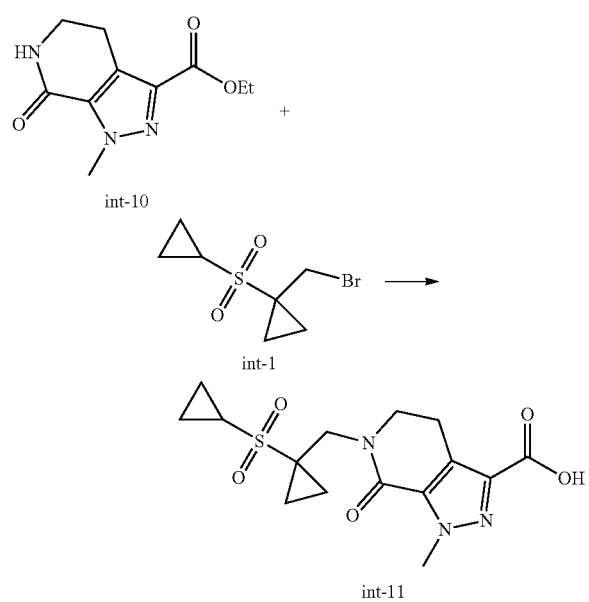

To a solution of ethyl 1-methyl-7-oxo-4,5,6,7-tetrahydro-1H-pyrazolo[3,4-c]pyridine-3-carboxylate (int-10) (1.0 g, 4.5 mmol, 1.0 equiv) in DMF (10 mL) was added NaH (60% in mineral oil, 360 mg, 9.0 mmol, 2.0 equiv) and 1-(bromomethyl)-1-(cyclopropylsulfonyl)cyclopropane (int-1) (2.2 g, 9.0 mmol, 2.0 equiv) at 25° C. (gas evolution). The resulting mixture was stirred at 25° C. for 12 h, then it was quenched with water (2 mL) and adjusted pH 2 with 1 N HCl before it was extracted with EtOAc (2×30 mL). The combined organic extracts were washed with brine (3×20 mL), dried over $Na_2SO_4$, filtered and concentrated to afford 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11). TLC $R_f$=0.2 (1:10 MeOH/DCM). MS (ESI): m/z 354.1 $[M+H]^+$.

Intermediate 12 ethyl 6-((1-(cyclopropylsulfonyl)cyclopropyl) methyl)-1-methyl-7-oxo-4,5,6,7-tetrahydro-1H-pyrazolo[3,4-c]pyridine-3-carboxylate (Int-12)

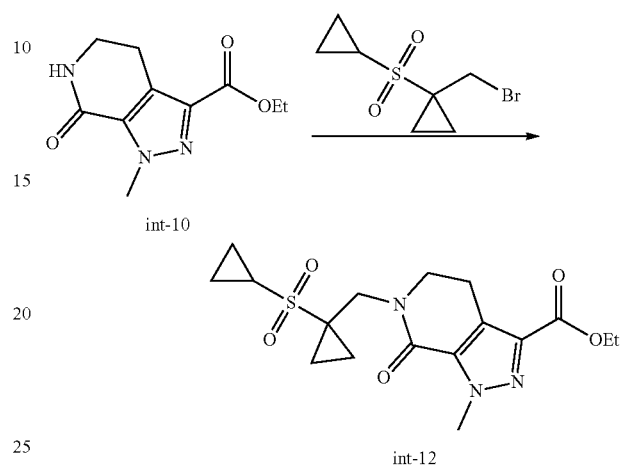

ethyl 6-((1-(cyclopropylsulfonyl)cyclopropyl)methyl)-1-methyl-7-oxo-4,5,6,7-tetrahydro-1H-pyrazolo[3,4-c]pyridine-3-carboxylate (int-12) was obtained using the procedure for intermediate (int-6), except intermediate (int-5) was replaced with ethyl 1-methyl-7-oxo-4,5,6,7-tetrahydro-1H-pyrazolo[3,4-c]pyridine-3-carboxylate (int-10). MS (ESI): m/z 382.1 $[M+H]^+$.

Intermediate 13 ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (Int-13)

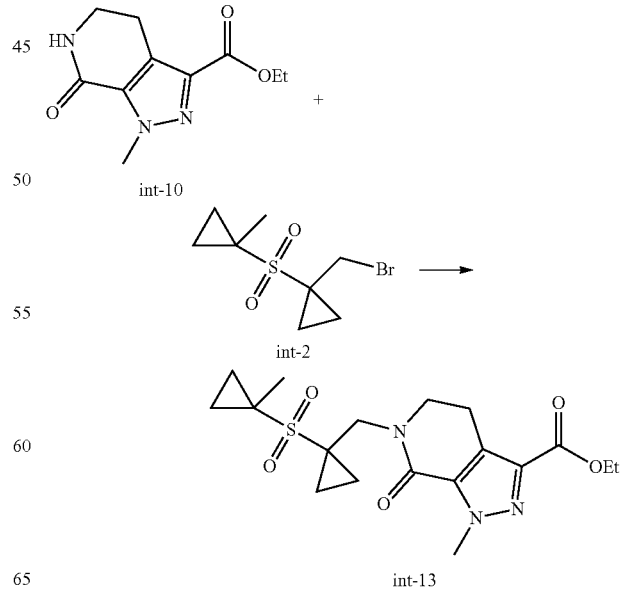

Ethyl 1-methyl-6-((1-(((1-methylcyclopropyl)sulfonyl)cyclopropyl)methyl)-7-oxo-4,5,6,7-tetrahydro-1H-pyrazolo[3,4-c]pyridine-3-carboxylate (int-13) was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with 1-(bromomethyl)-1-((1-methylcyclopropyl)sulfonyl)cyclopropane (int-2). TLC $R_f$=0.5 (EtOAc). $^1$H NMR (400 MHz, CDCl$_3$) δ 4.44 (m, 2H), 4.23 (s, 3H), 4.12 (s, 2H), 3.72-3.69 (m, 2H), 3.14-3.09 (m, 2H), 1.64-1.62 (m, 3H), 1.53-1.52 (m, 2H), 1.47-1.46 (m, 2H), 1.40 (m, 3H), 1.04 (m, 2H), 0.88-0.87 (m, 2H). MS (ESI): m/z 396.1 [M+H]$^+$.

Intermediate 14

1-methyl-6-((1-(((1-methylcyclopropyl)sulfonyl)cyclopropyl)methyl)-7-oxo-4,5,6,7-tetrahydro-1H-pyrazolo[3,4-c]pyridine-3-carboxylic acid (Int-14)

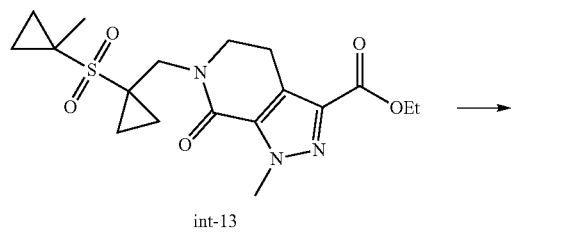

int-13

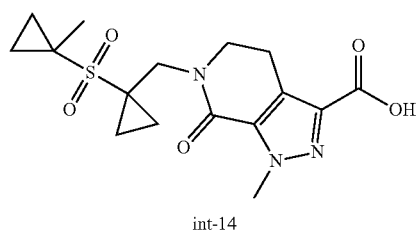

int-14

To a solution of ethyl 1-methyl-6-((1-(((1-methylcyclopropyl)sulfonyl)cyclopropyl)methyl)-7-oxo-4,5,6,7-tetrahydro-1H-pyrazolo[3,4-c]pyridine-3-carboxylate (int-13) (470 mg, 1.23 mmol, 1.0 equiv) in THF (3 mL) added a solution of NaOH (99 mg, 2.46 mmol, 2.0 equiv) in H$_2$O (1 mL). The reaction mixture was stirred at 25° C. for 16 h before it was acidified to pH 3-4 with 1 N HCl, then the mixture was diluted with water (30 mL) and extracted with EtOAc (3×50 mL). The combined organic extracts were washed with brine (2×10 mL), dried over Na$_2$SO$_4$, filtered and concentrated to afford 1-methyl-6-((1-(((1-methylcyclopropyl)sulfonyl)cyclopropyl)methyl)-7-oxo-4,5,6,7-tetrahydro-1H-pyrazolo[3,4-c]pyridine-3-carboxylic acid (int-14). TLC $R_f$=0.1 (EtOAc). $^1$H NMR (400 MHz, DMSO-d$_6$) δ 12.87 (br s, 1H), 4.10 (s, 3H), 4.01 (s, 2H), 3.64 (m, 2H), 2.96 (m, 2H), 1.53 (s, 3H), 1.25-1.22 (m, 4H), 1.04 (m, 2H), 0.92 (m, 2H). MS (ESI): m/z 368.1 [M+H]$^+$.

Intermediate 15

1-(bromomethyl)-1-((difluoromethyl)sulfonyl)cyclopropane (Int-15)

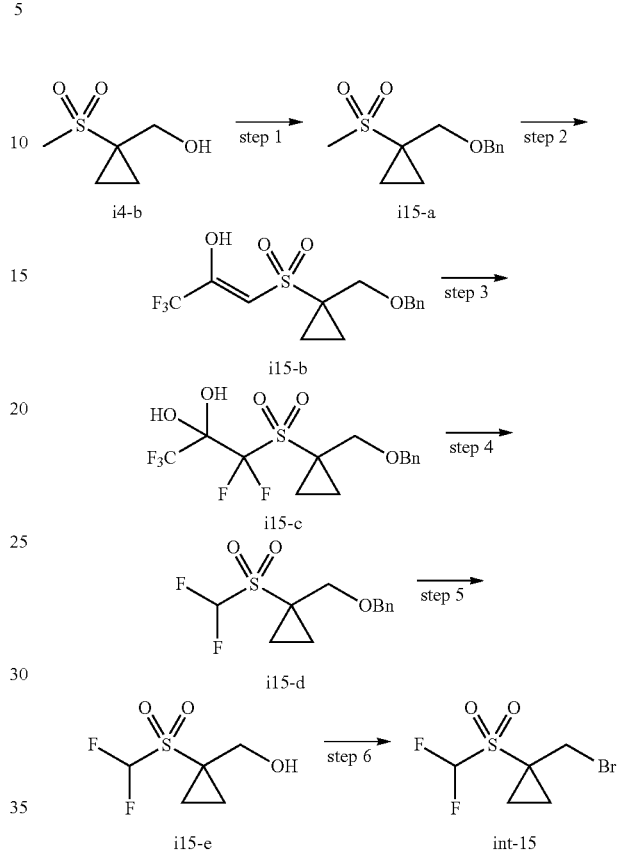

Step 1: (((1-(Methylsulfonyl)cyclopropyl)methoxy)methyl)benzene (i15-a) was obtained using the procedure described for intermediate (i2-a), except (1-(cyclopropylsulfonyl)cyclopropyl)methanol was replaced with (1-(methylsulfonyl)cyclopropyl)methanol (i4-b). TLC $R_f$=0.7 (50% EtOAc/petroleum ether). $^1$H NMR (400 MHz, MeOH-d$_4$) δ 7.42-7.24 (m, 5H), 4.58 (s, 2H), 3.81 (s, 2H), 3.05 (s, 3H), 1.45-1.39 (m, 2H), 1.11-1.03 (m, 2H). MS (ESI): m/z 263.1 [M+Na]$^+$.

Step 2: (Z)-1-((1-((Benzyloxy)methyl)cyclopropyl)sulfonyl)-3,3,3-trifluoroprop-1-en-2-ol (i15-b). A solution of LiHMDS (1.0 M in THF, 12 mL, 12.5 mmol, 1.2 equiv) in THF (30 mL) was cooled to −65° C. before a solution of (((1-(methylsulfonyl)cyclopropyl)methoxy)methyl)benzene (15-a) (2.5 g, 10.4 mmol, 1.0 equiv) in THF (10 mL) was added dropwise. The mixture was stirred at −65° C. for 1 h, then 2,2,2-trifluoroethyl 2,2,2-trifluoroacetate (3.05 g, 15.6 mmol, 1.5 equiv) was added dropwise. After 30 min at −65° C., the reaction mixture was quenched with 1 M H$_2$SO$_4$ (40 mL) and stirred at 25° C. for 16 h. The mixture was extracted with EtOAc (3×50 mL), then the combined organic extracts were dried over Na$_2$SO$_4$, filtered and concentrated. The residue was purified by RP-HPLC to give (Z)-1-((1-((benzyloxy)methyl)cyclopropyl)sulfonyl)-3,3,3-trifluoroprop-1-en-2-ol (i15-b). $^1$H NMR (400 MHz, DMSO-d$_6$) δ 7.39-7.22 (m, 5H), 4.62 (s, 1H), 4.57-4.43 (m, 2H), 3.80 (m, 2H), 3.69 (s, 1H), 1.42-1.37 (m, 1H), 1.26-1.21 (m, 1H), 1.10-1.06 (m, 1H), 0.81-0.77 (m, 1H). MS (ESI): m/z 353.9 [M+H]$^+$.

Step 3: 1-((1-(((Benzyloxy)methyl)cyclopropyl)sulfonyl)-1,1,3,3,3-pentafluoropropane-2,2-diol (i15-c). In each of eight identical reactions, a solution of (Z)-1-((1-(((benzyloxy)methyl)cyclopropyl)sulfonyl)-3,3,3-trifluoroprop-1-en-2-ol (115-b) (100 mg, 0.29 mmol, 1.0 equiv) in MeCN (2 mL) was treated with Selectfluor® (263 mg, 0.74 mmol, 2.6 equiv). Each mixture was stirred at 40° C. for 24 h before it was diluted with MeCN (3 mL) and purified by RP-HPLC. The pure material was combined to give 1-((1-(((benzyloxy)methyl)cyclopropyl)sulfonyl)-1,1,3,3,3-pentafluoropropane-2,2-diol (i15-c). $^1$H NMR (400 MHz, DMSO-$d_6$) δ 7.41-7.21 (m, 5H), 4.55-4.45 (m, 2H), 3.88 (s, 2H), 1.56-1.45 (m, 2H), 1.36-1.27 (m, 2H).

Step 4: (((1-(((Difluoromethyl)sulfonyl)cyclopropyl)methoxy)methyl)benzene (i15-d). A solution of 1-((1-(((benzyloxy)methyl)cyclopropyl)sulfonyl)-1,1,3,3,3-pentafluoropropane-2,2-diol (115-c) (300 mg, 0.768 mmol, 1.0 equiv) in THF (2 mL) and H$_2$O (2 mL) was treated with Et$_3$N (311 mg, 3.07 mmol, 4.0 equiv) and stirred for 0.5 h at 30° C. The reaction solution was purified by RP-HPLC to give (((1-(((difluoromethyl)sulfonyl)cyclopropyl)methoxy)methyl)benzene (i15-d). $^1$H NMR (400 MHz, DMSO-$d_6$) δ 7.44-7.27 (m, 5H), 7.18-6.86 (m, 1H), 4.55 (s, 2H), 3.72 (s, 2H), 1.44-1.38 (m, 2H), 1.32-1.27 (m, 2H). MS (ESI): m/z 294.0 [M+NH$_4$].

Step 5. (1-((Difluoromethyl)sulfonyl)cyclopropyl)methanol (i15-e) was obtained using the procedure described in step 2 of the synthesis of intermediate (int-2), except (((1-((1-methylcyclopropyl)sulfonyl)cyclopropyl)methoxy)methyl)benzene (i2-b) was replaced with (((1-(((difluoromethyl)sulfonyl)cyclopropyl)methoxy)methyl)benzene (115-d). TLC R$_f$=0.2 (25% EtOAc/petroleum ether).

Step 6: 1-(Bromomethyl)-1-(((difluoromethyl)sulfonyl)cyclopropane (int-15) was obtained using the procedure described step 4 of the synthesis of intermediate (int-1), except (1-(Cyclopropylsulfonyl)cyclopropyl)methanol (i1-c) was replaced with (1-((Difluoromethyl)sulfonyl)cyclopropyl)methanol (i15-e). $^1$H NMR (400 MHz, CDCl$_3$) δ 6.70-6.36 (m, 1H), 3.85 (s, 2H), 1.93-1.85 (m, 2H), 1.41-1.33 (m, 2H).

Intermediate 16

Ethyl 6-((1-(((difluoromethyl)sulfonyl)cyclopropyl)methyl)-1-methyl-7-oxo-4,5,6,7-tetrahydro-1H-pyrazolo[3,4-c]pyridine-3-carboxylate (Int-16)

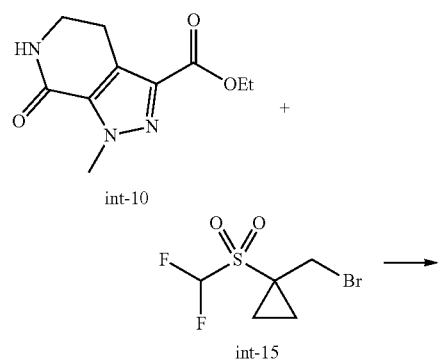

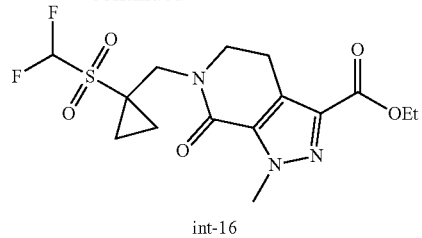

Ethyl 6-((1-(((difluoromethyl)sulfonyl)cyclopropyl)methyl)-1-methyl-7-oxo-4,5,6,7-tetrahydro-1H-pyrazolo[3,4-c]pyridine-3-carboxylate (int-16) was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with 1-(bromomethyl)-1-(((difluoromethyl)sulfonyl)cyclopropane (int-15). $^1$H NMR (400 MHz, CDCl$_3$) δ 6.61-6.27 (m, 1H), 4.42 (m, 2H), 4.23 (s, 3H), 4.01 (s, 2H), 3.78 (m, 2H), 3.15 (m, 2H), 1.73-1.67 (m, 2H), 1.41 (m, 3H), 1.37-1.32 (m, 2H). MS (ESI): m/z 392.0 [M+H]$^+$.

Intermediate 17

6-((1-(((difluoromethyl)sulfonyl)cyclopropyl)methyl)-1-methyl-7-oxo-4,5,6,7-tetrahydro-1H-pyrazolo[3,4-c]pyridine-3-carboxylic acid (Int-17)

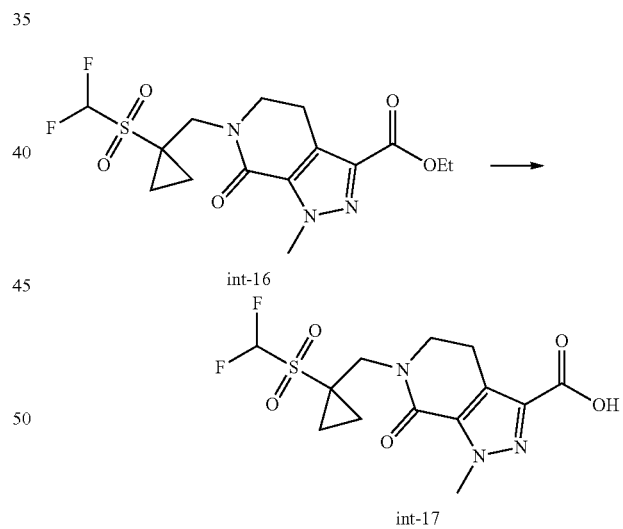

6-((1-(((Difluoromethyl)sulfonyl)cyclopropyl)methyl)-1-methyl-7-oxo-4,5,6,7-tetrahydro-1H-pyrazolo[3,4-c]pyridine-3-carboxylic acid (int-17) was obtained using the procedure described in the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-(((difluoromethyl)sulfonyl)cyclopropyl)methyl)-1-methyl-7-oxo-4,5,6,7-tetrahydro-1H-pyrazolo[3,4-c]pyridine-3-carboxylate (int-17). MS (ESI): m/z 364.0 [M+H]$^+$.

Intermediate 18 ethyl(Z)-2-chloro-2-(2-methylhydrazono)acetate (Int-18)

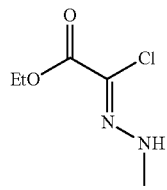

(int-18)

Ethyl (Z)-2-chloro-2-(2-methylhydrazono)acetate (int-18) was obtained using the procedure described for the synthesis of (Z)-Ethyl 2-chloro-2-(2-cyclopropylhydrazono) acetate (int-8), except in step 1 cyclopropylhydrazine dihydrochloride was replaced methylhydrazine. $^1$H NMR (500 MHz, CDCl$_3$) δ 6.43 (s, 1H), 4.36 (q, J=7.0 Hz, 2H), 3.28 (s, 3H), 1.36 (t, J=7.0 Hz, 3H). MS (ESI): m/z 165.1 [M+H]$^+$.

Intermediate 19

Ethyl 1,5-dimethyl-7-oxo-4,5,6,7-tetrahydro-1H-pyrazolo[3,4-c]pyridine-3-carboxylate (int-19)

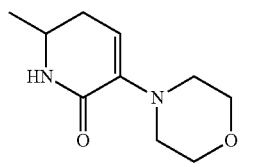

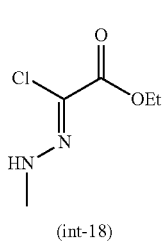

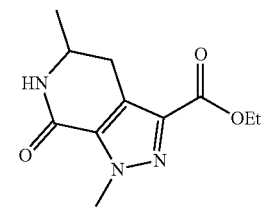

(int-18)    (int-19)

A solution of 6-methyl-3-morpholino-5,6-dihydropyridin-2(1H)-one (5 g, 25.48 mmol, crude, 1.0 equiv) in toluene (50 mL) was treated with Et$_3$N (7.73 g, 76.43 mmol, 3.0 equiv) and ethyl (Z)-2-chloro-2-(2-methylhydrazono)acetate (int-18) (5.03 g, 30.57 mmol, 1.2 equiv). The resulting mixture was stirred at 120° C. for 5 h, then it was concentrated and the residue was purified by RP-HPLC to afford ethyl 1,5-dimethyl-7-oxo-4,5,6,7-tetrahydro-1H-pyrazolo[3,4-c]pyridine-3-carboxylate (int-19). $^1$H NMR (400 MHz, CDCl$_3$) δ 5.43 (br s, 1H), 4.43 (q, J=7.2 Hz, 2H), 4.25 (s, 3H), 3.98-3.88 (m, 1H), 3.26 (dd, J=4.8, 16.8 Hz, 1H), 2.74 (dd, J=11.2, 16.4 Hz, 1H), 1.44-1.44 (m, 1H), 1.42 (t, J=7.2 Hz, 2H), 1.37 (d, J=6.4 Hz, 3H). MS (ESI): m/z 238.1 [M+H]$^+$.

Intermediate 20

1,5-dimethyl-6-((1-(methylsulfonyl)cyclopropyl)methyl)-7-oxo-4,5,6,7-tetrahydro-1H-pyrazolo[3,4-c]pyridine-3-carboxylic acid (Int-20)

1,5-dimethyl-6-((1-(methylsulfonyl)cyclopropyl)methyl)-7-oxo-4,5,6,7-tetrahydro-1H-pyrazolo[3,4-c]pyridine-3-carboxylic acid (int-20) was obtained using the procedure described in the synthesis of (int-11), except ethyl 1-methyl-7-oxo-4,5,6,7-tetrahydro-1H-pyrazolo[3,4-c]pyridine-3-carboxylate (int-10) was replaced with ethyl 1,5-dimethyl-7-oxo-4,5,6,7-tetrahydro-1H-pyrazolo[3,4-c]pyridine-3-carboxylate (int-19) and 1-(bromomethyl)-1-(cyclopropylsulfonyl)cyclopropane (int-1) was replaced with 1-(bromomethyl)-1-(methylsulfonyl)cyclopropane (int-4). MS (ESI): m/z 342.2 [M+H]$^+$

Intermediate 21 ethyl 1-cyclopropyl-6-((1-(cyclopropylsulfonyl)cyclopropyl)methyl)-7-oxo-4,5,6,7-tetrahydro-1H-pyrazolo[3,4-c]pyridine-3-carboxylate (Int-21)

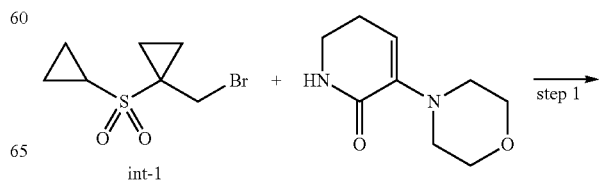

131

-continued

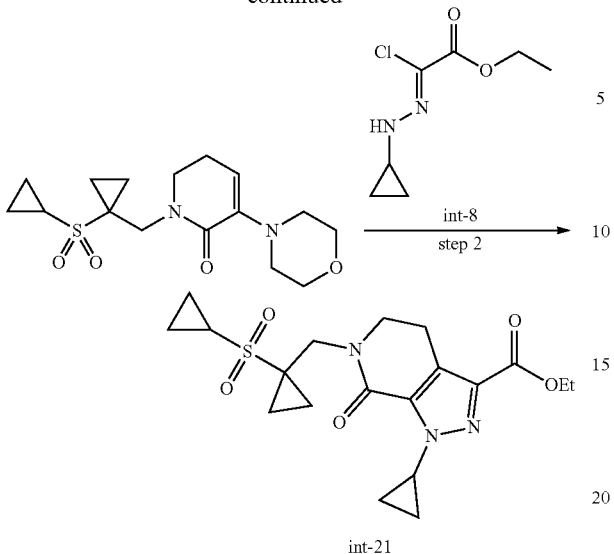

int-21

Step 1: 1-((1-(Cyclopropylsulfonyl)cyclopropyl)methyl)-3-morpholino-5,6-dihydropyridin-2(1H)-one. A solution of 3-morpholino-5,6-dihydropyridin-2(1H)-one (2.2 g, 12.1 mmol, 1.0 equiv) in DMF (22 mL) was cooled to 0° C. before NaH (60% in mineral oil, 590 mg, 14.5 mmol, 1.2 equiv) was added portion wise (gas evolution). The mixture was stirred at 25° C. for 0.5 h, then it was cooled to 0° C. before 1-(bromomethyl)-1-(cyclopropylsulfonyl)cyclopropane (int-1) (4.4 g, 18.1 mmol, 1.2 equiv) was added. After stirring at 25° C. for 12 h, the mixture was poured into water (30 mL) and extracted with EtOAc (4×30 mL). The combined organic extracts were dried over Na$_2$SO$_4$, filtered and concentrated. The residue was purified by column chromatography (SiO$_2$, 30-50% EtOAc/petroleum ether) to afford 1-((1-(cyclopropylsulfonyl)cyclopropyl)methyl)-3-morpholino-5,6-dihydropyridin-2(1H)-ones. MS (ESI): m/z 341.1 [M+H]$^+$.

Step 2: Ethyl 1-cyclopropyl-6-((1-(cyclopropylsulfonyl)cyclopropyl)methyl)-7-oxo-4,5,6,7-tetrahydro-1H-pyrazolo[3,4-c]pyridine-3-carboxylate (int-21) was obtained using the procedure described for the synthesis of intermediate (int-19), except 6-methyl-3-morpholino-5,6-dihydropyridin-2(1H)-one was replaced with 1-((1-(cyclopropylsulfonyl)cyclopropyl)methyl)-3-morpholino-5,6-dihydropyridin-2(1H)-one and ethyl (Z)-2-chloro-2-(2-methylhydrazono)acetate (int-18) was replaced with (Z)-Ethyl 2-chloro-2-(2-cyclopropylhydrazono)acetate (int-8). TLC R$_f$=0.3 (50% EtOAc/petroleum ether). MS (ESI): m/z 408.2 [M+H]$^+$.

Intermediate 22

(Z)-Ethyl 2-bromo-2-(2-(4-methoxybenzyl)hydrazono)acetate (Int-22)

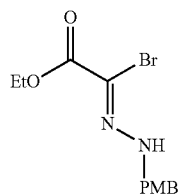

132

(Z)-Ethyl 2-bromo-2-(2-(4-methoxybenzyl)hydrazono)acetate (int-22) was obtained using the procedure described for the synthesis of (Z)-Ethyl 2-chloro-2-(2-cyclopropylhydrazono)acetate (int-8), except in step 1 cyclopropylhydrazine dihydrochloride was replaced with (4-methoxybenzyl)hydrazine and in step 2 NCS was replaced with NBS. TLC R$_f$=0.4 (1:10 EtOAc/petroleum ether). $^1$H NMR (400 MHz, DMSO-d$_6$) δ 8.53 (s, 1H), 7.20 (d, J=8.4 Hz, 2H), 6.92-6.89 (m, 2H), 4.50-4.49 (m, 2H), 4.22-4.17 (m, 2H), 3.73 (s, 3H), 1.24-1.20 (m, 3H).

Intermediate 23 ethyl 1-(4-methoxybenzyl)-7-oxo-4,5,6,7-tetrahydro-1H-pyrazolo[3,4-c]pyridine-3-carboxylate (Int-23)

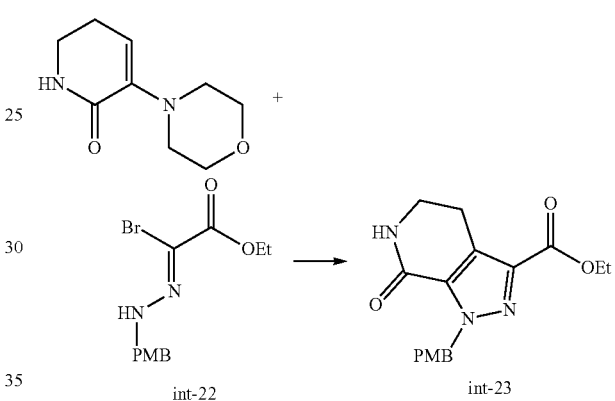

Ethyl 1-(4-methoxybenzyl)-7-oxo-4,5,6,7-tetrahydro-1H-pyrazolo[3,4-c]pyridine-3-carboxylate (int-23) was obtained using the method described for intermediate (int-10), except ethyl (Z)-2-bromo-2-(2-methylhydrazono)acetate (int-9) was replaced with ((Z)-Ethyl 2-bromo-2-(2-(4-methoxybenzyl)hydrazono)acetate (int-22). $^1$H NMR (400 MHz, CDCl$_3$) δ 7.40 (d, J=8.8 Hz, 2H), 6.84-6.81 (m, 2H), 5.78 (s, 1H), 5.75 (s, 2H), 4.45-4.39 (m, 2H), 3.77 (s, 3H), 3.58-3.54 (m, 2H), 3.11-3.08 (m, 2H), 1.43-1.39 (m, 3H). MS (ESI): m/z 330.2 [M+H]$^+$.

Intermediate 24

6-((1-(Cyclopropylsulfonyl)cyclopropyl)methyl)-1-(4-methoxybenzyl)-7-oxo-4,5,6,7-tetrahydro-1H-pyrazolo[3,4-c]pyridine-3-carboxylic acid (Int-24)

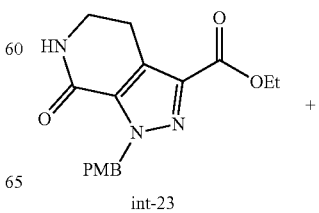

133

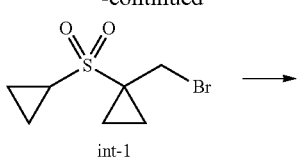

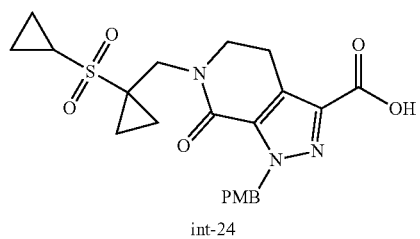

6-((1-(Cyclopropylsulfonyl)cyclopropyl)methyl)-1-(4-methoxybenzyl)-7-oxo-4,5,6,7-tetrahydro-1H-pyrazolo[3,4-c]pyridine-3-carboxylic acid (int-24) was obtained using the method described for the synthesis of (int-11), except ethyl 1-methyl-7-oxo-4,5,6,7-tetrahydro-1H-pyrazolo[3,4-c]pyridine-3-carboxylate (int-10) was replaced with ethyl 1-(4-methoxybenzyl)-7-oxo-4,5,6,7-tetrahydro-1H-pyrazolo[3,4-c]pyridine-3-carboxylate (int-23). $^1$H NMR (400 MHz, DMSO-$d_6$) δ 13.04-12.42 (m, 1H), 7.24 (d, J=8.7 Hz, 2H), 6.86 (d, J=8.8 Hz, 2H), 5.67 (s, 2H), 4.05 (s, 2H), 3.71 (s, 3H), 3.68 (s, 2H), 3.00-2.96 (m, 2H), 2.72 (s, 7H), 1.90 (s, 1H), 1.31-1.20 (m, 4H), 1.00-0.93 (m, 4H). MS (ESI): m/z 460.2 [M+H]$^+$.

Intermediate 25

4-(((2-Bromoethyl)amino)methyl)benzonitrile (Int-25)

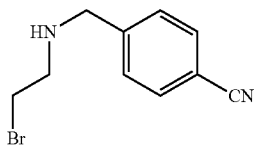

A solution of 4-formylbenzonitrile (4.8 g, 36.6 mmol, 1.0 equiv) in DCM (96 mL) was cooled to 0° C. before 2-bromoethylamine hydrobromide (11.6 g, 56.6 mmol, 1.55 equiv) was added. The reaction mixture was stirred at 0° C. for 0.5 h, then NaBH(OAc)$_3$ (23 g, 110 mmol, 3.0 equiv) and AcOH (231 mg, 3.7 mmol, 0.1 equiv) were added and the mixture was stirred at 25° C. for 12 h. The mixture was washed with water (2×100 mL), then the organic layer was dried over Na$_2$SO$_4$, filtered and concentrated to afford crude 4-(((2-bromoethyl)amino)methyl)benzonitrile (int-25). MS (ESI): m/z 239.2 [M+H]$^+$.

134

Intermediate 26 ethyl(Z)-2-chloro-2-(2-(4-methoxybenzyl)hydrazono)acetate (Int-26)

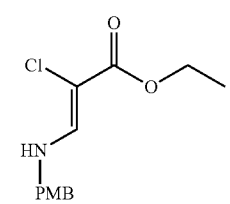

ethyl (Z)-2-chloro-2-(2-(4-methoxybenzyl)hydrazono)acetate (int-26) was obtained using the procedure described for the synthesis of (Z)-Ethyl 2-chloro-2-(2-cyclopropylhydrazono)acetate (int-8), except in step 1 cyclopropylhydrazine dihydrochloride was replaced with (4-methoxybenzyl)hydrazine. TLC R$_f$=0.5 (1:5 EtOAc/petroleum ether). MS (ESI): m/z 271.0 [M+H]$^+$.

Intermediate 27 ethyl 1-(4-methoxybenzyl)-6-((1-(methylsulfonyl)cyclopropyl)methyl)-7-oxo-4,5,6,7-tetrahydro-1H-pyrazolo[3,4-c]pyridine-3-carboxylate (Int-27)

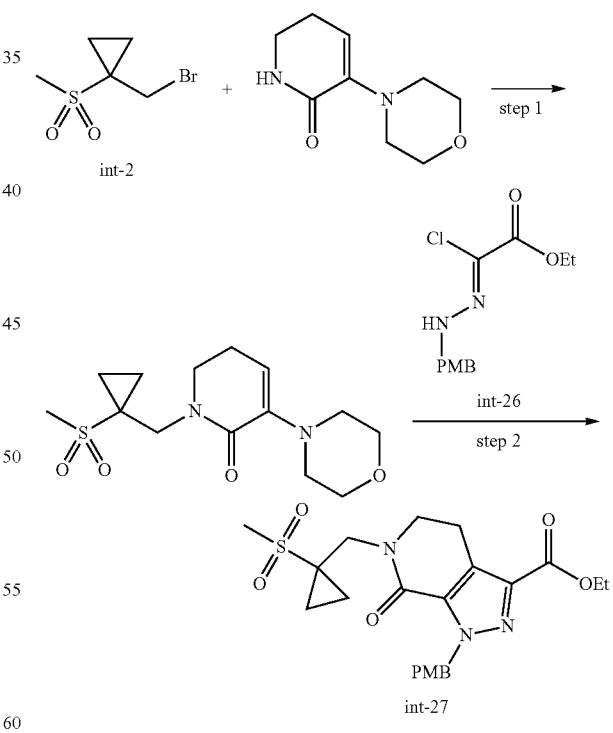

Step 1:1-((1-(Methylsulfonyl)cyclopropyl)methyl)-3-morpholino-5,6-dihydropyridin-2(1H)-one was obtained using the method described for the synthesis of 1-((1-(cyclopropylsulfonyl)cyclopropyl)methyl)-3-morpholino-5,6-dihydropyridin-2(1H)-one in step 1 of the synthesis of intermediate (int-21), except 1-(bromomethyl)-1-(cyclopropylsulfonyl)cyclopropane (int-1) was replaced with 1-(bromomethyl)-1-((1-methylcyclopropyl)sulfonyl)cyclopropane (int-2). TLC R$_f$=0.5 (67% EtOAc/petroleum ether). MS (ESI): m/z 315.3 [M+H]$^+$.

Step 2: Ethyl 1-(4-methoxybenzyl)-6-((1-(methylsulfonyl)cyclopropyl)methyl)-7-oxo-4,5,6,7-tetrahydro-1H-pyrazolo[3,4-c]pyridine-3-carboxylate (int-27) was obtained using the procedure described for the synthesis of intermediate (int-19), except 6-methyl-3-morpholino-5,6-dihydropyridin-2(1H)-one was replaced with 1-((1-(Methylsulfonyl)cyclopropyl)methyl)-3-morpholino-5,6-dihydropyridin-2(1H)-one and ethyl (Z)-2-chloro-2-(2-methylhydrazono)acetate (int-18) was replaced with ethyl (Z)-2-chloro-2-(2-(4-methoxybenzyl)hydrazono)acetate (int-26). TLC R$_f$=0.5 (EtOAc). MS (ESI): m/z 462.1 [M+H]$^+$.

Intermediate 28

1-(bromomethyl)-1-((2-methylbut-3-en-2-yl)sulfonyl)cyclopropane (Int-28)

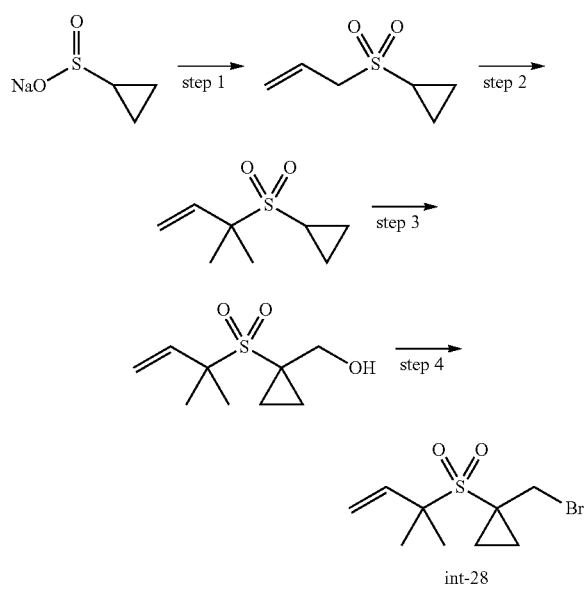

Step 1: A solution of sodium cyclopropanesulfinate (1.112 g, 8.68 mmol, 1.05 equiv) and tetrabutylammonium bromide (0.133 g, 0.413 mmol 0.05 equiv) in water (4 mL) was treated with allyl bromide (1 g, 8.27 mmol, 1.0 equiv) and the resulting biphasic solution was allowed to stir at rt for 24 h. The mixture was diluted with Et$_2$O (10 mL), the aqueous layer was removed and back-extracted with Et$_2$O (5 mL), then the combined org extracts were washed once with brine, dried with MgSO$_4$, filtered and evaporated to give (allylsulfonyl)cyclopropane. The product was sufficiently pure to be taken on without purification, but it can be purified by column chromatography (SiO$_2$, 0-50% EtOAc/heptane). TLC R$_f$=0.3 (2:3 EtOAc/heptane). $^1$H NMR (500 MHz, CDCl$_3$) δ 5.97 (ddt, J=14.9, 10.2, 7.4 Hz, 1H), 5.51-5.43 (m, 2H), 3.76 (d, J=7.4 Hz, 2H), 2.41 (tt, J=8.0, 4.9 Hz, 1H), 1.24 (dt, J=6.3, 3.2 Hz, 2H), 1.06-0.99 (m, 2H). MS (ESI): m/z 147.1 [M+H]$^+$.

Step 2: An solution of LiHMDS (1.0 M in THF) (30.0 mL, 30.0 mmol, 2.25 equiv) was allowed to cool to −78° C. before a solution of (allylsulfonyl)cyclopropane (1.95 g, 13.34 mmol, 1.0 equiv) in THF (5 mL) was added dropwise over 10-15 min, followed by a rinse with THF (5 mL). The resulting solution was allowed to stir at −78° C. for 15 min, then MeI (1.835 mL, 29.3 mmol, 2.2 equiv) was added dropwise over 5 min. The resulting mixture was allowed to stir at −78° C. for 30 min. The flask was removed from the cooling bath and the reaction was quenched with 60 mL saturated NH$_4$Cl. The resulting mixture was allowed to warm to rt, then a few mLs of water were added to dissolve the salts. The organic layer was separated and the aqueous layer was extracted with EtOAc (3×15 mL). The combined organic extracts were washed once with brine, dried with MgSO$_4$, filtered and evaporated to give crude product. The material was purified by column chromatography (SiO$_2$, 0-50% EtOAc/heptane) to provide ((2-methylbut-3-en-2-yl)sulfonyl)cyclopropane. TLC R$_f$=0.45 (2:3 EtOAc/heptane). $^1$H NMR (500 MHz, CDCl$_3$) δ 6.13 (ddd, J=15.2, 10.7, 4.1 Hz, 1H), 5.43-5.35 (m, 2H), 2.34 (dt, J=7.7, 4.5 Hz, 1H), 1.53 (s, 6H), 1.18 (s, 2H), 0.98 (d, J=7.7 Hz, 2H). MS (ESI): m/z 175.2 [M+H]$^+$.

Step 3: A solution of ((2-methylbut-3-en-2-yl)sulfonyl)cyclopropane (175 mg, 1.00 mmol, 1.0 equiv) in THF (2 mL) was allowed to cool to −78° C. before a solution of LDA (2.0 M in THF/heptane/ethylbenzene, 1.00 mL, 2.00 mmol, 2.0 equiv) was added dropwise down the inside wall of the vial over 5 min. The resulting mixture was allowed to stir well at −78° C. for 45 min before the vial was removed from the cooling bath and paraformaldehyde (151 mg, 5.02 mmol, 5.0 equiv) was immediately added in one portion. The vial was capped and allowed to warm to rt with efficient stirring. TLC showed complete conversion of the starting material within 15 min. The reaction was quenched with 3 mL saturated NH$_4$Cl to give a biphasic solution that contained an insoluble white precipitate. The organic layer was separated and the aqueous layer was extracted with EtOAc (2×2 mL). The combined organic extracts were washed once with brine, dried with MgSO$_4$, filtered and evaporated to give (1-((2-methylbut-3-en-2-yl)sulfonyl)cyclopropyl)methanol. This material was taken on without purification, but it can be purified by column chromatography (SiO$_2$, 0-60% EtOAc/heptane). $^1$H NMR (500 MHz, CDCl$_3$) δ 6.28 (dd, J=17.5, 10.7 Hz, 1H), 5.44-5.36 (m, 2H), 3.81 (d, J=6.2 Hz, 2H), 2.80 (t, J=6.4 Hz, 1H), 1.55 (d, J=7.9 Hz, 8H), 1.05-0.99 (m, 2H).

Step 4: 1-(Bromomethyl)-1-((2-methylbut-3-en-2-yl)sulfonyl)cyclopropane (int-28) was obtained using the method described in step 4 of the synthesis of intermediate (int-1), except (1-(Cyclopropylsulfonyl)cyclopropyl)methanol (1-c) was replaced with (1-((2-methylbut-3-en-2-yl)sulfonyl)cyclopropyl)methanol. TLC R$_f$=0.6 (1:1 EtOAc/petroleum ether). $^1$H NMR (400 MHz, CDCl$_3$) δ 6.29-6.22 (m, 1H), 5.44-5.38 (m, 2H), 3.94 (s, 2H), 1.69-1.66 (m, 2H), 1.56 (s, 6H), 1.24-1.21 (m, 2H).

Intermediate 29 ethyl 6-((1-((1-hydroxy-2-methylpropan-2-yl)sulfonyl)cyclopropyl)methyl)-1-(4-methoxybenzyl)-7-oxo-4,5,6,7-tetrahydro-1H-pyrazolo[3,4-c]pyridine-3-carboxylate (Int-29)

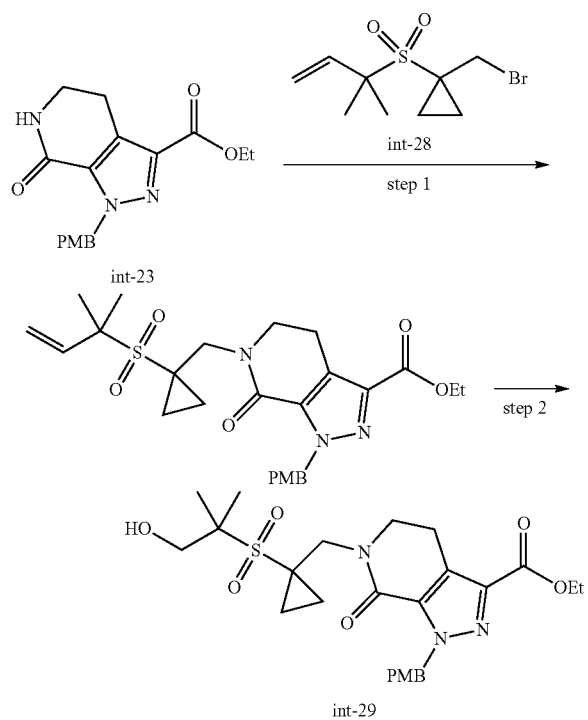

Step 1: Ethyl 1-(4-methoxybenzyl)-6-((1-((2-methylbut-3-en-2-yl)sulfonyl)cyclopropyl)methyl)-7-oxo-4,5,6,7-tetrahydro-1H-pyrazolo[3,4-c]pyridine-3-carboxylate was obtained using the method described in the synthesis of intermediate (int-6), except ethyl 1-methyl-7-oxo-6,7-dihydro-1H-pyrazolo[3,4-c]pyridine-3-carboxylate (int-5) was replaced with ethyl 1-(4-methoxybenzyl)-7-oxo-4,5,6,7-tetrahydro-1H-pyrazolo[3,4-c]pyridine-3-carboxylate (int-23) and 1-(bromomethyl)-1-(cyclopropylsulfonyl)cyclopropane (int-1) was replaced with 1-(bromomethyl)-1-((2-methylbut-3-en-2-yl)sulfonyl)cyclopropane (int-28). TLC R$_f$=0.5 (EtOAc). $^1$H NMR (400 MHz, CDCl$_3$) δ 7.34-7.30 (m, 2H), 6.82-6.80 (m, 2H), 6.26-6.16 (m, 1H), 5.71 (s, 2H), 5.46-5.39 (m, 2H), 4.46-4.37 (m, 2H), 4.05 (s, 2H), 3.76 (s, 3H), 3.68-3.64 (m, 2H), 3.08-3.05 (m, 2H), 1.56 (s, 6H), 1.54-1.52 (m, 2H), 1.41-1.37 (m, 3H), 1.01-0.98 (m, 2H).

Step 2: A solution of ethyl 1-(4-methoxybenzyl)-6-((1-((2-methylbut-3-en-2-yl)sulfonyl)cyclopropyl)methyl)-7-oxo-4,5,6,7-tetrahydro-1H-pyrazolo[3,4-c]pyridine-3-carboxylate (2.4 g, 4.65 mmol, 1.0 equiv) in DCM (10 mL) and EtOH (30 mL) was cooled to −70° C. before a stream of ozone in oxygen was bubbled through (20 min). Excess ozone was removed by bubbling oxygen through for 10 min, then the solution was allowed to warm to 0° C. and NaBH$_4$ (1.06 g, 27.90 mmol, 6.0 equiv) was added. The reaction mixture was stirred at 0° C. for 0.5 h before it was quenched with saturated NH$_4$C (20 mL) and extracted with EtOAc. The combined organic extracts were dried with Na$_2$SO$_4$, filtered and concentrated to give ethyl 6-((1-((1-hydroxy-2-methylpropan-2-yl)sulfonyl)cyclopropyl)methyl)-1-(4-methoxybenzyl)-7-oxo-4,5,6,7-tetrahydro-1H-pyrazolo[3,4-c]pyridine-3-carboxylate (int-29). TLC R$_f$=0.3 (EtOAc). MS (ESI): m/z 520.2 [M+H]$^+$.

Intermediate 30

6-((1-((1-hydroxy-2-methylpropan-2-yl)sulfonyl)cyclopropyl)methyl)-1-(4-methoxybenzyl)-7-oxo-4,5,6,7-tetrahydro-1H-pyrazolo[3,4-c]pyridine-3-carboxylic acid (Int-30)

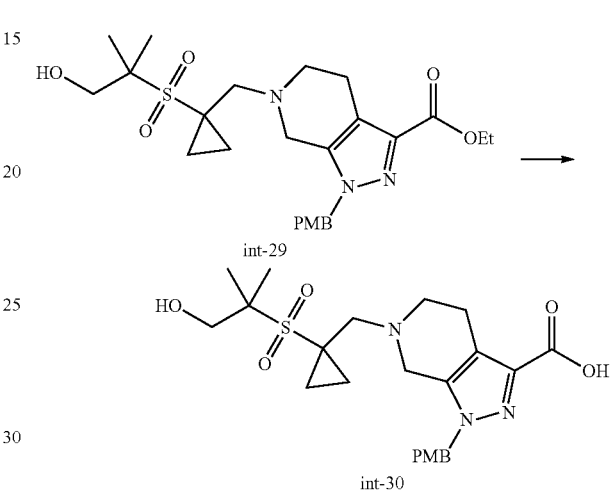

6-((1-((1-hydroxy-2-methylpropan-2-yl)sulfonyl)cyclopropyl)methyl)-1-(4-methoxybenzyl)-7-oxo-4,5,6,7-tetrahydro-1H-pyrazolo[3,4-c]pyridine-3-carboxylic acid (int-30) was obtained using the method described in the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-((1-hydroxy-2-methylpropan-2-yl)sulfonyl)cyclopropyl)methyl)-1-(4-methoxybenzyl)-7-oxo-4,5,6,7-tetrahydro-1H-pyrazolo[3,4-c]pyridine-3-carboxylate (int-29). MS (ESI): m/z 492.1 [M+H]$^+$.

Intermediate 31

(2-((1-(bromomethyl)cyclopropyl)sulfonyl)-2-methylpropoxy)(tert-butyl)diphenylsilane (Int-31)

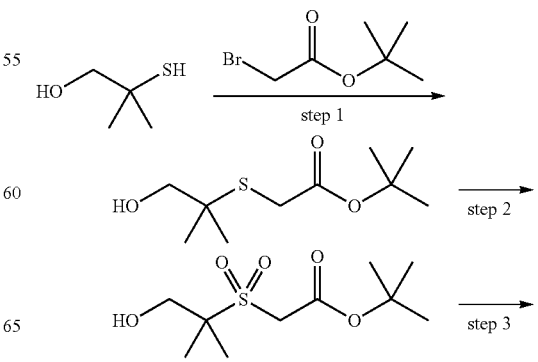

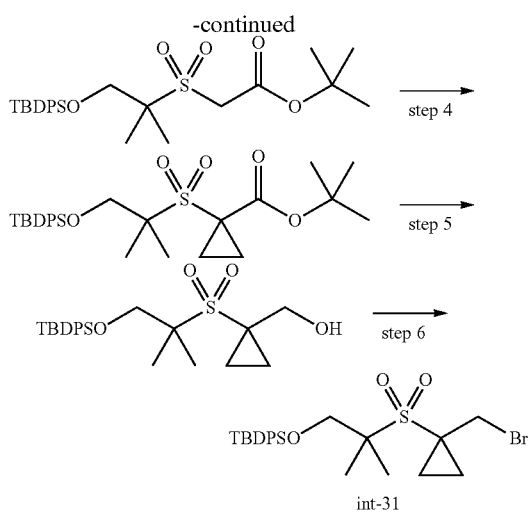

Step 1: Triethylamine (122 g, 1.2 mol, 1.2 equiv) was added dropwise to a solution of 2-mercapto-2-methylpropan-1-ol (106 g, 1 mol, 1.0 equiv) and tert-butyl 2-bromoacetate (195 g, 1 mol, 1.0 equiv) in MeOH (400 mL) over 30 min at 25° C. The reaction mixture was stirred at 25° C. for 12 h before it was concentrated. The residue was dissolved in EtOAc (20 mL) and the solids were removed by filtration, then the filtrate was concentrated and distilled under reduced pressure to give tert-butyl 2-((1-hydroxy-2-methylpropan-2-yl)thio)acetate. TLC $R_f$=0.4 (1:5 EtOAc/petroleum ether). MS (ESI): m/z 243.2 [M+Na]$^+$.

Step 2: Oxone® (280 g, 0.46 mol, 2.0 equiv) was added to a solution of tert-butyl 2-((1-hydroxy-2-methylpropan-2-yl)thio)acetate (50 g, 0.23 mol, 1.0 equiv) in acetone (0.4 L) and H$_2$O (1 L) and the mixture was stirred for 12 h at 25° C. After the solids were removed by filtration, the filtrate was diluted with 10% Na$_2$SO$_3$ (1 L) and EtOAc (1 L), then the layers were separated. The aqueous layer was extracted with EtOAc (3×30 mL), then the combined organic extracts were washed with brine (2×50 mL), dried with Na$_2$SO$_4$, filtered and concentrated. The crude material was purified by column chromatography (SiO$_2$, 5-15% EtOAc/petroleum ether), then the eluent was concentrated to dryness, washed with petroleum ether (20 mL) and dried to give tert-butyl 2-((1-hydroxy-2-methylpropan-2-yl)sulfonyl)acetate. TLC $R_f$=0.3 (25% EtOAc/petroleum ether). $^1$H NMR (400 MHz, CDCl$_3$) δ 4.06 (s, 2H), 3.84 (br d, J=4.5 Hz, 2H), 3.23 (br s, 1H), 1.52 (s, 9H), 1.43 (s, 6H).

Step 3: A solution of tert-butyl 2-((1-hydroxy-2-methylpropan-2-yl)sulfonyl)acetate (25 g, 99 mmol, 1.0 equiv), DMAP (1.2 g, 10 mmol, 0.1 equiv) and imidazole (13.5 g, 198 mmol, 2.0 equiv) in DCM (250 mL) was stirred at 25° C. for 0.5 h before TBDPSCl (55 g, 198 mmol, 2.0 equiv) was added. After the reaction was stirred at 25° C. for 1.5 h, the mixture was washed with water (3×150 mL). The organic layer was washed with brine, dried with Na$_2$SO$_4$, filtered and concentrated. The crude material was purified by column chromatography (SiO$_2$, 0-5% EtOAc/petroleum ether), the eluent was concentrated to dryness, washed with petroleum ether (20 mL) and dried to give tert-butyl 2-((1-((tert-butyldiphenylsilyl)oxy)-2-methylpropan-2-yl)sulfonyl)acetate. TLC $R_f$=0.3 (1:10 EtOAc/petroleum ether). $^1$H NMR (400 MHz, CDCl$_3$) δ 7.71-7.65 (m, 4H), 7.45-7.37 (m, 6H), 4.25 (s, 2H), 3.82 (s, 2H), 1.52 (s, 9H), 1.37 (s, 6H), 1.10 (s, 9H). MS (ESI): m/z 513.2 [M+Na]$^+$.

Step 4: tert-Butyl 1-((1-((tert-butyldiphenylsilyl)oxy)-2-methylpropan-2-yl)sulfonyl)cyclopropanecarboxylate was obtained in a manner similar to that for benzyl 1-(cyclopropylsulfonyl)cyclopropanecarboxylate. TLC $R_f$=0.2 (1:5 EtOAc/petroleum ether). $^1$H NMR (400 MHz, CDCl$_3$) δ 7.70-7.62 (m, 4H), 7.42-7.38 (m, 6H), 3.91 (s, 2H), 1.73-1.66 (m, 2H), 1.52 (s, 6H), 1.49-1.44 (m, 2H), 1.39 (s, 8H), 1.10 (s, 9H).

Step 5: A solution of tert-butyl 1-((1-((tert-butyldiphenylsilyl)oxy)-2-methylpropan-2-yl)sulfonyl)cyclopropanecarboxylate (3 g, 5.8 mmol, 1.0 equiv) in THF (30 mL) was cooled to 0° C. before LiAlH$_4$ (0.44 g, 11.6 mmol, 2.0 equiv) was added portion wise. The reaction mixture was stirred at 0° C. for 2 h, then it was quenched by the sequential addition of water (0.5 mL) (gas evolution), 10% NaOH (1.5 mL) and water (0.5 mL). After the mixture was warmed to rt, the solids were removed by filtration and the filter cake was rinsed with EtOAc. The filtrate was concentrated and the crude material was purified by column chromatography (SiO$_2$, 0-15% EtOAc/petroleum ether), then the eluent was concentrated to dryness, washed with petroleum ether (20 mL) and dried to give (1-((1-((tert-butyldiphenylsilyl)oxy)-2-methylpropan-2-yl)sulfonyl)cyclopropyl)methanol. TLC $R_f$=0.2 (25% EtOAc/petroleum ether). $^1$H NMR (400 MHz, CDCl$_3$) δ 7.68-7.63 (m, 4H), 7.49-7.37 (m, 6H), 3.89 (s, 2H), 3.79 (d, J=5.1 Hz, 2H), 2.77 (br t, J=5.6 Hz, 1H), 1.54-1.49 (m, 2H), 1.48 (s, 6H), 1.10 (s, 9H), 0.97 (d, J=1.9 Hz, 2H).

Step 6: (2-((1-(Bromomethyl)cyclopropyl)sulfonyl)-2-methylpropoxy)(tert-butyl)diphenylsilane (int-31) was obtained using the method described in step 4 in the synthesis of intermediate (int-1), except (1-(Cyclopropylsulfonyl)cyclopropyl)methanol (i1-c) was replaced with (1-((1-((tert-butyldiphenylsilyl)oxy)-2-methylpropan-2-yl)sulfonyl)cyclopropyl)methanol. $^1$H NMR (400 MHz, DMSO-d$_6$) δ 7.63-7.61 (m, 4H), 7.49-7.45 (m, 6H), 4.04 (s, 2H), 3.83 (s, 2H), 1.57-1.53 (m, 2H), 1.42 (s, 6H), 1.24-1.21 (m, 2H), 1.03 (s, 9H). MS (ESI): m/z 531.1 [M+Na]$^+$.

Intermediate 32

6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid (Int-32)

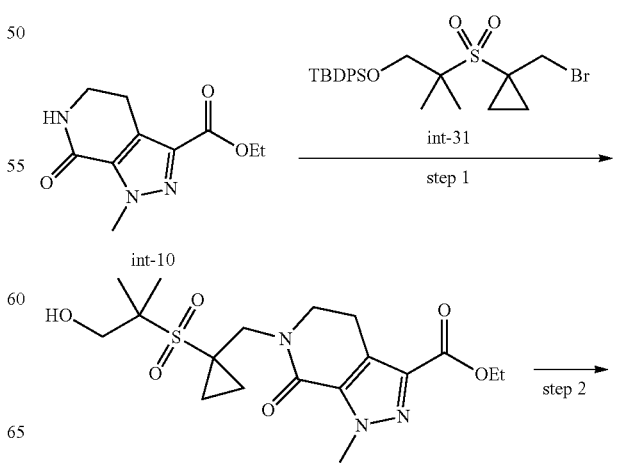

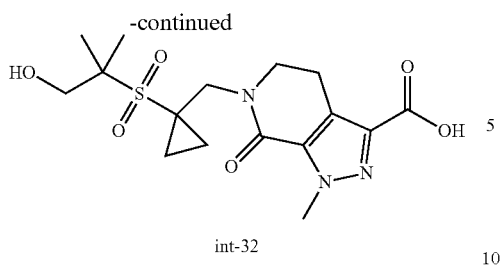

int-32

Step 1: Ethyl 6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate was obtained using the method described in the synthesis of intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with (2-((1-(Bromomethyl)cyclopropyl)sulfonyl)-2-methylpropoxy)(tert-butyl)diphenylsilane (int-31). $^1$H NMR (400 MHz, CDCl$_3$) δ 4.41 (m, 2H), 4.25-4.20 (m, 3H), 4.17 (s, 2H), 3.86 (s, 2H), 3.73 (m, 2H), 3.12 (m, 2H), 1.64-1.56 (m, 2H), 1.51 (s, 6H), 1.40 (m, 3H), 1.13-1.01 (m, 2H). MS (ESI): m/z 414.2 [M+H]$^+$.

Step 2: 6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid (int-32) was obtained using the method described in the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate. TLC R$_f$=0.2 (1:10 MeOH/EtOAc). MS (ESI): m/z 386.1 [M+H]$^+$.

Intermediate 33 tert-butyl 2-methyl-2-((1-(((methylsulfonyl)oxy)methyl)cyclopropyl)sulfonyl)propanoate (Int-33)

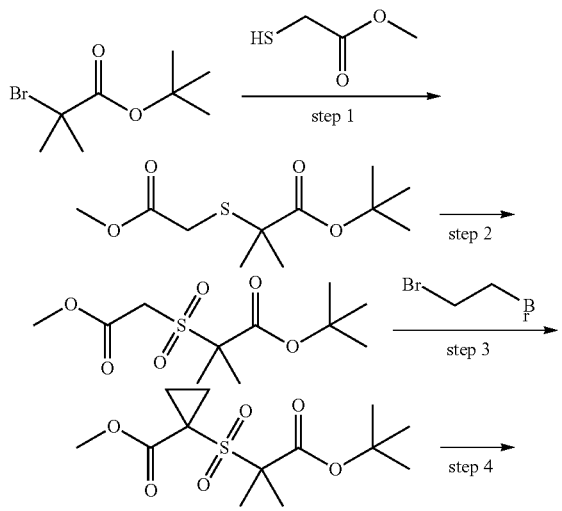

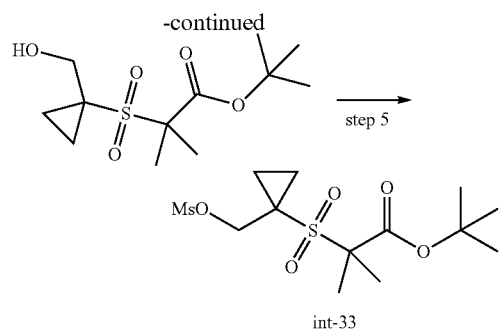

int-33

Step 1: A solution of methyl 2-mercaptoacetate (44.06 g, 415 mmol, 1.03 equiv) in MeOH (1350 mL) was treated with KOH pellets (23 g, 403 mmol, 1.0 equiv), followed by tert-butyl 2-bromo-2-methylpropanoate (90 g, 403 mmol, 1.0 equiv). The reaction was heated at 65° C. for 18 h and then cooled to rt before the precipitate was removed by filtration. The filter cake was rinsed with MeOH (540 mL) and the filtrate was concentrated under reduced pressure. The residue was dissolved in DCM (1350 mL) and the organic layer was washed with water (2×540 mL). The combined aqueous washes were back-extracted with DCM (2×250 mL) and the combined organic extracts were washed with brine (2×750 mL), dried over Na$_2$SO$_4$ and concentrated under reduced pressure. The residue was purified by column chromatography (SiO$_2$, 0-5% EtOAc/petroleum ether), then the eluent was concentrated to dryness, washed with petroleum ether (300 mL) and dried to give tert-butyl 2-((2-methoxy-2-oxoethyl)thio)-2-methylpropanoate. TLC R$_f$=0.3 (1:10 EtOAc/petroleum ether). $^1$H NMR (400 MHz, CDCl$_3$) δ 3.72 (s, 3H), 3.44 (s, 2H), 1.47 (s, 6H), 1.46 (s, 9H). MS (ESI): m/z 271.0 [M+Na]$^+$.

Step 2: tert-Butyl 2-((2-methoxy-2-oxoethyl)sulfonyl)-2-methylpropanoate was obtained using the method described in step 2 of the synthesis of intermediate (int-31), except tert-butyl 2-((1-hydroxy-2-methylpropan-2-yl)thio)acetate was replaced with tert-butyl 2-((2-methoxy-2-oxoethyl)thio)-2-methylpropanoate. TLC R$_f$=0.3 (1:5 EtOAc/petroleum ether). $^1$H NMR (400 MHz, DMSO-d$_6$) δ 4.49 (s, 2H), 3.72 (s, 3H), 1.51 (s, 6H), 1.45 (s, 9H). MS (ESI): m/z 225.0 [M+H-$^t$Bu]$^+$.

Step 3: Methyl 1-((1-(tert-butoxy)-2-methyl-1-oxopropan-2-yl)sulfonyl)cyclopropanecarboxylate was obtained using the method described in step 1 of the synthesis of intermediate (int-1), except benzyl 2-(cyclopropylsulfonyl)acetate was replaced with tert-Butyl 2-((2-methoxy-2-oxoethyl)sulfonyl)-2-methylpropanoate. TLC R$_f$=0.5 (25% EtOAc/petroleum ether). $^1$H NMR (400 MHz, DMSO-d$_6$) δ 3.69 (s, 3H), 1.67 (t, J=2.8 Hz, 2H), 1.66-1.63 (m, 2H), 1.56 (s, 6H), 1.42 (s, 9H).

Step 4: Lithium tri-tert-butoxyaluminum hydride (1.0 M in THF, 105 mL, 105 mmol, 2.0 equiv) was added to a solution of methyl 1-((1-(tert-butoxy)-2-methyl-1-oxopropan-2-yl)sulfonyl)cyclopropanecarboxylate (16 g, 52.2 mmol, 1.0 equiv) in THF (240 mL) at 20° C., then the reaction mixture was heated at 50° C. for 4 h. The reaction mixture was poured into 10% KHSO$_4$ (500 mL) and the resulting mixture was extracted with EtOAc (2×150 mL). The combined organic extracts were washed with brine (2×150 mL), dried with Na$_2$SO$_4$, filtered and concentrated. The crude was purified by column chromatography (SiO$_2$, 5-25% EtOAc/petroleum ether), then the eluent was concentrated to dryness, washed with EtOAc (20 mL) and dried to give tert-butyl 2-((1-(hydroxymethyl)cyclopropyl)sulfonyl)-2-methylpropanoate. TLC R$_f$=0.5 (25% EtOAc/petroleum ether). $^1$H NMR (400 MHz, DMSO-d$_6$) δ 5.23 (br s, 1H), 3.81 (s, 2H), 3.40 (br s, 35H), 1.56 (s, 6H), 1.43 (s, 9H), 1.26-1.20 (m, 2H), 1.14-1.08 (m, 2H). Step 5: To a solution of tert-butyl 2-((1-(hydroxymethyl)cyclopropyl)sulfonyl)-2-methylpropanoate (1 g, 3.6 mmol, 1.0 equiv) and Et$_3$N (1.1 g, 11 mmol, 3.0 equiv) in DCM (10 mL) was added MsCl (0.71 g, 6.2 mmol, 1.7 equiv) at 0° C. After the reaction mixture was stirred at 0° C. for 1 h, it was warmed to rt and stirred for 2 h. The reaction mixture was poured into saturated NaHCO$_3$ (10 mL), then the organic layer was separated and washed with brine (2×5 mL), dried over Na$_2$SO$_4$, filtered and concentrated to give tert-butyl 2-methyl-2-((1-(((methylsulfonyl)oxy)methyl)cyclopropyl)sulfonyl)propanoate (int-33). TLC R$_f$=0.5 (50% EtOAc/petroleum ether). $^1$H NMR (400 MHz, DMSO-d$_6$) δ 4.57 (s, 2H), 3.21 (s, 3H), 1.57 (s, 6H), 1.54-1.49 (m, 2H), 1.44 (s, 9H), 1.38-1.32 (m, 2H).

Intermediate 34

Ethyl 6-((1-((1-(tert-butoxy)-2-methyl-1-oxopropan-2-yl)sulfonyl)cyclopropyl)methyl)-1-methyl-7-oxo-4,5,6,7-tetrahydro-1H-pyrazolo[3,4-c]pyridine-3-carboxylate (Int-34)

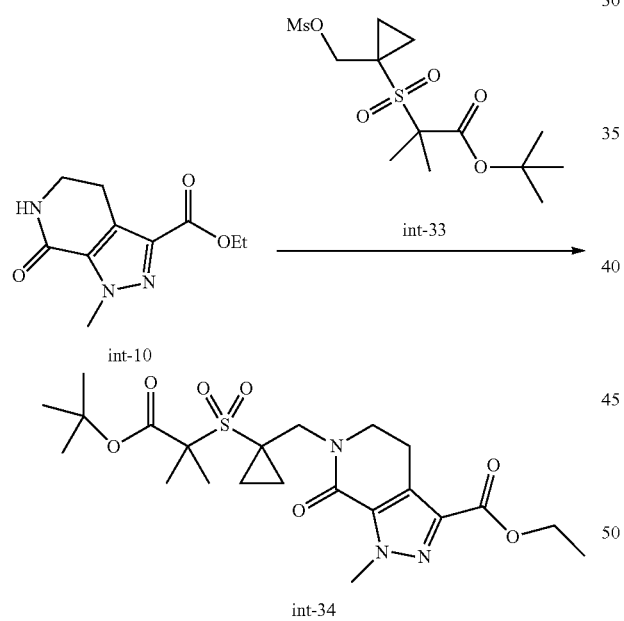

Ethyl 6-((1-((1-(tert-butoxy)-2-methyl-1-oxopropan-2-yl)sulfonyl)cyclopropyl)methyl)-1-methyl-7-oxo-4,5,6,7-tetrahydro-1H-pyrazolo[3,4-c]pyridine-3-carboxylate (int-34) was obtained using the method described in the synthesis of intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with tert-butyl 2-methyl-2-((1-(((methylsulfonyl)oxy)methyl)cyclopropyl)sulfonyl)propanoate (int-33). MS (ESI): m/z 484.0 [M+H]$^+$.

Intermediate 35

(2-(1-((1-(Bromomethyl)cyclopropyl)sulfonyl)cyclopropyl)ethoxy)triisopropylsilane (Int-35)

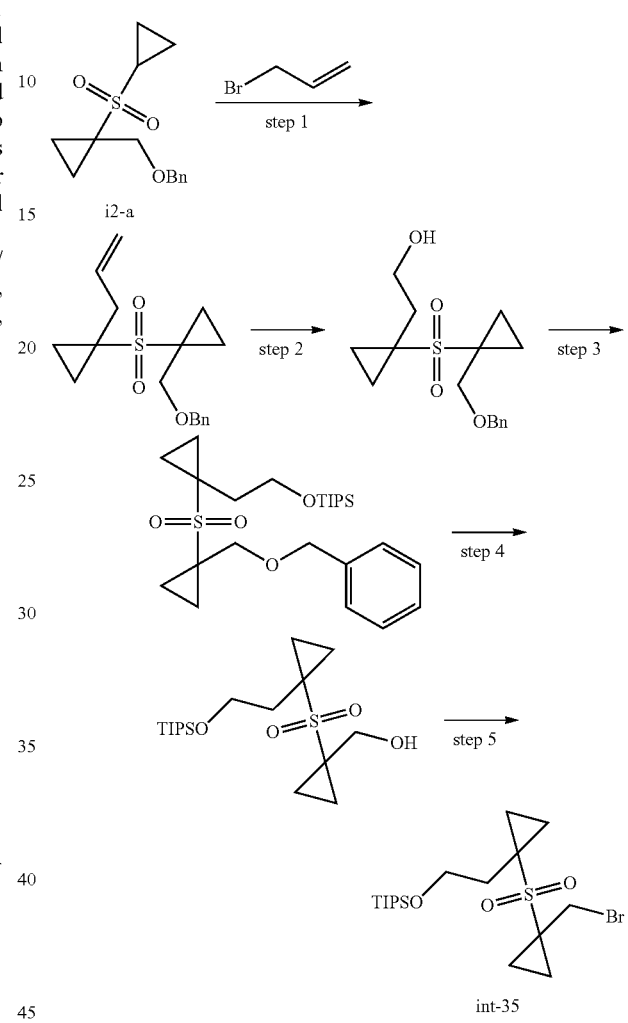

Step 1: n-BuLi (2.5 M in hexanes, 38 mL, 95 mmol, 1.2 equiv) was added dropwise to the solution of (((1-(cyclopropylsulfonyl)cyclopropyl)methoxy)methyl)benzene (i2-a) (21.00 g, 78.84 mmol, 1.0 equiv) in THF (200 mL) at −60° C. under N$_2$. The reaction was stirred at −60° C. for 30 min, then allyl bromide (28.61 g, 236 mmol, 3.0 equiv) was added to the mixture at −60° C. After the addition, the resulting mixture was stirred at 25° C. for 1 h before it was quenched with saturated NH$_4$Cl (100 mL) and extracted with EtOAc (3×100 mL). The combined organic extracts were washed with brine, dried over Na$_2$SO$_4$, filtered and concentrated to provide (((1-((1-allylcyclopropyl)sulfonyl)cyclopropyl)methoxy)methyl)benzene. TLC R$_f$=0.6 (50% EtOAc/petroleum ether). $^1$H NMR (400 MHz, CDCl$_3$) δ 7.43-7.30 (m, 5H), 5.64-5.55 (m, 1H), 5.09-4.94 (m, 2H), 4.53 (s, 2H), 3.77 (s, 2H), 2.76 (d, J=7.2 Hz, 2H), 1.58-1.52 (m, 2H), 1.42-1.34 (m, 2H), 1.12-1.03 (m, 2H), 0.85-0.76 (m, 2H).

Step 2: 2-(1-((1-((Benzyloxy)methyl)cyclopropyl)sulfonyl)cyclopropyl)ethanol was obtained using the method described in step 2 in the synthesis of intermediate (int-29), except ethyl 1-(4-methoxybenzyl)-6-((1-((2-methylbut-3-en-2-yl)sulfonyl)cyclopropyl)methyl)-7-oxo-4,5,6,7-tetrahydro-1H-pyrazolo[3,4-c]pyridine-3-carboxylate was replaced with (((1-((1-allylcyclopropyl)sulfonyl)cyclopropyl)methoxy)methyl)benzene. TLC $R_f$=0.4 (50% EtOAc/petroleum ether). MS (ESI): m/z 311.3 [M+H]$^+$.

Step 3: (2-(1-((1-(((Benzyloxy)methyl)cyclopropyl)sulfonyl)cyclopropyl)ethoxy)triisopropylsilane was obtained using the method described in step 5 of Example 105, except 4-((4-(1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridin-3-yl)-1H-1,2,3-triazol-1-yl)methyl)benzonitrile was replaced with 2-(1-((1-((benzyloxy)methyl)cyclopropyl)sulfonyl)cyclopropyl)ethanol. TLC $R_f$=0.8 (25% EtOAc/petroleum ether). $^1$H NMR (400 MHz, MeOH-d$_4$) δ 8.09-8.03 (m, 1H), 7.54-7.47 (m, 1H), 7.38-7.26 (m, 3H), 4.73-4.47 (m, 2H), 3.87-3.74 (m, 3H), 2.24-2.12 (m, 2H), 1.44-1.29 (m, 4H), 1.15-0.98 (m, 23H).

Step 4: (1-((1-(2-((Triisopropylsilyl)oxy)ethyl)cyclopropyl)sulfonyl)cyclopropyl)methanol was obtained using the method described in step 3 for the synthesis of intermediate (int-2), except (((1-((1-methylcyclopropyl)sulfonyl)cyclopropyl)methoxy)methyl)benzene (i2-b) was replaced with (2-(1-((1-((benzyloxy)methyl)cyclopropyl)sulfonyl)cyclopropyl)ethoxy)triisopropylsilane. TLC $R_f$=0.6 (50% EtOAc/petroleum ether). $^1$H NMR (400 MHz, MeOH-d$_4$) δ 3.94-3.86 (m, 4H), 2.21 (t, J=6.8 Hz, 2H), 1.44-1.32 (m, 4H), 1.18-1.04 (m, 25H).

Step 5: (2-(1-((1-(Bromomethyl)cyclopropyl)sulfonyl)cyclopropyl)ethoxy)triisopropylsilane (int-35) was obtained using the method described in step 4 for the synthesis of intermediate (int-1), except (1-(Cyclopropylsulfonyl)cyclopropyl)methanol (1-c) was replaced with (1-((1-(2-((Triisopropylsilyl)oxy)ethyl)cyclopropyl)sulfonyl)cyclopropyl)methanol. TLC $R_f$=0.8 (25% EtOAc/petroleum ether). $^1$H NMR (400 MHz, MeOH-d$_4$) δ 3.98-3.87 (m, 4H), 2.23 (t, J=6.6 Hz, 2H), 1.70-1.63 (m, 2H), 1.51-1.44 (m, 2H), 1.35-1.28 (m, 2H), 1.25-1.20 (m, 2H), 1.16-1.06 (m, 21H).

Intermediate 36

((1-((1-(Bromomethyl)cyclopropyl)sulfonyl)-2-methylpropan-2-yl)oxy)(tert-butyl)dimethylsilane
(Int-36)

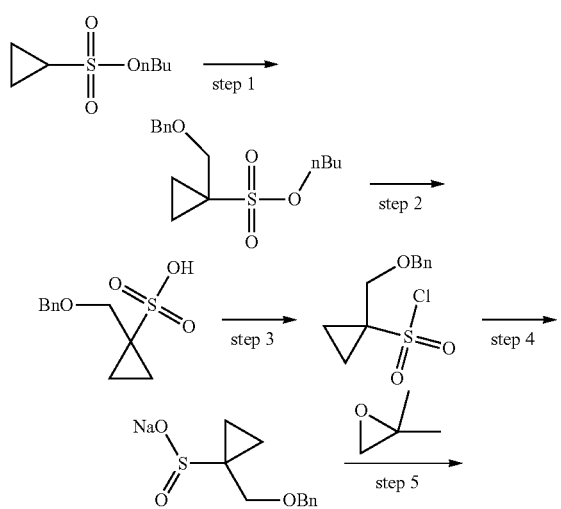

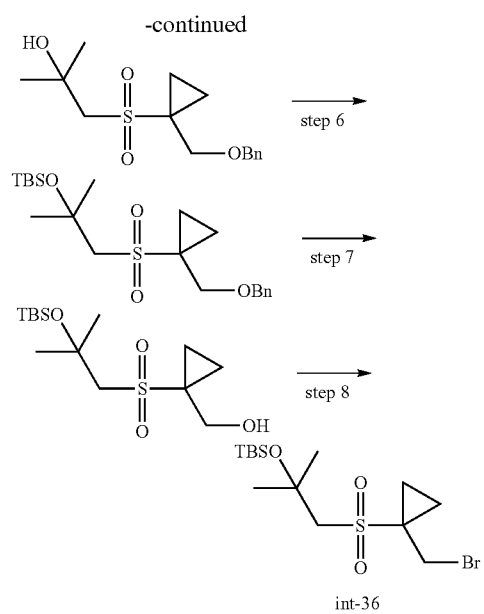

Step 1: To a solution of n-butyl cyclopropanesulfonate (5 g, 28.1 mmol, 1.0 equiv) in THF (100 mL) at −78° C. was added n-BuLi (2.5 M in hexanes, 13.46 mL, 33.7 mmol, 1.2 equiv) dropwise at −78° C. over 10-15 min. The resulting solution was allowed to stir at −78° C. for 30 min, then BOMCl (7.80 mL, 33.7 mmol, 1.2 equiv) was added in one portion. The resulting solution was allowed to slowly warm to rt and stir at rt overnight, then the flask was placed in an ice bath and the reaction was quenched with brine (100 mL) and diluted with EtOAc (100 mL). After the layers were separated, the aqueous layer was extracted with EtOAc (30 mL), then the combined organic extracts were dried with MgSO$_4$, filtered and concentrated. The residue was purified by column chromatography (SiO$_2$, 0-30% EtOAc/heptane) to afford butyl 1-((benzyloxy)methyl)cyclopropane-1-sulfonate. $^1$H NMR (500 MHz, CDCl$_3$) δ 7.34 (dt, J=12.7, 7.2 Hz, 5H), 4.55 (s, 2H), 4.23 (t, J=6.6 Hz, 2H), 3.79 (s, 2H), 1.66 (p, J=6.9 Hz, 2H), 1.48 (d, J=6.2 Hz, 2H), 1.37 (q, J=7.5 Hz, 2H), 1.10 (s, 2H), 0.90 (t, J=7.4 Hz, 3H). MS (ESI): m/z 299.2 [M+H]$^+$.

Step 2: A mixture of butyl 1-((benzyloxy)methyl)cyclopropane-1-sulfonate (6.4 g, 21.5 mmol, 1.0 equiv) and potassium thiocyanate (2.189 g, 22.5 mmol, 1.05 equiv) in DME (100 mL) and water (100 mL) was stirred at 90° C. overnight. After the solution was cooled, it was diluted with Et$_2$O (200 mL) and the aqueous layer was removed, then the organic layer was extracted with water (50 mL). The combined aqueous extracts were concentrated and dried under high vacuum to provide potassium 1-((benzyloxy)methyl)cyclopropane-1-sulfonate. $^1$H NMR (500 MHz, D$_2$O) δ 7.48-7.36 (m, 5H), 4.63 (s, 2H), 3.79 (s, 2H), 1.26-1.20 (m, 2H), 0.94-0.88 (m, 2H). MS (ESI): m/z 260.1 [M+H$_2$O]$^+$.

Step 3: To a mixture of potassium 1-((benzyloxy)methyl)cyclopropane-1-sulfonate (5.7 g, 20.26 mmol, 1.0 equiv) in DMF (5.5 mL) was added SOCl$_2$ (55 mL) (exothermic). The resulting mixture was stirred at 77° C. for 1 h before it was concentrated. The residue was taken up in EtOAc (250 mL) and washed with brine (2×50 mL), then the organic layer was dried over Na$_2$SO$_4$, filtered and concentrated to provide 1-((benzyloxy)methyl)cyclopropane-1-sulfonyl chloride. $^1$H NMR (400 MHz, CDCl$_3$) δ 7.40-7.27 (m, 5H), 4.61 (s, 2H), 4.00 (s, 2H), 1.82-1.76 (m, 2H), 1.43-1.37 (m, 2H).

Step 4: To a solution of Na₂SO₃ (3.48 g, 27.6 mmol, 1.0 equiv) in water (15 mL) was added NaHCO₃ (4.64 g, 55.2 mmol, 2.0 equiv). After the resulting mixture was stirred at 50° C. for 45 min, 1-((benzyloxy)methyl)cyclopropane-1-sulfonyl chloride (7.2 g, 27.6 mmol) was added. The resulting mixture was stirred at 50° C. overnight before it was concentrated. The residue was suspended in MeOH (150 mL), the solids were removed by filtration, and the filter cake washed with MeOH (3×50 mL). The filtrate was concentrated to provide sodium 1-((benzyloxy)methyl)cyclopropane-1-sulfinate. $^1$H NMR (400 MHz, DMSO-d₆) δ 7.29 (d, J=1.9 Hz, 5H), 4.44 (s, 2H), 3.62 (s, 2H), 0.62 (d, J=2.5 Hz, 2H), 0.22 (d, J=2.5 Hz, 2H). MS (ESI): m/z 227.1 [M+H]⁺.

Step 5: A biphasic solution of sodium 1-((benzyloxy)methyl)cyclopropane-1-sulfinate (1 g, 4.03 mmol, 1.0 equiv), isobutylene oxide (436 mg, 6.04 mmol, 1.5 equiv) and Bu₄NBr (649 mg, 2.01 mmol, 0.5 equiv) in CHCl₃ (30 mL) and H₂O (30 mL) was stirred at 100° C. for 12 h, then the mixture was extracted with CH₂Cl₂ (3×20 mL). The combined organic extracts were washed with brine (50 mL), dried over Na₂SO₄, filtered and concentrated. The residue was purified by RP-HPLC to give 1-((1-((benzyloxy)methyl)cyclopropyl)sulfonyl)-2-methylpropan-2-ol. TLC $R_f$=0.2 (50% EtOAc/petroleum ether). $^1$H NMR (400 MHz, CDCl₃) δ 7.42-7.30 (m, 5H), 4.57 (s, 2H), 3.79 (s, 2H), 3.74 (s, 1H), 3.44 (s, 2H), 1.55-1.50 (m, 2H), 1.41 (s, 6H), 1.03-0.96 (m, 2H). MS (ESI): m/z 299.3 [M+H]⁺.

Step 6: To a solution of 1-((1-((benzyloxy)methyl)cyclopropyl)sulfonyl)-2-methylpropan-2-ol (220 mg, 0.74 mmol, 1.0 equiv) in DCM (3 mL) was added TBSOTf (390 mg, 1.47 mmol, 2.0 equiv) and 2,6-lutidine (316 mg, 2.95 mmol, 4.0 equiv). The mixture was stirred at 25° C. for 2 h before the reaction was diluted with water (20 mL) and extracted with DCM (3×10 mL). The combined organic extracts were washed with brine (20 mL), dried over Na₂SO₄, filtered and concentrated. The residue was purified by column chromatography (SiO₂, 10-25% EtOAc/petroleum ether) to give ((1-((1-((benzyloxy)methyl)cyclopropyl)sulfonyl)-2-methylpropan-2-yl)oxy)(tert-butyl)dimethylsilane. TLC $R_f$=0.8 (50% EtOAc/petroleum ether). $^1$H NMR (400 MHz, CDCl₃) δ 7.41-7.30 (m, 5H), 4.55 (s, 2H), 3.77 (s, 2H), 3.43 (s, 2H), 1.52-1.46 (m, 8H), 0.99-0.92 (m, 2H), 0.85 (s, 9H), 0.08 (s, 6H).

Step 7: (1-((2-((tert-Butyldimethylsilyl)oxy)-2-methylpropyl)sulfonyl)cyclopropyl)methanol was obtained using the method described in step 3 for the synthesis of intermediate (int-2), except (((1-((1-methylcyclopropyl)sulfonyl)cyclopropyl)methoxy)methyl)benzene (i2-b) was replaced with ((1-((1-((benzyloxy)methyl)cyclopropyl)sulfonyl)-2-methylpropan-2-yl)oxy)(tert-butyl)dimethylsilane. TLC $R_f$=0.5 (25% EtOAc/petroleum ether). $^1$H NMR (400 MHz, CDCl₃) δ 3.89 (d, J=6.0 Hz, 2H), 3.34 (s, 2H), 1.54 (s, 6H), 1.52-1.47 (m, 2H), 1.03-0.99 (m, 2H), 0.89-0.88 (m, 9H), 0.14 (s, 6H).

Step 8: ((1-((1-(Bromomethyl)cyclopropyl)sulfonyl)-2-methylpropan-2-yl)oxy)(tert-butyl)dimethylsilane (int-36) was obtained using the method described in step 4 for the synthesis of intermediate (int-1), except (1-(cyclopropylsulfonyl)cyclopropyl)methanol (i1-c) was replaced with (1-((2-((tert-butyldimethylsilyl)oxy)-2-methylpropyl)sulfonyl)cyclopropyl)methanol. TLC $R_f$=0.8 (25% EtOAc/petroleum ether). $^1$H NMR (400 MHz, CDCl₃) δ 3.89 (s, 2H), 3.44 (s, 2H), 1.79-1.73 (m, 2H), 1.55 (s, 6H), 1.21-1.15 (m, 2H), 0.88 (s, 9H), 0.14 (s, 6H).

Intermediate 37

((1s, 3s)-3-((1-(Bromomethyl)cyclopropyl)sulfonyl)cyclobutoxy)triisopropylsilane (Int-37)

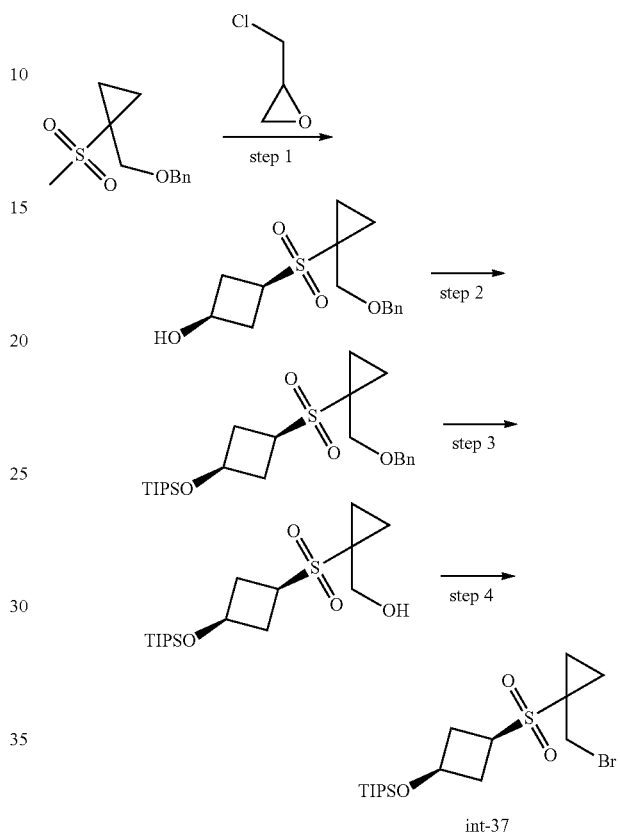

Step 1: To a solution of (((1-(methylsulfonyl)cyclopropyl)methoxy)methyl)benzene (7 g, 29.1 mmol, 1.0 equiv) in THF (90 mL) was added n-BuLi (2.5 M in hexanes, 11.7 mL, 29.1 mmol, 1.0 equiv,) at −60° C. under an atmosphere of N₂. After 30 min at −60° C., this solution was added dropwise to a solution of epichlorohydrin (2.6 g, 29.1 mmol, 1.0 equiv) in THF (10 mL) at −60° C., and the mixture was stirred at 20° C. for 16 h. The reaction was diluted with saturated NH₄Cl (50 mL) at 10° C., and the mixture was extracted with EtOAc (50 mL). The organic layer was dried over Na₂SO₄, filtered and concentrated. The residue was purified by RP-HPLC to afford (1s, 3s)-3-((1-((benzyloxy)methyl)cyclopropyl)sulfonyl)cyclobutan-1-ol. $^1$H NMR (400 MHz, CDCl₃) δ 7.41-7.28 (m, 5H), 4.59 (s, 2H), 3.80 (s, 2H), 1.92-1.86 (m, 2H), 1.74-1.68 (m, 2H), 1.29-1.24 (m, 2H), 1.20-1.14 (m, 2H). MS (ESI): m/z 297.1 [M+H]⁺.

Step 2: To a solution of (1s, 3s)-3-((1-((benzyloxy)methyl)cyclopropyl)sulfonyl)cyclobutan-1-ol (250 mg, 0.84 mmol, 1.0 equiv) in CH₂Cl₂ (2 mL) was added imidazole (172 mg, 2.53 mmol, 3.0 equiv) and DMAP (51 mg, 0.42 mmol, 0.5 equiv). The reaction mixture was stirred at 25° C. for 1 h before TIPSCl (487 mg, 2.53 mmol, 3.0 equiv) was added. After 15 h, the residue was concentrated and purified by RP-HPLC to give ((1s, 3s)-3-((1-((Benzyloxy)methyl)cyclopropyl)sulfonyl)cyclobutoxy)triisopropylsilane. $^1$H NMR (400 MHz, CDCl₃) δ 7.39-7.28 (m, 5H), 4.50 (s, 2H), 4.02-3.90 (m, 2H), 3.82-3.77 (m, 2H), 1.59-1.55 (m, 2H), 1.51-1.46 (m, 6H), 1.12-0.95 (m, 23H), MS (ESI): m/z 453.1 [M+H]⁺.

Step 3: (1-(((1s, 3s)-3-((Triisopropylsilyl)oxy)cyclobutyl) sulfonyl)cyclopropyl)methanol was obtained using the method described in step 3 for the synthesis of intermediate (int-2), except (((1-((1-methylcyclopropyl)sulfonyl)cyclopropyl)methoxy)methyl)benzene (i2-b) was replaced with ((1s, 3s)-3-((1-((Benzyloxy)methyl)cyclopropyl)sulfonyl) cyclobutoxy)triisopropylsilane. TLC $R_f$=0.5 (1:5 EtOAc/petroleum ether). ¹H NMR (400 MHz, CDCl₃) δ 7.18 (s, 1H), 4.22-4.12 (m, 1H), 3.73 (s, 2H), 3.47-3.36 (m, 1H), 2.57-2.45 (m, 2H), 2.44-2.33 (m, 2H), 1.39-1.32 (m, 2H), 1.05-0.91 (m, 31H), 0.90-0.84 (m, 2H).

Step 4: ((1s, 3s)-3-((1-(Bromomethyl)cyclopropyl)sulfonyl)cyclobutoxy)triisopropylsilane (int-37) was obtained using the method described in step 4 for the synthesis of intermediate (int-1), except (1-(cyclopropylsulfonyl)cyclopropyl)methanol (1-c) was replaced with 1-(((1s, 3s)-3-((Triisopropylsilyl)oxy)cyclobutyl)sulfonyl)cyclopropyl) methanol. ¹H NMR (400 MHz, CDCl₃) δ 4.31-4.23 (m, 1H), 3.82 (s, 2H), 3.69 (m, 1H), 2.71-2.61 (m, 2H), 2.53-2.42 (m, 2H), 1.77-1.70 (m, 2H), 1.17-1.11 (m, 2H), 1.08-1.00 (m, 22H).

Intermediate 38

((1r, 3r)-3-((1-(Bromomethyl)cyclopropyl)sulfonyl) cyclobutoxy)triisopropylsilane (Int-38)

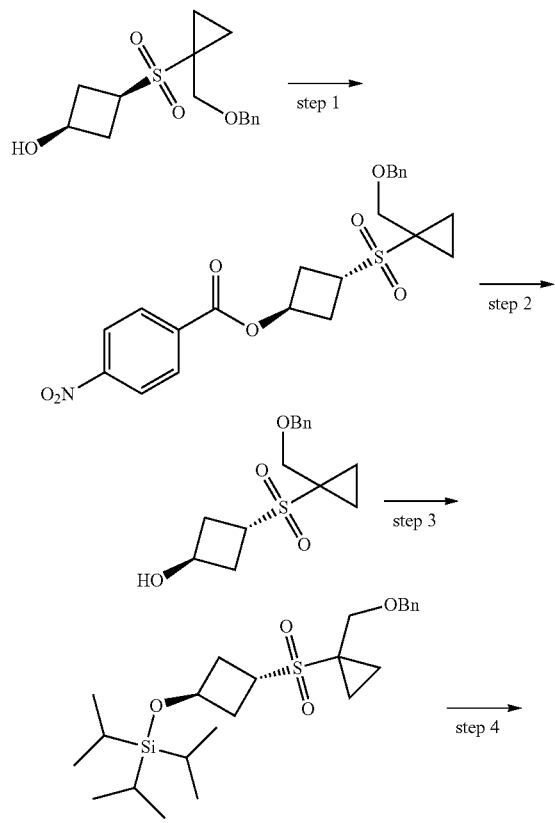

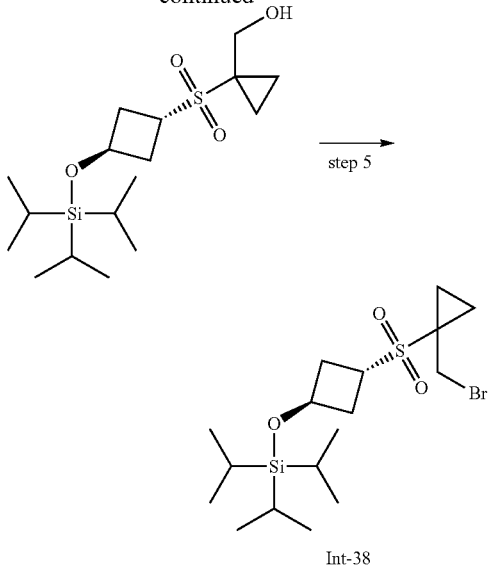

Step 1: To a suspension of (1s, 3s)-3-((1-((benzyloxy)methyl)cyclopropyl)sulfonyl)cyclobutan-1-ol (1.5 g, 5.06 mmol, 1.0 equiv) in THF (20 mL) was added 4-nitro-benzoic acid (845 mg, 5.06 mmol, 1.0 equiv) and PPh₃ (1.3 g, 5.06 mmol, 1.0 equiv). The reaction was cooled to 0° C. and DIAD (1.0 g, 5.06 mmol, 1.0 equiv) was added dropwise at 0° C. The reaction was stirred at 30° C. for 16 h before saturated NaHCO₃ (50 mL) was added at 10° C. The mixture was extracted with EtOAc (3×30 mL), the combined organic extracts were dried with Na₂SO₄, filtered, and concentrated. Purification by RP-HPLC afforded (1r, 3r)-3-((1-((benzyloxy)methyl)cyclopropyl)sulfonyl)cyclobutyl 4-nitrobenzoate. TLC $R_f$=0.5 (25% EtOAc/petroleum ether). ¹H NMR (400 MHz, CDCl₃) δ 8.32-8.27 (m, 2H), 8.21-8.15 (m, 2H), 7.37-7.25 (m, 5H), 5.45-5.36 (m, 1H), 4.57-4.52 (m, 2H), 4.30-4.21 (m, 1H), 3.73 (s, 2H), 3.15-3.03 (m, 2H), 2.66-2.55 (m, 2H), 1.57-1.51 (m, 2H), 1.02-0.96 (m, 2H). MS (ESI): m/z 463.1 [M+H]⁺.

Step 2: To a solution of (1r, 3r)-3-((1-((benzyloxy)methyl)cyclopropyl)sulfonyl)cyclobutyl 4-nitrobenzoate. (1.0 g, 2.24 mmol, 1.0 equiv) in THF (5 mL) was added NaOH (450 mg, 11.2 mmol, 5.0 equiv) in H₂O (5 mL). The reaction was stirred at 25° C. for 16 h before being concentrated. Purification by RP-HPLC afforded (1r, 3r)-3-((1-((benzyloxy)methyl)cyclopropyl)sulfonyl)cyclobutan-1-ol. TLC $R_f$=0.3 (25% EtOAc/petroleum ether). ¹H NMR (400 MHz, CDCl₃) δ 7.53-7.29 (m, 7H), 4.66-4.56 (m, 2H), 4.52 (s, 2H), 4.16-4.06 (m, 1H), 3.70 (s, 2H), 2.91-2.80 (m, 2H), 2.36-2.28 (m, 2H), 1.52-1.46 (m, 3H), 0.98-0.93 (m, 2H).

Step 3: ((1r, 3r)-3-((1-((Benzyloxy)methyl)cyclopropyl) sulfonyl)cyclobutoxy)triisopropylsilane was obtained using the method described in step 2 of the synthesis of intermediate (int-37), except (1s, 3s)-3-((1-((benzyloxy)methyl)cyclopropyl)sulfonyl)cyclobutan-1-ol was replaced with (1r, 3r)-3-((1-((benzyloxy)methyl)cyclopropyl)sulfonyl)cyclobutan-1-ol. TLC $R_f$=0.8 (1:5 EtOAc/petroleum ether). ¹H NMR (400 MHz, CDCl₃) δ 7.41-7.28 (m, 7H), 4.59-4.53 (m, 2H), 4.52 (s, 2H), 4.12-3.99 (m, 1H), 3.71 (s, 2H), 2.84 (ddd, J=4.5, 7.2, 14.3 Hz, 2H), 2.35-2.27 (m, 1H), 1.53-1.44 (m, 3H), 1.06-1.00 (m, 27H), 0.97-0.92 (m, 2H).

Step 4: (1-(((1r, 3r)-3-((Triisopropylsilyl)oxy)cyclobutyl) sulfonyl)cyclopropyl)methanol was obtained using the method described in step 3 of the synthesis of intermediate (int-37), except ((1s, 3s)-3-((1-((benzyloxy)methyl)cyclopropyl)sulfonyl)cyclobutoxy)triisopropylsilane was replaced with ((1r, 3r)-3-((1-((benzyloxy)methyl)cyclopropyl)sulfonyl)cyclobutoxy)triisopropylsilane. TLC R$_f$=0.3 (25% EtOAc/petroleum ether). $^1$H NMR (400 MHz, CDCl$_3$) δ 4.66-4.49 (m, 1H), 4.16-3.96 (m, 2H), 3.82 (s, 2H), 2.87 (m, 2H), 2.50-2.31 (m, 2H), 1.52-1.45 (m, 2H), 1.07-1.02 (m, 22H), 1.01-0.98 (m, 2H).

Step 5: ((1r, 3r)-3-((1-(Bromomethyl)cyclopropyl)sulfonyl)cyclobutoxy)triisopropylsilane (int-38) was obtained using the method described in step 4 of the synthesis of intermediate (int-37), except 1-(((1s, 3s)-3-((triisopropylsilyl)oxy)cyclobutyl)sulfonyl)cyclopropyl)methanol was replaced with (1-(((1r, 3r)-3-((triisopropylsilyl)oxy)cyclobutyl)sulfonyl)cyclopropyl)methanol. TLC R$_f$=0.7 (25% EtOAc/petroleum ether). $^1$H NMR (400 MHz, CDCl$_3$) δ 4.66-4.50 (m, 1H), 4.24-4.07 (m, 1H), 3.81 (s, 2H), 2.87 (m, 2H), 2.54-2.39 (m, 2H), 1.81-1.74 (m, 2H), 1.20-1.14 (m, 2H), 1.05 (d, J=8.2 Hz, 19H).

Intermediate 39

Benzyl(1-(bromomethyl)cyclopropyl)sulfane (Int-39)

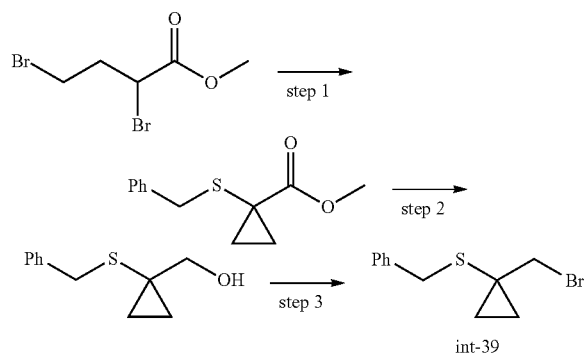

Step 1: To a mixture of methyl 2,4-dibromobutanoate (11.50 g, 35.39 mmol, 1.0 equiv), K$_2$CO$_3$ (14.68 g, 106.18 mmol, 3.0 equiv) and n-Bu$_4$NHSO$_4$ (2.40 g, 7.07 mmol, 0.2 equiv) in toluene (50 mL) was added benzyl mercaptan (3.96 g, 31.86 mmol, 0.9 equiv). The mixture was stirred at 120° C. for 3 h before it was concentrated. The residue was purified by column chromatography (SiO$_2$, 0-25% EtOAc/petroleum ether) to afford methyl 1-(benzylthio)cyclopropanecarboxylate. TLC R$_f$=0.6 (1:10 EtOAc/petroleum ether). $^1$H NMR (400 MHz, CDCl$_3$) δ 7.35-7.20 (m, 6H), 3.92 (s, 2H), 3.65 (s, 3H), 1.53 (d, J=3.2 Hz, 2H), 1.10-1.05 (m, 2H). MS (ESI): m/z 223.1 [M+H]$^+$.

Step 2: To a solution of methyl 1-(benzylthio)cyclopropanecarboxylate (3 g, 13.50 mmol, 1.0 equiv) in THF (30 mL) was added LiAlH$_4$ (2.05 g, 53.98 mmol, 4.0 equiv) at 0° C. under N$_2$ (gas evolution). The mixture was stirred at 25° C. for 2 h, then it was cooled to 0° C. and the reaction was quenched by the cautious, dropwise addition of water (2 mL) (gas evolution) and 15% NaOH (2 mL). The solids were removed by filtration, then the filter cake was washed with EtOAc (2×30 mL) and the filtrate was concentrated. The residue was purified by column chromatography (SiO$_2$, 0-50% EtOAc/petroleum ether) to afford 1-(benzylthio)cyclopropyl)methanol. TLC R$_f$=0.3 (25% EtOAc/petroleum ether). $^1$H NMR (400 MHz, CDCl$_3$) δ 7.33 (s, 4H), 7.26-7.22 (m, 1H), 3.83 (s, 2H), 3.38 (d, J=6.4 Hz, 2H), 2.02-1.96 (m, 1H), 0.86 (s, 2H), 0.82-0.76 (m, 2H). MS (ESI): m/z 177.0 [M+H-H$_2$O]$^+$.

Step 3: A solution of 1-(benzylthio)cyclopropyl)methanol (2.20 g, 11.32 mmol, 1.0 equiv) in DCM (20 mL) was cooled to 0° C. before it was treated with PBr$_3$ (3.37 g, 12.46 mmol, 1.1 equiv). The mixture was stirred at 25° C. for 2 h, then it was poured to ice water (100 mL) and extracted with EtOAc (2×100 mL). The combined organic extracts were dried over Na$_2$SO$_4$, concentrated and the residue was purified by column chromatography (SiO$_2$, 0-25% EtOAc/petroleum ether) to afford benzyl(1-(bromomethyl)cyclopropyl)sulfane (int-39). TLC R$_f$=0.7 (1:10 EtOAc/petroleum ether). $^1$H NMR (400 MHz, CDCl$_3$) δ 7.38-7.28 (m, 4H), 7.26-7.21 (m, 1H), 3.91 (s, 2H), 3.45 (s, 2H), 1.12-1.05 (m, 2H), 1.02-0.96 (m, 2H).

Intermediate 40

3-((1-(Bromomethyl)cyclopropyl)sulfonyl)-3-methyloxetane (Int-40)

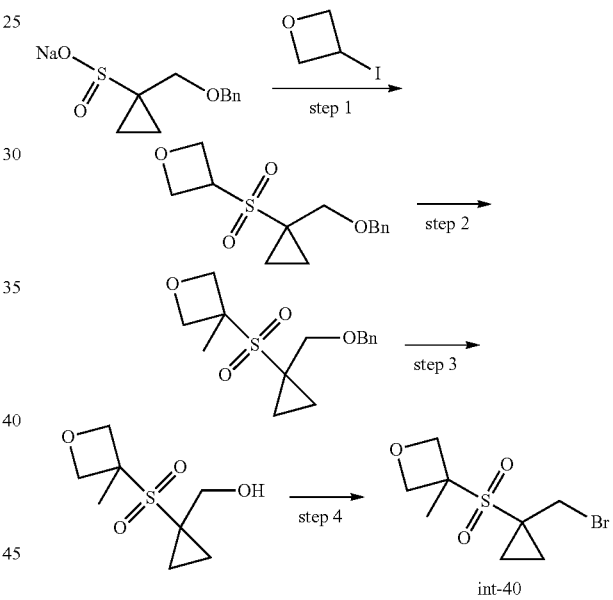

Step 1: A solution of sodium 1-((benzyloxy)methyl)cyclopropane-1-sulfinate (10.00 g, 40.28 mmol, 1.0 equiv) and 3-iodooxetane (9.63 g, 52.36 mmol, 1.3 equiv) in DMF (50 mL) was treated with Cs$_2$CO$_3$ (19.69 g, 60.42 mmol, 1.5 equiv) and the resulting mixture was allowed to stir at 110° C. for 12 h. The reaction was diluted with water (50 mL) and extracted with EtOAc (3×50 mL), then the combined organic extracts were washed with brine (50 mL), dried over Na$_2$SO$_4$, filtered and concentrated. The crude residue was purified by RP-HPLC to give 3-((1-((benzyloxy)methyl)cyclopropyl)sulfonyl)oxetane. $^1$H NMR (400 MHz, CDCl$_3$) δ 7.36-7.17 (m, 5H), 4.93-4.86 (m, 2H), 4.69-4.54 (m, 3H), 4.40 (s, 2H), 3.59 (s, 2H), 1.47-1.39 (m, 2H), 0.93-0.86 (m, 2H). MS (ESI): m/z 300.3 [M+H$_2$O]$^+$.

Step 2: A solution of 3-((1-((benzyloxy)methyl)cyclopropyl)sulfonyl)oxetane (300 mg, 1.06 mmol, 1.0 equiv) in THF (3 mL) was cooled to −70° C. before LiHMDS (1.6 mL, 1.6 mmol, 1.5 equiv) was added dropwise. The mixture was stirred at −70° C. for 1 h, then MeI (0.13 mL, 2.12 mmol, 2.0 equiv) was added and the mixture was stirred for 1 h at 25° C. The mixture was quenched with saturated NH₄Cl (10 mL) and extracted with EtOAc (3×10 mL). The combined organic extracts were washed with brine (10 mL), dried over Na₂SO₄, filtered and concentrated. The residue was purified by column chromatography (SiO₂, 10-25% EtOAc/petroleum ether) to give 3-((1-((benzyloxy)methyl) cyclopropyl)sulfonyl)-3-methyloxetane. TLC R$_f$=0.6 (50% EtOAc/petroleum ether). ¹H NMR (400 MHz, CDCl₃) δ 7.33-7.19 (m, 5H), 5.05 (d, J=7.2 Hz, 2H), 4.36 (s, 2H), 4.20 (d, J=7.2 Hz, 2H), 3.58 (s, 2H), 1.78 (s, 3H), 1.47-1.41 (m, 2H), 0.94-0.85 (m, 2H).

Step 3: (1-((3-Methyloxetan-3-yl)sulfonyl)cyclopropyl) methanol was obtained using the method described in step 3 for the synthesis of intermediate (int-2), except (((1-((1-methylcyclopropyl)sulfonyl)cyclopropyl)methoxy)methyl) benzene (i2-b) was replaced with 3-((1-((benzyloxy)methyl) cyclopropyl)sulfonyl)-3-methyloxetane. TLC R$_f$=0.1 (50% EtOAc/petroleum ether). ¹H NMR (400 MHz, CDCl₃) 55.23 (d, J=7.2 Hz, 2H), 4.46 (d, J=7.2 Hz, 2H), 3.84 (s, 2H), 1.90 (s, 3H), 1.55-1.49 (m, 2H), 1.05-0.99 (m, 2H).

Step 4: 3-((1-(Bromomethyl)cyclopropyl)sulfonyl)-3-methyloxetane (int-40) was obtained using the method described in step 4 for the synthesis of intermediate (int-1), except (1-(cyclopropylsulfonyl)cyclopropyl)methanol (1-c) was replaced with (1-((3-methyloxetan-3-yl)sulfonyl)cyclopropyl)methanol. TLC R$_f$=0.8 (50% EtOAc/petroleum ether). ¹H NMR (400 MHz, CDCl₃) δ 5.27 (d, J=7.0 Hz, 2H), 4.55 (d, J=7.3 Hz, 2H), 3.81 (s, 2H), 1.95 (s, 3H), 1.84-1.78 (m, 2H), 1.24-1.18 (m, 2H).

Intermediate 41

((3-((1-(bromomethyl)cyclopropyl)sulfonyl)oxetan-3-yl)methoxy)triisopropylsilane (Int-41)

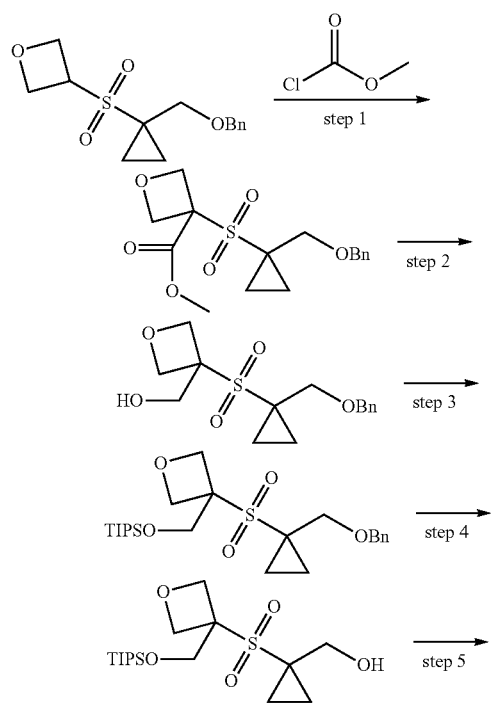

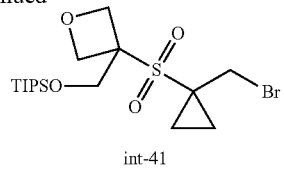

int-41

Step 1: To a solution of 3-((1-((benzyloxy)methyl)cyclopropyl)sulfonyl)oxetane (5.00 g, 17.7 mmol, 1.0 equiv) in THF (50 mL) at −70° C. was added LiHMDS (1.0 M in THF, 53.1 mL, 53.1 mmol, 3.0 equiv) dropwise. The mixture was stirred at −70° C. for 1 h before methyl chloroformate (3.35 g, 35.42 mmol, 2.0 equiv) was added, then the mixture was stirred at 25° C. for 1 h. The reaction was quenched with water (100 mL) and extracted with EtOAc (3×50 mL). The combined organic extracts were washed with brine (50 mL), dried over Na₂SO₄, filtered and concentrated. The crude residue was purified by RP-HPLC to give 3-((1-((benzyloxy)methyl)cyclopropyl)sulfonyl)oxetane-3-carboxylate. ¹H NMR (400 MHz, CDCl₃) δ 7.41-7.29 (m, 5H), 5.18 (d, J=8.0 Hz, 2H), 4.86 (d, J=8.0 Hz, 2H), 4.47 (s, 2H), 3.83 (s, 3H), 3.65 (s, 2H), 1.57-1.52 (m, 2H), 1.05-0.99 (m, 2H). MS (ESI): m/z 358.3 [M+H₂O]—.

Step 2: A solution of 3-((1-((benzyloxy)methyl)cyclopropyl)sulfonyl)oxetane-3-carboxylate (3.50 g, 10.28 mmol, 1.0 equiv) in THF (40 mL) was cooled to 0° C. before LiAlH₄ (737 mg, 20.56 mmol, 2.0 equiv) was added portion wise. The mixture was stirred at 25° C. for 1 h before it was quenched by the sequential addition of water (1 mL) (gas evolution), 2 N NaOH (2 mL) and water (1 mL). The mixture was dried over Na₂SO₄, filtered and concentrated. The residue was purified by column chromatography (SiO₂, 10-25% EtOAc/petroleum ether) to give (3-((1-((benzyloxy)methyl)cyclopropyl)sulfonyl)oxetan-3-yl)methanol. TLC R$_f$=0.4 (50% EtOAc/petroleum ether). ¹H NMR (400 MHz, CDCl₃) δ 7.43-7.25 (m, 6H), 5.05 (d, J=7.6 Hz, 2H), 4.48-4.40 (m, 4H), 4.29 (d, J=6.0 Hz, 2H), 3.69 (s, 2H), 2.80 (t, J=6.0 Hz, 1H), 1.65-1.59 (m, 2H), 1.07-1.00 (m, 2H).

Step 3: To a stirred solution of (3-((1-((benzyloxy)methyl)cyclopropyl)sulfonyl)oxetan-3-yl)methanol (1.00 g, 3.20 mmol, 1.0 equiv) in DMF (10 mL) was added imidazole (1.09 g, 16.01 mmol, 5.0 equiv) and TIPSCl (1.23 g, 6.40 mmol, 2.0 equiv) at 25° C., then the mixture was stirred at 80° C. for 12 h. The mixture was quenched with water (30 mL), and then extracted with EtOAc (3×30 mL). The combined organic extracts were washed with brine (30 mL), dried over Na₂SO₄, filtered and concentrated. The residue was purified by RP-HPLC to give ((3-((1-((benzyloxy)methyl)cyclopropyl)sulfonyl)oxetan-3-yl)methoxy)triisopropylsilane. TLC R$_f$=0.5 (25% EtOAc/petroleum ether). ¹H NMR (400 MHz, CDCl₃) δ 7.39-7.26 (m, 5H), 5.01 (d, J=7.2 Hz, 2H), 4.82 (d, J=6.8 Hz, 2H), 4.43 (s, 2H), 4.13 (s, 2H), 3.62 (s, 2H), 1.50-1.44 (m, 2H), 1.16-1.04 (m, 18H), 0.95-0.89 (m, 2H). MS (ESI): m/z 486.4 [M+H₂O]⁺.

Step 4: (1-((3-(((Triisopropylsilyl)oxy)methyl)oxetan-3-yl)sulfonyl)cyclopropyl)methanol was obtained using the method described in step 3 for the synthesis of intermediate (int-2), except (((1-((1-methylcyclopropyl)sulfonyl)cyclopropyl)methoxy)methyl)benzene (i2-b) was replaced with ((3-((1-((benzyloxy)methyl)cyclopropyl)sulfonyl)oxetan-3-yl)methoxy)triisopropylsilane. TLC R$_f$=0.1 (25% EtOAc/petroleum ether). ¹H NMR (400 MHz, CDCl₃) δ 5.13 (d, J=7.2 Hz, 2H), 4.76 (d, J=7.2 Hz, 2H), 4.28 (s, 2H), 3.83 (d, J=4.4 Hz, 2H), 2.59 (t, J=4.8 Hz, 1H), 1.56-1.50 (m, 2H), 1.23-1.05 (m, 25H), 1.04-0.99 (m, 2H).

Step 5: ((3-((1-(Bromomethyl)cyclopropyl)sulfonyl)oxetan-3-yl)methoxy)triisopropylsilane (int-41) was obtained using the method described in step 4 for the synthesis of intermediate (int-2), except (1-((3-(((triisopropylsilyl)oxy)methyl)oxetan-3-yl)sulfonyl)cyclopropyl)methanol. TLC $R_f$=0.8 (25% EtOAc/petroleum ether). $^1$H NMR (400 MHz, CDCl$_3$) δ 5.13 (d, J=7.2 Hz, 2H), 4.95 (d, J=7.2 Hz, 2H), 4.22 (s, 2H), 3.83 (s, 2H), 3.69 (s, 1H), 1.78-1.73 (m, 2H), 1.23-1.10 (m, 26H).

Intermediate 42

5-((1-(Bromomethyl)cyclopropyl)sulfonyl)-2,2,5-trimethyl-1,3-dioxane (Int-42)

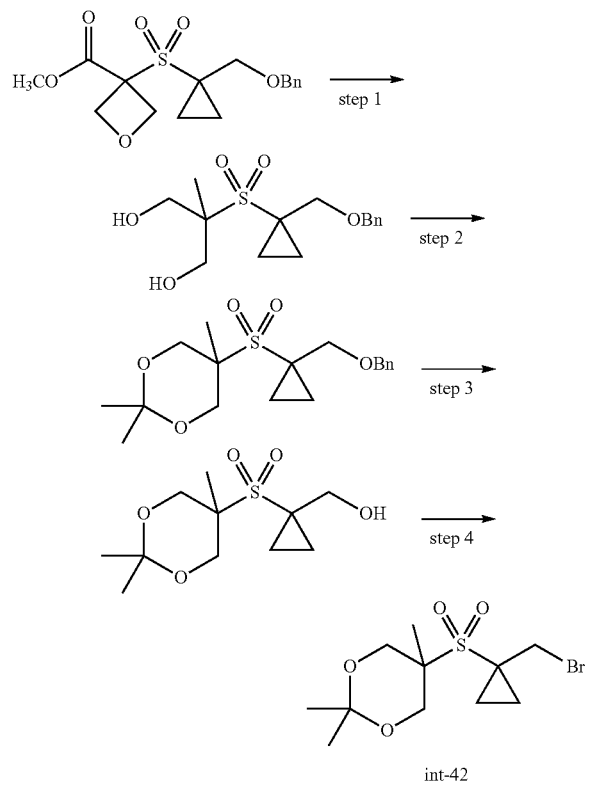

int-42

Step 1: (3-((1-((Benzyloxy)methyl)cyclopropyl)sulfonyl)oxetan-3-yl)methanol. To a stirred solution of 3-((1-((benzyloxy)methyl)cyclopropyl)sulfonyl)oxetane-3-carboxylate (16.00 g, 47.0 mmol, 1.0 equiv) in THF (160 mL) was added LiAlH$_4$ (8.92 g, 235.0 mmol, 5.0 equiv) at 25° C. After the mixture was stirred at 25° C. for 12 h, it was quenched with water (100 mL) (gas evolution) and adjusted to pH 1-2 with 1 N HCl. The mixture was extracted with EtOAc (3×100 mL), then the combined organic extracts were washed with brine (100 mL), dried over Na$_2$SO$_4$, filtered and concentrated. The residue was purified by column chromatography (SiO$_2$, 15-50% EtOAc/petroleum ether) to give 2-((1-((benzyloxy)methyl)cyclopropyl)sulfonyl)-2-methylpropane-1,3-diol. TLC $R_f$=0.3 (25% EtOAc/petroleum ether). $^1$H NMR (400 MHz, MeOH-d$_4$) δ 7.41-7.26 (m, 5H), 4.55 (s, 2H), 4.04-3.97 (m, 2H), 3.93-3.85 (m, 4H), 1.60-1.52 (m, 2H), 1.44-1.38 (m, 3H), 1.17-1.09 (m, 2H).

Step 2: To a stirred solution of 2-((1-((benzyloxy)methyl)cyclopropyl)sulfonyl)-2-methylpropane-1,3-diol (14.00 g, 44.5 mmol, 1.0 equiv) in THF (140 mL) was added 2,2-dimethoxypropane (46.38 g, 445.3 mmol, 10.0 equiv) and p-TsOH·H$_2$O (1.69 g, 8.9 mmol, 0.2 equiv) at 25° C. The mixture was stirred at 25° C. for 6 h before it was diluted with water (100 mL) and extracted with EtOAc (3×100 mL). The combined organic extracts were washed with brine (100 mL), dried over Na$_2$SO$_4$, filtered and concentrated. The residue was purified by purified by column chromatography (SiO$_2$, 10-35% EtOAc/petroleum ether) to give 5-((1-((benzyloxy)methyl)cyclopropyl)sulfonyl)-2,2,5-trimethyl-1,3-dioxane. TLC $R_f$=0.8 (25% EtOAc/petroleum ether). $^1$H NMR (400 MHz, MeOH-d$_4$) δ 7.45-7.24 (m, 4H), 4.54 (s, 2H), 4.44-4.38 (m, 1H), 4.41 (d, J=12.2 Hz, 1H), 3.83 (s, 2H), 3.79 (d, J=12.2 Hz, 2H), 1.56 (s, 3H), 1.54-1.49 (m, 2H), 1.38 (d, J=12.6 Hz, 6H), 1.20-1.14 (m, 2H).

Step 3: (1-((2,2,5-Trimethyl-1,3-dioxan-5-yl)sulfonyl)cyclopropyl)methanol was obtained using the method described in step 3 for the synthesis of intermediate (int-2), except (((1-((1-methylcyclopropyl)sulfonyl)cyclopropyl)methoxy)methyl)benzene (i2-b) was replaced with 5-((1-((benzyloxy)methyl)cyclopropyl)sulfonyl)-2,2,5-trimethyl-1,3-dioxane. TLC $R_f$=0.2 (25% EtOAc/petroleum ether). $^1$H NMR (400 MHz, MeOH-d$_4$) δ 4.46 (d, J=12.2 Hz, 2H), 3.93 (s, 2H), 3.87 (d, J=12.6 Hz, 2H), 1.58 (s, 3H), 1.49-1.45 (m, 5H), 1.40 (s, 3H), 1.17-1.11 (m, 2H).

Step 4: 5-((1-(Bromomethyl)cyclopropyl)sulfonyl)-2,2,5-trimethyl-1,3-dioxane (int-42) was obtained using the method described in step 4 for the synthesis of intermediate (int-1), except (1-(Cyclopropylsulfonyl)cyclopropyl)methanol (1-c) was replaced with (1-((2,2,5-trimethyl-1,3-dioxan-5-yl)sulfonyl)cyclopropyl)methanol. TLC $R_f$=0.8 (25% EtOAc/petroleum ether). $^1$H NMR (400 MHz, MeOH-d$_4$) δ 4.33 (d, J=13.6 Hz, 2H), 4.23 (s, 2H), 3.97 (d, J=13.6 Hz, 2H), 1.75-1.70 (m, 2H), 1.48 (s, 3H), 1.44 (s, 3H), 1.39 (s, 3H), 1.38-1.34 (m, 2H).

Intermediate 43

4-(2-((1-(Bromomethyl)cyclopropyl)sulfonyl)propan-2-yl)-2,2-dimethyl-1,3-dioxolane (Int-43)

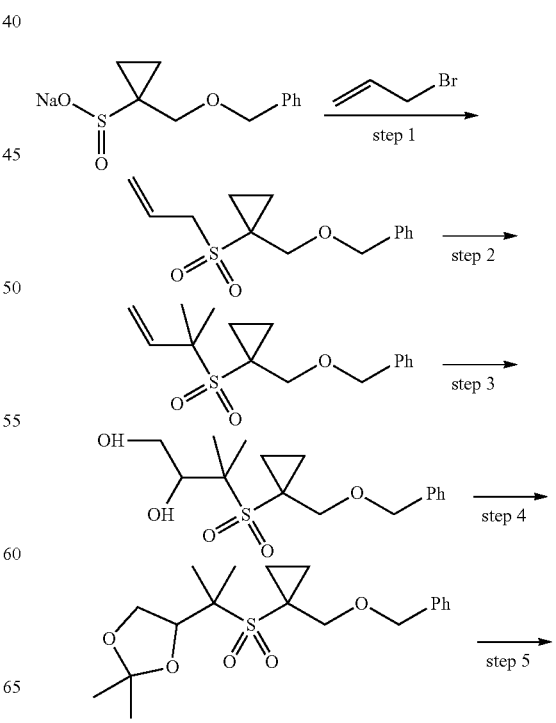

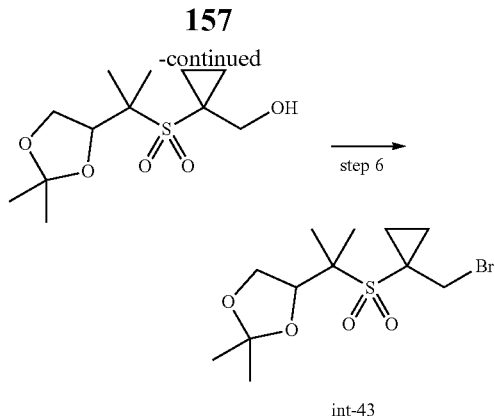

Step 1: To a solution of sodium 1-((benzyloxy)methyl)cyclopropane-1-sulfinate (19 g, 76.5 mmol, 1.0 equiv) in DMF (100 mL) was added allyl bromide (14 g, 115 mmol, 1.5 equiv) dropwise. The reaction mixture was stirred at 25° C. for 12 h before it was diluted with water (150 mL) and extracted with TMBE (3×50 mL). The combined organic extracts were washed with water (100 mL) and brine, then dried with $Na_2SO_4$, filtered and concentrated. The crude was purified by column chromatography ($SiO_2$, 5-10% EtOAc/petroleum ether), then the eluent was concentrated to dryness, washed with petroleum ether (20 mL) and dried to give of (((1-(allylsulfonyl)cyclopropyl)methoxy)methyl)benzene. TLC $R_f$=0.3 (1:5 EtOAc/petroleum ether). $^1$H NMR (400 MHz, $CDCl_3$) δ 7.44-7.29 (m, 5H), 5.99-5.84 (m, 1H), 5.46-5.35 (m, 2H), 4.57 (s, 2H), 3.97 (d, J=7.5 Hz, 2H), 3.77 (s, 2H), 1.54-1.45 (m, 2H), 1.01-0.89 (m, 2H).

Step 2: (((1-((2-Methylbut-3-en-2-yl)sulfonyl)cyclopropyl)methoxy)methyl)benzene was obtained using the method described in step 2 of the synthesis of intermediate (int-26), except, (allylsulfonyl)cyclopropane was replaced with (((1-(allylsulfonyl)cyclopropyl)methoxy)methyl)benzene. TLC $R_f$=0.4 (1:5 EtOAc/petroleum ether). $^1$H NMR (400 MHz, $CDCl_3$) δ 7.43-7.28 (m, 5H), 6.20 (dd, J=10.7, 17.5 Hz, 1H), 5.37-5.23 (m, 2H), 4.47 (s, 2H), 3.79 (s, 2H), 1.55 (s, 8H), 1.17-1.02 (m, 2H).

Step 3: A solution of (((1-((2-methylbut-3-en-2-yl)sulfonyl)cyclopropyl)methoxy)methyl)benzene (11 g, 37.4 mmol, 1.0 equiv) in acetone (570 mL) and $H_2O$ (63 mL) was treated with NMO (13.2 g, 112 mmol, 3.0 equiv) and $OsO_4$ (1% in t-BuOH, 24 mL, 1.9 mmol, 0.05 equiv). After 12 h at 25° C., the reaction was quenched with saturated aqueous $Na_2SO_3$, the solids were removed by filtration and the filtrate was extracted with EtOAc (3×250 mL). The combined organic extracts were washed with water (200 mL) and brine, dried with $Na_2SO_4$, filtered and concentrated. The crude was purified by column chromatography ($SiO_2$, 0-10% EtOAc/petroleum ether), then the eluent was concentrated to dryness, washed with petroleum ether (20 mL) and dried to give 3-((1-((benzyloxy)methyl)cyclopropyl)sulfonyl)-3-methylbutane-1,2-diol. TLC $R_f$=0.6 (1:5 EtOAc/petroleum ether). $^1$H NMR (400 MHz, $CDCl_3$) δ 7.41-7.28 (m, 5H), 4.56-4.46 (m, 2H), 4.27 (td, J=3.4, 7.2 Hz, 1H), 3.98-3.81 (m, 2H), 3.75-3.57 (m, 3H), 2.31 (br s, 1H), 1.70-1.55 (m, 2H), 1.52 (s, 3H), 1.45 (s, 3H), 1.18-1.02 (m, 2H).

Step 4: 4-(2-((1-((Benzyloxy)methyl)cyclopropyl)sulfonyl)propan-2-yl)-2,2-dimethyl-1,3-dioxolane was obtained using the method described in step 2 for the synthesis of Intermediate (int-42), except 2-((1-((benzyloxy)methyl)cyclopropyl)sulfonyl)-2-methylpropane-1,3-diol was replaced with 3-((1-((benzyloxy)methyl)cyclopropyl)sulfonyl)-3-methylbutane-1,2-diol. TLC $R_f$=0.5 (1:5 EtOAc/petroleum ether). $^1$H NMR (400 MHz, $CDCl_3$) δ 7.40-7.28 (m, 5H), 4.60 (t, J=6.8 Hz, 1H), 4.51 (s, 2H), 4.02 (dd, J=6.5, 8.9 Hz, 1H), 3.95-3.84 (m, 2H), 3.82-3.73 (m, 1H), 1.65-1.56 (m, 2H), 1.54 (s, 3H), 1.41 (s, 3H), 1.39 (s, 3H), 1.34 (s, 3H), 1.15-1.05 (m, 2H).

Step 5: (1-((2-(2,2-Dimethyl-1,3-dioxolan-4-yl)propan-2-yl)sulfonyl)cyclopropyl)methanol was obtained using the method described in step 3 for the synthesis of intermediate (int-2), except (((1-((1-methylcyclopropyl)sulfonyl)cyclopropyl)methoxy)methyl)benzene (i2-b) was replaced with 4-(2-((1-((Benzyloxy)methyl)cyclopropyl)sulfonyl)propan-2-yl)-2,2-dimethyl-1,3-dioxolane. TLC $R_f$=0.2 (1:5 EtOAc/petroleum ether). $^1$H NMR (400 MHz, $CDCl_3$) δ 4.56 (dd, J=6.5, 7.8 Hz, 1H), 4.08 (dd, J=6.5, 8.6 Hz, 1H), 3.91 (dd, J=6.0, 14.8 Hz, 2H), 3.79 (dd, J=7.9, 8.5 Hz, 1H), 3.24-3.18 (m, 1H), 1.65-1.59 (m, 2H), 1.55 (s, 3H), 1.45 (s, 3H), 1.41 (s, 3H), 1.36 (s, 3H), 1.12-1.05 (m, 2H).

Step 6: 4-(2-((1-(Bromomethyl)cyclopropyl)sulfonyl)propan-2-yl)-2,2-dimethyl-1,3-dioxolane (int-43) was obtained using the method described in step 4 for the synthesis of intermediate (int-1), except (1-(cyclopropylsulfonyl)cyclopropyl)methanol (1-c) was replaced with (1-((2-(2,2-Dimethyl-1,3-dioxolan-4-yl)propan-2-yl)sulfonyl)cyclopropyl)methanol. TLC $R_f$=0.6 (1:5 EtOAc/petroleum ether). $^1$H NMR (400 MHz, $CDCl_3$) δ 4.54 (t, J=7.0 Hz, 1H), 4.12-4.02 (m, 3H), 3.80 (t, J=8.1 Hz, 1H), 1.79-1.68 (m, 2H), 1.54 (s, 3H), 1.45 (s, 3H), 1.40 (s, 3H), 1.38 (s, 3H), 1.27 (br d, J=15.3 Hz, 2H).

Intermediate 44

4-(1-((1-(bromomethyl)cyclopropyl)sulfonyl)cyclopropyl)-2,2-dimethyl-1,3-dioxolane (Int-44)

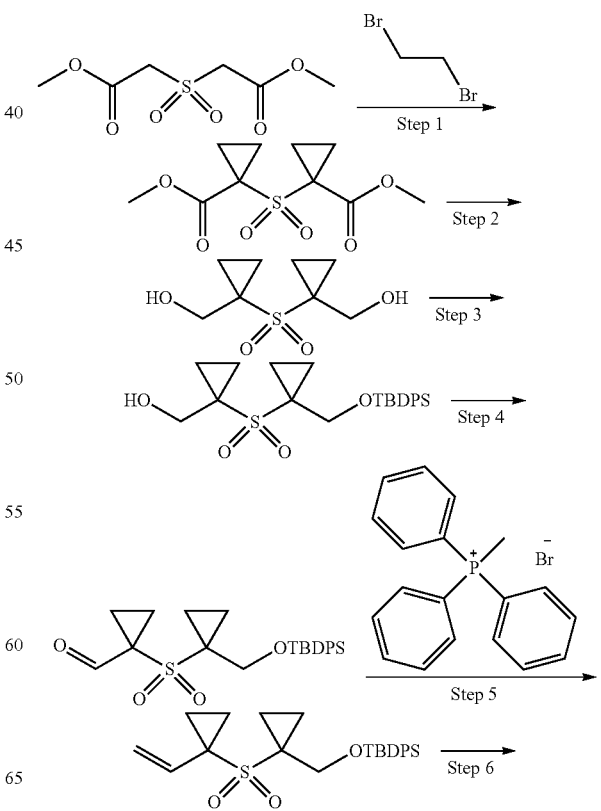

-continued

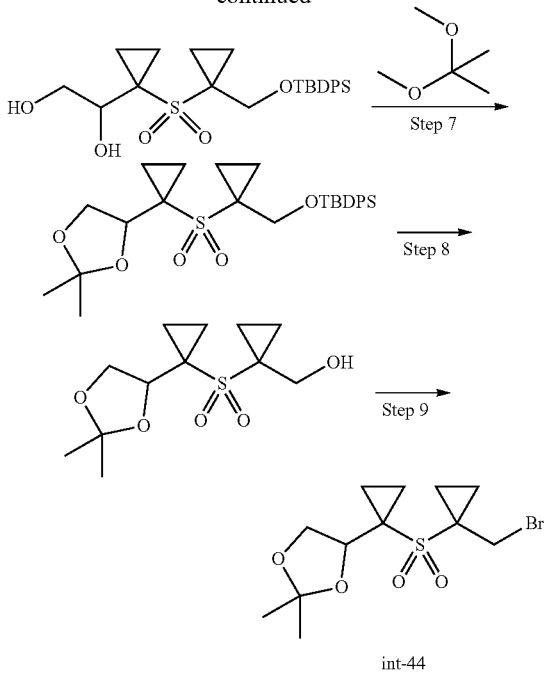

int-44

Step 1: A mixture of dimethyl 2,2'-sulfonyldiacetate (13 g, 61.84 mmol, 1.0 equiv), 1,2-dibromoethane (34.85 g, 185 mmol, 3.0 equiv) and K$_2$CO$_3$ (34.19 g, 247 mmol, 4.0 equiv) in DMF (100 mL) was stirred at 60° C. for 16 h before the solids were removed by filtration. The filtrate was concentrated and purified by column chromatography (SiO$_2$, 10-15% EtOAc/petroleum ether), then the eluent was concentrated to dryness, washed with petroleum ether (500 mL) and dried to give dimethyl 1,1'-sulfonyldicyclopropanecarboxylate. TLC R$_f$=0.7 (50% EtOAc/petroleum ether). $^1$H NMR (400 MHz, CDCl$_3$) δ 3.82-3.72 (m, 6H), 2.09-2.00 (m, 4H), 1.85-1.77 (m, 4H).

Step 2: To a solution of dimethyl 1,1'-sulfonyldicyclopropanecarboxylate (5.0 g, 19.06 mmol, 1.0 equiv) in THF (100 mL) was added LiAlH$_4$ (2.89 g, 76.25 mmol, 4.0 equiv). The mixture was stirred at 25° C. for 1 h, then it was cooled to 0° C. and the reaction was quenched by the cautious, dropwise addition of water (3 mL) (gas evolution) and 15% NaOH (3 mL). The solids were removed by filtration and the filtrate was concentrated to give of (sulfonylbis(cyclopropane-1,1-diyl))dimethanol. TLC R$_f$=0.2 (50% EtOAc/petroleum ether). $^1$H NMR (400 MHz, CDCl$_3$) δ 3.88-3.81 (m, 4H), 1.56-1.47 (m, 4H), 1.07-0.97 (m, 4H).

Step 3: To a stirred solution of (sulfonylbis(cyclopropane-1,1-diyl))dimethanol (3 g, 14.54 mmol, 1.0 equiv) and NaH (60% in mineral oil, 581 mg, 14.54 mmol, 1.0 equiv) in THF (50 mL) was added TBDPSCl (4 g, 14.54 mmol, 1.0 equiv) at 0° C. The mixture was stirred at 25° C. for 1 h before the solids were removed by filtration. The filtrate was purified by RP-HPLC to give of (1-((1-(((tert-butyldiphenylsilyl)oxy)methyl)cyclopropyl)sulfonyl)cyclopropyl)methanol. TLC R$_f$=0.4 (1:5 EtOAc/petroleum ether). $^1$H NMR (400 MHz, CDCl$_3$) δ 7.64 (dd, J=1.4, 7.9 Hz, 4H), 7.55-7.35 (m, 6H), 3.99 (s, 2H), 3.85 (d, J=6.0 Hz, 2H), 2.93 (t, J=6.0 Hz, 1H), 1.53-1.46 (m, 4H), 1.09 (s, 9H), 1.04-0.97 (m, 4H).

Step 4: A mixture of 1-((1-(((tert-butyldiphenylsilyl)oxy) methyl)cyclopropyl)sulfonyl)cyclopropyl)methanol (3.5 g, 7.87 mmol, 1.0 equiv) and IBX (6.6 g, 23.61 mmol, 3.0 equiv) in EtOAc (100 mL) was stirred at 50° C. for 16 h before the solids were removed by filtration. The filtrate was concentrated to give 1-((1-(((tert-butyldiphenylsilyl)oxy) methyl)cyclopropyl)sulfonyl)cyclopropanecarbaldehyde. TLC R$_f$=0.6 (1:5 EtOAc/petroleum ether). $^1$H NMR (400 MHz, CDCl$_3$) δ 9.96 (s, 1H), 7.59-7.46 (m, 5H), 7.45-7.28 (m, 7H), 3.94-3.84 (m, 2H), 1.82-1.74 (m, 3H), 1.63-1.56 (m, 3H), 1.46-1.38 (m, 3H), 0.97 (s, 9H), 0.84-0.77 (m, 2H).

Step 5: A mixture of methyltriphenylphosphonium bromide (5.04 g, 14.12 mmol, 2.4 equiv) in dry THF (50 mL) was cooled to 0° C. before t-BuOK (2.22 g, 19.8 mmol, 3.4 equiv) was added portion wise over 10 min. The mixture was allowed to stir at rt for 1 h, then it was cooled to 0° C. before a solution of 1-((1-(((tert-butyldiphenylsilyl)oxy)methyl)cyclopropyl)sulfonyl)cyclopropanecarbaldehyde (2.5 g, 5.85 mmol, 1.0 equiv) in THF (50 mL) was added dropwise over 5 min. After 1 h, the reaction was quenched with saturated NH$_4$Cl (100 mL), then the layers were separated and the aqueous layer was extracted with EtOAc (3×50 mL). The combined organic extracts were dried with Na$_2$SO$_4$, filtered, and concentrated. The crude product was purified by RP-HPLC to give tert-butyldiphenyl((1-((1-vinylcyclopropyl) sulfonyl)cyclopropyl)methoxy)silane. TLC R$_f$=0.5 (25% EtOAc/petroleum ether). $^1$H NMR (400 MHz, CDCl$_3$) δ 7.67-7.61 (m, 4H), 7.50-7.38 (m, 6H), 6.27 (m, 1H), 5.20 (d, J=10.4 Hz, 1H), 5.08 (d, J=17.0 Hz, 1H), 4.07 (s, 2H), 1.54-1.46 (m, 2H), 1.43-1.34 (m, 2H), 1.15-1.10 (m, 2H), 1.09-1.03 (m, 10H), 1.02-0.94 (m, 2H).

Step 6: To a bi-phasic solution of tert-butyldiphenyl((1-((1-vinylcyclopropyl)sulfonyl)cyclopropyl)methoxy)silane (2 g, 4.54 mmol, 1.0 equiv) in DCM (10 mL) and water (3 mL) was added NMO (0.9 g, 7.72 mmol, 1.7 equiv) and K$_2$OsO$_4$·2H$_2$O (133 mg, 0.45 mmol, 0.1 equiv). The mixture was stirred vigorously at 25° C. for 1 h. The mixture was concentrated and purified by RP-HPLC to give 1-(1-((1-(((tert-butyldiphenylsilyl)oxy)methyl)cyclopropyl)sulfonyl) cyclopropyl)ethane-1,2-diol. TLC R$_f$=0.3 (50% EtOAc/petroleum ether). $^1$H NMR (400 MHz, CDCl$_3$) δ 7.72-7.60 (m, 4H), 7.55-7.38 (m, 6H), 4.16-4.10 (m, 1H), 4.08-3.93 (m, 2H), 3.72-3.63 (m, 1H), 3.56 (dd, J=6.4, 11.5 Hz, 1H), 1.62-1.39 (m, 4H), 1.23-1.15 (m, 1H), 1.10-1.01 (m, 3H).

Step 7: tert-Butyl((1-((1-(2,2-dimethyl-1,3-dioxolan-4-yl) cyclopropyl)sulfonyl)cyclopropyl)methoxy)diphenylsilane was obtained using the method described in step 2 for the synthesis of Intermediate (int-42), except 2-((1-((benzyloxy) methyl)cyclopropyl)sulfonyl)-2-methylpropane-1,3-diol was replaced with 1-(1-((1-(((tert-butyldiphenylsilyl)oxy) methyl)cyclopropyl)sulfonyl)cyclopropyl)ethane-1,2-diol. TLC R$_f$=0.5 (1:10 EtOAc/petroleum ether). $^1$H NMR (400 MHz, CDCl$_3$) δ 7.73-7.59 (m, 4H), 7.55-7.36 (m, 6H), 4.83 (t, J=6.5 Hz, 1H), 4.26-4.10 (m, 2H), 3.90-3.75 (m, 2H), 1.48-1.38 (m, 2H), 1.36 (s, 3H), 1.34 (s, 3H), 1.33-1.22 (m, 2H), 1.02-0.88 (m, 2H).

Step 8: (1-((1-(2,2-Dimethyl-1,3-dioxolan-4-yl)cyclopropyl)sulfonyl)cyclopropyl)methanol was obtained using the method described in step 5 of Example 105, except 4-((4-(1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridin-3-yl)-1H-1,2,3-triazol-1-yl)methyl)benzonitrile was replaced with tert-Butyl((1-((1-(2,2-dimethyl-1,3-dioxolan-4-yl)cyclopropyl)sulfonyl) cyclopropyl)methoxy)diphenylsilane. TLC R$_f$=0.3 (25% EtOAc/petroleum ether). $^1$H NMR (400 MHz, CDCl$_3$) δ 4.87-4.74 (m, 1H), 4.10-4.05 (m, 1H), 3.89 (m, 2H), 3.58 (m, 1H), 3.01 (m, 1H), 1.62-1.55 (m, 2H), 1.53-1.46 (m, 2H), 1.40 (s, 3H), 1.39-1.37 (m, 3H), 1.37-1.32 (m, 1H), 1.18 (m, 1H), 1.09-0.92 (m, 2H).

Step 9: 4-(1-(((1-(Bromomethyl)cyclopropyl)sulfonyl)cyclopropyl)-2,2-dimethyl-1,3-dioxolane (int-44) was obtained using the method described in step 4 for the synthesis of intermediate (int-1), except (1-(cyclopropylsulfonyl)cyclopropyl)methanol (i1-c) was replaced with (1-((1-(2,2-dimethyl-1,3-dioxolan-4-yl)cyclopropyl)sulfonyl)cyclopropyl)methanol. TLC R$_f$=0.5 (1:5 EtOAc/petroleum ether). $^1$H NMR (400 MHz, CDCl$_3$) δ 4.89-4.76 (m, 1H), 4.17 (dd, J=6.2, 8.8 Hz, 1H), 3.96 (d, J=11.8 Hz, 1H), 3.83-3.72 (m, 2H), 1.84-1.73 (m, 1H), 1.70-1.62 (m, 1H), 1.56-1.50 (m, 1H), 1.50-1.42 (m, 2H), 1.39 (s, 3H), 1.39-1.37 (m, 3H), 1.36-1.30 (m, 1H), 1.23-1.13 (m, 1H), 1.04 (ddd, J=4.4, 7.0, 9.0 Hz, 1H).

Intermediate 45 tert-butyl (R)-4-(2-((1-(bromomethyl)cyclopropyl)sulfonyl)propan-2-yl)-2,2-dimethyloxazolidine-3-carboxylate (Int-45)

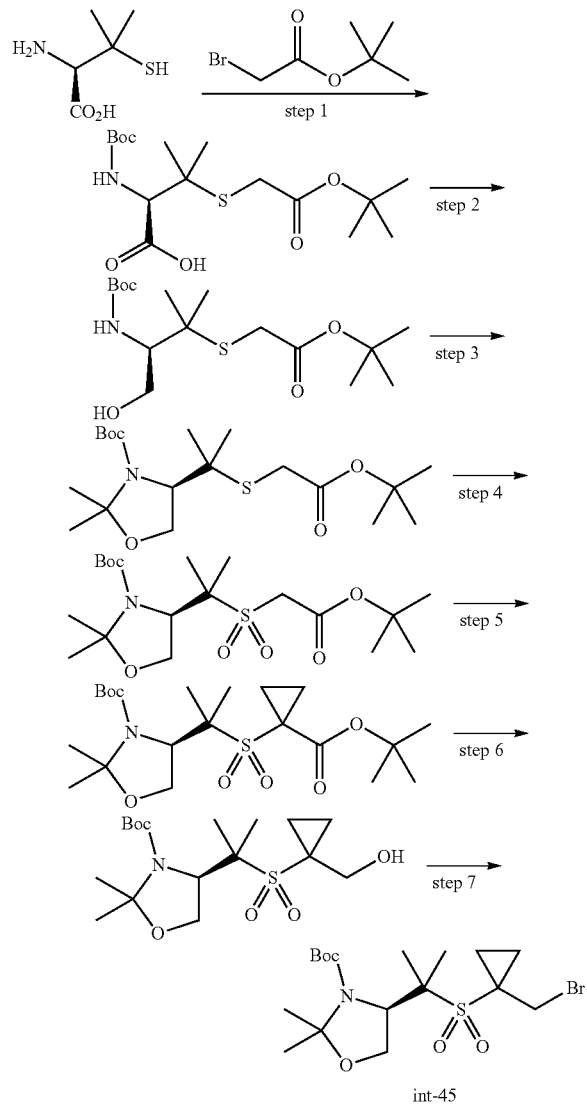

Step 1: A solution of (R)-2-amino-3-mercapto-3-methylbutanoic acid (L-penicillamine) (1.492 g, 10 mmol, 1.0 equiv) in NaOH (1 M, 20 mL, 20 mmol, 2.0 equiv) was treated with Boc$_2$O (2.182 g, 10 mmol, 1.0 equiv) and dioxane (10 mL), then the biphasic solution was stirred at rt for 90 min. To the cloudy solution was added tert-butyl bromoacetate (1.951 g, 10 mmol, 1.0 equiv), and the resulting biphasic solution was stirred well at rt overnight. The mixture was diluted with water (150 mL), neutralized with 1 N HCl (11 mL), then extracted with EtOAc (5×40 mL). The combined organic extracts were washed once each with water and brine, dried with MgSO$_4$, filtered and evaporated to provide (R)-3-((2-(tert-butoxy)-2-oxoethyl)thio)-2-((tert-butoxycarbonyl)amino)-3-methylbutanoic acid. $^1$H NMR (500 MHz, CDCl$_3$) δ 55.58 (d, J=8.3 Hz, 1H), 4.31 (d, J=8.1 Hz, 1H), 3.47 (d, J=17.2 Hz, 1H), 3.34 (d, J=17.0 Hz, 1H), 1.51-1.39 (m, 24H). MS(ESI): m/z 364.3 [M+H]$^+$.

Step 2: A solution of crude (R)-3-((2-(tert-butoxy)-2-oxoethyl)thio)-2-((tert-butoxycarbonyl)amino)-3-methylbutanoic acid (3.8 g, 10.45 mmol, 1.0 equiv) in THF (50 mL) was cooled to −10° C. before Et$_3$N (1.594 mL, 11.50 mmol, 1.1 equiv) and isobutyl chloroformate (1.510 mL, 11.50 mmol, 1.1 equiv) were added. The resulting slurry was stirred at −10° C. for 30 min, then the solids were removed by filtration and the filter cake was rinsed with THF (2×5 mL). The filtrate was added dropwise over 10-15 min to a stirred solution of NaBH$_4$ (1.187 g, 31.4 mmol, 3.0 equiv) in water (10 mL) (gas evolution) at between −10° C. and 0° C. After 5 min, the reaction was quenched with 1N HCl (30 mL) (gas evolution), then the mixture was diluted with EtOAc (150 mL) and the layers were separated. The organic layer was washed once each with saturated NaHCO$_3$ and brine, then dried with MgSO$_4$, filtered and evaporated to give crude tert-butyl (R)-2-((3-((tert-butoxycarbonyl)amino)-4-hydroxy-2-methylbutan-2-yl)thio)acetate. MS (ESI): m/z 350.3 [M+H]$^+$.

Step 3: A solution of crude tert-butyl (R)-2-((3-((tert-butoxycarbonyl)amino)-4-hydroxy-2-methylbutan-2-yl)thio)acetate (3.8 g, 10.45 mmol, 1.0 equiv) was azeotroped once from toluene (25 mL), then the residue was redissolved in toluene (25 mL) and treated with 2,2-dimethoxypropane (6.43 mL, 52.3 mmol, 5.0 equiv) and p-TsOH·H$_2$O (0.099 g, 0.523 mmol, 0.05 equiv). The reaction was stirred at rt overnight before it was concentrated and dried under high vacuum to give crude tert-butyl (R)-4-(2-((2-(tert-butoxy)-2-oxoethyl)thio)propan-2-yl)-2,2-dimethyloxazolidine-3-carboxylate. MS (ESI): m/z 390.3 [M+H]$^+$.

Step 4: A mixture of crude tert-butyl (R)-4-(2-((2-(tert-butoxy)-2-oxoethyl)thio)propan-2-yl)-2,2-dimethyloxazolidine-3-carboxylate (4.4 g, 10.45 mmol, 1.0 equiv) and NaHCO$_3$ (7.03 g, 84 mmol, 8.0 equiv) in acetone (30 mL) was cooled to 0° C. before Oxone® (14.46 g, 23.52 mmol, 2.25 equiv) and water (10 mL) were added (gas evolution). The resulting mixture was stirred at 0° C. for 10 min, then at rt for 1 h before it was cooled to 0° C. and quenched with 10% Na$_2$SO$_3$ (15 mL). After 15 min at rt, the mixture was returned to the ice bath and neutralized with 1 N HCl (15 mL) before it was diluted with water (75 mL) and EtOAc (50 mL). The layers were separated, then the aqueous layer was extracted with EtOAc (4×25 mL). The combined organic extracts were washed with brine, dried with MgSO$_4$, filtered and concentrated to give tert-butyl (R)-4-(2-((2-(tert-butoxy)-2-oxoethyl)sulfonyl)propan-2-yl)-2,2-dimethyloxazolidine-3-carboxylate. $^1$H NMR (500 MHz, CDCl$_3$) δ 4.59 (t, J=8.3 Hz, 1H), 4.40 (dd, J=30.2, 10.3 Hz, 1H), 4.12-4.01 (m, 1H), 3.94 (dd, J=10.3, 5.7 Hz, 2H), 1.59 (s, 3H), 1.47 (dd, J=24.1, 7.1 Hz, 28H). MS (ESI): m/z 422.2 [M+H]$^+$.

Step 5: A solution of tert-butyl (R)-4-(2-((2-(tert-butoxy)-2-oxoethyl)sulfonyl)propan-2-yl)-2,2-dimethyloxazolidine- 3-carboxylate (3.1 g, 7.35 mmol, 1.0 equiv) in DMF (15 mL) was treated with K$_2$CO$_3$ (3.05 g, 22.06 mmol, 3.0 equiv) and 1,2-dibromoethane (1.267 mL, 14.71 mmol, 2.0 equiv) and the resulting mixture was stirred at 100° C. overnight. The reaction was diluted with water (150 mL) and extracted with EtOAc (4×40 mL), then the combined organic extracts were washed twice with 1:1 water-brine, once with brine, dried with MgSO$_4$, filtered and concentrated to give crude tert-butyl (R)-4-(2-((1-(tert-butoxycarbonyl)cyclopropyl)sulfonyl)propan-2-yl)-2,2-dimethyloxazolidine-3-carboxylate. $^1$H NMR (500 MHz, CDCl$_3$) δ 4.48 (d, J=10.3 Hz, 1H), 3.97 (dd, J=10.3, 6.0 Hz, 1H), 1.81-1.70 (m, 2H), 1.59 (d, J=7.3 Hz, 6H), 1.51 (s, 6H), 1.48 (s, 18H), 1.44 (d, J=4.5 Hz, 2H). MS (ESI): m/z 448.2 [M+H]$^+$.

Step 6: A solution of crude tert-butyl (R)-4-(2-((1-(tert-butoxycarbonyl)cyclopropyl)sulfonyl)propan-2-yl)-2,2-dimethyloxazolidine-3-carboxylate (3.31 g, 7.35 mmol, 1.0 equiv) in THF (29 mL) was cooled to 0° C. before LiAlH$_4$ (1.0 M in THF, 14.71 mL, 14.71 mmol, 2.0 equiv) was added dropwise over 10-15 min (gas evolution). The resulting solution was stirred at 0° C. for 3 h before it was quenched by the sequential addition of 0.6 mL water (gas evolution), 1.2 mL 2 N NaOH, and 1.8 mL water. The slurry was stirred at rt for 15 min, then MgSO$_4$ was added and the solids were removed by filtration through Celite®. The filter cake was rinsed with EtOAc and the filtrate was concentrated to give of crude tert-butyl (R)-4-(2-((1-(hydroxymethyl)cyclopropyl)sulfonyl)propan-2-yl)-2,2-dimethyloxazolidine-3-carboxylate. $^1$H NMR (500 MHz, CDCl$_3$) δ 4.73 (d, J=5.7 Hz, 1H), 4.45 (d, J=10.2 Hz, 1H), 4.06 (dd, J=13.9, 6.5 Hz, 1H), 4.01-3.93 (m, 2H), 3.81 (t, J=6.7 Hz, 1H), 1.52-1.47 (m, 23H), 1.18 (dd, J=10.0, 5.2 Hz, 1H), 1.13-1.08 (m, 1H). MS (ESI): m/z 378.3 [M+H]$^+$.

Step 7: tert-butyl (R)-4-(2-((1-(bromomethyl)cyclopropyl)sulfonyl)propan-2-yl)-2,2-dimethyloxazolidine-3-carboxylate (int-45) was obtained using the method described in step 4 for the synthesis of intermediate (int-1), except (1-(cyclopropylsulfonyl)cyclopropyl)methanol (i1-c) was replaced with tert-butyl (R)-4-(2-((1-(hydroxymethyl)cyclopropyl)sulfonyl)propan-2-yl)-2,2-dimethyloxazolidine-3-carboxylate. MS (ESI): m/z 440.3 [M+H]$^+$.

Intermediate 46 ethyl 7-oxo-1-(2-(((triisopropylsilyl)oxy)ethyl)-4,5,6,7-tetrahydro-1H-pyrazolo[3,4-c]pyridine-3-carboxylate (Int-46)

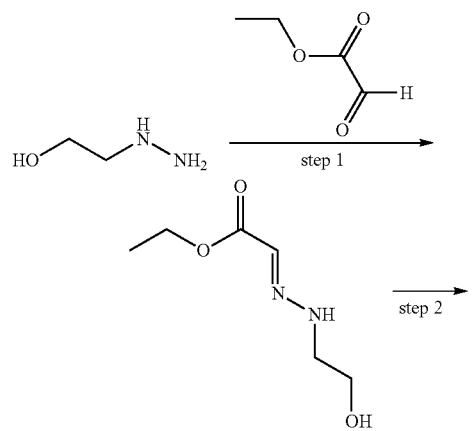

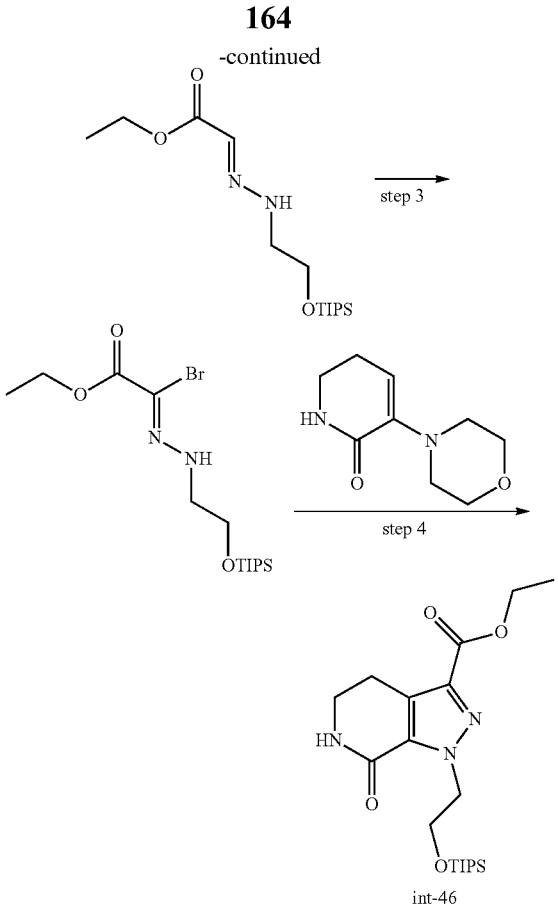

Step 1: A solution of ethyl 2-oxoacetate (200 g, 980 mmol, 1.0 equiv) in THF (500 mL) was cooled to 0° C. before 2-hydrazinylethanol (75 g, 980 mmol, 1.0 equiv) was added. The reaction mixture was stirred at 25° C. for 12 h before it was concentrated. The mixture was diluted with EtOAc (300 mL) and washed with water (2×100 mL), dried over anhydrous Na$_2$SO$_4$, and concentrated under reduced pressure. The residue was purified by column chromatography (SiO$_2$, 75-100% EtOAc/petroleum ether) to provide (E)-ethyl 2-(2-(2-hydroxyethyl)hydrazono)acetate. TLC R$_f$=0.3 (EtOAc). $^1$H NMR (400 MHz, CDCl$_3$) δ 7.35 (br s, 1H), 6.79 (s, 1H), 4.29-4.21 (m, 2H), 3.89-3.86 (m, 2H), 3.39 (br s, 2H), 1.33-1.30 (m, 3H). MS (ESI): m/z 187.1 [M+H]$^+$.

Step 2: To a solution of (E)-ethyl 2-(2-(2-hydroxyethyl)hydrazono)acetate (50 g, 312 mmol, 1.0 equiv) in DCM (500 mL) was added imidazole (85 g, 1248 mmol, 4.0 equiv), DMAP (19 g, 156 mmol, 0.5 equiv) and TIPSCl (120 g, 624 mmol, 2.0 equiv). The mixture was stirred at 25° C. for 12 h before it was washed with water (100 mL). The organic layer was dried with Na$_2$SO$_4$, filtered and concentrated, then the residue was purified by column chromatography (SiO$_2$, 50-100% EtOAc/petroleum ether) to give (E)-ethyl 2-(2-(2-((triisopropylsilyl)oxy)ethyl)hydrazono)acetate. TLC R$_f$=0.6 (75% EtOAc/petroleum ether). $^1$H NMR (400 MHz, DMSO-d$_6$) δ 8.81-8.79 (m, 1H), 6.79 (s, 1H), 4.11-4.06 (m, 2H), 3.80-3.77 (m, 2H), 3.32-3.28 (m, 2H), 1.21-1.17 (m, 3H), 1.03-0.98 (m, 21H).

Step 3: A solution of (E)-ethyl 2-(2-(2-((triisopropylsilyl)oxy)ethyl)hydrazono)acetate (35 g, 110.58 mmol, 1.0 equiv) in EtOAc (350 mL) was cooled to 0° C. before NBS (21 g, 116.11 mmol, 1.05 equiv) was added portion wise. The reaction mixture was stirred at 25° C. for 0.5 h, then the solids were removed by filtration. The filtrate was diluted with water (50 mL) and extracted with EtOAc (2×250 mL). The combined organic extracts were dried over Na₂SO₄, filtered and concentrated under reduced pressure. The residue was purified by column chromatography (SiO₂, petroleum ether) to afford (Z)-ethyl 2-bromo-2-(2-(2-((triisopropylsilyl)oxy)ethyl)hydrazono) acetate. TLC $R_f$=0.6 (1:10 EtOAc/petroleum ether). ¹H NMR (400 MHz, DMSO-d₆) δ 8.07-8.05 (m, 1H), 4.21-4.16 (m, 2H), 3.82-3.79 (m, 2H), 3.50-3.47 (m, 2H), 1.24-1.20 (m, 3H), 1.06-0.99 (m, 21H).

Step 4: A solution of 3-morpholino-5,6-dihydropyridin-2 (1H)-one (14.66 g, 80.47 mmol, 1.0 equiv) and (Z)-ethyl 2-bromo-2-(2-(2-((triisopropylsilyl)oxy)ethyl)hydrazono) acetate (35 g, 88.52 mmol, 1.1 equiv) in EtOAc (150 mL) was cooled to 0° C. before Et₃N (20.82 g, 205.80 mmol, 2.6 equiv) was added. The mixture was stirred at 25° C. for 0.5 h, then at 80° C. for 1.5 h before the precipitate was removed by filtration. The filtrate was diluted with water (50 mL) and extracted with EtOAc (2×150 mL), then the combined organic extracts were dried over Na₂SO₄, filtered and concentrated. The residue was suspended in 25% EtOAc/petroleum ether (30 mL) and stirred at 25° C. for 0.5 h, then the solid was collected by filtration. The filter cake was purified by RP-HPLC to afford ethyl 7-oxo-1-(2-((triisopropylsilyl) oxy)ethyl)-4,5,6,7-tetrahydro-1H-pyrazolo[3,4-c]pyridine-3-carboxylate (int-46). ¹H NMR (400 MHz, CDCl₃) δ 5.71 (br s, 1H), 4.83-4.80 (m, 2H), 4.45-4.40 (m, 2H), 4.11-4.09 (m, 2H), 3.59-3.55 (m, 2H), 3.13-3.09 (m, 2H), 1.42-1.39 (t, J=7.1 Hz, 3H), 1.07-0.95 (m, 21H). MS (ESI): m/z 410.4 [M+H]⁺.

Intermediate 47 ethyl 1-(2-hydroxypropyl)-7-oxo-4,5,6,7-tetrahydro-1H-pyrazolo[3,4-c]pyridine-3-carboxylate (Int-47)

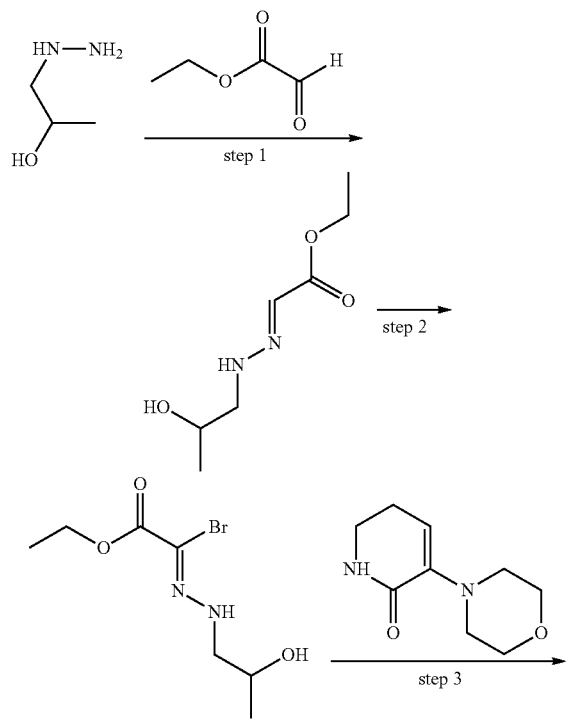

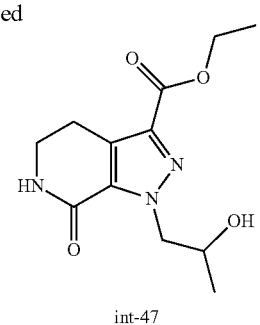

int-47

Step 1: A solution of ethyl 2-oxoacetate (50% in toluene, 48 g, 233 mmol, 1.0 equiv) in THF (210 mL) was cooled to ° C., then 1-hydrazinylpropan-2-ol (21 g, 233 mmol, 1.0 equiv) was added. The reaction mixture was stirred at 25° C. for 12 h before it was concentrated. The residue was diluted with EtOAc (300 mL) and washed with water (2×100 mL), then dried over Na₂SO₄, filtered and concentrated under reduced pressure. The residue was purified by column chromatography (SiO₂, 75-100% EtOAc/petroleum ether) to provide (E)-ethyl 2-(2-(2-hydroxypropyl)hydrazono)acetate. TLC $R_f$=0.3 (EtOAc). ¹H NMR (400 MHz, CDCl₃) δ 7.16-7.11 (m, 1H), 6.81 (s, 1H), 4.29-4.23 (m, 2H), 4.13-4.10 (m, 1H), 3.37-3.33 (m, 1H), 3.17-3.15 (m, 1H), 1.33-1.29 (m, 3H), 1.26-1.24 (m, 3H).

Step 2: A solution of (E)-ethyl 2-(2-(2-hydroxypropyl) hydrazono)acetate (6.3 g, 36.17 mmol, 1.0 equiv) in EtOAc (60 mL) was cooled to 0° C. before NBS (6.76 g, 37.99 mmol, 1.05 equiv) was added portion wise. The reaction mixture was stirred at 25° C. for 0.5 h, then the precipitate was removed by filtration. The filtrate was diluted with water (10 mL) and extracted with EtOAc (2×50 mL), then the combined organic extracts were dried over Na₂SO₄, filtered and concentrated. The residue was purified by column chromatography (SiO₂, petroleum ether) to afford (Z)-ethyl 2-bromo-2-(2-(2-hydroxypropyl)hydrazono)acetate. TLC $R_f$=0.6 (50% EtOAc/petroleum ether). ¹H NMR (400 MHz, CDCl₃) δ 7.09-6.91 (m, 1H), 4.35-4.30 (m, 2H), 4.08-4.05 (m, 1H), 3.61-3.57 (m, 1H), 3.42-3.36 (m, 1H), 1.36-1.32 (m, 3H), 1.22 (d, J=6.4 Hz, 3H).

Step 3 A solution of 3-morpholino-5,6-dihydropyridin-2 (1H)-one (1.91 g, 10.47 mmol, 1.0 equiv) and (Z)-ethyl 2-bromo-2-(2-(2-hydroxypropyl)hydrazono)acetate (5.30 g, 20.94 mmol, 2.0 equiv) in EtOAc (20 mL) was cooled to 0° C. before Et₃N (2.65 g, 26.18 mmol, 2.5 equiv) was added. The mixture was stirred at 25° C. for 0.5 h, then at 80° C. for 1.5 h. The precipitate was removed by filtration, then the filtrate was diluted with water (8 mL) and extracted with EtOAc (2×20 mL). The combined organic extracts were dried over Na₂SO₄, filtered and concentrated. The residue was purified by RP-HPLC to afford ethyl 1-(2-hydroxypropyl)-7-oxo-4,5,6,7-tetrahydro-1H-pyrazolo[3,4-c]pyridine-3-carboxylate (int-47). ¹H NMR (400 MHz, CDCl₃) δ 5.78 (s, 1H), 4.69-4.66 (m, 1H), 4.61-4.58 (m, 1H), 4.46-4.40 (m, 2H), 4.28-4.17 (m, 1H), 3.64-3.60 (m, 2H), 3.17-3.13 (m, 2H), 1.43-1.39 (m, 3H), 1.27 (d, J=6.4 Hz, 3H). MS (ESI): m/z 268.1 [M+H]⁺.

Intermediate 48 ethyl(Z)-2-chloro-2-(2-((1-hydroxycyclopropyl)methyl)hydrazono)acetate (Int-48)

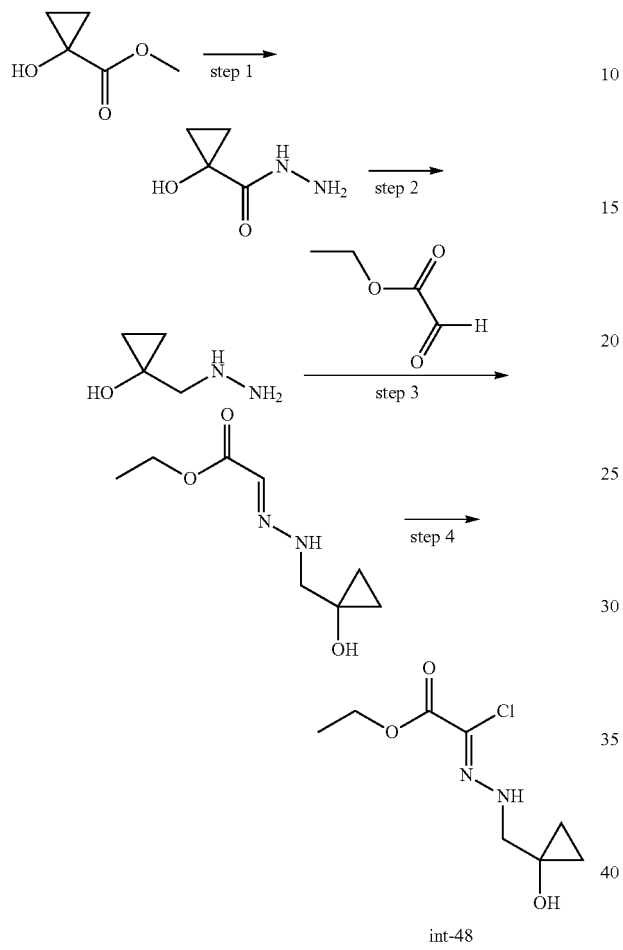

int-48

Step 1: A solution of methyl 1-hydroxycyclopropanecarboxylate (8 g, 68.9 mmol, 1.0 equiv) and hydrazine monohydrate (17 g, 344.4 mmol, 5.0 equiv) in MeOH (40 mL) was stirred at 60° C. for 16 h before it was concentrated to provide a solid. The resulting 8 g of crude material was washed with EtOAc (10 mL) and dried under vacuum to provide 1-hydroxycyclopropanecarbohydrazide. TLC $R_f$=0.4 (1:10 MeOH/EtOAc). $^1$H NMR (400 MHz, DMSO-$d_6$) δ 9.04-8.78 (m, 1H), 6.09 (br s, 1H), 4.22 (br s, 2H), 1.04-0.97 (m, 2H), 0.85-0.78 (m, 2H).

Step 2: A solution of 1-hydroxycyclopropanecarbohydrazide (4 g, 34.4 mmol, 1.0 equiv) in THF (40 mL) was cooled to 0° C. before BH$_3$.SMe$_2$ (34.4 mL, 344 mmol, 10.0 equiv) was added dropwise. The reaction was stirred at 60° C. for 16 h before it was cooled to 0° C. and quenched by the slow addition of MeOH (50 mL) (gas evolution). The solids were removed by filtration, then the filtrate was concentrated to provide an oil. This material was dissolved in MeOH (50 mL) and heated at 80° C. for 5 h. The solution was concentrated to provide crude 1-(hydrazinylmethyl)cyclopropanol. TLC $R_f$=0.8 (1:10 MeOH/EtOAc). $^1$H NMR (400 MHz, CDCl$_3$) δ 2.91 (s, 2H), 0.83 (t, J=6.0 Hz, 2H), 0.55-0.50 (m, 2H).

Step 3: A mixture of ethyl-2-oxoacetate (8 g, 39.1 mmol, 1.0 equiv), Et$_3$N (4 g, 39.1 mmol, 1.0 equiv) and MgSO$_4$ (9.4 g, 78.3 mmol, 2.0 equiv) in THF (40 mL) was cooled to 0° C. before 1-(hydrazinylmethyl)cyclopropanol (4 g, 39.1 mmol, 1.0 equiv) was added. The reaction mixture was stirred at 25° C. for 16 h, then the solids were removed by filtration and the filtrate was concentrated under reduced pressure. The residue was purified by column chromatography (SiO$_2$, 15-50% EtOAc/petroleum ether) to afford ethyl (E)-2-(2-((1-hydroxycyclopropyl)methyl)hydrazono)acetate. TLC $R_f$=0.7 (EtOAc). $^1$H NMR (400 MHz, DMSO-$d_6$) δ 8.92 (br t, J=4.2 Hz, 1H), 6.76 (s, 1H), 5.44 (s, 1H), 4.13-4.06 (m, 2H), 3.26 (d, J=4.3 Hz, 2H), 1.20 (t, J=7.1 Hz, 3H), 0.62-0.57 (m, 2H), 0.51-0.45 (m, 2H). MS (ESI): m/z 187.1 [M+H]$^+$.

Step 4: A solution of ethyl (E)-2-(2-((1-hydroxycyclopropyl)methyl)hydrazono)acetate (300 mg, 1.6 mmol, 1.0 equiv) in DMF (3 mL) was treated with NCS (236 mg, 1.77 mmol, 1.1 equiv) and the resulting mixture was stirred at 50° C. for 1 h. The reaction solution was diluted with water and extracted with EtOAc (5 mL), then the aqueous layer was back-extracted with EtOAc (2×5 mL). The combined organic extracts were washed with brine (5 mL), dried over Na$_2$SO$_4$ and concentrated. The residue was purified by column chromatography (SiO$_2$, 10-15% EtOAc/petroleum ether) to give ethyl (Z)-2-chloro-2-(2-((1-hydroxycyclopropyl)methyl)hydrazono)acetate (int-48). TLC $R_f$=0.7 (75% EtOAc/petroleum ether). $^1$H NMR (400 MHz, CDCl$_3$) δ 6.84 (br s, 1H), 4.34 (q, J=7.2 Hz, 2H), 3.62 (d, J=4.4 Hz, 2H), 2.88-2.32 (m, 1H), 1.36 (m, 3H), 0.91-0.86 (m, 2H), 0.69-0.64 (m, 2H). MS (ESI): m/z 221.0 [M+H]$^+$.

Intermediate 49

Ethyl 1-((1-hydroxycyclopropyl)methyl)-7-oxo-4,5,6,7-tetrahydro-1H-pyrazolo[3,4-c]pyridine-3-carboxylate (Int-49)

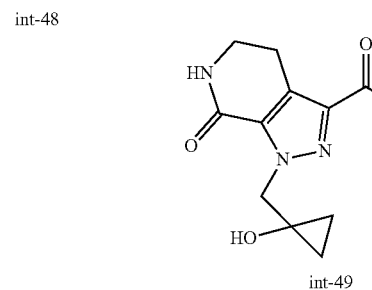

int-49

A solution of 3-morpholino-5,6-dihydropyridin-2(1H)-one (100 mg, 0.548 mmol, 1.0 equiv) and Et$_3$N (166 mg, 1.64 mmol, 3.0 equiv) in toluene (1 mL) was treated with ethyl (Z)-2-chloro-2-(2-((1-hydroxycyclopropyl)methyl)hydrazono)acetate (int-48) (130 mg, 0.589 mmol, 1.1 equiv) and the mixture was stirred at 110° C. for 12 h. The reaction was concentrated and the residue was purified by RP-HPLC (NH3.H2O) to give ethyl 1-((1-hydroxycyclopropyl)methyl)-7-oxo-4,5,6,7-tetrahydro-1H-pyrazolo[3,4-c]pyridine-3-carboxylate (int-49). $^1$H NMR (400 MHz, CDCl$_3$) δ 5.76 (br s, 1H), 4.77 (s, 2H), 4.43 (m, 2H), 4.37 (br s, 1H), 3.63 (m, 2H), 3.16 (m, 2H), 1.41 (t, J=7.2 Hz, 3H), 0.89-0.76 (m, 4H). MS (ESI): m/z 280.0 [M+H]$^+$.

Intermediate 50 ethyl (Z)-2-chloro-2-(2-(2-hydroxy-2-methylpropyl)hydrazono)acetate (Int-50)

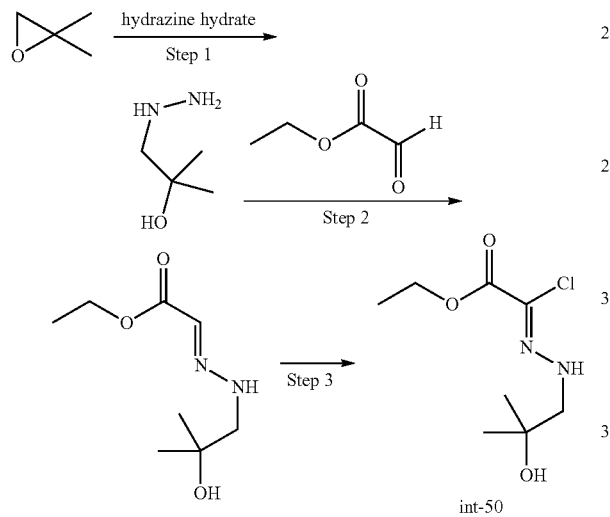

Step 1: A mixture of sodium hydroxide (1 N, 12 drops) and hydrazine monohydrate (34.8 g, 695 mmol, 5.0 equiv) was treated with 2,2-dimethyloxirane (10 g, 139 mmol, 1.0 equiv) before the reaction was stirred at 95° C. for 16 h. Hydrazine monohydrate was removed under reduced pressure, then the residue was suspended in THF (16 mL) and MTBE (16 mL) and the precipitate was removed by filtration. The filtrate was concentrated to provide 1-hydrazinyl-2-methylpropan-2-ol. TLC R$_f$=0.3 (33% MeOH/CH$_2$Cl$_2$). $^1$H NMR (400 MHz, CDCl$_3$) δ 4.81 (br s, 1H), 3.22 (br s, 3H), 2.70 (s, 2H), 1.18 (s, 6H).

Step 2: (E)-Ethyl 2-(2-(2-hydroxy-2-methylpropyl)hydrazono)acetate. A mixture of ethyl 2-oxoacetate (5.88 g, 28.8 mmol, 1.0 equiv) and MgSO$_4$ (6.9 g, 57.6 mmol, 2.0 equiv) in THF (30 ml) was cooled to 0° C., then 1-hydrazinyl-2-methylpropan-2-ol (3 g, 28.8 mmol, 1.0 equiv) and Et$_3$N (3.2 g, 31.7 mmol, 1.1 equiv) were added. The reaction mixture was stirred at 25° C. for 12 h before it was diluted with EtOAc (50 mL) and washed with water (3×20 mL). The organic layer was dried over Na$_2$SO$_4$, filtered and concentrated under reduced pressure. The residue was purified by column chromatography (SiO$_2$, 30-100% EtOAc/petroleum ether) to afford ethyl (E)-2-(2-(2-hydroxy-2-methylpropyl)hydrazono)acetate. TLC R$_f$=0.5 (75% EtOAc/petroleum ether). $^1$H NMR (400 MHz, CDCl$_3$) δ 7.24 (br s, 1H), 6.80 (s, 1H), 4.27-4.21 (m, 2H), 3.23 (d, J=4.4 Hz, 2H), 1.30-1.28 (m, 3H), 1.27 (s, 6H).

Step 3: (Z)-Ethyl 2-chloro-2-(2-(2-hydroxy-2-methylpropyl)hydrazono)acetate. A solution of ethyl (E)-2-(2-(2-hydroxy-2-methylpropyl)hydrazono)acetate (3.2 g, 17 mmol, 1.0 equiv) in DMF (20 mL) at 50° C. was treated with NCS (2.5 g, 18.7 mmol, 1.1 equiv) and stirred at 50° C. for 0.5 h. The mixture was diluted with water and extracted with EtOAc (2×30 mL), then the combined organic extracts were dried over Na$_2$SO$_4$, filtered and concentrated. The residue was purified by column chromatography (SiO$_2$, 10-60% EtOAc/petroleum ether) to afford ethyl (Z)-2-chloro-2-(2-(2-hydroxy-2-methylpropyl)hydrazono)acetate (int-50). TLC R$_f$=0.5 (50% EtOAc/petroleum ether). $^1$H NMR (400 MHz, CDCl$_3$) δ 6.91 (br s, 1H), 4.34-4.28 (m, 2H), 4.06 (s, 1H), 3.47 (d, J=5.2 Hz, 2H), 1.33 (t, J=7.2 Hz, 3H), 1.24 (s, 6H).

Intermediate 51 ethyl 1-(2-hydroxy-2-methylpropyl)-7-oxo-4,5,6,7-tetrahydro-1H-pyrazolo[3,4-c]pyridine-3-carboxylate (Int-51)

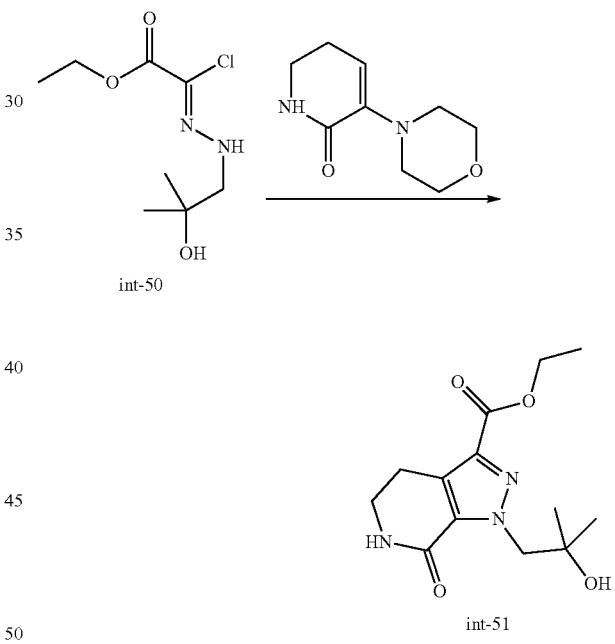

To a solution of 3-morpholino-5,6-dihydropyridin-2(1H)-one (1 g, 5.5 mmol, 1.0 equiv) in toluene (10 mL) was added Et$_3$N (1.67 g, 16.5 mmol, 3.0 equiv) and ethyl (Z)-2-chloro-2-(2-(2-hydroxy-2-methylpropyl)hydrazono)acetate (int-50) (1.5 g, 6.6 mmol, 1.2 equiv). The mixture was stirred at 120° C. for 6 h before it was concentrated under reduced pressure. The mixture was diluted with water and extracted with EtOAc (2×30 mL), then the combined organic extracts were dried over Na$_2$SO$_4$, filtered and concentrated. The residue was purified by RP-HPLC (FA) to afford ethyl 1-(2-hydroxy-2-methylpropyl)-7-oxo-4,5,6,7-tetrahydro-1H-pyrazolo[3,4-c]pyridine-3-carboxylate (int-51). $^1$H NMR (400 MHz, CDCl$_3$) δ 6.01 (br s, 1H), 4.63 (s, 2H), 4.44-4.39 (m, 2H), 3.63-3.59 (m, 2H), 3.14 (t, J=6.8 Hz, 2H), 1.40 (t, J=7.2 Hz, 3H), 1.24-1.22 (m, 6H). MS (ESI): m/z 282.2 [M+H]$^+$.

Intermediate 52 ethyl(Z)-2-bromo-2-(2-(3-hydroxypropyl)hydrazono)acetate (Int-52

Intermediate 53 ethyl 1-(3-hydroxypropyl)-7-oxo-4,5,6,7-tetrahydro-1H-pyrazolo[3,4-c]pyridine-3-carboxylate (Int-53)

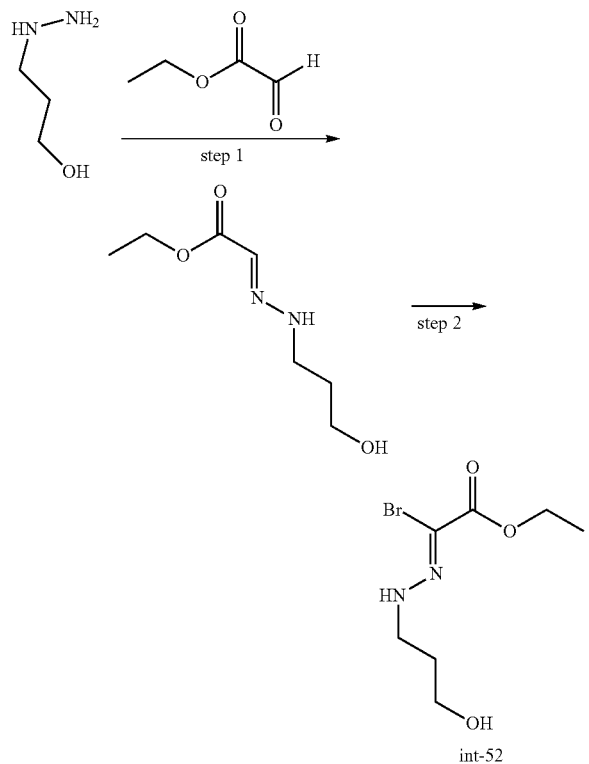

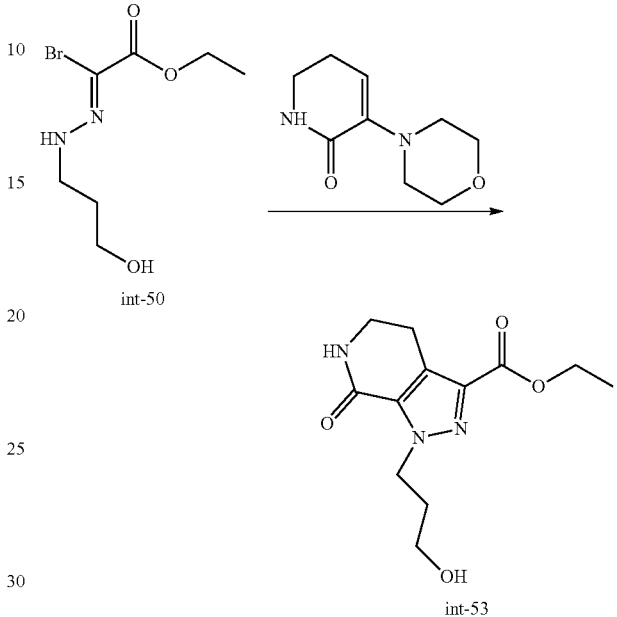

Step 1: Ethyl 2-oxoacetate (11.32 g, 55.5 mmol, 1 equiv) were dissolved in THF (50 ml), and to the solution was added 3-hydrazinylpropan-1-ol (5.00 g, 55.5 mmol, 1 equiv) at 0° C. The reaction mixture was stirred at 25° C. for 12 h. The reaction mixture was concentrated in vacuo and the residue was dissolved in ethyl acetate (80 mL), washed with water (2×30 mL), dried over anhydrous $Na_2SO_4$, filtered and concentrated in vacuo to give a crude residue. The residue was purified by silica gel chromatography to afford ethyl (E)-2-(2-(3-hydroxypropyl)hydrazono)acetate. TLC $R_f$=0.3 (EtOAc). $^1$H NMR (400 MHz, $CDCl_3$) δ 7.19 (s, 1H), 6.73 (s, 1H), 4.30-4.23 (m, 2H), 3.79-3.76 (m, 2H), 3.39-3.35 (m, 2H), 1.92-1.86 (m, 2H), 1.31 (t, J=7.1 Hz, 3H).

Step 2: (Z)-Ethyl 2-bromo-2-(2-(3-hydroxypropyl)hydrazono)acetate. A solution of ethyl (E)-2-(2-(3-hydroxypropyl)hydrazono)acetate (3.5 g, 20.09 mmol, 1.0 equiv) in EtOAc (35 mL) was cooled to 0° C., then NBS (3.75 g, 21.09 mmol, 1.04 equiv) was added slowly. The reaction mixture was stirred at 25° C. for 0.5 h. The mixture was filtered, and the filtrate was diluted with water (5 mL) and extracted with EtOAc (2×30 mL). The combined organic extracts were dried over $Na_2SO_4$, filtered and concentrated. The residue was purified by silica gel chromatography (petroleum ether) to afford ethyl (Z)-2-bromo-2-(2-(3-hydroxypropyl)hydrazono)acetate (int-52). TLC $R_f$=0.4 (1:5 EtOAc/petroleum ether). $^1$H NMR (400 MHz, $CDCl_3$) δ 6.94 (s, 1H), 4.36-4.30 (m, 2H), 3.78-3.75 (m, 2H), 3.69-3.67 (m, 2H), 1.93-1.86 (m, 2H), 1.36-1.33 (m, 3H).

Ethyl 1-(3-hydroxypropyl)-7-oxo-4,5,6,7-tetrahydro-1H-pyrazolo[3,4-c]pyridine-3-carboxylate (int-53) was obtained using the method described for the synthesis of intermediate (int-51), except ethyl (Z)-2-chloro-2-(2-(2-hydroxy-2-methylpropyl)hydrazono)acetate (int-50) was replaced with ethyl (Z)-2-bromo-2-(2-(3-hydroxypropyl)hydrazono)acetate (int-52). $^1$H NMR (400 MHz, $CDCl_3$) δ 6.17 (s, 1H), 4.78-4.74 (m, 2H), 4.43-4.40 (m, 2H), 3.63-3.59 (m, 2H), 3.50-3.47 (m, 2H), 3.15-3.11 (m, 2H), 2.14-2.05 (m, 2H), 1.43-1.39 (m, 3H). MS (ESI): m/z 268.1 $[M+H]^+$.

Synthesis of Exemplary Compounds

Example 1

N-(4-Cyanobenzyl)-6-((1-(cyclopropylsulfonyl)cyclopropyl)methyl)-1-methyl-7-oxo-6,7-dihydro-1H-pyrazolo[3,4-c]pyridine-3-carboxamide (1)

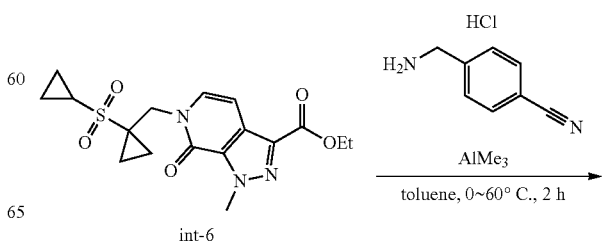

-continued

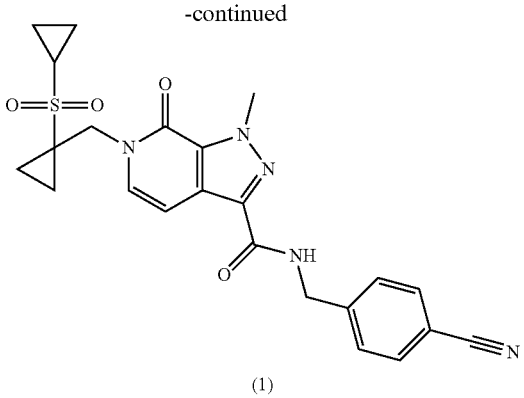

(1)

A solution of 4-(aminomethyl)benzonitrile hydrochloride (81 mg, 0.48 mmol, 3.0 equiv) in toluene (1.2 mL) was cooled to 0° C. before AlMe₃ (1.0 M in toluene, 0.48 mL, 0.48 mmol, 3.0 equiv) was added dropwise, followed by ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6) (50 mg, 0.16 mmol, 1.0 equiv) in one portion. After the reaction was stirred at 60° C. for 2 h, it was cooled to 0° C. and quenched with water (1 mL). The mixture was extracted with EtOAc (3×1 mL), then the combined organic extracts were dried over Na₂SO₄, filtered and concentrated. The crude was purified by RP-HPLC to give N-(4-cyanobenzyl)-6-((1-(cyclopropylsulfonyl)cyclopropyl)methyl)-1-methyl-7-oxo-6,7-dihydro-1H-pyrazolo[3,4-c]pyridine-3-carboxamide (1). TLC $R_f$=0.3 (67% EtOAc/petroleum ether). ¹H NMR (400 MHz, CDCl₃) δ 7.74-7.59 (m, J=8.3 Hz, 2H), 7.53-7.43 (m, J=8.2 Hz, 2H), 7.35 (br t, J=6.1 Hz, 1H), 7.21 (d, J=7.3 Hz, 1H), 7.13 (d, J=7.3 Hz, 1H), 4.72 (d, J=6.2 Hz, 2H), 4.58 (s, 2H), 4.38 (s, 3H), 2.39 (ddd, J=3.1, 4.9, 8.0 Hz, 1H), 1.56-1.52 (m, 2H), 1.25-1.14 (m, 4H), 1.04-0.95 (m, 2H). MS (ESI): m/z 466.2 [M+H]⁺.

Example 2

N-(4-Cyanobenzyl)-1-methyl-6-((1-(methylsulfonyl)cyclopropyl)methyl)-7-oxo-6,7-dihydro-1H-pyrazolo[3,4-c]pyridine-3-carboxamide (2)

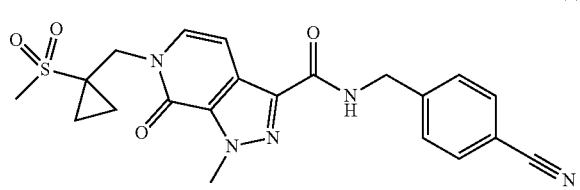

(2)

N-(4-Cyanobenzyl)-1-methyl-6-((1-(methylsulfonyl)cyclopropyl)methyl)-7-oxo-6,7-dihydro-1H-pyrazolo[3,4-c]pyridine-3-carboxamide (2) was obtained using the procedure described in Example 1, except intermediate (int-6) was replaced with intermediate (int-7). TLC $R_f$=0.2 (67% EtOAc/petroleum ether). ¹H NMR (400 MHz, CDCl₃) δ 7.69-7.62 (m, J=8.3 Hz, 2H), 7.53-7.44 (m, J=8.3 Hz, 2H), 7.35 (br t, J=6.2 Hz, 1H), 7.23 (d, J=7.3 Hz, 1H), 7.14 (d, J=7.2 Hz, 1H), 4.72 (d, J=6.2 Hz, 2H), 4.50 (s, 2H), 4.39 (s, 3H), 2.81 (s, 3H), 1.59-1.55 (m, 2H), 1.32-1.27 (m, 2H). MS (ESI): m/z 440.2 [M+H]⁺.

Example 3

N-(4-cyanobenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide (3)

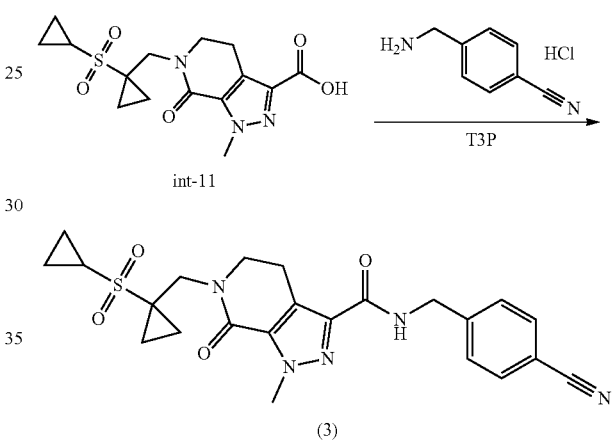

To a solution of 6-((1-cycloprosulfonccloropyl)methyl)-1-meth 17-oxo-4,5,6,7-tetrahydro-1H-pyrazolo[3,4-c]pyridine-3-carboxylic acid (int-11)(45 mg, 0.13 mmol, 1.0 equiv) and 4-(aminomethyl)benzonitrile hydrochloride (27 mg, 0.16 mmol, 1.2 equiv) in DMF (0.5 mL) was added T3P (248 mg, 0.39 mmol, 3.0 equiv) and DIPEA (84 mg, 0.65 mmol, 5.0 equiv). The reaction mixture was stirred at 25° C. for 2 h before it was diluted with water (2 mL) and extracted with EtOAc (2×5 mL). The combined organic extracts were dried over Na₂SO₄, filtered and concentrated. The residue was purified by RP-HPLC to afford N-(4-cyanobenzyl)-6-((16-(cyclopropylsulfonyl)cyclopropyl)methyl)-1-methyl-7-oxo-4,5,6,7-tetrahydro-1H-pyrazolo[3,4-c]pyridine-3-carboxamide (3). ¹H NMR (400 MHz, CDCl₃) 7.63 (d, J=8.4 Hz, 2H), 7.45 (d, J=8.4 Hz, 2H), 7.30-7.28 (m, 1H), 4.65 (d, J=6.4 Hz, 2H), 4.16 (s, 3H), 4.07 (s, 2H), 3.77-3.73 (m, 2H), 3.21-3.17 (m, 2H), 2.77-2.73 (m, 1H), 1.52-1.51 (m, 2H), 1.24-1.22 (m, 2H), 1.08-1.04 (m, 4H). MS (ESI): m/z 468.1 [M+H]⁺.

Compounds given in Table 1 below were prepared following procedures analogous to those described in Example 3 for compound (3).

TABLE 1

| Example/Compound Number | Compound Structure and Name | Physical Data MS (m/z), $^1$H NMR |
|---|---|---|
| 4 | 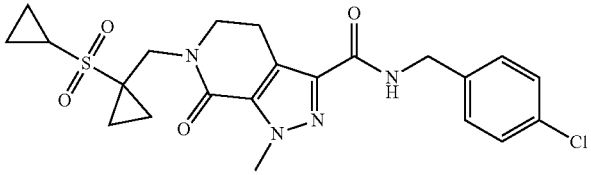 [SMILES: Cn1nc(C(=O)NCc2ccc(Cl)cc2)c2c1C(=O)N(CC1(S(=O)(=O)C3CC3)CC1)CC2]<br>N-(4-Chlorobenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 477.1 [M + H]$^+$. $^1$H NMR (400 MHz, DMSO-d$_6$) δ 8.84 (t, J = 6.2 Hz, 1H), 7.38-7.30 (m, 4H), 4.37 (d, J = 6.4 Hz, 2H), 4.11 (s, 3H), 4.02 (s, 2H), 3.66 (t, J = 6.8 Hz, 2H), 2.99 (t, J = 6.8 Hz, 2H), 2.95-2.91 (m, 1H), 1.29-1.26 (m, 2H), 1.10-0.98 (m, 6H). |
| 5 | 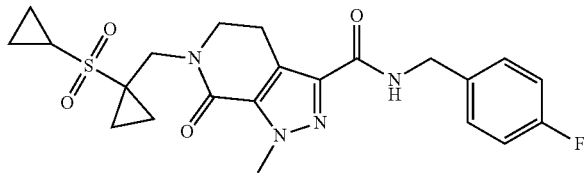 [SMILES: Cn1nc(C(=O)NCc2ccc(F)cc2)c2c1C(=O)N(CC1(S(=O)(=O)C3CC3)CC1)CC2]<br>6-((1-(Cyclopropylsulfonyl)cyclopropyl)methyl)-N-(4-fluorobenzyl)-1-methyl-7-oxo-4,5,6,7-tetrahydro-1H-pyrazolo[3,4-c]pyridine-3-carboxamide | MS (ESI): m/z 461.1 [M + H]$^+$. $^1$H NMR (400 MHz, DMSO-d$_6$) δ 8.82-8.79 (m, 1H), 7.35-7.31 (m, 2H), 7.15-7.10 (m, 2H), 4.37 (d, J = 6.4 Hz, 2H), 4.11 (s, 3H), 4.02 (s, 2H), 3.66 (t, J = 6.8 Hz, 2H), 2.99 (t, J = 6.8 Hz, 2H), 2.95-2.91 (m, 1H), 1.29-1.23 (m, 2H), 1.10-1.00 (m, 6H). |
| 6 | 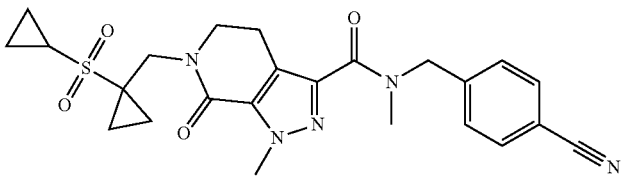 [SMILES: CN(Cc1ccc(C#N)cc1)C(=O)c1nn(C)c2c1CCN(CC1(S(=O)(=O)C3CC3)CC1)C2=O]<br>N-(4-Cyanobenzyl)-6-((1-(cyclopropylsulfonyl)cyclopropyl)methyl)-N,1-dimethyl-7-oxo-4,5,6,7-tetrahydro-1H-pyrazolo[3,4-c]pyridine-3-carboxamide | MS (ESI): m/z 482.2 [M + H]$^+$. $^1$H NMR (400 MHz, DMSO-d$_6$) δ 7.83 (d, J = 7.2 Hz, 2H), 7.47-7.46 (m, 2H), 5.10 (s, 1H), 4.74 (s, 1H), 4.10 (s, 2H), 4.03-4.00 (m, 3H), 3.67-3.66 (m, 2H), 3.25 (s, 3H), 2.93-2.92 (m, 2H), 2.90-2.89 (m, 1H), 1.28 (s, 2H), 1.09-1.01 (m, 6H). |
| 7 | 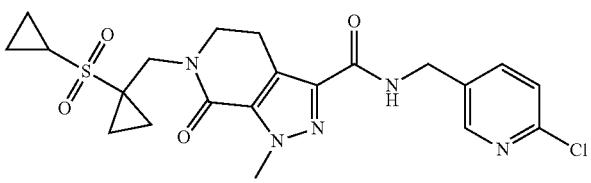 [SMILES: Cn1nc(C(=O)NCc2ccc(Cl)nc2)c2c1C(=O)N(CC1(S(=O)(=O)C3CC3)CC1)CC2]<br>N-((6-Chloropyridin-3-yl)methyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 478.0 [M + H]$^+$. $^1$H NMR (500 MHz, CDCl$_3$) δ 8.40 (d, J = 2.4 Hz, 1H), 7.70 (dd, J = 8.2, 2.5 Hz, 1H), 7.32 (d, J = 8.2 Hz, 1H), 7.26-7.22 (m, 1H), 4.61 (d, J = 6.3 Hz, 2H), 4.18 (s, 3H), 4.09 (s, 2H), 3.77 (t, J = 6.9 Hz, 2H), 3.21 (t, J = 6.9 Hz, 2H), 2.80-2.73 (m, 1H), 1.56-1.50 (m, 2H), 1.29-1.23 (m, 2H), 1.10 (dt, J = 7.8, 3.3 Hz, 2H), 1.08-1.05 (m, 2H). |
| 8 | 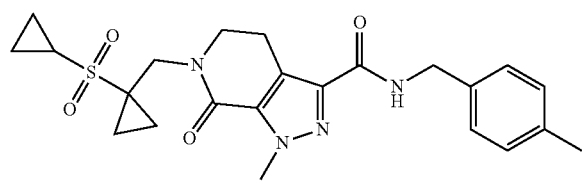 [SMILES: Cc1ccc(CNC(=O)c2nn(C)c3c2CCN(CC2(S(=O)(=O)C4CC4)CC2)C3=O)cc1]<br>6-((1-(Cyclopropylsulfonyl)cyclopropyl)methyl)-1-methyl-N-(4-methylbenzyl)-7-oxo-4,5,6,7-tetrahydro-1H-pyrazolo[3,4-c]pyridine-3-carboxamide | MS (ESI): m/z 457.0 [M + H]$^+$. $^1$H NMR (500 MHz, DMSO-d$_6$) δ 8.70 (t, J = 6.3 Hz, 1H), 7.18 (d, J = 8.0 Hz, 2H), 7.10 (d, J = 7.9 Hz, 2H), 4.34 (d, J = 6.3 Hz, 2H), 4.11 (s, 3H), 4.02 (s, 2H), 3.66 (t, J = 6.8 Hz, 2H), 2.99 (t, J = 6.8 Hz, 2H), 2.94 (ddd, J = 12.8, 7.9, 5.0 Hz, 1H), 2.26 (s, 3H), 1.27 (q, J = 4.8 Hz, 2H), 1.12-0.97 (m, 6H). |

TABLE 1-continued

| Example/Compound Number | Compound Structure and Name | Physical Data MS (m/z), $^1$H NMR |
|---|---|---|
| 9 | 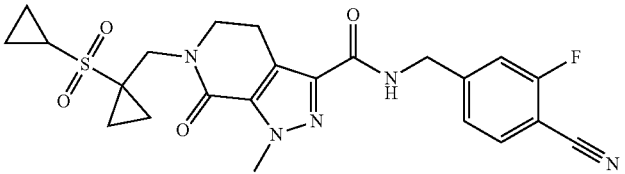<br>N-(4-Cyano-3-fluorobenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 486.0 [M + H]$^+$. $^1$H NMR (500 MHz, DMSO-d$_6$) δ 8.98 (t, J = 6.2 Hz, 1H), 7.91-7.84 (m, 1H), 7.40 (d, J = 10.4 Hz, 1H), 7.35-7.30 (m, 1H), 4.47 (s, 2H), 4.13 (s, 3H), 4.02 (s, 2H), 3.67 (t, J = 6.8 Hz, 2H), 2.99 (t, J = 6.8 Hz, 2H), 2.97-2.91 (m, 1H), 1.30-1.25 (m, 2H), 1.11-1.07 (m, 2H), 1.07-0.98 (m, 4H). |
| 10 | 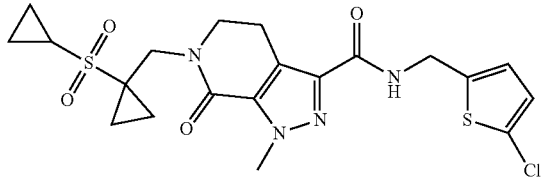 [SMILES: Cn1nc(C(=O)NCc2ccc(Cl)s2)c2c1C(=O)N(CC1(S(=O)(=O)C3CC3)CC1)CC2]<br>N-((5-Chlorothiophen-2-yl)methyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 483.0 [M + H]$^+$. $^1$H NMR (500 MHz, DMSO-d$_6$) δ 8.90 (t, J = 6.2 Hz, 1H), 6.93 (d, J = 3.7 Hz, 1H), 6.84 (d, J = 3.7 Hz, 1H), 4.45 (d, J = 6.1 Hz, 2H), 4.11 (s, 3H), 4.02 (s, 2H), 3.67 (t, J = 6.8 Hz, 2H), 3.00 (t, J = 6.8 Hz, 2H), 2.94 (ddd, J = 12.7, 7.8, 5.0 Hz, 1H), 1.27 (q, J = 4.8 Hz, 2H), 1.11-1.07 (m, 2H), 1.02 (ddd, J = 15.9, 6.6, 3.4 Hz, 4H). |
| 11 | 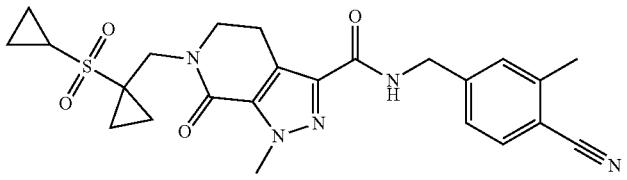 [SMILES: Cc1cc(CNC(=O)c2nn(C)c3c2CCN(CC2(S(=O)(=O)C4CC4)CC2)C3=O)ccc1C#N]<br>N-(4-Cyano-3-methylbenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 482.4 [M + H]$^+$. $^1$H NMR (400 MHz, DMSO-d$_6$) δ 8.92 (t, J = 6.4 Hz, 1H), 7.71 (d, J = 8.0 Hz, 1H), 7.36 (s, 1H), 7.29 (d, J = 8.0 Hz, 1H), 4.43 (d, J = 6.0 Hz, 2H), 4.13 (s, 3H), 4.03 (s, 2H), 3.67 (t, J = 6.8 Hz, 2H), 3.03-2.91 (m, 3H), 2.46 (s, 3H), 1.32-1.25 (m, 2H), 1.12-0.98 (m, 6H). |
| 12 | 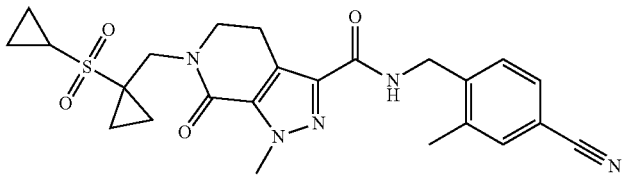 [SMILES: Cc1cc(C#N)ccc1CNC(=O)c1nn(C)c2c1CCN(CC1(S(=O)(=O)C3CC3)CC1)C2=O]<br>N-(4-Cyano-2-methylbenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 482.1 [M + H]$^+$. $^1$H NMR (400 MHz, DMSO-d$_6$) 8.87 (t, J = 6.0 Hz, 1H), 7.66-7.60 (m, 2H), 7.37 (d, J = 8.0 Hz, 1H), 4.43 (d, J = 6.2 Hz, 2H), 4.14 (s, 3H), 4.03 (s, 2H), 3.68 (t, J = 6.8 Hz, 2H), 3.03-2.93 (m, 3H), 2.37 (s, 3H), 1.32-1.26 (m, 2H), 1.13-0.98 (m, 6H). |
| 13 | 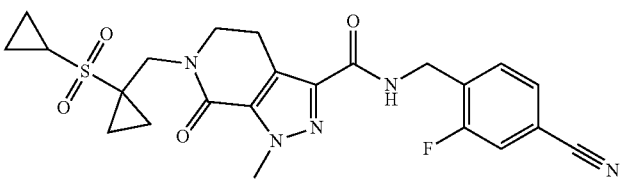 [SMILES: Cn1nc(C(=O)NCc2ccc(C#N)cc2F)c2c1C(=O)N(CC1(S(=O)(=O)C3CC3)CC1)CC2]<br>N-(4-Cyano-2-fluorobenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 486.0 [M + H]$^+$. $^1$H NMR (400 MHz, DMSO-d$_6$) δ 8.93 (t, J = 6.2 Hz, 1H), 7.83 (m, 1H), 7.67 (m, 1H), 7.50 (m, 1H), 4.50 (d, J = 6.0 Hz, 2H), 4.14 (s, 3H), 4.03 (s, 2H), 3.67 (m, 2H), 3.02-2.91 (m, 3H), 1.30-1.26 (m, 2H), 1.12-1.08 (m, 2H), 1.07-1.00 (m, 4H). |

TABLE 1-continued

| Example/ Compound Number | Compound Structure and Name | Physical Data MS (m/z), ¹H NMR |
|---|---|---|
| 14 | 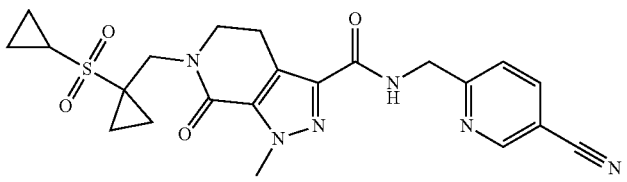 [SMILES: Cn1nc(C(=O)NCc2ccc(C#N)cn2)c2c1C(=O)N(CC1(S(=O)(=O)C3CC3)CC1)CC2]<br>N-((5-Cyanopyridin-2-yl)methyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 469.0 [M + H]⁺. ¹H NMR (400 MHz, DMSO-$d_6$) δ 8.99-8.88 (m, 2H), 8.26 (dd, J = 2.4, 8.4 Hz, 1H), 7.49 (d, J = 8.2 Hz, 1H), 4.59 (d, J = 6.0 Hz, 2H), 4.15 (s, 3H), 4.04 (s, 2H), 3.68 (t, J = 6.8 Hz, 2H), 3.03-2.91 (m, 3H), 1.32-1.25 (m, 2H), 1.14-0.98 (m, 6H). |
| 15 | 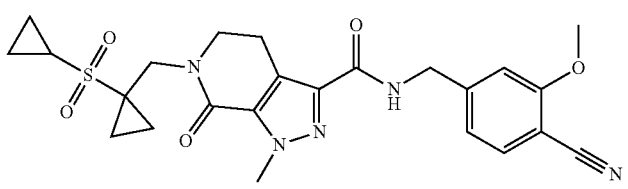<br>N-(4-Cyano-3-methoxybenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 498.2 [M + H]⁺. ¹H NMR (400 MHz, CDCl₃) δ 7.53 (d, J = 7.8 Hz, 1H), 6.99 (d, J = 7.8 Hz, 1H), 6.95 (s, 1H), 4.63 (d, J = 6.4 Hz, 2H), 4.17 (s, 3H), 4.08 (s, 2H), 3.93 (s, 3H), 3.76 (t, J = 6.8 Hz, 2H), 3.21 (t, J = 6.8 Hz, 2H), 2.82-2.71 (m, 1H), 1.56-1.49 (m, 2H), 1.28-1.21 (m, 2H), 1.13-1.00 (m, 4H). |
| 16 | 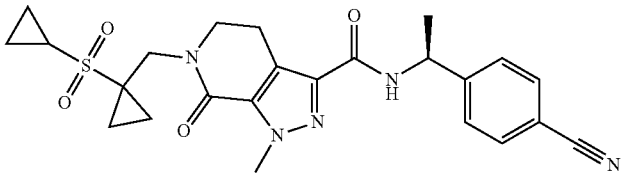 [SMILES: C[C@H](NC(=O)c1nn(C)c2c1CCN(CC1(S(=O)(=O)C3CC3)CC1)C2=O)c1ccc(C#N)cc1]<br>(S)-N-(1-(4-Cyanophenyl)ethyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 482.2 [M + H]⁺. ¹H NMR (400 MHz, CDCl₃) δ 7.68-7.61 (m, 2H), 7.49 (d, J = 8.2 Hz, 2H), 7.12 (d, J = 7.6 Hz, 1H), 5.25 (m, 1H), 4.19 (s, 3H), 4.07 (m, 2H), 3.73 (m, 2H), 3.15 (m, 2H), 2.80-2.68 (m, 1H), 1.59 (d, J = 7.0 Hz, 3H), 1.54-1.48 (m, 2H), 1.29-1.21 (m, 2H), 1.11-1.06 (m, 2H), 1.06-1.01 (m, 2H). Chiral SFC Separation Condition: (DEA)_5_40_3ML_T35 Column: Chiralcel OD-3 50 × 4.6 mm I.D., 3 um Mobile phase: ethanol (0.05% DEA) in CO2 from 5% to 40% Flow rate: 3 mL/min Wavelength: 220 nm. SFC (C-07336-144-P2A_2, OD-3_5CM_ETOH(DEA)_5_40_3ML_T35.M): Rt = 2.255, ee% = 93.27 |
| 17 | 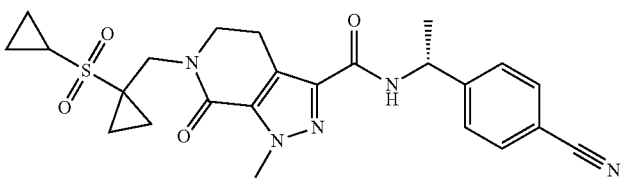 [SMILES: C[C@@H](NC(=O)c1nn(C)c2c1CCN(CC1(S(=O)(=O)C3CC3)CC1)C2=O)c1ccc(C#N)cc1]<br>(R)-N-(1-(4-Cyanophenyl)ethyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 482.2 [M + H]⁺. ¹H NMR (400 MHz, CDCl₃) δ 7.68-7.60 (m, 2H), 7.49 (d, J = 8.0 Hz, 2H), 7.12 (br d, J = 7.6 Hz, 1H), 5.25 (m, 1H), 4.19 (s, 3H), 4.07 (m, 2H), 3.77-3.69 (m, 2H), 3.15 (m, 2H), 2.75 (m, 1H), 1.59 (d, J = 7.0 Hz, 3H), 1.54-1.49 (m, 2H), 1.27-1.21 (m, 2H), 1.11-1.06 (m, 2H), 1.06-1.00 (m, 2H). SFC (OD-3_5CM_ETOH(DEA)_5_40_3ML_T35.M): Rt = 1.729, ee% = 100.00 |
| 18 | 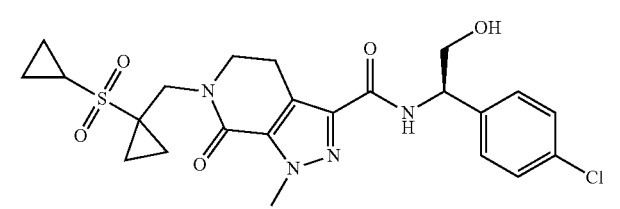 [SMILES: Cn1nc(C(=O)N[C@@H](CO)c2ccc(Cl)cc2)c2c1C(=O)N(CC1(S(=O)(=O)C3CC3)CC1)CC2]<br>(R)-N-(1-(4-Chlorophenyl)-2-hydroxyethyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 507.3 [M + H]⁺. ¹H NMR (400 MHz, DMSO-$d_6$) δ 8.41 (d, J = 8.0 Hz, 1H), 7.41-7.34 (m, 4H), 5.02-4.94 (m, 2H), 4.14 (s, 3H), 4.02 (s, 2H), 3.74- (m, 4H), 2.98-2.89 (m, 3H), 1.30-1.25 (m, 2H), 1.11-1.06 (m, 2H), 1.06-0.99 (m, 4H). Chiral HPLC separation condition: Column: Chiralcel OJ-3 50 × 4.6 mm I.D., 3 um Mobile phase: ethanol (0.05% DEA) in CO2 from 5% to 40% Flow rate: 3 mL/min Wavelength: 220 nm. SFC: Rt = 1.836, 91% ee, OJ-3_5CM_ETOH(DEA)_5_40_3ML_T35.M; |

TABLE 1-continued

| Example/ Compound Number | Compound Structure and Name | Physical Data MS (m/z), ¹H NMR |
|---|---|---|
| 19 | 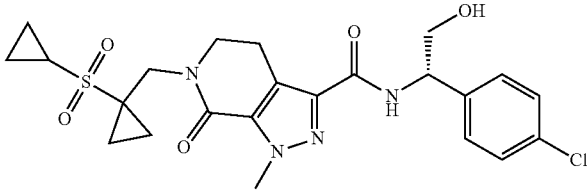 [SMILES: Cn1nc(C(=O)N[C@H](CO)c2ccc(Cl)cc2)c2c1C(=O)N(CC1(S(=O)(=O)C3CC3)CC1)CC2]<br>(S)-N-(1-(4-Chlorophenyl)-2-hydroxyethyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide | MS (ESI): m/z 507.2 [M + H]⁺. ¹H NMR (400 MHz, DMSO-$d_6$) δ 8.41 (d, J = 8.0 Hz, 1H), 7.37 (m, 4H), 5.01-4.94 (m, 2H), 4.14 (s, 3H), 4.02 (s, 2H), 3.69-3.63 (m, 4H), 2.97-2.91 (m, 3H), 1.27-1.26 (m, 2H), 1.08-1.06 (m, 2H), 1.04-1.00 (m, 4H).<br>SFC: Rt = 1.683, 100% ee, OJ-3_5CM_ETOH(DEA)_5_40_3ML_135.M; |
| 20 | 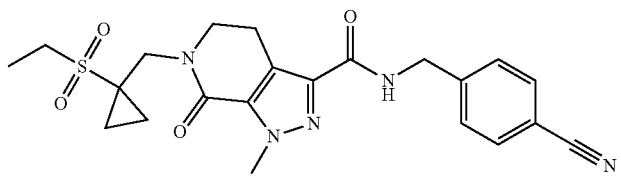 [SMILES: CCS(=O)(=O)C1(CN2CCc3c(C(=O)NCc4ccc(C#N)cc4)nn(C)c3C2=O)CC1]<br>N-(4-Cyanobenzyl)-6-((1-(ethylsulfonyl)cyclopropyl)methyl)-1-methyl-7-oxo-4,5,6,7-tetrahydro-1H-pyrazolo[3,4-c]pyridine-3-carboxamide | MS (ESI): m/z 456.3 [M + H]⁺. ¹H NMR (400 MHz, CDCl₃) δ 7.64 (d, J = 8.2 Hz, 2H), 7.45 (d, J = 8.2 Hz, 2H), 7.31-7.28 (m, 1H), 4.66 (d, J = 6.3 Hz, 2H), 4.17 (s, 3H), 3.96 (s, 2H), 3.75 (t, J = 6.9 Hz, 2H), 3.27 (q, J = 7.4 Hz, 2H), 3.20 (t, J = 6.9 Hz, 2H), 1.57-1.51 (m, 2H), 1.42 (t, J = 7.5 Hz, 3H), 1.08-1.02 (m, 2H). |
| 21 | 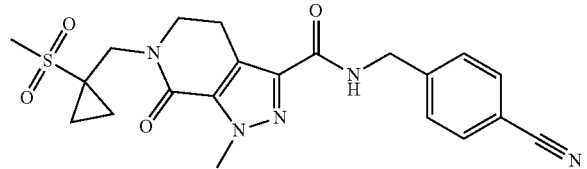 [SMILES: Cn1nc(C(=O)NCc2ccc(C#N)cc2)c2c1C(=O)N(CC1(S(C)(=O)=O)CC1)CC2]<br>N-(4-Cyanobenzyl)-1-methyl-6-((1-(methylsulfonyl)cyclopropyl)methyl)-7-oxo-4,5,6,7-tetrahydro-1H-pyrazolo[3,4-c]pyridine-3-carboxamide | MS (ESI): m/z 442.2 [M + H]⁺. ¹H NMR (400 MHz, DMSO-$d_6$) δ 8.96 (t, J = 6.2 Hz, 1H), 7.78 (d, J = 8.4 Hz, 2H), 7.47 (d, J = 8.0 Hz, 2H), 4.46 (d, J = 6.4 Hz, 2H), 4.12 (s, 3H), 3.96 (s, 2H), 3.66 (t, J = 7.0 Hz, 2H), 3.11 (s, 3H), 2.98 (t, J = 6.8 Hz, 2H), 1.30-1.27 (m, 2H), 1.11-1.10 (m, 2H). |
| 22 | 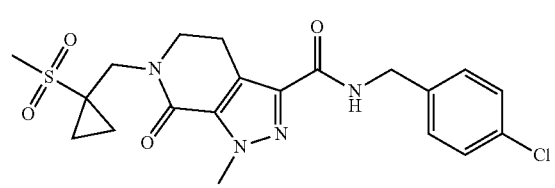 [SMILES: Cn1nc(C(=O)NCc2ccc(Cl)cc2)c2c1C(=O)N(CC1(S(C)(=O)=O)CC1)CC2]<br>N-(4-Chlorobenzyl)-1-methyl-6-((1-(methylsulfonyl)cyclopropyl)methyl)-7-oxo-4,5,6,7-tetrahydro-1H-pyrazolo[3,4-c]pyridine-3-carboxamide | MS (ESI): m/z 451.1 [M + H]⁺. ¹H NMR (400 MHz, DMSO-$d_6$) δ 8.85 (t, J = 6.2 Hz, 1H), 7.38-7.30 (m, 4H), 4.37 (d, J = 6.4 Hz, 2H), 4.11 (s, 3H), 3.96 (s, 2H), 3.66 (t, J = 6.8 Hz, 2H), 3.11 (s, 3 H), 2.99 (t, J = 6.8 Hz, 2 H), 1.30-1.27 (m, 2 H), 1.11-1.08 (m, 2 H). |
| 23 | 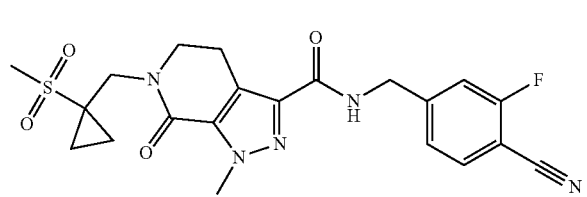 [SMILES: Cn1nc(C(=O)NCc2ccc(C#N)c(F)c2)c2c1C(=O)N(CC1(S(C)(=O)=O)CC1)CC2]<br>N-(4-Cyano-3-fluorobenzyl)-1-methyl-6-((1-(methylsulfonyl)cyclopropyl)methyl)-7-oxo-4,5,6,7-tetrahydro-1H-pyrazolo[3,4-c]pyridine-3-carboxamide | MS (ESI): m/z 460.3 [M + H]⁺. ¹H NMR (400 MHz, CDCl₃) δ 7.62-7.58 (m, 1H), 7.35-7.31 (m, 1H), 7.25-7.20 (m, 2H), 4.66 (d, J = 6.4 Hz, 2H), 4.18 (s, 3H), 3.98 (s, 2H), 3.78-3.75 (m, 2H), 3.22-3.18 (m, 2H), 3.08 (s, 3H), 1.58-1.55 (m, 2H), 1.10-1.07 (m, 2H). |

Example 24

4-cyanobenzyl 6-((1-(cyclopropylsulfonyl)cyclopropyl)methyl)-1-methyl-7-oxo-4,5,6,7-tetrahydro-1H-pyrazolo[3,4-c]pyridine-3-carboxylate (24)

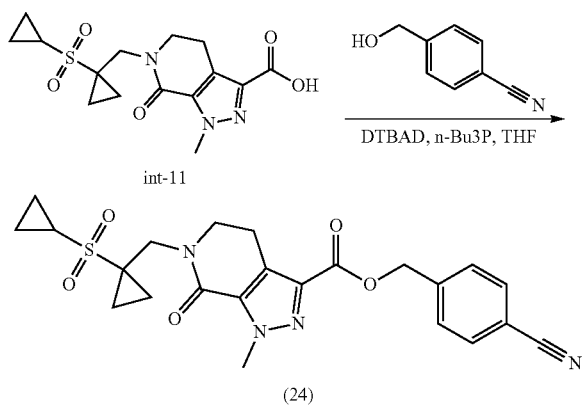

A solution of 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) (100 mg, 0.283 mmol, 1.0 equiv), 4-(hydroxymethyl)benzonitrile (57 mg, 0.424 mmol, 1.5 equiv) and PBu₃ (86 mg, 0.424 mmol, 1.5 equiv) in THF (1 mL) was cooled to 0° C. before di-tert-butyl azodicarboxylate (DTBAD) (98 mg, 0.424 mmol, 1.5 equiv) was added. After 1 h at 25° C., the reaction mixture was concentrated and the residue was purified by RP-HPLC. The material obtained was triturated with MTBE to afford 4-cyanobenzyl 6-((1-(cyclopropylsulfonyl)cyclopropyl)methyl)-1-methyl-7-oxo-4,5,6,7-tetrahydro-1H-pyrazolo[3,4-c]pyridine-3-carboxylate (24). $^1$H NMR (400 MHz, CDCl₃) δ 7.68 (d, J=8.0 Hz, 2H), 7.55 (d, J=8.4 Hz, 2H), 5.43 (s, 2H), 4.25 (s, 3H), 4.07 (s, 2H), 3.77 (m, 2H), 3.12 (m, 2H), 2.82-2.61 (m, 1H), 1.56-1.49 (m, 2H), 1.30-1.20 (m, 2H), 1.14-0.99 (m, 4H). MS (ESI): m/z 469.4 [M+H]⁺.

Example 25

4-(2-(6-((1-(cyclopropylsulfonyl)cyclopropyl)methyl)-1-methyl-7-oxo-4,5,6,7-tetrahydro-1H-pyrazolo[3,4-c]pyridin-3-yl)-2-oxoethoxy)benzonitrile (25)

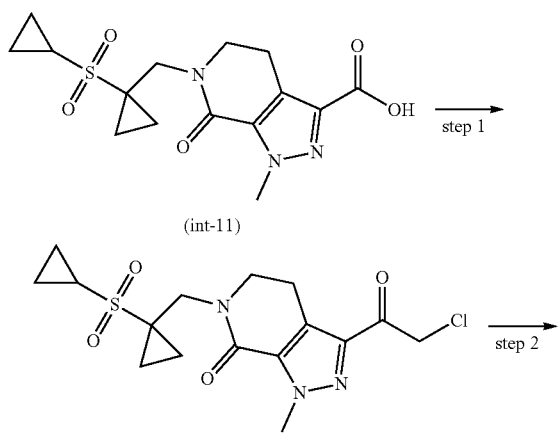

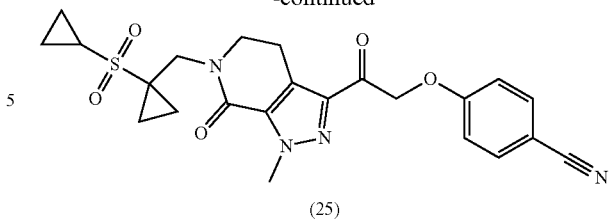

Step 1: 3-(2-Chloroacetyl)-6-((1-(cyclopropylsulfonyl)cyclopropyl)methyl)-1-methyl-1,4,5,6-tetrahydro-7H-pyrazolo[3,4-c]pyridin-7-one. To a mixture of 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) (235 mg, 0.665 mmol, 1.0 equiv) in oxalyl chloride (1.1 mL, 13.3 mmol, 20 equiv) was added DMF (10.3 µL, 0.132 mmol, 0.2 equiv) at rt. After 3 h, the reaction was concentrated and the crude residue was dissolved in 1:1 THF-MeCN (2 mL) and cooled to 0° C. A solution of TMSCHN₂ (2.0 M in hexanes, 665 µL, 1.33 mmol, 2.0 equiv) and Et₃N (184 µL, 1.33 mmol, 2.0 equiv) was added dropwise. The mixture was stirred at 0° C. for 2 h before HCl (4.0 M in Et₂O, 8.7 mL, 34.8 mmol, 52 equiv) was added. The mixture was stirred at 0° C. for 1 h before it was partitioned between saturated NaHCO₃ (100 mL) and CH₂Cl₂ (200 mL). The layers were separated and the aqueous phase was extracted with CH₂Cl₂ (100 mL), then the combined organic extracts were dried with Na₂SO₄, filtered and concentrated. The residue was purified by column chromatography (SiO₂, 0-100% EtOAc/heptane) to afford 3-(2-chloroacetyl)-6-((1-(cyclopropylsulfonyl)cyclopropyl)methyl)-1-methyl-1,4,5,6-tetrahydro-7H-pyrazolo[3,4-c]pyridin-7-one. $^1$H NMR (500 MHz, CDCl₃) δ 4.79 (s, 2H), 4.22 (s, 3H), 4.07 (s, 2H), 3.76 (t, J=6.9 Hz, 2H), 3.17 (t, J=6.9 Hz, 2H), 2.81-2.69 (m, 1H), 1.53-1.50 (m, 2H), 1.29-1.20 (m, 2H), 1.11-1.06 (m, 2H), 1.06-1.00 (m, 2H), 0.88 (t, J=6.7 Hz, 1H). MS (ESI): m/z 386.1 [M+H]⁺.

Step 2: 4-(2-(6-((1-(Cyclopropylsulfonyl)cyclopropyl)methyl)-1-methyl-7-oxo-4,5,6,7-tetrahydro-1H-pyrazolo[3,4-c]pyridin-3-yl)-2-oxoethoxy)benzonitrile (25). A mixture of 3-(2-chloroacetyl)-6-((1-(cyclopropylsulfonyl)cyclopropyl)methyl)-1-methyl-1,4,5,6-tetrahydro-7H-pyrazolo[3,4-c]pyridin-7-one (12 mg, 31 µmol, 1.0 equiv), K₂CO₃ (6.45 mg, 47 µmol, 1.5 equiv) and 4-hydroxybenzonitrile (5.56 mg, 47 µmol, 1.5 equiv) in MeCN (311 µL) was heated at 60° C. for 14 h before it was concentrated. The residue was partitioned between EtOAc (2 mL) and H₂O (2 mL), the layers were separated, and then the aqueous phase was extracted with EtOAc (3×5 mL). The combined organic extracts were dried with MgSO₄, filtered, and concentrated. The residue was purified by column chromatography (SiO₂, 0-100% EtOAc/heptane) to afford 4-(2-(6-((1-(Cyclopropylsulfonyl)cyclopropyl)methyl)-1-methyl-7-oxo-4,5,6,7-tetrahydro-1H-pyrazolo[3,4-c]pyridin-3-yl)-2-oxoethoxy)benzonitrile (25). $^1$H NMR (500 MHz, CDCl₃) δ 7.59 (d, J=8.6 Hz, 2H), 7.00 (d, J=8.7 Hz, 2H), 5.41 (s, 2H), 4.24 (s, 3H), 4.07 (s, 2H), 3.76 (t, J=6.9 Hz, 2H), 3.16 (t, J=6.9 Hz, 2H), 2.78 (tt, J=8.3, 4.8 Hz, 1H), 1.54-1.50 (m, 2H), 1.26-1.21 (m, 3H), 1.11-1.06 (m, 2H), 1.05-1.02 (m, 2H). MS (ESI): m/z 469.2 [M+H]⁺.

Example 26

4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,3,4-oxadiazol-2-yl)methyl)benzonitrile (26)

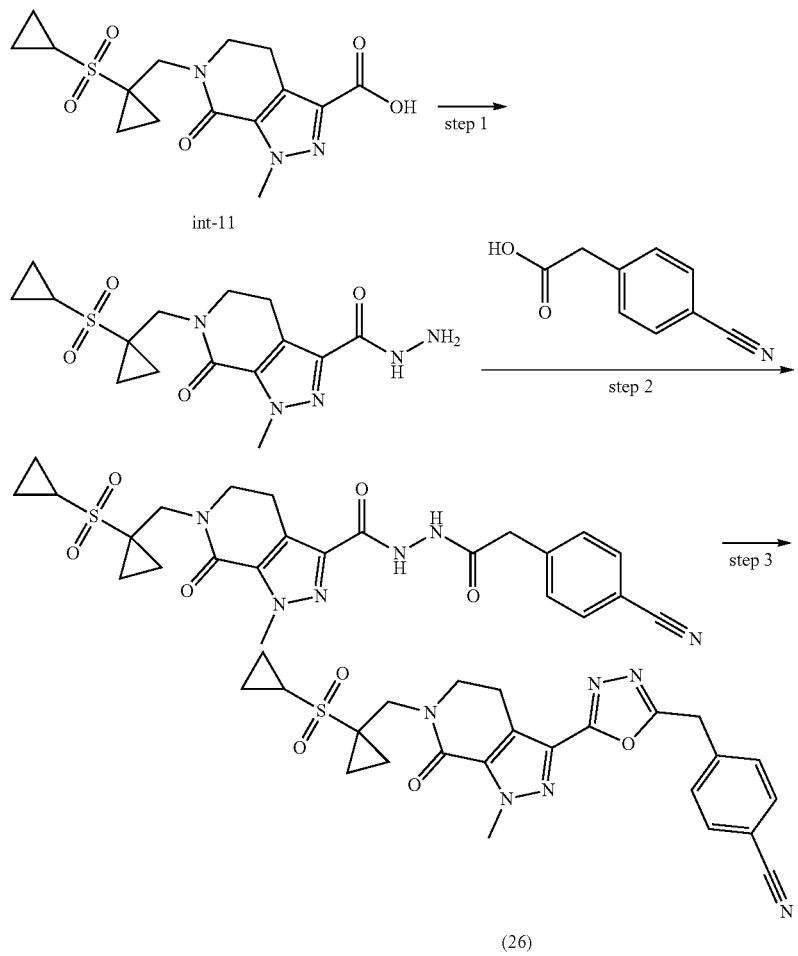

(26)

Step 1: 6-((1-(Cyclopropylsulfonyl)cyclopropyl)methyl)-1-methyl-7-oxo-4,5,6,7-tetrahydro-1H-pyrazolo[3,4-c]pyridine-3-carbohydrazide. To a solution of 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) (300 mg, 0.849 mmol, 1.0 equiv), HOBt (345 mg, 2.55 mmol, 3.0 equiv), EDCI (489 mg, 2.55 mmol, 3.0 equiv) in DMF (2 mL) was added a solution of NH$_2$NH$_2$—H$_2$O (425 mg, 8.49 mmol, 10 equiv) in DMF (1 mL) dropwise at 25° C. The mixture was stirred at 25° C. for 2 h, then it was filtered and purified by RP-HPLC to afford 6-((1-(cyclopropylsulfonyl)cyclopropyl)methyl)-1-methyl-7-oxo-4,5,6,7-tetrahydro-1H-pyrazolo[3,4-c]pyridine-3-carbohydrazide.

Step 2: N'-(2-(4-Cyanophenyl)acetyl)-6-((1-(cyclopropylsulfonyl)cyclopropyl)methyl)-1-methyl-7-oxo-4,5,6,7-tetrahydro-1H-pyrazolo[3,4-c]pyridine-3-carbohydrazide was obtained using the procedure detailed in step 1, except (int-11) was replaced with 2-(4-cyanophenyl)acetic acid and hydrazine was replaced with 6-((1-(Cyclopropylsulfonyl)cyclopropyl)methyl)-1-methyl-7-oxo-4,5,6,7-tetrahydro-1H-pyrazolo[3,4-c]pyridine-3-carbohydrazide. $^1$H NMR (400 MHz, CDCl$_3$) δ 9.02-8.85 (m, 1H), 8.26 (br s, 1H), 7.65 (m, 2H), 7.53-7.43 (m, 2H), 4.17 (s, 3H), 4.06 (s, 2H), 3.78-3.74 (m, 2H), 3.74 (s, 2H), 3.14 (m, 2H), 2.80-2.67 (m, 1H), 1.56-1.49 (m, 2H), 1.25-1.21 (m, 2H), 1.12-1.01 (m, 4H). MS (ESI): m/z 511.2 [M+H]$^+$.

Step 3: 4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,3,4-oxadiazol-2-yl)methyl)benzonitrile (26). To a solution of N'-(2-(4-Cyanophenyl)acetyl)-6-((1-(cyclopropylsulfonyl)cyclopropyl)methyl)-1-methyl-7-oxo-4,5,6,7-tetrahydro-1H-pyrazolo[3,4-c]pyridine-3-carbohydrazide (140 mg, 0.27 mmol, 1.0 equiv) and pyridine (100 µL, 1.1 mmol, 4.0 equiv) in DCM (1.5 mL) was added Tf$_2$O (140 µL, 0.82 mmol, 3.0 equiv) at rt. After stirring for 2 h at rt, the mixture was concentrated and purified by RP-HPLC to afford 4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,3,4-oxadiazol-2-yl)methyl)benzonitrile (26). $^1$H NMR (400 MHz, CDCl$_3$) δ 7.69-7.61 (m, 2H), 7.48 (d, J=8.4 Hz, 2H), 4.35 (s, 2H), 4.26 (s, 3H), 4.11-4.07 (m, 2H), 3.85-3.79 (m, 2H), 3.21 (m, 2H), 2.77 (m, 1H), 1.56-1.51 (m, 2H), 1.26-1.22 (m, 2H), 1.11-1.05 (m, 4H). MS (ESI): m/z 493.2 [M+H]$^+$.

Example 27

4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,2,4-oxadiazol-3-yl)methyl)benzonitrile (27)

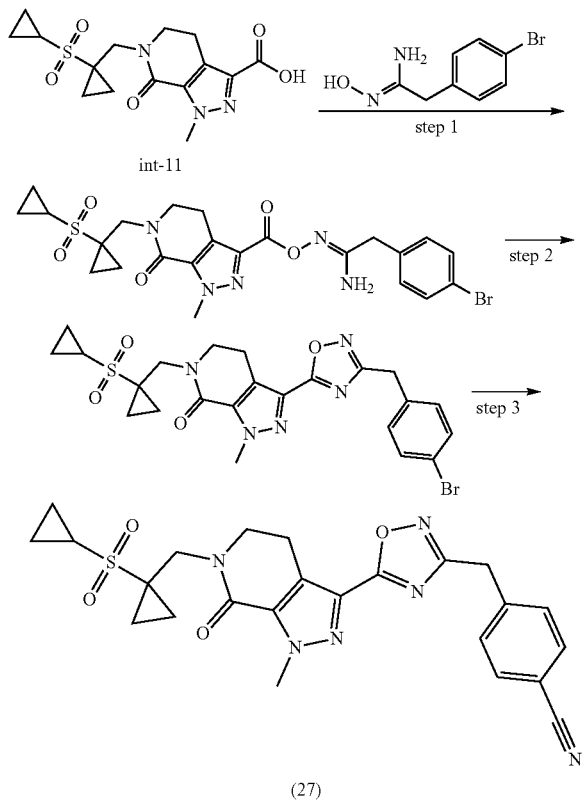

Step 1: (Z)-2-(4-Bromophenyl)-N'-((6-((1-(cyclopropylsulfonyl)cyclopropyl)methyl)-1-methyl-7-oxo-4,5,6,7-tetrahydro-1H-pyrazolo[3,4-c]pyridine-3-carbonyl)oxy)acetimidamide was obtained using the procedure detailed in step 1 of Example 26, except hydrazine was replaced with (Z)-2-(4-bromophenyl)-N'-hydroxyacetimidamide. $^1$H NMR (400 MHz, CDCl$_3$) δ 7.49 (d, J=8.4 Hz, 2H), 7.23 (d, J=8.4 Hz, 2H), 4.97-4.73 (m, 1H), 4.86 (br s, 1H), 4.23 (s, 3H), 4.08 (s, 2H), 3.78 (m, 2H), 3.61 (s, 2H), 3.19 (m, 2H), 2.77-2.68 (m, 1H), 1.54-1.52 (m, 2H), 1.27-1.23 (m, 2H), 1.12-1.04 (m, 4H). MS (ESI): m/z 564.2 [M+H]$^+$.

Step 2: 3-(3-(4-Bromobenzyl)-1,2,4-oxadiazol-5-yl)-6-((1-(cyclopropylsulfonyl)cyclopropyl)methyl)-1-methyl-5,6-dihydro-1H-pyrazolo[3,4-c]pyridin-7(4H)-one. A solution of (Z)-2-(4-Bromophenyl)-N'-((6-((1-(cyclopropylsulfonyl)cyclopropyl)methyl)-1-methyl-7-oxo-4,5,6,7-tetrahydro-1H-pyrazolo[3,4-c]pyridine-3-carbonyl)oxy)acetimidamide (244 mg, 446 µmol, 1.0 equiv) and Et$_3$N (223 µL, 2.23 mmol, 5.0 equiv) in dioxane (5 mL) was stirred at 80° C. for 12 h before it was diluted with H$_2$O (10 mL) and extracted with EtOAc (3×15 mL). The combined organic extracts were washed with brine (10 mL), dried with Na$_2$SO$_4$, filtered and concentrated. Purification by RP-HPLC afforded 3-(3-(4-Bromobenzyl)-1,2,4-oxadiazol-5-yl)-6-((1-(cyclopropylsulfonyl)cyclopropyl)methyl)-1-methyl-5,6-dihydro-1H-pyrazolo[3,4-c]pyridin-7(4H)-one. $^1$H NMR (400 MHz, CDCl$_3$) δ 7.45 (d, J=8.3 Hz, 2H), 7.25 (s, 2H), 4.28 (s, 3H), 4.13-4.06 (m, 4H), 3.82 (t, J=6.8 Hz, 2H), 3.19 (t, J=6.8 Hz, 2H), 2.79-2.68 (m, 1H), 1.56-1.52 (m, 2H), 1.29-1.22 (m, 3H), 1.12-1.04 (m, 4H). MS (ESI): m/z 546.0 [M+H]$^+$.

Step 3: 4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,2,4-oxadiazol-3-yl)methyl)benzonitrile (27). To a mixture of 3-(3-(4-bromobenzyl)-1,2,4-oxadiazol-5-yl)-6-((1-(cyclopropylsulfonyl)cyclopropyl)methyl)-1-methyl-5,6-dihydro-1H-pyrazolo[3,4-c]pyridin-7(4H)-one (50 mg, 0.092 mmol, 1.0 equiv) in dioxane (1 mL) and H$_2$O (0.2 mL) was added XPhos (15 mg, 0.036 mmol, 0.4 equiv), K$_4$Fe(CN)$_6$ (101 mg, 0.275 mmol, 3.0 equiv), K$_2$CO$_3$ (40 mg, 0.275 mmol, 3.0 equiv) and Pd(OAc)$_2$ (4 mg, 0.018 mmol, 0.2 equiv). The reaction mixture was degassed and placed under N$_2$ before it was stirred at 120° C. for 12 h. The mixture was filtered and purified by RP-HPLC to afford 4-((5-(6-((1-(cyclopropylsulfonyl)cyclopropyl)methyl)-1-methyl-7-oxo-4,5,6,7-tetrahydro-1H-pyrazolo[3,4-c]pyridin-3-yl)-1,2,4-oxadiazol-3-yl)methyl)benzonitrile (27). $^1$H NMR (400 MHz, CDCl$_3$) δ 7.63 (d, J=8.4 Hz, 2H), 7.50 (d, J=8.0 Hz, 2H), 4.28 (s, 3H), 4.21 (s, 2H), 4.09 (s, 2H), 3.83 (m, 2H), 3.19 (m, 2H), 2.78-2.70 (m, 1H), 1.55-1.53 (m, 2H), 1.28-1.22 (m, 2H), 1.13-1.05 (m, 4H). MS (ESI): m/z 493.2 [M+H]$^+$.

Example 28

4-((3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,2,4-oxadiazol-5-yl)methyl)benzonitrile (28)

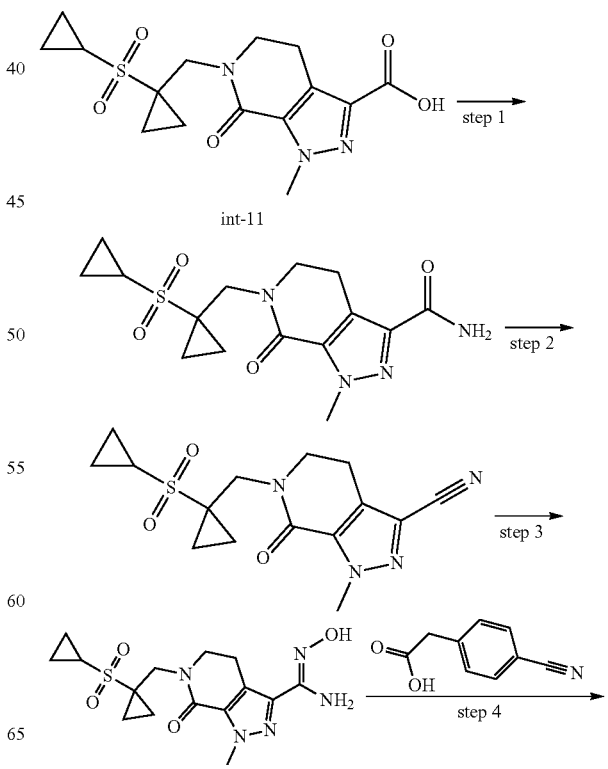

-continued

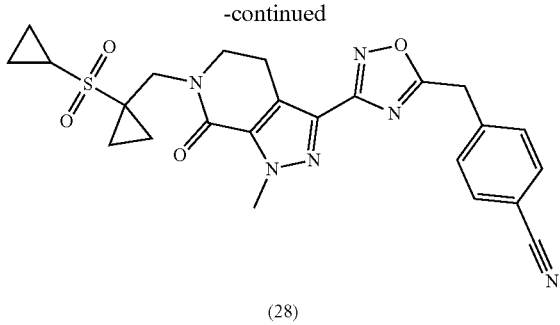

(28)

Step 1: 6-((1-(Cyclopropylsulfonyl)cyclopropyl)methyl)-1-methyl-7-oxo-4,5,6,7-tetrahydro-1H-pyrazolo[3,4-c]pyridine-3-carboxamide. To a solution of 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) (300 mg, 0.85 mmol, 1.0 equiv) and HATU (970 mg, 2.55 mmol, 3.0 equiv), DIEA (1097 mg, 8.49 mmol, 10.0 equiv) in DMF (3 mL) was added NH₄Cl (227 mg, 4.24 mmol, 5.0 equiv). The reaction mixture was stirred at 25° C. for 2 h, then it was filtered and purified by RP-HPLC to afford 6-((1-(cyclopropylsulfonyl)cyclopropyl)methyl)-1-methyl-7-oxo-4,5,6,7-tetrahydro-1H-pyrazolo[3,4-c]pyridine-3-carboxamide. $^1$H NMR (400 MHz, CDCl$_3$) δ 6.71 (br s, 1H), 5.42 (br s, 1H), 4.18 (s, 3H), 4.08 (s, 2H), 3.78-3.71 (m, 2H), 3.21-3.15 (m, 2H), 2.79-2.69 (m, 1H), 1.55-1.48 (m, 2H), 1.27-1.22 (m, 2H), 1.12-1.02 (m, 4H). MS (ESI): m/z 353.1 [M+H]$^+$.

Step 2: 6-((1-(Cyclopropylsulfonyl)cyclopropyl)methyl)-1-methyl-7-oxo-4,5,6,7-tetrahydro-1H-pyrazolo[3,4-c]pyridine-3-carbonitrile. To a solution of 6-((1-(cyclopropylsulfonyl)cyclopropyl)methyl)-1-methyl-7-oxo-4,5,6,7-tetrahydro-1H-pyrazolo[3,4-c]pyridine-3-carboxamide (220 mg, 0.62 mmol, 1.0 equiv) in THF (2.5 mL) was added pyridine (0.13 mL, 1.56 mmol, 2.5 equiv) and TFAA (0.1 mL, 1.56 mmol, 2.5 equiv). The reaction mixture was stirred at 25° C. for 12 h before it was concentrated. Purification by RP-HPLC afforded 6-((1-(cyclopropylsulfonyl)cyclopropyl)methyl)-1-methyl-7-oxo-4,5,6,7-tetrahydro-1H-pyrazolo[3,4-c]pyridine-3-carbonitrile. $^1$H NMR (400 MHz, CDCl$_3$) δ 4.22 (s, 3H), 4.12-3.98 (m, 2H), 3.81 (m, 2H), 2.99 (m, 2H), 2.74 (m, 1H), 1.55-1.51 (m, 2H), 1.28-1.21 (m, 2H), 1.13-1.01 (m, 4H). MS (ESI): m/z 335.1 [M+H]$^+$.

Step 3: (Z)-6-((1-(Cyclopropylsulfonyl)cyclopropyl)methyl)-N'-hydroxy-1-methyl-7-oxo-4,5,6,7-tetrahydro-1H-pyrazolo[3,4-c]pyridine-3-carboximidamide. To a solution of 6-((1-(cyclopropylsulfonyl)cyclopropyl)methyl)-1-methyl-7-oxo-4,5,6,7-tetrahydro-1H-pyrazolo[3,4-c]pyridine-3-carbonitrile (90 mg, 0.27 mmol, 1.0 equiv) in EtOH (1.5 mL) was added NH₂OH.HCl (28 mg, 0.32 mmol, 1.2 equiv) and Et₃N (82 mg, 0.81 mmol, 3.0 equiv). The reaction mixture was heated at 80° C. for 2 h before it was concentrated and purified by RP-HPLC to afford (Z)-6-((1-(cyclopropylsulfonyl)cyclopropyl)methyl)-N'-hydroxy-1-methyl-7-oxo-4,5,6,7-tetrahydro-1H-pyrazolo[3,4-c]pyridine-3-carboximidamid. $^1$H NMR (400 MHz, CDCl$_3$) δ 6.52 (br s, 1H), 5.17 (s, 2H), 4.16 (s, 3H), 4.08 (s, 2H), 3.72 (m, 2H), 3.02 (m, 2H), 2.75-2.66 (m, 1H), 1.53-1.49 (m, 2H), 1.27-1.22 (m, 2H), 1.11-1.04 (m, 4H). MS (ESI): m/z 368.1 [M+H]$^+$.

Step 4: 4-((3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,2,4-oxadiazol-5-yl)methyl)benzonitrile (28). To a solution of (Z)-6-((1-(Cyclopropylsulfonyl)cyclopropyl)methyl)-N'-hydroxy-1-methyl-7-oxo-4,5,6,7-tetrahydro-1H-pyrazolo[3,4-c]pyridine-3-carboximidamide (60 mg, 0.163 mmol, 1.0 equiv), CDI (79 mg, 0.490 mmol, 3.0 equiv) and Et₃N (66 mg, 0.653 mmol, 4.0 equiv) in DCE (0.6 mL) was added 2-(4-cyanophenyl)acetic acid (53 mg, 0.327 mmol, 2.0 equiv). The reaction mixture stirred at 25° C. for 2 h before it was heated at 80° C. for 4 h. The mixture was diluted with H₂O (5 mL) and extracted with CH₂Cl₂ (4×5 mL), then the combined organic extracts were dried with Na₂SO₄, filtered, and concentrated. The residue was purified by RP-HPLC to afford 4-((3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,2,4-oxadiazol-5-yl)methyl)benzonitrile (28). $^1$H NMR (400 MHz, CDCl$_3$) δ 7.66 (d, J=8.0 Hz, 2H), 7.50 (d, J=8.4 Hz, 2H), 4.38 (s, 2H), 4.27 (s, 3H), 4.10 (s, 2H), 3.81 (m, 2H), 3.15 (m, 2H), 2.77-2.69 (m, 1H), 1.54-1.52 (m, 2H), 1.28-1.23 (m, 2H), 1.13-1.06 (m, 4H). MS (ESI): m/z 493.2 [M+H]$^+$.

Example 29 and Example 30

4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-2H-tetrazol-2-yl)methyl)benzonitrile (29) and 4-((5-(6-((1-(cyclopropylsulfonyl)cyclopropyl)methyl)-1-methyl-7-oxo-4,5,6,7-tetrahydro-1H-pyrazolo[3,4-c]pyridin-3-yl)-1H-tetrazol-1-yl)methyl)benzonitrile (30)

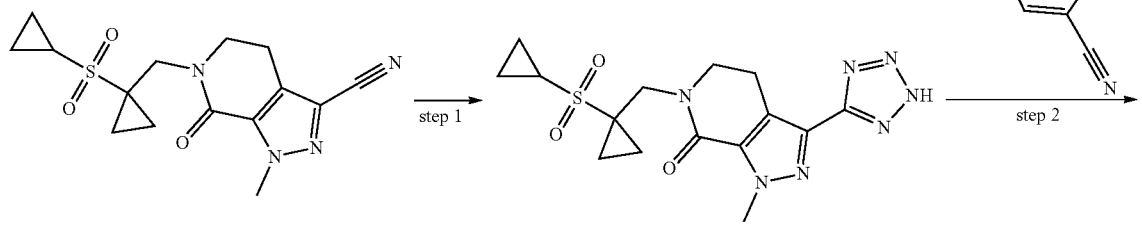

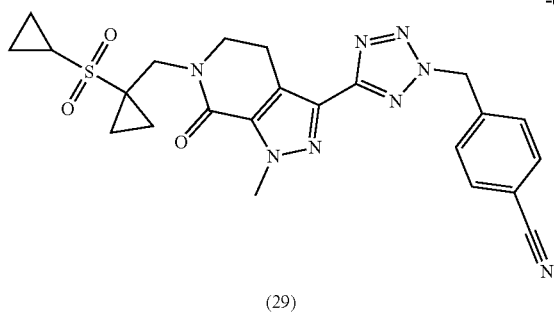

(29)

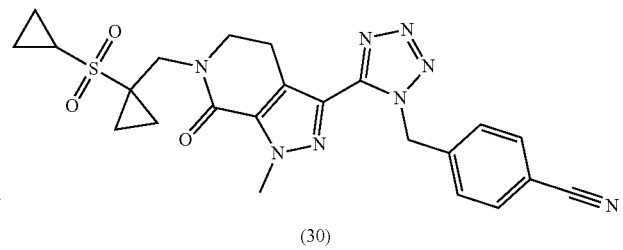

(30)

Step 1: 6-((1-(Cyclopropylsulfonyl)cyclopropyl)methyl)-1-methyl-3-(2H-tetrazol-5-yl)-1,4,5,6-tetrahydro-7H-pyrazolo[3,4-c]pyridin-7-one. A mixture of 6-((1-(cyclopropylsulfonyl)cyclopropyl)methyl)-1-methyl-7-oxo-4,5,6,7-tetrahydro-1H-pyrazolo[3,4-c]pyridine-3-carbonitrile (see step 2 of Example 28) (140 mg, 0.42 mmol, 1.0 equiv), NaN$_3$ (90 mg, 1.38 mmol, 3.3 equiv) and NH$_4$Cl (82 mg, 1.26 mmol, 3.0 equiv) in DMF (2 mL) was heated at 100° C. for 3 h. The reaction mixture was concentrated the residue was purified by RP-HPLC to afford 6-((1-(cyclopropylsulfonyl)cyclopropyl)methyl)-1-methyl-3-(2H-tetrazol-5-yl)-1,4,5,6-tetrahydro-7H-pyrazolo[3,4-c]pyridin-7-one. $^1$H NMR (400 MHz, CDCl$_3$) δ 3.92 (s, 3H), 3.87 (br s, 2H), 3.42 (br s, 2H), 2.90 (br s, 2H), 2.84 (s, 1H), 2.79-2.69 (m, 1H), 1.37-1.21 (m, 2H), 1.16-1.06 (m, 2H), 1.00 (br d, J=7.0 Hz, 2H), 0.88 (br s, 2H). MS (ESI): m/z 378.1 [M+H]$^+$.

Step 2: 4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-2H-tetrazol-2-yl)methyl)benzonitrile (29) and 4-((5-(6-((1-(cyclopropylsulfonyl)cyclopropyl)methyl)-1-methyl-7-oxo-4,5,6,7-tetrahydro-1H-pyrazolo[3,4-c]pyridin-3-yl)-1H-tetrazol-1-yl)methyl)benzonitrile (30). A mixture of 6-((1-(cyclopropylsulfonyl)cyclopropyl)methyl)-1-methyl-3-(2H-tetrazol-5-yl)-1,4,5,6-tetrahydro-7H-pyrazolo[3,4-c]pyridin-7-one (120 mg, 0.32 mmol, 1.0 equiv), 4-(bromomethyl)benzonitrile (125 mg, 0.64 mmol, 2.0 equiv) and K$_2$CO$_3$ (132 mg, 0.96 mmol, 3.0 equiv) in DMF (2 mL) was stirred at rt for 1 h. The reaction mixture was filtered and purified by RP-HPLC and SFC to afford:

4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-2H-tetrazol-2-yl)methyl)benzonitrile (29): $^1$H NMR (500 MHz, DMSO-d$_6$) δ 7.89 (d, J=8.0 Hz, 2H), 7.57 (d, J=7.9 Hz, 2H), 6.13 (s, 2H), 4.14 (s, 3H), 4.05 (s, 2H), 3.73 (t, J=6.9 Hz, 2H), 3.06 (t, J=6.7 Hz, 2H), 2.94 (s, 1H), 1.29 (s, 2H), 1.11 (s, 2H), 1.08-1.00 (m, 4H). MS (ESI): m/z 493.1 [M+H]$^+$.

and 4-((5-(6-((1-(cyclopropylsulfonyl)cyclopropyl)methyl)-1-methyl-7-oxo-4,5,6,7-tetrahydro-1H-pyrazolo[3,4-c]pyridin-3-yl)-1H-tetrazol-1-yl)methyl)benzonitrile (30): $^1$H NMR (500 MHz, DMSO-d$_6$) δ 7.83 (d, J=8.2 Hz, 2H), 7.50 (d, J=8.0 Hz, 2H), 6.15 (s, 2H), 4.17 (s, 3H), 4.06 (s, 2H), 3.76 (t, J=6.8 Hz, 2H), 3.12 (t, J=6.8 Hz, 2H), 2.95 (ddd, J=12.7, 7.8, 4.9 Hz, 1H), 1.32-1.26 (m, 2H), 1.15-1.09 (m, 2H), 1.09-0.98 (m, 4H). MS (ESI): m/z 493.2 [M+H]$^+$.

Example 31

4-(3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (31)

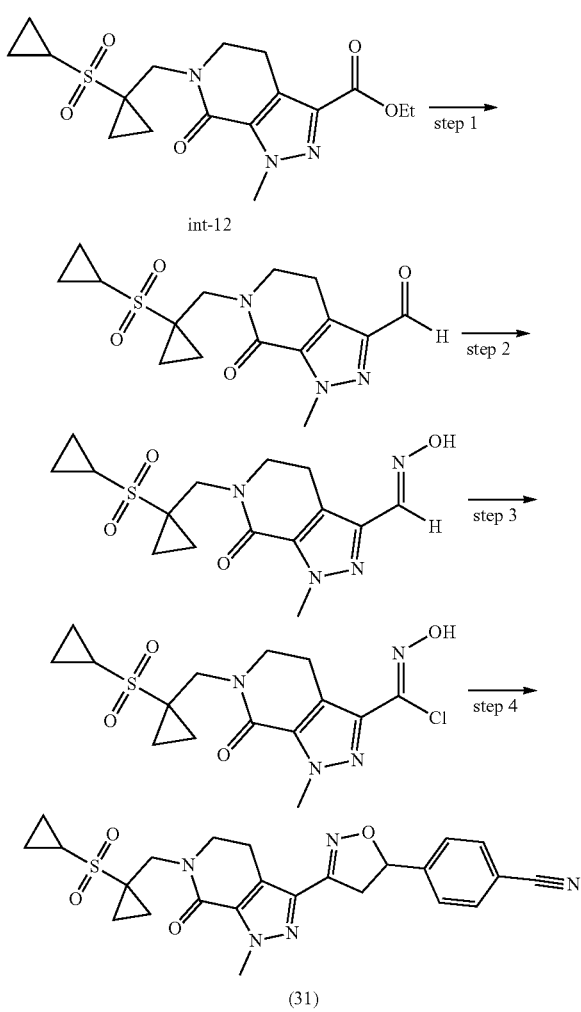

(31)

Step 1: 6-((1-(Cyclopropylsulfonyl)cyclopropyl)methyl)-1-methyl-7-oxo-4,5,6,7-tetrahydro-1H-pyrazolo[3,4-c]pyridine-3-carbaldehyde. A solution of ethyl 6-((1-(cyclopropylsulfonyl)cyclopropyl)methyl)-1-methyl-7-oxo-4,5,6,7- tetrahydro-1H-pyrazolo[3,4-c]pyridine-3-carboxylate (int-12) (600 mg, 1.57 mmol, 1.0 equiv) in THF (10 mL) was cooled to −70° C. before DIBAL-H (1.0 M in THF, 4.72 mL, 4.72 mmol, 3.0 equiv) was added dropwise. After 2 h at −70° C., MeOH (10 mL) was added and the reaction mixture was warmed to rt. The solution was diluted with H$_2$O (20 mL) and extracted with EtOAc (3×20 mL). The combined organic extracts were dried with Na$_2$SO$_4$, filtered, and concentrated to provide crude 4-(3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile. MS (ESI): m/z 338.3 [M+H]$^+$.

Step 2: (E)-6-((1-(Cyclopropylsulfonyl)cyclopropyl)methyl)-1-methyl-7-oxo-4,5,6,7-tetrahydro-1H-pyrazolo[3,4-c]pyridine-3-carbaldehyde oxime. To a solution of NH$_2$OH.HCl (151 mg, 1.42 mmol, 1.2 equiv) in MeOH (5 mL) was added Na$_2$CO$_3$ (302 mg, 2.85 mmol, 2.4 equiv), followed by a solution of 6-((1-(cyclopropylsulfonyl)cyclopropyl)methyl)-1-methyl-7-oxo-4,5,6,7-tetrahydro-1H-pyrazolo[3,4-c]pyridine-3-carbaldehyde (400 mg, 1.19 mmol, 1.0 equiv) in MeOH (10 mL). The mixture was stirred at 20° C. for 3 h before it was poured into H$_2$O (5 mL) and extracted with EtOAc (3×15 mL). The combined organic extracts were dried with Na$_2$SO$_4$, filtered, and concentrated to provide crude (E)-6-((1-(Cyclopropylsulfonyl)cyclopropyl)methyl)-1-methyl-7-oxo-4,5,6,7-tetrahydro-1H-pyrazolo[3,4-c]pyridine-3-carbaldehyde oxime. MS (ESI): m/z 353.3 [M+H]$^+$.

Step 3: (Z)-6-((1-(Cyclopropylsulfonyl)cyclopropyl)methyl)-N-hydroxy-1-methyl-7-oxo-4,5,6,7-tetrahydro-1H-pyrazolo[3,4-c]pyridine-3-carbimidoyl chloride. To a solution of (E)-6-((1-(Cyclopropylsulfonyl)cyclopropyl)methyl)-1-methyl-7-oxo-4,5,6,7-tetrahydro-1H-pyrazolo[3,4-c]pyridine-3-carbaldehyde oxime (400 mg, 1.14 mmol, 1.0 equiv) in DMF (8 mL), NCS (159 mg, 1.19 mmol, 1.0 equiv) was added portion wise. The mixture was stirred at 20° C. for 1 h before it was poured into H$_2$O (8 mL) and extracted with EtOAc (3×10 mL). The combined organic extracts were dried with Na$_2$SO$_4$, filtered, and concentrated to afford (Z)-6-((1-(Cyclopropylsulfonyl)cyclopropyl)methyl)-N-hydroxy-1-methyl-7-oxo-4,5,6,7-tetrahydro-1H-pyrazolo[3,4-c]pyridine-3-carbimidoyl chloride. MS (ESI): m/z 387.0 [M+H]$^+$.

Step 4: 4-(3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (31). To a solution of (Z)-6-((1-(Cyclopropylsulfonyl)cyclopropyl)methyl)-N-hydroxy-1-methyl-7-oxo-4,5,6,7-tetrahydro-1H-pyrazolo[3,4-c]pyridine-3-carbimidoyl chloride (400 mg, 1.03 mmol, 1.0 equiv) and 4-vinylbenzonitrile (200 mg, 1.55 mmol, 1.5 equiv) in THF (6 mL) was added Et$_3$N (136 mg, 1.34 mmol, 1.3 equiv). The mixture was stirred at 60° C. for 4 h before saturated NH$_4$Cl (5 mL) was added and the mixture was extracted with EtOAc (3×5 mL). The combined organic extracts were dried with Na$_2$SO$_4$, filtered, and concentrated. The residue was purified by column chromatography (SiO$_2$, 10-100% EtOAc/petroleum ether) to afford 4-(3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (31). $^1$H NMR (400 MHz, CDCl$_3$) δ 7.77-7.60 (m, 2H), 7.51-7.42 (m, 2H), 5.74-5.70 (m, 1H), 4.15 (s, 3H), 4.10-4.05 (m, 2H), 3.90 (dd, J=11.1, 17.2 Hz, 1H), 3.77 (t, J=6.8 Hz, 2H), 3.42-3.40 (m, 1H), 3.13-3.09 (m, 2H), 2.75-2.73 (m, 1H), 1.55 (s, 1H), 1.54-1.47 (m, 2H), 1.27-1.20 (m, 3H), 1.12 (br s, 1H), 1.12-1.01 (m, 3H). MS (ESI): m/z 480.1 [M+H]$^+$.

Example 32 and Example 33

(R)-4-(3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (32) and (S)-4-(3-(6-((1-(cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (33)

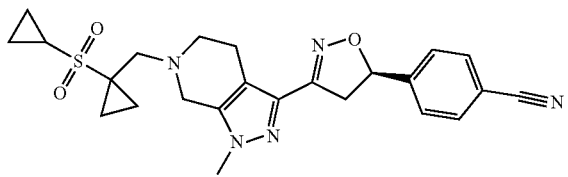

(32)

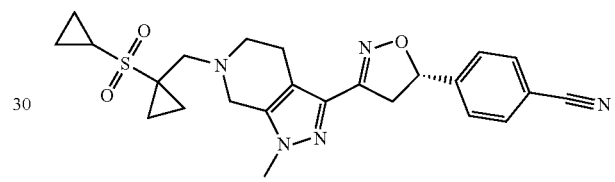

(33)

(R)-4-(3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (32) and (S)-4-(3-(6-((1-(cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (33) were obtained by chiral SFC of 4-(3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (31). (OJ-3_MeOH+ACN (DEA)_40_3 mL-35T Column: Chiralcel OJ-3 50×4.6 mm I.D., 3 um Mobile phase: 40% methanol+ACN (0.05% DEA) in CO$_2$ Flow rate: 3 mL/min Wavelength: 220 nm). (R)-4-(3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (32): Rt=1.31 min, >99% ee, $^1$H NMR (400 MHz, CDCl$_3$) δ 7.68 (d, J=8.4, 2H), 7.50 (d, J=8.4 Hz, 2H), 5.75-5.71 (m, 1H), 4.16 (s, 3H), 4.09 (s, 2H), 3.91-3.86 (m, 1H), 3.78 (t, J=6.8 Hz, 2H), 3.43-3.90 (m, 1H), 3.12 (t, J=6.8 Hz, 2H), 2.76-2.73 (m, 1H), 1.56-1.49 (m, 2H), 1.29-1.21 (m, 2H), 1.13-1.03 (m, 4H). MS (ESI): m/z 480.1 [M+H]$^+$.

(S)-4-(3-(6-((1-(cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (33): Rt=0.993 min, 99% ee, $^1$H NMR (400 MHz, CDCl$_3$) δ 7.67 (d, J=8.2 Hz, 2H), 7.50 (d, J=8.2 Hz, 2H), 5.75-5.70 (m, 1H), 4.16 (s, 3H), 4.09 (s, 2H), 3.93-3.86 (m, 1H), 3.78 (t, J=6.8 Hz, 2H), 3.48-3.33 (m, 1H), 3.12 (t, J=6.8 Hz, 2H), 2.81-2.70 (m, 1H), 1.58-1.48 (m, 2H), 1.29-1.20 (m, 2H), 1.12-1.00 (m, 4H). MS (ESI): m/z 480.1 [M+H]$^+$.

Example 34

4-((3-(6-((1-(Cyclopropylsulfonyl)cyclopropyl)methyl)-1-methyl-7-oxo-4,5,6,7-tetrahydro-1H-pyrazolo[3,4-c]pyridin-3-yl)isoxazol-5-yl)methyl)benzonitrile (34)

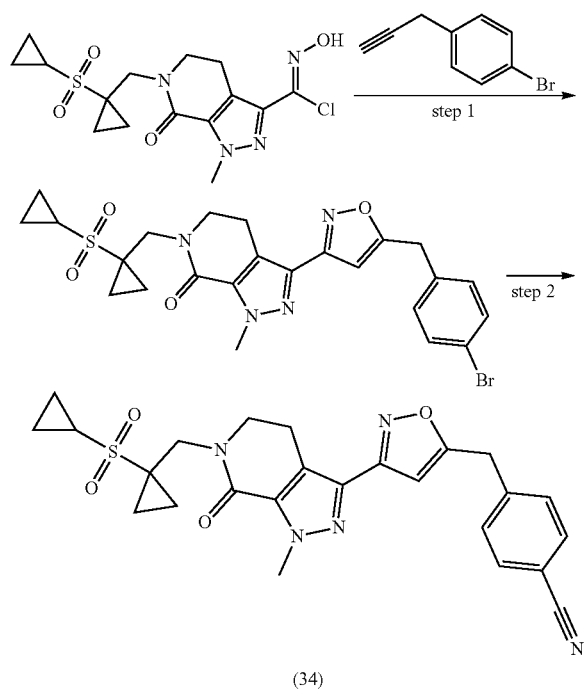

(34)

Step 1: 3-(5-(4-Bromobenzyl)isoxazol-3-yl)-6-((1-(cyclopropylsulfonyl)cyclopropyl)methyl)-1-methyl-5,6-dihydro-1H-pyrazolo[3,4-c]pyridin-7(4H)-one. A mixture of (Z)-6-((1-(cyclopropylsulfonyl)cyclopropyl)methyl)-N-hydroxy-1-methyl-7-oxo-4,5,6,7-tetrahydro-1H-pyrazolo[3,4-c]pyridine-3-carbimidoyl chloride (see step 3 of Example 31) (500 mg, 1.29 mmol, 1.0 equiv), 1-bromo-4-(prop-2-yn-1-yl)benzene (378 mg, 1.94 mmol, 1.5 equiv) and i-Pr$_2$NEt (0.28 mL, 1.68 mmol, 1.3 equiv) in THF (6 mL) was stirred at 60° C. for 4 h. The mixture was diluted with saturated NH$_4$Cl (5 mL) and extracted with EtOAc (3×15 mL), then the combined organic extracts were dried with Na$_2$SO$_4$, filtered, and concentrated. The residue was purified by column chromatography (SiO$_2$, 10-100% EtOAc/petroleum ether) to afford 3-(5-(4-Bromobenzyl)isoxazol-3-yl)-6-((1-(cyclopropylsulfonyl)cyclopropyl)methyl)-1-methyl-5,6-dihydro-1H-pyrazolo[3,4-c]pyridin-7(4H)-one. MS (ESI): m/z 547.1 [M+H]$^+$.

Step 2: 4-((3-(6-((1-(Cyclopropylsulfonyl)cyclopropyl)methyl)-1-methyl-7-oxo-4,5,6,7-tetrahydro-1H-pyrazolo[3,4-c]pyridin-3-yl)isoxazol-5-yl)methyl)benzonitrile (34) was obtained using the procedure described in step 3 of Example 27, except 3-(3-(4-bromobenzyl)-1,2,4-oxadiazol-5-yl)-6-((1-(cyclopropylsulfonyl)cyclopropyl)methyl)-1-methyl-5,6-dihydro-1H-pyrazolo[3,4-c]pyridin-7(4H)-one was replaced with 3-(5-(4-Bromobenzyl)isoxazol-3-yl)-6-((1-(cyclopropylsulfonyl)cyclopropyl)methyl)-1-methyl-5,6-dihydro-1H-pyrazolo[3,4-c]pyridin-7(4H)-one. $^1$H NMR (400 MHz, CDCl$_3$) δ 7.65 (d, J=8.2 Hz, 2H), 7.41 (d, J=8.2 Hz, 2H), 6.41 (s, 1H), 4.20 (s, 5H), 4.11-4.05 (m, 2H), 3.82-3.73 (m, 2H), 3.15 (t, J=6.8 Hz, 2H), 2.76-2.69 (m, 1H), 1.55-1.46 (m, 2H), 1.29-1.17 (m, 2H), 1.14-1.02 (m, 4H). MS (ESI): m/z 492.4 [M+H]$^+$.

Example 35

4-((4-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1H-1,2,3-triazol-1-yl)methyl)benzonitrile (35)

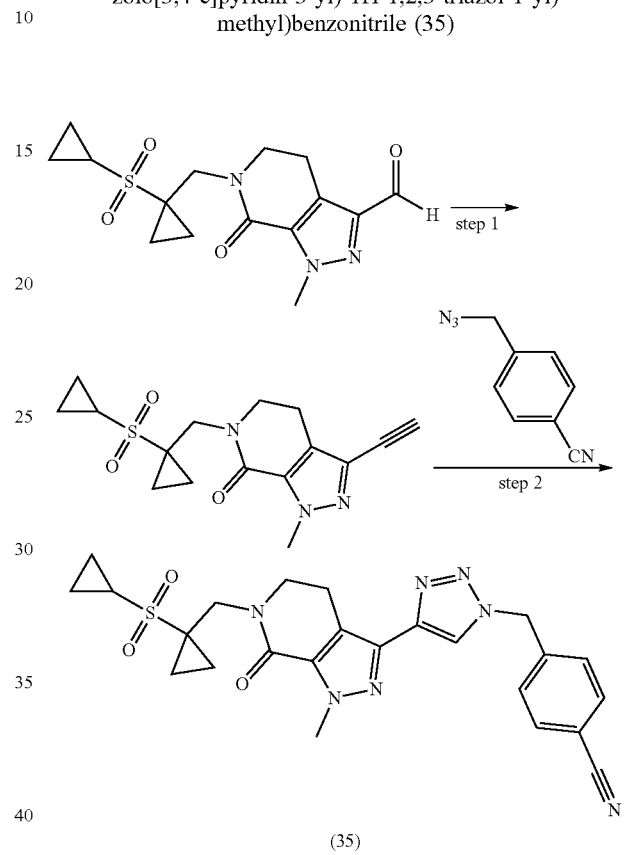

(35)

Step 1: 6-((1-(Cyclopropylsulfonyl)cyclopropyl)methyl)-3-ethynyl-1-methyl-5,6-dihydro-1H-pyrazolo[3,4-c]pyridin-7(4H)-one. To a solution of 6-((1-(cyclopropylsulfonyl)cyclopropyl)methyl)-1-methyl-7-oxo-4,5,6,7-tetrahydro-1H-pyrazolo[3,4-c]pyridine-3-carbaldehyde (see step 1 of Example 31) (450 mg, 1.33 mmol, 1.0 equiv) and dimethyl (1-diazo-2-oxopropyl)phosphonate (384 mg, 2.00 mmol, 1.5 equiv) in MeOH (10 ml) was added K$_2$CO$_3$ (369 mg, 2.67 mmol) at 20° C. The mixture was stirred at 20° C. for 12 h before it was poured into H$_2$O (10 mL) and extracted with EtOAc (3×10 mL). The combined organic extracts were washed with brine, dried with Na$_2$SO$_4$, filtered and concentrated to provide 6-((1-(cyclopropylsulfonyl)cyclopropyl)methyl)-3-ethynyl-1-methyl-5,6-dihydro-1H-pyrazolo[3,4-c]pyridin-7(4H)-one. TLC R$_f$=0.5 (50% EtOAc/petroleum ether). MS (ESI): m/z 334 [M+H]$^+$.

Step 2: 4-((4-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1H-1,2,3-triazol-1-yl)methyl)benzonitrile (35). A mixture of 6-((1-(cyclopropylsulfonyl)cyclopropyl)methyl)-3-ethynyl-1-methyl-5,6-dihydro-1H-pyrazolo[3,4-c]pyridin-7(4H)-one (350 mg, 1.05 mmol, 1.0 equiv), 4-(azidomethyl)benzonitrile (332 mg, 2.10 mmol, 2.0 equiv), CuSO$_4$.5H$_2$O (39 mg, 0.13 mmol, 0.12 equiv) and sodium ascorbate (42 mg, 0.21 mmol, 0.2 equiv) in DMF (6 mL) and H₂O (3 mL) was stirred at 80° C. for 5 h. The reaction mixture was cooled and diluted with water (10 mL) before the aqueous phase was extracted with EtOAc (3×10 mL). The combined organic extracts were washed with brine (5 mL), dried with Na₂SO₄, filtered, and concentrated. The residue was purified by RP-HPLC to give 4-((4-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1H-1,2,3-triazol-1-yl)methyl)benzonitrile (35). ¹H NMR (400 MHz, DMSO-d₆) δ 8.56 (s, 1H), 7.87 (d, J=8.2 Hz, 2H), 7.50 (d, J=8.2 Hz, 2H), 5.82-5.71 (m, 2H), 4.09 (s, 3H), 4.05 (s, 2H), 3.73 (t, J=6.8 Hz, 2H), 3.06 (t, J=6.8 Hz, 2H), 3.01-2.90 (m, 1H), 1.35-1.26 (m, 2H), 1.15-1.09 (m, 2H), 1.08-0.98 (m, 4H). MS (ESI): m/z 492.2 [M+H]⁺.

Example 36

6-((1-(Cyclopropylsulfonyl)cyclopropyl)methyl)-3-(1-((4,4-difluorocyclohexyl)methyl)-1H-1,2,3-triazol-4-yl)-1-methyl-5,6-dihydro-1H-pyrazolo[3,4-c]pyridin-7(4H)-one (36)

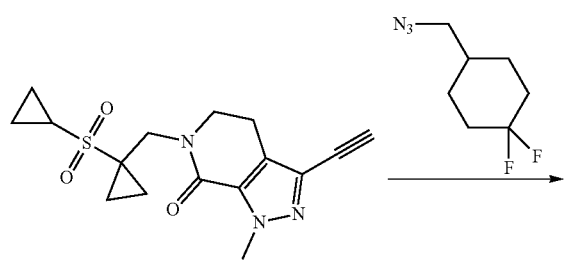

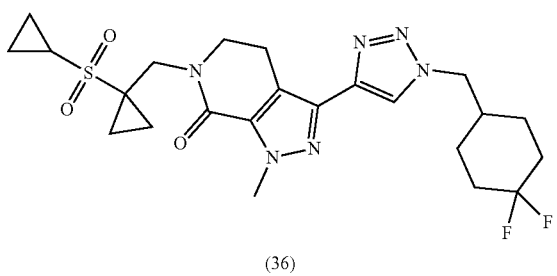

(36)

6-((1-(Cyclopropylsulfonyl)cyclopropyl)methyl)-3-(1-((4,4-difluorocyclohexyl)methyl)-1H-1,2,3-triazol-4-yl)-1-methyl-5,6-dihydro-1H-pyrazolo[3,4-c]pyridin-7(4H)-one (36) was obtained using the procedure described in step 2 of Example 35, except 4-(azidomethyl)benzonitrile was replaced with 4-(azidomethyl)-1,1-difluorocyclohexane. ¹H NMR (400 MHz, DMSO-d₆) δ 7.86 (s, 1H), 4.30 (d, J=7.2 Hz, 2H), 4.20 (s, 3H), 4.11 (s, 2H), 3.80 (t, J=6.8 Hz, 2H), 3.28 (t, J=6.8 Hz, 2H), 2.78-2.67 (m, 1H), 2.20-2.05 (m, 3H), 1.83-1.70 (m, 3H), 1.55-1.48 (m, 2H), 1.47-1.35 (m, 2H), 1.30-1.21 (m, 2H), 1.15-1.04 (m, 4H). MS (ESI): m/z 509.4 [M+H]⁺.

Example 37

N-(4-Chlorophenoxy)-1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxamide (37)

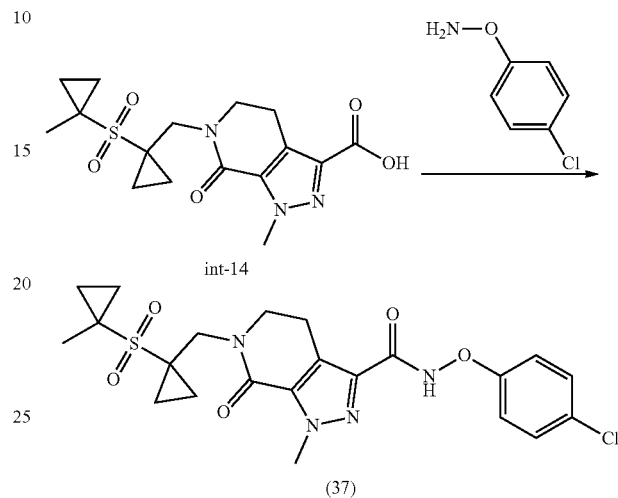

N-(4-Chlorophenoxy)-1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxamide (37) was obtained using the procedure described in step 1 of Example 28, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylic acid (int-14) and NH₄Cl was replaced with O-(4-chlorophenyl)hydroxylamine. ¹H NMR (400 MHz, CDCl₃) δ 9.57 (s, 1H), 7.28 (s, 2H), 7.26-7.25 (m, 2H), 7.11-7.08 (m, 2H), 4.20 (s, 3H), 4.13 (s, 2H), 3.72 (m, 2H), 3.17 (m, 2H), 1.62 (s, 3H), 1.55-1.52 (m, 2H), 1.47 (m, 2H), 1.05-1.03 (m, 2H), 0.88-0.86 (m, 2H). MS (ESI): m/z 493.1 [M+H]⁺.

Example 38

N-(4-Cyanobenzyl)-6-((1-(((difluoromethyl)sulfonyl)cyclopropyl)methyl)-1-methyl-7-oxo-4,5,6,7-tetrahydro-1H-pyrazolo[3,4-c]pyridine-3-carboxamide (38)

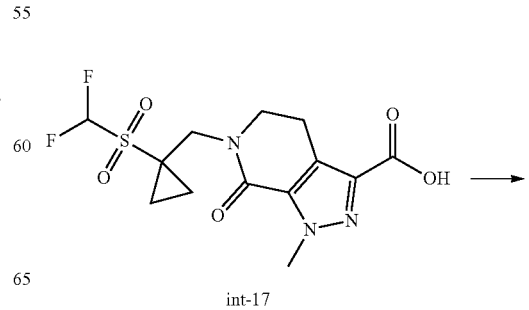

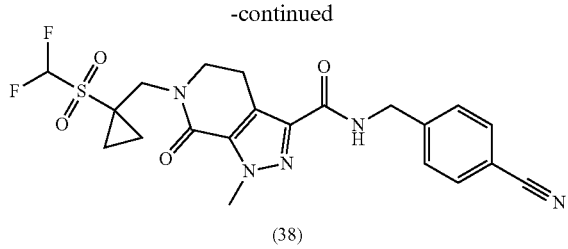

(38)

N-(4-Cyanobenzyl)-6-((1-((difluoromethyl)sulfonyl)cyclopropyl)methyl)-1-methyl-7-oxo-4,5,6,7-tetrahydro-1H-pyrazolo[3,4-c]pyridine-3-carboxamide (38) was obtained using the procedure described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((Difluoromethyl)sulfonyl)cyclopropyl)methyl)-1-methyl-7-oxo-4,5,6,7-tetrahydro-1H-pyrazolo[3,4-c]pyridine-3-carboxylic acid (int-17). $^1$H NMR (400 MHz, CDCl$_3$) δ 7.64 (m, 2H), 7.46 (m, 2H), 7.29 (m, 1H), 6.66-6.34 (m, 1H), 4.66 (m, 2H), 4.16 (s, 3H), 4.01 (s, 2H), 3.76 (m, 2H), 3.21 (t, J=6.8 Hz, 2H), 1.74-1.66 (m, 2H), 1.36-1.27 (m, 2H). MS (ESI): m/z 478.1 [M+H]$^+$.

Example 39

N-(4-Chlorobenzyl)-6-((1-((difluoromethyl)sulfonyl)cyclopropyl)methyl)-1-methyl-7-oxo-4,5,6,7-tetrahydro-1H-pyrazolo[3,4-c]pyridine-3-carboxamide (39)

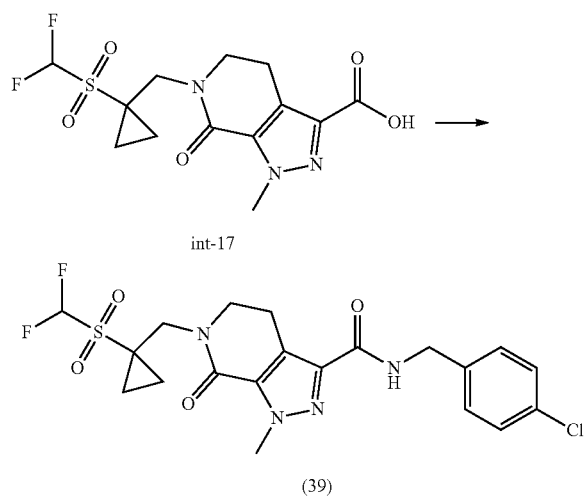

N-(4-Chlorobenzyl)-6-((1-((difluoromethyl)sulfonyl)cyclopropyl)methyl)-1-methyl-7-oxo-4,5,6,7-tetrahydro-1H-pyrazolo[3,4-c]pyridine-3-carboxamide (39) was obtained using the procedure described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((Difluoromethyl)sulfonyl)cyclopropyl)methyl)-1-methyl-7-oxo-4,5,6,7-tetrahydro-1H-pyrazolo[3,4-c]pyridine-3-carboxylic acid (int-17) and 4-(aminomethyl)benzonitrile hydrochloride was replaced with (4-chlorophenyl)methanamine. $^1$H NMR (400 MHz, CDCl$_3$) δ 7.34-7.28 (m, 4H), 7.18 (m, 1H), 6.64-6.35 (m, 1H), 4.57 (m, 2H), 4.15 (s, 3H), 4.01 (s, 2H), 3.75 (t, J=6.8 Hz, 2H), 3.22 (t, J=6.8 Hz, 2H), 1.72-1.66 (m, 2H), 1.34-1.28 (m, 2H). MS (ESI): m/z 487.2 [M+H]$^+$.

Example 40

N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide (40)

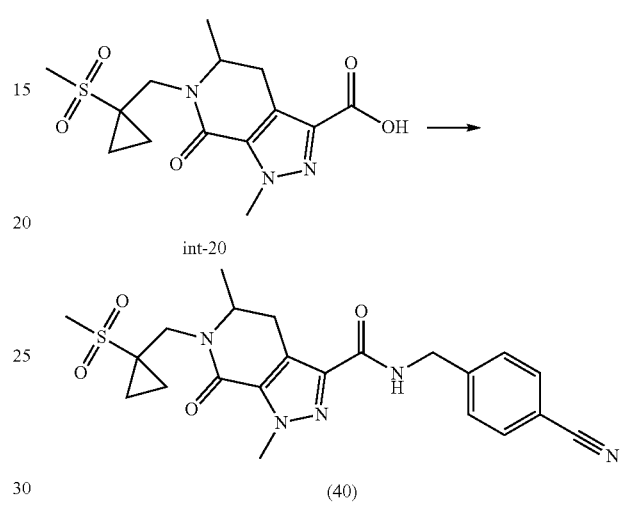

(40)

N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide (40) was obtained using the procedure described in step 1 of Example 28, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 1,5-dimethyl-6-((1-(methylsulfonyl)cyclopropyl)methyl)-7-oxo-4,5,6,7-tetrahydro-1H-pyrazolo[3,4-c]pyridine-3-carboxylic acid (int-20). MS (ESI): m/z 456.3 [M+H]$^+$ Example 41 and Example 42

(R)- or (S)—N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide (41) and (R)- or (S)—N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide (42)

(41)

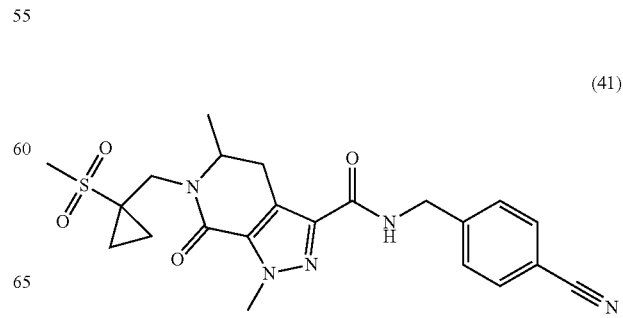

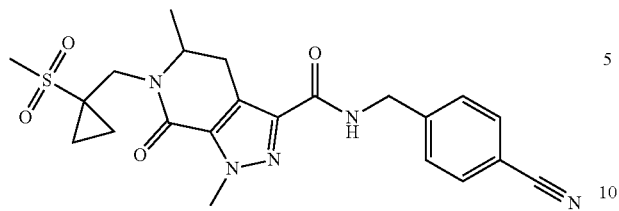

(42)

(R)- or (S)—N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide (41) and (R)- or (S)—N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide (42) were obtained by SFC separation of N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide (40). Unless otherwise indicated, examples indicate relative stereochemistry.

SFC: Chiralpak AD-3, 5-40% (MeOH+0.05% Et$_2$NH), 3 mL/min (R)- or (S)—N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide (41): Peak 1: SFC Rt=3.033 min, AD-3S_3_5_40_3ML_T35. $^1$H NMR (400 MHz, CDCl$_3$) δ 7.64 (d, J=8.4 Hz, 2H), 7.46 (d, J=8.8 Hz, 2H), 7.30 (t, J=6.4 Hz, 1H), 4.66 (d, J=6.4 Hz, 2H), 4.44 (d, J=14.8 Hz, 1H), 4.18 (s, 3H), 4.13-4.08 (m, 1H), 3.45 (d, J=14.4 Hz, 1H), 3.28-3.25 (m, 2H), 3.00 (s, 3H), 1.57-1.54 (m, 1H), 1.52-1.46 (m, 1H), 1.28-1.25 (m, 1H), 1.23 (d, J=6.8 Hz, 3H), 1.03-0.97 (m, 1H). MS (ESI): m/z 456.3 [M+H]$^+$.

(R)- or (S)—N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide (42): Peak 2: SFC Rt=4.134 min, AD-3S_3_5_40_3ML_T35. $^1$H NMR (400 MHz, CDCl$_3$) δ 7.64 (d, J=8.4 Hz, 2H), 7.46 (d, J=8.8 Hz, 2H), 7.30 (t, J=6.4 Hz, 1H), 4.66 (d, J=6.4 Hz, 2H), 4.44 (d, J=14.8 Hz, 1H), 4.18 (s, 3H), 4.13-4.08 (m, 1H), 3.45 (d, J=14.4 Hz, 1H), 3.28-3.25 (m, 2H), 3.00 (s, 3H), 1.57-1.54 (m, 1H), 1.52-1.46 (m, 1H), 1.28-1.25 (m, 1H), 1.23 (d, J=6.8 Hz, 3H), 1.01-0.97 (m, 1H). MS (ESI): m/z 456.4 [M+H]$^+$.

Example 43

N-(4-Cyanobenzyl)-1-cyclopropyl-6-((1-(cyclopropylsulfonyl)cyclopropyl)methyl)-7-oxo-4,5,6,7-tetrahydro-1H-pyrazolo[3,4-c]pyridine-3-carboxamide (43)

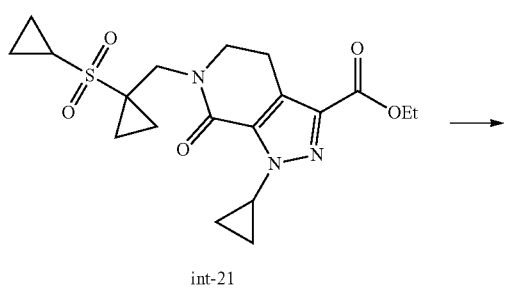

int-21

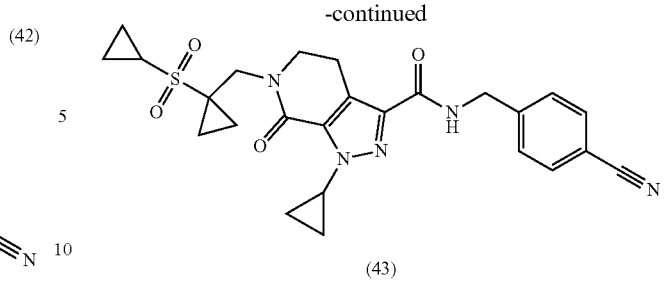

(43)

N-(4-Cyanobenzyl)-1-cyclopropyl-6-((1-(cyclopropylsulfonyl)cyclopropyl)methyl)-7-oxo-4,5,6,7-tetrahydro-1H-pyrazolo[3,4-c]pyridine-3-carboxamide (43) was obtained using the procedure described in Example 1, except ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6) was replaced with ethyl 1-cyclopropyl-6-((1-(cyclopropylsulfonyl)cyclopropyl)methyl)-7-oxo-4,5,6,7-tetrahydro-1H-pyrazolo[3,4-c]pyridine-3-carboxylate (int-21). TLC R$_f$=0.2 (50% EtOAc/petroleum ether). $^1$H NMR (400 MHz, CDCl$_3$) δ 7.63 (d, J=8.4 Hz, 2H), 7.44 (d, J=8.0 Hz, 2H), 7.24-7.21 (m, 1H), 4.64 (d, J=6.4 Hz, 2H), 4.57-4.52 (m, 1H), 4.09 (s, 2H), 3.75-3.72 (m, 2H), 3.20-3.17 (m, 2H), 2.78-2.74 (m, 1H), 1.53-1.50 (m, 2H), 1.28-1.22 (m, 6H), 1.10-1.03 (m, 6H). MS (ESI): m/z 494.2 [M+H]$^+$.

Example 44

N-(4-Chlorobenzyl)-6-((1-(cyclopropylsulfonyl)cyclopropyl)methyl)-7-oxo-4,5,6,7-tetrahydro-1H-pyrazolo[3,4-c]pyridine-3-carboxamide (44)

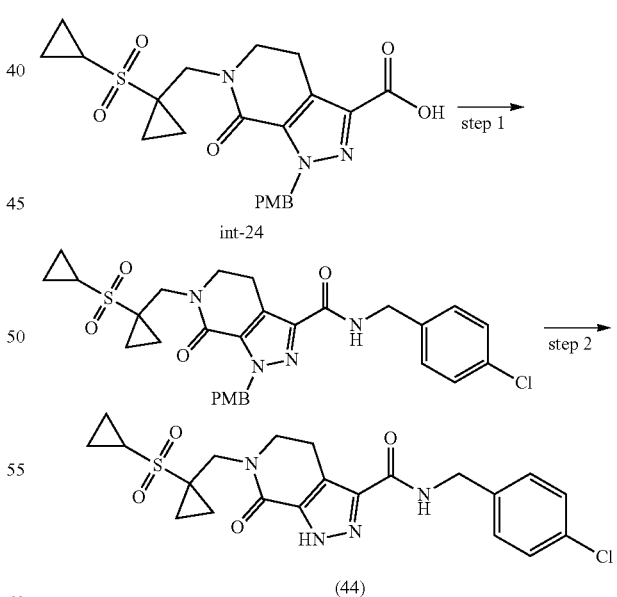

Step 1: N-(4-Chlorobenzyl)-6-((1-(cyclopropylsulfonyl)cyclopropyl)methyl)-1-(4-methoxybenzyl)-7-oxo-4,5,6,7-tetrahydro-1H-pyrazolo[3,4-c]pyridine-3-carboxamide was obtained using the procedure described in step 1 of Example 28, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-(Cyclopropylsulfonyl)cyclopropyl)methyl)-1-(4-methoxybenzyl)-7-oxo-4,5,6,7-tetrahydro-1H-pyrazolo[3,4-c]pyridine-3-carboxylic acid (int-24) and NH₄Cl was replaced with (4-chlorophenyl)methanamine. MS (ESI): m/z 583.0 [M+H]⁺.

Step 2: A solution of N-(4-chlorobenzyl)-6-((1-(cyclopropylsulfonyl)cyclopropyl)methyl)-1-(4-methoxybenzyl)-7-oxo-4,5,6,7-tetrahydro-1H-pyrazolo[3,4-c]pyridine-3-carboxamide (110 mg, 0.19 mmol, 1.0 equiv) in TFA (2 mL) was stirred at 80° C. for 2 h before it was concentrated. The residue was purified by RP-HPLC to afford N-(4-Chlorobenzyl)-6-((1-(cyclopropylsulfonyl)cyclopropyl)methyl)-7-oxo-4,5,6,7-tetrahydro-1H-pyrazolo[3,4-c]pyridine-3-carboxamide (44). ¹H NMR (400 MHz, DMSO-d₆) δ 8.75 (br s, 1H), 7.41-7.24 (m, 4H), 4.38 (br d, J=6.1 Hz, 2H), 4.02 (s, 2H), 3.63 (br t, J=6.7 Hz, 2H), 3.06-2.86 (m, 3H), 1.29-1.22 (m, 2H), 1.11-1.05 (m, 2H), 1.05-0.94 (m, 4H). MS (ESI): m/z 463.2 [M+H]⁺.

Example 45

N-(4-Cyanobenzyl)-6-((1-(cyclopropylsulfonyl)cyclopropyl)methyl)-7-oxo-4,5,6,7-tetrahydro-1H-pyrazolo[3,4-c]pyridine-3-carboxamide (45)

(45)

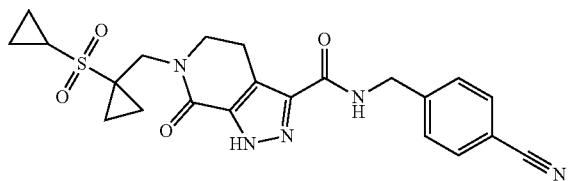

N-(4-Cyanobenzyl)-6-((1-(cyclopropylsulfonyl)cyclopropyl)methyl)-7-oxo-4,5,6,7-tetrahydro-1H-pyrazolo[3,4-c]pyridine-3-carboxamide (45) was obtained using the methods described for N-(4-chlorobenzyl)-6-((1-(cyclopropylsulfonyl)cyclopropyl)methyl)-7-oxo-4,5,6,7-tetrahydro-1H-pyrazolo[3,4-c]pyridine-3-carboxamide (44) except (4-chlorophenyl)methanamine was replaced with 4-(aminomethyl)benzonitrile hydrochloride. TLC $R_f$=0.4 (EtOAc). ¹H NMR (400 MHz, DMSO-d₆) δ 8.76 (s, 1H), 7.79-7.77 (m, 2H), 7.48 (d, J=8.4 Hz, 2H), 4.47 (d, J=6.0 Hz, 2H), 4.01 (s, 2H), 3.60-3.58 (m, 2H), 2.97-2.93 (m, 3H), 1.25-1.24 (m, 2H), 1.06-1.00 (m, 6H). MS (ESI): m/z 454.2 [M+H]⁺.

Example 46

4-((8-((1-(Methylsulfonyl)cyclopropyl)methyl)-1,7-dioxo-3,4,7,8,9,10-hexahydropyrido[3',4':3,4]pyrazolo[1,5-a]pyrazin-2(1H)-yl)methyl)benzonitrile (46)

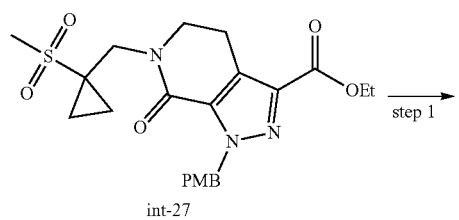

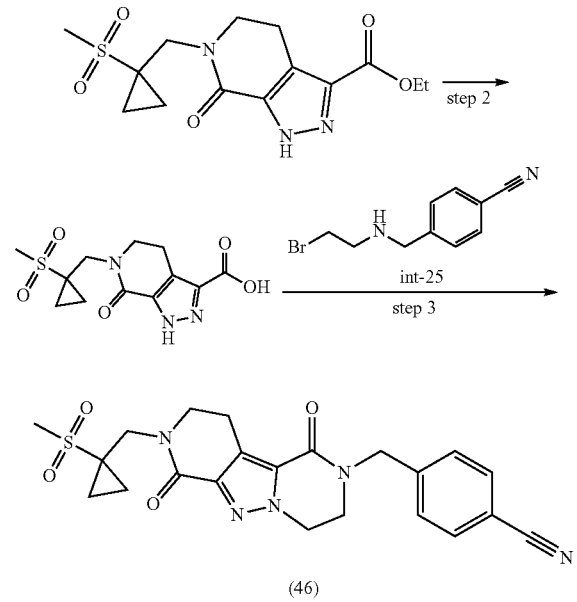

Step 1: Ethyl 6-((1-(methylsulfonyl)cyclopropyl)methyl)-7-oxo-4,5,6,7-tetrahydro-1H-pyrazolo[3,4-c]pyridine-3-carboxylate was obtained using the PMB deprotection method described in step 2 of Example 44, except N-(4-chlorobenzyl)-6-((1-(cyclopropylsulfonyl)cyclopropyl)methyl)-1-(4-methoxybenzyl)-7-oxo-4,5,6,7-tetrahydro-1H-pyrazolo[3,4-c]pyridine-3-carboxamide was replaced with ethyl 1-(4-methoxybenzyl)-6-((1-(methylsulfonyl)cyclopropyl)methyl)-7-oxo-4,5,6,7-tetrahydro-1H-pyrazolo[3,4-c]pyridine-3-carboxylate (int-27). TLC $R_f$=0.3 (EtOAc). ¹H NMR (400 MHz, CDCl₃) δ 12.04 (s, 1H), 4.44-4.39 (m, 2H), 4.02 (s, 2H), 3.84-3.81 (m, 2H), 3.18-3.15 (m, 2H), 3.07 (s, 3H), 1.59-1.57 (m, 3H), 1.41 (t, 2H), 1.13-1.10 (m, 2H). MS (ESI): m/z 342.2 [M+H]⁺.

Step 2: 6-((1-(Methylsulfonyl)cyclopropyl)methyl)-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-(methylsulfonyl)cyclopropyl)methyl)-7-oxo-4,5,6,7-tetrahydro-1H-pyrazolo[3,4-c]pyridine-3-carboxylate. TLC $R_f$=0.2 (1:10 MeOH/EtOAc). MS (ESI): m/z 313.9 [M+H]⁺.

Step 3: 4-((8-((1-(Methylsulfonyl)cyclopropyl)methyl)-1,7-dioxo-3,4,7,8,9,10-hexahydropyrido[3',4':3,4]pyrazolo[1,5-a]pyrazin-2(1H)-yl)methyl)benzonitrile (46) was obtained using the method described in step 1 of Example 28, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-(Methylsulfonyl)cyclopropyl)methyl)-7-oxo-4,5,6,7-tetrahydro-1H-pyrazolo[3,4-c]pyridine-3-carboxylic acid and NH₄Cl was replaced with 4-(((2-Bromoethyl)amino)methyl)benzonitrile (int-25). ¹H NMR (400 MHz, CDCl₃) δ 7.67 (d, J=8.0 Hz, 2H), 7.44 (d, J=8.4 Hz, 2H), 4.80 (s, 2H), 4.44-4.41 (m, 2H), 4.03 (s, 2H), 3.81-3.77 (m, 2H), 3.72-3.69 (m, 2H), 3.21-3.18 (m, 2H), 3.08 (s, 3H), 1.55-1.54 (m, 2H), 1.10-1.07 (m, 2H). MS (ESI): m/z 454.4 [M+H]⁺.

Example 47

N-(4-Cyanobenzyl)-6-((1-(cyclopropylsulfonyl)cyclopropyl)methyl)-1-((1-(hydroxymethyl)cyclopropyl)methyl)-7-oxo-4,5,6,7-tetrahydro-1H-pyrazolo[3,4-c]pyridine-3-carboxamide (47)

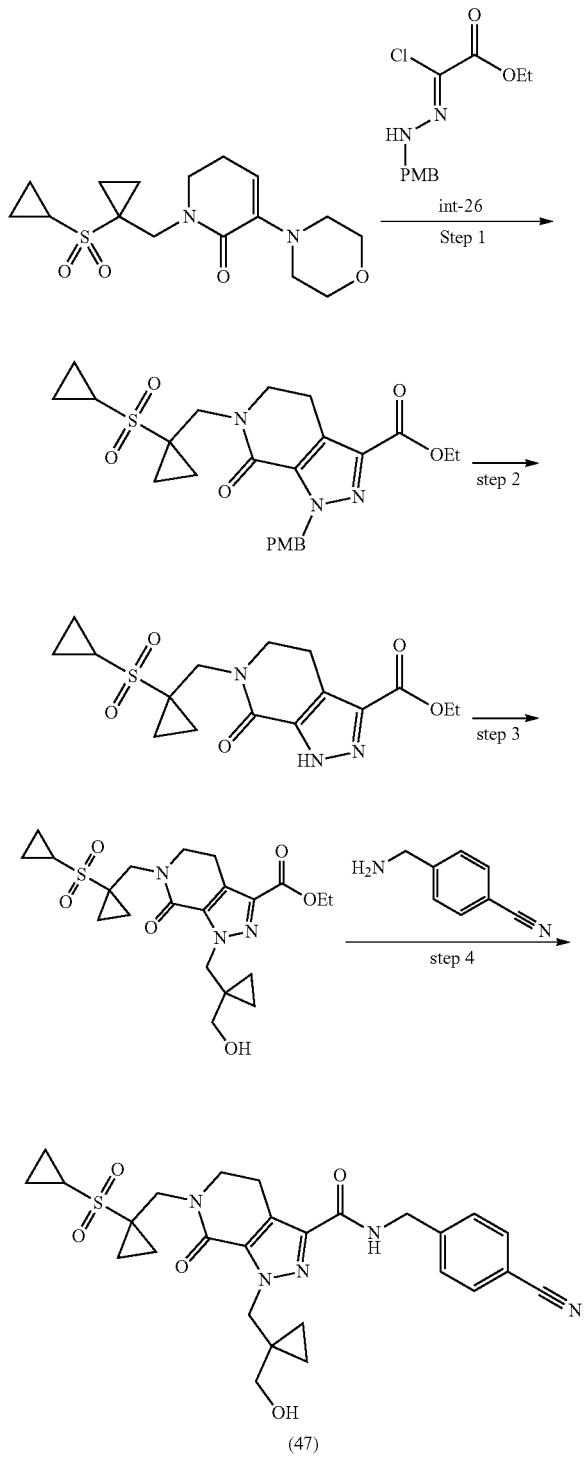

Step 1: Ethyl 6-((1-(cyclopropylsulfonyl)cyclopropyl)methyl)-1-(4-methoxybenzyl)-7-oxo-4,5,6,7-tetrahydro-1H-pyrazolo[3,4-c]pyridine-3-carboxylate was obtained using the method described for intermediate (int-16), except 6-methyl-3-morpholino-5,6-dihydropyridin-2(1H)-one was replaced with 1-((1-(cyclopropylsulfonyl)cyclopropyl)methyl)-3-morpholino-5,6-dihydropyridin-2(1H)-one (see step 1 in synthesis of intermediate (int-19) and ethyl (Z)-2-chloro-2-(2-methylhydrazono)acetate (int-18) was replaced with ethyl (Z)-2-chloro-2-(2-(4-methoxybenzyl)hydrazono)acetate (int-26). TLC $R_f$=0.5 (EtOAc). $^1$H NMR (400 MHz, CDCl$_3$) δ 7.27 (d, J=8.7 Hz, 2H), 6.77-6.72 (m, 2H), 5.68 (s, 2H), 4.33 (q, J=7.1 Hz, 2H), 4.02-3.94 (m, 1H), 3.99 (s, 1H), 3.69 (s, 3H), 3.66 (t, J=6.9 Hz, 2H), 3.04 (t, J=6.9 Hz, 2H), 2.62 (tt, J=4.9, 8.0 Hz, 1H), 1.47-1.39 (m, 2H), 1.32 (t, J=7.2 Hz, 3H), 1.19-1.11 (m, 2H), 1.01-0.90 (m, 4H).

Step 2: Ethyl 6-((1-(cyclopropylsulfonyl)cyclopropyl)methyl)-7-oxo-4,5,6,7-tetrahydro-1H-pyrazolo[3,4-c]pyridine-3-carboxylate was obtained using the PMB deprotection method described in step 2 of Example 44, except N-(4-chlorobenzyl)-6-((1-(cyclopropylsulfonyl)cyclopropyl)methyl)-1-(4-methoxybenzyl)-7-oxo-4,5,6,7-tetrahydro-1H-pyrazolo[3,4-c]pyridine-3-carboxamide was replaced with ethyl 6-((1-(cyclopropylsulfonyl)cyclopropyl)methyl)-1-(4-methoxybenzyl)-7-oxo-4,5,6,7-tetrahydro-1H-pyrazolo[3,4-c]pyridine-3-carboxylate. TLC $R_f$=0.3 (EtOAc). $^1$H NMR (400 MHz, CDCl$_3$) δ 4.42 (q, J=7.1 Hz, 2H), 4.13 (s, 2H), 3.83 (t, J=6.9 Hz, 2H), 3.17 (t, J=7.0 Hz, 2H), 2.78 (tt, J=4.9, 8.0 Hz, 1H), 1.57-1.52 (m, 2H), 1.42 (t, J=7.2 Hz, 3H), 1.26-1.20 (m, 2H), 1.15-1.10 (m, 2H), 1.10-1.06 (m, 2H).

Step 3: To a solution of ethyl 6-((1-(cyclopropylsulfonyl)cyclopropyl)methyl)-7-oxo-4,5,6,7-tetrahydro-1H-pyrazolo[3,4-c]pyridine-3-carboxylate (150 mg, 0.41 mmol, 1.0 equiv), n-Bu$_3$P (124 mg, 0.62 mmol, 1.5 equiv) and 1,1-bis(hydroxymethyl)cyclopropane (125 mg, 1.23 mmol, 3.0 equiv) in THF (2 mL) was added DIAD (124 mg, 0.62 mmol, 1.5 equiv) at 0° C. The mixture was stirred at 25° C. for 6 h before it was diluted with water (5 mL) and extracted with EtOAc (3×2 mL). The combined organic extracts were dried with Na$_2$SO$_4$, filtered and concentrated. The residue was purified by RP-HPLC to afford ethyl 6-((1-(cyclopropylsulfonyl)cyclopropyl)methyl)-1-((1-(hydroxymethyl)cyclopropyl)methyl)-7-oxo-4,5,6,7-tetrahydro-1H-pyrazolo[3,4-c]pyridine-3-carboxylate. MS (ESI): m/z 452.0 [M+H]$^+$.

Step 4: N-(4-Cyanobenzyl)-6-((1-(cyclopropylsulfonyl)cyclopropyl)methyl)-1-((1-(hydroxymethyl)cyclopropyl)methyl)-7-oxo-4,5,6,7-tetrahydro-1H-pyrazolo[3,4-c]pyridine-3-carboxamide (47) was obtained using the procedure described in Example 1, except ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6) was replaced with 6-((1-(cyclopropylsulfonyl)cyclopropyl)methyl)-1-((1-(hydroxymethyl)cyclopropyl)methyl)-7-oxo-4,5,6,7-tetrahydro-1H-pyrazolo[3,4-c]pyridine-3-carboxylate. $^1$H NMR (400 MHz, CDCl$_3$) δ 7.65 (d, J=12 Hz, 2H), 7.47 (d, J=8.0 Hz, 2H), 4.67 (d, J=8.0 Hz, 2H), 4.54 (s, 2H), 4.10 (s, 2H), 3.81-3.76 (m, 2H), 3.23 (d, J=4.0 Hz, 3H), 2.92-2.84 (m, 1H), 1.54 (s, 2H), 1.48-1.39 (m, 2H), 1.24 (d, J=4.0 Hz, 2H), 1.10 (d, J=4.0 Hz, 2H), 1.05-1.01 (m, 2H), 0.94 (m, 1H), 0.82-0.77 (m, 2H), 0.59-0.53 (m, 2H). MS (ESI): m/z 538.0 [M+H]$^+$.

Example 48

N-(4-Cyanobenzyl)-1-((1-(hydroxymethyl)cyclopropyl)methyl)-6-((1-(methylsulfonyl)cyclopropyl)methyl)-7-oxo-4,5,6,7-tetrahydro-1H-pyrazolo[3,4-c]pyridine-3-carboxamide (48)

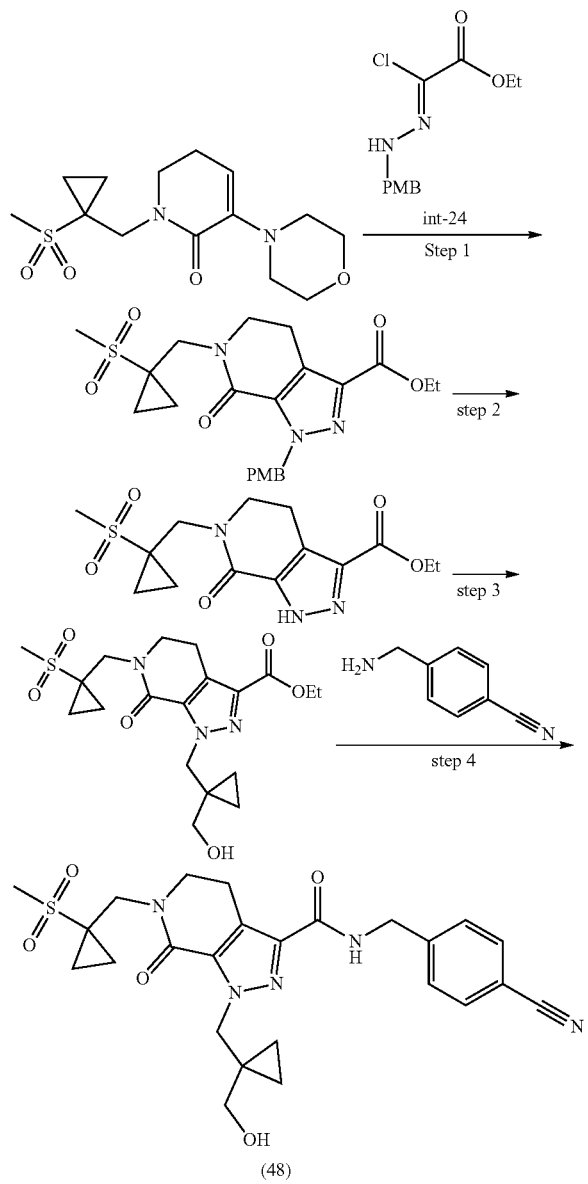

N-(4-Cyanobenzyl)-1-((1-(hydroxymethyl)cyclopropyl)methyl)-6-((1-(methylsulfonyl)cyclopropyl)methyl)-7-oxo-4,5,6,7-tetrahydro-1H-pyrazolo[3,4-c]pyridine-3-carboxamide (48) was obtained using the method described for the synthesis of N-(4-Cyanobenzyl)-6-((1-(cyclopropylsulfonyl)cyclopropyl)methyl)-1-((1-(hydroxymethyl)cyclopropyl)methyl)-7-oxo-4,5,6,7-tetrahydro-1H-pyrazolo[3,4-c]pyridine-3-carboxamide (47), except in step 1 where 1-((1-(cyclopropylsulfonyl)cyclopropyl)methyl)-3-morpholino-5,6-dihydropyridin-2(1H)-one was replaced with 1-((1-(methylsulfonyl)cyclopropyl)methyl)-3-morpholino-5,6-dihydropyridin-2(1H)-one. $^1$H NMR (400 MHz, DMSO-d$_6$) δ 8.89-8.86 (m, 1H), 7.80 (d, J=8.0 Hz, 2H), 7.49 (d, J=8.4 Hz, 2H), 4.60 (s, 2H), 4.50 (d, J=6.0 Hz, 2H), 3.97 (s, 2H), 3.69-3.65 (m, 2H), 3.34-3.30 (m, 2H), 3.11 (s, 3H), 3.00-2.97 (m, 2H), 1.29-1.26 (m, 2H), 1.10-1.09 (m, 2H), 0.60-0.57 (m, 2H), 0.42-0.40 (m, 2H). MS (ESI): m/z 512.4 [M+H]$^+$.

Example 49

N-(4-Cyanobenzyl)-6-((1-((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide (49)

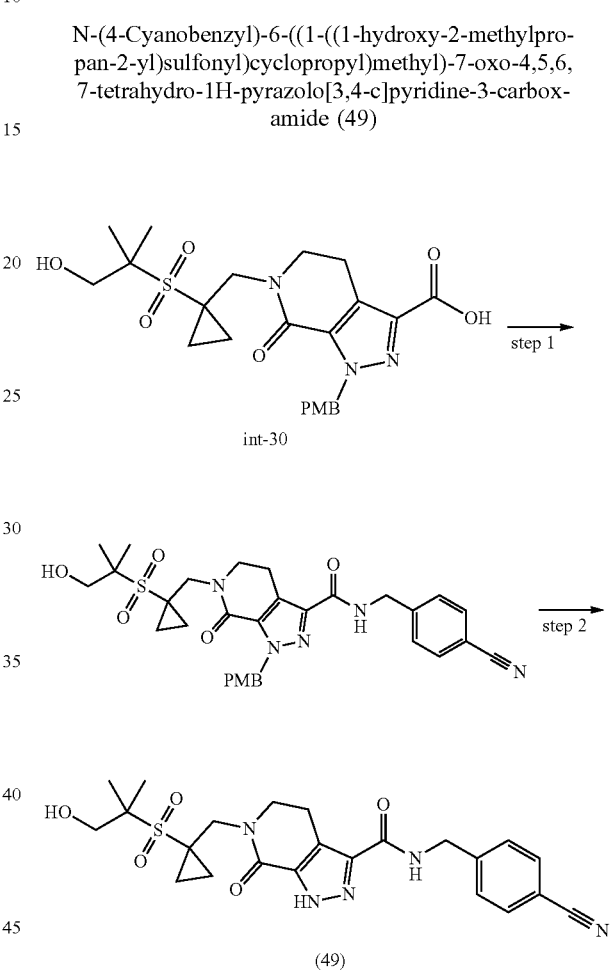

Step 1: N-(4-Cyanobenzyl)-6-((1-((1-hydroxy-2-methylpropan-2-yl)sulfonyl)cyclopropyl)methyl)-1-(4-methoxybenzyl)-7-oxo-4,5,6,7-tetrahydro-1H-pyrazolo[3,4-c]pyridine-3-carboxamide was obtained using the method described in step 1 of Example 26, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((1-hydroxy-2-methylpropan-2-yl)sulfonyl)cyclopropyl)methyl)-1-(4-methoxybenzyl)-7-oxo-4,5,6,7-tetrahydro-1H-pyrazolo[3,4-c]pyridine-3-carboxylic acid (int-30) and hydrazine was replaced with 4-(aminomethyl)benzonitrile hydrochloride. TLC R$_f$=0.3 (EtOAc). $^1$H NMR (400 MHz, DMSO-d$_6$) b 8.91-8.88 (m, 1H), 7.78-7.75 (m, 2H), 7.47 (d, J=8.4 Hz, 2H), 7.21 (d, J=8.8 Hz, 2H), 6.88-6.85 (m, 2H), 5.65 (s, 2H), 5.32 (br s, 1H), 4.46 (d, J=6.0 Hz, 2H), 4.09 (s, 2H), 3.71 (s, 3H), 3.63-3.59 (m, 4H), 3.00-2.96 (m, 2H), 1.32-1.30 (m, 8H), 0.99-0.96 (m, 2H).

Step 2: N-(4-Cyanobenzyl)-6-((1-((1-hydroxy-2-methyl-propan-2-yl)sulfonyl)cyclopropyl)methyl)-7-oxo-4,5,6,7-tetrahydro-1H-pyrazolo[3,4-c]pyridine-3-carboxamide (49) was obtained using the PMB deprotection method described in step 2 of Example 44, except N-(4-chlorobenzyl)-6-((1-(cyclopropylsulfonyl)cyclopropyl)methyl)-1-(4-methoxy-benzyl)-7-oxo-4,5,6,7-tetrahydro-1H-pyrazolo[3,4-c]pyri-dine-3-carboxamide was replaced with N-(4-Cyanobenzyl)-6-((1-((1-hydroxy-2-methylpropan-2-yl)sulfonyl)cyclopropyl)methyl)-1-(4-methoxybenzyl)-7-oxo-4,5,6,7-tetrahydro-1H-pyrazolo[3,4-c]pyridine-3-carboxamide. $^1$H NMR (400 MHz, DMSO-d$_6$) δ 8.93-8.92 (m, 1H), 7.78 (d, J=8.0 Hz, 2H), 7.48 (d, J=8.0 Hz, 2H), 5.31 (br s, 1H), 4.48 (d, J=6.0 Hz, 2H), 4.09 (s, 2H), 3.65-3.60 (m, 4H), 2.99-2.96 (m, 2H), 1.34 (m, 8H), 1.04-0.98 (m, 2H). MS (ESI): m/z 486.3 [M+H]$^+$.

Example 50

N-(4-Chlorobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (50)

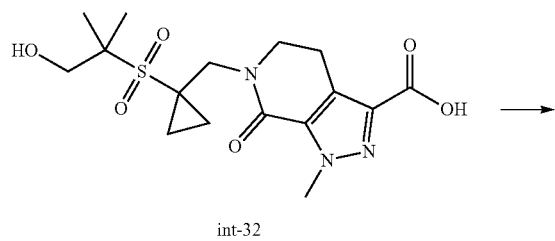

int-32

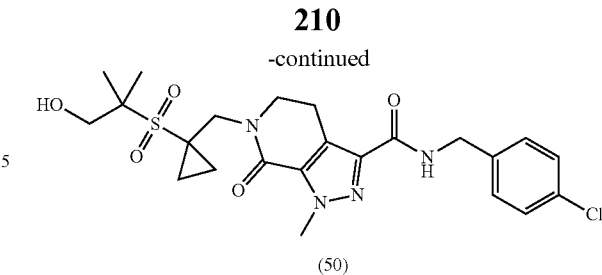

(50)

N-(4-Chlorobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (50) was obtained using the method described in step 1 of Example 26, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid (int-32) and hydrazine was replaced with (4-chlorophenyl)methanamine. MS (ESI): m/z 509.3 [M+H]$^+$. $^1$H NMR (400 MHz, CDCl$_3$) δ 7.34-7.28 (m, 4H), 7.16 (s, 1H), 4.57 (d, J=6.1 Hz, 2H), 4.17 (s, 2H), 4.14 (s, 3H), 3.86 (br d, J=5.0 Hz, 2H), 3.71 (t, J=6.8 Hz, 2H), 3.20 (t, J=6.9 Hz, 2H), 3.13 (br s, 1H), 1.60 (br s, 2H), 1.51 (s, 6H), 1.27 (s, 1H), 1.11-1.05 (m, 2H).

Compounds given in Table 2 below were prepared following procedures analogous to those described in Example 50 for compound (50) using the appropriate amine in place of (4-chlorophenyl)methanamine.

TABLE 2

| Example/Compound Number | Compound Structure and Name | Physical Data MS (m/z), $^1$H NMR |
|---|---|---|
| 51 | N-((6-Chloropyridin-3-yl)methyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 510.4 [M + H]$^+$. $^1$H NMR (400 MHz, CDCl$_3$) δ 8.38 (d, J = 2.3 Hz, 1H), 7.68 (dd, J = 2.5, 8.2 Hz, 1H), 7.31 (d, J = 8.2 Hz, 1H), 7.22 (s, 1H), 4.59 (d, J = 6.3 Hz, 2H), 4.17 (s, 2H), 4.15 (s, 3H), 3.86 (d, J = 6.3 Hz, 2H), 3.72 (t, J = 6.9 Hz, 2H), 3.18 (t, J = 6.8 Hz, 2H), 3.14-3.05 (m, 1H), 1.62-1.58 (m, 2H), 1.51 (s, 6H), 1.12-1.00 (m, 2H). |
| 52 | N-(4-Cyanobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 500.4 [M + H]$^+$. $^1$H NMR (400 MHz, CDCl$_3$) δ 7.64 (d, J = 8.3 Hz, 2H), 7.46 (d, J = 8.3 Hz, 2H), 7.29 (br s, 1H), 4.66 (d, J = 6.4 Hz, 2H), 4.17 (s, 2H), 4.16 (s, 3H), 3.86 (d, J = 5.9 Hz, 2H), 3.72 (t, J = 6.9 Hz, 2H), 3.19 (t, J = 6.9 Hz, 2H), 3.14 (s, 1H), 1.60 (d, J = 2.3 Hz, 2H), 1.51 (s, 6H), 1.12-1.03 (m, 2H). |

US 11,667,613 B2

TABLE 2-continued

| Example/ Compound Number | Compound Structure and Name | Physical Data MS (m/z), $^1$H NMR |
|---|---|---|
| 53 | 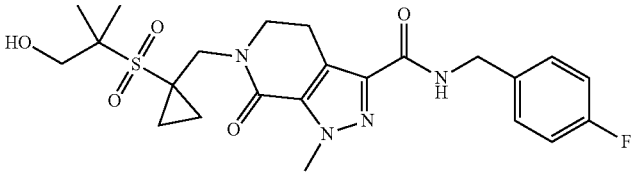 [SMILES: Cn1nc(C(=O)NCc2ccc(F)cc2)c2c1C(=O)N(CC1(S(=O)(=O)C(C)(C)CO)CC1)CC2]<br>N-(4-Fluorobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 493.2 [M + H]$^+$. $^1$H NMR (400 MHz, CDCl$_3$) δ 7.36-7.29 (m, 2H), 7.20-7.10 (m, 1H), 7.07-7.00 (m, 2H), 4.57 (d, J = 6.1 Hz, 2H), 4.17 (s, 2H), 4.14 (s, 3H), 3.86 (s, 2H), 3.71 (t, J = 6.9 Hz, 2H), 3.20 (t, J = 6.8 Hz, 2H), 1.62-1.56 (m, 2H), 1.51 (s, 6H), 1.11-1.02 (m, 2H). |
| 54 | 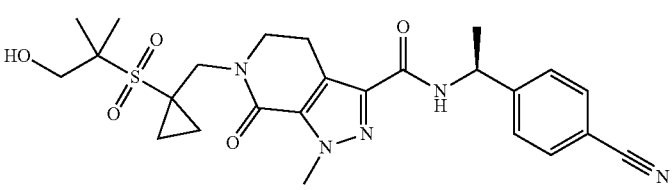 [SMILES: C[C@H](NC(=O)c1nn(C)c2c1CCN(CC1(S(=O)(=O)C(C)(C)CO)CC1)C2=O)c1ccc(C#N)cc1]<br>(S)-N-(1-(4-Cyanophenyl)ethyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 514.1 [M + H]$^+$. $^1$H NMR (400 MHz, CDCl$_3$) δ 7.74-7.59 (m, 2H), 7.49 (d, J = 8.2 Hz, 2H), 7.11 (d, J = 7.6 Hz, 1H), 5.26 (m, 1H), 4.21-4.11 (m, 5H), 3.86 (d, J = 6.4 Hz, 2H), 3.73-3.65 (m, 2H), 3.17-3.09 (m, 3H), 1.61-1.58 (m, 5H), 1.51 (s, 6H), 1.12-1.00 (m, 2H). SFC: C-07508-092-P2A_1, Rt = 1.960, ee = 100%, OD-3_5CM MEOH(DEA)_5_40_3ML_AT35.M |
| 55 | 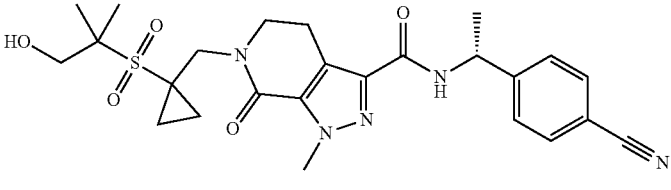 [SMILES: C[C@@H](NC(=O)c1nn(C)c2c1CCN(CC1(S(=O)(=O)C(C)(C)CO)CC1)C2=O)c1ccc(C#N)cc1]<br>(R)-N-(1-(4-Cyanophenyl)ethyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 514.1 [M + H]$^+$. $^1$H NMR (400 MHz, CDCl$_3$) δ 7.64 (m, 2H), 7.49 (d, J = 7.8 Hz, 2H), 7.11 (m, 1H), 5.26 (m, 1H), 4.17 (s, 5H), 3.86 (s, 2H), 3.69 (m, 2H), 3.14 (m, 3H), 1.59 (d, J = 6.6 Hz, 5H), 1.51 (s, 7H), 1.06 (br s, 2H). SFC: C-07508-092-P1A_1, Rt = 1.724, ee = 100%, OD-3_5CM_MEOH(DEA)_5_40_3ML_AT35.M |

Example 56

N-(4-Cyanobenzyl)-6-((1-((1-hydroxy-2-methylpropan-2-yl-1,1-d$_2$)sulfonyl)cyclopropyl)methyl)-1-methyl-7-oxo-4,5,6,7-tetrahydro-1H-pyrazolo[3,4-c]pyridine-3-carboxamide (56)

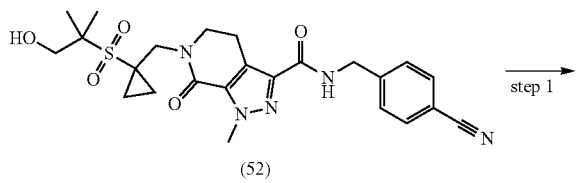

(52)

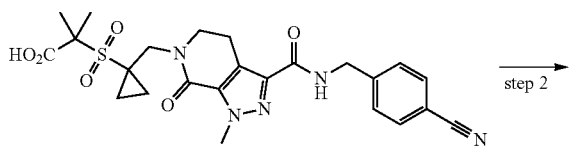

step 1 step 2

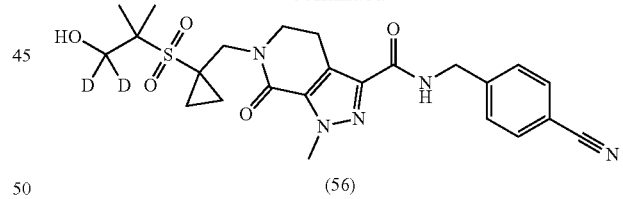

(56)

Step 1: N-(4-cyanobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (52) (50 mg, 0.100 mmol, 1.0 equiv), NMO (117 mg, 1.001 mmol, 10 equiv), and water (18.03 µl, 1.001 mmol, 10 equiv) were dissolved in MeCN (1 mL), then TPAP (3.52 mg, 10.01 µmol, 0.1 equiv) was added. The solution was stirred at rt for 15 min before the reaction mixture was quenched with i-PrOH (5 mL). The solution was diluted with water (1 mL) and acidified to pH -3 with 1 N KHSO$_4$. The aqueous layer was extracted with EtOAc (2×25 mL), then the combined organic extracts were dried over MgSO$_4$, filtered and concentrated to give 48 mg of crude material. After trituration with diethyl ether, the solid was collected by filtration to provide 2-((1-((3-((4-cyanobenzyl)carbamoyl)-

1-methyl-7-oxo-4,5-dihydro-1H-pyrazolo[3,4-c]pyridin-6(7H)-yl)methyl)cyclopropyl)sulfonyl)-2-methylpropanoic acid. MS (ESI): m/z 514.5 [M+H]$^+$.

Step 2: A mixture of 2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropanoic acid (40 mg, 0.0785 mmol, 1.0 equiv) and NMM (11.55 μL, 0.105 mmol, 1.34 equiv) in THF (1 mL) was cooled to −5° C., then isobutyl chloroformate (13.80 μL, 0.105 mmol, 1.34 equiv) was added. After 10 min at −5° C., the solids were removed by filtration and the filter cake was washed with a small amount of cold THF. The filtrate was cooled to 0° C. before it was treated with a solution of NaBD$_4$ (6.70 mg, 0.160 mmol, 2.04 equiv) in D$_2$O (26 μL). After 15 min at 0° C., the reaction mixture was partitioned between EtOAc (10 mL) and water (10 mL) and the layers were separated. The aqueous layer was extracted with EtOAc (3×10 mL), then the combined organic extracts were washed with brine (20 mL), dried over Na$_2$SO$_4$, filtered and concentrated. The residue was purified by RP-HPLC to provide N-(4-Cyanobenzyl)-6-((1-((1-hydroxy-2-methylpropan-2-yl-1,1-d$_2$)sulfonyl)cyclopropyl)methyl)-1-methyl-7-oxo-4,5,6,7-tetrahydro-1H-pyrazolo[3,4-c]pyridine-3-carboxamide (56). $^1$H NMR (500 MHz, DMSO-d$_6$) δ 8.94 (t, J=6.3 Hz, 1H), 7.78 (d, J=8.3 Hz, 2H), 7.47 (d, J=8.3 Hz, 2H), 4.46 (d, J=6.3 Hz, 2H), 4.09 (d, J=9.3 Hz, 5H), 3.61 (t, J=6.8 Hz, 2H), 2.97 (t, J=6.8 Hz, 2H), 1.36-1.29 (m, 8H), 1.02-0.95 (m, 2H). MS (ESI): m/z 502.1 [M+H]$^+$.

Example 57

2-((1-((3-((4-Cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropyl acetate (57)

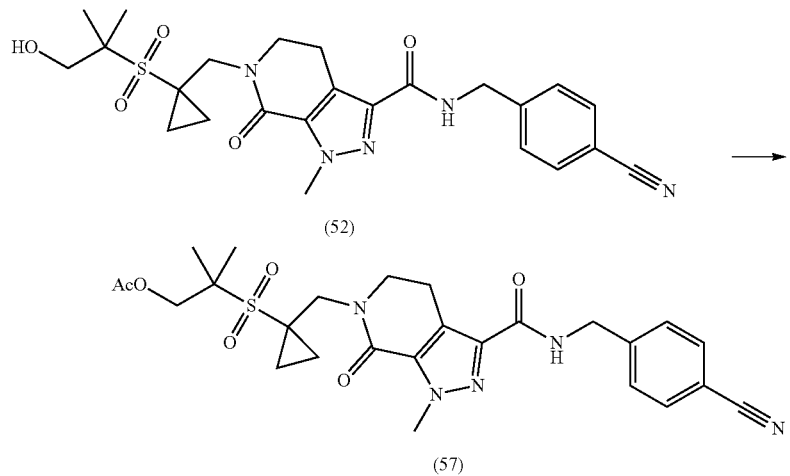 [SMILES: Cn1nc(C(=O)NCc2ccc(C#N)cc2)c2c1C(=O)N(CC1(S(=O)(=O)C(C)(C)CO)CC1)CC2 ; CC(=O)OCC(C)(C)S(=O)(=O)C1(CN2CCc3c(C(=O)NCc4ccc(C#N)cc4)nn(C)c3C2=O)CC1]

To a solution of N-(4-cyanobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (52) (110 mg, 0.22 mmol, 1.0 equiv) in DCM (1 mL) was added acetic anhydride (112 mg, 1.10 mmol, 5.0 equiv) and pyridine (87 mg, 1.10 mmol, 5.0 equiv). The reaction mixture was stirred at 25° C. for 2 h, then it was diluted with water (3 mL) and extracted with EtOAc (3×30 mL). After the combined organic extracts were dried with Na$_2$SO$_4$, filtered and concentrated, the residue was purified by RP-HPLC to afford 2-((1-((3-((4-Cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropyl acetate (57). $^1$H NMR (400 MHz, CDCl$_3$) δ 7.64 (d, J=8.4 Hz, 2H), 7.46 (d, J=8.0 Hz, 2H), 7.33-7.29 (m, 1H), 4.66 (d, J=6.4 Hz, 2H), 4.35 (s, 2H), 4.19 (s, 2H), 4.15 (s, 3H), 3.74-3.70 (m, 2H), 3.20-3.16 (m, 2H), 2.20 (s, 3H), 1.60-1.57 (m, 2H), 1.52 (s, 6H), 1.10-1.07 (m, 2H). MS (ESI): m/z 542.2 [M+H]$^+$.

Example 58

N-(4-Cyanobenzyl)-6-((1-((1-(difluoromethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (58)

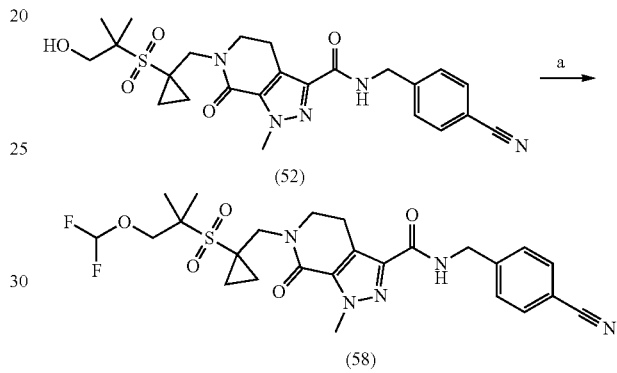

A mixture of N-(4-cyanobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (52) (50 mg, 0.100 mmol, 1.0 equiv) and CuI (3.81 mg, 0.020 mmol, 0.2 equiv) in MeCN (1.0 mL) was heated to 50° C., then a solution of FSO$_2$CF$_2$CO$_2$H (26.7 mg, 0.150 mmol, 1.5 equiv) in 300 μL MeCN was added dropwise over 10 min. The reaction mixture was heated for an additional 30 min at 50° C. before it was concentrated.

The residue was diluted with EtOAc (5 mL) and the solids were removed by filtration. The filtrate was concentrated to give a crude oil that was purified by RP-HPLC to afford N-(4-Cyanobenzyl)-6-((1-((1-(difluoromethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (58). $^1$H NMR (500 MHz, DMSO-$d_6$) δ 8.96 (t, J=6.3 Hz, 1H), 7.84-7.77 (m, 2H), 7.49 (d, J=8.4 Hz, 2H), 6.80 (t, J=75.2 Hz, 1H), 4.48 (d, J=6.3 Hz, 2H), 4.12 (s, 3H), 4.09 (s, 2H), 4.08 (s, 2H), 3.63 (t, J=6.8 Hz, 2H), 2.99 (t, J=6.8 Hz, 2H), 1.45 (s, 6H), 1.40-1.34 (m, 2H), 1.09-1.03 (m, 2H). MS (ESI): m/z 550.1 [M+H]$^+$.

Example 59

N-(4-Cyanobenzyl)-6-((1-((2-cyanopropan-2-yl)sulfonyl)cyclopropyl)methyl)-1-methyl-7-oxo-4,5,6,7-tetrahydro-1H-pyrazolo[3,4-c]pyridine-3-carboxamide (59)

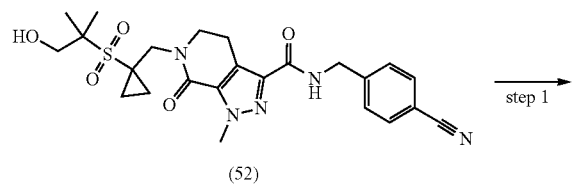

(52)

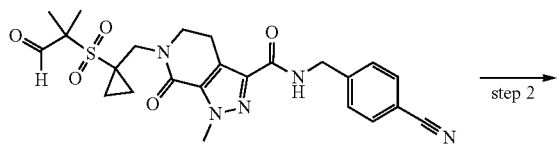

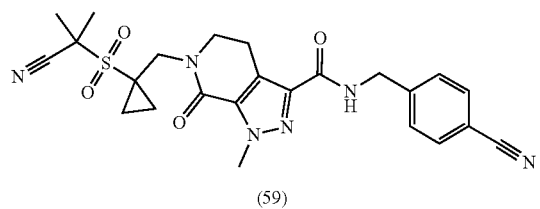

(59)

Step 1: A suspension of Dess-Martin periodinane (50.8 mg, 0.110 mmol, 1.1 equiv) in CH$_2$Cl$_2$ (2.0 mL) was treated with N-(4-cyanobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (52) (50 mg, 0.100 mmol, 1.0 equiv). After 2 h at 23° C., saturated Na$_2$SO$_3$ (1.0 mL) and saturated NaHCO$_3$ (1.0 mL) were added, and then the biphasic mixture was stirred for 30 min. The mixture was diluted with CH$_2$Cl$_2$ (3 mL), the layers were separated, and then the aqueous layer was extracted with CH$_2$Cl$_2$(2×4 mL). The combined organic extracts were dried with MgSO$_4$, filtered, and concentrated to afford N-(4-cyanobenzyl)-1-methyl-6-((1-((2-methyl-1-oxopropan-2-yl)sulfonyl)cyclopropyl)methyl)-7-oxo-4,5,6,7-tetrahydro-1H-pyrazolo[3,4-c]pyridine-3-carboxamide. H NMR (500 MHz, CDCl$_3$) δ 9.78 (s, 1H), 7.63 (d, J=8.2 Hz, 2H), 7.45 (d, J=8.0 Hz, 2H), 4.65 (d, J=6.3 Hz, 2H), 4.14 (s, 3H), 3.96 (s, 2H), 3.67 (t, J=6.9 Hz, 2H), 3.16 (t, J=6.9 Hz, 2H), 1.62 (56H), 1.51-1.48 (m, 2H), 1.14-1.08 (m, 2H). MS(ESI): m/z 498.5 [M+H]$^+$. Šiška, P.; Fodran, P.; Szolcsányi, P. Tetrahedron 2014, 70, 6420-6427.

Step 2: 4 solution of N-(4-cyanobenzyl)-1-methyl-6-((1-((2-methyl-1-oxopropan-2-yl)sulfonyl)cyclopropyl)methyl)-7-oxo-4,5,6,7-tetrahydro-1H-pyrazolo[3,4-c]pyridine-3-carboxamide (40 mg, 0.080 mmol, 1.0 equiv) in THF (804 μL) and NH$_4$H (347 μL) was stirred at 23° C. for 5 min, then I$_2$ (61.2 mg, 0.241 mmol, 3.0 equiv) was added and the reaction mixture was heated to 50° C. for 5 h. Saturated Na$_2$S$_2$O$_3$(20 mL) was added and the aqueous phase was extracted with CH$_2$Cl$_2$ (3×15 mL). The combined organic extracts were washed with brine, dried over anhydrous Na$_2$SO$_4$ and concentrated. The residue was purified by column chromatography (SiO$_2$, 40-90% EtOAc/heptane) to afford N-(4-Cyanobenzyl)-6-((1-((2-cyanopropan-2-yl)sulfonyl)cyclopropyl)methyl)-1-methyl-7-oxo-4,5,6,7-tetrahydro-1H-pyrazolo[3,4-c]pyridine-3-carboxamide (59). $^1$H NMR (500 MHz, CDCl$_3$) δ 7.63 (d, J=8.2 Hz, 2H), 7.45 (d, J=8.2 Hz, 2H), 4.66 (d, J=6.3 Hz, 2H), 4.31 (s, 2H), 4.15 (s, 3H), 3.76 (t, J=6.8 Hz, 2H), 3.19 (t, J=6.8 Hz, 2H), 1.85 (s, 6H), 1.73-1.64 (m, 2H), 1.32-1.24 (m, 3H). MS (ESI): m/z 495.5 [M+H]$^+$.

Example 60

N-(4-Cyanobenzyl)-6-((1-((1-(3-fluoroazetidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (60)

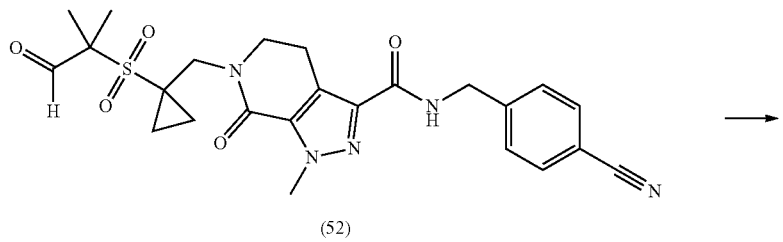

(52)

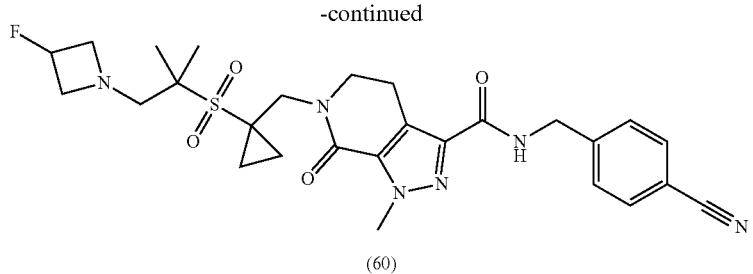

(60)

A solution of N-(4-cyanobenzyl)-1-methyl-6-((1-((2-methyl-1-oxopropan-2-yl)sulfonyl)cyclopropyl)methyl)-7-oxo-4,5,6,7-tetrahydro-1H-pyrazolo[3,4-c]pyridine-3-carboxamide (52) (20 mg, 0.04 mmol, 1.0 equiv) and 3-fluoroazetidine (16.4 mg, 0.147 mmol, 3.67 equiv) in DCM (2 mL) was stirred at rt for 45 min before NaBH(OAc)$_3$ (200 mg, 0.944 mmol, 23 equiv) was added. After 1 h at rt, saturated NaHCO$_3$ (2 mL) was added and the biphasic mixture was stirred for 30 min. The organic layer was removed, and the aqueous layer was extracted with DCM (2 mL), then the combined organic extracts were dried over anhydrous Na$_2$SO$_4$, filtered and concentrated. The residue was purified by RP-HPLC to give N-(4-Cyanobenzyl)-6-((1-((1-(3-fluoroazetidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (60). MS (ESI): m/z 557.3 [M+H]$^+$.

Compounds given in Table 3 below were prepared following procedures analogous to those described in Examples 56-60.

TABLE 3

| Example/Compound Number | Compound Structure and Name | Physical Data MS (m/z), $^1$H NMR |
|---|---|---|
| 61 | N-(4-Cyanobenzyl)-1-methyl-6-((1-((2-methyl-1-morpholinopropan-2-yl)sulfonyl)cyclopropyl)methyl)-7-oxo-4,5,6,7-tetrahydro-1H-pyrazolo[3,4-c]pyridine-3-carboxamide | MS (ESI): m/z 569.4 [M + H]$^+$. $^1$H NMR (500 MHz, DMSO-d$_6$) δ 7.79 (d, J = 8.4 Hz, 1H), 7.48 (d, J = 8.3 Hz, 1H), 4.47 (d, J = 6.4 Hz, 2H), 4.11 (d, J = 6.3 Hz, 5H), 2.98 (t, J = 6.8 Hz, 1H), 2.54 (s, 9H). |
| 62 | (R)-N-(4-cyanobenzyl)-6-((1-((1-(3-methoxypyrrolidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 583.3 [M + H]$^+$. $^1$H NMR (500 MHz, DMSO-d$_6$) δ 8.97 (t, J = 6.2 Hz, 1H), 7.80 (d, J = 8.3 Hz, 2H), 7.49 (d, J = 8.2 Hz, 2H), 6.55 (s, 5H), 4.48 (d, J = 6.3 Hz, 2H), 4.12 (d, J = 9.4 Hz, 5H), 2.99 (t, J = 6.8 Hz, 1H), 1.54 (s, 4H), 1.40 (s, 2H), 1.25 (s, 1H), 1.09 (s, 2H). |
| 63 | 6-((1-((1-(6-Oxa-3-azabicyclo[3.1.1]heptan-3-yl)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 581.3 [M + H]$^+$. $^1$H NMR (500 MHz, DMSO-d6) δ 8.96 (t, J = 6.4 Hz, 1H), 7.86-7.77 (m, 2H), 7.49 (d, J = 8.2 Hz, 2H), 4.48 (d, J = 6.2 Hz, 2H), 4.42 (s, 1H), 4.18-4.10 (m, 5H), 3.16 (d, J = 11.4 Hz, 1H), 3.06-2.94 (m, 4H), 1.77 (s, 1H), 1.47 (s, 6H), 1.35 (s, 2H), 1.04 (s, 2H). |

TABLE 3-continued

| Example/ Compound Number | Compound Structure and Name | Physical Data MS (m/z), ¹H NMR |
|---|---|---|
| 64 | 6-((1-((1-(2-Oxa-5-azabicyclo[2.2.1]heptan-5-yl)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 581.3 [M + H]$^+$. $^1$H NMR (500 MHz, DMSO-d6) δ 8.97 (s, 1H), 7.80 (d, J = 8.2 Hz, 2H), 7.49 (d, J = 8.1 Hz, 2H), 4.48 (d, J = 6.2 Hz, 2H), 4.13 (s, 5H), 3.64 (s, 6H), 3.00 (s, 1H), 1.77 (s, 2H), 1.37 (m, 6H). |
| 65 | N-(4-Cyanobenzyl)-6-((1-((1-(3-hydroxyazetidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 555.2 [M + H]$^+$. $^1$H NMR (500 MHz, DMSO-d6) δ 8.97 (t, J = 6.3 Hz, 1H), 7.86-7.78 (m, 2H), 7.49 (d, J = 8.2 Hz, 2H), 4.48 (d, J = 6.2 Hz, 4H), 4.13 (s, 3H), 4.09 (s, 2H), 3.64 (t, J = 6.8 Hz, 5H), 3.01 (t, J = 6.7 Hz, 2H), 1.52 (s, 6H), 1.42 (d, J = 7.0 Hz, 2H), 1.14 (s, 2H). |
| 66 | N-(4-Cyanobenzyl)-6-((1-((1-(3-methoxyazetidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 569.4 [M + H]$^+$. $^1$H NMR (500 MHz, DMSO-d$_6$) δ 7.89-7.77 (m, 2H), 7.49 (d, J = 8.3 Hz, 2H), 6.56 (s, 2H), 4.48 (d, J = 6.4 Hz, 8H), 4.13 (s, 11H), 1.51 (s, 3H), 1.41 (s, 1H), 1.13 (s, 1H). |
| 67 | N-(4-Cyanobenzyl)-1-methyl-6-((1-((2-methyl-1-(2-oxa-6-azaspiro[3.3]heptan-6-yl)propan-2-yl)sulfonyl)cyclopropyl)methyl)-7-oxo-4,5,6,7-tetrahydro-1H-pyrazolo[3,4-c]pyridine-3-carboxamide | MS (ESI): m/z 581.3 [M + H]$^+$. $^1$H NMR (500 MHz, DMSO-d6) δ 8.97 (t, J = 6.3 Hz, 1H), 7.86-7.78 (m, 2H), 7.49 (d, J = 8.2 Hz, 2H), 4.48 (d, J = 6.2 Hz, 2H), 4.22-4.15 (m, 2H), 4.13 (s, 3H), 4.09 (s, 2H), 4.05-3.99 (m, 2H), 3.73 (d, J = 5.0 Hz, 2H), 3.64 (t, J = 6.8 Hz, 4H), 3.00 (t, J = 6.8 Hz, 2H), 1.53 (s, 5H), 1.42 (q, J = 5.1 Hz, 2H), 1.17-1.11 (m, 2H). |
| 68 | N-(4-Cyanobenzyl)-6-((1-((1-(3-hydroxypyrrolidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 569.3 [M + H]$^+$. $^1$H NMR (500 MHz, DMSO-d6) δ 8.98 (d, J = 6.5 Hz, 1H), 7.87-7.76 (m, 2H), 7.49 (d, J = 8.2 Hz, 2H), 6.55 (s, 4H), 4.48 (d, J = 6.3 Hz, 2H), 4.12 (d, J = 10.2 Hz, 5H), 3.81 (s, 2H), 3.64 (s, 4H), 3.00 (d, J = 6.9 Hz, 2H), 1.77 (s, 1H), 1.62 (s, 4H), 1.43 (s, 2H), 1.15 (s, 2H). |

TABLE 3-continued

| Example/Compound Number | Compound Structure and Name | Physical Data MS (m/z), ¹H NMR |
|---|---|---|
| 69 | 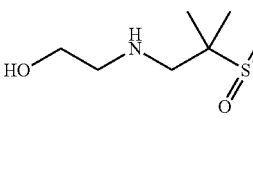<br>N-(4-Cyanobenzyl)-6-((1-((1-((2-hydroxyethyl)amino)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 543.5 [M + H]⁺. ¹H NMR (500 MHz, CDCl₃) δ 7.63 (d, J = 7.9 Hz, 2H), 7.45 (d, J = 8.0 Hz, 2H), 4.65 (d, J = 6.1 Hz, 2H), 4.21 (s, 2H), 4.14 (s, 3H), 3.70 (t, J = 6.8 Hz, 2H), 3.67-3.62 (m, 2H), 3.17 (t, J = 7.2 Hz, 2H), 2.98 (s, 2H), 2.84-2.78 (m, 2H), 1.53 (s, 6H), 1.26 (s, 2H), 1.04 (s, 2H). |

Example 70

6-((1-((1-Amino-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (70)

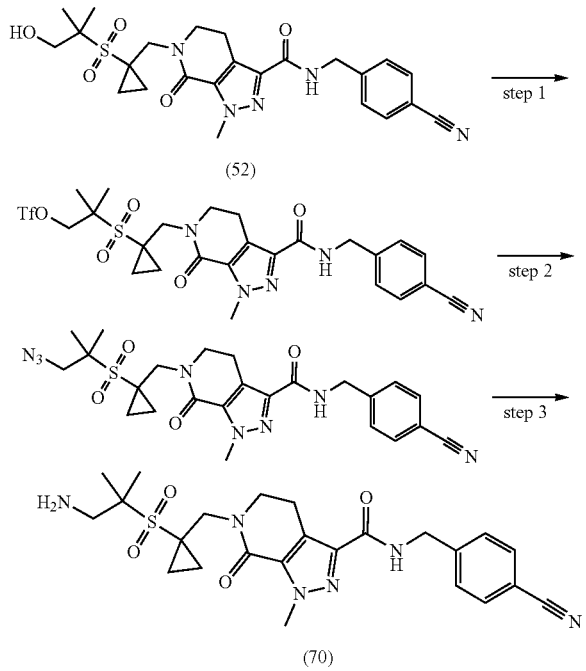

Step 1: To a solution of N-(4-cyanobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (52) (500 mg, 1.0 mmol, 1.0 equiv) in DCM (5 mL) was added pyridine (237 mg, 3.0 mmol, 3.0 equiv) and Tf₂O (564 mg, 2.0 mmol, 2.0 equiv) at 0° C. The mixture was stirred at 25° C. for 2 h before it was concentrated. The residue was purified by column chromatography (SiO₂, 25-75% EtOAc/petroleum ether) to afford 2-((1-((3-((4-cyanobenzyl)carbamoyl)-1-methyl-7-oxo-1,4,5,7-tetrahydro-6H-pyrazolo[3,4-c]pyridin-6-yl)methyl)cyclopropyl)sulfonyl)-2-methylpropyl trifluoromethanesulfonate. ¹H NMR (400 MHz, CDCl₃) δ 7.64 (d, J=8.0 Hz, 2H), 7.46 (d, J=8.0 Hz, 2H), 7.30-7.27 (m, 1H), 4.72 (s, 2H), 4.66 (d, J=6.4 Hz, 2H), 4.16 (s, 3H), 4.13 (s, 2H), 3.72-3.69 (m, 2H), 3.21-3.17 (m, 2H), 1.62 (s, 6H), 1.61-1.59 (m, 2H), 1.15-1.12 (m, 2H). MS (ESI): m/z 632.0 [M+H]⁺.

Step 2: A mixture of 2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropyl trifluoromethanesulfonate (530 mg, 0.84 mmol, 1.0 equiv) and NaN₃ (300 mg, 4.61 mmol, 5.5 equiv) in DMF (5 mL) was stirred at 80° C. for 2 h. After the mixture was diluted with water (5 mL) and extracted with EtOAc (2×30 mL), the combined organic extracts were dried with Na₂SO₄, filtered and concentrated to afford 6-((1-((1-Azido-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide. ¹H NMR (400 MHz, CDCl₃) δ 7.64 (d, J=8.4 Hz, 2H), 7.45 (d, J=8.4 Hz, 2H), 7.30-7.28 (m, 1H), 4.66 (d, J=6.4 Hz, 2H), 4.17 (s, 2H), 4.15 (s, 3H), 3.73-3.70 (m, 4H), 3.20-3.16 (m, 2H), 1.62-1.56 (m, 2H), 1.54 (s, 6H), 1.11-1.08 (m, 2H). MS (ESI): m/z 525.1 [M+H]⁺.

Step 3: A mixture of 6-((1-((1-azido-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (300 mg, 0.57 mmol, 1.0 equiv) and 10% Pd/C (30 mg, 0.028 mmol, 0.05 equiv) in EtOAc (12 mL) was placed under a H₂ atmosphere (15 psi), then the mixture was stirred at 25° C. for 30 min. The mixture was filtered and the filtrate was concentrated to afford 6-((1-((1-Amino-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (70). ¹H NMR (400 MHz, CDCl₃) δ 7.64 (d, J=8.0 Hz, 2H), 7.46 (d, J=8.4 Hz, 2H), 7.30-7.28 (m, 1H), 4.66 (d, J=6.0 Hz, 2H), 4.19 (s, 2H), 4.16 (s, 3H), 3.74-3.70 (m, 2H), 3.20-3.16 (m, 2H), 3.10 (s, 2H), 1.58-1.57 (m, 2H), 1.50 (s, 6H), 1.07-1.04 (m, 2H). MS (ESI): m/z 499.3 [M+H]⁺.

Compounds given in Table 4 below were prepared by derivatization of 6-((1-((1-Amino-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (70) either directly with the appropriate acylating agent (e.g. see Example 3), or via EDC-mediated amide coupling (e.g. see Example 26) with an N-Boc amino acid followed by Boc deprotection.

TABLE 4

| Example/Compound Number | Compound Structure and Name | Physical Data MS (m/z), $^1$H NMR |
|---|---|---|
| 71 | 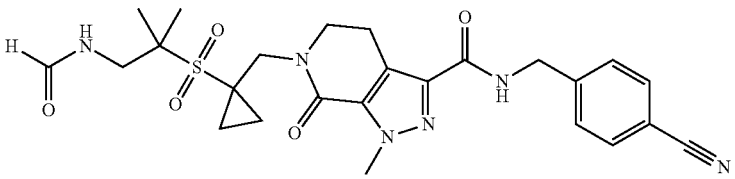 [SMILES: Cn1nc(C(=O)NCc2ccc(C#N)cc2)c2c1C(=O)N(CC1(S(=O)(=O)C(C)(C)CNC=O)CC1)CC2]<br>N-(4-Cyanobenzyl)-6-((1-(((1-formamido-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 527.2 [M + H]$^+$. $^1$H NMR (400 MHz, CDCl$_3$) δ 8.27 (d, J = 1.6 Hz, 1H), 7.65-7.63 (m, 2H), 7.46 (d, J = 8.4 Hz, 2H), 7.30-7.27 (m, 1H), 6.58 (s, 1H), 4.66 (d, J = 6.4 Hz, 2H), 4.16 (s, 5H), 3.76 (d, J = 6.0 Hz, 2H), 3.72-3.69 (m, 2H), 3.21-3.17 (m, 2H), 1.58-1.57 (m, 2H), 1.55 (s, 6H), 1.11-1.08 (m, 2H). |
| 72 | 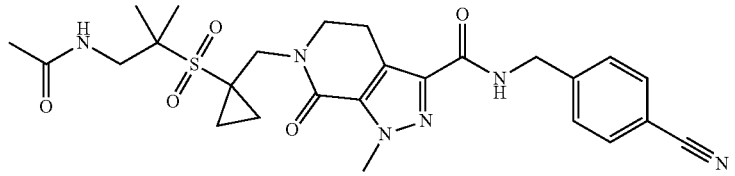 [SMILES: CC(=O)NCC(C)(C)S(=O)(=O)C1(CN2CCc3c(C(=O)NCc4ccc(C#N)cc4)nn(C)c3C2=O)CC1]<br>6-((1-(((1-Acetamido-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 541.0 [M + H]$^+$. $^1$H NMR (400 MHz, CDCl$_3$) δ 7.64 (d, J = 8.0 Hz, 2H), 7.46 (d, J = 8.4 Hz, 2H), 7.30-7.29 (m, 1H), 6.46-6.43 (m, 1H), 4.66 (d, J = 6.0 Hz, 2H), 4.16 (s, 5H), 3.72-3.69 (m, 4H), 3.21-3.17 (m, 2H), 2.03 (s, 3H), 1.57-1.56 (m, 2H), 1.53 (s, 6H), 1.11-1.07 (m, 2H). |
| 73 | 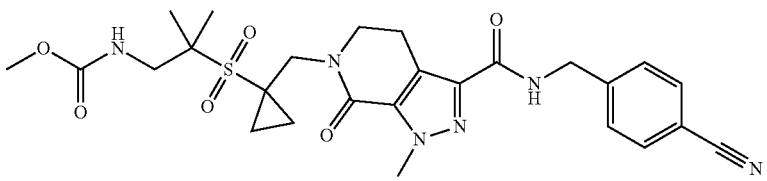 [SMILES: COC(=O)NCC(C)(C)S(=O)(=O)C1(CN2CCc3c(C(=O)NCc4ccc(C#N)cc4)nn(C)c3C2=O)CC1]<br>Methyl (2-((1-(((3-((4-cyanobenzyl)carbamoyl)-1-methyl-7-oxo-1,4,5,7-tetrahydro-6H-pyrazolo[3,4-c]pyridin-6-yl)methyl)cyclopropyl)sulfonyl)-2-methylpropyl)carbamate | MS (ESI): m/z 557.2 [M + H]$^+$. $^1$H NMR (400 MHz, CDCl$_3$) δ 7.64 (d, J = 8.4 Hz, 2H), 7.46 (d, J = 8.4 Hz, 2H), 4.67-4.66 (m, 2H), 4.16-4.14 (m, 5H), 3.72-3.70 (m, 2H), 3.69 (s, 3H), 3.64-3.63 (m, 2H), 3.20-3.17, (m, 2H), 1.55-1.53 (m, 2H), 1.53 (s, 6H), 1.09-1.08 (m, 2H). |
| 74 | 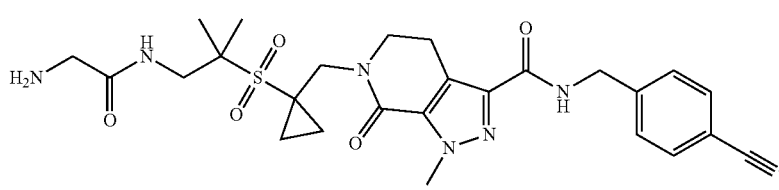<br>6-((1-(((1-(2-Aminoacetamido)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide. | MS (ESI): m/z 556.2 [M + H]$^+$. $^1$H NMR (400 MHz, CDCl$_3$) δ 8.11 (br s, 1H), 7.95-7.92 (m, 1H), 7.64 (d, J = 8.0 Hz, 2H), 7.45 (d, J = 8.4 Hz, 2H), 7.31-7.28 (m, 1H), 4.66 (d, J = 6.4 Hz, 2H), 4.17-4.15 (m, 5H), 3.75-3.69 (m, 4H), 3.43 (s, 2H), 3.20-3.17 (m, 2H), 1.59-1.56 (m, 2H), 1.53 (s, 6H), 1.11-1.08 (m, 2H). |
| 75 | 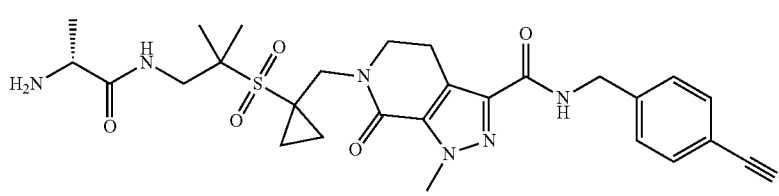<br>(R)-6-((1-(((1-(2-Aminopropanamido)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide. | MS (ESI): m/z 570.2 [M + H]$^+$. $^1$H NMR (400 MHz, CDCl$_3$) δ 8.05 (s, 1H), 7.95 (s, 1H), 7.64 (d, J = 8.0 Hz, 2H), 7.46 (d, J = 8.4 Hz, 2H), 7.31-7.29 (m, 1H), 4.66 (d, J = 6.4 Hz, 2H), 4.17-4.15 (m, 5H), 3.73-3.69 (m, 4H), 3.57-3.53 (m, 1H), 3.20-3.17 (m, 2H), 1.60-1.57 (m, 2H), 1.52 (s, 6H), 1.36 (d, J = 7.2 Hz, 3H), 1.11-1.09 (m, 2H). SFC (C-06637-140-P1B_1, AD-3-IPA(DEA)-40-3 mL-35T) Rt = 1.155 min, EE value: 100% |

TABLE 4-continued

| Example/ Compound Number | Compound Structure and Name | Physical Data MS (m/z), $^1$H NMR |
|---|---|---|
| 76 | 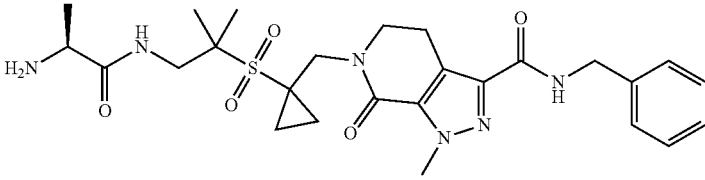<br>(S)-6-((1-((1-(2-Aminopropanamido)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 570.2 [M + H]$^+$.<br>$^1$H NMR (400 MHz, CDCl$_3$) δ 8.07 (s, 1H), 7.94-7.93 (m, 1H), 7.64 (d, J = 8.4 Hz, 2H), 7.46 (d, J = 8.4 Hz, 2H), 7.31-7.29 (m, 1H), 4.66 (d, J = 6.4 Hz, 2H), 4.17-4.12 (m, 5H), 3.73-3.69 (m, 4H), 3.58-3.56 (m, 1H), 3.19-3.17 (m, 2H), 1.60-1.57 (m, 2H), 1.52 (s, 6H), 1.37 (d, J = 6.8 Hz, 3H), 1.11-1.08 (m, 2H). SFC (C-06637-141-P1B_1, AD-3-IPA(DEA)-40-3mL-35T) Rt = 1.506 min, EE value: 100% |
| 77 | 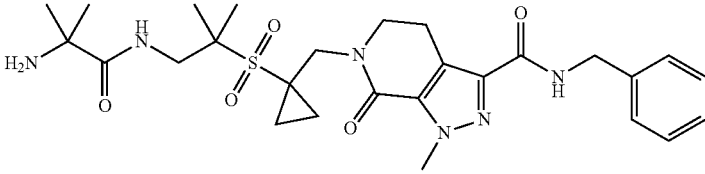<br>6-((1-((1-(2-Amino-2-methylpropanamido)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 584.1 [M + H]$^+$.<br>$^1$H NMR (400 MHz, CDCl$_3$) δ 8.30 (br s, 1H), 7.64 (d, J = 8.4 Hz, 2H), 7.46 (d, J = 8.4 Hz, 2H), 7.29-7.28 (m, 1H), 4.66 (d, J = 6.4 Hz, 2H), 4.17-4.15 (m, 5H), 3.73-3.67 (m, 4H), 3.20-3.13 (m, 2H), 1.60-1.57 (m, 2H), 1.51 (s, 6H), 1.37 (s, 6H), 1.11-1.08 (m, 2H). |
| 78 | 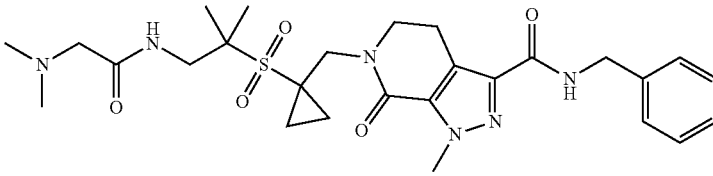<br>N-(4-Cyanobenzyl)-6-((1-((1-(2-(dimethylamino)acetamido)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 584.2 [M + H]$^+$.<br>$^1$H NMR (400 MHz, DMSO-d$_6$) δ 8.97-8.94 (m, 1H), 7.86-7.83 (m, 1H), 7.78 (d, J = 8.0 Hz, 2H), 7.47 (d, J = 8.0 Hz, 2H), 4.46 (d, J = 6.4 Hz, 2H), 4.11 (s, 3H), 4.07 (s, 2H), 3.63-3.60 (m, 2H), 3.57-3.55 (m 2H), 3.00-2.98 (m, 2 H), 2.89 (s, 2H), 2.20 (s, 6H), 1.36 (s, 6H), 1.36-1.34 (m 1H), 1.07-1.04 (m, 2 H). |

Example 79

N-(4-cyanobenzyl)-6-((1-((1-(1-fluoro-2-hydroxy-ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (79)

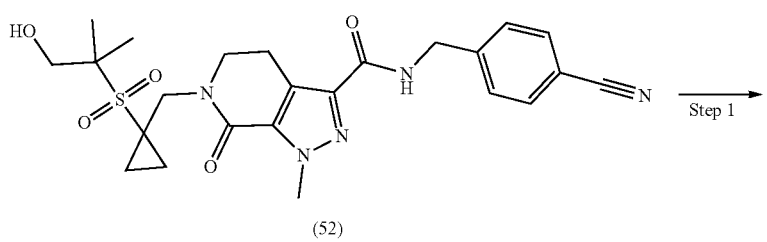

(52)

Step 1 →

-continued

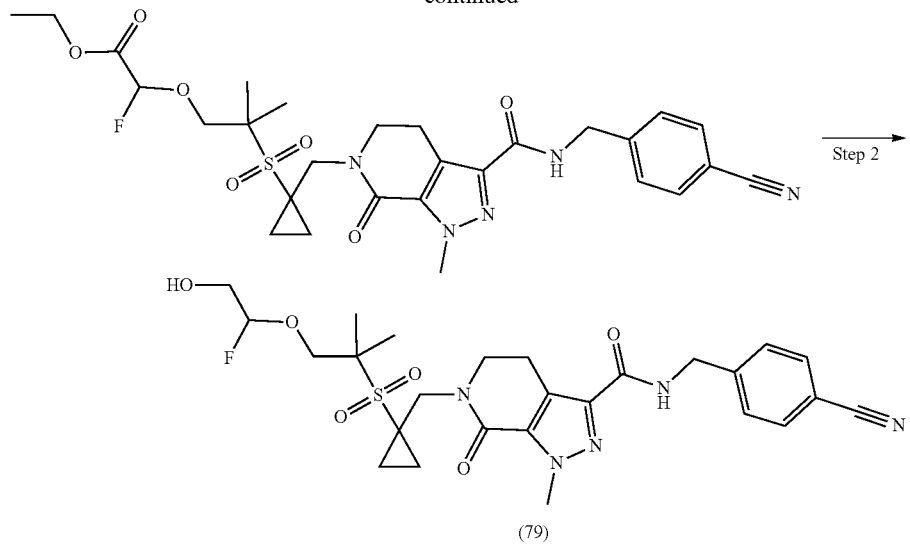

(79)

Step 1: A solution of N-(4-cyanobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (52) (500 mg, 1.0 mmol, 1.0 equiv) in THF (5 mL) was cooled to 0° C. before NaH (60% in mineral oil, 80 mg, 2.0 mmol, 2.0 equiv) was added (gas evolution). The mixture was stirred at 0° C. for 30 min, then ethyl 2-bromo-2-fluoroacetate (370 mg, 2.0 mmol, 2.0 equiv) was added and the mixture was stirred at 60° C. for 4.5 h. The reaction was diluted with H$_2$O (5 mL) and extracted with EtOAc (3×10 mL), then the combined organic extracts were dried over Na$_2$SO$_4$, filtered and concentrated. The residue was purified by RP-HPLC to give ethyl 2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)-2-fluoroacetate. TLC R$_f$=0.5 (EtOAc). $^1$H NMR (400 MHz, CDCl$_3$) δ 7.65 (d, J=8.2 Hz, 2H), 7.47 (d, J=8.2 Hz, 2H), 7.33-7.29 (m, 1H), 5.66-5.48 (m, 1H), 4.67 (d, J=6.4 Hz, 2H), 4.35 (q, J=7.2 Hz, 2H), 4.16 (s, 3H), 4.14-4.11 (m, 2H), 4.01-3.92 (m, 1H), 3.77-3.71 (m, 2H), 3.18 (t, J=6.8 Hz, 2H), 1.66-1.59 (m, 2H), 1.55 (s, 6H), 1.37 (t, J=7.2 Hz, 3H), 1.14-1.05 (m, 2H). MS (ESI): m/z 604.3 [M+H]$^+$.

Step 2: A solution of ethyl 2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)-2-fluoroacetate (500 mg, 0.83 mmol, 1.0 equiv) in THF (5 mL) was cooled to −30° C. before a solution of NaBH$_4$ (157 mg, 4.14 mmol, 5.0 equiv) in H$_2$O (5 mL) was added slowly (gas evolution). The resulting mixture was stirred at 20° C. for 1 h, then it was poured into water (5 mL) and extracted with EtOAc (3×10 mL). The combined organic extracts were dried over Na$_2$SO$_4$, filtered and concentrated. The residue was purified by RP-HPLC to give N-(4-cyanobenzyl)-6-((1-((1-((1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (79). TLC R$_f$=0.3 (EtOAc). MS (ESI): m/z 562.4 [M+H]$^+$.

Example 80 and Example 81

(R)- or (S)—N-(4-Cyanobenzyl)-6-((1-((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (80)

and (R)- or (S)—N-(4-cyanobenzyl)-6-((1-((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (81)

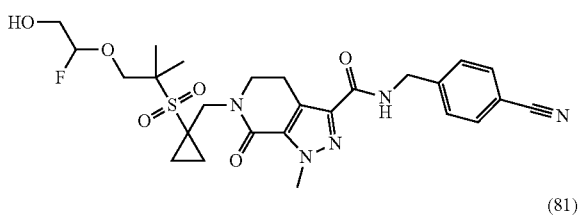

(80)

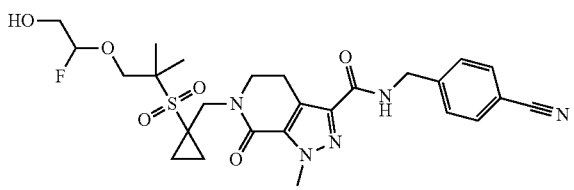

(81)

(R)- or(S)—N-(4-Cyanobenzyl)-6-((1-((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (80) and (R)- or (S)—N-(4-cyanobenzyl)-6-((1-((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]

pyridine-3-carboxamide (81) were obtained by chiral SFC separation of N-(4-cyanobenzyl)-6-((1-((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (79).

Unless otherwise indicated, examples indicate relative stereochemistry.

SFC: CHIRALCEL OJ-3, 5-40% MeOH (0.05% Et$_2$NH), 3 mL/min

Example (80) SFC: Rt=1.923 min, ee 100%, $^1$H NMR (400 MHz, CDCl$_3$) δ 7.65 (d, J=8.2 Hz, 2H), 7.47 (d, J=8.2 Hz, 2H), 7.30 (m, 1H), 5.49-5.23 (m, 1H), 4.67 (d, J=6.4 Hz, 2H), 4.33-4.23 (m, 2H), 4.15 (s, 3H), 4.12-4.10 (m, 1H), 3.89-3.84 (m, 1H), 3.80-3.78 (m, 2H), 3.74-3.67 (m, 2H), 3.20-3.17 (m, 2H), 1.57-1.55 (m, 2H), 1.54 (s, 6H), 1.02 (t, J=5.6 Hz, 2H). MS (ESI): m/z 562.4 [M+H]$^+$.

Example (81) SFC: Rt=2.001 min, ee 88%, $^1$H NMR (400 MHz, CDCl$_3$) δ 7.65 (d, J=8.2 Hz, 2H), 7.47 (d, J=8.2 Hz, 2H), 7.30 (br s, 1H), 5.47-5.23 (m, 1H), 4.67 (d, J=6.4 Hz, 2H), 4.31-4.23 (m, 2H), 4.15 (s, 3H), 4.12 (d, J=11.2 Hz, 1H), 3.86 (dd, J=1.6, 11.2 Hz, 1H), 3.80 (br dd, J=4.3, 8.7 Hz, 2H), 3.74-3.62 (m, 2H), 3.47 (br s, 1H), 3.19 (t, J=6.9 Hz, 2H), 1.58 (br d, J=1.3 Hz, 2H), 1.55 (d, J=2.4 Hz, 6H), 1.02 (t, J=5.6 Hz, 2H). MS (ESI): m/z 562.4 [M+H]$^+$.

Example 82 and Example 83

(R)- or (S)-6-((1-((1-(2-amino-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (82)

and (R)- or (S)-6-((1-((1-(2-amino-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (83)

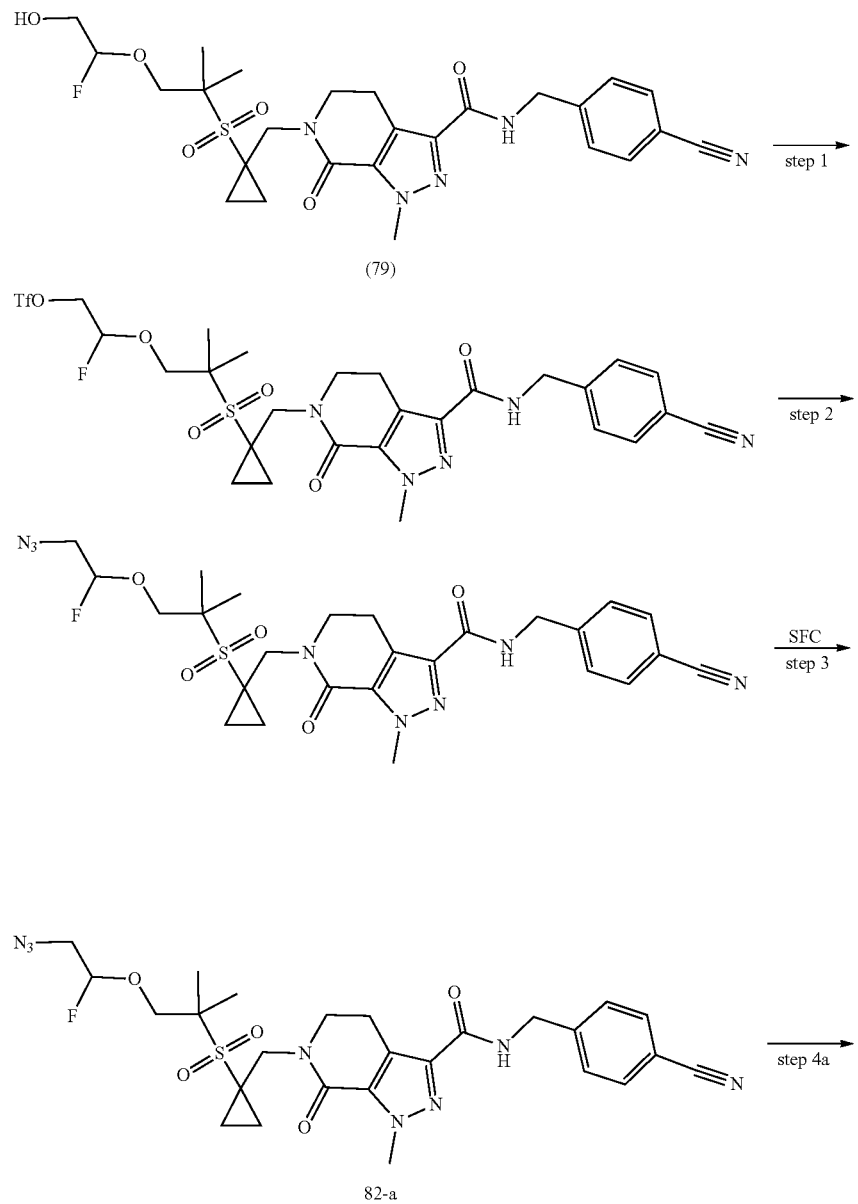

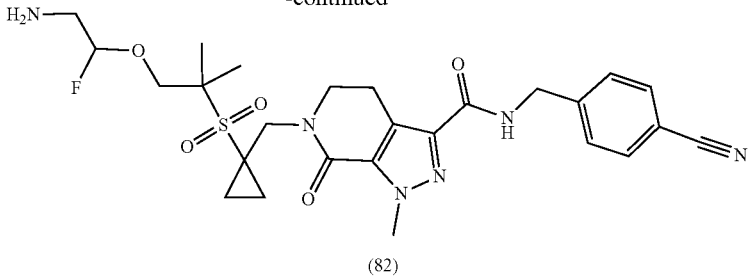

(82)

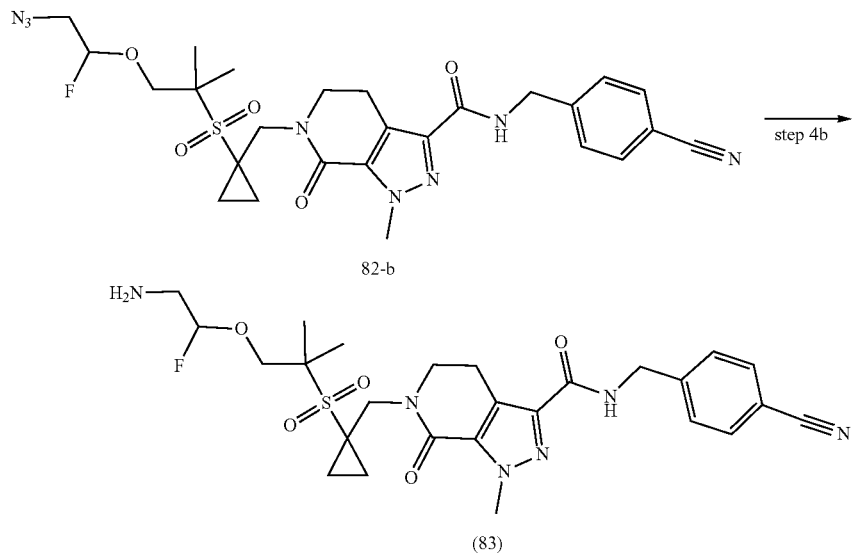

82-b (83)

Step 1: A solution of N-(4-cyanobenzyl)-6-((1-(((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (79)(550 mg, 0.98 mmol, 1.0 equiv) and Et₃N (0.21 mL, 1.47 mmol, 1.5 equiv) in DCM (10 mL) was cooled to 0° C. before Tf₂O (0.18 mL, 1.08 mmol, 1.1 equiv) was added dropwise. The resulting mixture was stirred at 20° C. for 1 h before the reaction mixture was poured into water (10 mL) and extracted by DCM (3×10 mL). The combined organic extracts were dried over Na₂SO₄, filtered and concentrated. The residue was purified by column chromatography (SiO₂, 50% EtOAc/petroleum ether) to give 2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)-2-fluoroethyl trifluoromethanesulfonate. TLC R$_f$=0.3 (50% EtOAc/petroleum ether).

Step 2: A mixture of 2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)-2-fluoroethyl trifluoromethanesulfonate (350 mg, 0.50 mmol, 1.0 equiv) and NaN₃ (66 mg, 1.01 mmol, 1.0 equiv) in DMF (5 mL) was stirred at 80° C. for 3 h. The reaction mixture was poured into water (10 mL) and extracted with EtOAc (3×15 mL), then the combined organic extracts were dried over Na₂SO₄, filtered and concentrated. The residue was purified by prep-TLC (SiO₂, EtOAc) to give (6-((1-((1-(2-azido-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide. TLC R$_f$=0.5 (EtOAc). MS (ESI): m/z 587.3 [M+H]⁺.

Step 3: (6-((1-((1-(2-azido-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (250 mg, 0.43 mmol) was subjected to chiral SFC separation to give (R)- or (S)-6-((1-((1-(2-azido-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (82-a) and (R)- or (S)-6-((1-((1-(2-azido-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (82-b).
Unless otherwise indicated, examples indicate relative stereochemistry.
SFC: AmyCoat, 60% EtOH (0.05% Et₂NH), 3 mL/min
(82-a): (R)- or (S)-6-((1-((1-(2-azido-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide. Chiral SFC peak 1: Rt=1.100 min, ee 100%. MS (ESI): m/z 587.2 [M+H]⁺.
(82-b): (R)- or (S)-6-((1-((1-(2-azido-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide Chiral SFC peak 2: Rt=1.496 min, ee 100%. MS (ESI): m/z 587.3 [M+H]⁺.

Step 4a: A mixture of (R)- or (S)-6-((1-((1-(2-azido-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (82-a) (100 mg, 0.17 mmol) and Pd/C (50 mg) in EtOAc (10 mL) was stirred at 20° C. under a hydrogen atmosphere for 2 h before the suspension was filtered through a pad of Celite®.

The filter cake was washed with EtOAc (10 mL) and the combined filtrates were concentrated. The residue was purified by RP-HPLC to give (R)- or (S)-6-((1-((1-(2-amino-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (82). TLC R$_f$=0.3 (1:10 MeOH/EtOAc). $^1$H NMR (400 MHz, CDCl$_3$) δ 7.56 (d, J=8.2 Hz, 2H), 7.38 (d, J=8.2 Hz, 2H), 7.21 (br s, 1H), 5.29-5.05 (m, 1H), 4.58 (d, J=6.4 Hz, 2H), 4.10 (m, 2H), 4.08-4.06 (m, 3H), 4.06-4.01 (m, 1H), 3.80-3.74 (m, 1H), 3.64 (t, J=6.8 Hz, 2H), 3.16-3.07 (m, 2H), 2.91 (m, 1H), 1.54-1.49 (m, 2H), 1.48-1.41 (m, 6H), 1.02-0.97 (m, 2H). MS (ESI): m/z 561.3 [M+H]$^+$. SFC Rt=2.814 min, 100% ee [CHIRALPAK IC-3, 40% EtOH (0.05% Et$_2$NH), 3 mL/min]. Unless otherwise indicated, examples indicate relative stereochemistry.

Step 4b: (R)- or (S)-6-((1-((1-(2-Amino-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (83) was obtained using the method used to obtain (R)- or (S)-6-((1-((1-(2-amino-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (82), except (R)- or (S)-6-((1-((1-(2-azido-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (82-a) was replaced with (R)- or (S)-6-((1-((1-(2-azido-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (82-b). TLC R$_f$=0.3 (1:10 MeOH/EtOAc). $^1$H NMR (400 MHz, CDCl$_3$) δ 7.56 (d, J=8.2 Hz, 2H), 7.38 (d, J=8.2 Hz, 2H), 7.24-7.20 (m, 1H), 5.34-5.13 (m, 1H), 4.58 (d, J=6.2 Hz, 2H), 4.09 (s, 2H), 4.06 (s, 3H), 4.03 (m, 1H), 3.84-3.75 (m, 1H), 3.67-3.59 (m, 2H), 3.09 (t, J=6.8 Hz, 2H), 3.01-2.92 (m, 1H), 2.97 (m, 1H), 2.47 (br s, 2H), 1.53-1.48 (m, 2H), 1.46 (d, J=8.2 Hz, 6H), 1.03-0.94 (m, 2H). MS (ESI): m/z 561.3 [M+H]$^+$. SFC Rt=3.214 min, 68% ee [CHIRALPAK IC-3, 40% EtOH (0.05% Et$_2$NH), 3 mL/min]. Unless otherwise indicated, examples indicate relative stereochemistry.

Example 84: N-(4-Cyanobenzyl)-6-((1-((1-(1,1-difluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (84)

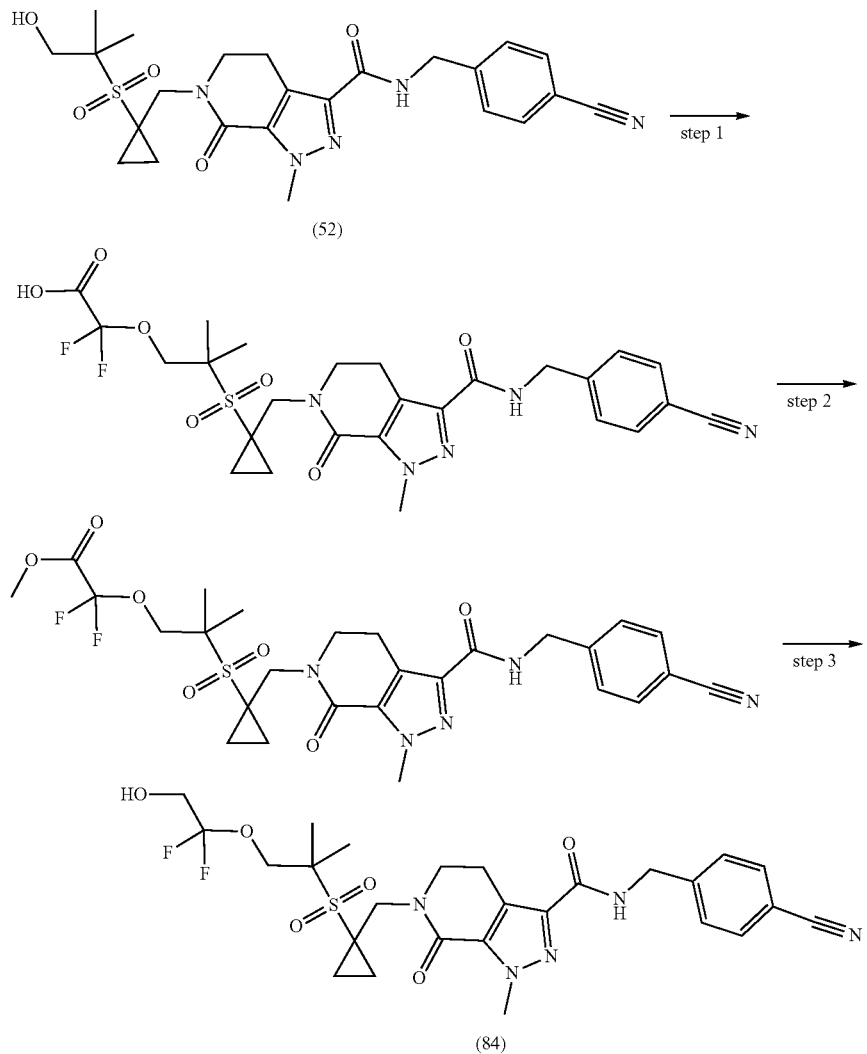

Step 1: 2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)-2,2-difluoroacetic acid was obtained using the method described in step 1 of Example 79, except ethyl 2-bromo-2-fluoroacetate was replaced with potassium 2-bromo-2,2-difluoroacetate. MS (ESI): m/z 594.2 [M+H]$^+$.

Step 2: To a mixture of 2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)-2,2-difluoroacetic acid (400 mg, 0.67 mmol, 1.0 equiv) in toluene (4 mL) and MeOH (1 mL) was added TMS diazomethane (2.0 M in hexanes, 1.3 mL, 2.6 mmol, 3.9 equiv) at 25° C. The mixture was stirred at 25° C. for 1 h before it was quenched with AcOH (0.2 mL) and concentrated to methyl 2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)-2,2-difluoroacetate. MS (ESI): m/z 608.3 [M+H]$^+$.

Step 3: N-(4-cyanobenzyl)-6-((1-((1-(1,1-difluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (84) was obtained using the method described in step 2 of Example 79, except ethyl 2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)-2-fluoroacetate was replaced with methyl 2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)-2,2-difluoroacetate. A 50 mg portion of the product was purified by RP-HPLC. $^1$H NMR (400 MHz, CDCl$_3$) δ 7.64 (d, J=8.0 Hz, 2H), 7.45 (d, J=8.0 Hz, 2H), 7.25 (m, 1H), 4.66 (m, 2H), 4.37 (m, 1H), 4.28 (s, 2H), 4.13 (s, 3H), 4.10 (s, 2H), 3.93 (m, 2H), 3.68 (m, 2H), 3.19 (m, 2H), 1.56 (br s, 2H), 1.54 (s, 6H), 1.02-0.95 (m, 2H). MS (ESI): m/z 580.2 [M+H]$^+$.

Example 85

6-((1-((1-(2-Amino-1,1-difluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (85)

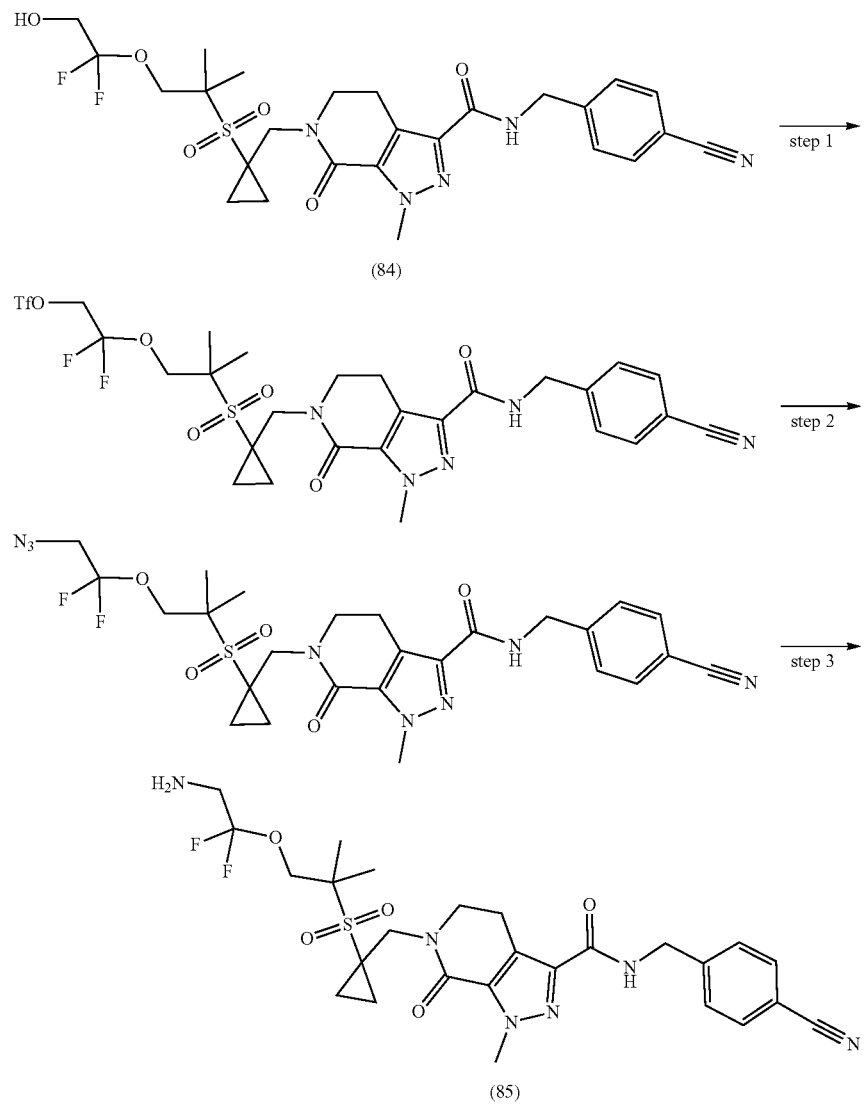

Step 1: 2-(2-((1-((3-((4-cyanobenzyl)carbamoyl)-1-methyl-7-oxo-1,4,5,7-tetrahydro-6H-pyrazolo[3,4-c]pyridin-6-yl)methyl)cyclopropyl)sulfonyl)-2-methylpropoxy)-2,2-difluoroethyl trifluoromethanesulfonate was obtained using the method described in step 1 of Example 82, except N-(4-cyanobenzyl)-6-((1-(((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (79) was replaced with N-(4-cyanobenzyl)-6-((1-(((1-(1,1-difluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (84). MS (ESI): m/z 712.0 [M+H]$^+$.

Step 2: 6-((1-(((1-(2-Azido-1,1-difluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide was obtained using the method described in step 2 of Example 82, except 2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)-2-fluoroethyl trifluoromethanesulfonate was replaced with 2-(2-((1-((3-((4-cyanobenzyl)carbamoyl)-1-methyl-7-oxo-1,4,5,7-tetrahydro-6H-pyrazolo[3,4-c]pyridin-6-yl)methyl)cyclopropyl)sulfonyl)-2-methylpropoxy)-2,2-difluoroethyl trifluoromethanesulfonate. MS (ESI): m/z 605.1 [M+H]$^+$.

Step 3: 6-((1-(((1-(2-Amino-1,1-difluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (85) was obtained using the method described in step 4a of Example 82, except (R)-6-((1-(((1-(2-Amino-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide was replaced with 6-((1-(((1-(2-Azido-1,1-difluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide. $^1$H NMR (400 MHz, CDCl$_3$) δ 7.66-7.62 (m, 2H), 7.46 (m, 2H), 7.29 (br s, 1H), 4.66 (d, J=6.0 Hz, 2H), 4.19-4.10 (m, 7H), 3.71 (m, 2H), 3.21-3.10 (m, 4H), 1.61-1.57 (m, 2H), 1.54 (s, 6H), 1.10-1.04 (m, 2H). MS (ESI): m/z 579.2 [M+H]$^+$.

Example 86

N-(4-Cyanobenzyl)-6-((1-((1-(2-hydroxy-2-methylpropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (86)

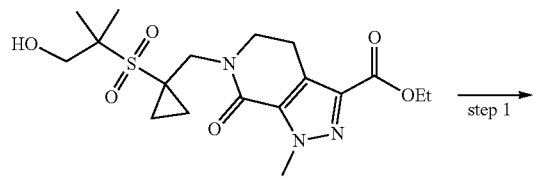

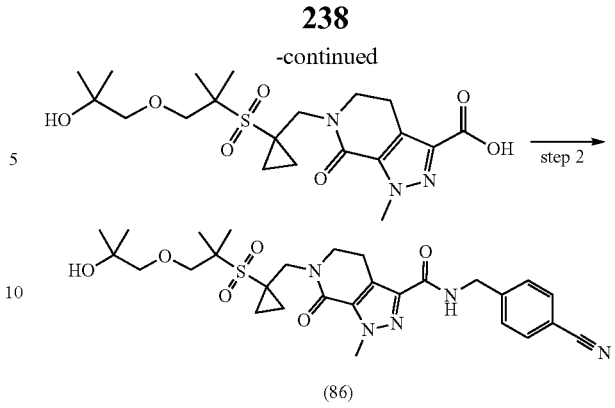

Step 1: A solution of ethyl 6-((1-(1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate (see step 1 of intermediate (int-32) synthesis) (200 mg, 0.48 mmol, 1.0 equiv) in DMF (5 mL) was cooled to 0° C. before NaH (60% in mineral oil, 39 mg, 0.97 mmol, 2.0 equiv) was added (gas evolution). The mixture was stirred at 25° C. for 0.5 h, then 2,2-dimethyloxirane (70 mg, 0.97 mmol, 2.0 equiv) was added and the mixture was stirred at 100° C. in a sealed tube for 12 h. The reaction was diluted with H$_2$O (3 mL) and extracted with EtOAc (3×10 mL), then the combined organic extracts were dried over Na$_2$SO$_4$, filtered and concentrated. The residue was purified by RP-HPLC to give 6-((1-(((1-(2-hydroxy-2-methylpropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid. MS (ESI): m/z 458.2 [M+H]$^+$.

Step 2: N-(4-Cyanobenzyl)-6-((1-(((1-(2-hydroxy-2-methylpropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (86) was obtained using the method described in step 1 of Example 26, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-(((1-(2-hydroxy-2-methylpropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid and hydrazine was replaced with 4-(aminomethyl)benzonitrile hydrochloride. $^1$H NMR (400 MHz, MeOH-d$_4$) δ 7.74-7.68 (m, 2H), 7.53 (d, J=8.4 Hz, 2H), 4.61 (s, 2H), 4.21 (s, 2H), 4.19-4.14 (m, 3H), 3.81-3.70 (m, 4H), 3.38 (s, 2H), 3.10 (t, J=6.8 Hz, 2H), 1.52 (s, 8H), 1.25 (s, 6H), 1.17-1.09 (m, 2H). MS (ESI): m/z 572.5 [M+H]$^+$.

Example 87

N-(4-Cyanobenzyl)-6-((1-((1-(2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (87)

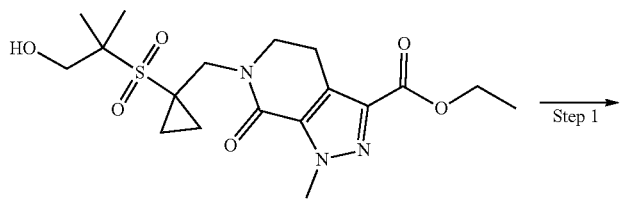

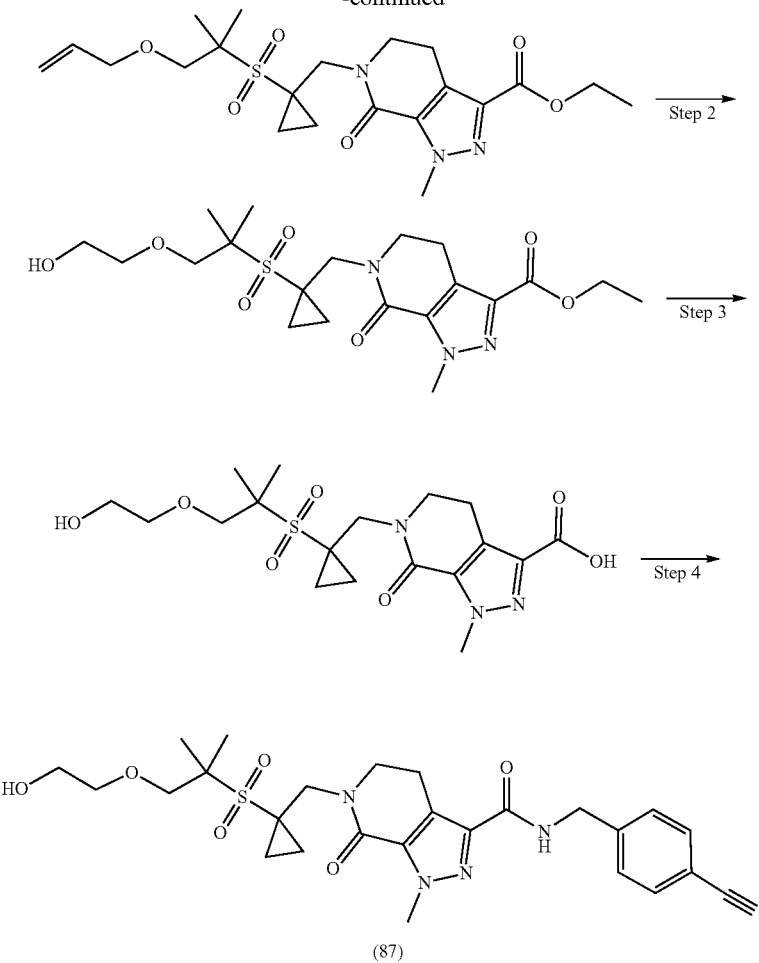

Step 1: To a solution of ethyl 6-((1-(((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate (see step 1 of intermediate (int-32) synthesis) (1.5 g, 3.63 mmol, 1.0 equiv) and 3-bromoprop-1-ene (877 mg, 7.26 mmol, 2.0 equiv) in THF (10 mL) was added NaH (60% in mineral oil, 290 mg, 7.26 mmol, 2.0 equiv) at 25° C. (gas evolution). The mixture was stirred at 20° C. for 16 h before it was poured into $H_2O$ (10 mL) and extracted with EtOAc (3×15 mL). The combined organic extracts were dried over $Na_2SO_4$, filtered and concentrated to give ethyl 6-((1-(((1-(allyloxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylate. MS (ESI): m/z 454.2 [M+H]⁺.

Step 2: Ethyl 6-((1-(((1-(2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylate was obtained using the method described in step 2 in the synthesis of intermediate (int-29), except ethyl 1-(4-methoxybenzyl)-6-((1-((2-methylbut-3-en-2-yl)sulfonyl)cyclopropyl)methyl)-7-oxo-4,5,6,7-tetrahydro-1H-pyrazolo[3,4-c]pyridine-3-carboxylate was replaced with ethyl 6-((1-((1-(allyloxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylate. TLC $R_f$=0.4 (EtOAc). MS (ESI): m/z 458.4 [M+H]⁺.

Step 3: 6-((1-(((1-(2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid was obtained using the method described in the synthesis of intermediate (int-14), except ethyl 1-methyl-6-((1-(((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-((1-(allyloxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylate. MS (ESI): m/z 430.2 [M+H]⁺.

Step 4: N-(4-Cyanobenzyl)-6-((1-((1-(2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (87) was obtained using the method described in step 1 of Example 26, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-(((1-(2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid and hydrazine was replaced with 4-(aminomethyl)benzonitrile hydrochloride. H NMR (400 MHz, $CDCl_3$) δ 7.63 (d, J=8.2 Hz, 2H), 7.45 (d, J=8.2 Hz, 2H), 7.31-7.27 (m, 1H), 4.65 (d, J=6.4 Hz, 2H), 4.26 (s, 2H), 4.14 (s, 3H), 3.87-3.76 (m, 2H), 3.72-3.68 (m, 2H), 3.66 (s, 3H), 3.63-3.59 (m, 2H), 3.43-3.33 (m, 1H), 3.16 (t, J=6.8 Hz, 2H), 1.56-1.52 (m, 2H), 1.50 (s, 6H), 1.03-0.96 (m, 2H). MS (ESI): m/z 544.3 [M+H]⁺.

Example 88

N-(4-Chlorobenzyl)-6-((1-((1-(2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (88)

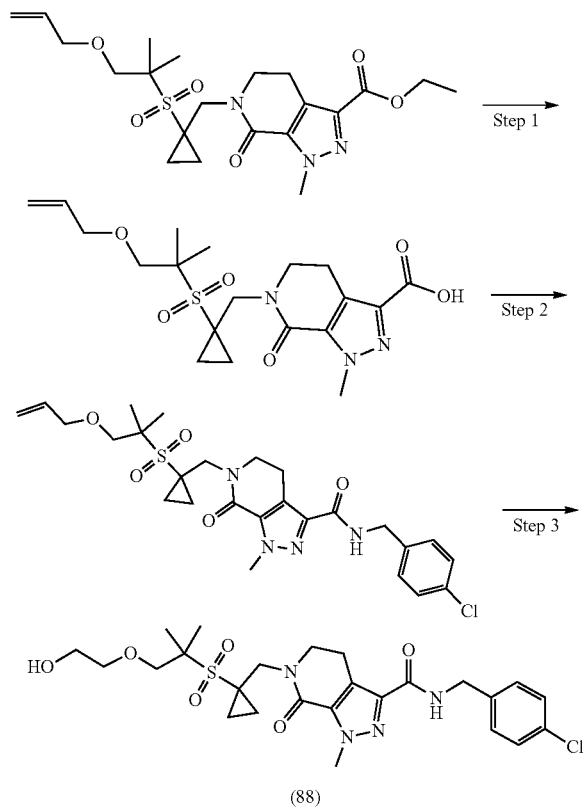

Step 1: 6-((1-((1-(Allyloxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid was obtained using the method described in the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-((1-(allyloxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylate. $^1$H NMR (400 MHz, DMSO-d$_6$) δ 14.53-11.01 (m, 1H), 5.93 (br s, 1H), 5.32 (br d, J=16.4 Hz, 1H), 5.19 (br d, J=8.4 Hz, 1H), 4.08 (br s, 3H), 4.05 (br s, 4H), 3.61 (br s, 4H), 2.95 (br s, 2H), 1.38 (br s, 6H), 1.34 (br s, 2H), 1.00 (br s, 2H). MS (ESI): m/z 426.2 [M+H]$^+$.

Step 2: 6-((1-((1-(Allyloxy)-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide was obtained using the method described in step 1 of Example 26, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((1-(Allyloxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid and hydrazine was replaced with (4-chlorophenyl)methanamine. $^1$H NMR (400 MHz, CDCl$_3$) δ 7.34-7.27 (m, 4H), 7.16 (m, 1H), 6.03-5.83 (m, 1H), 5.36-5.29 (m, 1H), 5.24 (m, 1H), 4.57 (d, J=6.0 Hz, 2H), 4.16 (s, 2H), 4.14 (s, 3H), 4.08-4.03 (m, 2H), 3.73 (m, 2H), 3.63 (s, 2H), 3.17 (m, 2H), 1.65-1.54 (m, 4H), 1.50 (s, 6H), 1.11-1.03 (m, 2H). MS (ESI): m/z 549.2 [M+H]$^+$.

Step 3. N-(4-Chlorobenzyl)-6-((1-((1-(2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (88) was obtained using the method described in step 2 in the synthesis of intermediate (int-29), except ethyl 1-(4-methoxybenzyl)-6-((1-((2-methylbut-3-en-2-yl)sulfonyl)cyclopropyl)methyl)-7-oxo-4,5,6,7-tetrahydro-1H-pyrazolo[3,4-c]pyridine-3-carboxylate was replaced with 6-((1-((1-(Allyloxy)-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide. $^1$H NMR (400 MHz, CDCl$_3$) δ 7.38-7.28 (m, 4H), 7.21-7.13 (m, 1H), 4.56 (d, J=6.0 Hz, 2H), 4.27 (s, 2H), 4.22-4.16 (m, 1H), 4.16-4.08 (m, 3H), 3.88-3.78 (m, 2H), 3.74-3.68 (m, 2H), 3.66 (s, 2H), 3.64-3.59 (m, 2H), 3.24-3.14 (m, 2H), 1.60-1.46 (m, 8H), 1.08-0.97 (m, 2H). MS (ESI): m/z 553.3 [M+H]$^+$.

Example 89

N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (89)

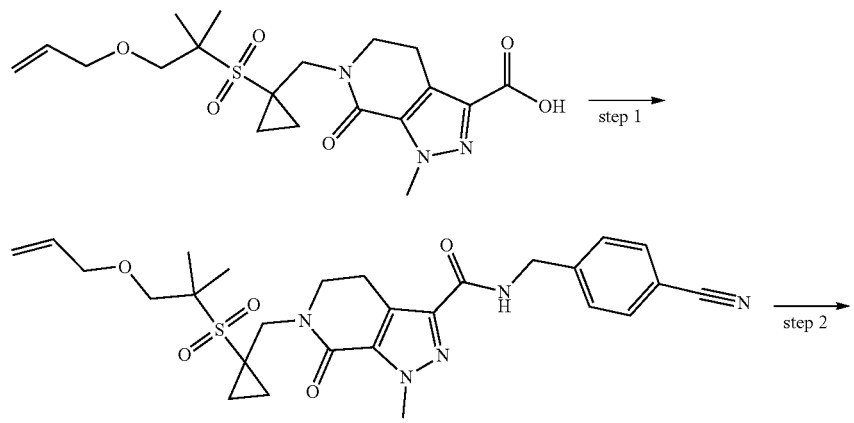

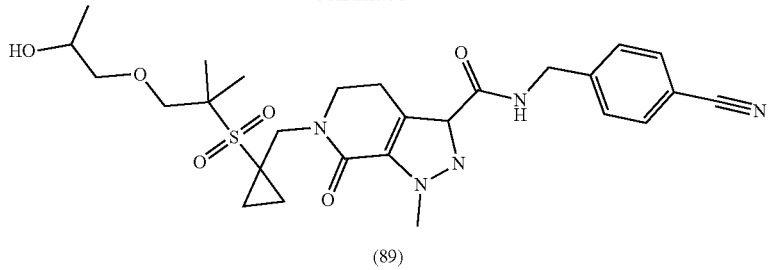

(89)

Step 1: 6-((1-((1-(Allyloxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide was obtained using the method described in step 1 of Example 26, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((1-(allyloxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid and hydrazine was replaced with 4-(aminomethyl)benzonitrile hydrochloride. MS (ESI): m/z 540.2 [M+H]$^+$.

Step 2: A solution of 6-((1-((1-(allyloxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (300 mg, 0.56 mmol, 1.0 equiv) in THF (5 mL) was cooled to 0° C. before a solution of Hg(OAc)$_2$ (354 mg, 1.11 mmol, 2.0 equiv) in H$_2$O (2 mL) was added. The mixture was stirred at 20° C. for 4 h, then a solution of NaBH$_4$ (53 mg, 1.39 mmol, 2.5 equiv) in H$_2$O (3 mL) was slowly added. The mixture was stirred at 20° C. for 1 h before it was poured into water (10 mL) and extracted with EtOAc (3×15 mL). The combined organic extracts were dried over Na$_2$SO$_4$, filtered and concentrated. The residue was purified by prep-TLC (SiO$_2$, EtOAc) to give N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (89). TLC R$_f$=0.3 (EtOAc). MS (ESI): m/z 558.1 [M+H]$^+$.

Example 90 and Example 91

(R)- or (S)—N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (90)

and (R)- or (S)—N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (91)

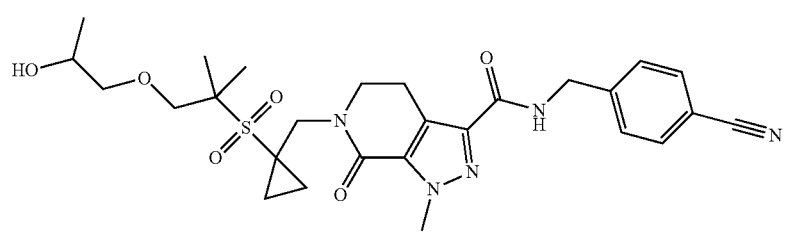

(90)

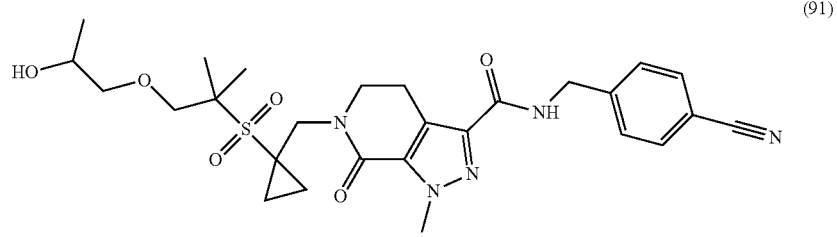

(91)

(R)- or (S)—N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (90) and (R)- or (S)—N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (91) were obtained by chiral SFC separation of N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (89). Unless otherwise indicated, examples indicate relative stereochemistry.

SFC: CHIRALPAK IC-3, 40% EtOH (0.05% Et$_2$NH), 3 mL/min.

(R)- or (S)—N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (90) SFC: Rt=4.943 min, ee 100%, $^1$H NMR (400 MHz, CDCl$_3$) δ 7.68-7.61 (d, J=8.4 Hz, 2H), 7.47 (d, J=8.4 Hz, 2H), 7.30 (br s, 1H), 4.67 (d, J=6.4 Hz, 2H), 4.26 (d, J=2.0 Hz, 2H), 4.16 (s, 3H), 4.07 (br t, J=6.2 Hz, 1H), 3.75-3.63 (m, 4H), 3.50 (m, 1H), 3.37 (m, 1H), 3.30 (br s, 1H), 3.18 (t, J=6.8 Hz, 2H), 1.59-1.55 (m, 2H), 1.53 (d, J=7.8 Hz, 6H), 1.20 (d, J=6.4 Hz, 3H), 1.07-0.98 (m, 2H). MS (ESI): m/z 558.4 [M+H]$^+$.

(R)- or (S)—N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (91). SFC: Rt=6.035 min. ee 97%, $^1$H NMR (400 MHz, CDCl$_3$) δ 7.65 (d, J=8.2 Hz, 2H), 7.47 (d, J=8.2 Hz, 2H), 7.30 (br s, 1H), 4.67 (d, J=6.4 Hz, 2H), 4.26 (s, 2H), 4.16 (s, 3H), 4.11-4.02 (m, 1H), 3.78-3.62 (m, 4H), 3.54-3.46 (m, 1H), 3.37 (m, 1H), 3.18 (t, J=6.8 Hz, 2H), 1.59-1.55 (m, 2H), 1.54-1.46 (m, 6H), 1.20 (d, J=6.54 Hz, 3H), 1.07-0.97 (m, 2H). MS (ESI): m/z 558.4 [M+H]$^+$.

Example 92

6-((1-(((1-(2-Aminoethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (92)

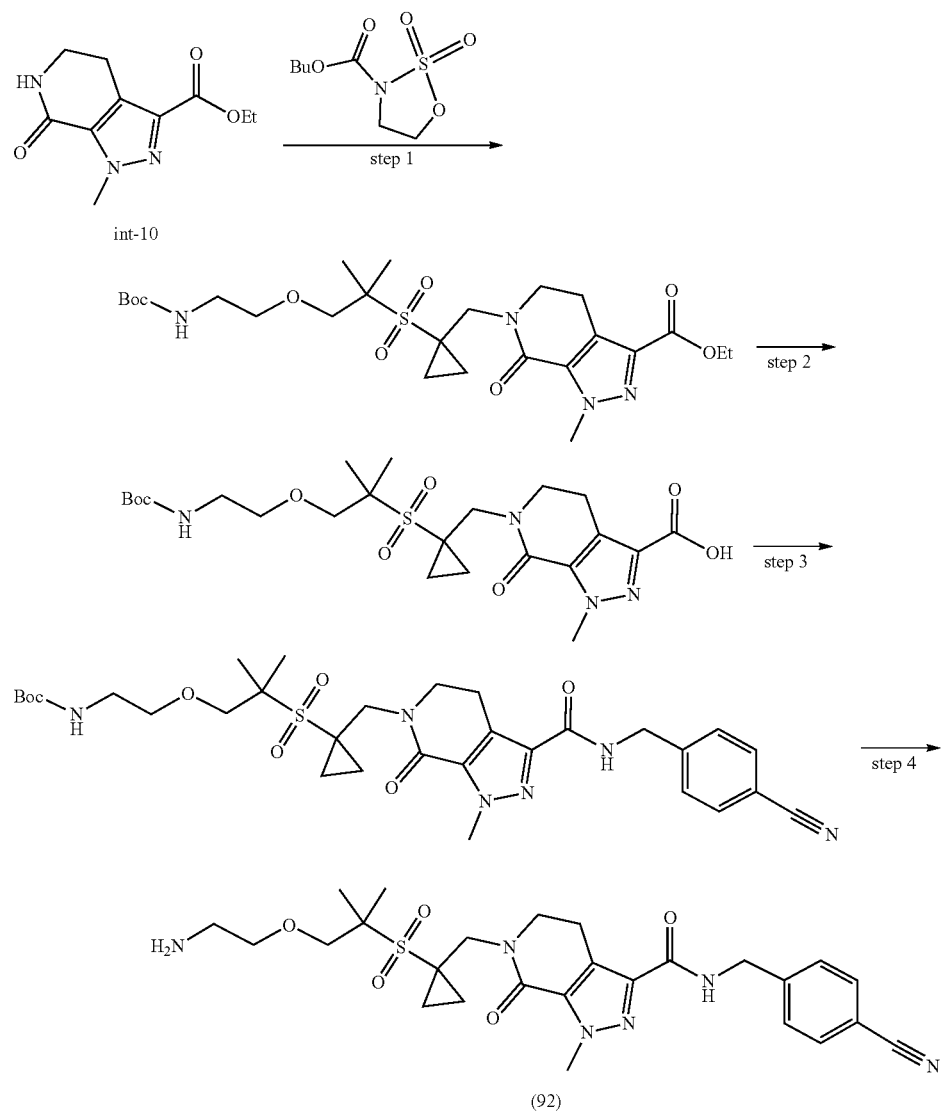

Step 2: 6-((1-((1-(2-((tert-Butoxycarbonyl)amino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid was obtained using the method described in the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-((1-(2-((tert-butoxycarbonyl)amino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylate. MS (ESI): m/z 429.2 [M-Boc+H]⁺.

Step 3: tert-Butyl (2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)ethyl)carbamate was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((1-(2-((tert-Butoxycarbonyl)amino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid. ¹H NMR (400 MHz, CDCl₃) b 4.40 (q, J=7.1 Hz, 2H), 4.30 (s, 2H), 4.21 (s, 3H), 4.18-4.14 (m, 2H), 3.73 (br t, J=6.8 Hz, 2H), 3.10 (br t, J=6.7 Hz, 2H), 1.58 (br s, 3H), 1.51 (s, 6H), 1.50 (s, 9H), 1.44-1.34 (m, 4H), 1.14-1.05 (m, 2H). MS (ESI): m/z 543.2 [M-Boc+H]⁺.

Step 4: A solution of HCl in MeOH (0.05 mL, 0.187 mmol, 3.0 equiv) was slowly added into a solution of tert-butyl (2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)ethyl) carbamate (40 mg, 0.062 mmol, 1.0 equiv) in DCM (2 mL). After 2 h at 25° C., the reaction mixture was adjusted to pH 8 with saturated NaHCO₃, then the mixture was filtered and purified by RP-HPLC to give 6-((1-((1-(2-Aminoethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (92). ¹H NMR (400 MHz, MeOH-d₄) δ 7.72-7.67 (m, 2H), 7.52 (d, J=8.4 Hz, 2H), 4.59 (s, 2H), 4.18 (s, 2H), 4.16 (s, 3H), 3.75-3.68 (m, 4H), 3.57 (t, J=5.4 Hz, 2H), 3.09 (t, J=6.8 Hz, 2H), 2.88 (t, J=5.4 Hz, 2H), 1.49-1.48 (m, 2H), 1.53-1.46 (m, 8H), 1.12-1.06 (m, 2H). MS (ESI): m/z 543.4 [M+H]⁺.

Compounds given in Table 5 below were prepared using methods analogous to those described in Example 92.

TABLE 5

| Example/Compound Number | Compound Structure and Name | Physical Data MS (m/z), ¹H NMR |
|---|---|---|
| 93 | 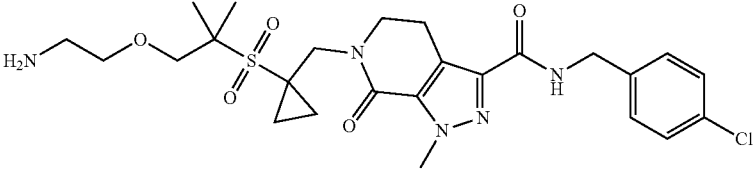 [SMILES: Cn1nc(C(=O)NCc2ccc(Cl)cc2)c2c1C(=O)N(CC1(S(=O)(=O)C(C)(C)COCCN)CC1)CC2]<br>6-((1-((1-(2-Aminoethoxy)-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide. | MS (ESI): m/z 552.3 [M + H]⁺. ¹H NMR (400 MHz, MeOH-d₄) δ 7.33-7.25 (m, 4H), 4.47 (s, 2H), 4.15 (s, 2H), 4.12 (s, 3H), 3.72-3.65 (m, 4H), 3.55 (t, J = 5.4 Hz, 2H), 3.06 (t, J = 6.8 Hz, 2H), 2.86 (t, J = 5.4 Hz, 2H), 1.50-1.43 (m, 8H), 1.09-1.03 (m, 2H). |
| 94 | 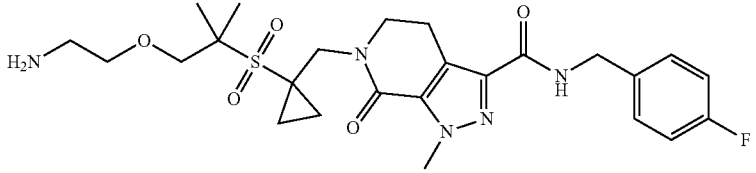 [SMILES: Cn1nc(C(=O)NCc2ccc(F)cc2)c2c1C(=O)N(CC1(S(=O)(=O)C(C)(C)COCCN)CC1)CC2]<br>6-((1-((1-(2-aminoethoxy)-2-methylpropan-2-yl)sulfonyl)cyclopropyl)methyl)-N-(4-fluorobenzyl)-1-methyl-7-oxo-4,5,6,7-tetrahydro-1H-pyrazolo[3,4-c]pyridine-3-carboxamide | MS (ESI): m/z 536.1 [M + H]⁺. ¹H NMR (400 MHz, MeOH-d₄) δ 7.38-7.35 (m, 2H), 7.09-7.00 (m, 2H), 4.51 (s, 2H), 4.20 (s, 2H), 4.16 (s, 3H), 3.78-3.69 (m, 4H), 3.67-3.56 (m, 2H), 3.11 (t, J = 6.8 Hz, 2H), 2.94 (t, J = 5.4 Hz, 2H), 1.58-1.44 (m, 8H), 1.15-1.02 (m, 2H). |
| 95 | 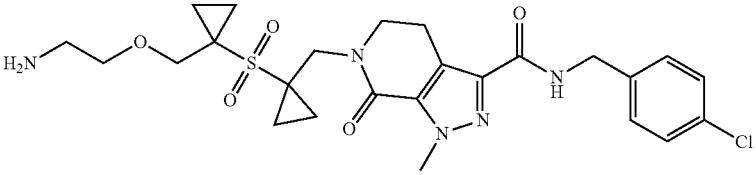 [SMILES: Cn1nc(C(=O)NCc2ccc(Cl)cc2)c2c1C(=O)N(CC1(S(=O)(=O)C3(COCCN)CC3)CC1)CC2]<br>6-((1-((1-((2-Aminoethoxy)methyl)cyclopropyl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide | MS (ESI): m/z 550.4 [M + H]⁺. ¹H NMR (400 MHz, MeOH-d₄) δ 7.34 (s, 4H), 4.52 (s, 2H), 4.17 (s, 5H), 3.82 (s, 2H), 3.72 (t, J = 6.8 Hz, 2H), 3.58 (t, J = 5.4 Hz, 2H), 3.11 (t, J = 6.8 Hz, 2H), 2.92 (t, J = 5.4 Hz, 2H), 1.52-1.46 (m, 4H), 1.21-1.16 (m, 2H), 1.14-1.10 (m, 2H), |

TABLE 5-continued

| Example/ Compound Number | Compound Structure and Name | Physical Data MS (m/z), ¹H NMR |
|---|---|---|
| 96 | 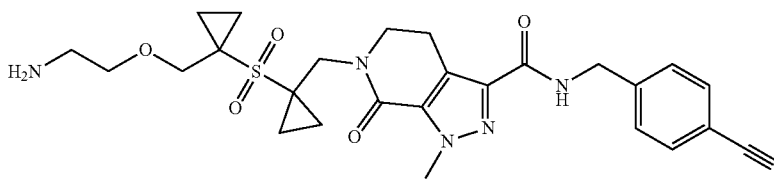<br>6-((1-(((1-((2-aminoethoxy)methyl)cyclopropyl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide. | MS (ESI): m/z 541.4 [M + H]⁺. ¹H NMR (400 MHz, DMSO-$d_6$) δ 8.97 (t, J = 6.4 Hz, 1H), 7.79 (d, J = 7.4 Hz, 2H), 7.48 (d, J = 8.0 Hz, 2H), 4.47 (d, J = 6.0 Hz, 2H), 4.12 (s, 3H), 4.04 (s, 2H), 3.71 (s, 2H), 3.62 (br t, J = 6.6 Hz, 2H), 3.42 (t, J = 5.8 Hz, 2H), 2.98 (br t, J = 6.8 Hz, 2H), 2.72 (t, J = 5.8 Hz, 2H), 1.32 (br s, 4H), 1.16-1.11 (m, 2H), 1.06-1.01 (m, 2H). |
| 97 | 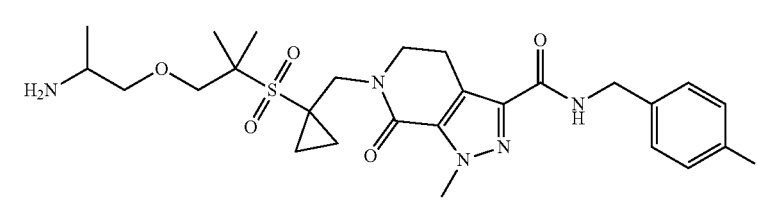<br>(R)-or (S)-6-((1-(((1-(2-Aminopropoxy)-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide. | MS (ESI): m/z 566.5 [M + H]⁺. ¹H NMR (400 MHz, CDCl₃) δ 7.36-7.26 (m, 4H), 7.19 (br t, J = 6.2 Hz, 1H), 4.57 (d, J = 6.2 Hz, 2H), 4.18 (s, 2H), 4.14 (s, 3H), 3.80-3.68 (m, 3H), 3.66-3.61 (m, 1H), 3.46-3.37 (m, 1H), 3.28-3.13 (m, 4H), 1.72 (br s, 2H), 1.61-1.56 (m, 2H), 1.53 (s, 3H), 1.51 (s, 3H), 1.11-1.02 (m, 5H). SFC $R_t$ = 1.278 min, 100% ee [CHIRALPAK AS-3, 20% EtOH (0.05% Et₂NH), 3 mL/min]. |
| 98 | 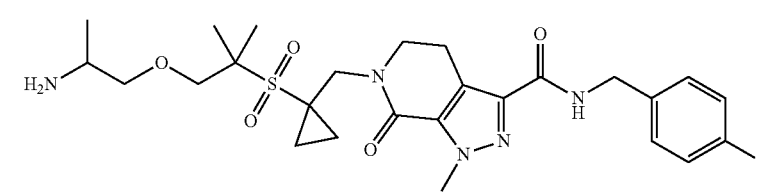<br>(R)-or (S)-6-((1-(((1-(2-Aminopropoxy)-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide | MS (ESI): m/z 566.5 [M + H]⁺. ¹H NMR (400 MHz, CDCl₃) δ 7.38-7.24 (m, 5H), 7.18 (br t, J = 6.2 Hz, 1H), 4.58 (d, J = 6.2 Hz, 2H), 4.18 (s, 2H), 4.14 (s, 3H), 3.79-3.67 (m, 3H), 3.67-3.58 (m, 1H), 3.47-3.33 (m, 1H), 3.29-3.14 (m, 4H), 1.63 (br s, 2H), 1.60-1.57 (m, 2H), 1.53 (s, 3H), 1.51 (s, 3H), 1.12-1.02 (m, 5H). SFC $R_t$ = 1.523 min, 96% ee [CHIRALPAK AS-3, 20% EtOH (0.05% Et₂NH), 3 mL/min]. |
| 99 | 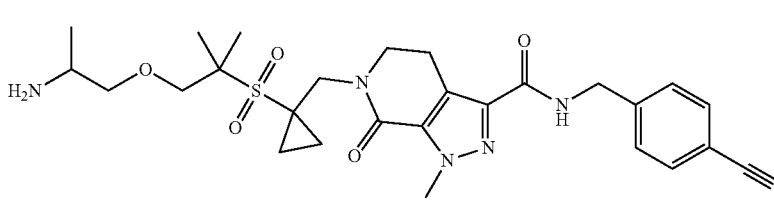<br>(R)-or (S)-6-((1-(((1-(2-Aminopropoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 557.2 [M + H]⁺. ¹H NMR (400 MHz, MeOH-$d_4$) δ 7.59 (d, J = 8.4 Hz, 2H), 7.42 (d, J = 8.4 Hz, 2H), 4.50 (s, 2H), 4.08 (s, 2H), 4.06 (s, 3H), 3.70-3.50 (m, 4H), 3.38 (m, 1H), 3.18-3.06 (m, 1H), 2.99 (t, J = 6.8 Hz, 2H), 1.41 (s, 3H), 1.39 (s, 5H), 1.05-0.95 (m, 5H). SFC $R_t$ = 2.874 min, 100% ee [CHIRALPAK AS-3, 10-40% EtOH (0.05% Et₂NH), 3 mL/min]. |

TABLE 5-continued

| Example/Compound Number | Compound Structure and Name | Physical Data MS (m/z), ¹H NMR |
|---|---|---|
| 100 | 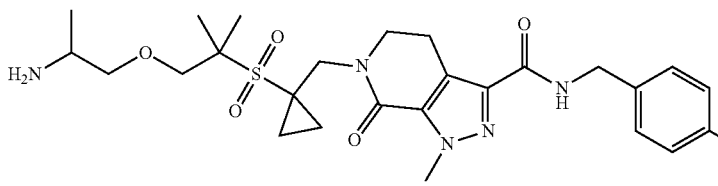<br>(R)- or (S)-6-((1-(((1-(2-Aminopropoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 557.3 [M + H]⁺. ¹H NMR (400 MHz, MeOH-$d_4$) δ 7.64-7.52 (m, 2H), 7.42 (d, J = 8.4 Hz, 2H), 4.50 (s, 2H), 4.13-4.01 (m, 5H), 3.70-3.53 (m, 4H), 3.38 (m, 1H), 3.16-3.07 (m, 1H), 2.99 (t, J = 6.8 Hz, 2H), 1.41 (s, 3H), 1.41-1.36 (m, 5H) 1.05-0.98 (m, 5H). SFC $R_t$ = 3.054 min, 93% ee [CHIRALPAK AS-3, 10-40% EtOH (0.05% Et₂NH), 3 mL/min]. |

Example 101

N-(4-Cyanobenzyl)-1-methyl-6-((1-((2-methyl-1-(2-(methylamino)ethoxy)propan-2-yl)sulfonyl)cyclopropyl)methyl)-7-oxo-4,5,6,7-tetrahydro-1H-pyrazolo[3,4-c]pyridine-3-carboxamide (101)

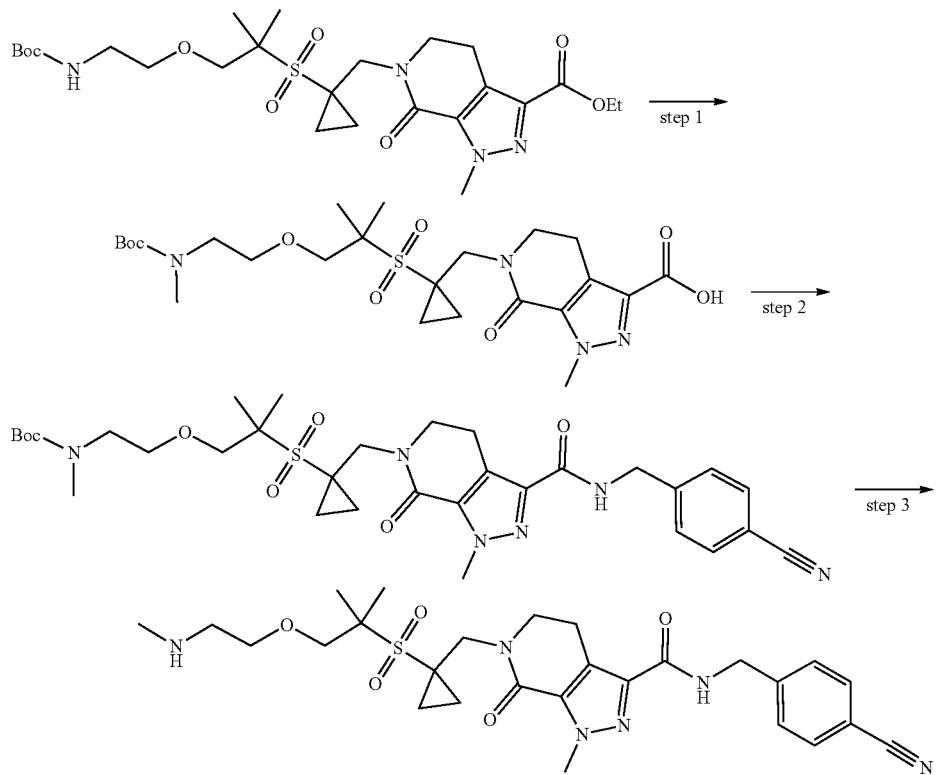

Step 1: A mixture of NaH (60% in mineral oil, 91 mg, 2.27 mmol, 3.0 equiv) in DMF (5 mL) was cooled to 0° C. before 6-((1-(((1-(2-((tert-butoxycarbonyl)amino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid (400 mg, 0.76 mmol, 1.0 equiv) was added (gas evolution). The mixture was stirred at 0° C. for 1 h, then at 25° C. for 30 min. The solution was cooled to 0° C., then MeI (0.22 mL, 3.78 mmol, 5.0 equiv) was added. The mixture was stirred at rt for 10 h before it was diluted with H₂O (2 mL) and extracted with EtOAc (3×2 mL). The combined organic extracts were dried with Na₂SO₄, filtered and concentrated to provide crude 6-((1-(((1-(2-((tert-butoxycarbonyl)(methyl)amino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid. MS (ESI): m/z 443.2 [M-Boc+H]⁺.

Step 2: tert-Butyl (2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)ethyl)(methyl)carbamate was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-(((1-(2-((tert-butoxycarbonyl)

(methyl)amino)ethoxy)-2-methylpropan-2-yl)sulfonyl) cyclopropyl)methyl)-1-methyl-7-oxo-4,5,6,7-tetrahydro-1H-pyrazolo[3,4-c]pyridine-3-carboxylic acid. MS (ESI): m/z 557.2 [M-Boc+H]⁺.

Step 3: N-(4-Cyanobenzyl)-1-methyl-6-((1-((2-methyl-1-(2-(methylamino)ethoxy)propan-2-yl)sulfonyl)cyclopropyl)methyl)-7-oxo-4,5,6,7-tetrahydro-1H-pyrazolo[3,4-c]pyridine-3-carboxamide (101) was obtained using the method described in step 4 of Example 92, except tert-butyl (2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)ethyl) carbamate was replaced with 6-((1-((1-(2-((tert-butoxycarbonyl)(methyl)amino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid. H NMR (400 MHz, MeOH-d₄) δ 7.70 (d, J=8.2 Hz, 2H), 7.53 (d, J=8.2 Hz, 2H), 4.61 (s, 2H), 4.20 (s, 2H), 4.18 (s, 3H), 3.76-3.70 (m, 4H), 3.68 (t, J=5.2 Hz, 2H), 3.10 (t, J=6.8 Hz, 2H), 2.94-2.89 (m, 2H), 2.51 (d, J=1.4 Hz, 3H), 1.51 (s, 8H), 1.13-1.07 (m, 2H). MS (ESI): m/z 557.0 [M+H]⁺.

Example 102

6-((1-((1-(Azetidin-3-yloxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (102)

Step 1: A mixture of ethyl 6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate (100 mg, 0.24 mmol, 1.0 equiv), CsOH.H₂O (244 mg, 1.45 mmol, 6.0 equiv) and tert-butyl 3-iodoazetidine-1-carboxylate (205 mg, 0.73 mmol, 3.0 equiv) in DMSO (1.5 mL) was stirred at 80° C. for 12 h, then it was diluted with saturated NH₄Cl (1 mL), filtered and purified by RP-HPLC to give 6-((1-((1-((1-(tert-butoxycarbonyl)azetidin-3-yl)oxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid). MS (ESI): m/z 441.2 [M-Boc+H]⁺.

Step 2: tert-Butyl 3-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)azetidine-1-carboxylate was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((1-((1-(tert-butoxycarbonyl)azetidin-3-yl)oxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid). MS (ESI): m/z 555.5 [M-Boc+H]⁺.

Step 3: 6-((1-((1-(Azetidin-3-yloxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyri-

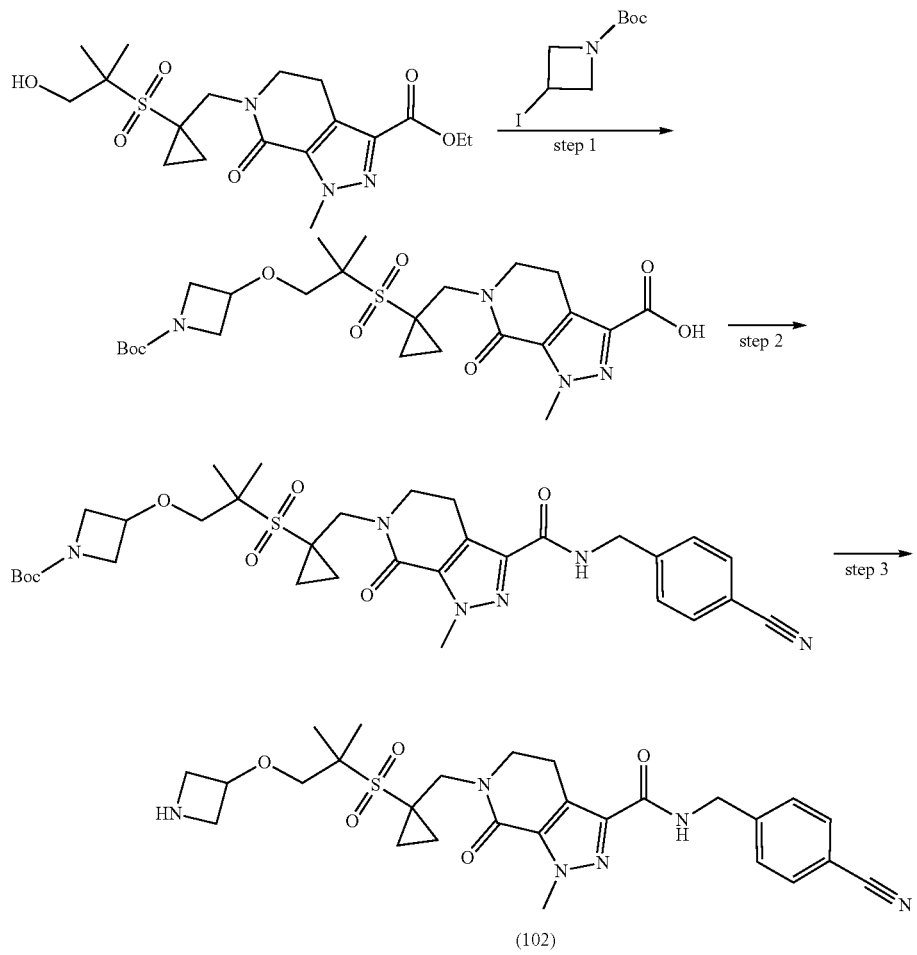

(102)

dine-3-carboxamide (102) was obtained using the method described in step 4 of Example 92, except tert-butyl (2-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)ethyl) carbamate was replaced with tert-butyl 3-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropoxy)azetidine-1-carboxylate. $^1$H NMR (400 MHz, MeOH-d$_4$) δ 8.41 (br s, 1H), 7.56 (d, J=8.2 Hz, 2H), 7.38 (d, J=8.2 Hz, 2H), 7.26-7.20 (m, 1H), 4.58 (d, J=6.4 Hz, 2H), 4.40 (br s, 1H), 4.10 (s, 3H), 4.06 (s, 4H), 3.93 (br s, 3H), 3.62 (br t, J=6.8 Hz, 3H), 3.53 (s, 2H), 3.10 (br t, J=6.8 Hz, 2H), 1.49-1.45 (m, 2H), 1.43 (s, 5H), 1.01-0.91 (m, 2H). MS (ESI): m/z 555.2 [M+H]$^+$.

Example 103

6-((1-((1-(2-Amino-2-methylpropoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (103)

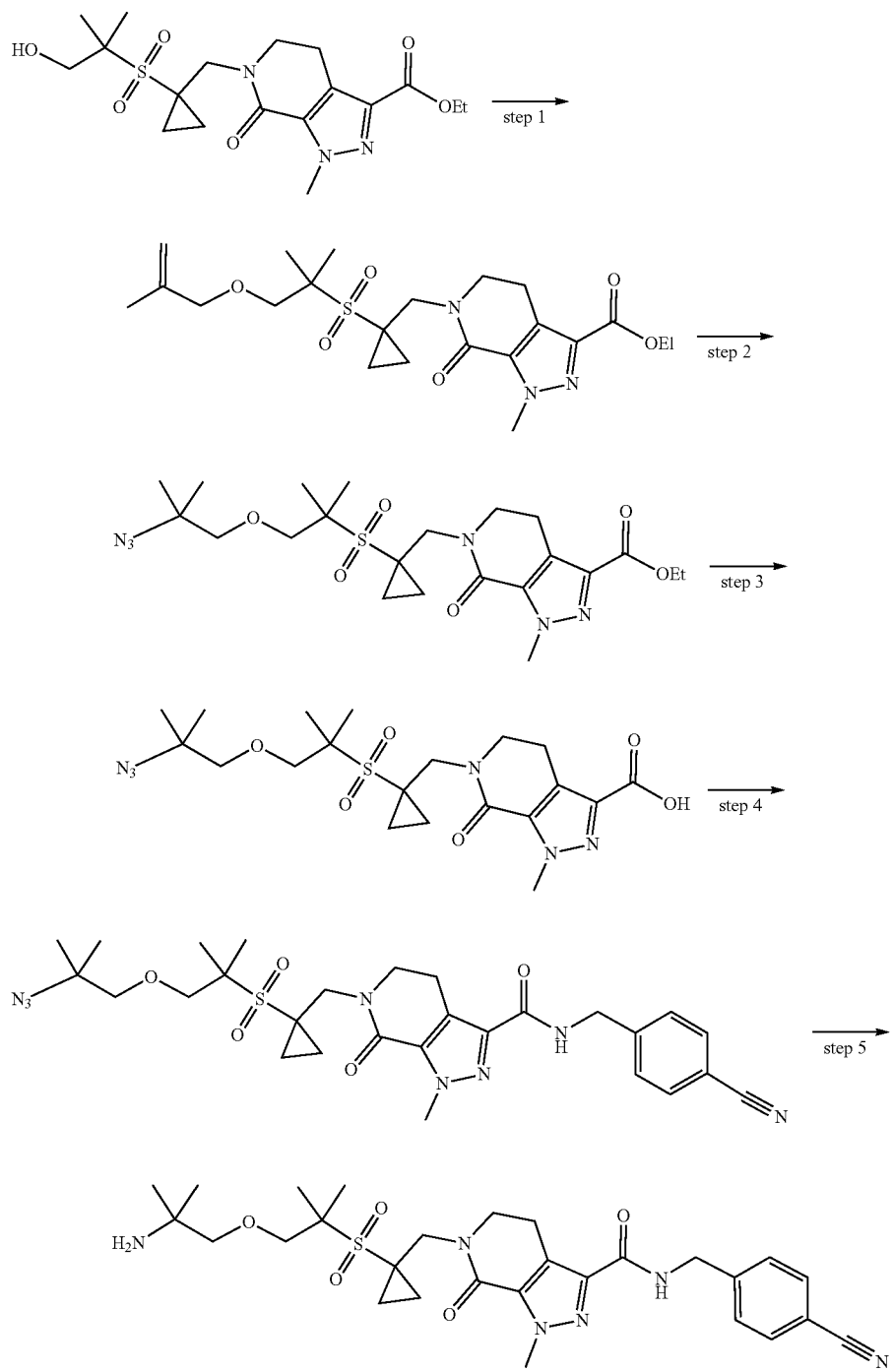

tep 1: A mixture of ethyl 6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate (1.00 g, 2.42 mmol, 1.0 equiv), Ag$_2$O (0.84 g, 3.63 mmol, 1.5 equiv) and 3-bromo-2-methylprop-1-ene (1.31 g, 9.67 mmol, 4.0 equiv) in DMF (10 mL) was stirred at 25° C. for 12 h before it was diluted with H$_2$O (10 mL). The aqueous mixture was extracted with EtOAc (3×15 mL), then the combined organic extracts were dried with Na$_2$SO$_4$, filtered and concentrated. The residue was purified by column chromatography (SiO$_2$, 1:5 EtOAc/petroleum ether) to afford ethyl 1-methyl-6-((1-((2-methyl-1-((2-methylallyl)oxy)propan-2-yl)sulfonyl)cyclopropyl)methyl)-7-oxo-4,5,6,7-tetrahydro-1H-pyrazolo[3,4-c]pyridine-3-carboxylate. TLC R$_f$=0.6 (1:5 EtOAc/petroleum ether). $^1$H NMR (400 MHz, CDCl$_3$) δ 5.02-4.90 (m, 2H), 4.41 (m, 2H), 4.27-4.18 (m, 3H), 4.15 (s, 2H), 3.98-3.90 (m, 2H), 3.75 (t, J=6.8 Hz, 2H), 3.65-3.55 (m, 2H), 3.10 (t, J=6.8 Hz, 2H), 1.76 (s, 3H), 1.60-1.56 (m, 2H), 1.50 (s, 6H), 1.40 (t, J=7.2 Hz, 3H), 1.13-1.01 (m, 2H).

Step 2: Co(BF$_4$)$_2$.6H$_2$O (17 mg, 0.051 mmol, 0.06 equiv) and potassium (E)-2-((3,5-di-tert-butyl-2-hydroxybenzylidene)amino)-2-methylpropanoate (19 mg, 0.051 mmol, 0.06 equiv) were dissolved in EtOH (5 mL) at 20° C. under N$_2$. After 10 min, ethyl 1-methyl-6-((1-((2-methyl-1-((2-methylallyl)oxy)propan-2-yl)sulfonyl)cyclopropyl)methyl)-7-oxo-4,5,6,7-tetrahydro-1H-pyrazolo[3,4-c]pyridine-3-carboxylate (400 mg, 0.855 mmol, 1.0 equiv) was added, followed by tosyl azide (506 mg, 2.566 mmol, 3.0 equiv) and t-BuOOH (5.5 M in decane, 0.05 mL, 0.257 mmol, 0.3 equiv). After 5 mins, 1,1,3,3-tetramethyldisiloxane (TMDSO) (345 mg, 2.566 mmol, 3.0 equiv) was added dropwise. The resulting solution was stirred at 20° C. for 6 h before it was quenched with H$_2$O (5 mL). Saturated NaHCO$_3$ (4 mL) and brine (5 mL) were added and the reaction mixture was extracted with EtOAc (3×10 mL). The combined organic extracts were dried over Na$_2$SO$_4$, filtered and concentrated. The residue was purified by column chromatography (SiO$_2$, 0-75% EtOAc/petroleum ether) to afford ethyl 6-((1-((1-(2-azido-2-methylpropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylate. MS (ESI): m/z 511.1 [M+H]$^+$.

Note: potassium (E)-2-((3,5-di-tert-butyl-2-hydroxybenzylidene)amino)-2-methylpropanoate was obtained using methods similar to those described in Waser, J.; Nambu, H.; Carreira, E. M. Cobalt-catalyzed hydroazidation of olefins: convenient access to alkyl azides. *J. Am. Chem. Soc.* 2005, 127, 8294-8295 and in Waser, J.; Gaspar, B.; Nambu, H.; Carreira, E. M. Hydrazines and azides via the metal-catalyzed hydrohydrazination and hydroazidation of olefins *J. Am. Chem. Soc.* 2006, 128, 11693-11712.

Specifically, potassium hydroxide (0.5 M in EtOH, 9.3 mL, 4.6 mmol, 1.1 equiv) was added to a suspension of 2-amino-2-methylpropanoic acid (0.45 g, 4.4 mmol, 1.1 equiv) in ethanol (50 mL) at 23° C. under argon. After 30 min, 3,5-di-tert-butyl-salicylaldehyde (197) (1.0 g, 4.4 mmol, 1.0 equiv) was added and the reaction mixture was stirred at 23° C. for 10 h and the solvent was removed under reduced pressure. The isolated solid was further dried in high vacuo for 8 h to furnish 43, which was used without further purification.

Step 3: 6-((1-((1-(2-azido-2-methylpropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-((1-(2-azido-2-methylpropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylate. MS (ESI): m/z 483.3 [M+H]$^+$.

Step 4: 6-((1-((1-(2-Azido-2-methylpropoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((1-(2-Azido-2-methylpropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid. MS (ESI): m/z 597.2 [M+H]$^+$.

Step 5: 6-((1-((1-(2-Amino-2-methylpropoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (103) was obtained using the method described in step 3 of Example 70, except 6-((1-((1-azido-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide was replaced with 6-((1-((1-(2-Azido-2-methylpropoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide. $^1$H NMR (400 MHz, CDCl$_3$) δ 7.63 (d, J=8.2 Hz, 2H), 7.45 (d, J=8.2 Hz, 2H), 7.31-7.28 (m, 1H), 4.66 (d, J=6.2 Hz, 2H), 4.18 (s, 2H), 4.15 (s, 3H), 3.76-3.68 (m, 4H), 3.29 (s, 2H), 3.17 (t, J=6.8 Hz, 2H), 1.97 (br s, 2H), 1.61-1.55 (m, 2H), 1.53 (s, 6H), 1.17 (s, 6H), 1.08-1.03 (m, 2H). MS (ESI): m/z 571.3 [M+H]$^+$.

Example 104

N-(4-Cyanobenzyl)-6-((1-((1-(2-(dimethylamino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (104)

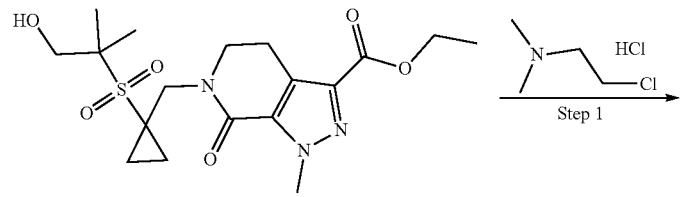

Step 1

-continued

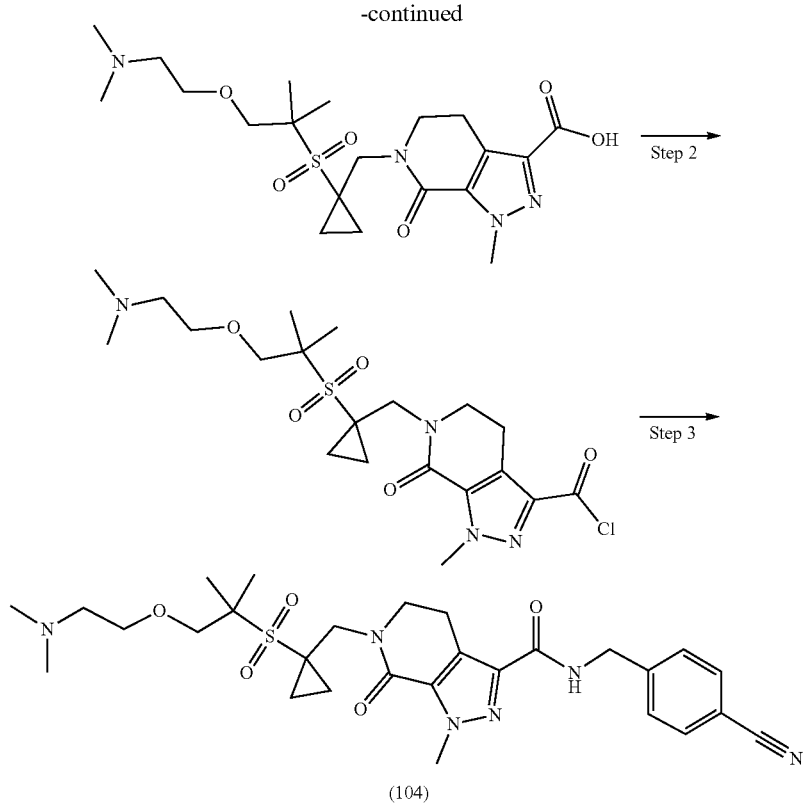

(104)

Step 2: 6-((1-((1-(2-(Dimethylamino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carbonyl chloride. A solution of 6-((1-((1-(2-(dimethylamino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid (110 mg, 0.241 mmol, 1.0 equiv) in SOCl$_2$ (1.5 mL) was stirred at 60° C. for 14 h before the reaction was concentrated to provide crude 6-((1-((1-(2-(dimethylamino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carbonyl chloride. MS (ESI): m/z 471.3 [M+H]$^+$.

Step 3: A mixture of 6-((1-((1-(2-(dimethylamino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carbonyl chloride (200 mg, 0.092 mmol, 1.0 equiv) and 4-(aminomethyl)benzonitrile hydrochloride (47 mg, 0.276 mmol, 3.0 equiv) in DMF (0.5 mL) was stirred at 40° C. for 12 h. The reaction was diluted with water (6 mL) and extracted with EtOAc (3×3 mL), then the combined the organic extracts were concentrated. The residue was purified by RP-HPLC to provide N-(4-Cyanobenzyl)-6-((1-((1-(2-(dimethylamino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (104). $^1$H NMR (400 MHz, MeOH-d$_4$) δ 7.69 (d, J=8.2 Hz, 2H), 7.51 (d, J=8.2 Hz, 2H), 4.59 (s, 1H), 4.61-4.58 (m, 1H), 4.19-4.15 (m, 5H), 3.78-3.64 (m, 7H), 3.35 (s, 2H), 3.25 (s, 1H), 3.09 (m, 2H), 2.68 (m, 2H), 2.34 (s, 6H), 1.54-1.46 (m, 8H), 1.13-1.08 (m, 2H). MS (ESI): m/z 571.5 [M+H]$^+$.

Example 105

4-((4-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-1H-1,2,3-triazol-1-yl)methyl)benzonitrile (105)

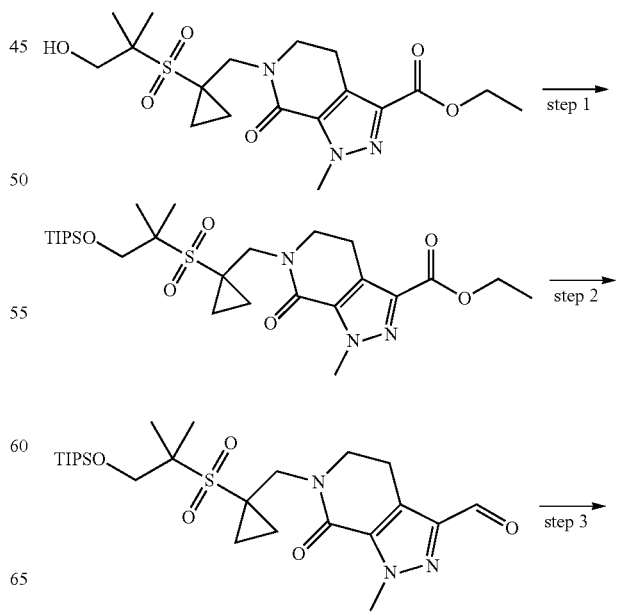

-continued

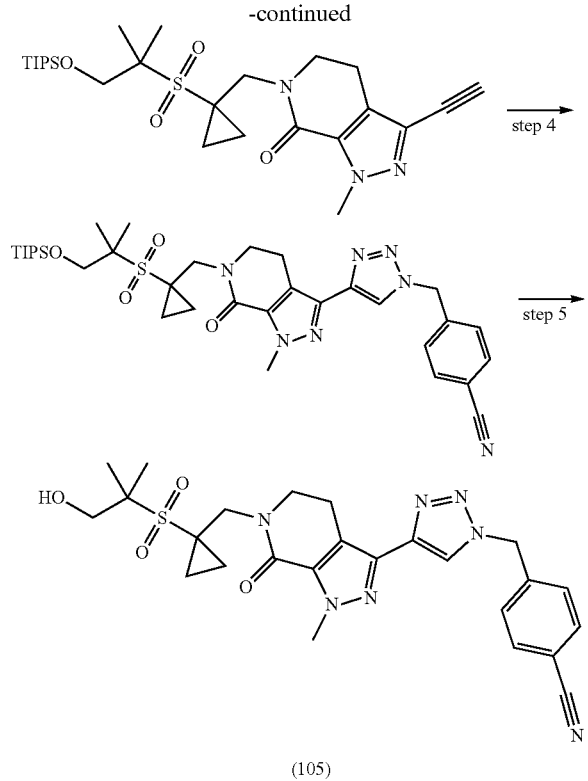

(105)

Step 1: A solution of ethyl 6-((1-((1-hydroxy-2-methyl-propan-2-yl)sulfonyl)cyclopropyl)methyl)-1-methyl-7-oxo-4,5,6,7-tetrahydro-1H-pyrazolo[3,4-c]pyridine-3-carboxylate (1.2 g, 2.90 mmol, 1.0 equiv) and DMAP (709 mg, 5.80 mmol, 2.0 equiv) in DMF (10 mL) was cooled to before TIPSOTf (1.16 g, 3.77 mmol, 1.3 equiv) was added dropwise. After the reaction was stirred at 80° C. for 2 h, the mixture was poured into H$_2$O (10 mL) and extracted with EtOAc (3×20 mL), then the combined organic extracts were dried with Na$_2$SO$_4$, filtered and concentrated. The residue was purified by column chromatography (SiO$_2$, 10-100% EtOAc/petroleum ether) to afford ethyl 1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridine-3-carboxylate. $^1$H NMR (400 MHz, CDCl$_3$) δ 4.42 (q, J=7.2 Hz, 2H), 4.22 (s, 3H), 4.17 (s, 2H), 3.97 (s, 2H), 3.75 (t, J=6.8 Hz, 2H), 3.11 (t, J=6.8 Hz, 2H), 1.62-1.57 (m, 3H), 1.52 (s, 7H), 1.41 (t, J=7.2 Hz, 3H), 1.13-1.02 (m, 21H). MS (ESI): m/z 570.3 [M+H]$^+$.

Step 2: 1-Methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridine-3-carbaldehyde was obtained using the method described in step 1 of Example 31, except ethyl 6-((1-(cyclopropylsulfonyl)cyclopropyl)methyl)-1-methyl-7-oxo-4,5,6,7-tetrahydro-1H-pyrazolo[3,4-c]pyridine-3-carboxylate (int-12) was replaced with ethyl 1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridine-3-carboxylate. MS (ESI): m/z 526.5 [M+H]$^+$.

Step 3. 3-Ethynyl-1-methyl-6-((1-((2-methyl-1-((triisopropylsilyl)oxy)propan-2-yl)sulfonyl)cyclopropyl)methyl)-5,6-dihydro-1H-pyrazolo[3,4-c]pyridin-7(4H)-one was obtained using the method described in step 1 of Example 35, except 6-((1-(cyclopropylsulfonyl)cyclopropyl)methyl)-1-methyl-7-oxo-4,5,6,7-tetrahydro-1H-pyrazolo[3,4-c]pyridine-3-carbaldehyde was replaced with 1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridine-3-carbaldehyde. MS (ESI): m/z 522.3 [M+H]$^+$.

Step 4: 4-((4-(1-Methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridin-3-yl)-1H-1,2,3-triazol-1-yl)methyl)benzonitrile was obtained using the method described in step 2 of Example 35, except 6-((1-(cyclopropylsulfonyl)cyclopropyl)methyl)-3-ethynyl-1-methyl-5,6-dihydro-1H-pyrazolo[3,4-c]pyridin-7(4H)-one was replaced with 3-ethynyl-1-methyl-6-((1-((2-methyl-1-((triisopropylsilyl)oxy)propan-2-yl)sulfonyl)cyclopropyl)methyl)-5,6-dihydro-1H-pyrazolo[3,4-c]pyridin-7(4H)-one. TLC R$_f$=0.4 (50% EtOAc/petroleum ether). MS (ESI): m/z 680.3 [M+H]$^+$.

Step 5: To a solution of 4-((4-(1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridin-3-yl)-1H-1,2,3-triazol-1-yl)methyl)benzonitrile (150 mg, 0.22 mmol, 1.0 equiv) in THF (2 mL) was added Bu$_4$NF (1.0 M in THF, 0.22 mL, 0.22 mmol, 1.0 equiv). The reaction was stirred at 25° C. for 2 h before it was poured into H$_2$O (5 mL) and extracted with EtOAc (2×5 mL). The combined organic extracts were dried over Na$_2$SO$_4$, filtered and concentrated. The residue was purified by column chromatography (SiO$_2$, 0-50% EtOAc/petroleum ether) to afford 4-((4-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-1H-1,2,3-triazol-1-yl)methyl)benzonitrile (105). TLC R$_f$=0.2 (50% EtOAc/petroleum ether). $^1$H NMR (400 MHz, CDCl$_3$) δ 7.86 (s, 1H), 7.71-7.64 (m, 2H), 7.39 (d, J=8.4 Hz, 2H), 5.67-5.60 (m, 2H), 4.20 (s, 2H), 4.15 (s, 3H), 3.87 (s, 2H), 3.75 (t, J=6.8 Hz, 2H), 3.25 (t, J=6.8 Hz, 2H), 3.21-3.07 (m, 1H), 1.61-1.55 (m, 2H), 1.52 (s, 6H), 1.13-1.07 (m, 2H). MS (ESI): m/z 524.4 [M+H Example 106

4-(3-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (106)

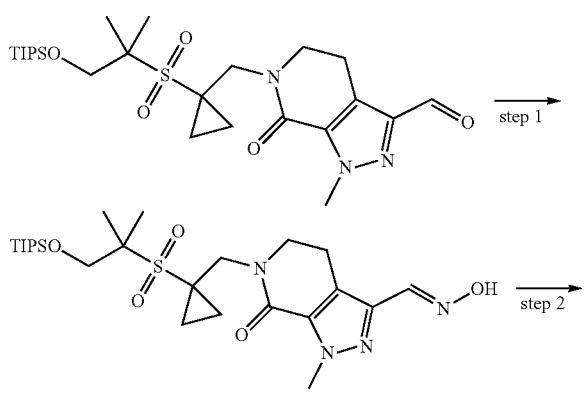

-continued

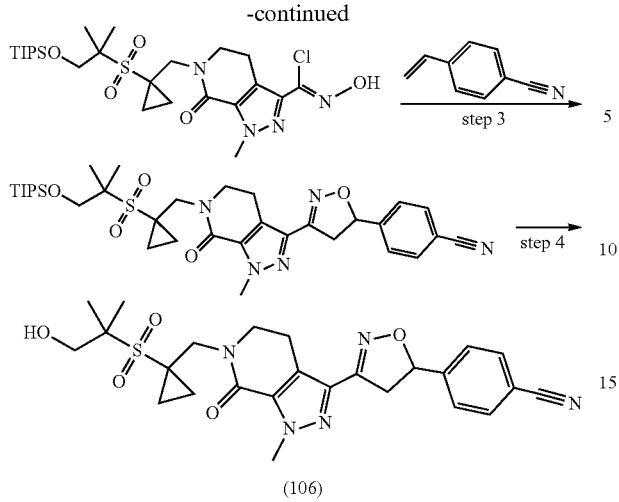

(106)

Step 1: (E)-1-Methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridine-3-carbaldehyde oxime was obtained using the method described in step 2 of Example 31, except 6-((1-(cyclopropylsulfonyl)cyclopropyl)methyl)-1-methyl-7-oxo-4,5,6,7-tetrahydro-1H-pyrazolo[3,4-c]pyridine-3-carbaldehyde was replaced with 1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridine-3-carbaldehyde. MS (ESI): m/z 541.3 [M+H]+.

Step 2: (Z)—N-Hydroxy-1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridine-3-carbimidoyl chloride was obtained using the method described in step 3 of Example 31, except (E)-6-((1-(cyclopropylsulfonyl)cyclopropyl)methyl)-1-methyl-7-oxo-4,5,6,7-tetrahydro-1H-pyrazolo[3,4-c]pyridine-3-carbaldehyde oxime was replaced with (E)-1-Methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridine-3-carbaldehyde oxime. MS (ESI): m/z 575.3 [M+H]+.

Step 3: 4-(3-(1-Methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridin-3-yl)-4,5-dihydroisoxazol-5-yl)benzonitrile was obtained using the method described in step 4 of Example 31, except (Z)-6-((1-(cyclopropylsulfonyl)cyclopropyl)methyl)-N-hydroxy-1-methyl-7-oxo-4,5,6,7-tetrahydro-1H-pyrazolo[3,4-c]pyridine-3-carbimidoyl chloride was replaced with (Z)—N-Hydroxy-1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridine-3-carbimidoyl chloride. MS (ESI): m/z 668.4 [M+H]+.

Step 4: 4-(3-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (106) was obtained using the method described in step 5 of Example 105, except 4-((4-(1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridin-3-yl)-1H-1,2,3-triazol-1-yl)methyl)benzonitrile was replaced with 4-(3-(1-Methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridin-3-yl)-4,5-dihydroisoxazol-5-yl)benzonitrile.
MS (ESI): m/z 512.1 [M+H]+.

Example 107 and Example 108

(R)-4-(3-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (107)

and (S)-4-(3-(6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (108)

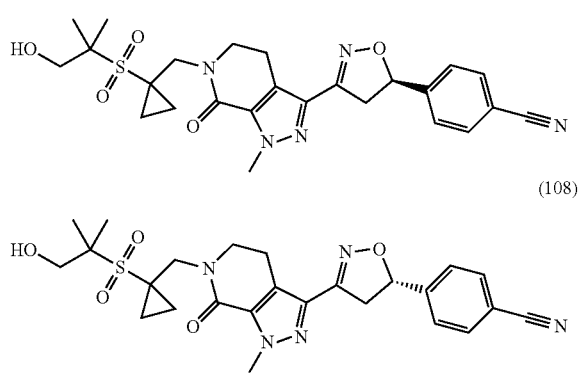

(R)-4-(3-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (107) and (S)-4-(3-(6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (108) were obtained by chiral separation of 4-(3-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile.

SFC: CHIRALCEL OJ-3, 60% MeOH (0.05% Et2NH), 3 mL/min (R)-4-(3-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (107). SCF: >99% ee, Rt=1.252; $^1$H NMR (400 MHz, CDCl3) δ 7.70-7.64 (m, 2H), 7.50 (d, J=8.2 Hz, 2H), 5.74 (m, 1H), 4.18 (s, 2H), 4.14 (s, 3H), 3.95-3.88 (m, 1H), 3.86 (s, 2H), 3.74 (m, 2H), 3.40 (m, 1H), 3.11 (m, 2H), 1.62-1.56 (m, 3H), 1.51 (s, 6H), 1.10-1.04 (m, 2H). MS (ESI): m/z 512.1 [M+H]+.

(S)-4-(3-(6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile (108). SCF: >99% ee, Rt=1.777); $^1$H NMR (400 MHz, CDCl3) δ 7.67 (d, J=8.2 Hz, 2H), 7.49 (d, J=8.2 Hz, 2H), 5.74 (m, 1H), 4.18 (s, 2H), 4.14 (s, 3H), 3.95-3.88 (m, 1H), 3.86 (s, 2H), 3.74 (t, J=6.8 Hz, 2H), 3.40 (m, 1H), 3.10 (t, J=6.8 Hz, 2H), 1.62-1.57 (m, 3H), 1.51 (s, 6H), 1.11-1.05 (m, 2H). MS (ESI): m/z 512.1 [M+H]+.

Example 109

6-((1-((1-Amino-2-methyl-1-oxopropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide (109)

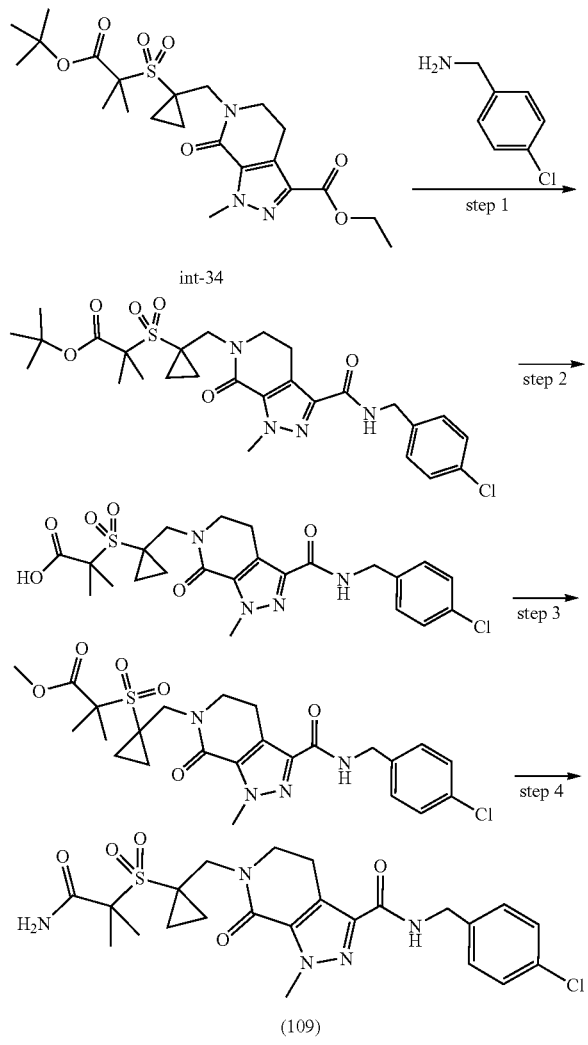

Step 1: tert-butyl 2-((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-2-methylpropanoate was obtained using the method described in Example 1, except ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6) was replaced with ethyl 6-((1-((1-(tert-butoxy)-2-methyl-1-oxopropan-2-yl)sulfonyl)cyclopropyl)methyl)-1-methyl-7-oxo-4,5,6,7-tetrahydro-1H-pyrazolo[3,4-c]pyridine-3-carboxylate (int-34) and 4-(aminomethyl)benzonitrile hydrochloride was replaced with (4-chlorophenyl)methanamine. TLC $R_f$=0.2 (50% EtOAc/petroleum ether). MS (ESI): m/z 579.0 [M+H]$^+$.

Step 2: A solution of tert-butyl 2-((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-2-methylpropanoate (250 mg, 0.43 mmol, 1.0 equiv) in 4 M HCl in Dioxane (5 mL) was stirred at 60° C. for 12 h. The mixture was concentrated to afford crude 2-((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-2-methylpropanoic acid. TLC $R_f$=0.2 (1:10 MeOH/EtOAc). MS (ESI): m/z 523.1 [M+H]$^+$.

Step 3: A solution of 2-((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-2-methylpropanoic acid in MeOH (2 mL) was treated with SOCl$_2$ (0.12 mL, 1.65 mmol, 3.8 equiv) at 25° C. The mixture was stirred at 70° C. for 6 h before it was quenched with water (2 mL) and extracted with EtOAc (2×20 mL). The combined organic extracts were dried over Na$_2$SO$_4$, filtered and concentrated. The residue was purified by prep-TLC (SiO$_2$, 50% EtOAc/petroleum ether) to afford methyl 2-((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-2-methylpropanoate. TLC $R_f$=0.5 (50% EtOAc/petroleum ether). MS (ESI): m/z 537.1 [M+H]$^+$.

Step 4: A solution of methyl 2-((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-2-methylpropanoate (50 mg, 0.09 mmol, 1.0 equiv) in 4 M NH$_3$ in MeOH (5 mL) was stirred at 80° C. for 12 h in a sealed tube before it was concentrated. The residue was purified by RP-HPLC to afford 6-((1-((1-amino-2-methyl-1-oxopropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide (109). $^1$H NMR (400 MHz, CDCl$_3$) δ 7.32-7.28 (m, 4H), 7.18-7.15 (m, 1H), 6.82 (s, 1H), 5.59 (s, 1H), 4.56 (d, J=14 Hz, 2H), 4.12 (s, 3H), 4.10 (s, 2H), 3.69-3.65 (m, 2H), 3.18-3.15 (m, 2H), 1.72 (s, 6H), 1.58-1.55 (m, 2H), 1.14-1.12 (m, 2H). MS (ESI): m/z 522.0 [M+H]$^+$.

Example 110

N-(4-Chlorobenzyl)-1-methyl-6-((1-((2-methyl-1-(methylamino)-1-oxopropan-2-yl)sulfonyl)cyclopropyl)methyl)-7-oxo-4,5,6,7-tetrahydro-1H-pyrazolo[3,4-c]pyridine-3-carboxamide (110)

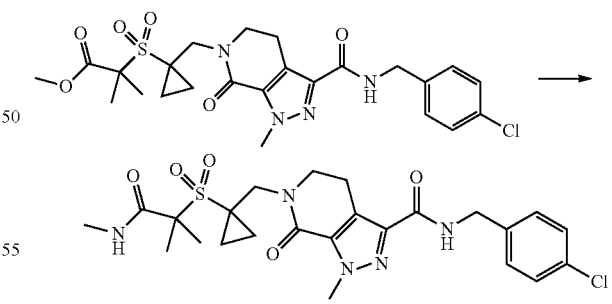

N-(4-Chlorobenzyl)-1-methyl-6-((1-((2-methyl-1-(methylamino)-1-oxopropan-2-yl)sulfonyl)cyclopropyl)methyl)-7-oxo-4,5,6,7-tetrahydro-1H-pyrazolo[3,4-c]pyridine-3-carboxamide (110) was obtained using the methods described for the synthesis of compound (109) in Example 109, except in step 4 NH$_3$ was replaced with methylamine. $^1$H NMR (400 MHz, CDCl$_3$) δ 7.32-7.28 (m, 4H), 7.18-7.15 (m, 1H), 6.76-6.75 (m, 1H), 4.56 (d, J=6 Hz, 2H), 4.12 (s, 3H), 4.10 (s, 2H), 3.68-3.65 (m, 2H), 3.18-3.15 (m, 2H), 2.86 (d, J=4

Hz, 3H), 1.70 (s, 6H), 1.51-1.48 (m, 2H), 1.13-1.10 (m, 2H). MS (ESI): m/z 536.1 [M+H]⁺.

Example 111 and Example 112

(R)- or (S)—N-(4-Cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide (111)

and (R)- or (S)—N-(4-Cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide (112)

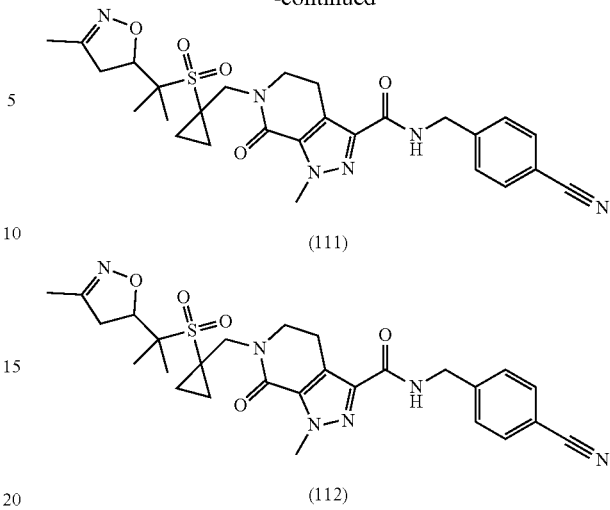

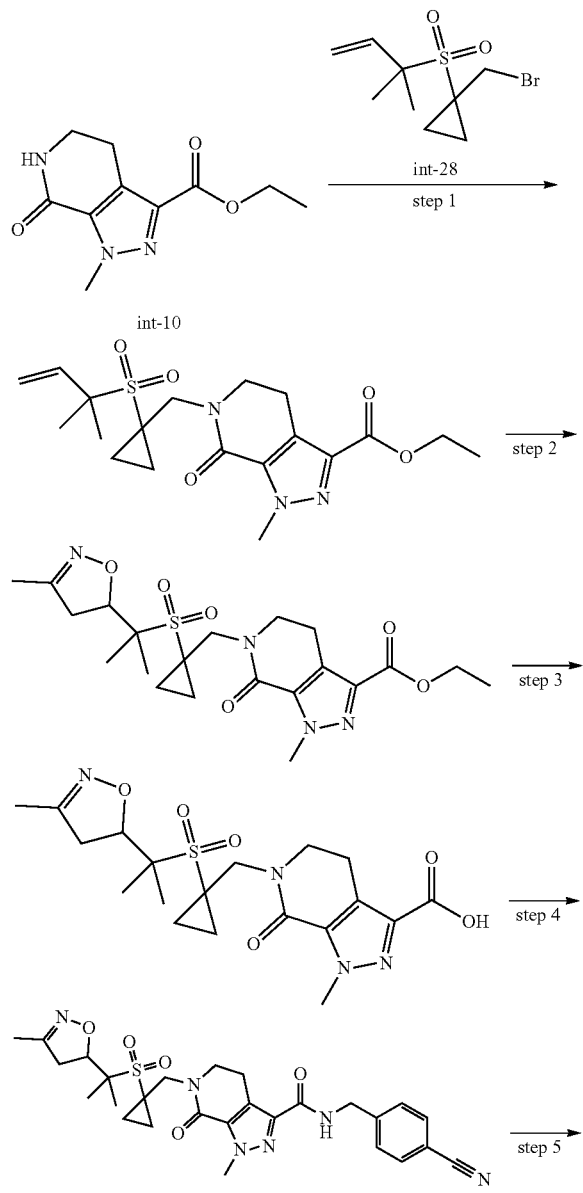

Step 1: Ethyl 1-methyl-6-((1-((2-methylbut-3-en-2-yl)sulfonyl)cyclopropyl)methyl)-7-oxo-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with 1-(bromomethyl)-1-((2-methylbut-3-en-2-yl)sulfonyl)cyclopropane (int-28). H NMR (500 MHz, CDCl₃) δ 6.24 (dd, J=17.5, 10.7 Hz, 1H), 5.52-5.43 (m, 2H), 4.43 (q, J=7.1 Hz, 2H), 4.23 (s, 3H), 4.10 (s, 2H), 3.73 (t, J=6.9 Hz, 2H), 3.12 (t, J=6.8 Hz, 2H), 1.54 (s, 1H), 1.43 (t, J=7.1 Hz, 3H), 1.06 (d, J=2.1 Hz, 2H). MS (ESI): m/z 410.3 [M+H]⁺.

Step 2: To a solution of NCS (82 mg, 0.611 mmol, 5.0 equiv) in DCE (2.2 ml) was added pyridine (0.593 μL, 7.33 μmol, 0.06 equiv), followed by acetaldehyde oxime (37 μL, 0.608 mmol, 5.0 equiv). The reaction mixture was stirred at rt for 30 min before ethyl 1-methyl-6-((1-((2-methylbut-3-en-2-yl)sulfonyl)cyclopropyl)methyl)-7-oxo-4,5,6,7-tetrahydro-1H-pyrazolo[3,4-c]pyridine-3-carboxylate (50 mg, 0.122 mmol, 1.0 equiv) was added. The temperature was raised to 65° C., then Et₃N (20.42 μL, 0.147 mmol, 1.2 equiv) was added and the mixture was stirred at 65° C. for 3 h. The reaction was diluted with water (2 mL) and the layers were separated. The aqueous layer was extracted with DCM (2×2 mL) and the combined organic extracts were dried over MgSO₄, filtered and concentrated to provide crude ethyl 1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxylate. ¹H NMR (500 MHz, CDCl₃) δ 4.43 (q, J=7.1 Hz, 1H), 4.30-4.18 (m, 2H), 4.09 (s, 1H), 3.81-3.68 (m, 3H), 3.19-3.05 (m, 2H), 2.80 (s, 2H), 2.29 (s, 2H), 2.02 (s, 1H), 1.67-1.55 (m, 4H), 1.48-1.39 (m, 3H), 1.09-1.00 (m, 1H). MS (ESI): m/z 467.8 [M+H]⁺.

Step 3: 1-Methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxylic acid was obtained using the procedure for intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced ethyl 1-methyl-6-((1-((2-(3-methyl-4,5-dihydroisoxazol-5-yl)propan-2-yl)sulfonyl)cyclopropyl) methyl)-7-oxo-4,5,6,7-tetrahydro-1H-pyrazolo[3,4-c]pyridine-3-carboxylate. $^1$H NMR (500 MHz, CDCl$_3$) δ 4.30-4.08 (m, 3H), 3.83-3.65 (m, 1H), 3.16-3.01 (m, 2H), 2.05 (m, 2H), 1.31-1.16 (m, 6H), 1.12 (s, 2H), 0.88 (m, 2H). MS (ESI): m/z 439.2 [M+H]$^+$.

Step 4. The racemic product (N-(4-Cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxylic acid.

Step 5: (R)- or (S)—N-(4-Cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide (111) and (R)- or (S)—N-(4-Cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide (112) were obtained by chiral SFC separation of racemic (N-(4-cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide. Unless otherwise indicated, examples indicate relative stereochemistry.

SFC: CHIRALPAK AD, 60% EtOH, 5 mL/min (R)- or (S)—N-(4-Cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide (111). 100% ee. Rt=3.24 min. MS (ESI): m/z 553.2 [M+H]$^+$.

(R)- or (S)—N-(4-Cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide (112), 83% ee. Rt=4.09 min. MS (ESI): m/z 553.2 [M+H]$^+$.

Example 113

N-(4-Cyanobenzyl)-6-((1-((4-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (113)

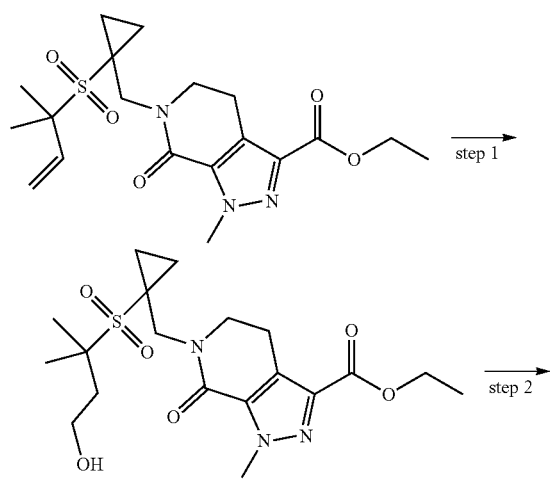

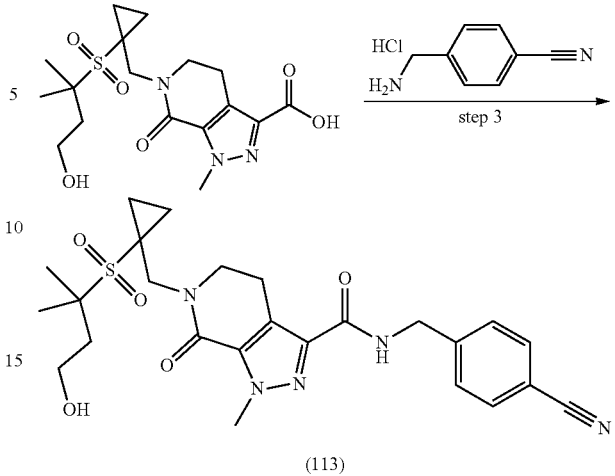

(113)

Step 1: A solution of ethyl 1-methyl-6-((1-((2-methylbut-3-en-2-yl)sulfonyl)cyclopropyl)methyl)-7-oxo-4,5,6,7-tetrahydro-1H-pyrazolo[3,4-c]pyridine-3-carboxylate (see Example 112) (500 mg, 1.22 mmol, 1.0 equiv) in THF (5.0 mL) was cooled to -10° C. before BH$_3$ (1.0 M in THF, 1.83 mL, 1.83 mmol, 1.5 equiv) was added, then the mixture was stirred at 25° C. for 16 h. The solution was re-cooled to −10° C., then a solution of NaOH (3.0 M, 0.40 mL, 1.22 mmol, 1.0 equiv) was added dropwise, followed by H$_2$O$_2$ (30%, 166 mg, 1.47 mmol, 1.2 equiv). The mixture was stirred at 25° C. for 3 h to complete the oxidation. The reaction mixture was purified by RP-HPLC to afford ethyl 6-((1-((4-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxylate. $^1$H NMR (400 MHz, CDCl$_3$) δ 4.45-4.39 (m, 2H), 4.22 (s, 3H), 4.19 (s, 2H), 3.88 (m, 2H), 3.73 (m, 2H), 3.12 (m, 2H), 2.19-2.13 (m, 2H), 1.63-1.58 (m, 2H), 1.56 (s, 5H), 1.43-1.39 (m, 4H), 1.10-1.05 (m, 2H). MS (ESI): m/z 428.2 [M+H]$^+$.

Step 2: 6-((1-((4-Hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-((4-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxylate. MS (ESI): m/z 400.2 [M+H]$^+$.

Step 3: N-(4-Cyanobenzyl)-6-((1-((4-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (113) was obtained using the method described in step 1 of Example 26, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((4-Hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxylic acid and hydrazine was replaced with 4-(aminomethyl)benzonitrile hydrochloride. TLC R$_f$=0.4 (EtOAc). $^1$H NMR (400 MHz, CDCl$_3$) δ 7.64 (d, J=8.0 Hz, 2H), 7.46 (d, J=8.0 Hz, 2H), 7.31-7.27 (m, 1H), 4.66 (d, J=6.4 Hz, 2H), 4.19 (s, 2H), 4.15 (s, 3H), 3.87 (t, J=6.4 Hz, 2H), 3.72 (t, J=6.8 Hz, 2H), 3.18 (t, J=6.8 Hz, 2H), 2.16 (t, J=6.4 Hz, 2H), 1.62-1.58 (m, 2H), 1.56 (s, 6H), 1.09-1.03 (m, 2H). MS (ESI): m/z 514.2 [M+H]$^+$.

Example 114

N-(4-cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide (114)

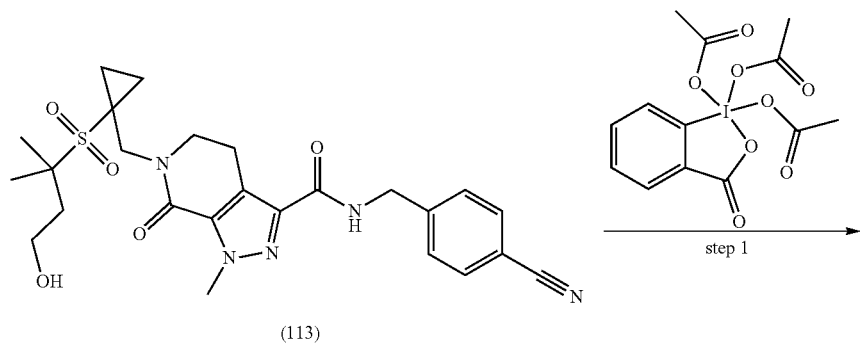

(113)

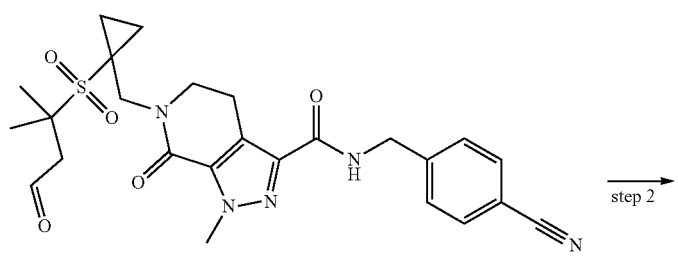

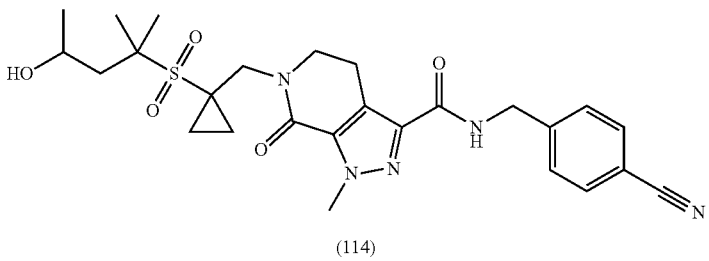

(114)

Step 1: To a solution of N-(4-cyanobenzyl)-6-((1-((4-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (113) (200 mg, 0.389 mmol, 1.0 equiv) in DCM (5.0 mL) was added Dess-Martin periodane (198 mg, 0.467 mmol, 1.2 equiv) at 0° C. The mixture was stirred at 15° C. for 1 h before it was filtered and concentrated to afford crude N-(4-cyanobenzyl)-1-methyl-6-((1-((2-methyl-4-oxobutan-2-yl)sulfonyl)cyclopropyl)methyl)-7-oxo-4,5,6,7-tetrahydro-1H-pyrazolo[3,4-c]pyridine-3-carboxamide. TLC $R_f$=0.7 (EtOAc).

Step 2: To a solution of CeCl$_3$ (216 mg, 0.879 mmol, 3.0 equiv) in THF (5 mL) was added MeMgBr (3.0 M in Et$_2$O, 0.2 mL, 0.6 mmol, 2.0 equiv) at −78° C., then the reaction mixture was stirred at −78° C. for 15 min before a solution of N-(4-cyanobenzyl)-1-methyl-6-((1-((2-methyl-4-oxobutan-2-yl)sulfonyl)cyclopropyl)methyl)-7-oxo-4,5,6,7-tetrahydro-1H-pyrazolo[3,4-c]pyridine-3-carboxamide (150 mg, 0.293 mmol, 1.0 equiv) in THF (0.2 mL) was added. After the reaction was stirred at −78° C. for 15 min, it was quenched with saturated NH$_4$Cl (30 mL) and extracted with EtOAc (3×30 mL). The combined organic extracts were dried over Na$_2$SO$_4$, filtered and concentrated. The residue was purified by prep-TLC (SiO$_2$, EtOAc) to afford N-(4-cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide. TLC $R_f$=0.4 (EtOAc). $^1$H NMR (400 MHz, CDCl$_3$) δ 7.64 (d, J=8.2 Hz, 2H), 7.46 (d, J=8.0 Hz, 2H), 4.66 (d, J=6.4 Hz, 2H), 4.19 (d, J=3.6 Hz, 2H), 4.15 (s, 3H), 3.72 (t, J=6.8 Hz, 2H), 3.18 (t, J=6.8 Hz, 2H), 2.12-2.00 (m, 1H), 1.97-1.87 (m, 1H), 1.63 (s, 3H), 1.61-1.58 (m, 2H), 1.57 (s, 3H), 1.30-1.25 (m, 3H), 1.11-1.02 (m, 2H). MS (ESI): m/z 528.1 [M+H]$^+$.

Example 115 and Example 116

(R)- or (S)—N-(4-Cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide (115)

and (R)- or (S)—N-(4-Cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide (116)

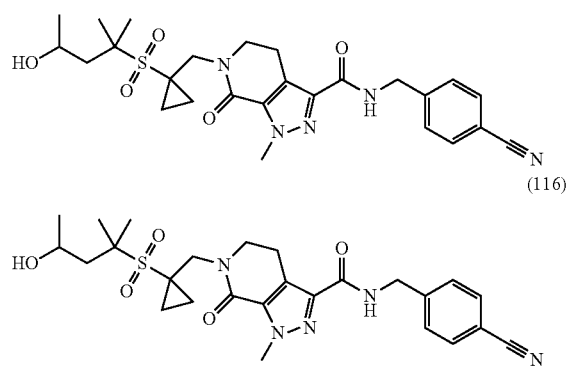

(R)- or (S)—N-(4-Cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide (115) and (R)- or (S)—N-(4-Cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide (116) were obtained by chiral SFC separation of N-(4-cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide.

Unless otherwise indicated, examples indicate relative stereochemistry. SFC: AmyCoat, 40% EtOH (0.05% Et$_2$NH), 3 mL/min (R)- or (S)—N-(4-cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide (115). Rt=1.584 mins, ee value=100%. $^1$H NMR (400 MHz, CDCl$_3$) δ 7.64 (br d, J=8.0 Hz, 2H), 7.46 (br d, J=7.6 Hz, 2H), 4.66 (br d, J=6.4 Hz, 2H), 4.24-4.12 (m, 6H), 3.72 (br t, J=6.8 Hz, 2H), 3.18 (br t, J=6.8 Hz, 2H), 2.12-2.00 (m, 1H), 1.98-1.88 (m, 1H), 1.63 (s, 3H), 1.59 (m, 2H), 1.57 (s, 3H), 1.27 (br d, J=6.0 Hz, 4H), 1.09-1.04 (m, 2H). MS (ESI): m/z 528.3 [M+H]$^+$.

(R)- or (S)—N-(4-cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide (116). SFC (C-07330-076-P2A1_2, Amycoat-EtOH(DEA)-40-3 mL-35T.Icm) Rt=2.000 mins, ee value=100%. $^1$H NMR (400 MHz, CDCl$_3$) δ 7.64 (br d, J=7.8 Hz, 2H), 7.46 (br d, J=8.0 Hz, 2H), 4.66 (br d, J=6.0 Hz, 2H), 4.28-4.10 (m, 6H), 3.72 (br t, J=6.8 Hz, 2H), 3.28-3.15 (br t, J=6.8 Hz, 2H), 2.06 (m, 1H), 2.00-1.89 (m, 1H), 1.63 (s, 3H), 1.59 (br s, 2H), 1.56 (s, 3H), 1.27 (br d, J=6.0 Hz, 4H), 1.07 (br s, 2H). MS (ESI): m/z 528.2 [M+H]$^+$.

Example 117

N-(4-Cyanobenzyl)-6-((1-((1-(2-hydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide (117)

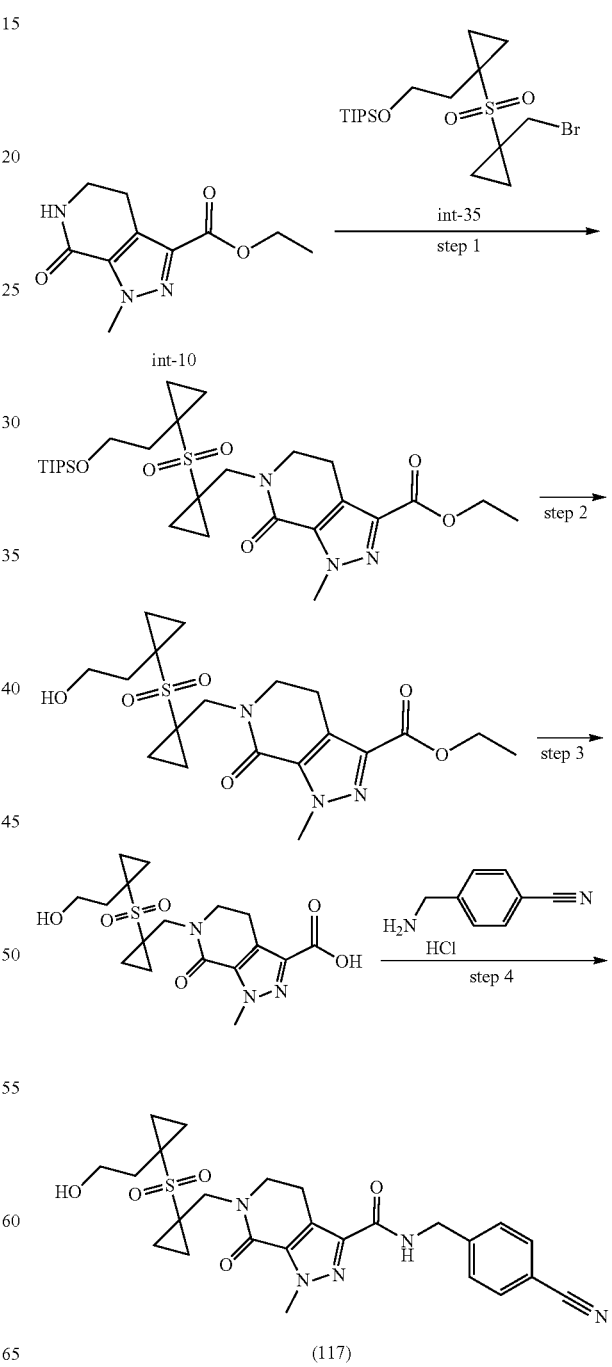

Step 1: Ethyl 1-methyl-7-oxo-6-((1-((1-(2-((triisopropylsilyl)oxy)ethyl)cyclopropyl)sulfonyl)cyclopropyl)methyl)-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with ((2-(1-((1-(bromomethyl)cyclopropyl)sulfonyl)cyclopropyl)ethoxy)triisopropylsilane (int-35). MS (ESI): m/z 582.5 [M+H]+.

Step 2: Ethyl 6-((1-((1-(2-hydroxyethyl)cyclopropyl)sulfonyl)cyclopropyl)methyl)-1-methyl-7-oxo-4,5,6,7-tetrahydro-1H-pyrazolo[3,4-c]pyridine-3-carboxylate was obtained using the method described in step 5 of Example 105, except 4-((4-(1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridin-3-yl)-1H-1,2,3-triazol-1-yl)methyl)benzonitrile was replaced with ethyl 1-methyl-7-oxo-6-((1-((1-(2-((triisopropylsilyl)oxy)ethyl)cyclopropyl)sulfonyl)cyclopropyl)methyl)-4,5,6,7-tetrahydro-1H-pyrazolo[3,4-c]pyridine-3-carboxylate. MS (ESI): m/z 426.0 [M+H]+.

Step 3: 6-((1-((1-(2-Hydroxyethyl)cyclopropyl)sulfonyl)cyclopropyl)methyl)-1-methyl-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-((1-(2-hydroxyethyl)cyclopropyl)sulfonyl)cyclopropyl)methyl)-1-methyl-7-oxo-4,5,6,7-tetrahydro-1H-pyrazolo[3,4-c]pyridine-3-carboxylate. 1H NMR (400 MHz, DMSO-d6) δ 12.93 (br s, 1H), 4.60 (t, J=5.2 Hz, 1H), 4.11 (s, 3H), 4.03 (s, 2H), 3.63 (t, J=6.8 Hz, 2H), 3.58-3.49 (m, 2H), 2.96 (t, J=6.8 Hz, 2H), 2.10 (t, J=7.0 Hz, 2H), 1.30-1.19 (m, 4H), 1.13-1.02 (m, 4H). MS (ESI): m/z 398.2 [M+H]+.

Step 4: N-(4-Cyanobenzyl)-6-((1-((1-(2-hydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide (117) was obtained using the method described in step 1 of Example 26, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((1-(2-Hydroxyethyl)cyclopropyl)sulfonyl)cyclopropyl)methyl)-1-methyl-7-oxo-4,5,6,7-tetrahydro-1H-pyrazolo[3,4-c]pyridine-3-carboxylic acid and hydrazine was replaced with 4-(aminomethyl)benzonitrile hydrochloride. 1H NMR (400 MHz, DMSO-d6) δ 8.95 (t, J=6.2 Hz, 1H), 7.79 (d, J=8.4 Hz, 2H), 7.48 (d, J=8.4 Hz, 2H), 4.61 (br s, 1H), 4.47 (d, J=6.2 Hz, 2H), 4.12 (s, 3H), 4.03 (s, 2H), 3.62 (t, J=6.8 Hz, 2H), 3.54 (t, J=6.8 Hz, 2H), 2.98 (t, J=6.8 Hz, 2H), 2.10 (t, J=6.8 Hz, 2H), 1.30-1.18 (m, 4H), 1.13-1.02 (m, 4H). MS (ESI): m/z 512.4 [M+H]+.

Example 118

N-(4-Cyanobenzyl)-6-((1-((2-hydroxy-2-methylpropyl)sulfonyl)cyclopropyl)methyl)-1-methyl-7-oxo-4,5,6,7-tetrahydro-1H-pyrazolo[3,4-c]pyridine-3-carboxamide (118)

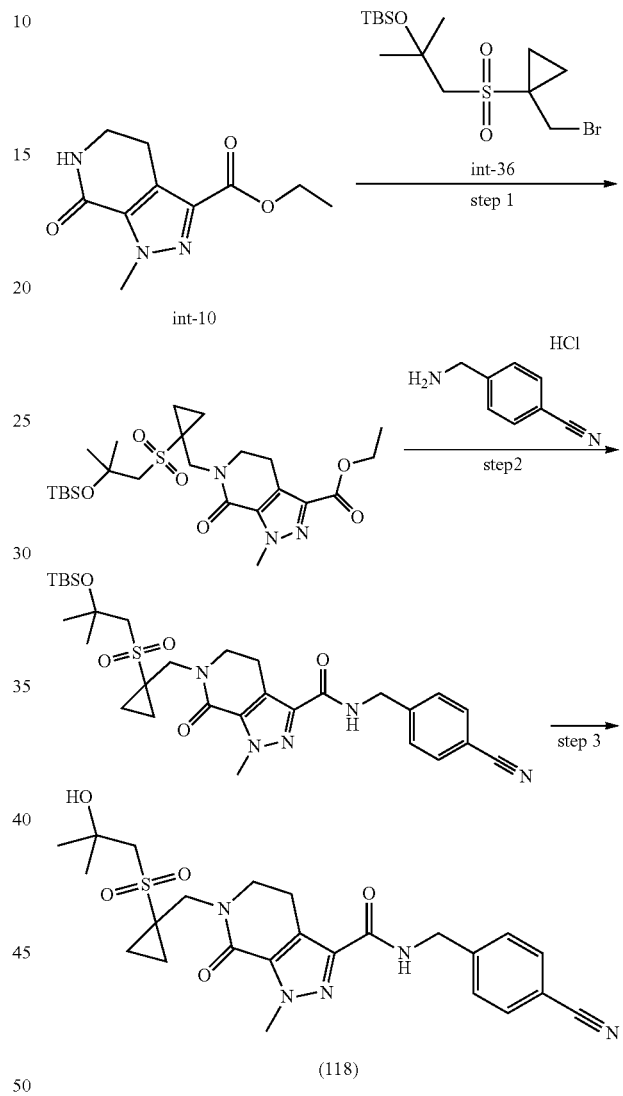

Step 1: Ethyl 6-((1-((2-((tert-butyldimethylsilyl)oxy)-2-methylpropyl)sulfonyl)cyclopropyl)methyl)-1-methyl-7-oxo-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with ((1-((1-(bromomethyl)cyclopropyl)sulfonyl)-2-methylpropan-2-yl)oxy)(tert-butyl)dimethylsilane (int-36). 1H NMR (400 MHz, CDCl3) δ 4.44-4.39 (m, 2H), 4.24 (s, 3H), 3.94 (s, 2H), 3.78 (t, J=6.8 Hz, 2H), 3.35 (s, 2H), 3.15 (t, J=6.8 Hz, 2H), 1.52 (s, 8H), 1.41 (t, J=7.2 Hz, 3H), 1.07 (d, J=1.8 Hz, 2H), 0.84 (s, 9H), 0.11 (s, 6H). MS (ESI): m/z 528.4 [M+H]+.

Step 2: 6-((1-((2-((tert-Butyldimethylsilyl)oxy)-2-methylpropyl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide was obtained using the method described in Example 1, except ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6) was replaced with ethyl 6-((1-((2-((tert-butyldimethylsilyl)oxy)-2-methylpropyl)sulfonyl)cyclopropyl)methyl)-1-methyl-7-oxo-4,5,6,7-tetrahydro-1H-pyrazolo[3,4-c]pyridine-3-carboxylate. ¹H NMR (400 MHz, CDCl₃) δ 7.63 (d, J=8.4 Hz, 2H), 7.50-7.41 (m, 1H), 7.45 (d, J=8.4 Hz, 1H), 4.66 (d, J=6.4 Hz, 2H), 4.16 (s, 3H), 3.95 (s, 2H), 3.76 (t, J=6.8 Hz, 2H), 3.38 (s, 2H), 3.20 (t, J=6.8 Hz, 2H), 1.52 (s, 8H), 1.08-1.01 (m, 2H), 0.84 (s, 9H), 0.12 (s, 6H). MS (ESI): m/z 636.4 [M+Na]⁺.

Step 3: N-(4-Cyanobenzyl)-6-((1-((2-hydroxy-2-methylpropyl)sulfonyl)cyclopropyl)methyl)-1-methyl-7-oxo-4,5,6,7-tetrahydro-1H-pyrazolo[3,4-c]pyridine-3-carboxamide (118) was obtained using the method described in step 5 of Example 105, except 4-((4-(1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridin-3-yl)-1H-1,2,3-triazol-1-yl)methyl)benzonitrile was replaced with 6-((1-((2-((tert-Butyldimethylsilyl)oxy)-2-methylpropyl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide. ¹H NMR (400 MHz, MeOH-d₄) δ 7.70 (d, J=8.4 Hz, 2H), 7.52 (d, J=8.4 Hz, 2H), 4.60 (s, 2H), 4.18 (s, 3H), 4.03 (s, 2H), 3.76 (t, J=6.8 Hz, 2H), 3.58 (s, 1H), 3.13-3.09 (m, 4H), 1.47-1.42 (m, 6H), 1.15-1.12 (m, 2H), 1.05-1.01 (m, 2H). MS (ESI): m/z 500.4 [M+H]⁺.

Example 119

N-(4-Cyanobenzyl)-6-((1-(((1s, 3s)-3-hydroxycyclobutyl)sulfonyl)cyclopropyl)methyl)-1-methyl-7-oxo-4,5,6,7-tetrahydro-1H-pyrazolo[3,4-c]pyridine-3-carboxamide (119)

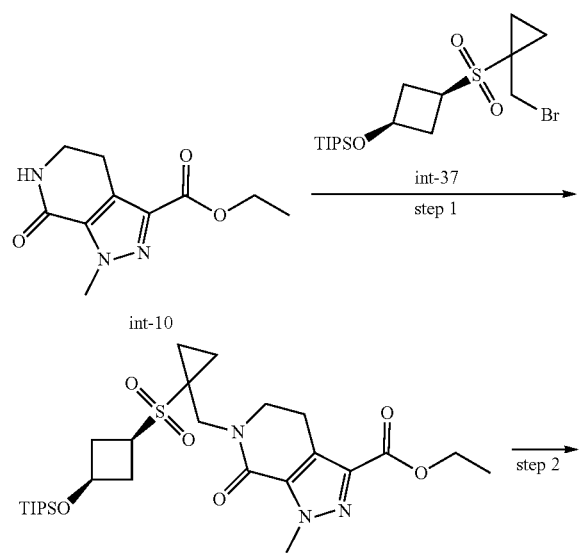

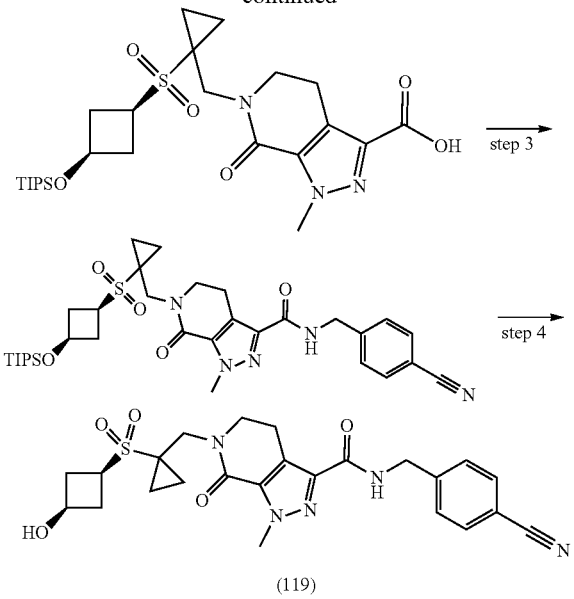

(119)

Step 1: Ethyl 1-methyl-7-oxo-6-((1-(((1s, 3s)-3-((triisopropylsilyl)oxy)cyclobutyl)sulfonyl)cyclopropyl)methyl)-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with ((1s, 3s)-3-((1-(Bromomethyl)cyclopropyl)sulfonyl)cyclobutoxy)triisopropylsilane (int-37). MS (ESI): m/z 568.4 [M+H]⁺.

Step 2: 1-Methyl-7-oxo-6-((1-(((1s, 3s)-3-((triisopropylsilyl)oxy)cyclobutyl)sulfonyl)cyclopropyl)methyl)-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 1-methyl-7-oxo-6-((1-(((1s, 3s)-3-((triisopropylsilyl)oxy)cyclobutyl)sulfonyl)cyclopropyl)methyl)-4,5,6,7-tetrahydro-1H-pyrazolo[3,4-c]pyridine-3-carboxylate. ¹H NMR (400 MHz, CDCl₃) δ 4.35-4.27 (m, 1H), 4.24 (s, 3H), 3.94 (s, 2H), 3.76 (t, J=6.8 Hz, 2H), 3.70-3.60 (m, 1H), 3.14 (t, J=6.8 Hz, 2H), 2.70-2.59 (m, 2H), 2.54-2.42 (m, 2H), 1.54-1.48 (m, 2H), 1.10-1.01 (m, 22H), 1.00-0.97 (m, 3H). MS (ESI): m/z 540.2 [M+H]⁺.

Step 3: N-(4-Cyanobenzyl)-1-methyl-7-oxo-6-((1-(((1s, 3s)-3-((triisopropylsilyl)oxy)cyclobutyl)sulfonyl)cyclopropyl)methyl)-4,5,6,7-tetrahydro-1H-pyrazolo[3,4-c]pyridine-3-carboxamide was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced 1-methyl-7-oxo-6-((1-(((1s, 3s)-3-((triisopropylsilyl)oxy)cyclobutyl)sulfonyl)cyclopropyl)methyl)-4,5,6,7-tetrahydro-1H-pyrazolo[3,4-c]pyridine-3-carboxylic acid. MS (ESI): m/z 654.2 [M+H]⁺.

Step 4: N-(4-Cyanobenzyl)-6-((1-(((1s, 3s)-3-hydroxycyclobutyl)sulfonyl)cyclopropyl)methyl)-1-methyl-7-oxo-4,5,6,7-tetrahydro-1H-pyrazolo[3,4-c]pyridine-3-carboxamide (119) was obtained using the method described in step 5 of Example 105, except 4-((4-(1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridin-3-yl)-1H-1,2,3-triazol-1-yl)methyl)benzonitrile was replaced with N-(4-cyanobenzyl)-1-methyl-7-oxo-6-((1-(((1s, 3s)-3-((triisopropylsilyl)oxy)cyclobutyl)sulfonyl)cyclopropyl)methyl)-4,5,6,7-tetrahydro-1H-pyrazolo[3,4-c]pyridine-3-carboxamide. $^1$H NMR (400 MHz, CDCl$_3$) δ 7.64 (d, J=8.0 Hz, 2H), 7.45 (d, J=8.0 Hz, 2H), 7.31-7.28 (m, 1H), 4.66 (d, J=6.4 Hz, 2H), 4.34-4.23 (m, 1H), 4.16 (s, 3H), 3.93 (s, 2H), 3.85-3.75 (m, 1H), 3.72 (m, 2H), 3.19 (m, 2H), 2.76 (m, 2H), 2.50-2.39 (m, 2H), 2.26-2.15 (m, 1H), 1.53-1.48 (m, 2H), 1.03-0.97 (m, 2H). MS (ESI): m/z 498.2 [M+H]$^+$.

Example 120

N-(4-Cyanobenzyl)-6-((1-(((1r, 3r)-3-hydroxycyclobutyl)sulfonyl)cyclopropyl)methyl)-1-methyl-7-oxo-4,5,6,7-tetrahydro-1H-pyrazolo[3,4-c]pyridine-3-carboxamide (120)

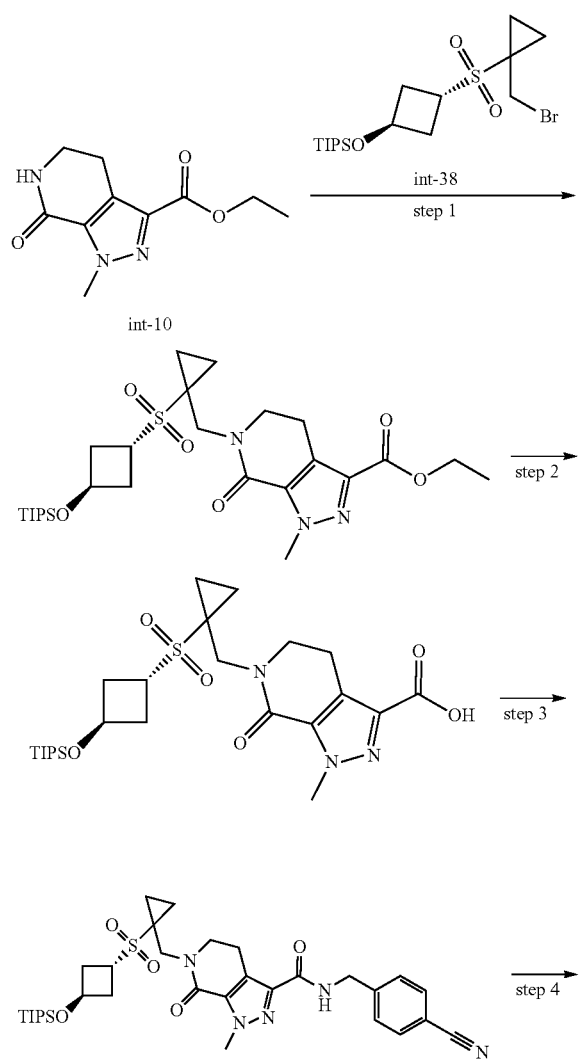

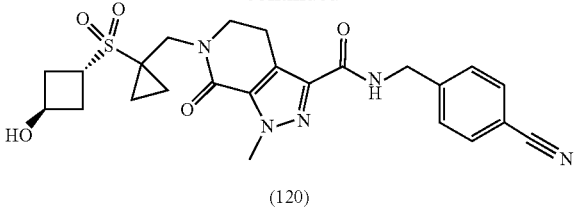

(120)

Step 1: Ethyl 1-methyl-7-oxo-6-((1-(((1r, 3r)-3-((triisopropylsilyl)oxy)cyclobutyl)sulfonyl)cyclopropyl)methyl)-4,5,6,7-tetrahydro-1H-pyrazolo[3,4-c]pyridine-3-carboxylate was obtained using the method described in step 1 of Example 119, except ((1s, 3s)-3-((1-(bromomethyl)cyclopropyl)sulfonyl)cyclobutoxy)triisopropylsilane (int-37) was replaced with ((1r, 3r)-3-((1-(bromomethyl)cyclopropyl)sulfonyl)cyclobutoxy)triisopropylsilane (int-38). TLC R$_f$=0.4 (25% EtOAc/petroleum ether). $^1$H NMR (400 MHz, CDCl$_3$) δ 4.54 (br s, 1H), 4.41 (J=7.2 Hz, 2H), 4.31-4.18 (m, 3H), 3.84-3.53 (m, 3H), 3.34-3.17 (m, 1H), 3.16-3.03 (m, 1H), 1.68-1.62 (m, 2H), 1.61 (s, 6H), 1.56 (s, 6H), 1.49 (s, 8H), 1.43-1.39 (m, 3H), 1.38 (s, 2H), 1.09 (s, 2H).

Step 2: 1-Methyl-7-oxo-6-((1-(((1r, 3r)-3-((triisopropylsilyl)oxy)cyclobutyl)sulfonyl)cyclopropyl)methyl)-4,5,6,7-tetrahydro-1H-pyrazolo[3,4-c]pyridine-3-carboxylic acid was obtained using the method described in step 2 of Example 119, except ethyl 1-methyl-7-oxo-6-((1-(((1s, 3s)-3-((triisopropylsilyl)oxy)cyclobutyl)sulfonyl)cyclopropyl)methyl)-4,5,6,7-tetrahydro-1H-pyrazolo[3,4-c]pyridine-3-carboxylate was replaced with ethyl 1-methyl-7-oxo-6-((1-(((1r, 3r)-3-((triisopropylsilyl)oxy)cyclobutyl)sulfonyl)cyclopropyl)methyl)-4,5,6,7-tetrahydro-1H-pyrazolo[3,4-c]pyridine-3-carboxylate. TLC R$_f$=0.2 (1:10 MeOH/EtOAc). $^1$H NMR (400 MHz, CDCl$_3$) δ 4.58 (J=6.2 Hz, 1H), 4.24 (s, 3H), 4.10 (t, J=3.8 Hz, 1H), 3.93 (s, 2H), 3.80-3.72 (m, 2H), 3.15 (t, J=6.8 Hz, 2H), 2.84 (m, 2H), 2.49-2.38 (m, 2H), 1.59-1.50 (m, 2H), 1.16-0.95 (m, 27H).

Step 3: N-(4-Cyanobenzyl)-1-methyl-7-oxo-6-((1-(((1r, 3r)-3-((triisopropylsilyl)oxy)cyclobutyl)sulfonyl)cyclopropyl)methyl)-4,5,6,7-tetrahydro-1H-pyrazolo[3,4-c]pyridine-3-carboxamide was obtained using the method described in step 3 of Example 119, except 1-methyl-7-oxo-6-((1-(((1s, 3s)-3-((triisopropylsilyl)oxy)cyclobutyl)sulfonyl)cyclopropyl)methyl)-4,5,6,7-tetrahydro-1H-pyrazolo[3,4-c]pyridine-3-carboxylic acid was replaced with 1-methyl-7-oxo-6-((1-(((1r, 3r)-3-((triisopropylsilyl)oxy)cyclobutyl)sulfonyl)cyclopropyl)methyl)-4,5,6,7-tetrahydro-1H-pyrazolo[3,4-c]pyridine-3-carboxylic acid. TLC R$_f$=0.4 (25% EtOAc/petroleum ether). $^1$H NMR (400 MHz, CDCl$_3$) δ 7.64 (d, J=8.4 Hz, 2H), 7.46 (d, J=8.4 Hz, 2H), 4.66 (d, J=6.2 Hz, 2H), 4.59 (m, 1H), 4.16 (s, 3H), 4.15-4.06 (m, 1H), 4.05-3.90 (m, 2H), 3.81-3.69 (m, 2H), 3.19 (m, 2H), 2.84 (m, 2H), 2.50-2.38 (m, 2H), 2.36 (s, 4H), 1.55-1.48 (m, 2H), 1.10-0.99 (m, 23H).

Step 4: N-(4-Cyanobenzyl)-6-((1-(((1r, 3r)-3-hydroxycyclobutyl)sulfonyl)cyclopropyl)methyl)-1-methyl-7-oxo-4,5,6,7-tetrahydro-1H-pyrazolo[3,4-c]pyridine-3-carboxamide (120) was obtained using the method described in step 3 of Example 119, except N-(4-cyanobenzyl)-1-methyl-7-oxo-6-((1-(((1s, 3s)-3-((triisopropylsilyl)oxy)cyclobutyl)sulfonyl)cyclopropyl)methyl)-4,5,6,7-tetrahydro-1H-pyrazolo[3,4-c]pyridine-3-carboxamide was replaced with N-(4-cyanobenzyl)-1-methyl-7-oxo-6-((1-(((1r, 3r)-3-((triisopropylsilyl)oxy)cyclobutyl)sulfonyl)cyclopropyl)methyl)-4,5,6,7-tetrahydro-1H-pyrazolo[3,4-c]pyridine-3-carboxamide.

TLC R*f*=0.3 (50% EtOAc/petroleum ether). ¹H NMR (400 MHz, CDCl₃) δ 7.64 (d, J=8.2 Hz, 2H), 7.46 (d, J=8.0 Hz, 2H), 7.31-7.28 (m, 1H), 4.66 (d, J=6.4 Hz, 2H), 4.61 (m, 1H), 4.23 (m, 1H), 4.16 (s, 3H), 3.93 (s, 2H), 3.73 (m, 2H), 3.25-3.14 (m, 2H), 2.94-2.80 (m, 2H), 2.42 (m, 2H), 1.55-1.47 (m, 3H), 1.08-1.01 (m, 2H). MS (ESI): m/z 498.4 [M+H]⁺.

Example 121

N-(4-Chlorobenzyl)-1-methyl-7-oxo-6-((1-sulfamoylcyclopropyl)methyl)-4,5,6,7-tetrahydro-1H-pyrazolo[3,4-c]pyridine-3-carboxamide (121)

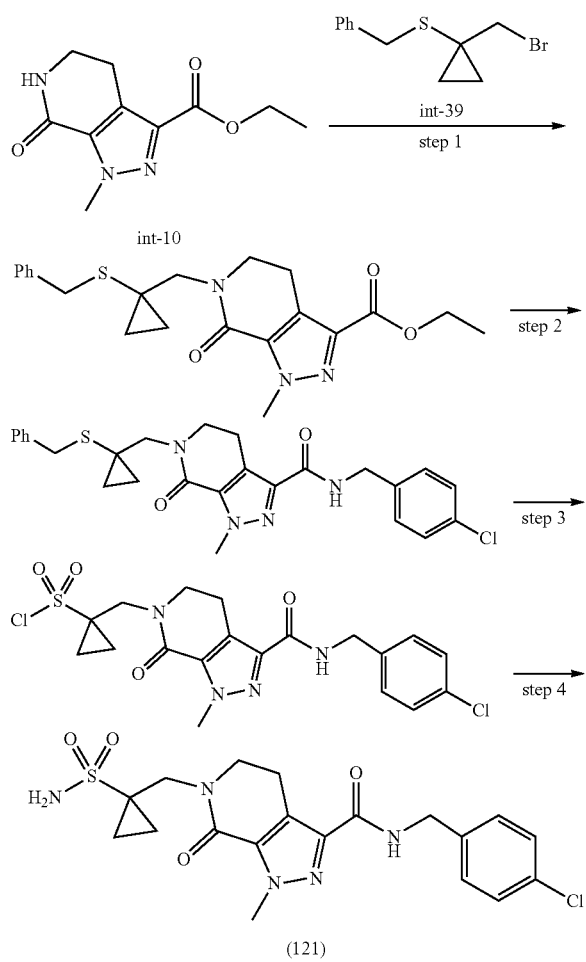

Step 1: Ethyl 6-((1-(benzylthio)cyclopropyl)methyl)-1-methyl-7-oxo-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with benzyl(1-(bromomethyl)cyclopropyl)sulfane (int-39). TLC R*f*=0.3 (50% EtOAc/petroleum ether). ¹H NMR (400 MHz, CDCl₃) δ 7.33 (s, 5H), 4.42 (q, J=7.2 Hz, 2H), 4.28 (s, 3H), 3.91 (s, 2H), 3.69-3.61 (m, 2H), 3.55 (s, 2H), 3.17-3.08 (m, 2H), 1.42 (t, J=7.0 Hz, 3H). MS (ESI): m/z 400.3 [M+H]⁺.

Step 2: 6-((1-(Benzylthio)cyclopropyl)methyl)-N-(4-chlorobenzyl)-1-methyl-7-oxo-4,5,6,7-tetrahydro-1H-pyrazolo[3,4-c]pyridine-3-carboxamide was obtained using the method described in Example 1, except ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6) was replaced with ethyl 6-((1-(benzylthio)cyclopropyl)methyl)-1-methyl-7-oxo-4,5,6,7-tetrahydro-1H-pyrazolo[3,4-c]pyridine-3-carboxylate and 4-(aminomethyl)benzonitrile hydrochloride was replaced with (4-chlorophenyl)methanamine. TLC R*f*=0.25 (1:10 EtOAc/petroleum ether). ¹H NMR (400 MHz, CDCl₃) δ 7.35-7.29 (m, 7H), 7.25-7.16 (m, 2H), 4.58 (d, J=6.2 Hz, 2H), 4.20 (s, 3H), 3.91 (s, 2H), 3.63 (t, J=6.8 Hz, 2H), 3.57-3.54 (m, 2H), 3.19 (t, J=6.8 Hz, 2H), 0.86 (s, 4H). MS (ESI): m/z 495.3 [M+H]⁺.

Step 3: A 2 dram vial charged with a mixture of 6-((1-(benzylthio)cyclopropyl)methyl)-N-(4-chlorobenzyl)-1-methyl-7-oxo-4,5,6,7-tetrahydro-1H-pyrazolo[3,4-c]pyridine-3-carboxamide (300 mg, 0.606 mmol, 1.0 equiv) in DCM (3 mL) was cooled to 0° C. A second 2 dram vial was charged with NCS (404 mg, 3.03 mmol, 5.0 equiv) in DCM (3 mL) before concentrated HCl (368 mg, 3.636 mmol, 6.0 equiv) was added dropwise over a few minutes. After 5 min, the NCS/HCl solution was added to first vial dropwise at 0° C. The vial was removed from bath and allowed to stir at rt for 1 h. The reaction was poured into water (20 mL), and then extracted with DCM (3×20 mL). The combined organic extracts were washed with brine (20 mL), dried over Na₂SO₄, filtered and concentrated to give crude 1-((3-((4-chlorobenzyl)carbamoyl)-1-methyl-7-oxo-4,5-dihydro-1H-pyrazolo[3,4-c]pyridin-6(7H)-yl)methyl)cyclopropane-1-sulfonyl chloride. MS (ESI): m/z 471.0 [M+H]⁺.

Step 4: A solution of NH₃ in THF (0.5 M, 20.0 mL, 10.0 mmol, 11.5 equiv) was cooled to −25° C. before 1-((3-((4-chlorobenzyl)carbamoyl)-1-methyl-7-oxo-4,5-dihydro-1H-pyrazolo[3,4-c]pyridin-6(7H)-yl)methyl)cyclopropane-1-sulfonyl chloride (410 mg, 0.869 mmol, 1.0 equiv) was added in one portion. The resulting mixture was stirred at 25° C. for 16 h, then the reaction mixture was concentrated and the residue was purified by RP-HPLC to afford N-(4-chlorobenzyl)-1-methyl-7-oxo-6-((1-sulfamoylcyclopropyl)methyl)-4,5,6,7-tetrahydro-1H-pyrazolo[3,4-c]pyridine-3-carboxamide (121). ¹H NMR (400 MHz, DMSO-d₆) δ 8.85 (t, J=6.2 Hz, 1H), 7.41-7.27 (m, 4H), 6.95-6.87 (m, 2H), 4.37 (d, J=6.4 Hz, 2H), 4.10 (s, 3H), 3.93 (s, 2H), 3.67 (t, J=6.8 Hz, 2H), 2.97 (t, J=6.8 Hz, 2H), 1.23-1.14 (m, 2H), 1.04-0.93 (m, 2H). MS (ESI): m/z 452.2 [M+H]⁺.

Example 122

(E)-N-(4-Chlorobenzyl)-6-((1-(N-((dimethylamino)methylene)sulfamoyl)cyclopropyl)methyl)-1-methyl-7-oxo-4,5,6,7-tetrahydro-1H-pyrazolo[3,4-c]pyridine-3-carboxamide (122)

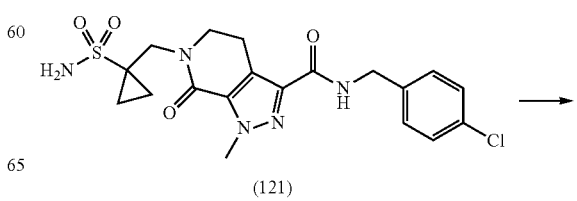

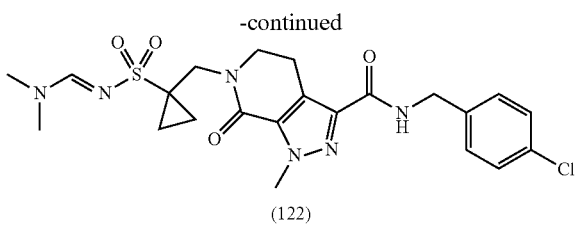

(122)

A solution of N-(4-chlorobenzyl)-1-methyl-7-oxo-6-((1-sulfamoylcyclopropyl)methyl)-4,5,6,7-tetrahydro-1H-pyrazolo[3,4-c]pyridine-3-carboxamide (121) (80 mg, 0.177 mmol, 1.0 equiv) in DMF-DMA (1 mL) was stirred at 90° C. for 2 h. The mixture was purified by RP-HPLC to give (E)-N-(4-chlorobenzyl)-6-((1-(N-((dimethylamino)methylene)sulfamoyl)cyclopropyl)methyl)-1-methyl-7-oxo-4,5,6,7-tetrahydro-1H-pyrazolo[3,4-c]pyridine-3-carboxamide (122). $^1$H NMR (400 MHz, DMSO-$d_6$) δ 8.85 (t, J=6.2 Hz, 1H), 7.95 (s, 1H), 7.42-7.28 (m, 4H), 4.38 (d, J=6.2 Hz, 2H), 4.12 (s, 3H), 3.83 (s, 2H), 3.69 (br t, J=6.8 Hz, 2H), 3.08 (s, 3H), 3.02-2.96 (m, 2H), 2.87 (s, 3H), 1.25-1.16 (m, 2H), 1.05-0.95 (m, 2H). MS (ESI): m/z 507.0 [M+H]$^+$.

Example 123

N-(4-Cyanobenzyl)-1-methyl-6-((1-(N-methylsulfamoyl)cyclopropyl)methyl)-7-oxo-4,5,6,7-tetrahydro-1H-pyrazolo[3,4-c]pyridine-3-carboxamide (123)

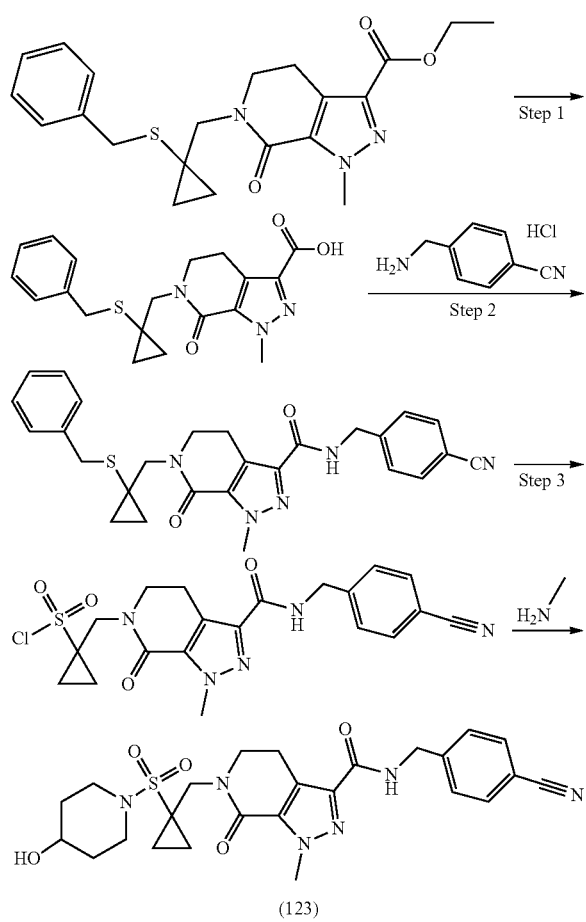

(123)

Step 1: 6-((1-(Benzlthio)cyclopropyl)methyl)-1-methyl-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-(benzylthio)cyclopropyl)methyl)-1-methyl-7-oxo-4,5,6,7-tetrahydro-1H-pyrazolo[3,4-c]pyridine-3-carboxylate. MS (ESI): m/z 372.0 [M+H]$^+$.

Step 2: 6-((1-(Benzylthio)cyclopropyl)methyl)-N-(4-cyanobenzyl)-1-methyl-7-oxo-4,5,6,7-tetrahydro-1H-pyrazolo[3,4-c]pyridine-3-carboxamide was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced 6-((1-(benzylthio)cyclopropyl)methyl)-1-methyl-7-oxo-4,5,6,7-tetrahydro-1H-pyrazolo[3,4-c]pyridine-3-carboxylic acid. $^1$H NMR (400 MHz, CDCl$_3$) δ 8.33 (s, 1H), 7.63 (d, J=8.2 Hz, 2H), 7.46 (d, J=8.2 Hz, 2H), 7.34-7.28 (m, 4H), 7.26-7.19 (m, 1H), 4.66 (d, J=6.4 Hz, 2H), 4.20 (s, 3H), 3.90 (s, 2H), 3.62 (t, J=6.8 Hz, 2H), 3.55 (s, 2H), 3.17 (t, J=6.8 Hz, 2H), 1.94-1.55 (m, 2H), 1.43-1.25 (m, 2H), 0.86 (s, 4H). MS (ESI): m/z 486.0 [M+H]$^+$.

Step 3: 1-((3-((4-cyanobenzyl)carbamoyl)-1-methyl-7-oxo-1,4,5,7-tetrahydro-6H-pyrazolo[3,4-c]pyridin-6-yl)methyl)cyclopropane-1-sulfonyl chloride was obtained using the method described in step 3 of Example 121, except (6-((1-(benzylthio)cyclopropyl)methyl)-N-(4-chlorobenzyl)-1-methyl-7-oxo-4,5,6,7-tetrahydro-1H-pyrazolo[3,4-c]pyridine-3-carboxamide) was replaced with 6-((1-(benzylthio)cyclopropyl)methyl)-N-(4-cyanobenzyl)-1-methyl-7-oxo-4,5,6,7-tetrahydro-1H-pyrazolo[3,4-c]pyridine-3-carboxamide. TLC R$_f$=0.4 (50% EtOAc/petroleum ether). MS (ESI): m/z 461.9 [M+H]$^+$.

Step 4: 1-((3-((4-cyanobenzyl)carbamoyl)-1-methyl-7-oxo-1,4,5,7-tetrahydro-6H-pyrazolo[3,4-c]pyridin-6-yl)methyl)cyclopropane-1-sulfonyl chloride (150 mg, 0.32 mmol, 1.0 equiv) was added portion wise to a solution of methylamine (2.0 M in THF, 0.49 mL, 0.98 mmol, 3.0 equiv) and DIEA (126 mg, 0.97 mmol, 3.0 equiv) in DCM (1.5 mL) at 25° C. under N$_2$, the resulting mixture was stirred at 25° C. for 12 h. The reaction was filtered and concentrated, then the residue was purified by RP-HPLC to afford N-(4-cyanobenzyl)-1-methyl-6-((1-(N-methylsulfamoyl)cyclopropyl)methyl)-7-oxo-4,5,6,7-tetrahydro-1H-pyrazolo[3,4-c]pyridine-3-carboxamide (123). $^1$H NMR (400 MHz, DMSO-$d_6$) δ 8.97 (m, 1H), 7.79 (d, J=4.0 Hz, 2H), 7.48 (m, 2H), 7.01 (m, 1H), 4.47 (m, 2H), 4.12 (s, 3H), 3.90 (s, 2H), 3.67 (m, 2H), 2.98 (m, 2H), 2.73-2.62 (m, 3H), 1.21-1.13 (m, 2H), 1.07-0.99 (m, 2H). MS (ESI): m/z 457.2 [M+H]$^+$.

Other compounds in Table 6 below were prepared following procedures analogous to those described for Compound (123) in Example 123. For analogs derived from diamine building blocks, the corresponding mono-Boc diamine was used in the sulfonamide formation and the final compound was revealed by deprotection with HCl in dioxane.

TABLE 6

| Example/Compound Number | Compound Structure and Name | Physical Data MS (m/z), $^1$H NMR, and/or $^{19}$F NMR |
|---|---|---|
| 124 | 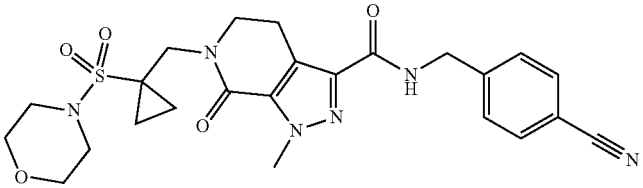 [SMILES: Cn1nc(C(=O)NCc2ccc(C#N)cc2)c2c1C(=O)N(CC1(S(=O)(=O)N3CCOCC3)CC1)CC2]<br>N-(4-Cyanobenzyl)-1-methyl-6-((1-(morpholinosulfonyl)cyclopropyl)methyl)-7-oxo-4,5,6,7-tetrahydro-1H-pyrazolo[3,4-c]pyridine-3-carboxamide | MS (ESI): m/z 513.2 [M + H]$^+$. $^1$H NMR (400 MHz, DMSO-d$_6$) δ 8.96 (m, 1H), 7.78 (d, J = 8.4 Hz, 2H), 7.47 (d, J = 8.0 Hz, 2H), 4.46 (d, J = 6.4 Hz, 2H), 4.11 (s, 3H), 3.91 (s, 2H), 3.63 (m, 6H), 3.28-3.21 (m, 4H), 2.97 (m, 2H), 1.28-1.20 (m, 2H) 2H), 1.09-1.01 (m, 2H). |
| 125 | 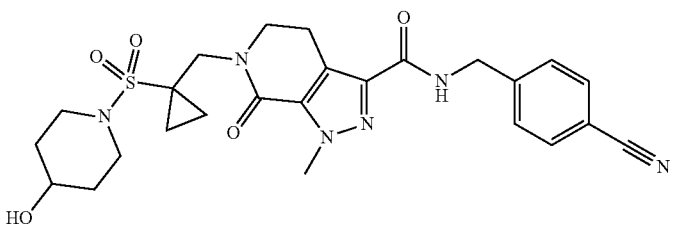 [SMILES: Cn1nc(C(=O)NCc2ccc(C#N)cc2)c2c1C(=O)N(CC1(S(=O)(=O)N3CCC(O)CC3)CC1)CC2]<br>N-(4-Cyanobenzyl)-6-((1-((4-hydroxypiperidin-1-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 527.3 [M + H]$^+$. $^1$H NMR (400 MHz, CDCl$_3$) δ 7.64 (d, J = 8.0 Hz, 2H), 7.46 (d, J = 8.0 Hz, 2H), 4.66 (d, J = 6.4 Hz, 2H), 4.16 (s, 3H), 3.97 (s, 2H), 3.93 (m, 1H), 3.73 (t, J = 6.8 Hz, 2H), 3.70-3.62 (m, 2H), 3.25-3.20 (m, 2H), 3.20-3.16 (m, 2H), 1.98 (m, 2H), 1.72-1.63 (m, 2H), 1.46-1.39 (m, 2H), 1.08-1.01 (m, 2H). |
| 126 | 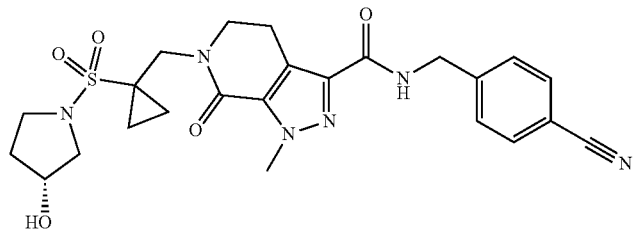 [SMILES: Cn1nc(C(=O)NCc2ccc(C#N)cc2)c2c1C(=O)N(CC1(S(=O)(=O)N3CC[C@@H](O)C3)CC1)CC2]<br>(R)-N-(4-Cyanobenzyl)-6-((1-((3-hydroxypyrrolidin-1-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 513.3 [M + H]$^+$. $^1$H NMR (400 MHz, CDCl$_3$) δ 7.64 (d, J = 8.0 Hz, 2H), 7.46 (d, J = 8.0 Hz, 2H), 7.32-7.27 (m, 1H), 4.66 J = 6.4 Hz, 2H), 4.50 (br s, 1H), 4.29 (d, J = 14.8 Hz, 1H), 4.16 (s, 3H), 3.84-3.74 (m, 1H), 3.73-3.59 (m, 2H), 3.59-3.50 (m, 2H), 3.49-3.43 (m, 2H), 3.21 (m, 2H), 2.15-2.01 (m, 2H), 1.56-1.48 (m, 2H), 1.07-0.93 (m, 2H). SFC R$_t$ = 3.671 min, 100% ee, [CHIRALPAK AD-3, 5-40% i-PrOH (0.05% Et$_2$NH), 3 mL/min]. |
| 127 | 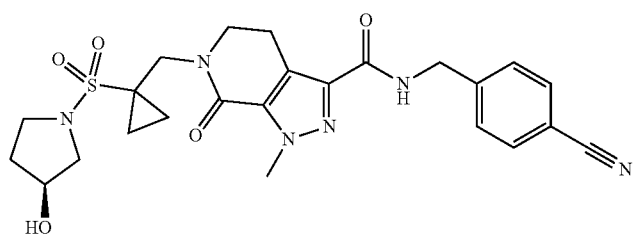 [SMILES: Cn1nc(C(=O)NCc2ccc(C#N)cc2)c2c1C(=O)N(CC1(S(=O)(=O)N3CC[C@H](O)C3)CC1)CC2]<br>(S)-N-(4-Cyanobenzyl)-6-((1-((3-hydroxypyrrolidin-1-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 513.3 [M + H]$^+$. $^1$H NMR (400 MHz, CDCl$_3$) δ 7.64 (d, J = 8.0 Hz, 2H), 7.46 (d, J = 8.0 Hz, 2H), 7.32-7.27 (m, 1H), 4.66 (d, J = 6.4 Hz, 2H), 4.49 (br s, 1H), 4.29 (d, J = 14.8 Hz, 1H), 4.16 (s, 3H), 3.84-3.75 (m, 1H), 3.73-3.60 (m, 2H), 3.60-3.49 (m, 2H), 3.53-3.41 (m, 2H), 3.25-3.17 (m, 2H), 2.12-2.04 (m, 2H), 1.58-1.48 (m, 2H), 1.06-0.95 (m, 2H). SFC R$_t$ = 3.594 min, 100% ee, [CHIRALPAK AD-3, 5-40% i-PrOH (0.05% Et$_2$NH), 3 mL/min] |
| 128 | 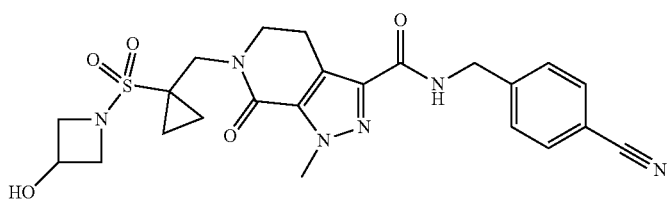 [SMILES: Cn1nc(C(=O)NCc2ccc(C#N)cc2)c2c1C(=O)N(CC1(S(=O)(=O)N3CC(O)C3)CC1)CC2]<br>N-(4-Cyanobenzyl)-6-((1-((3-hydroxyazetidin-1-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 499.3 [M + H]$^+$. $^1$H NMR (400 MHz, CDCl$_3$) δ 7.64 (d, J = 8.2 Hz, 2H), 7.46 (d, J = 8.2 Hz, 2H), 7.33-7.28 (m, 1H), 4.66 (d, J = 6.4Hz, 2H), 4.64-4.54 (m, 1H), 4.16 (s, 3H), 4.15-4.11 (m, 2H), 3.93-3.89 (s, 2H), 3.91 (m, 2H), 3.77 (t, J = 6.8 Hz, 2H), 3.20 (t, J = 6.8 Hz, 2H), 2.59 (br d, J = 7.2 Hz, 1H), 1.46-1.35 (m, 2H), 1.17-1.05 (m, 2H). |

TABLE 6-continued

| Example/ Compound Number | Compound Structure and Name | Physical Data MS (m/z), $^1$H NMR, and/or $^{19}$F NMR |
|---|---|---|
| 129 | 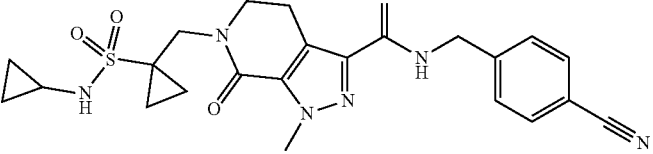<br>N-(4-cyanobenzyl)-6-((1-(N-cyclopropylsulfamoyl)cyclopropyl)methyl)-1-methyl-7-oxo-4,5,6,7-tetrahydro-1H-pyrazolo[3,4-c]pyridine-3-carboxamide | MS (ESI): m/z 483.3 [M + H]$^+$. $^1$H NMR (400 MHz, CDCl$_3$) δ 7.64 (d, J = 8.2 Hz, 2H), 7.45 (d, J = 8.2 Hz, 2H), 7.30 (m, 1H), 6.20 (s, 1H), 4.66 (d, J = 6.4 Hz, 2H), 4.16 (s, 3H), 3.91 (s, 2H), 3.73 (m, 2H), 3.19 (m 2H), 2.64-2.55 (m, 1H), 1.60 (br s, 2H), 1.00-0.94 (m, 2H), 0.85-0.78 (m, 2H), 0.75-0.69 (m, 2H). |
| 130 | 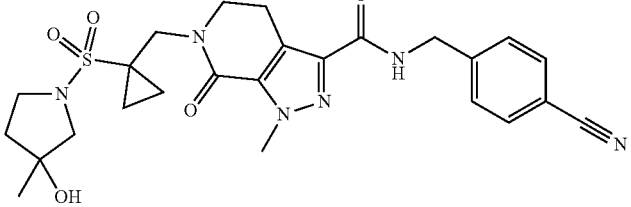<br>(R)- or (S)-N-(4-Cyanobenzyl)-6-((1-((3-hydroxy-3-methylpyrrolidin-1-yl)sulfonyl)cyclopropyl)methyl)-1-methyl-7-oxo-4,5,6,7-tetrahydro-1H-pyrazolo[3,4-c]pyridine-3-carboxamide<br>Unless otherwise indicated, examples indicate relative stereochemistry | MS (ESI): m/z 527.3 [M + H]$^+$. $^1$H NMR (400 MHz, DMSO-d$_6$) δ 8.95 (t, J = 6.4 Hz, 1H), 7.78 (d, J = 8.0 Hz, 2H), 7.47 (d, J = 8.2 Hz, 2H), 4.92 (s, 1H), 4.46 (d, J = 6.4 Hz, 2H), 4.11 (s, 3H), 3.97-3.87 (m, 2H), 3.64 (t, J = 6.8 Hz, 2H), 3.50-3.37 (m, 2H), 3.27-3.12 (m, 2H), 2.97 (t, J = 6.8 Hz, 2H), 1.89-1.75 (m, 2H), 1.29 (s, 3H), 1.22-1.15 (m, 2H), 1.07-0.98 (m, 2H). SFC R$_t$ = 2.398 min, 100% ee, [CHIRALPAK AS-3, 5-40% MeOH (0.05% Et$_2$NH), 3 mL/min]. |
| 131 | 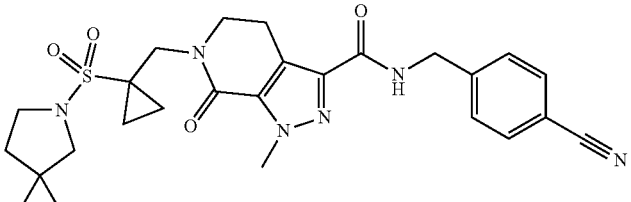<br>(R)- or (S)-N-(4-Cyanobenzyl)-6-((1-((3-hydroxy-3-methylpyrrolidin-1-yl)sulfonyl)cyclopropyl)methyl)-1-methyl-7-oxo-4,5,6,7-tetrahydro-1H-pyrazolo[3,4-c]pyridine-3-carboxamide<br>Unless otherwise indicated, examples indicate relative stereochemistry | MS (ESI): m/z 527.3 [M + H]$^+$. $^1$H NMR (400 MHz, DMSO-d$_6$) δ 8.95 (t, J = 6.4 Hz, 1H), 7.78 (d, J = 8.2 Hz, 2H), 7.47 (d, J = 8.2 Hz, 2H), 4.92 (s, 1H), 4.46 (d, J = 6.4 Hz, 2H), 4.11 (s, 3H), 3.96-3.86 (m, 2H), 3.64 (t, J = 6.8 Hz, 2H), 3.52-3.37 (m, 2H), 3.27-3.13 (m, 2H), 2.97 (t, J = 6.8 Hz, 2H), 1.89-1.74 (m, 2H), 1.29 (s, 3H), 1.24-1.16 (m, 2H), 1.07-0.99 (m, 2H). SFC R$_t$ = 2.518 min, 100% ee, [CHIRALPAK AS-3, 5-40% MeOH (0.05% Et$_2$NH), 3 mL/min] |
| 132 | 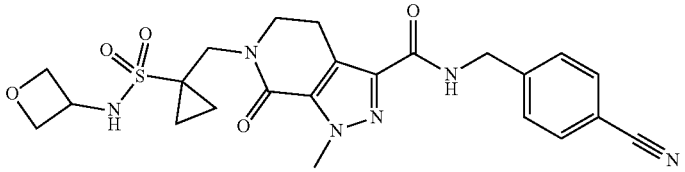 [SMILES: Cn1nc(C(=O)NCc2ccc(C#N)cc2)c2c1C(=O)N(CC1(S(=O)(=O)NC3COC3)CC1)CC2]<br>N-(4-Cyanobenzyl)-1-methyl-6-((1-(N-(oxetan-3-yl)sulfamoyl)cyclopropyl)methyl)-7-oxo-4,5,6,7-tetrahydro-1H-pyrazolo[3,4-c]pyridine-3-carboxamide | MS (ESI): m/z 499.1 [M + H]$^+$. $^1$H NMR (400 MHz, CDCl$_3$) δ 7.65 (d, J = 8.0 Hz, 2H), 7.46 (d, J = 8.0 Hz, 2H), 7.32-7.29 (m, 1H), 6.80 (d, J = 8.4 Hz, 1H), 4.89-4.86 (m, 2H), 4.80-4.76 (m, 2H), 4.74-4.68 (m, 1H), 4.67 (d, J = 6.4 Hz, 2H), 4.20 (s, 2H), 3.84 (s, 2H), 3.74-3.70 (m, 2H), 3.22-3.19 (m, 2H), 1.48-1.45 (m, 2H), 0.93-0.90 (m, 2H). |

TABLE 6-continued

| Example/ Compound Number | Compound Structure and Name | Physical Data MS (m/z), ¹H NMR, and/or ¹⁹F NMR |
|---|---|---|
| 133 | N-(4-Cyanobenzyl)-1-methyl-7-oxo-6-((1-(piperazin-1-ylsulfonyl)cyclopropyl)methyl)-4,5,6,7-tetrahydro-1H-pyrazolo[3,4-c]pyridine-3-carboxamide | MS (ESI): m/z 512.0 [M + H]⁺. ¹H NMR (400 MHz, DMSO-d₆) δ 8.94 (m, 1H), 7.78 (d, J = 8.0 Hz, 2H), 7.47 (m, 2H), 4.46 (d, J = 6.0 Hz, 2H), 4.11 (s, 3H), 3.95-3.83 (m, 2H), 3.63 (m, 2H), 3.45 (m, 1H), 3.25 (m, 1H), 3.20-3.09 (m, 3H), 2.97 (t, J = 6.7 Hz, 2H), 2.75-2.69 (m, 3H), 1.27-1.17 (m, 2H), 1.08-0.99 (m, 2H). |
| 134 | 6-((1-(N-(3-Aminopropyl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 500.2 [M + H]⁺. ¹H NMR (400 MHz, DMSO-d₆) δ 8.94 (br s, 1H), 7.78 (br d, J = 8.0 Hz, 2H), 7.47 (br d, J = 8.0 Hz, 2H), 4.46 (br d, J = 6.0 Hz, 2H), 4.11 (s, 3H), 3.90 (s, 2H), 3.62 (br s, 2H), 3.06 (m, 2H), 2.98 (br d, J = 6.4 Hz, 2H), 2.61 (m, 2H), 1.63-1.51 (m, 2H), 1.17 (br s, 2H), 1.01 (br s, 2H). |
| 135 | 6-((1-(N-(2-Aminoethyl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 486.0 [M + H]⁺. ¹H NMR (400 MHz, DMSO-d₆) δ 8.95 (m, 1H), 7.78 (d, J = 8.0 Hz, 2H), 7.47 (m, 2H), 4.46 (d, J = 6.0 Hz, 2H), 4.12 (s, 3H), 3.91 (s, 2H), 3.66 (m, 2H), 3.04 (m, 3H), 2.97 (m, 2H), 2.71-2.67 (m, 1H), 1.17 (br s, 2H), 1.02 (br s, 2H). |
| 136 | N-(4-Cyanobenzyl)-1-methyl-6-((1-((4-methylpiperazin-1-yl)sulfonyl)cyclopropyl)methyl)-7-oxo-4,5,6,7-tetrahydro-1H-pyrazolo[3,4-c]pyridine-3-carboxamide | MS (ESI): m/z 526.0 [M + H]⁺. ¹H NMR (400 MHz, DMSO-d₆) δ 8.94-8.92 (m, 1H), 7.78 (d, J = 8.0 Hz, 2H), 7.47 (d, J = 8.8 Hz, 2H), 4.46 (d, J = 5.6 Hz, 2H), 4.11 (s, 3H), 3.89 (s, 2H), 3.68-3.58 (m, 2H), 3.25 (s, 4H), 2.97 (m, 2H), 2.39-2.33 (m, 3H), 2.18 (s, 3H), 1.25-1.17 (m, 2H), 1.04 (s, 2H). |
| 137 | N-(4-Cyanobenzyl)-1-methyl-7-oxo-6-((1-(N-(piperidin-4-yl)sulfamoyl)cyclopropyl)methyl)-4,5,6,7-tetrahydro-1H-pyrazolo[3,4-c]pyridine-3-carboxamide | MS (ESI): m/z 526.3 [M + H]⁺. ¹H NMR (400 MHz, DMSO-d₆) δ 8.95 (t, J = 6.2 Hz, 1H), 7.78 (d, J = 8.2 Hz, 2H), 7.47 (d, J = 8.0 Hz, 2H), 7.14 (br s, 1H), 4.46 (br d, J = 6.0 Hz, 2H), 4.11 (s, 3H), 3.89 (s, 2H), 3.66 (br t, J = 6.8 Hz, 2H), 3.15 (br s, 1H), 2.97 (br t, J = 6.8 Hz, 2H), 2.89 (br d, J = 12.2 Hz, 2H), 2.43 (m, 2H), 1.79 (br d, J = 10.4 Hz, 2H), 1.33 (m, 2H), 1.21-1.13 (m, 2H), 1.04-0.96 (m, 2H). |

TABLE 6-continued

| Example/ Compound Number | Compound Structure and Name | Physical Data MS (m/z), ¹H NMR, and/or ¹⁹F NMR |
|---|---|---|
| 138 | 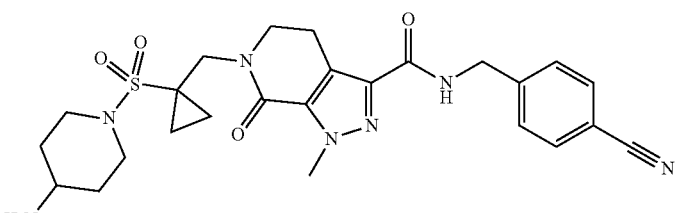<br>6-((1-(((4-Aminopiperidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 526.2 [M + H]⁺. ¹H NMR (400 MHz, DMSO-d₆) δ 8.95 (br t, J = 6.2 Hz, 1H), 7.78 (d, J = 8.0 Hz, 2H), 7.47 (br d, J = 8.0 Hz, 2H), 4.46 (br d, J = 6.0 Hz, 2H), 4.11 (s, 3H), 3.87 (s, 2H), 3.67-3.61 (m, 2H), 3.61-3.56 (m, 2H), 3.01-2.96 (m, 2H), 2.95-2.89 (m, 2H), 2.78-2.68 (m, 1H), 1.74 (br d, J = 10.4 Hz, 2H), 1.31-1.21 (m, 2H), 1.20 (br s, 2H), 1.02 (br s, 2H). |
| 139 | 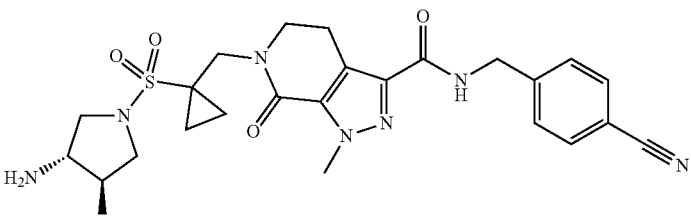<br>6-((1-(((3R,4R)-3-Amino-4-hydroxypyrrolidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 528.4 [M + H]⁺. ¹H NMR (400 MHz, DMSO-d₆) δ 8.93 (m, 1H), 7.78 (d, J = 8.0 Hz, 2H), 7.47 (br d, J = 8.0 Hz, 2H), 5.17 (br s, 1H), 4.46 (br d, J = 6.0 Hz, 2H), 4.11 (s, 3H), 4.01-3.87 (m, 2H), 3.84 (br s, 1H), 3.65 (m, 2H), 3.57 (m, 1H), 3.48 (m, 1H), 3.20 (br d, J = 2.2 Hz, 1H), 3.17-3.11 (m, 1H), 3.07 (m, 1H), 2.97 (m, 2H), 1.20 (br s, 2H), 1.02 (br s, 2H SFC R₁ = 2.434 min, 100% ee, [CHIRALPAK AD-3, 5-40% i-PrOH (0.05% Et₂NH), 3 mL/min]. |
| 140 | 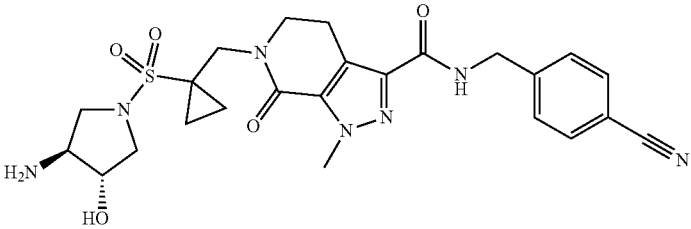 [SMILES: Cn1nc(C(=O)NCc2ccc(C#N)cc2)c2c1C(=O)N(CC1(S(=O)(=O)N3C[C@H](N)[C@@H](O)C3)CC1)CC2]<br>6-((1-(((3S,4S)-3-Amino-4-hydroxypyrrolidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 528.4 [M + H]⁺. ¹H NMR (400 MHz, DMSO-d₆) δ 8.93 (m, 1H), 7.78 (br d, J = 8.0 Hz, 2H), 7.47 (br d, J = 8.0 Hz, 2H), 5.18 (br s, 1H), 4.46 (br d, J = 6.0 Hz, 2H), 4.11 (s, 3H), 4.02-3.87 (m, 2H), 3.84 (br s, 1H), 3.64 (m, 2H), 3.57 (m, 1H), 3.48 (m, 1H), 3.20 (br s, 1H), 3.15 (br d, J = 9.2 Hz, 1H), 3.07 (br d, J = 9.2 Hz, 1H), 2.97 (m, 2H), 1.20 (br s, 2H), 1.02 (br s, 2H). SFC R₁ = 2.543 min, 95.8% ee, [CHIRALPAK AD-3, 5-40% i-PrOH (0.05% Et₂NH), 3 mL/min]. |
| 141 | 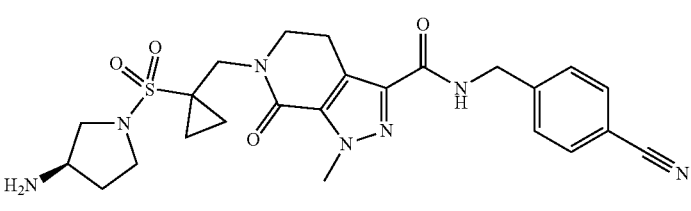 [SMILES: Cn1nc(C(=O)NCc2ccc(C#N)cc2)c2c1C(=O)N(CC1(S(=O)(=O)N3CC[C@@H](N)C3)CC1)CC2]<br>(R)-6-((1-(((3-Aminopyrrolidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 512.2 [M + H]⁺. ¹H NMR (400 MHz, DMSO-d₆) δ 8.95 J = 6.2 Hz, 1H), 7.78 (d, J = 8.4 Hz, 2H), 7.47 (d, J = 8.0 Hz, 2H), 4.46 (br d, J = 6.2 Hz, 2H), 4.11 (s, 3H), 3.97-3.85 (m, 2H), 3.64 (m, 2H), 3.51-3.40 (m, 5H), 3.00-2.96 (m, 2H), 2.96-2.92 (m, 1H), 1.96 (m, 1H), 1.62 (m, 1H), 1.26-1.13 (m, 2H), 1.10-0.96 (m, 2H). SFC R₁ = 3.778 min, 100% ee, [CHIRALPAK AD-3, 3-40% MeOH (0.05% Et₂NH), 3 mL/min]. |

TABLE 6-continued

| Example/ Compound Number | Compound Structure and Name | Physical Data MS (m/z), ¹H NMR, and/or ¹⁹F NMR |
|---|---|---|
| 142 | 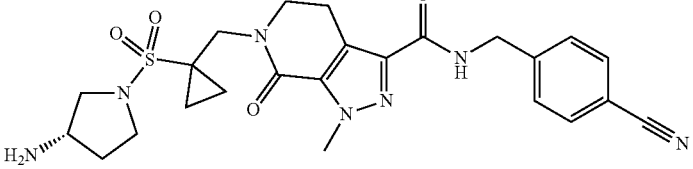(S)-6-((1-((3-Aminopyrrolidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 512.2 [M + H]⁺. ¹H NMR (400 MHz, DMSO-d₆) δ 8.95 J = 6.2 Hz, 1H), 7.78 (d, J = 8.0 Hz, 2H), 7.47 (d, J = 8.4 Hz, 2H), 4.46 (br d, J = 6.0 Hz, 2H), 4.11 (s, 3H), 3.98-3.84 (m, 2H), 3.64 (m, 2H), 3.51-3.40 (m, 5H), 3.01-2.96 (m, 1H), 2.96-2.92 (m, 1H), 1.96 (m, 1H), 1.62 (m, 1H), 1.24-1.16 (m, 2H), 1.08-1.00 (m, 2H). SFC R$_t$ = 5.826 min, 100% ee, [CHIRALPAK AD-3, 3-40% MeOH (0.05% Et₂NH), 3 mL/min]. |
| 143 | 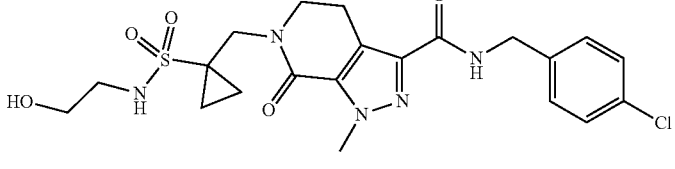N-(4-Chlorobenzyl)-6-((1-(N-(2-hydroxyethyl)sulfamoyl)cyclopropyl)methyl)-1-methyl-7-oxo-4,5,6,7-tetrahydro-1H-pyrazolo[3,4-c]pyridine-3-carboxamide | MS (ESI): m/z 496.2 [M + H]⁺. ¹H NMR (400 MHz, DMSO-d₆) δ 8.84 (m, 1H), 7.39-7.37 (m, 2H), 7.32-7.30 (m, 2H), 7.08 (s, 1H), 4.79 (s, 1H), 4.37 (br d, J = 6.0 Hz, 2H), 4.11 (s, 3H), 3.92 (s, 2H), 3.67 (m, 2H), 3.47 (m, 2H), 3.06 (m, 2H), 2.98 (m, 2H), 1.21-1.14 (m, 2H), 1.07-0.98 (m, 2H). |
| 144 | 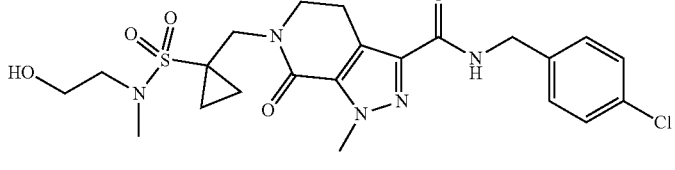N-(4-Chlorobenzyl)-6-((1-(N-(2-hydroxyethyl)-N-methylsulfamoyl)cyclopropyl)methyl)-1-methyl-7-oxo-4,5,6,7-tetrahydro-1H-pyrazolo[3,4-c]pyridine-3-carboxamide | MS (ESI): m/z 510.1 [M + H]⁺. ¹H NMR (400 MHz, DMSO-d₆) δ 8.84 (m, 1H), 7.43-7.34 (m, 2H), 7.34-7.25 (m, 2H), 4.80 (m, 1H), 4.37 (d, J = 6.0 Hz, 2H), 4.10 (s, 3H), 3.90 (s, 2H), 3.63 (m, 2H), 3.55 (m, 2H), 3.24 (m, 2H), 2.98 (m, 2H), 2.89 (s, 3H), 1.31-1.15 (m, 2H), 1.07-0.93 (m, 2H). |
| 145 | 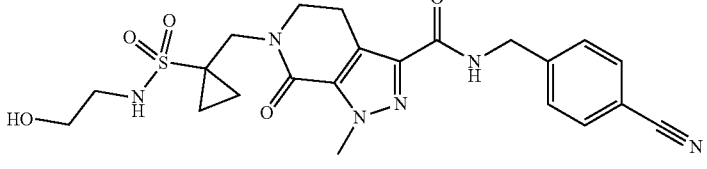N-(4-Cyanobenzyl)-6-((1-(N-(2-hydroxyethyl)sulfamoyl)cyclopropyl)methyl)-1-methyl-7-oxo-4,5,6,7-tetrahydro-1H-pyrazolo[3,4-c]pyridine-3-carboxamide | MS (ESI): m/z 487.0 [M + H]⁺. ¹H NMR (400 MHz, DMSO-d₆) δ 8.94 (m, 1H), 7.78 (d, J = 8.0 Hz, 2H), 7.47 (d, J = 8.0 Hz, 2H), 7.07 (br s, 1H), 4.79 (m, 1H), 4.46 (br d, J = 6.4 Hz, 2H), 4.12 (s, 3H), 3.92 (s, 2H), 3.67 (m, 2H), 3.47 (m, 2H), 3.06 (m, 2H), 2.97 (m, 2H), 1.23-1.13 (m, 2H), 1.07-0.96 (m, 2H). |
| 146 | 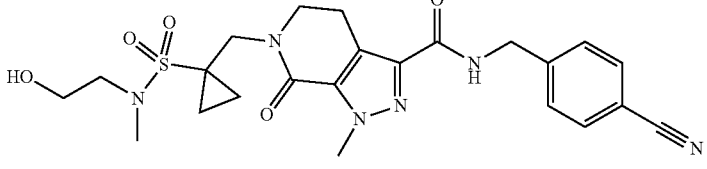N-(4-Cyanobenzyl)-6-((1-(N-(2-hydroxyethyl)-N-methylsulfamoyl)cyclopropyl)methyl)-1-methyl-7-oxo-4,5,6,7-tetrahydro-1H-pyrazolo[3,4-c]pyridine-3-carboxamide | MS (ESI): m/z 501.0 [M + H]⁺. ¹H NMR (400 MHz, DMSO-d₆) δ 9.12-8.87 (m, 1H), 7.78 (br d, J = 8.0 Hz, 2H), 7.47 (br d, J = 7.6 Hz, 2H), 5.00-4.74 (m, 1H), 4.46 (br d, J = 5.6 Hz, 2H), 4.11 (br s, 3H), 3.90 (br s, 2H), 3.63 (m, 2H), 3.55 (br d, J = 5.4 Hz, 2H), 3.29-3.20 (m, 2H), 3.04-2.94 (m, 2H), 2.89 (br s, 3H), 1.22 (br s, 2H), 1.02 (br s, 2H). |

TABLE 6-continued

| Example/ Compound Number | Compound Structure and Name | Physical Data MS (m/z), ¹H NMR, and/or ¹⁹F NMR |
|---|---|---|
| 147 | 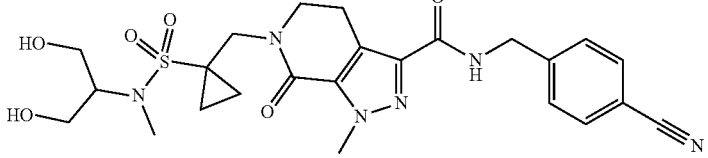<br>N-(4-Cyanobenzyl)-6-((1-(N-(1,3-dihydroxypropan-2-yl)-N-methylsulfamoyl)cyclopropyl)methyl)-1-methyl-7-oxo-4,5,6,7-tetrahydro-1H-pyrazolo[3,4-c]pyridine-3-carboxamide | MS (ESI): m/z 531.4 [M + H]⁺. ¹H NMR (400 MHz, CDCl₃) δ 7.64 (d, J = 8.2 Hz, 2H), 7.45 (d, J = 8.2 Hz, 2H), 7.30 (br t, J = 6.2 Hz, 1H), 6.12 (br d, J = 5.4 Hz, 1H), 4.66 (d, J = 6.2 Hz, 2H), 4.17 (s, 3H), 3.99 (s, 2H), 3.81 (br d, J = 3.6 Hz, 2H), 3.73 (m, 2H), 3.66-3.57 (m, 3H), 3.41 (s, 3H), 3.19 (t, J = 7.0 Hz, 2H), 1.55-1.46 (m, 2H), 0.98-0.93 (m, 2H). |
| 148 | 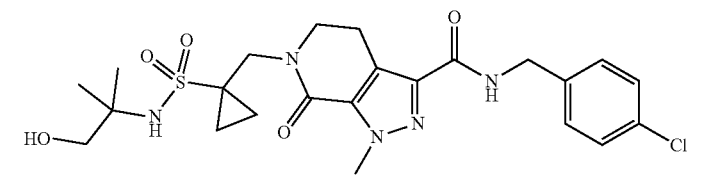 [SMILES: Cn1nc(C(=O)NCc2ccc(Cl)cc2)c2c1C(=O)N(CC1(S(=O)(=O)NC(C)(C)CO)CC1)CC2]<br>N-(4-Chlorobenzyl)-6-((1-(N-(1-hydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxamide | MS (ESI): m/z 523.9 [M + H]⁺. ¹H NMR (400 MHz, DMSO-d₆) δ 8.85 (br s, 1H), 7.34 (br d, J = 14.8 Hz, 4H), 6.56 (br s, 1H), 4.94 (m, 1H), 4.38 (m, 2H), 4.11 (m, 3H), 3.95 (m, 2H), 3.67 (m, 2H), 3.31 (m, 2H), 2.97 (m, 2H), 1.21 (m, 8H), 1.04 (m, 2H). |
| 149 | 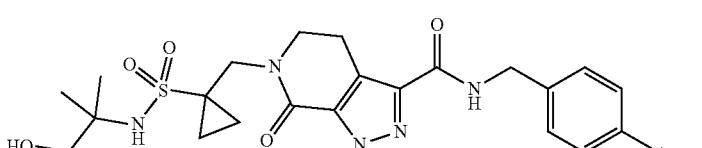<br>N-(4-Cyanobenzyl)-6-((1-(N-(1-hydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxamide | MS (ESI): m/z 515.2 [M + H]⁺. ¹H NMR (400 MHz, DMSO-d₆) δ 8.95 (m, 1H), 7.79 (d, J = 8.4 Hz, 2H), 7.48 (d, J = 8.4 Hz, 2H), 6.56 (s, 1H), 4.94 (m, 1H), 4.47 (d, J = 6.4 Hz, 2H), 4.12 (s, 3H), 3.96 (s, 2H), 3.67 (t, J = 6.8 Hz, 2H), 3.31 (m, 2H), 2.97 (t, J = 6.8 Hz, 2H), 1.24-1.16 (m, 8H), 1.08-1.02 (m, 2H). |
| 150 | 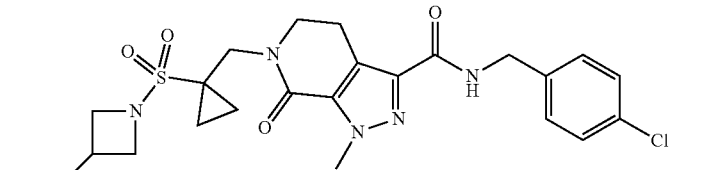<br>N-(4-Chlorobenzyl)-6-((1-((3-hydroxyazetidin-1-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 508.0 [M + H]⁺. ¹H NMR (400 MHz, CDCl₃) δ 7.34-7.31 (m, 2H), 7.31-7.28 (m, 2H), 7.23-7.16 (m, 1H), 4.64-4.57 (m, 2H), 4.56 (s, 1H), 4.14 (s, 3H), 4.14-4.08 (m, 2H), 3.95 (s, 2H), 3.91 (m, 2H), 3.76 (m, 2H), 3.21 (m, 2H), 3.00-2.81 (m, 1H), 1.43-1.37 (m, 2H), 1.14-1.07 (m, 2H). |
| 151 | 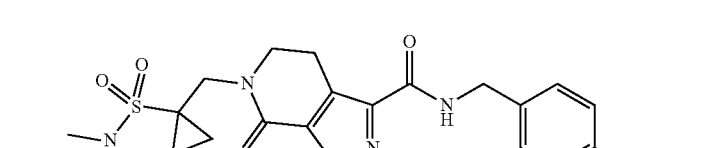<br>N-(4-Chlorobenzyl)-1-methyl-6-((1-(N-methylsulfamoyl)cyclopropyl)methyl)-7-oxo-4,5,6,7-tetrahydro-1H-pyrazolo[3,4-c]pyridine-3-carboxamide | MS (ESI): m/z 465.9 [M + H]⁺. ¹H NMR (400 MHz, DMSO-d₆) δ 8.84 (m, 1H), 7.39-7.34 (m, 2H), 7.34-7.27 (m, 2H), 6.99 (m, 1H), 4.37 (d, J = 6.2 Hz, 2H), 4.10 (s, 3H), 3.89 (s, 2H), 3.66 (m, 2H), 2.97 (m, 2H), 2.65 (s, 3H), 1.19-1.12 (m, 2H), 1.05-0.96 (m, 2H). |

TABLE 6-continued

| Example/ Compound Number | Compound Structure and Name | Physical Data MS (m/z), $^1$H NMR, and/or $^{19}$F NMR |
|---|---|---|
| 152 | 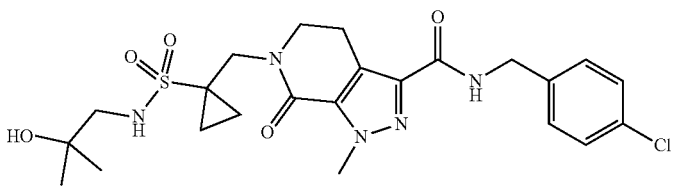 [SMILES: Cn1nc(C(=O)NCc2ccc(Cl)cc2)c2c1C(=O)N(CC1(S(=O)(=O)NCC(C)(C)O)CC1)CC2]<br>N-(4-Chlorobenzyl)-6-((1-(N-(2-hydroxy-2-methylpropyl)sulfamoyl)cyclopropyl)methyl)-1-methyl-7-oxo-4,5,6,7-tetrahydro-1H-pyrazolo[3,4-c]pyridine-3-carboxamide | MS (ESI): m/z 524.1 [M + H]$^+$. $^1$H NMR (400 MHz, DMSO-d$_6$) δ 8.85 (m, 1H), 7.40-7.34 (m, 2H), 7.34-7.27 (m, 2H), 6.86 (m, 1H), 4.51 (s, 1H), 4.37 (d, J = 6.4 Hz, 2H), 4.11 (s, 3H), 3.92 (s, 2H), 3.67 (m, 2H), 2.98 (m, 2H), 2.91 (d, J = 6.4 Hz, 2H), 1.23-1.15 (m, 2H), 1.13-1.07 (m, 1H), 1.10 (s, 6H), 1.05-0.97 (m, 2H). |
| 153 | 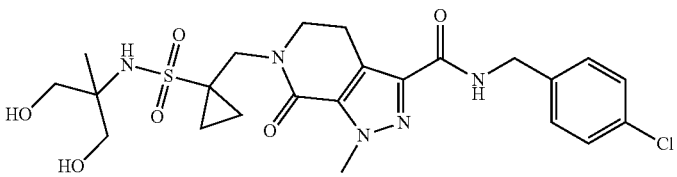 [SMILES: Cn1nc(C(=O)NCc2ccc(Cl)cc2)c2c1C(=O)N(CC1(S(=O)(=O)NC(C)(CO)CO)CC1)CC2]<br>N-(4-Chlorobenzyl)-6-((1-(N-(1,3-dihydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxamide | MS (ESI): m/z 540.1 [M + H]$^+$. $^1$H NMR (400 MHz, DMSO-d$_6$) δ 8.85 (m, 1H), 7.40-7.27 (m, 4H), 6.37 (s, 1H), 4.79 (s, 2H), 4.37 (m, 2H), 4.11 (s, 3H), 3.98 (s, 2H), 3.67 (m, 2H), 3.44-3.40 (m, 4H), 2.97 (m, 2H), 1.23-1.12 (m, 5H), 1.05 (m, 2H). |
| 253 | 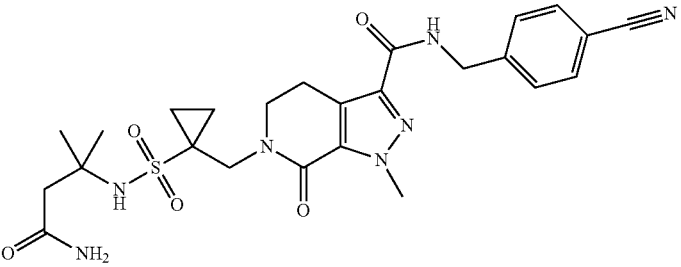 [SMILES: Cn1nc(C(=O)NCc2ccc(C#N)cc2)c2c1C(=O)N(CC1(S(=O)(=O)NC(C)(C)CC(N)=O)CC1)CC2]<br>(253)<br>6-((1-(N-(4-amino-2-methyl-4-oxobutan-2-yl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide | LCMS (ESI): m/z 542.2 [M + H]$^+$ |
| 254 | 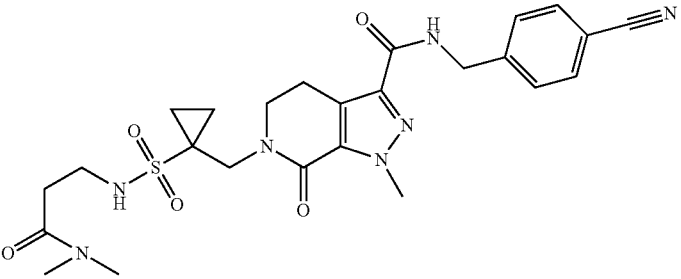 [SMILES: CN(C)C(=O)CCNS(=O)(=O)C1(CN2CCc3c(C(=O)NCc4ccc(C#N)cc4)nn(C)c3C2=O)CC1]<br>(254)<br>N-(4-cyanobenzyl)-6-((1-(N-(3-(dimethylamino)-3-oxopropyl)sulfamoyl)cyclopropyl)methyl)-1-methyl-7-oxo-4,5,6,7-tetrahydro-1H-pyrazolo[3,4-c]pyridine-3-carboxamide | $^1$H NMR (400 MHz, DMSO-d6) δ 8.94 (t, J = 6.3 Hz, 1H), 7.84-7.70 (m, 2H), 7.57-7.31 (m, 2H), 7.02 (t, J = 6.0 Hz, 1H), 4.47 (d, J = 6.3 Hz, 2H), 4.12 (s, 2H), 3.91 (s, 2H), 3.67 (t, J = 6.8 Hz, 2H), 3.22 (q, J = 6.7 Hz, 2H), 2.96 (d, J = 14.1 Hz, 3H), 2.81 (s, 3H), 1.18 (q, J = 4.7, 4.3 Hz, 1H), 1.15-0.83 (m, 2H). $^{19}$F NMR (376 MHz, DMSO-d6) δ −75.15. LCMS (ESI): m/z 542.2 [M + H]$^+$ |

TABLE 6-continued

| Example/ Compound Number | Compound Structure and Name | Physical Data MS (m/z), $^1$H NMR, and/or $^{19}$F NMR |
|---|---|---|
| 255 | 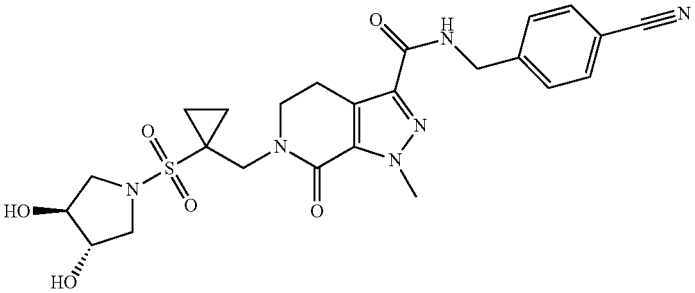 [SMILES: Cn1nc(C(=O)NCc2ccc(C#N)cc2)c2c1C(=O)N(CC1(S(=O)(=O)N3C[C@H](O)[C@@H](O)C3)CC1)CC2]<br>(255)<br>N-(4-cyanobenzyl)-6-((1-(((3S,4S)-3,4-dihydroxypyrrolidin-1-yl)sulfonyl)cyclopropyl)methyl)-1-methyl-7-oxo-4,5,6,7-tetrahydro-1H-pyrazolo[3,4-c]pyridine-3-carboxamide | $^1$H NMR (400 MHz, DMSO-d6) δ 8.94 (t, J = 6.3 Hz, 1H), 7.97-7.63 (m, 2H), 7.59-7.35 (m, 2H), 7.02 (t, J = 6.0 Hz, 1H), 4.47 (d, J = 6.3 Hz, 2H), 4.12 (s, 3H), 3.91 (s, 2H), 3.67 (t, J = 6.8 Hz, 2H), 3.22 (q, J = 6.7 Hz, 2H), 2.96 (d, J = 14.1 Hz, 5H), 2.81 (s, 3H), 1.18 (q, J = 4.7, 4.3 Hz, 2H), 1.10-0.80 (m, 2H). $^{19}$F NMR (376 MHz, DMSO-d6) δ −75.15. LCMS (ESI): m/z 529.2 [M + H]$^+$ |
| 256 | 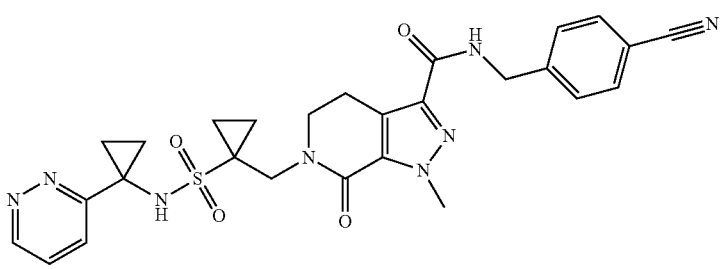 [SMILES: Cn1nc(C(=O)NCc2ccc(C#N)cc2)c2c1C(=O)N(CC1(S(=O)(=O)NC3(c4cccnn4)CC3)CC1)CC2]<br>(256)<br>N-(4-cyanobenzyl)-1-methyl-7-oxo-6-((1-(N-(1-(pyridazin-3-yl)cyclopropyl)sulfamoyl)cyclopropyl)methyl)-4,5,6,7-tetrahydro-1H-pyrazolo[3,4-c]pyridine-3-carboxamide | $^1$H NMR (400 MHz, DMSO-d6) δ 8.94 (t, J = 6.2 Hz, 1H), 8.00-7.72 (m, 2H), 7.46 (dd, J = 19.9, 8.2 Hz, 2H), 6.91 (d, J = 8.1 Hz, 1H), 4.62-4.34 (m, 5H), 4.15-4.05 (m, 11H), 4.00 (d, J = 6.9 Hz, 2H), 3.78-3.62 (m, 2H), 3.48 (d, J = 5.6 Hz, 2H), 2.97 (t, J = 6.8 Hz, 3H), 2.60 (s, 3H), 1.34-1.15 (m, 2H), 1.10-0.86 (m, 2H). $^{19}$F NMR (376 MHz, DMSO-d6) δ −74.51 (d, J = 16.4 Hz), −75.22. $^{19}$F NMR (376 MHz, Methanol-d4) δ −77.70--77.90 (m). LCMS (ESI): m/z 561.2 [M + H]$^+$ |
| 257 | 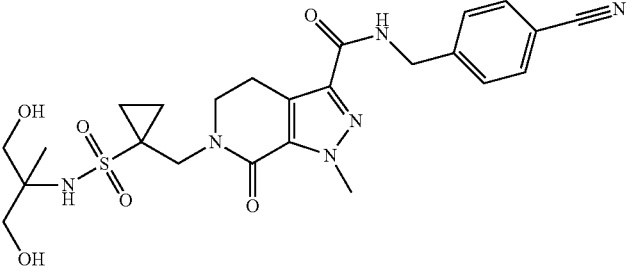 [SMILES: Cn1nc(C(=O)NCc2ccc(C#N)cc2)c2c1C(=O)N(CC1(S(=O)(=O)NC(C)(CO)CO)CC1)CC2]<br>(257)<br>N-(4-cyanobenzyl)-6-((1-(N-(1,3-dihydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxamide | $^1$H NMR (400 MHz, Methanol-d4) δ 8.92 (t, J = 6.3 Hz, 1H), 8.08 (dt, J = 5.6, 1.2 Hz, 1H), 7.78-7.67 (m, 3H), 7.62-7.50 (m, 3H), 4.62 (d, J = 7.1 Hz, 1H), 4.62 (s, 2H), 4.16 (d, J = 28.4 Hz, 5H), 4.07-3.94 (m, 2H), 3.82 (t, J = 6.8 Hz, 2H), 3.41 (tt, J = 8.2, 2.5 Hz, 2H), 3.12 (t, J = 6.8 Hz, 2H), 1.56-1.44 (m, 2H), 1.33-1.18 (m, 2H), 0.98-0.88 (m, 2H). LCMS (ESI): m/z 530.6 [M + H]$^+$ |

TABLE 6-continued

| Example/ Compound Number | Compound Structure and Name | Physical Data MS (m/z), $^1$H NMR, and/or $^{19}$F NMR |
|---|---|---|
| 258 | 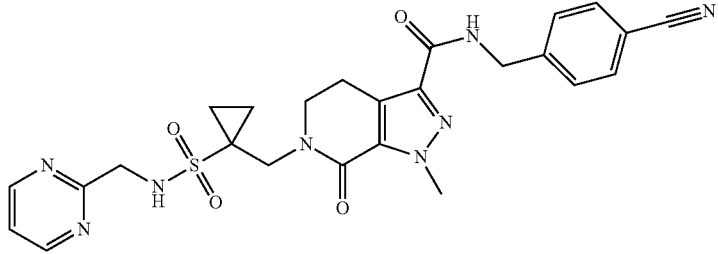<br>(258)<br>N-(4-cyanobenzyl)-1-methyl-7-oxo-6-((1-(N-(pyrimidin-2-ylmethyl)sulfamoyl)cyclopropyl)methyl)-4,5,6,7-tetrahydro-1H-pyrazolo[3,4-c]pyridine-3-carboxamide | $^1$H NMR (400 MHz, Methanol-d4) δ 8.79 (d, J = 4.9 Hz, 2H), 7.80-7.60 (m, 2H), 7.61-7.45 (m, 2H), 7.40 (t, J = 5.0 Hz, 1H), 4.59 (d, J = 21.5 Hz, 3H), 4.19 (s, 2H), 4.04 (s, 2H), 3.77 (t, J = 6.9 Hz, 2H), 3.09 (t, J = 6.9 Hz, 2H), 1.30 (q, J = 4.8 Hz, 2H), 1.09-0.81 (m, 2H). $^{19}$F NMR (376 MHz, Methanol-d4) δ −77.99. LCMS (ESI): m/z 532.2 [M + H]$^+$ |
| 259 | 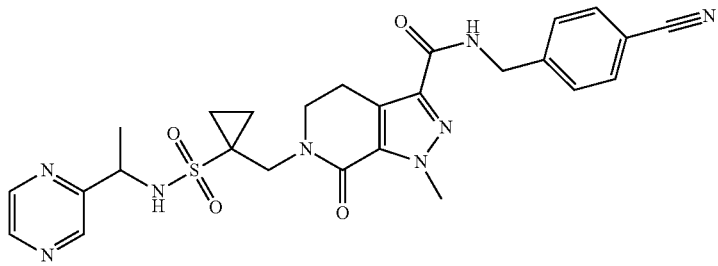 [SMILES: CC(NS(=O)(=O)C1(CN2CCc3c(C(=O)NCc4ccc(C#N)cc4)nn(C)c3C2=O)CC1)c1cnccn1]<br>(259)<br>N-(4-cyanobenzyl)-1-methyl-7-oxo-6-((1-(N-(1-(pyrazin-2-yl)ethyl)sulfamoyl)cyclopropyl)methyl)-4,5,6,7-tetrahydro-1H-pyrazolo[3,4-c]pyridine-3-carboxamide | $^1$H NMR (400 MHz, DMSO-d6) δ 8.94 (t, J = 6.3 Hz, 1H), 8.77 (d, J = 1.5 Hz, 1H), 8.63-8.54 (m, 2H), 7.91 (d, J = 8.4 Hz, 1H), 7.83-7.76 (m, 2H), 7.48 (d, J = 8.1 Hz, 2H), 4.77-4.64 (m, 1H), 4.47 (d, J = 6.2 Hz, 2H), 4.12 (s, 3H), 3.95 (d, J = 14.8 Hz, 1H), 3.73-3.59 (m, 11H), 2.94 (t, J = 6.8 Hz, 2H), 1.51 (d, J = 6.9 Hz, 3H), 1.27-1.16 (m, 1H), 1.10-0.97 (m, 2H), 0.80-0.70 (m, 1H). $^{19}$F NMR (376 MHz, DMSO-d6) δ −75.09. LCMS (ESI): m/z 549.6 [M + H]$^+$ |
| 260 | 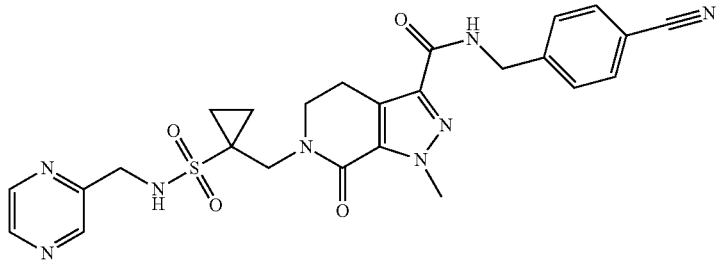 [SMILES: Cn1nc(C(=O)NCc2ccc(C#N)cc2)c2c1C(=O)N(CC1(S(=O)(=O)NCc3cnccn3)CC1)CC2]<br>(260)<br>N-(4-cyanobenzyl)-1-methyl-7-oxo-6-((1-(N-(pyrazin-2-ylmethyl)sulfamoyl)cyclopropyl)methyl)-4,5,6,7-tetrahydro-1H-pyrazolo[3,4-c]pyridine-3-carboxamide | $^1$H NMR (400 MHz, DMSO-d6) δ 8.94 (t, J = 6.3 Hz, 1H), 8.73 (d, J = 1.5 Hz, 1H), 8.64-8.55 (m, 2H), 7.88 (t, J = 6.2 Hz, 1H), 7.83-7.76 (m, 2H), 7.52-7.45 (m, 2H), 4.44 (dd, J = 22.9, 6.2 Hz, 4H), 4.12 (s, 4H), 3.65 (t, J = 6.8 Hz, 3H), 2.96 (t, J = 6.8 Hz, 2H), 1.23-1.15 (m, 2H), 1.01-0.93 (m, 2H). $^{19}$F NMR (376 MHz, DMSO) δ −32.26, −75.28, −75.29, −75.30, −75.70, −188.83. LCMS (ESI): m/z 535.1 [M + H]$^+$ |

TABLE 6-continued

| Example/Compound Number | Compound Structure and Name | Physical Data MS (m/z), $^1$H NMR, and/or $^{19}$F NMR |
|---|---|---|
| 261 | 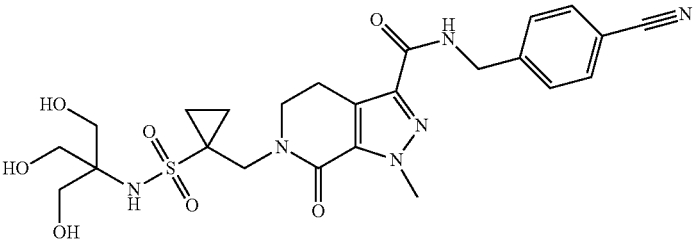 [SMILES: Cn1nc(C(=O)NCc2ccc(C#N)cc2)c2c1C(=O)N(CC1(S(=O)(=O)NC(CO)(CO)CO)CC1)CC2]<br>(261)<br>N-(4-cyanobenzyl)-6-((1-(N-(1,3-dihydroxy-2-(hydroxymethyl)propan-2-yl)sulfamoyl)cyclopropyl)methyl)-1-methyl-7-oxo-4,5,6,7-tetrahydro-1H-pyrazolo[3,4-c]pyridine-3-carboxamide | $^1$H NMR (400 MHz, DMSO-d$_6$) δ 8.98-8.90 (m, 1H), 7.83-7.76 (m, 2H), 7.48 (d, J = 8.2 Hz, 2H), 7.14 (s, 0H), 6.21 (s, 1H), 4.47 (d, J = 6.2 Hz, 2H), 4.12 (d, J = 2.6 Hz, 3H), 4.07-3.92 (m, 4H), 3.69 (td, J = 6.8, 3.6 Hz, 5H), 3.61 (s, 5H), 2.97 (t, J = 6.8 Hz, 2H), 1.76 (s, 0H), 1.21 (q, J = 4.9, 4.2 Hz, 2H), 1.07-0.99 (m, 2H), 0.08 (s, 0H). $^{19}$F NMR (376 MHz, DMSO-d6) δ −74.59 (d, J = 3.5 Hz), −74.91. LCMS (ESI): m/z 547.2 [M + H]$^+$ |

Example 154

N-(4-Chlorobenzyl)-6-((1-(N-(1,3-dihydroxy-2-methylpropan-2-yl)-N-methylsulfamoyl)cyclopropyl)methyl)-1-methyl-7-oxo-4,5,6,7-tetrahydro-1H-pyrazolo[3,4-c]pyridine-3-carboxamide (154)

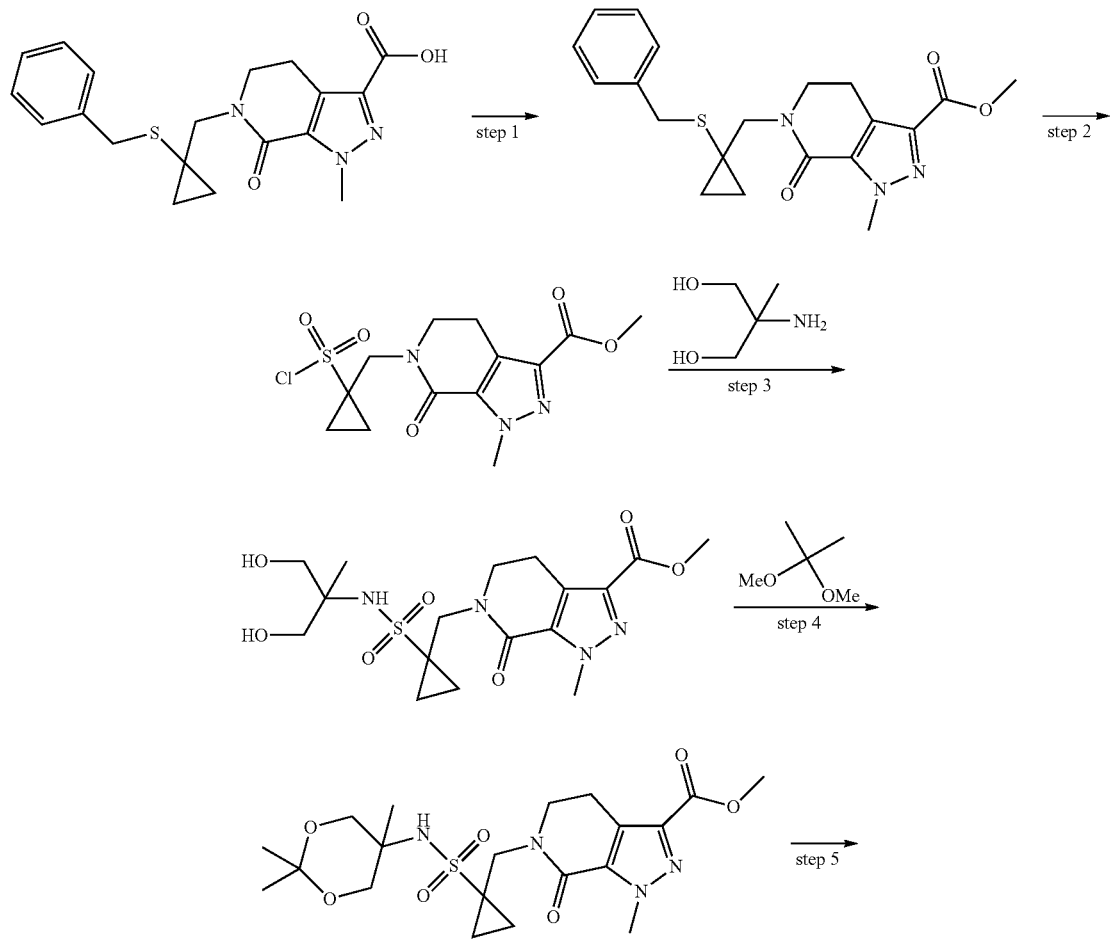

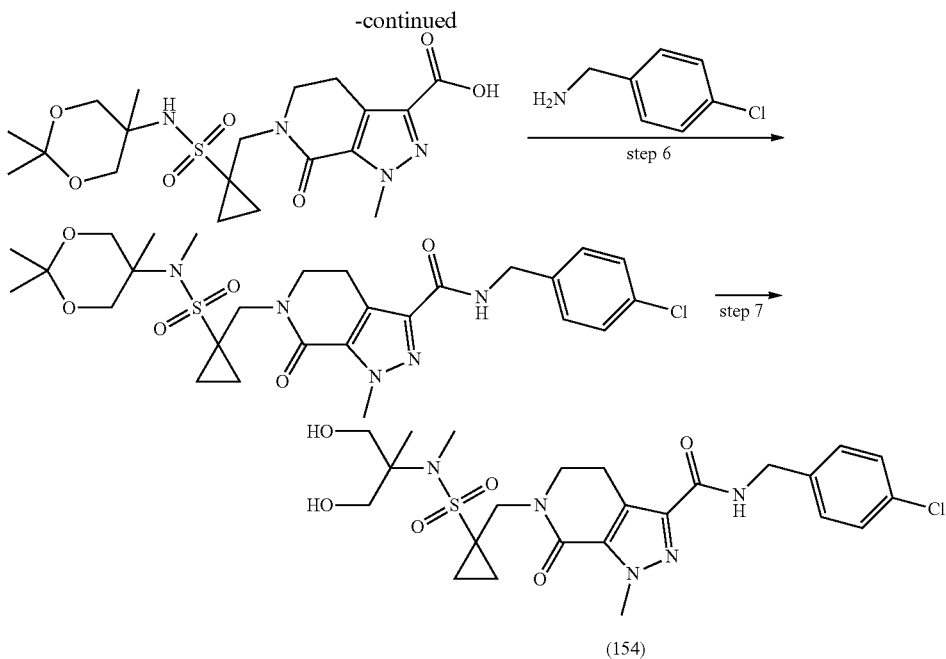

(154)

Step 1: To a solution of 6-((1-(benzylthio)cyclopropyl)methyl)-1-methyl-7-oxo-4,5,6,7-tetrahydro-1H-pyrazolo[3,4-c]pyridine-3-carboxylic acid (450 mg, 1.21 mmol, 1.0 equiv) in MeOH (5 mL) was added SOCl$_2$(0.11 mL, 1.45 mmol, 1.2 equiv) dropwise at 25° C., then the resulting solution was stirred at 80° C. for 1 h. The mixture was concentrated to afford methyl 6-((1-(benzylthio)cyclopropyl)methyl)-1-methyl-7-oxo-4,5,6,7-tetrahydro-1H-pyrazolo[3,4-c]pyridine-3-carboxylate. TLC R$_f$=0.5 (50% EtOAc/petroleum ether). MS (ESI): m/z 386.1 [M+H]$^+$.

Step 2: Methyl 6-((1-(chlorosulfonyl)cyclopropyl)methyl)-1-methyl-7-oxo-4,5,6,7-tetrahydro-1H-pyrazolo[3,4-c]pyridine-3-carboxylate was obtained using the method described in step 3 of Example 121, except (6-((1-(benzylthio)cyclopropyl)methyl)-N-(4-chlorobenzyl)-1-methyl-7-oxo-4,5,6,7-tetrahydro-1H-pyrazolo[3,4-c]pyridine-3-carboxamide) was replaced with methyl 6-((1-(benzylthio)cyclopropyl)methyl)-1-methyl-7-oxo-4,5,6,7-tetrahydro-1H-pyrazolo[3,4-c]pyridine-3-carboxylate. Used immediately in step 3. TLC R$_f$=0.5 (25% EtOAc/petroleum ether.

Step 3 Methyl 6-((1-(N-(1,3-dihydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxylate was obtained using the method described in step 4 of Example 123, except 1-((3-((4-cyanobenzyl)carbamoyl)-1-methyl-7-oxo-1,4,5,7-tetrahydro-6H-pyrazolo[3,4-c]pyridin-6-yl)methyl)cyclopropane-1-sulfonyl chloride was replaced with methyl 6-((1-(chlorosulfonyl)cyclopropyl)methyl)-1-methyl-7-oxo-4,5,6,7-tetrahydro-1H-pyrazolo[3,4-c]pyridine-3-carboxylate and methylamine was replaced with 2-amino-2-methylpropane-1,3-diol. MS (ESI): m/z 431.1 [M+H]$^+$.

Step 4: A solution of methyl 6-((1-(N-(1,3-dihydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxylate (200 mg, 0.38 mmol, 1.0 equiv) and 2,2-dimethoxypropane (198 mg, 1.90 mmol, 5.0 equiv) in THF (2 mL) was treated with p-TsOH·H$_2$O (11 mg, 0.06 mmol, 0.16 equiv) at 25° C. The mixture was stirred at 25° C. for 2 h before it was quenched with NaHCO$_3$, then it was filtered and purified by RP-HPLC to give methyl 1-methyl-7-oxo-6-((1-(N-(2,2,5-trimethyl-1,3-dioxan-5-yl)sulfamoyl)cyclopropyl)methyl)-4,5,6,7-tetrahydro-1H-pyrazolo[3,4-c]pyridine-3-carboxylate. TLC R$_f$=0.6 (50% EtOAc/petroleum ether). $^1$H NMR (400 MHz, CDCl$_3$) δ 4.26 (s, 3H), 4.07 (s, 2H), 3.94 (s, 3H), 3.91-3.83 (m, 2H), 3.80-3.70 (m, 4H), 3.14 (t, J=6.8 Hz, 2H), 1.54 (s, 3H), 1.51-1.48 (m, 2H), 1.47 (s, 3H), 1.29 (s, 3H), 1.04-0.99 (m, 2H).

Step 5: To a solution of methyl 1-methyl-7-oxo-6-((1-(N-(2,2,5-trimethyl-1,3-dioxan-5-yl)sulfamoyl)cyclopropyl)methyl)-4,5,6,7-tetrahydro-1H-pyrazolo[3,4-c]pyridine-3-carboxylate (50 mg, 0.11 mmol, 1.0 equiv) in THF (0.5 mL) was added NaH (60% in mineral oil, 21 mg, 0.53 mmol, 4.8 equiv) at 25° C. (gas evolution). The mixture was stirred at 25° C. for 0.5 h before iodomethane (301 mg, 2.13 mmol, 19.4 equiv) was added, then the mixture was stirred at 60° C. for 12 h. The reaction was quenched with water (1 mL), adjusted to pH 4-5 with 1 M HCl, then it was concentrated. The residue was purified by RP-HPLC to afford 1-methyl-6-((1-(N-methyl-N-(2,2,5-trimethyl-1,3-dioxan-5-yl)sulfamoyl)cyclopropyl)methyl)-7-oxo-4,5,6,7-tetrahydro-1H-pyrazolo[3,4-c]pyridine-3-carboxylic acid. MS (ESI): m/z 471.1 [M+H]$^+$.

Step 6: N-(4-Chlorobenzyl)-1-methyl-6-((1-(N-methyl-N-(2,2,5-trimethyl-1,3-dioxan-5-yl)sulfamoyl)cyclopropyl)methyl)-7-oxo-4,5,6,7-tetrahydro-1H-pyrazolo[3,4-c]pyridine-3-carboxamide was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 1-methyl-6-((1-(N-methyl-N-(2,2,5-trimethyl-1,3-dioxan-5-yl)sulfamoyl)cyclopropyl)methyl)-7-oxo-4,5,6,7-tetrahydro-1H-pyrazolo[3,4-c]pyridine-3-carboxylic acid and 4-(aminomethyl)benzonitrile hydrochloride was replaced with (4-chlorophenyl)methanamine. TLC R$_f$=0.6 (EtOAc). $^1$H NMR (400 MHz, CDCl$_3$) δ 7.35-7.28 (m, 4H), 7.19-7.15 (m, 1H), 4.57 (d, J=6.2 Hz, 2H), 4.29 (d, J=12.4 Hz, 2H), 4.17 (s, 2H), 4.14 (s, 3H), 3.75 (t, J=6.8 Hz, 2H), 3.69 (d, J=12.4 Hz, 2H), 3.19 (t, J=6.8 Hz, 2H), 2.92 (s, 3H), 1.52-1.49 (m, 2H), 1.44 (d, J=7.6 Hz, 6H), 1.33 (s, 3H), 1.14-1.07 (m, 2H).

Step 7: To a solution of N-(4-chlorobenzyl)-1-methyl-6-((1-(N-methyl-N-(2,2,5-trimethyl-1,3-dioxan-5-yl)sulfamoyl)cyclopropyl)methyl)-7-oxo-4,5,6,7-tetrahydro-1H-pyrazolo[3,4-c]pyridine-3-carboxamide (25 mg, 0.038 mmol, 1.0 equiv) in MeOH (0.3 mL) was added p-TsOH-H₂O (15 mg, 0.076 mmol, 2.0 equiv). The mixture was stirred at 25° C. for 2 h before it was quenched with NaHCO₃ and purified by RP-HPLC to afford N-(4-chlorobenzyl)-6-((1-(N-(1,3-dihydroxy-2-methylpropan-2-yl)-N-methylsulfamoyl)cyclopropyl)methyl)-1-methyl-7-oxo-4,5,6,7-tetrahydro-1H-pyrazolo[3,4-c]pyridine-3-carboxamide (154). TLC $R_f$=0.2 (EtOAc). $^1$H NMR (400 MHz, CDCl₃) δ 7.37-7.27 (m, 4H), 7.20 (m, 1H), 4.56 (d, J=6.2 Hz, 2H), 4.14 (s, 3H), 4.04 (s, 2H), 3.84 (m, 4H), 3.72 (m, 2H), 3.26-3.19 (m, 2H), 2.97 (s, 3H), 1.61-1.54 (m, 2H), 1.33 (s, 3H), 1.11-1.04 (m, 2H). MS (ESI): m/z 554.2 [M+H]⁺.

Example 155

N-(4-Cyanobenzyl)-1-methyl-7-oxo-6-((1-(N-(pyridin-2-yl)sulfamoyl)cyclopropyl)methyl)-4,5,6,7-tetrahydro-1H-pyrazolo[3,4-c]pyridine-3-carboxamide (155)

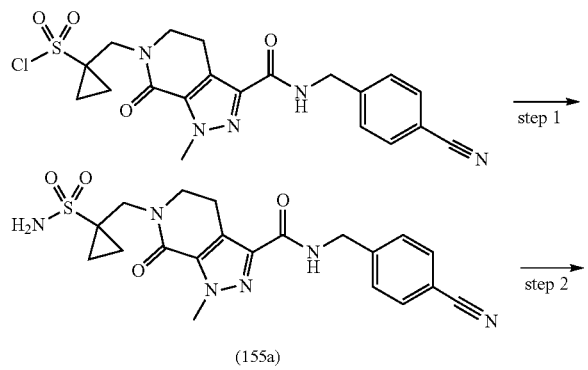

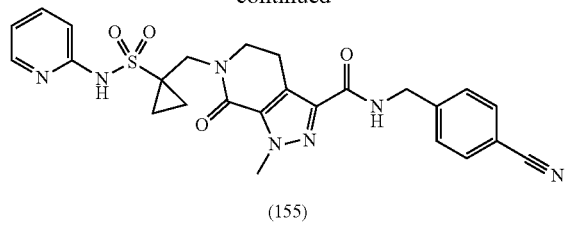

(155)

Step 1: N-(4-Cyanobenzyl)-1-methyl-7-oxo-6-((1-sulfamoylcyclopropyl)methyl)-4,5,6,7-tetrahydro-1H-pyrazolo[3,4-c]pyridine-3-carboxamide (155a) was obtained using the method described in step 4 of Example 123, except methylamine was replaced with NH₃. $^1$H NMR (400 MHz, DMSO-d₆) δ 8.98-8.88 (m, 1H), 7.83-7.76 (m, 2H), 7.47 (m, 2H), 6.91 (m, 1H), 4.46 (d, J=6.2 Hz, 2H), 4.15-4.10 (m, 3H), 3.97-3.89 (m, 2H), 3.71-3.56 (m, 2H), 3.02-2.91 (m, 2H), 1.25-1.12 (m, 2H), 1.05-0.94 (m, 2H). MS (ESI): m/z 443.1 [M+H]⁺.

Step 2: To a solution of N-(4-cyanobenzyl)-1-methyl-7-oxo-6-((1-sulfamoylcyclopropyl)methyl)-4,5,6,7-tetrahydro-1H-pyrazolo[3,4-c]pyridine-3-carboxamide (1.0 g, 2.26 mmol, 1.0 equiv) in DMF (10 mL) was added 2-bromopyridine (393 mg, 2.49 mmol, 1.1 equiv), N,N'-dimethylethylenediamine (100 mg, 1.14 mmol, 0.5 equiv), K₂CO₃ (937 mg, 6.78 mmol, 3.0 equiv) and CuF₂ (106 mg, 1.04 mmol, 0.46 equiv). The mixture was stirred under N₂ and heated at 130° C. for 2 h before it was diluted with water (50 mL) and extracted with EtOAc (2×100 mL). The combined organic extracts were dried over Na₂SO₄, filtered and concentrated. The residue was purified by RP-HPLC to afford N-(4-cyanobenzyl)-1-methyl-7-oxo-6-((1-(N-(pyridin-2-yl)sulfamoyl)cyclopropyl)methyl)-4,5,6,7-tetrahydro-1H-pyrazolo[3,4-c]pyridine-3-carboxamide (155). $^1$H NMR (400 MHz, DMSO-d₆) δ 8.93 (m, 1H), 8.01 (br d, J=4.4 Hz, 1H), 7.84-7.75 (m, 2H), 7.75-7.66 (m, 1H), 7.47 (d, J=8.2 Hz, 2H), 7.20 (br d, J=8.6 Hz, 1H), 6.86 (br s, 1H), 4.46 (d, J=6.2 Hz, 2H), 4.08 (s, 3H), 3.94 (s, 2H), 3.66 (m, 2H), 2.91 (m, 2H), 1.35-1.25 (m, 2H), 1.02 (m, 2H). MS (ESI): m/z 519.9 [M+H]⁺.

Compounds in Table 7 below were prepared following procedures analogous to those described for Compound (155) in Example 155.

TABLE 7

| Example/Compound Number | Compound Structure and Name | Physical Data MS (m/z), $^1$H NMR |
|---|---|---|
| 156 | N-(4-Cyanobenzyl)-1-methyl-6-((1-(N-(1-methyl-1H-pyrazol-3-yl)sulfamoyl)cyclopropyl)methyl)-7-oxo-4,5,6,7-tetrahydro-1H-pyrazolo[3,4-c]pyridine-3-carboxamide | MS (ESI): m/z 523.2 [M + H]⁺. $^1$H NMR (400 MHz, DMSO-d₆) δ 9.01-8.86 (m, 1H), 7.78 (br d, J = 7.6 Hz, 2H), 7.54 (br s, 1H), 7.47 (br d, J = 7.6 Hz, 2H), 5.98 (br s, 1H), 4.46 (br d, J = 5.76 Hz, 2H), 4.11 (s, 3H), 3.95 (br s, 2H), 3.71 (s, 3H), 3.66 (m, 2H), 2.95 (m, 2H), 1.14 (br s, 2H), 0.97 (br s, 2H). |

TABLE 7-continued

| Example/ Compound Number | Compound Structure and Name | Physical Data MS (m/z), ¹H NMR |
|---|---|---|
| 157 | N-(4-Cyanobenzyl)-1-methyl-6-((1-(N-(6-methylpyridin-2-yl)sulfamoyl)cyclopropyl)methyl)-7-oxo-4,5,6,7-tetrahydro-1H-pyrazolo[3,4-c]pyridine-3-carboxamide | MS (ESI): m/z 534.4 [M + H]⁺. ¹H NMR (400 MHz, DMSO-d₆) δ 8.92 (m, 1H), 7.90-7.74 (m, 2H), 7.59 (m, 1H), 7.47 (d, J = 8.4 Hz, 2H), 7.20-6.99 (m, 1H), 6.83-6.49 (m, 1H), 4.46 (d, J = 6.2 Hz, 2H), 4.08 (s, 3H), 3.94 (s, 2H), 3.66 (m, 2H), 2.90 (m, 2H), 2.29 (s, 3H), 1.29 (br s, 2H), 1.09-0.93 (m, 2H). |
| 158 | N-(4-Chlorobenzyl)-1-methyl-7-oxo-6-((1-(N-(pyridin-2-yl)sulfamoyl)cyclopropyl)methyl)-4,5,6,7-tetrahydro-1H-pyrazolo[3,4-c]pyridine-3-carboxamide | MS (ESI): m/z 529.3 [M + H]⁺. ¹H NMR (400 MHz, DMSO-d₆) δ 8.82 (m, 1H), 8.11-7.93 (m, 1H), 7.74-7.67 (m, 1H), 7.40-7.34 (m, 2H), 7.34-7.28 (m, 2H), 7.20 (br d, J = 8.4 Hz, 1H), 6.93-6.81 (m, 1H), 4.37 (d, J = 6.2 Hz, 2H), 4.07 (s, 3H), 3.94 (s, 2H), 3.66 (m, 2H), 2.91 (m, 2H), 1.30 (m, 2H), 1.07-0.95 (m, 2H). |
| 159 | N-(4-Cyanobenzyl)-6-((1-(N-(3-methoxypyridin-2-yl)sulfamoyl)cyclopropyl)methyl)-1-methyl-7-oxo-4,5,6,7-tetrahydro-1H-pyrazolo[3,4-c]pyridine-3-carboxamide | MS (ESI): m/z 550.0 [M + H]⁺. ¹H NMR (400 MHz, DMSO-d₆) δ 9.29 (br s, 1H), 8.93 (m, 1H), 7.85-7.75 (m, 2H), 7.47 (d, J = 8.4 Hz, 2H), 7.28 (br s, 1H), 7.15-6.49 (m, 1H), 4.46 (d, J = 6.2 Hz, 2H), 4.08 (br s, 3H), 3.99 (br s, 2H), 3.74 (br s, 3H), 3.67 (br s, 2H), 2.85 (br s, 2H), 1.46 (m, 2H), 1.10 (m, 2H). |
| 160 | N-(4-Cyanobenzyl)-6-((1-(N-(3-methoxy-6-methylpyridin-2-yl)sulfamoyl)cyclopropyl)methyl)-1-methyl-7-oxo-4,5,6,7-tetrahydro-1H-pyrazolo[3,4-c]pyridine-3-carboxamide | MS (ESI): m/z 564.0 [M + H]⁺. ¹H NMR (400 MHz, DMSO-d₆) δ 8.91 (m, 1H), 7.85-7.75 (m, 2H), 7.47 (d, J = 8.4 Hz, 2H), 7.20-7.06 (m, 1H), 6.87-6.68 (m, 1H), 4.46 (d, J = 6.0Hz, 2H), 4.17-4.05 (m, 3H), 3.99 (s, 2H), 3.71 (s, 3H), 3.66 (m, 2H), 2.82 (m, 2H), 2.30 (s, 3H), 1.50 (m, 2H), 1.16-1.05 (m, 2H). |
| 161 | N-(4-Cyanobenzyl)-1-methyl-6-((1-(N-(2-methylpyridin-3-yl)sulfamoyl)cyclopropyl)methyl)-7-oxo-4,5,6,7-tetrahydro-1H-pyrazolo[3,4-c]pyridine-3-carboxamide | MS (ESI): m/z 534.3 [M + H]⁺. ¹H NMR (400 MHz, DMSO-d₆) δ 8.94 (m, 1H), 8.22 (m, 1H), 7.78 (d, J = 8.4 Hz, 2H), 7.71 (d, J = 8.0 Hz, 1H), 7.47 (d, J = 8.4 Hz, 2H), 7.18 (m, 1H), 4.46 (d, J = 6.2 Hz, 2H), 4.11 (s, 3H), 3.97 (s, 2H), 3.67 (m, 2H), 2.95 (m, 2H), 2.54 (br s, 3H), 1.11-1.05 (m, 2H), 1.04-0.96 (m, 2H). |

TABLE 7-continued

| Example/Compound Number | Compound Structure and Name | Physical Data MS (m/z), ¹H NMR |
|---|---|---|
| 162 | 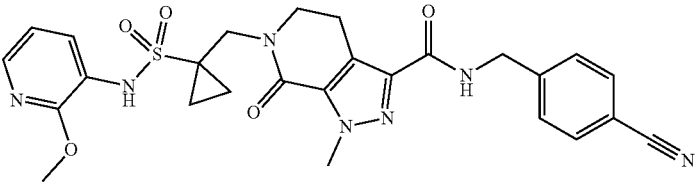<br>N-(4-Cyanobenzyl)-6-((1-(N-(2-methoxypyridin-3-yl)sulfamoyl)cyclopropyl)methyl)-1-methyl-7-oxo-4,5,6,7-tetrahydro-1H-pyrazolo[3,4-c]pyridine-3-carboxamide | MS (ESI): m/z 550.3 [M + H]⁺. ¹H NMR (400 MHz, DMSO-d₆) δ 8.95 (m, 1H), 7.96 (br d, J= 3.6 Hz, 1H), 7.83-7.76 (m, 2H), 7.65 (m, 1H), 7.48 (d, J = 8.4 Hz, 2H), 6.96 (m, 1H), 4.47 (d, J = 6.2 Hz, 2H), 4.12 (s, 3H), 4.01 (s, 2H), 3.92 (s, 3H), 3.68 (m, 2H), 2.95 (m, 2H), 1.06-0.99 (m, 2H), 0.97 (br d, J = 4.4 Hz, 2H). |
| 163 | 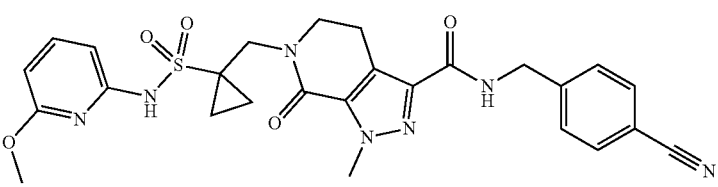<br>N-(4-Cyanobenzyl)-6-((1-(N-(6-methoxypyridin-2-yl)sulfamoyl)cyclopropyl)methyl)-1-methyl-7-oxo-4,5,6,7-tetrahydro-1H-pyrazolo[3,4-c]pyridine-3-carboxamide | MS (ESI): m/z 550.0 [M + H]⁺. ¹H NMR (400 MHz, DMSO-d₆) δ 10.23 (br s, 1H), 8.92 (m, 1H), 7.85-7.73 (m, 2H), 7.57 (m, 1H), 7.47 (d, J = 8.4 Hz, 2H), 6.64 (d, J = 7.6 Hz, 1H), 6.42 (d, J = 8.0 Hz, 1H), 4.46 (d, J = 6.2 Hz, 2H), 4.10 (s, 3H), 3.96 (s, 2H), 3.79 (s, 3H), 3.64 (m, 2H), 2.90 (m, 2H), 1.46-1.35 (m, 2H), 1.15-1.05 (m, 2H). |
| 164 | 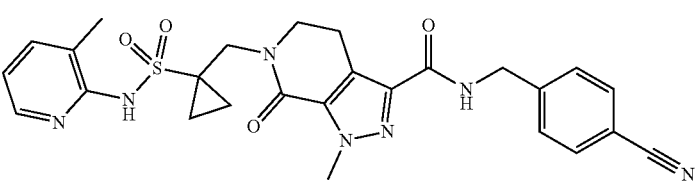<br>N-(4-Cyanobenzyl)-1-methyl-6-((1-(N-(3-methylpyridin-2-yl)sulfamoyl)cyclopropyl)methyl)-7-oxo-4,5,6,7-tetrahydro-1H-pyrazolo[3,4-c]pyridine-3-carboxamide | MS (ESI): m/z 534.3 [M + H]⁺. ¹H NMR (400 MHz, DMSO-d₆) δ 8.90 (m, 1H), 7.78 (d, J = 8.4 Hz, 2H), 7.76-7.67 (m, 1H), 7.59 (br d, J = 6.6 Hz, 1H), 7.47 (d, J = 8.4 Hz, 2H), 6.69 (m, 1H), 4.46 (d, J = 6.2 Hz, 2H), 4.05 (s, 3H), 3.96 (s, 2H), 3.71 (m, 2H), 2.94 (m, 2H), 2.17-2.01 (m, 3H), 1.27 (m, 2H), 0.98 (m, 2H). |

Example 165

N-(4-Cyanobenzyl)-1-methyl-6-((1-(N-(5-methyl-isoxazol-3-yl)sulfamoyl)cyclopropyl) methyl)-7-oxo-4,5,6,7-tetrahydro-1H-pyrazolo[3,4-c]pyridine-3-carboxamide (165)

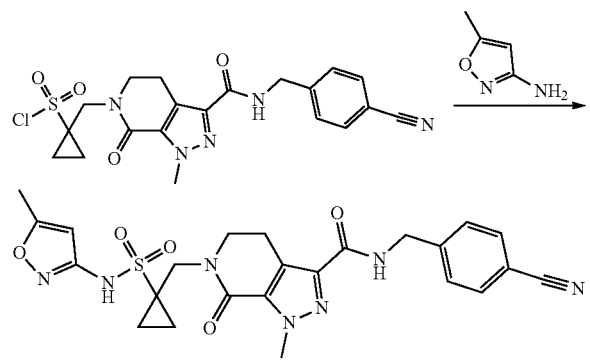

A solution of 5-methylisoxazol-3-amine (54 mg, 0.55 mmol, 5.0 equiv) in THF (1.0 mL) was cooled to 0° C. before LiHMDS (1.0 M in THF, 0.55 mL, 0.55 mmol, 5.0 equiv) was added dropwise. The reaction mixture was stirred at 25° C. for 30 min, then 1-((3-((4-cyanobenzyl)carbamoyl)-1-methyl-7-oxo-1,4,5,7-tetrahydro-6H-pyrazolo[3,4-c]pyridin-6-yl)methyl)cyclopropane-1-sulfonyl chloride (90 mg, 0.11 mmol, 55.21% purity, 1.0 equiv) was added. The resulting mixture was stirred at 25° C. for 1.5 h before it was concentrated in vacuum. The residue was purified by RP-HPLC to afford N-(4-cyanobenzyl)-1-methyl-6-((1-(N-(5-methylisoxazol-3-yl)sulfamoyl)cyclopropyl)methyl)-7-oxo-4,5,6,7-tetrahydro-1H-pyrazolo[3,4-c]pyridine-3-carboxamide (165). ¹H NMR (400 MHz, DMSO-d₆) δ 8.94 (m, 1H), 7.78 (d, J=8.0 Hz, 2H), 7.47 (d, J=8.2 Hz, 2H), 6.08 (s, 1H), 4.46 (d, J=6.4 Hz, 2H), 4.10 (s, 3H), 3.89 (s, 2H), 3.67 (m, 2H), 2.95 (m, 2H), 2.28 (s, 3H), 1.28-1.20 (m, 2H), 1.01 (m, 2H). MS (ESI): m/z 524.0 [M+H]⁺.

Compounds in Table 8 below were prepared following procedures analogous to those described for Compound (165) in Example 165.

TABLE 8

| Example/Compound Number | Compound Structure and Name | Physical Data MS (m/z), ¹H NMR |
|---|---|---|
| 166 | 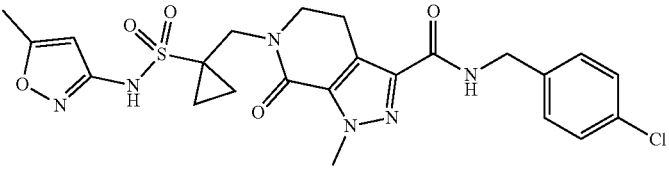<br>N-(4-Cyanobenzyl)-1-methyl-6-((1-(N-(5-methylisoxazol-3-yl)sulfamoyl)cyclopropyl)methyl)-7-oxo-4,5,6,7-tetrahydro-1H-pyrazolo[3,4-c]pyridine-3-carboxamide | MS (ESI): m/z 533.0 [M + H]⁺. ¹H NMR (400 MHz, DMSO-d₆) δ 8.84 (br s, 1H), 7.43-7.34 (m, 2H), 7.34-7.20 (m, 2H), 6.06 (s, 1H), 4.37 (br d, J = 5.6 Hz, 2H), 4.09 (s, 3H), 3.88 (br s, 2H), 3.68 (m, 2H), 2.95 (m, 2H), 2.26 (s, 3H), 1.22 (m, 2H), 0.97 (m, 2H). |
| 167 | 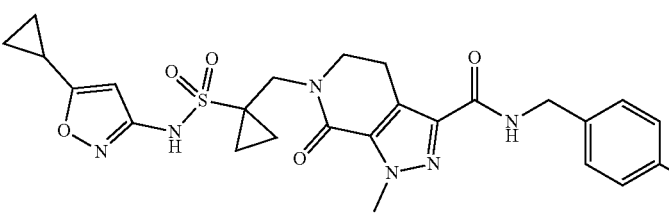<br>N-(4-Cyanobenzyl)-6-((1-(N-(5-cyclopropylisoxazol-3-yl)sulfamoyl)cyclopropyl)methyl)-1-methyl-7-oxo-4,5,6,7-tetrahydro-1H-pyrazolo[3,4-c]pyridine-3-carboxamide | MS (ESI): m/z 550.0 [M + H]⁺. ¹H NMR (400 MHz, DMSO-d₆) δ 8.92 (m, 1H), 7.78 (d, J = 8.4 Hz, 2H), 7.47 (d, J = 8.0 Hz, 2H), 5.89 (s, 1H), 4.46 (br d, J = 6.4 Hz, 2H), 4.09 (s, 3H), 3.82 (s, 2H), 3.73 (m, 2H), 2.94 (m, 2H), 1.96-1.85 (m, 1H), 1.10 (m, 2H), 0.96-0.87 (m, 2H), 0.86-0.77 (m, 2H), 0.76-0.67 (m, 2H). |

Example 168

N-(4-Cyanobenzyl)-1-methyl-6-((1-(oxetan-3-ylsulfonyl)cyclopropyl)methyl)-7-oxo-4,5,6,7-tetrahydro-1H-pyrazolo[3,4-c]pyridine-3-carboxamide (168)

(168)

Step 1: To a solution of Na₂SO₃ (180 mg, 1.43 mmol, 1.0 equiv) in water (2 mL) was added NaHCO₃ (240 mg, 2.86 mmol, 2.0 equiv). The resulting mixture was stirred at 50° C. for 1 h, then 1-((3-((4-cyanobenzyl)carbamoyl)-1-methyl-7-oxo-1,4,5,7-tetrahydro-6H-pyrazolo[3,4-c]pyridin-6-yl)methyl)cyclopropane-1-sulfonyl chloride (660 mg, 1.43 mmol, 1.0 equiv) was added. The resulting dark mixture was stirred at 50° C. for 12 h before it was concentrated. The residue was diluted with MeOH (20 mL), the solids were removed by filtration, and the filter cake was rinsed with MeOH (3×20 mL). The filtrate was concentrated and suspended in THF (20 mL). The solids were removed by filtration and the filter cake was rinsed with THF (3×20 mL), then the filtrate was concentrated to give sodium 1-((3-((4-cyanobenzyl)carbamoyl)-1-methyl-7-oxo-4,5-dihydro-1H-pyrazolo[3,4-c]pyridin-6(7H)-yl)methyl)cyclopropane-1-sulfinate. ¹H NMR (400 MHz, DMSO-d₆) δ 8.92-8.88 (m, 1H), 7.79 (d, J=8.2 Hz, 2H), 7.48 (d, J=8.2 Hz, 2H), 7.31-7.18 (m, 1H), 4.47 (br d, J=6.4 Hz, 2H), 4.11 (s, 3H), 3.79-3.74 (m, 2H), 2.93-2.89 (m, 2H), 0.66-0.56 (m, 2H), 0.32 (d, J=2.4 Hz, 2H).

Step 2: A mixture of sodium 1-((3-((4-cyanobenzyl)carbamoyl)-1-methyl-7-oxo-4,5-dihydro-1H-pyrazolo[3,4-c]pyridin-6(7H)-yl)methyl)cyclopropane-1-sulfinate (50 mg, 0.11 mmol, 1.0 equiv) and 3-bromooxetane (23 mg, 0.17 mmol, 1.55 equiv) in DMF (1 mL) was stirred at 100° C. for 12 h. The reaction mixture was concentrated and the residue was purified by RP-HPLC to give N-(4-cyanobenzyl)-1-methyl-6-((1-(oxetan-3-ylsulfonyl)cyclopropyl)methyl)-7-oxo-4,5,6,7-tetrahydro-1H-pyrazolo[3,4-c]pyridine-3-carboxamide (168). ¹H NMR (400 MHz, CDCl₃) δ 7.71 (d, J=8.4 Hz, 2H), 7.55-7.52 (m, 2H), 5.29-5.18 (m, 1H), 4.95 (d, J=7.2 Hz, 4H), 4.62 (s, 2H), 4.21-4.17 (m, 3H), 3.94 (s, 2H), 3.73 (m, 2H), 3.11 (m, 2H), 1.49-1.44 (m, 2H), 1.17-1.12 (m, 2H). MS (ESI): m/z 484.4 [M+H]⁺.

Compounds in Table 9 below were prepared following procedures analogous to those described for Compound (168) in Example 168.

TABLE 9

| Example/Compound Number | Compound Structure and Name | Physical Data MS (m/z), ¹H NMR |
|---|---|---|
| 169 | 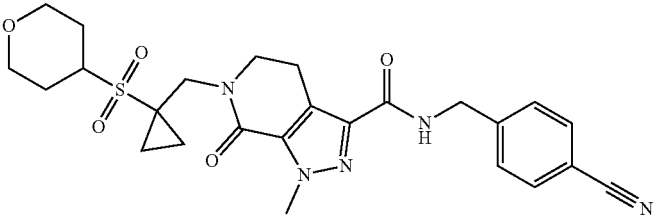<br>N-(4-Cyanobenzyl)-1-methyl-7-oxo-6-((1-((tetrahydro-2H-pyran-4-yl)sulfonyl)cyclopropyl)methyl)-4,5,6,7-tetrahydro-1H-pyrazolo[3,4-c]pyridine-3-carboxamide | MS (ESI): m/z 512.4 [M + H]⁺. ¹H NMR (400 MHz, MeOH-d₄) δ 7.59 (d, J = 8.2 Hz, 2H), 7.42 (d, J = 8.2 Hz, 2H), 4.50 (s, 2H), 4.07 (s, 3H), 4.05-3.93 (m, 3H), 3.92 (s, 2H), 3.64 (t, J = 6.8 Hz, 2H), 3.39 (m, 2H), 3.00 (t, J = 6.8 Hz, 2H), 1.93 (br d, J = 10.8 Hz, 2H), 1.71 (m, 2H), 1.33-1.28 (m, 2H), 1.19 (br d, J = 3.8 Hz, 3H), 1.06-0.99 (m, 2H). |
| 170 | 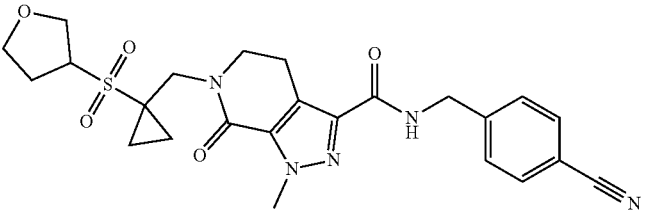<br>(R)- or (S)- N-(4-Cyanobenzyl)-1-methyl-7-oxo-6-((1-((tetrahydrofuran-3-yl)sulfonyl)cyclopropyl)methyl)-4,5,6,7-tetrahydro-1H-pyrazolo[3,4-c]pyridine-3-carboxamide<br>Unless otherwise indicated, examples indicate relative stereochemistry | MS (ESI): m/z 498.4 [M + H]⁺. ¹H NMR (400 MHz, CDCl₃) δ 7.66 (d, J = 8.0 Hz, 2H), 7.48 (d, J = 8.0 Hz, 2H), 7.30 (br s, 1H), 4.68 (d, J = 6.4 Hz, 2H), 4.41-4.33 (m, 1H), 4.18-4.03 (m, 5H), 3.96-3.90 (m, 4H), 3.76 (m, 2H), 3.23 (m, 2H), 2.47 (m, 1H), 2.35-2.33 (m, 1H), 1.57 (s, 2H), 1.06 (s, 2H). SFC R$_t$ = 5.756 min, 100% ee, [CHIRALPAK IC-3, 5-40% EtOH(0.05% Et₂NH), 3 mL/min]. |
| 171 | 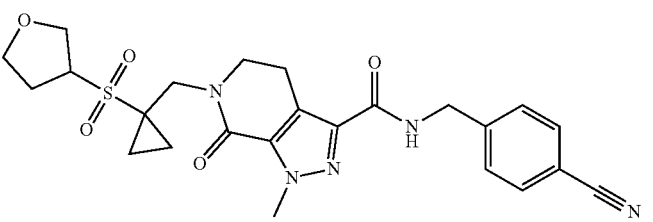<br>(R)- or (S)- N-(4-Cyanobenzyl)-1-methyl-7-oxo-6-((1-((tetrahydrofuran-3-yl)sulfonyl)cyclopropyl)methyl)-4,5,6,7-tetrahydro-1H-pyrazolo[3,4-c]pyridine-3-carboxamide Unless otherwise indicated, examples indicate relative stereochemistry | MS (ESI): m/z 498.4 [M + H]⁺. ¹H NMR (400 MHz, CDCl₃) δ 7.66 (d, J = 8.0 Hz, 2H), 7.48 (d, J = 8.0 Hz, 2H), 7.30 (s, 1H), 4.68 (d, J = 6.4 Hz, 2H), 4.38 (m, 1H), 4.19-4.14 (m, 5H), 4.02-3.90 (m, 4H), 3.75 (m, 2H), 3.23-3.19 (m, 2H), 2.45-2.42 (m, 1H), 2.34-2.31 (m, 1H), 1.56-1.54 (m, 2H), 1.09-1.06 (m, 2H). SFC R$_t$ = 9.621 min, 96% ee [CHIRALPAK IC-3, 5-40% EtOH(0.05% Et₂NH), 3 mL/min]. |

Example 172

N-(4-Cyanobenzyl)-1-methyl-6-((1-((3-methyl-oxetan-3-yl)sulfonyl)cyclopropyl) methyl)-7-oxo-4,5,6,7-tetrahydro-1H-pyrazolo[3,4-c]pyridine-3-carboxamide (172)

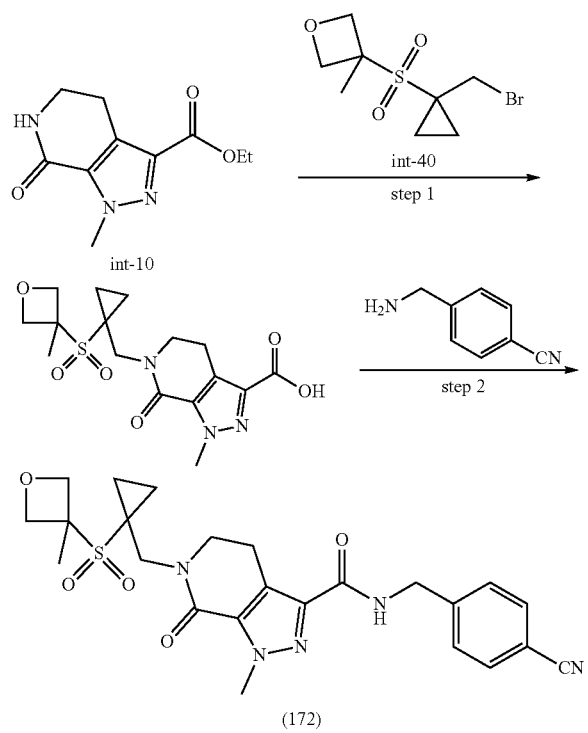

Step 1: 1-Methyl-6-((1-((3-methyloxetan-3-yl)sulfonyl)cyclopropyl)methyl)-7-oxo-4,5,6,7-tetrahydro-1H-pyrazolo[3,4-c]pyridine-3-carboxylic acid was obtained using the procedure described in the synthesis of (it-11), except 1-(bromomethyl)-1-(cyclopropylsulfonyl)cyclopropane (int-1) was replaced with 3-((1-(bromomethyl)cyclopropyl)sulfonyl)-3-methyloxetane (int-40). $^1$H NMR (400 MHz, CDCl$_3$) δ 5.23 (d, J=6.8 Hz, 2H), 4.49 (d, J=6.8 Hz, 2H), 4.23 (s, 3H), 3.92 (s, 2H), 3.72 (t, J=6.8 Hz, 2H), 3.50 (s, 3H), 3.14 (br t, J=6.8 Hz, 2H), 2.00 (s, 3H), 1.52-1.46 (m, 2H), 1.07-1.01 (m, 2H). MS (ESI): m/z 384.1 [M+H]$^+$.

Step 2: N-(4-Cyanobenzyl)-1-methyl-6-((1-((3-methyloxetan-3-yl)sulfonyl)cyclopropyl)methyl)-7-oxo-4,5,6,7-tetrahydro-1H-pyrazolo[3,4-c]pyridine-3-carboxamide (172) was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 1-Methyl-6-((1-((3-methyloxetan-3-yl)sulfonyl)cyclopropyl)methyl)-7-oxo-4,5,6,7-tetrahydro-1H-pyrazolo[3,4-c]pyridine-3-carboxylic acid. $^1$H NMR (400 MHz, CDCl$_3$) δ 7.64 (d, J=8.2 Hz, 2H), 7.46 (d, J=8.2 Hz, 2H), 5.23 (d, J=6.8 Hz, 2H), 4.66 (d, J=6.4 Hz, 2H), 4.49 (d, J=6.8 Hz, 2H), 4.15 (s, 3H), 3.91 (s, 2H), 3.69 (t, J=6.8 Hz, 2H), 3.19 (t, J=6.8 Hz, 2H), 2.00 (s, 3H), 1.52-1.45 (m, 2H), 1.06-0.98 (m, 2H). MS (ESI): m/z 498.4 [M+H]$^+$.

Example 173

N-(4-Cyanobenzyl)-6-((1-((3-(hydroxymethyl)oxetan-3-yl)sulfonyl)cyclopropyl)methyl)-1-methyl-7-oxo-4,5,6,7-tetrahydro-1H-pyrazolo[3,4-c]pyridine-3-carboxamide (173)

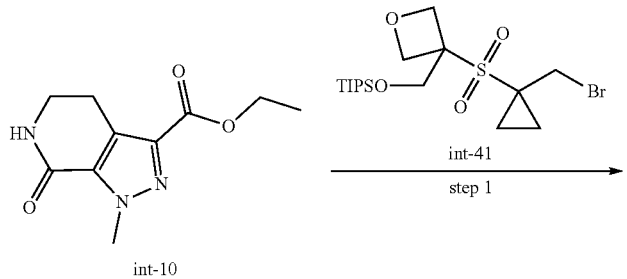

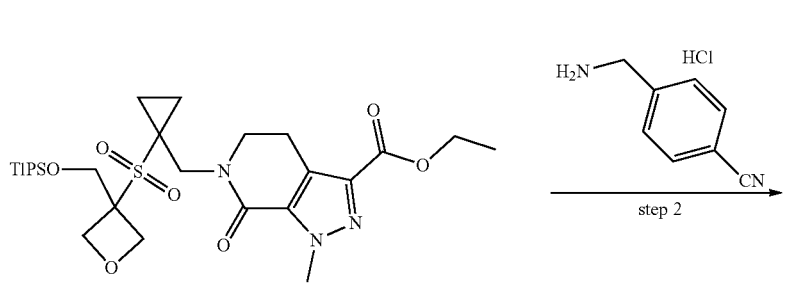

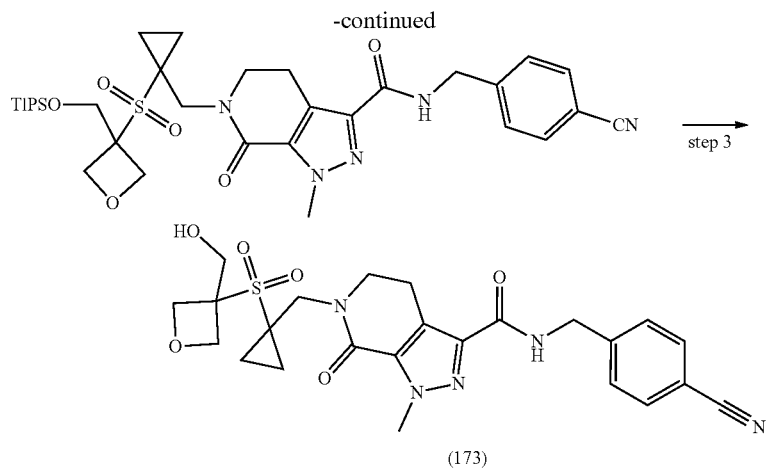

(173)

Step 1: Ethyl 1-methyl-7-oxo-6-((1-((3-(((triisopropylsilyl)oxy)methyl)oxetan-3-yl)sulfonyl)cyclopropyl)methyl)-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with ((3-((1-(Bromomethyl)cyclopropyl)sulfonyl)oxetan-3-yl)methoxy)triisopropylsilane (int-41). TLC $R_f$=0.5 (25% EtOAc/petroleum ether). $^1$H NMR (400 MHz, CDCl$_3$) δ 55.14-5.11 (m, 2H), 4.86 (d, J=6.8 Hz, 2H), 4.42 (q, J=7.2 Hz, 2H), 4.31 (s, 2H), 4.22 (s, 3H), 3.92 (s, 2H), 3.73 (t, J=6.8 Hz, 2H), 3.13 (t, J=6.8 Hz, 2H), 1.54-1.48 (m, 2H), 1.41 (t, J=7.2 Hz, 3H), 1.18-1.10 (m, 24H), 1.08-1.03 (m, 3H).

Step 2: N-(4-Cyanobenzyl)-1-methyl-7-oxo-6-((1-((3-(((triisopropylsilyl)oxy)methyl)oxetan-3-yl)sulfonyl)cyclopropyl)methyl)-4,5,6,7-tetrahydro-1H-pyrazolo[3,4-c]pyridine-3-carboxamide was obtained using the method described in Example 1, except ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6) was replaced with ethyl 1-methyl-7-oxo-6-((1-((3-(((triisopropylsilyl)oxy)methyl)oxetan-3-yl)sulfonyl)cyclopropyl)methyl)-4,5,6,7-tetrahydro-1H-pyrazolo[3,4-c]pyridine-3-carboxylate. MS (ESI): m/z 670.1 [M+H]$^+$.

Step 3: N-(4-Cyanobenzyl)-6-((1-((3-(hydroxymethyl)oxetan-3-yl)sulfonyl)cyclopropyl)methyl)-1-methyl-7-oxo-4,5,6,7-tetrahydro-1H-pyrazolo[3,4-c]pyridine-3-carboxamide (173) was obtained using the method described in step 5 of Example 105, except 4-((4-(1-methyl-6-((1-((2-methyl-1-(((triisopropylsilyl)oxy)propan-2-yl)sulfonyl)cyclopropyl)methyl)-7-oxo-4,5,6,7-tetrahydro-1H-pyrazolo[3,4-c]pyridin-3-yl)-1H-1,2,3-triazol-1-yl)methyl)benzonitrile was replaced with N-(4-Cyanobenzyl)-1-methyl-7-oxo-6-((1-((3-(((triisopropylsilyl)oxy)methyl)oxetan-3-yl)sulfonyl)cyclopropyl)methyl)-4,5,6,7-tetrahydro-1H-pyrazolo[3,4-c]pyridine-3-carboxamide. $^1$H NMR (400 MHz, DMSO-d$_6$) δ 8.95 (t, J=6.2 Hz, 1H), 7.78 (d, J=8.0 Hz, 2H), 7.47 (d, J=8.4 Hz, 2H), 5.83 (t, J=5.6 Hz, 1H), 4.87 (d, J=7.0 Hz, 2H), 4.64 (d, J=7.0 Hz, 2H), 4.46 (br d, J=6.4 Hz, 2H), 4.11 (s, 3H), 4.05 (br d, J=5.6 Hz, 2H), 3.85 (s, 2H), 3.60 (br t, J=6.8 Hz, 2H), 2.97 (br t, J=6.8 Hz, 2H), 1.32-1.23 (m, 2H), 1.08-0.98 (m, 2H). MS (ESI): m/z 514.4 [M+H]$^+$.

Example 174

6-((1-((3-(Aminomethyl)oxetan-3-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (174)

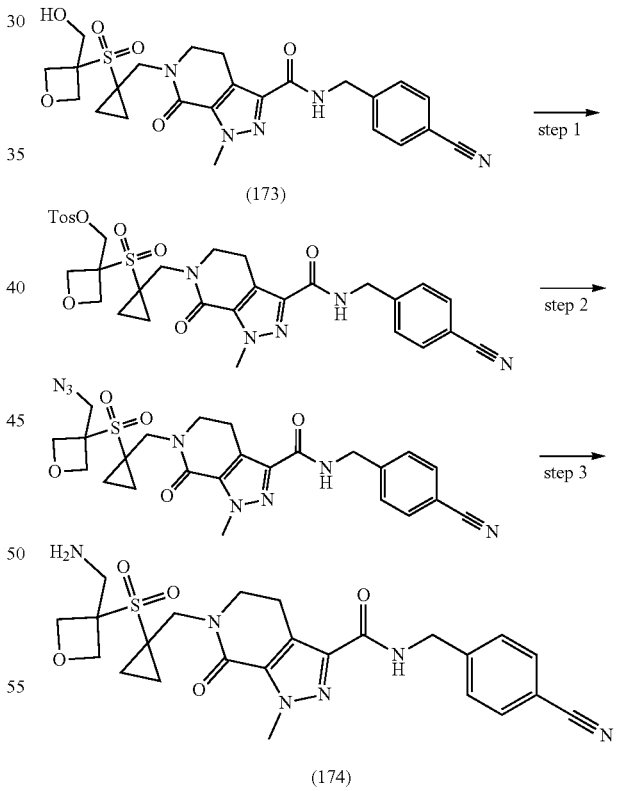

Step 1: A solution of N-(4-Cyanobenzyl)-6-((1-((3-(hydroxymethyl)oxetan-3-yl)sulfonyl)cyclopropyl)methyl)-1-methyl-7-oxo-4,5,6,7-tetrahydro-1H-pyrazolo[3,4-c]pyridine-3-carboxamide (173) (13 mg, 0.03 mmol, 1.0 equiv), Et$_3$N (39 mg, 0.15 mmol, 5.0 equiv), DMAP (2 mg, 0.015 mmol, 0.5 equiv) and p-TsCl (17 mg, 0.09 mmol, 3.0 equiv) in DCM (0.2 mL) was stirred at 25° C. for 12 h. The mixture was diluted with water (2 mL) and extracted with DCM (3×2 mL), then the combined organic extracts were washed with brine (2 mL), dried over Na$_2$SO$_4$, filtered and concentrated. The residue was purified by RP-HPLC to give (3-((1-((3-((4-cyanobenzyl)carbamoyl)-1-methyl-7-oxo-4,5-dihydro-1H-pyrazolo[3,4-c]pyridin-6(7H)-yl)methyl)cyclopropyl) sulfonyl)oxetan-3-yl)methyl 4-methylbenzenesulfonate. MS (ESI): m/z 668.3 [M+H]$^+$.

Step 2: A mixture of (3-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)oxetan-3-yl) methyl 4-methylbenzenesulfonate (18 mg, 0.027 mmol, 1.0 equiv) and NaN$_3$ (4 mg, 0.054 mmol, 2.0 equiv) in DMF (0.5 mL) was stirred at 80° C. for 12 h. The mixture was diluted with water (2 mL) and extracted with EtOAc (3×2 mL), then the combined organic extracts were washed with brine (2 mL), dried over Na$_2$SO$_4$, filtered and concentrated. The residue was purified by RP-HPLC to give 6-((1-((3-(azidomethyl)oxetan-3-yl)sulfonyl)cyclopropyl)methyl)-N-(4-cyanobenzyl)-1-methyl-7-oxo-4,5,6,7-tetrahydro-1H-pyrazolo [3,4-c]pyridine-3-carboxamide. MS (ESI): m/z 539.3 [M+H]$^+$.

Step 3: A solution of 6-((1-((3-(azidomethyl)oxetan-3-yl) sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (12 mg, 0.26 mmol, 1.0 equiv) and PPh$_3$ (10 mg, 0.40 mmol, 1.5 equiv) in THF (0.5 mL) and H$_2$O (0.1 mL) was stirred at 25° C. for 5 h. The mixture was diluted with water (3 mL) and extracted with EtOAc (3×3 mL), then the combined organic extracts were washed with brine (3 mL), dried over Na$_2$SO$_4$, filtered and concentrated. The residue was purified by RP-HPLC to give 6-((1-((3-(aminomethyl)oxetan-3-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (174). $^1$H NMR (400 MHz, DMSO-d$_6$) δ 8.97 (t, J=6.0 Hz, 1H), 7.79 (d, J=8.0 Hz, 2H), 7.48 (d, J=8.0 Hz, 2H), 4.85 (d, J=7.2 Hz, 2H), 4.73 (d, J=6.8 Hz, 2H), 4.47 (br d, J=6.2 Hz, 2H), 4.11 (s, 3H), 3.85 (s, 2H), 3.61 (br t, J=6.6 Hz, 2H), 3.22 (s, 2H), 3.02-2.93 (m, 2H), 1.30-1.21 (m, 2H), 1.07-1.00 (m, 2H). MS (ESI): m/z 513.3 [M+H]$^+$.

Example 175

N-(4-chlorobenzyl)-6-((1-(((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (175)

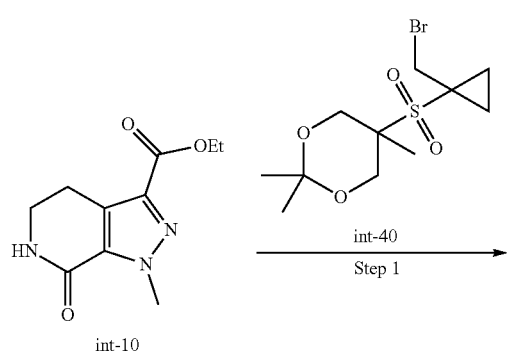

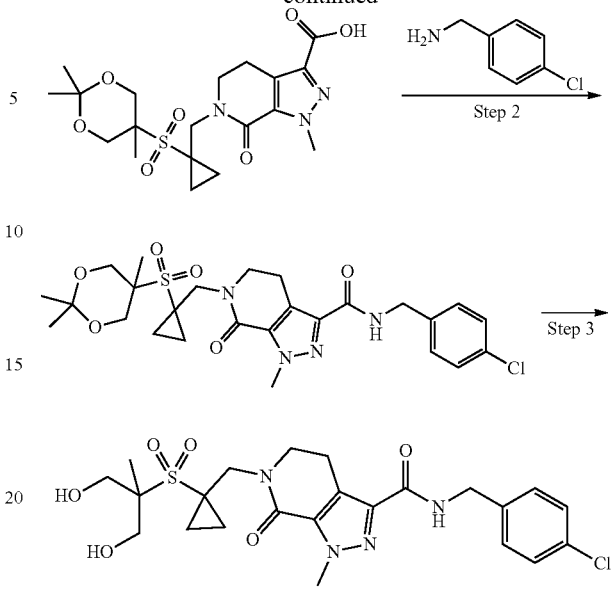

Step 1: 1-Methyl-7-oxo-6-((1-((2,2,5-trimethyl-1,3-dioxan-5-yl)sulfonyl)cyclopropyl)methyl)-4,5,6,7-tetrahydro-1H-pyrazolo[3,4-c]pyridine-3-carboxylic acid was obtained using the procedure described in the synthesis of (int-11), except 1-(bromomethyl)-1-(cyclopropylsulfonyl)cyclopropane (int-1) was replaced with 5-((1-(bromomethyl)cyclopropyl)sulfonyl)-2,2,5-trimethyl-1,3-dioxane (int-42). MS (ESI): m/z 441.9 [M+H]$^+$.

Step 2: N-(4-Chlorobenzyl)-1-methyl-7-oxo-6-((1-((2,2,5-trimethyl-1,3-dioxan-5-yl)sulfonyl)cyclopropyl)methyl)-4,5,6,7-tetrahydro-1H-pyrazolo[3,4-c]pyridine-3-carboxamide was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-9) was replaced with 1-methyl-7-oxo-6-((1-((2,2,5-trimethyl-1,3-dioxan-5-yl)sulfonyl) cyclopropyl)methyl)-4,5,6,7-tetrahydro-1H-pyrazolo[3,4-c] pyridine-3-carboxylic acid. MS (ESI): m/z 565.4 [M+H]$^+$.

Step 3: To a stirred solution of N-(4-chlorobenzyl)-1-methyl-7-oxo-6-((1-((2,2,5-trimethyl-1,3-dioxan-5-yl) sulfonyl)cyclopropyl)methyl)-4,5,6,7-tetrahydro-1H-pyrazolo[3,4-c]pyridine-3-carboxamide (70 mg, 0.124 mmol, 1.0 equiv) in MeOH (1 mL) at 25° C. was added concentrated HCl (12 M, 22 mg, 0.62 mmol, 5.0 equiv). The mixture was stirred at 25° C. for 12 h, then it was purified by RP-HPLC to give N-(4-chlorobenzyl)-6-((1-(((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (175). $^1$H NMR (400 MHz, MeOH-d$_4$) δ 7.38-7.31 (m, 4H), 4.52 (s, 2H), 4.26 (s, 2H), 4.16 (s, 3H), 4.01-3.95 (m, 2H), 3.93-3.87 (m, 2H), 3.77 (t, J=6.8 Hz, 2H), 3.10 (t, J=6.8 Hz, 2H), 1.58-1.51 (m, 2H), 1.43 (s, 3H), 1.17-1.08 (m, 2H). MS (ESI): m/z 525.4 [M+H]$^+$.

Compounds in Table 10 below were prepared following procedures analogous to those described for Compound (175) in Example 175.

TABLE 10

| Example/Compound Number | Compound Structure and Name | Physical Data MS (m/z), $^1$H NMR |
|---|---|---|
| 169 | 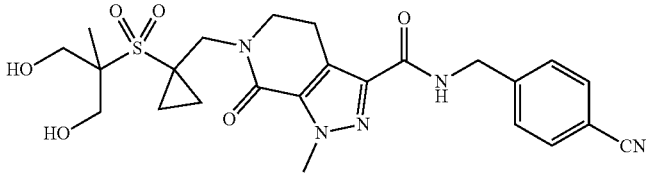 N-(4-Cyanobenzyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 516.5 [M + H]$^+$. $^1$H NMR (400 MHz, MeOH-d$_4$) δ 7.71 (d, J = 8.3 Hz, 2H), 7.53 (d, J = 8.3 Hz, 2H), 4.61 (s, 2H), 4.26 (s, 2H), 4.17 (s, 3H), 4.00-3.95 (m, 2H), 3.92-3.86 (m, 2H), 3.77 (t, J = 6.8 Hz, 2H), 3.10 (t, J = 6.8 Hz, 2H), 1.58-1.52 (m, 2H), 1.43 (s, 3H), 1.16-1.10 (m, 2H). |
| 170 | 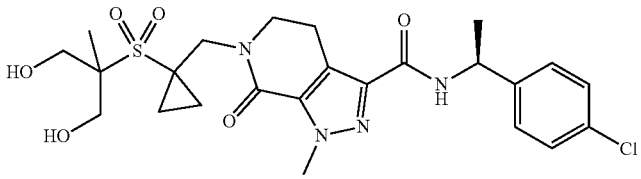 (S)-N-(1-(4-Chlorophenyl)ethyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 539.4 [M + H]$^+$. $^1$H NMR (500 MHz, MeOH-d$_4$) δ 8.43 (d, J = 8.1 Hz, NH), 7.38 (d, J = 8.3 Hz, 2H), 7.32 (d, J = 8.4 Hz, 2H), 5.16 (q, J = 6.9 Hz, 1H), 4.23 (s, 2H), 4.16 (s, 3H), 3.95 (d, J = 11.9 Hz, 2H), 3.87 (d, J = 11.8 Hz, 2H), 3.78-3.67 (m, 2H), 3.04 (t, J = 6.8 Hz, 2H), 1.58-1.49 (m, 5H), 1.40 (s, 3H), 1.13-1.05 (m, 2H). SFC R$_t$ = 2.35 min, 96% ee, (CHIRALCEL OJ-H, 20% EtOH, 5 mL/min). |
| 171 | 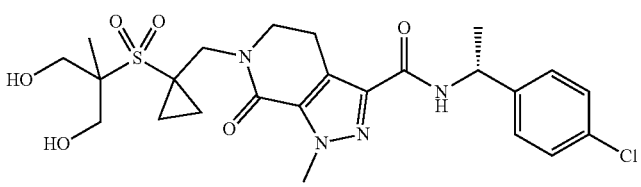 (R)-N-(1-(4-Chlorophenyl)ethyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 539.4 [M + H]$^+$. $^1$H NMR (400 MHz, MeOH-d$_4$) δ 8.43 (d, J = 8.1 Hz, 1H), 7.38 (d, J = 8.4 Hz, 2H), 7.31 (d, J = 8.4 Hz, 2H), 5.16 (q, J = 7.1 Hz, 1H), 4.23 (s, 2H), 4.15 (s, 3H), 3.95 (d, J = 11.8 Hz, 2H), 3.87 (d, J = 11.8 Hz, 2H), 3.73 (t, J = 6.8 Hz, 2H), 3.04 (t, J = 6.9 Hz, 2H), 1.60-1.47 (m, 5H), 1.40 (s, 3H), 1.13-1.05 (m, 2H). SFC R$_t$ = 1.86 min, 98% ee, (CHIRALCEL OJ-H, 20% EtOH, 5 mL/min). |

Example 179

N-(4-Cyanobenzyl)-6-((1-((1,3-dimethoxy-2-methyl-propan-2-yl)sulfonyl)cyclopropyl) methyl)-1-methyl-7-oxo-4,5,6,7-tetrahydro-1H-pyrazolo[3,4-c] pyridine-3-carboxamide (179)

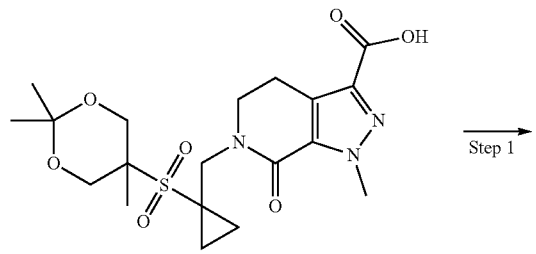

Step 1

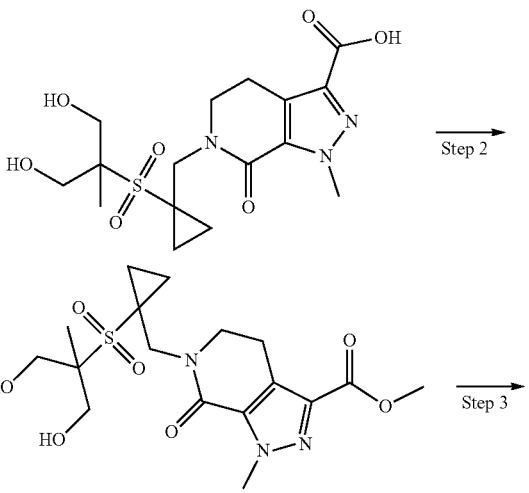

-continued

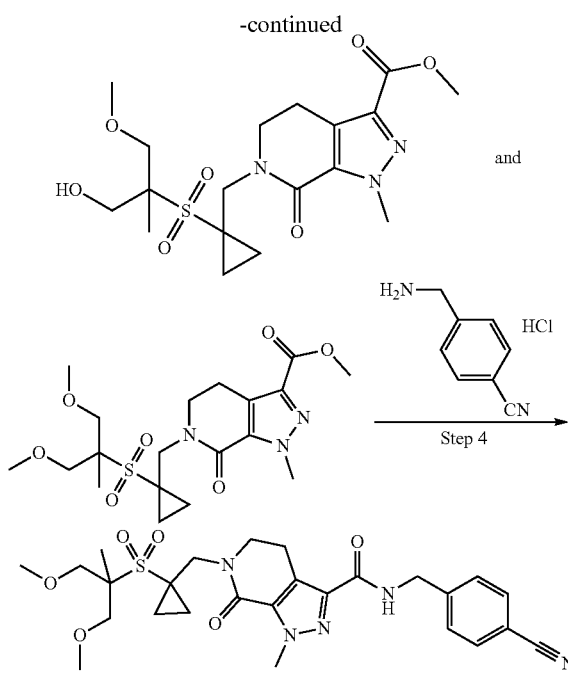

Step 1: 6-((1-((1,3-Dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid was obtained using the method described in step 3 of Example 175, except N-(4-cyanobenzyl)-1-methyl-7-oxo-6-((1-((2,2,5-trimethyl-1,3-dioxan-5-yl)sulfonyl)cyclopropyl)methyl)-4,5,6,7-tetrahydro-1H-pyrazolo[3,4-c]pyridine-3-carboxamide was replaced with 1-methyl-7-oxo-6-((1-((2,2,5-trimethyl-1,3-dioxan-5-yl)sulfonyl)cyclopropyl)methyl)-4,5,6,7-tetrahydro-1H-pyrazolo[3,4-c]pyridine-3-carboxylic acid. MS (ESI): m/z 402.1 [M+H]$^+$.

Step 2: To a stirred solution of 6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid (300 mg, 0.75 mmol, 1.0 equiv) in MeOH (5 mL) was added $SOCl_2$ (267 mg, 2.25 mmol, 3.0 equiv) at 25° C. The mixture was stirred at 80° C. for 12 h, then the mixture was concentrated and dissolved in DMF (5 mL) prior and purified by RP-HPLC to give methyl 6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate. $^1$H NMR (400 MHz, $CDCl_3$) δ 4.23 (s, 3H), 4.19 (s, 2H), 4.00-4.12 (m, 2H), 4.03-3.97 (m, 2H), 3.94 (s, 3H), 3.74 (t, J=6.8 Hz, 2H), 3.13 (t, J=6.8 Hz, 2H), 1.69-1.64 (m, 2H), 1.45 (s, 3H), 1.14-1.07 (m, 2H). MS (ESI): m/z 416.1 [M+H]$^+$.

Step 3: To a stirred solution of methyl 6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate (250 mg, 0.6 mmol, 1.0 equiv) in DMF (3 mL) was added NaH (60% in mineral oil, 48 mg, 1.2 mmol, 2.0 equiv) at 25° C. After 1 h at 25° C., MeI (85 mg, 0.6 mmol, 1.0 equiv) was added and the mixture was stirred for another 1 h. The mixture was quenched with water (20 mL) and extracted with EtOAc (2×20 mL). The combined organic extracts were dried over $Na_2SO_4$, filtered and concentrated. The residue was purified by RP-HPLC to give methyl 6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate (MS (ESI): m/z 430.3 [M+H]+) and methyl 6-((1-((1,3-dimethoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate (MS (ESI): m/z 444.1 [M+H]+).

Step 4: N-(4-Cyanobenzyl)-6-((1-((1,3-dimethoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (179) was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with methyl 6-((1-((1,3-dimethoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate. $^1$H NMR (400 MHz, $CDCl_3$) δ 7.64 (d, J=8.2 Hz, 2H), 7.46 (d, J=8.2 Hz, 2H), 4.66 (d, J=6.4 Hz, 2H), 4.16 (s, 5H), 3.78-3.72 (m, 4H), 3.68-3.61 (m, 2H), 3.41 (s, 6H), 3.17 (t, J=6.8 Hz, 2H), 1.55-1.59 (m, 2H), 1.45 (s, 3H), 1.11-1.05 (m, 2H). MS (ESI): m/z 544.4 [M+H]$^+$.

Example 180

N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (180)

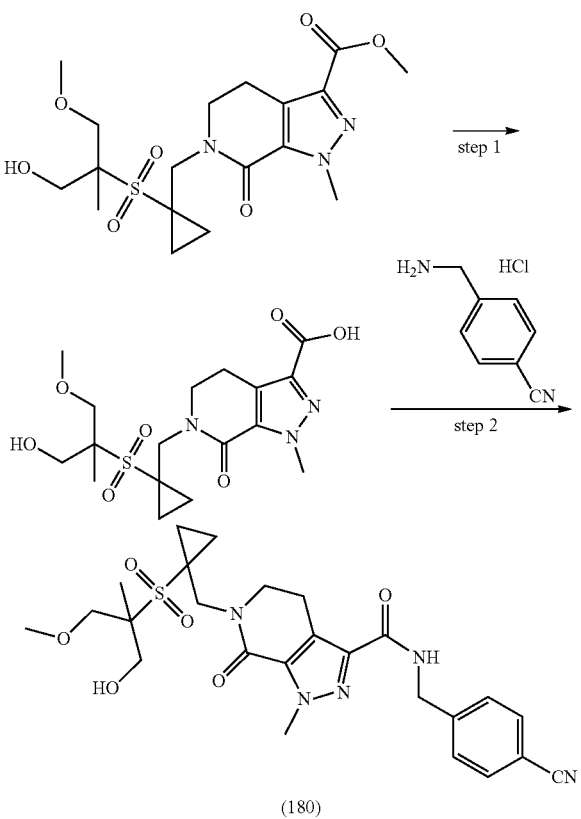

Step 1:6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with methyl 6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate.

Step 2: N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (180) was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylic acid. MS (ESI): m/z 530.1 [M+H]$^+$.

Example 181 and Example 182

(R)- or (S)—N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (181)

and (R)- or (S)—N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (182)

pan-2-yl)sulfonyl)cyclopropyl)methyl)-1-methyl-7-oxo-4,5,6,7-tetrahydro-1H-pyrazolo[3,4-c]pyridine-3-carboxamide (180).

Unless otherwise indicated, examples indicate relative stereochemistry. SFC: CHIRALPAK IC-3,5-40% MeOH (0.05% Et$_2$NH), 3 mL/min (R)- or (S)—N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (181). $^1$H NMR (400 MHz, MeOH-d$_4$) δ7.69 (d, J=8.4 Hz, 2H), 7.52 (d, J=8.4 Hz, 2H), 4.59 (s, 2H), 4.20-4.13 (m, 5H), 3.99 (d, J=11.6 Hz, 1H), 3.81 (d, J=11.6 Hz, 1H), 3.77-3.66 (m, 4H), 3.41 (s, 3H), 3.08 (t, J=6.8 Hz, 2H), 1.55-1.48 (m, 2H), 1.40 (s, 3H), 1.13-1.08 (m, 2H). MS (ESI): m/z 530.4 [M+H]$^+$. SFC: ee %=99%, Rt=5.932 min.

(R)- or (S)—N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (182). $^1$H NMR (400 MHz, MeOH-d$_4$) δ 7.69 (d, J=8.4 Hz, 2H), 7.52 (d, J=8.4 Hz, 2H), 4.59 (s, 2H), 4.21-4.13 (m, 5H), 3.99 (d, J=11.6 Hz, 1H), 3.81 (d, J=11.6 Hz, 1H), 3.77-3.65 (m, 4H), 3.41 (s, 3H), 3.08 (t, J=6.8 Hz, 2H), 1.55-1.48 (m, 2H), 1.40 (s, 3H), 1.13-1.08 (m, 2H). MS (ESI): m/z 530.4 [M+H]$^+$. SFC: ee %=98%, Rt=7.943 min.

Example 183

6-((1-((1-Amino-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (183)

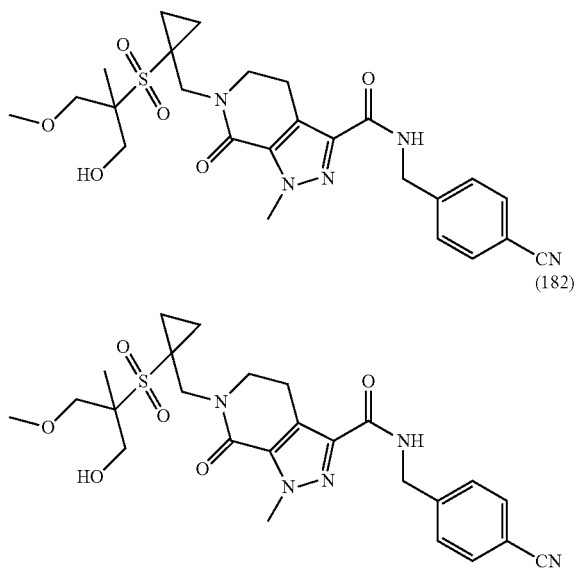

(R)- or(S)—N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (181) and (R)- or (S)—N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide (182) were obtained by chiral SFC separation of N-(4-Cyanobenzyl)-6-((1-((1-hydroxy-3-methoxy-2-methylpro-

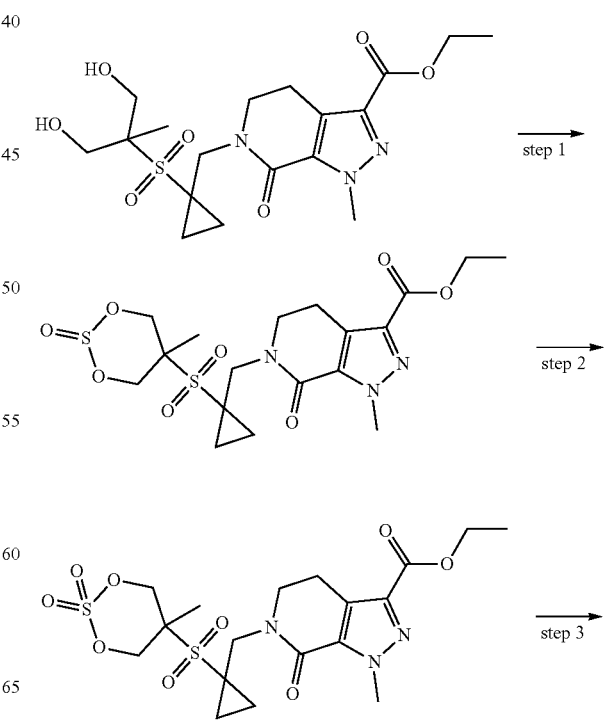

-continued

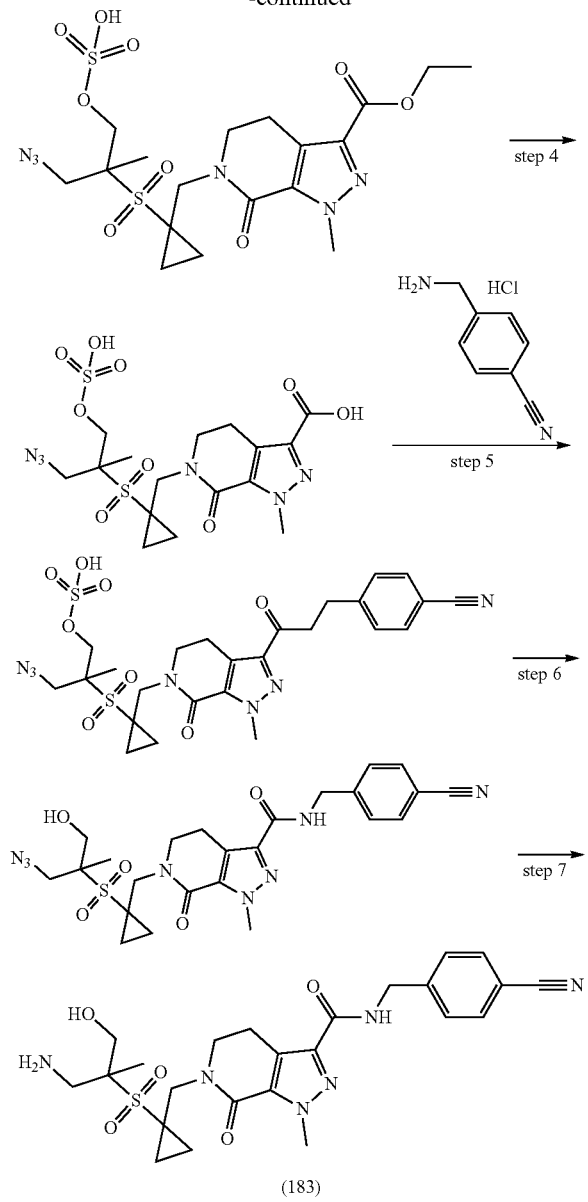

(183)

Step 1: To a solution of ethyl 6-((1-(((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate (3.40 g, 7.92 mmol, 1.0 equiv) in DCM (40 mL) was added $SOCl_2$ (1.7 mL, 23.75 mmol, 3.0 equiv). The reaction mixture was stirred at 25° C. for 3 h before it was diluted with water (10 mL) and adjusted to pH 8-9 with saturated $NaHCO_3$. The mixture was extracted with EtOAc (3×50 mL), washed with brine (50 mL), dried over $Na_2SO_4$, filtered and concentrated. The crude was purified by column chromatography ($SiO_2$, 10-50% EtOAc/petroleum ether) to give ethyl 1-methyl-6-((1-((5-methyl-2-oxido-1,3,2-dioxathian-5-yl)sulfonyl)cyclopropyl)methyl)-7-oxo-4,5,6,7-tetrahydro-1H-pyrazolo[3,4-c]pyridine-3-carboxylate. $^1$H NMR (400 MHz, $CDCl_3$) δ 5.32 (d, J=11.2 Hz, 1H), 4.84 (d, J=13.76 Hz, 2H), 4.51-4.39 (m, 5H), 4.26-4.22 (m, 6H), 4.18-4.13 (m, 1H), 3.99-3.91 (m, 1H), 3.80 (t, J=6.8 Hz, 2H), 3.72 (t, J=6.8 Hz, 1H), 3.19-3.11 (m, 3H), 1.79 (br d, J=2.0 Hz, 2H), 1.46-1.40 (m, 5H), 1.37 (s, 3H), 1.29-1.23 (m, 2H). MS (ESI): m/z 476.2 [M+H]$^+$.

Step 2: To a solution of ethyl 1-methyl-6-((1-((5-methyl-2-oxido-1,3,2-dioxathian-5-yl)sulfonyl)cyclopropyl)methyl)-7-oxo-4,5,6,7-tetrahydro-1H-pyrazolo[3,4-c]pyridine-3-carboxylate (2.40 g, 5.26 mmol, 1.0 equiv) in DCM (20 mL), MeCN (20 mL) and $H_2O$ (1 mL) was added $NaIO_4$ (1.57 g, 7.36 mmol, 1.4 equiv) and $RuCl_3$ (109 mg, 0.526 mmol, 0.1 equiv). The reaction mixture was stirred at 25° C. for 2 h before it diluted with water (40 mL) and extracted with EtOAc (3×40 mL). The combined organic extracts were washed with brine (40 mL), dried over $Na_2SO_4$, filtered and concentrated to give ethyl 1-methyl-6-((1-((5-methyl-2,2-dioxido-1,3,2-dioxathian-5-yl)sulfonyl)cyclopropyl)methyl)-7-oxo-4,5,6,7-tetrahydro-1H-pyrazolo[3,4-c]pyridine-3-carboxylate. MS (ESI): m/z 492.0 [M+H]$^+$.

Step 3: Ethyl 6-((1-((1-azido-2-methyl-3-(sulfooxy)propan-2-yl)sulfonyl)cyclopropyl)methyl)-1-methyl-7-oxo-4,5,6,7-tetrahydro-1H-pyrazolo[3,4-c]pyridine-3-carboxylate was obtained using the method described in step 2 of Example 174, except (3-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)oxetan-3-yl)methyl 4-methylbenzenesulfonate was replaced with ethyl 1-methyl-6-((1-((5-methyl-2,2-dioxido-1,3,2-dioxathian-5-yl)sulfonyl)cyclopropyl)methyl)-7-oxo-4,5,6,7-tetrahydro-1H-pyrazolo[3,4-c]pyridine-3-carboxylate. MS (ESI): m/z 535.1 [M+H]$^+$.

Step 4: 6-((1-((1-Azido-2-methyl-3-(sulfooxy)propan-2-yl)sulfonyl)cyclopropyl)methyl)-1-methyl-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-((1-azido-2-methyl-3-(sulfooxy)propan-2-yl)sulfonyl)cyclopropyl)methyl)-1-methyl-7-oxo-4,5,6,7-tetrahydro-1H-pyrazolo[3,4-c]pyridine-3-carboxylate. MS (ESI): m/z 507.2 [M+H]$^+$.

Step 5: 3-Azido-2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropyl hydrogen sulfate was obtained using the method described in step 1 of Example 26, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-((1-Azido-2-methyl-3-(sulfooxy)propan-2-yl)sulfonyl)cyclopropyl)methyl)-1-methyl-7-oxo-4,5,6,7-tetrahydro-1H-pyrazolo[3,4-c]pyridine-3-carboxylic and hydrazine was replaced with 4-(aminomethyl)benzonitrile hydrochloride. MS (ESI): m/z 612.4 [M+H]$^+$.

Step 6: A solution of 3-azido-2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropyl hydrogen sulfate (1.40 g, 2.26 mmol, 1.0 equiv) in MeOH (15 mL) at 25° C. was treated with $H_2SO_4$ (17 mg, 0.18 mmol, 0.08 equiv) and the reaction mixture was stirred at 60° C. for 2 h. The mixture was diluted with water (50 mL) and extracted with EtOAc (3×50 mL). The combined organic extracts were washed with brine (50 mL), dried over $Na_2SO_4$, filtered and concentrated. The residue was purified by column chromatography ($SiO_2$, 10-50% EtOAc/petroleum ether) to give 6-((1-((1-azido-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide. $^1$H NMR (400 MHz, DMSO-$d_6$) δ 8.96 (t, J=6.2 Hz, 1H), 7.79 (d, J=8.2 Hz, 2H), 7.48 (d, J=8.2 Hz, 2H), 5.53 (t, J=5.0 Hz, 1H), 4.47 (d, J=6.2 Hz, 2H), 4.17-4.04 (m, 5H), 3.91-3.67 (m, 6H), 3.63 (br t, J=6.8 Hz, 3H), 2.98 (br t, J=6.8 Hz, 2H), 1.39 (br s, 2H), 1.34 (s, 3H), 1.04 (br d, J=1.8 Hz, 2H). MS (ESI): m/z 541.4 [M+H]⁺.

Step 7: 6-((1-((1-Amino-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (183) was obtained using the method described in step 3 for the synthesis of intermediate (int-2), except (((1-((1-methylcyclopropyl)sulfonyl)cyclopropyl)methoxy)methyl)benzene (i2-b) was replaced with 6-((1-((1-azido-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide.

$^1$H NMR (400 MHz, DMSO-$d_6$) δ 8.95 (t, J=6.2 Hz, 1H), 7.79 (d, J=8.2 Hz, 2H), 7.48 (d, J=8.2 Hz, 2H), 4.47 (d, J=6.2 Hz, 2H), 4.15-4.09 (m, 5H), 3.83-3.77 (m, 1H), 3.74-3.68 (m, 1H), 3.62 (t, J=6.8 Hz, 2H), 3.18 (d, J=5.2 Hz, 1H), 3.09 (d, J=13.8 Hz, 1H), 2.97 (br t, J=6.8 Hz, 2H), 2.87 (d, J=13.8 Hz, 1H), 1.37-1.32 (m, 2H), 1.29 (s, 3H), 1.06-0.96 (m, 2H). MS (ESI): m/z 515.4 [M+H]⁺.

Compounds in Table 11 below were prepared following procedures analogous to those described for Compound (183) in Example 183.

TABLE 11

| Example/Compound Number | Compound Structure and Name | Physical Data MS (m/z), $^1$H NMR |
|---|---|---|
| 184 | 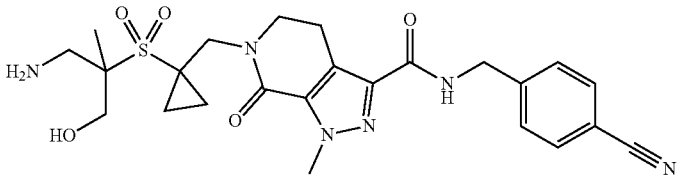<br>(R)- or (S)- 6-((1-((1-Amino-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 515.2 [M + H]⁺. $^1$H NMR (400 MHz, DMSO-$d_6$) δ 8.94 (t, J = 6.2 Hz, 1H), 7.79 (d, J = 8.0 Hz, 2H), 7.48 (d, J = 8.4 Hz, 2H), 4.47 (d, J = 6.2 Hz, 2H), 4.17-4.07 (m, 5H), 3.83-3.76 (m, 1H), 3.75-3.68 (m, 1H), 3.62 (t, J = 6.8 Hz, 2H), 3.17 (d, J = 5.0 Hz, 1H), 3.08 (d, J = 13.6 Hz, 1H), 2.97 (t, J = 6.6 Hz, 2H), 2.85 (d, J = 13.6 Hz, 1H), 1.36-1.31 (m, 2H), 1.29 (s, 3H), 1.02-0.95 (m, 2H). SFC $R_t$ = 3.634 min, 96.3% ee [AmyCoat, 50% EtOH (0.05% Et₂NH), 3 mL/min]. |
| 185 | 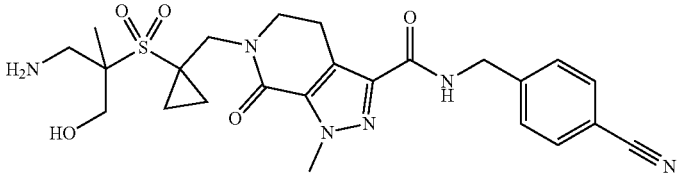<br>(R)- or (S)- 6-((1-((1-Amino-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 515.1 [M + H]⁺. $^1$H NMR (400 MHz, DMSO-$d_6$) δ 8.94 (t, J = 6.2 Hz, 1H), 7.79 (d, J = 8.4 Hz, 2H), 7.48 (d, J = 8.2 Hz, 2H), 4.47 (d, J = 6.2 Hz, 2H), 4.17-4.05 (m, 5H), 3.84-3.76 (m, 1H), 3.75-3.68 (m, 1H), 3.62 (t, J = 6.6 Hz, 2H), 3.17 (d, J = 5.2 Hz, 1H), 3.08 (d, J = 13.6 Hz, 1H), 2.97 (br t, J = 6.8 Hz, 2H), 2.85 (d, J = 13.6 Hz, 1H), 1.37-1.31 (m, 2H), 1.29 (s, 3H), 0.99 (br d, J = 2.0 Hz, 2H). SFC $R_t$ = 2.501 min, 100% ee [AmyCoat, 50% EtOH(0.05% Et₂NH), 3 mL/min]. |
| 186 | 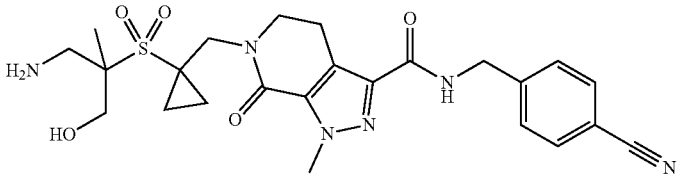<br>(R)- or (S)- 6-((1-((1-Amino-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 524.4 [M + H]⁺. $^1$H NMR (400 MHz, DMSO-$d_6$) δ 8.84 (t, J = 6.4 Hz, 1H), 7.42-7.26 (m, 4H), 4.38 (d, J = 6.4 Hz, 2H), 4.16-4.06 (m, 5H), 3.82-3.77 (m, 1H), 3.74-3.69 (m, 1H), 3.62 (t, J = 6.8 Hz, 2H), 3.07 (d, J = 13.6 Hz, 1H), 2.97 (t, J = 6.8 Hz, 2H), 2.85 (d, J = 13.6 Hz, 1H), 1.36-1.31 (m, 2H), 1.29 (s, 3H), 1.00-0.95 (m, 2H). |

TABLE 11-continued

| Example/Compound Number | Compound Structure and Name | Physical Data MS (m/z), $^1$H NMR |
|---|---|---|
| 187 | 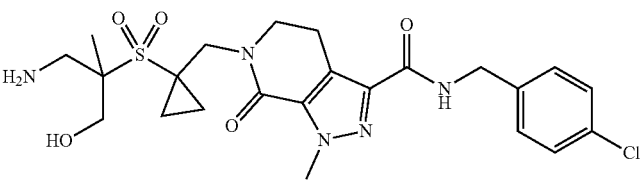<br>6-((1-((1-Amino-3-hydroxy-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide | MS (ESI): m/z 524.4 [M + H]$^+$. $^1$H NMR (400 MHz, DMSO-d$_6$) δ 8.83 (t, J = 6.4 Hz, 1H), 7.41-7.27 (m, 4H), 5.29 (br s, 1H), 4.38 (d, J = 6.4 Hz, 2H), 4.15-4.08 (m, 5H), 3.83-3.76 (m, 1H), 3.75-3.68 (m, 1H), 3.62 (t, J = 6.8 Hz, 2H), 3.08 (br d, J = 13.8 Hz, 1H), 2.98 (br t, J = 6.8 Hz, 2H), 2.85 (br d, J = 13.8 Hz, 1H), 1.59 (br s, 1H), 1.36-1.25 (m, 5H), 1.01-0.95 (m, 2H). SFC R$_t$ = 2.506 min, 100% ee [CHIRALPAK AD-3, 5-40% i-PrOH (0.05% Et$_2$NH), 3 mL/min]. |
| 188 | 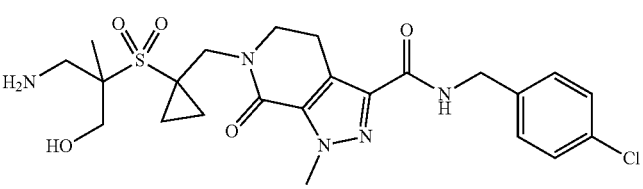<br>(R)- or (S)- 6-((1-((1-Amino-3-hydroxy-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 524.4 [M + H]$^+$. $^1$H NMR (400 MHz, DMSO-d$_6$) δ 8.83 (t, J = 6.4 Hz, 1H), 7.40-7.28 (m, 4H), 5.29 (br s, 1H), 4.38 (d, J = 6.2 Hz, 2H), 4.16-4.07 (m, 5H), 3.83-3.77 (m, 1H), 3.74-3.68 (m, 1H), 3.62 (t, J = 6.8 Hz, 2H), 3.08 (br d, J = 13.4 Hz, 1H), 2.98 (t, J = 6.8 Hz, 2H), 2.86 (br d, J = 13.8 Hz, 1H), 1.59 (br s, 2H), 1.36-1.31 (m, 2H), 1.29 (s, 3H), 1.02-0.96 (m, 2H). SFC R$_t$ = 2.424 min, 100% ee [CHIRALPAK AD-3, 5-40% i-PrOH (0.05% Et$_2$NH), 3 mL/min]. |

Example 189

N-(4-chlorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (189)

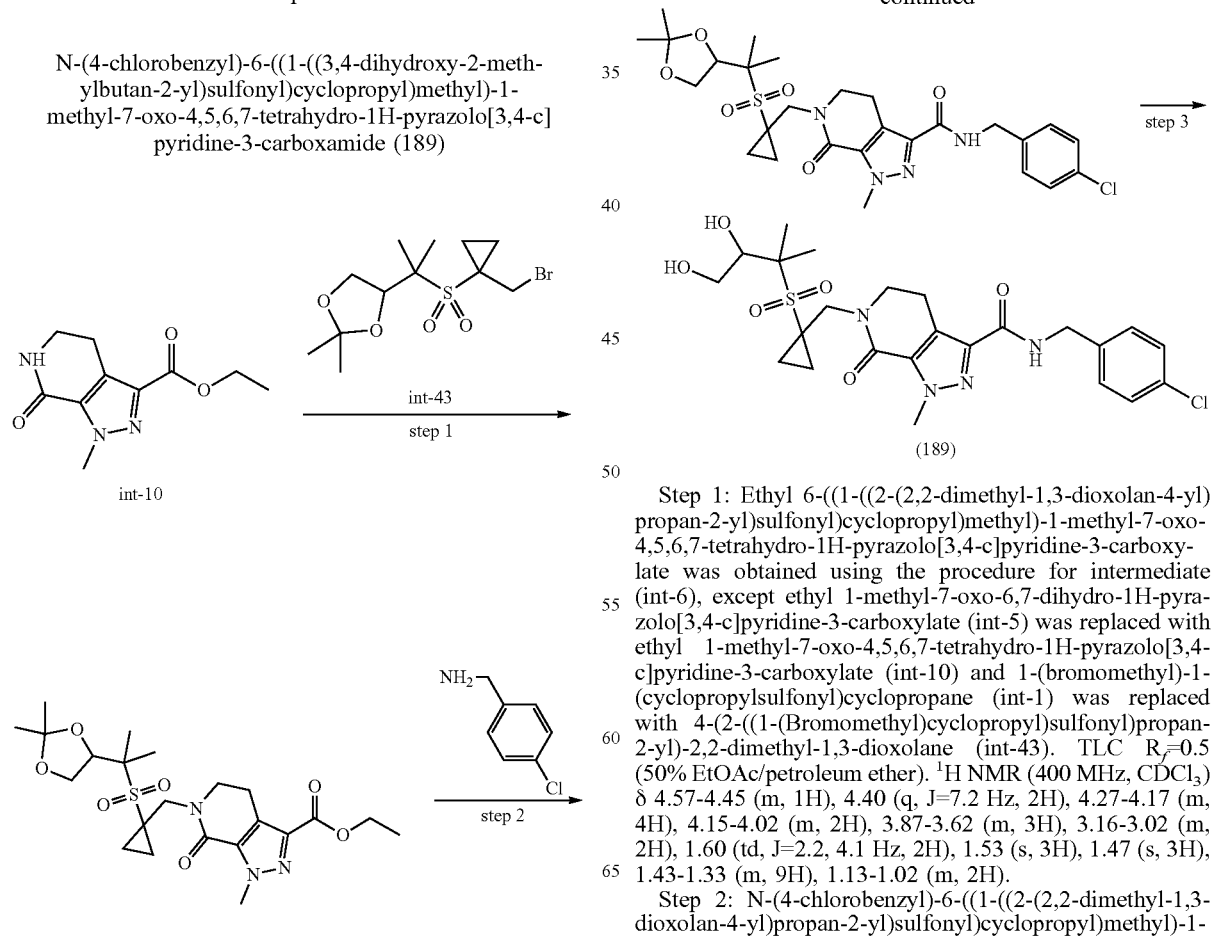

Step 1: Ethyl 6-((1-((2-(2,2-dimethyl-1,3-dioxolan-4-yl)propan-2-yl)sulfonyl)cyclopropyl)methyl)-1-methyl-7-oxo-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with 4-(2-((1-(Bromomethyl)cyclopropyl)sulfonyl)propan-2-yl)-2,2-dimethyl-1,3-dioxolane (int-43). TLC R$_f$=0.5 (50% EtOAc/petroleum ether). $^1$H NMR (400 MHz, CDCl$_3$) δ 4.57-4.45 (m, 1H), 4.40 (q, J=7.2 Hz, 2H), 4.27-4.17 (m, 4H), 4.15-4.02 (m, 2H), 3.87-3.62 (m, 3H), 3.16-3.02 (m, 2H), 1.60 (td, J=2.2, 4.1 Hz, 2H), 1.53 (s, 3H), 1.47 (s, 3H), 1.43-1.33 (m, 9H), 1.13-1.02 (m, 2H).

Step 2: N-(4-chlorobenzyl)-6-((1-((2-(2,2-dimethyl-1,3-dioxolan-4-yl)propan-2-yl)sulfonyl)cyclopropyl)methyl)-1- methyl-7-oxo-4,5,6,7-tetrahydro-1H-pyrazolo[3,4-c]pyridine-3-carboxamide was obtained using the method described in Example 1, except ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6) was replaced with Ethyl 6-((1-((2-(2,2-dimethyl-1,3-dioxolan-4-yl)propan-2-yl)sulfonyl)cyclopropyl)methyl)-1-methyl-7-oxo-4,5,6,7-tetrahydro-1H-pyrazolo[3,4-c]pyridine-3-carboxylate and 4-(aminomethyl)benzonitrile hydrochloride was replaced with 4-chlorophenyl)methanamine.

Step 3: N-(4-chlorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide was obtained using the method described in step 3 of Example 175, except N-(4-cyanobenzyl)-1-methyl-7-oxo-6-((1-((2,2,5-trimethyl-1,3-dioxan-5-yl)sulfonyl)cyclopropyl)methyl)-4,5,6,7-tetrahydro-1H-pyrazolo[3,4-c]pyridine-3-carboxamide was replaced with N-(4-chlorobenzyl)-6-((1-((2-(2,2-dimethyl-1,3-dioxolan-4-yl)propan-2-yl)sulfonyl)cyclopropyl)methyl)-1-methyl-7-oxo-4,5,6,7-tetrahydro-1H-pyrazolo[3,4-c]pyridine-3-carboxamide.

Example 190 and Example 191

(S)—N-(4-Chlorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (190)

and (R)—N-(4-Chlorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (191)

(190)

(191)

(S)—N-(4-Chlorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (190). MS (ESI): m/z 539.3 [M+H]$^+$. $^1$H NMR (400 MHz, CDCl$_3$) δ 7.34-7.27 (m, 4H), 7.18 (br t, J=6.1 Hz, 1H), 4.57 (d, J=6.1 Hz, 2H), 4.27-4.22 (m, 1H), 4.19 (td, J=3.6, 7.4 Hz, 1H), 4.16-4.09 (m, 4H), 3.89 (d, J=3.9 Hz, 1H), 3.81 (br dd, J=3.8, 7.2 Hz, 1H), 3.75-3.66 (m, 3H), 3.19 (t, J=6.9 Hz, 2H), 2.37-2.26 (m, 1H), 1.61 (td, J=2.5, 5.1 Hz, 2H), 1.57 (s, 3H), 1.50 (s, 3H), 1.09 (td, J=2.5, 4.7 Hz, 2H). SFC: Rt=1.667 min, 99% ee.

(R)—N-(4-Chlorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (191). MS (ESI): m/z 539.3[M+H]$^+$. $^1$H NMR (400 MHz, CDCl$_3$) δ 7.32 (d, J=8.0 Hz, 2H), 7.32-7.27 (s, 3H), 7.17 (br t, J=6.0 Hz, 1H), 4.57 (d, J=6.1 Hz, 2H), 4.27-4.22 (m, 1H), 4.19 (td, J=3.6, 7.4 Hz, 1H), 4.16-4.09 (s, 4H), 3.88 (d, J=3.6 Hz, 1H), 3.84-3.77 (m, 1H), 3.70 (t, J=6.9 Hz, 3H), 3.19 (t, J=6.9 Hz, 2H), 2.27 (brs, 1H), 1.63-1.60 (s, 2H), 1.57, 3H), 1.50 (s, 3H), 1.09 (td, J=2.5, 4.7 Hz, 2H). SFC: Rt=2.095 min, 98% ee.

The amide analogs in Table 12 below were prepared following the procedures analogous to those described for Compounds 189-191 in Examples 89-191. The stereochemistry was assigned by analogy to similar compounds with known stereochemistry as determined by X-ray crystallography.

TABLE 12

| Example/ Compound Number | Compound Structure and Name | Physical Data MS (m/z), $^1$H NMR |
|---|---|---|
| 192 | 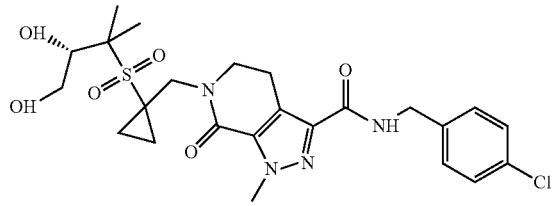<br>(S)-N-(4-Cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 530.4 [M + H]$^+$. $^1$H NMR (400 MHz, CDCl$_3$) δ 7.66-7.62 (m, J = 8.3 Hz, 2H), 7.48-7.43 (m, J = 8.2 Hz, 2H), 7.34-7.27 (m, 1H), 4.66 (d, J = 6.4 Hz, 2H), 4.28-4.21 (m, 1H), 4.19 (td, J = 3.4, 7.3 Hz, 1H), 4.15 (s, 3H), 4.14-4.09 (m, 1H), 3.88 (d, J = 3.6 Hz, 1H), 3.80 (br s, 1H), 3.75-3.65 (m, 3H), 3.18 (t, J = 6.9 Hz, 2H), 2.30 (br s, 1H), 1.61 (td, J = 2.6, 5.3 Hz, 3H), 1.57 (s, 3H), 1.50 (s, 3H), 1.09 (td, J = 2.3, 7.3 Hz, 2H). SFC R$_t$ = 3.787 min, 100% ee [CHIRALCEL OD-3, 5-40% i-PrOH (0.05% Et$_2$NH), 3 mL/min] |

TABLE 12-continued

| Example/Compound Number | Compound Structure and Name | Physical Data MS (m/z), ¹H NMR |
|---|---|---|
| 193 | (R)-N-(4-Cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide | MS (ESI): m/z 530.4 [M + H]⁺. ¹H NMR (400 MHz, CDCl₃) δ 7.68-7.60 (m, 2H), 7.49-7.42 (m, J = 8.2 Hz, 2H), 7.33-7.27 (m, 1H), 4.66 (d, J = 6.3 Hz, 2H), 4.28-4.22 (m, 1H), 4.19 (dd, J = 3.3, 7.4 Hz, 1H), 4.15 (s, 3H), 4.14-4.10 (m, 1H), 3.82 (dd, J = 3.3, 11.3 Hz, 1H), 3.74-3.66 (m, 3H), 3.18 (t, J = 6.8 Hz, 2H), 1.62 (td, J = 2.6, 5.1 Hz, 2H), 1.57 (s, 3H), 1.50 (s, 3H), 1.13-1.05 (m, 2H). SFC R$_t$ = 4.074 min, 93% ee [CHIRALCEL OD-3, 5-40% i-PrOH (0.05% Et₂NH), 3 mL/min] |

Example 194 and Example 195

(R)- or (S)—N-(4-Cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide (194)

and (R)- or (S)—N-(4-Cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide (195)

Step 1: Ethyl 6-((1-((1-(2,2-dimethyl-1,3-dioxolan-4-yl)cyclopropyl)sulfonyl)cyclopropyl)methyl)-1-methyl-7-oxo-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with 4-(1-((1-(Bromomethyl)cyclopropyl)sulfonyl)cyclopropyl)-2,2-dimethyl-1,3-dioxolane (int-44). TLC R$_f$=0.3 (75% EtOAc/petroleum ether). ¹H NMR (400 MHz, CDCl₃) δ 4.86 (t, J=6.8 Hz, 1H), 4.49-4.34 (m, 2H), 4.23 (s, 3H), 4.20-4.13 (m, 2H), 4.10-4.02 (m, 1H), 3.77-3.66 (m, 3H), 3.21-3.02 (m, 2H), 1.55-1.46 (m, 4H), 1.44-1.41 (m, 3H), 1.41 (s, 3H), 1.39 (s, 3H), 1.20-1.11 (m, 2H), 1.08-0.94 (m, 2H).

Step 2: N-(4-cyanobenzyl)-6-((1-((1-(2,2-dimethyl-1,3-dioxolan-4-yl)cyclopropyl)sulfonyl)cyclopropyl)methyl)-1-methyl-7-oxo-4,5,6,7-tetrahydro-1H-pyrazolo[3,4-c]pyridine-3-carboxamide was obtained the method described in Example 1, except ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6) was replaced with ethyl 6-((1-((1-(2,2-dimethyl-1,3-dioxolan-4-yl)cyclopropyl)sulfonyl)cyclopropyl)methyl)-1-methyl-7-oxo-4,5,6,7-tetrahydro-1H-pyrazolo[3,4-c]pyridine-3-carboxylate.

Step 3: N-(4-cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide was obtained using the method described in step 7 in Example 154, except N-(4-chlorobenzyl)-1-methyl-6-((1-(N-methyl-N-(2,2,5-trimethyl-1,3-dioxan-5-yl)sulfamoyl)cyclopropyl)methyl)-7-oxo-4,5,6,7-tetrahydro-1H-pyrazolo[3,4-c]pyridine-3-carboxamide was replaced with N-(4-cyanobenzyl)-6-((1-((1-(2,2-dimethyl-1,3-dioxolan-4-yl)cyclopropyl)sulfonyl)cyclopropyl)methyl)-1-methyl-7-oxo-4,5,6,7-tetrahydro-1H-pyrazolo[3,4-c]pyridine-3-carboxamide.

Step 4: (R)- or (S)—N-(4-Cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide (194) and (R)- or (S)—N-(4-Cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide (195) were obtained by chiral SFC separation of N-(4-cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide.

Unless otherwise indicated, examples indicate relative stereochemistry. SFC: CHIRALCEL OD-3,5-40% EtOH (0.05% Et$_2$NH), 3 mL/min (R)- or (S)—N-(4-Cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide (194). MS (ESI): m/z 528.2 [M+H]$^+$. $^1$H NMR (400 MHz, CDCl$_3$) δ 7.64 (d, J=8.4 Hz, 2H), 7.45 (d, J=8.4 Hz, 2H), 7.33-7.27 (m, 1H), 4.66 (d, J=6.4 Hz, 2H), 4.32 (s, 1H), 4.27-4.19 (m, 1H), 4.16 (s, 3H), 4.15-4.08 (m, 1H), 3.86 (s, 1H), 3.75-3.58 (m, 4H), 3.17 (t, J=6.8 Hz, 2H), 2.50 (s, 1H), 1.59-1.56 (m, 2H), 1.54-1.44 (m, 2H), 1.34-1.27 (m, 2H), 1.05-0.95 (m, 2H). SFC: Rt=3.380 min, ee=100%, (R)- or (S)—N-(4-Cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide (195). MS (ESI): m/z 528.2 [M+H]$^+$. $^1$H NMR (400 MHz, CDCl$_3$) δ 7.64 (d, J=8.4 Hz, 2H), 7.45 (d, J=8.4 Hz, 2H), 7.34-7.27 (m, 1H), 4.66 (d, J=6.4 Hz, 2H), 4.38-4.28 (m, 1H), 4.26-4.19 (m, 1H), 4.16 (s, 3H), 4.15-4.08 (m, 1H), 3.86 (s, 1H), 3.66 (t, J=6.8 Hz, 4H), 3.17 (t, J=6.8 Hz, 2H), 2.50 (s, 1H), 1.58 (s, 2H), 1.55-1.46 (m, 2H), 1.32 (s, 2H), 1.05-0.96 (m, 2H). SFC: Rt=3.492 min, ee=96%, The amide analogs in the Table 13 below were prepared following the procedures analogous to those described for Compounds (194) and (195) in Examples 194-195.

TABLE 13

| Example/Compound Number | Compound Structure and Name | Physical Data MS (m/z), $^1$H NMR |
|---|---|---|
| 196 | (R)- or (S)- N-(4-Chlorobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 537.2 [M + H]$^+$. $^1$H NMR (400 MHz, CDCl$_3$) δ 7.37-7.29 (m, 4H), 7.20 (t, J = 6.0 Hz, 1H), 4.58 (d, J = 6.2 Hz, 2H), 4.39-4.30 (m, 1H), 4.28-4.20 (m, 1H), 4.18-4.09 (m, 4H), 3.93 (br s, 1H), 3.77-3.59 (m, 4H), 3.26-3.15 (m, 2H), 2.53 (s, 1H), 1.60-1.49 (m, 4H), 1.39-1.28 (m, 2H), 1.08-0.94 (m, 2H). SFC R$_t$ = 3.455 min, 100% ee [CHIRALCEL OD-3, 5-40% EtOH (0.05% Et$_2$NH), 3 mL/min]. |
| 197 | (R)- or (S)- N-(4-Chlorobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 537.2 [M + H]$^+$. $^1$H NMR (400 MHz, CDCl$_3$) δ 7.37-7.29 (m, 4H), 7.19 (t, J = 6.0 Hz, 1H), 4.58 (d, J = 6.2 Hz, 2H), 4.40-4.31 (m, 1H), 4.28-4.20 (m, 1H), 4.16 (s, 4H), 3.91 (d, J = 3.6 Hz, 1H), 3.77-3.58 (m, 4H), 3.24-3.10 (m, 2H), 2.58-2.36 (m, 1H), 1.59-1.48 (m, 4H), 1.33 (d, J = 2.4 Hz, 2H), 1.07-0.94 (m, 2H). SFC R$_t$ = 3.559 min, 93% ee [CHIRALCEL OD-3, 5-40% EtOH (0.05% Et$_2$NH), 3 mL/min]. |

Example 198

(R)-6-((1-((4-amino-3-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (198)

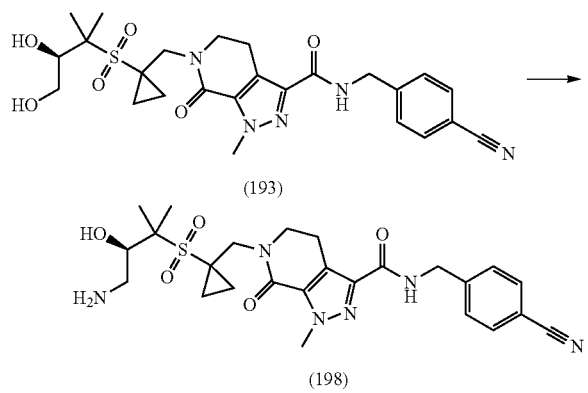

(193)

(198)

Et₃N (4.0 equiv.) was added to a solution of (R)—N-(4-cyanobenzyl)-6-((1-((3,4-dihydroxy-2-methyl butan-2-yl)sulfonyl)cyclopropyl)methyl) -1-methyl-7-oxo-4,5,6,7-tetrahydro-1H-pyrazolo[3,4-c]pyridine-3-carboxamide (193) (1.0 equiv.) in $CH_2Cl_2$ before adding TsCl (2.0 equiv.) in one portion at rt. After 5 h, the solution was concentrated, re-dissolved in MeOH, and $K_2CO_3$ (6.0 equiv.) was added in one portion. The resulting suspension was stirred vigorously for 90 min before being concentrated. The crude reaction mixture was partitioned between $CH_2Cl_2$ and $H_2O$ (5 mL each) and the aqueous phase was extracted (2×5 mL $CH_2Cl_2$). The combined organic extracts were dried ($MgSO_4$), filtered, and concentrated to afford the desired crude epoxide. A methanolic solution of the $NH_3$ (7.0 equiv.) was added to the crude epoxide and the solution was capped and heated to 60° C. for 2 h. The reaction mixture was concentrated to dryness and the crude solid was purified by RP-HPLC to obtain (R)-6-((1-((4-amino-3-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (198). MS (ESI): m/z 529.4 [M+H]⁺. ¹H NMR (400 MHz, CDCl₃) δ 7.64 (d, J=8.4 Hz, 2H), 7.46 (d, J=8.4 Hz, 2H), 4.66 (d, J=6.6 Hz, 2H), 4.28-4.17 (m, 2H), 4.15 (s, 3H), 3.98 (m, 1H), 3.77-3.67 (m, 2H), 3.18 (m, 2H), 3.00 (m, 1H), 2.67 (m, 1H), 1.63-1.60 (m, 2H), 1.51 (s, 3H), 1.44 (s, 3H), 1.14-1.03 (m, 2H). SFC: Rt=10.121 min, ee=100%, [CHIRALPAK IC-3, 5-35% EtOH (0.05% Et₂NH), 3 mL/min].

The compounds in Table 14 below were prepared following the procedures analogous to method described for Compound (198) in Example 198 using the appropriate diol and amine.

TABLE 14

| Example/ Compound Number | Compound Structure and Name | Physical Data MS (m/z), ¹H NMR |
|---|---|---|
| 199 | (R)- or (S)- 6-((1-((4-Amino-3-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 529.3 [M + H]⁺. ¹H NMR (400 MHz, CDCl₃) δ 7.64 (d, J = 8.2 Hz, 2H), 7.46 (d, J = 8.2 Hz, 2H), 4.66 (d, J = 6.6 Hz, 2H), 4.29-4.17 (m, 2H), 4.15 (s, 3H), 3.98 (m, 1H), 3.79-3.66 (m, 2H), 3.18 (t, J = 6.8 Hz, 2H), 3.01 (m, 1H), 2.67 (m, 1H), 1.61 (s, 3H), 1.52 (s, 3H), 1.44 (s, 3H), 1.11-1.02 (m, 2H). SFC R_t = 8.827 min, 100% ee [CHIRALPAK IC-3, 5-35% EtOH (0.05% Et₂NH), 3 mL/min]. |
| 200 | (R)- or (S)- 6-((1-((4-Amino-3-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 538.4 [M + H]⁺. ¹H NMR (400 MHz, CDCl₃) δ 7.37-7.29 (m, 4H), 7.19 (t, J = 6.2 Hz, 1H), 4.58 (d, J = 6.2 Hz, 2H), 4.32-4.18 (m, 2H), 4.15 (s, 3H), 3.98 (m, 1H), 3.80-3.66 (m, 2H), 3.20 (m, 2H), 3.00 (m, 1H), 2.68 (m, 1H), 1.62 (m, 2H), 1.53 (s, 3H), 1.45 (s, 3H), 1.14-1.05 (m, 2H). SFC R_t = 3.467 min, 100% ee [CHIRALPAK IC-3, 40% MeOH (0.05% Et₂NH), 3 mL/min]. |

TABLE 14-continued

| Example/ Compound Number | Compound Structure and Name | Physical Data MS (m/z), ¹H NMR |
|---|---|---|
| 201 | (R)- or (S)- 6-((1-((4-Amino-3-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 538.4 [M + H]⁺. ¹H NMR (400 MHz, CDCl₃) δ 7.35-7.28 (m, 4H), 7.17 (m, 1H), 4.57 (d, J = 6.2 Hz, 2H), 4.30-4.17 (m, 2H), 4.14 (s, 3H), 3.97 (m, 1H), 3.77-3.66 (m, 2H), 3.19 (m, 2H), 2.99 (m, 1H), 2.67 (m, 1H), 1.52 (s, 4H), 1.44 (s, 3H), 1.13-0.99 (m, 2H). SFC R₁ = 3.959 min, 100% ee [CHIRALPAK IC-3, 40% MeOH (0.05% Et₂NH), 3 mL/min]. |
| 202 | (R)- or (S)- N-(4-Cyanobenzyl)-6-((1-((3-hydroxy-2-methyl-4-(methylamino)butan-2-yl)sulfonyl)cyclopropyl)methyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 543.2 [M + H]⁺. ¹H NMR (500 MHz, DMSO-d₆) δ 8.95 (t, J = 6.3 Hz, 1H), 8.48 (s, 1H), 8.36 (s, 1H), 7.87-7.72 (m, 2H), 7.52-7.42 (m, 2H), 6.23 (s, 1H), 4.46 (d, J = 6.2 Hz, 2H), 4.10 (d, J = 6.4 Hz, 6H), 3.25 (d, J = 12.1 Hz, 1H), 3.06-2.94 (m, 3H), 2.60 (t, J = 5.4 Hz, 3H), 1.47 (s, 3H), 1.37 (s, 5H), 1.12-0.99 (m, 2H). |
| 203 | (R)- or (S)- N-(4-Cyanobenzyl)-6-((1-((3-hydroxy-2-methyl-4-(methylamino)butan-2-yl)sulfonyl)cyclopropyl)methyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 543.2 [M + H]⁺. ¹H NMR (500 MHz, DMSO-d₆) δ 8.97 (t, J = 6.3 Hz, 1H), 8.47 (s, 1H), 8.36 (s, 1H), 7.85-7.76 (m, 2H), 7.49 (d, J = 8.1 Hz, 2H), 6.23 (s, 1H), 4.48 (d, J = 6.3 Hz, 2H), 4.12 (d, J = 6.6 Hz, 6H), 3.25 (s, 2H), 3.01 (q, J = 7.6, 6.9 Hz, 3H), 2.62 (t, J = 5.4 Hz, 3H), 1.48 (s, 3H), 1.39 (s, 5H), 1.13-1.02 (m, 2H). |
| 204 | (R)- or (S)- N-(4-Chlorobenzyl)-6-((1-((3-hydroxy-2-methyl-4-(methylamino)butan-2-yl)sulfonyl)cyclopropyl)methyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 552.4 [M + H]⁺. ¹H NMR (500 MHz, DMSO-d₆) δ 8.85 (t, J = 6.3 Hz, 1H), 8.47 (s, 1H), 8.35 (s, 1H), 7.48-7.25 (m, 4H), 4.37 (d, J = 6.3 Hz, 2H), 4.10 (s, 5H), 3.74-3.55 (m, 2H), 3.23 (s, 1H), 3.02-2.89 (m, 2H), 2.60 (t, J = 5.4 Hz, 3H), 1.47 (s, 3H), 1.37 (s, 5H), 1.18-0.86 (m, 2H). |

TABLE 14-continued

| Example/ Compound Number | Compound Structure and Name | Physical Data MS (m/z), $^1$H NMR |
|---|---|---|
| 205 | 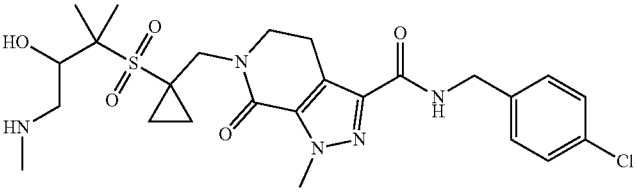<br>(R)- or (S)- N-(4-Chlorobenzyl)-6-((1-((3-hydroxy-2-methyl-4-(methylamino)butan-2-yl)sulfonyl)cyclopropyl)methyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 552.2 [M + H]$^+$. $^1$H NMR (500 MHz, DMSO-d$_6$) δ 8.85 (t, J = 6.3 Hz, 1H), 8.49 (s, 1H), 8.36 (s, 1H), 7.40-7.34 (m, 2H), 7.34-7.26 (m, 2H), 4.37 (d, J = 6.3 Hz, 2H), 4.10 (s, 6H), 3.61 (dq, J = 10.0, 5.9 Hz, 2H), 3.30-3.16 (m, 1H), 3.08-2.92 (m, 3H), 2.60 (t, J = 5.4 Hz, 3H), 1.47 (s, 3H), 1.37 (s, 5H), 1.14-0.97 (m, 2H). |
| 206 | 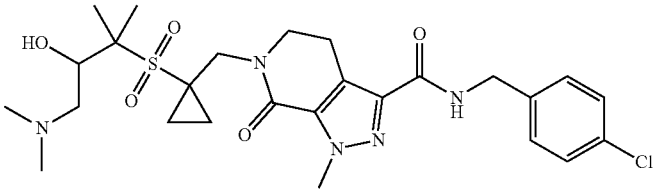<br>(R)- or (S)- N-(4-Chlorobenzyl)-6-((1-((4-(dimethylamino)-3-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 566.2 [M + H]$^+$. $^1$H NMR (400 MHz, CDCl$_3$) δ 7.26-7.20 (m, 4H), 7.08 (s, 1H), 4.49 (d, J = 6.2 Hz, 2H), 4.26-4.11 (m, 2H), 4.06 (s, 3H), 4.01 (m, 1H), 3.70-3.62 (m, 3H), 3.10 (m, 2H), 2.35-2.30 (m, 1H), 2.27 (s, 6H), 1.43 (s, 3H), 1.29 (s, 3H), 1.19 (s, 2H), 0.99 (s, 2H). SFC R$_t$ = 5.728 min, 85% ee [CHIRALPAK IC-3, 40% EtOH (0.05% Et$_2$NH), 3 mL/min]. |
| 207 | 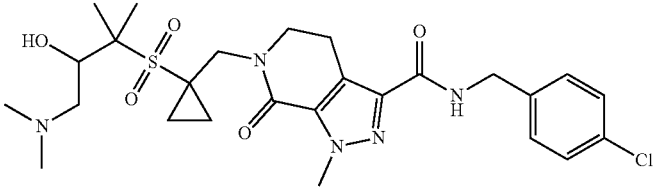<br>(R)- or (S)- N-(4-Chlorobenzyl)-6-((1-((4-(dimethylamino)-3-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide Unless otherwise indicated, examples indicate relative stereochemistry | MS (ESI): m/z 566.2 [M + H]$^+$. $^1$H NMR (400 MHz, CDCl$_3$) δ 7.34-7.28 (m, 4H), 7.16 (s, 1H), 4.57 (d, J = 6.2 Hz, 2H), 4.37-4.18 (m, 2H), 4.14 (s, 3H), 4.10 (m, 1H), 3.78-3.68 (m, 3H), 3.21-3.13 (m, 2H), 2.43 (s, 1H), 2.37 (s, 6H), 1.52 (s, 2H), 1.37 (s, 3H), 1.26 (d, J = 3.8 Hz, 2H), 1.08 (d, J = 2.2 Hz, 2H). SFC R$_t$ = 4.907 min, 100% ee [CHIRALPAK IC-3, 40% EtOH (0.05% Et$_2$NH), 3 mL/min]. |
| 208 | 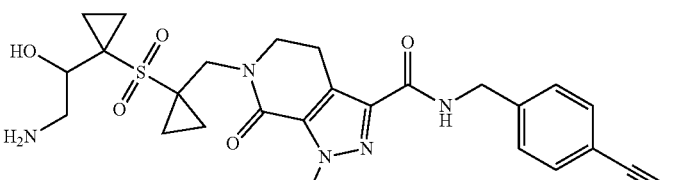<br>6-((1-((1-(2-Amino-1-hydroxyethyl)cyclopropyl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide | MS (ESI): m/z 527.3 [M + H]$^+$. $^1$H NMR (400 MHz, CDCl$_3$) δ 7.64 (d, J = 8.2 Hz, 2H), 7.45 (d, J = 8.2 Hz, 2H), 4.66 (d, J = 6.4 Hz, 2H), 4.27 (d, J = 14.4 Hz, 1H), 4.16 (s, 3H), 4.13-4.04 (m, 2H), 3.73-3.62 (m, 2H), 3.22-3.12 (m, 2H), 2.96 (dd, J = 3.6, 12.7 Hz, 1H), 2.69 (dd, J = 9.2, 12.6 Hz, 1H), 1.61-1.38 (m, 4H), 1.31-1.11 (m, 3H), 1.10-0.94 (m, 2H). |

TABLE 14-continued

| Example/ Compound Number | Compound Structure and Name | Physical Data MS (m/z), ¹H NMR |
|---|---|---|
| 209 | 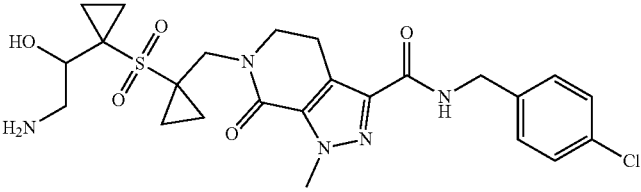 6-((1-((1-(2-Amino-1-hydroxyethyl)cyclopropyl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide | MS (ESI: m/z 536.2 [M + H]⁺. ¹H NMR (400 MHz, CDCl₃) δ 7.36-7.28 (m, 4H), 7.18 (br t, J = 6.1 Hz, 1H), 4.57 (d, J = 6.1 Hz, 2H), 4.28 (d, J = 14.4 Hz, 1H), 4.15 (s, 3H), 4.12-4.04 (m, 2H), 3.75-3.60 (m, 2H), 3.30-3.08 (m, 2H), 2.93 (dd, J = 4.0, 12.7 Hz, 1H), 2.67 (dd, J = 8.8, 12.6 Hz, 1H), 1.49-1.37 (m, 4H), 1.30-0.96 (m, 4H). |

Example 210

6-((1-((4-amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (210)

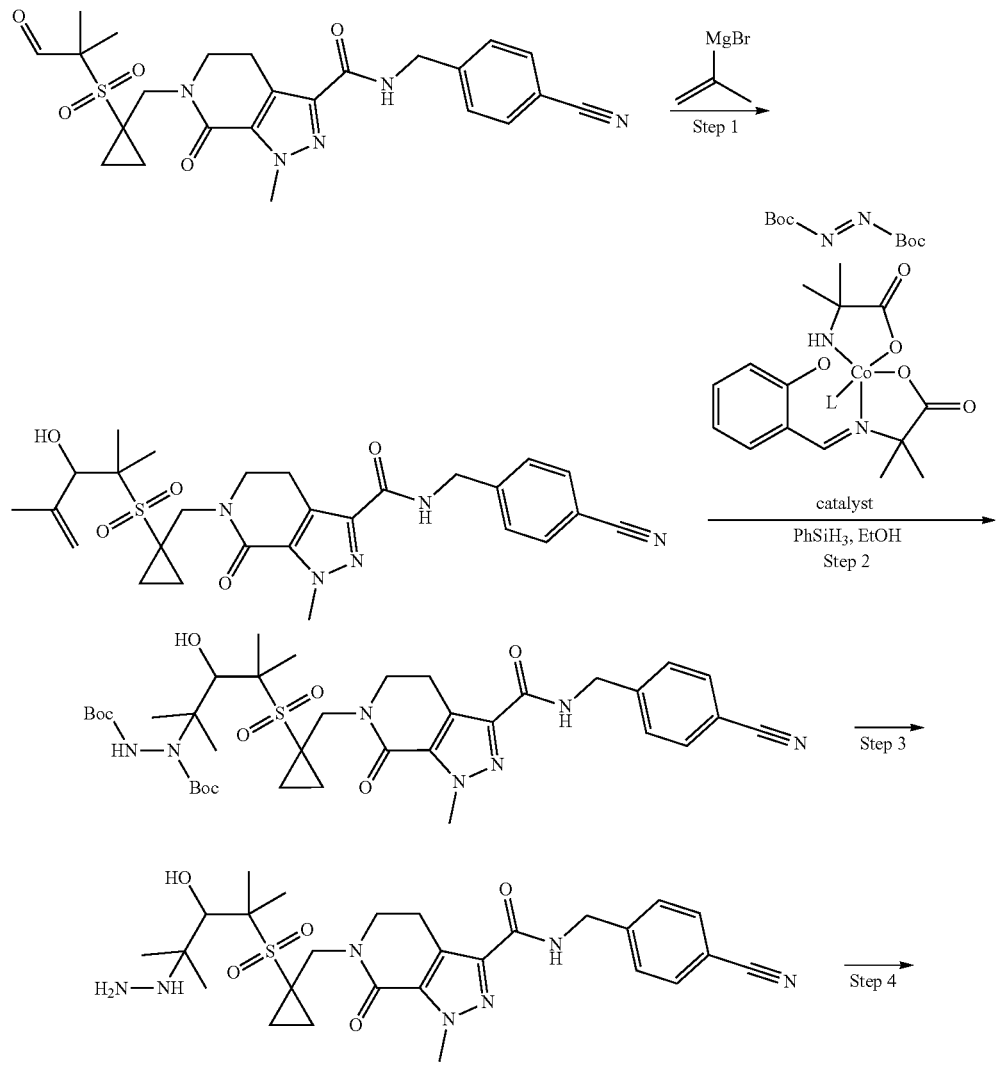

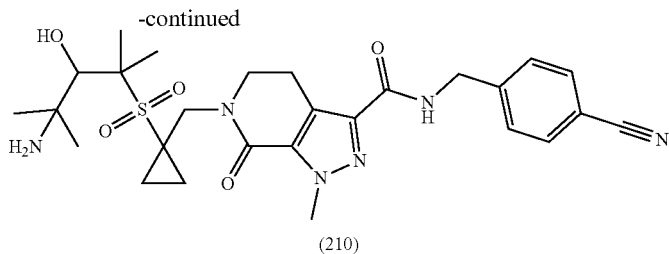

(210)

Step 1: To a solution of N-(4-cyanobenzyl)-1-methyl-6-((1-((2-methyl-1-oxopropan-2-yl)sulfonyl)cyclopropyl)methyl)-7-oxo-4,5,6,7-tetrahydro-1H-pyrazolo[3,4-c]pyridine-3-carboxamide (1.0 g, 2.01 mmol, 1.0 equiv) in THF (10 mL) was added prop-1-en-2-ylmagnesium bromide (584 mg, 4.02 mmol, 2.0 equiv) at 25° C. The reaction mixture was stirred at 25° C. for 2 h, then the solution was quenched with saturated NH$_4$Cl (20 mL) and extracted with EtOAc (3×10 mL). The combined organic extracts were washed with brine (10 mL), dried over Na$_2$SO$_4$, filtered and concentrated. The residue was purified by RP-HPLC to give (N-(4-cyanobenzyl)-6-((1-((3-hydroxy-2,4-dimethylpent-4-en-2-yl)sulfonyl)cyclopropyl)methyl)-1-methyl-7-oxo-4,5,6,7-tetrahydro-1H-pyrazolo[3,4-c]pyridine-3-carboxamide. $^1$H NMR (400 MHz, DMSO-d$_6$) δ 8.94 (t, J=6.2 Hz, 1H), 7.79 (d, J=8.2 Hz, 2H), 7.48 (d, J=8.2 Hz, 2H), 5.61 (d, J=3.8 Hz, 1H), 5.00 (br s, 2H), 4.47 (d, J=6.4 Hz, 3H), 4.26-4.17 (m, 1H), 4.14-4.06 (m, 4H), 3.67-3.57 (m, 2H), 3.10-2.95 (m, 2H), 1.80-1.70 (m, 3H), 1.45 (s, 3H), 1.38 (d, J=5.4 Hz, 2H), 1.16 (s, 3H), 0.98 (t, J=5.4 Hz, 2H). MS (ESI): m/z 540.0 [M+H]$^+$.

Step 2: To a solution of N-(4-cyanobenzyl)-6-((1-((3-hydroxy-2,4-dimethylpent-4-en-2-yl)sulfonyl)cyclopropyl)methyl)-1-methyl-7-oxo-4,5,6,7-tetrahydro-1H-pyrazolo[3,4-c]pyridine-3-carboxamide (650 mg, 1.20 mmol, 1.0 equiv) in EtOH (10 mL) was added cobalt catalyst (22 mg, 0.06 mmol, 0.05 equiv) and di-tert-butyl azodicarboxylate (416 mg, 1.81 mmol, 1.5 equiv) at 25° C. The reaction mixture was stirred at 25° C. for 10 min, then PhSiH$_3$ (130 mg, 1.20 mmol, 1.0 equiv) was added and the mixture was stirred another 2 h at 25° C. The reaction was diluted with water (10 mL) and extracted with EtOAc (3×10 mL). The combined organic extracts were washed with brine (10 mL), dried over Na$_2$SO$_4$, filtered and concentrated. The mixture was purified by RP-HPLC to give di-tert-butyl 1-(4-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-3-hydroxy-2,4-dimethylpentan-2-yl)hydrazine-1,2-dicarboxylate. $^1$H NMR (400 MHz, DMSO-d$_6$) δ 8.95 (br t, J=6.2 Hz, 1H), 7.79 (d, J=8.4 Hz, 2H), 7.48 (d, J=8.4 Hz, 2H), 4.47 (d, J=6.2 Hz, 2H), 4.25-4.15 (m, 1H), 4.11 (s, 3H), 3.63 (br d, J=5.2 Hz, 2H), 2.98 (br s, 2H), 1.55-1.22 (m, 35H). MS (ESI): m/z 572.5 [M-2Boc+H]$^+$.

Note: the cobalt catalyst was obtained using the methods described in Waser, J.; Gaspar, B.; Nambu, H.; Carreira, E. M. Hydrazines and azides via the metal-catalyzed hydrohydrazination and hydroazidation of olefins. *J. Am. Chem. Soc.* 2006, 128, 11693-11712.)

Step 3: To a solution of di-tert-butyl 1-(4-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)-3-hydroxy-2,4-dimethylpentan-2-yl)hydrazine-1,2-dicarboxylate (500 mg, 0.65 mmol, 1.0 equiv) in DCM (5 mL) was added TFA (1 mL) at 25° C. The reaction mixture was stirred at 25° C. for 12 h before it was diluted with water (10 mL) and the pH was adjusted to 8-9 with saturated Na$_2$CO$_3$. The biphasic mixture was concentrated, then the residue was diluted in DMF (10 mL) and the solids were removed by filtration. The filtrate phase was purified by RP-HPLC to give (N-(4-cyanobenzyl)-6-((1-((4-hydrazinyl-3-hydroxy-2,4-dimethylpentan-2-yl)sulfonyl)cyclopropyl)methyl)-1-methyl-7-oxo-4,5,6,7-tetrahydro-1H-pyrazolo[3,4-c]pyridine-3-carboxamide). $^1$H NMR (400 MHz, DMSO-d$_6$) δ 8.93 (t, J=6.2 Hz, 1H), 7.79 (d, J=8.2 Hz, 2H), 7.48 (d, J=8.2 Hz, 2H), 5.73 (br s, 1H), 4.47 (d, J=6.2 Hz, 2H), 4.23-4.15 (m, 1H), 4.11 (s, 4H), 4.07-4.01 (m, 1H), 3.69-3.58 (m, 2H), 2.98 (br t, J=6.8 Hz, 2H), 1.53-1.45 (m, 3H), 1.42-1.31 (m, 5H), 1.14 (s, 3H), 1.03-0.90 (m, 5H). MS (ESI): m/z 572.5 [M+H]$^+$.

Step 4: Zn dust (30 g) was activated by stirring with 5% HCl (40 mL) for 3 min, then the solid was isolated by filtration and washed with water (3×40 mL), acetone (2×30 mL) and Et$_2$O (2×30 mL) before it was dried for 2 h under high vacuum. A portion of this activated Zn dust (114 mg, 1.75 mmol, 10.0 equiv) was added to a solution of N-(4-cyanobenzyl)-6-((1-((4-hydrazinyl-3-hydroxy-2,4-dimethylpentan-2-yl)sulfonyl)cyclopropyl)methyl)-1-methyl-7-oxo-4,5,6,7-tetrahydro-1H-pyrazolo[3,4-c]pyridine-3-carboxamide (100 mg, 0.175 mmol, 1.0 equiv) in AcOH (5 mL) at 25° C., followed 10 min later by acetone (0.1 mL). The reaction was stirred at 25° C. for 1 h, then at 60° C. for 11 h. The reaction mixture was quenched with saturated NaHCO$_3$ (10 mL) and the mixture was extracted with EtOAc (3×10 mL). The combined organic extracts were washed with brine, dried over Na$_2$SO$_4$, filtered and concentrated. The residue was purified by RP-HPLC to give 6-((1-((4-amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (210). $^1$H NMR (400 MHz, MeOH-d$_4$) δ 7.71 (d, J=8.4 Hz, 2H), 7.54 (d, J=8.4 Hz, 2H), 4.61 (s, 3H), 4.32-4.20 (m, 2H), 4.18 (s, 3H), 3.91 (s, 1H), 3.76 (dt, J=3.1, 6.8 Hz, 2H), 3.37 (s, 1H), 3.11 (t, J=6.8 Hz, 2H), 1.62 (d, J=16.0 Hz, 6H), 1.60-1.54 (m, 2H), 1.30 (s, 3H), 1.25 (s, 3H), 1.17-1.05 (m, 2H). MS (ESI): m/z 557.5 [M+H]$^+$.

Example 211 and Example 212

(R)- or(S)-6-((1-((4-Amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (211)

and (R)- or(S)-6-((1-((4-Amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (212)

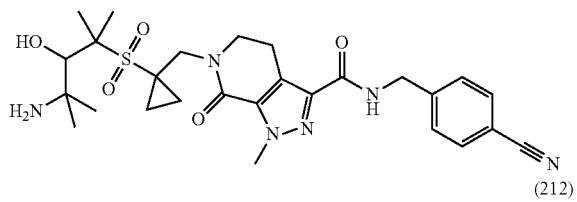
(211)

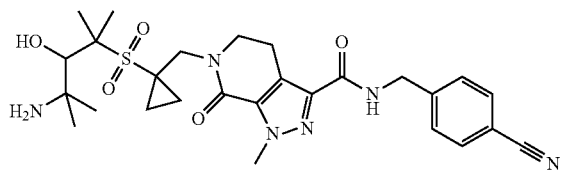
(212)

(R)- or (S)-6-((1-((4-Amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (211) and (R)- or (S)-6-((1-((4-Amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (212) were obtained by chiral SFC separation of 6-((1-((4-amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (210).

Unless otherwise indicated, examples indicate relative stereochemistry. SFC: CHIRALPAK IC-3, 60% MeOH (0.05% Et$_2$NH), 3 mL/min.

(R)- or (S)-6-((1-((4-Amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (211). MS (ESI): m/z 557.5 [M+H]$^+$. $^1$H NMR (400 MHz, MeOH-d$_4$) δ 7.69 (d, J=8.0 Hz, 2H), 7.51 (d, J=8.2 Hz, 2H), 4.59 (s, 2H), 4.29-4.11 (m, 5H), 3.90 (s, 1H), 3.78-3.69 (m, 2H), 3.37-3.33 (m, 1H), 3.09 (t, J=6.8 Hz, 2H), 1.62 (s, 3H), 1.58 (s, 3H), 1.55-1.50 (m, 2H), 1.29 (s, 3H), 1.24 (s, 3H), 1.12-1.06 (m, 2H). SFC: Rt=1.071 min, 98% ee.

(R)- or (S)-6-((1-((4-Amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (212). MS (ESI): m/z 557.5 [M+H]$^+$. $^1$H NMR (400 MHz, MeOH-d$_4$) δ 7.59 (d, J=8.0 Hz, 2H), 7.41 (d, J=8.0 Hz, 2H), 4.49 (s, 2H), 4.20-4.02 (m, 5H), 3.80 (s, 1H), 3.69-3.57 (m, 2H), 3.25 (s, 1H), 2.99 (t, J=6.8 Hz, 2H), 1.52 (s, 3H), 1.47 (s, 3H), 1.45-1.40 (m, 2H), 1.19 (s, 3H), 1.14 (s, 3H), 1.03-0.95 (m, 2H). SFC: Rt=1.754 min, 96% ee.

Example 213

(R)-6-((1-((3-amino-4-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (213)

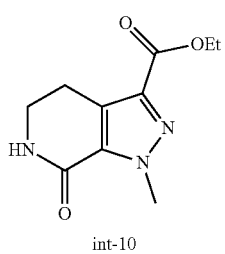
int-10

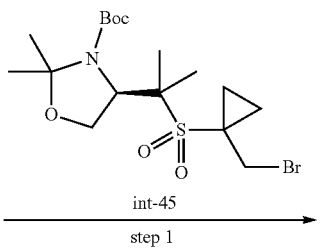
int-45 step 1

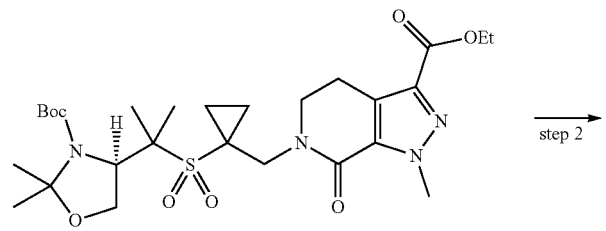
step 2

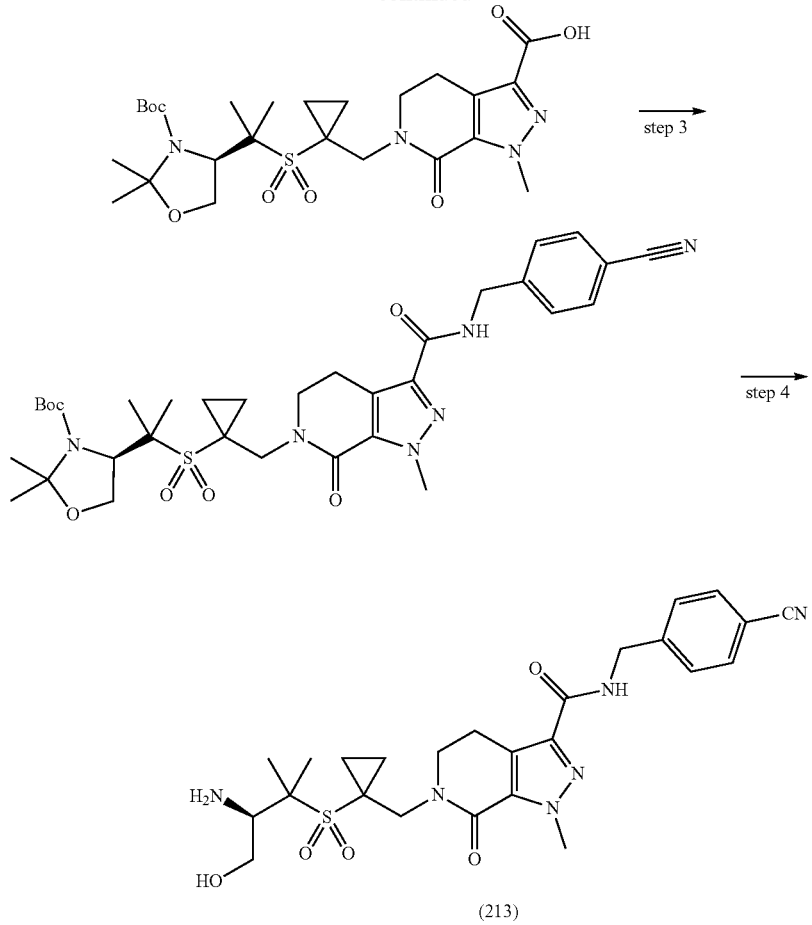

(213)

Step 1: (R)-tert-Butyl 4-(2-((1-((3-(ethoxycarbonyl)-1-methyl-7-oxo-4,5-dihydro-1H-pyrazolo[3,4-c]pyridin-6(7H)-yl)methyl)cyclopropyl)sulfonyl)propan-2-yl)-2,2-dimethyloxazolidine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-methyl-7-oxo-4,5,6,7-tetrahydro-1H-pyrazolo[3,4-c]pyridine-3-carboxylate (int-10) and 1-(bromomethyl)-1-(cyclopropylsulfonyl)cyclopropane (int-1) was replaced with tert-butyl (R)-4-(2-((1-(bromomethyl)cyclopropyl)sulfonyl)propan-2-yl)-2,2-dimethyloxazolidine-3-carboxylate (int-45). MS (ESI): m/z 583.7 [M+H]⁺.

Step 2: (R)-6-((1-((2-(3-(tert-Butoxycarbonyl)-2,2-dimethyloxazolidin-4-yl)propan-2-yl)sulfonyl)cyclopropyl)methyl)-1-methyl-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with (R)-tert-Butyl 4-(2-((1-((3-(ethoxycarbonyl)-1-methyl-7-oxo-4,5-dihydro-1H-pyrazolo[3,4-c]pyridin-6(7H)-yl)methyl)cyclopropyl)sulfonyl)propan-2-yl)-2,2-dimethyloxazolidine-3-carboxylate. MS (ESI): m/z 555.6 [M+H]⁺.

Step 3: (R)-tert-Butyl 4-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)propan-2-yl)-2,2-dimethyloxazolidine-3-carboxylate was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with (R)-6-((1-((2-(3-(tert-Butoxycarbonyl)-2,2-dimethyloxazolidin-4-yl)propan-2-yl)sulfonyl)cyclopropyl)methyl)-1-methyl-7-oxo-4,5,6,7-tetrahydro-1H-pyrazolo[3,4-c]pyridine-3-carboxylic acid. MS (ESI): m/z 669.6 [M+H]⁺.

Step 4: A solution of (R)-tert-Butyl 4-(2-((1-((3-((4-cyanobenzyl)carbamoyl)-1-methyl-7-oxo-4,5-dihydro-1H-pyrazolo[3,4-c]pyridin-6(7H)-yl)methyl)cyclopropyl)sulfonyl)propan-2-yl)-2,2-dimethyloxazolidine-3-carboxylate (55 mg, 0.082 mmol, 1.0 equiv) in TFA (2.5 mL) was stirred at rt for 5 min before it was concentrated. The residue was dissolved in MeOH (2 mL), filtered and purified by RP-HPLC to give (R)-6-((1-((3-Amino-4-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide (213). ¹H NMR (500 MHz, DMSO-d₆) δ 8.94 (t, J=6.1 Hz, 1H), 7.78 (d, J=7.5 Hz, 2H), 7.47 (d, J=7.9 Hz, 2H), 4.68 (s, 1H), 4.46 (d, J=6.0 Hz, 2H), 4.11 (s, 5H), 3.67 (s, 1H), 3.61 (t, J=6.6 Hz, 2H), 3.18 (s, 1H), 2.97 (t, J=6.5 Hz, 2H), 1.42 (s, 3H), 1.37 (s, 3H), 1.35-1.30 (m, 2H), 1.04-0.96 (m, 2H). MS (ESI): m/z 529.1 [M+H]⁺.

Example 214

(R)-6-((1-((3-Amino-4-hydroxy-2-methylbutan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide hydrochloride (214)

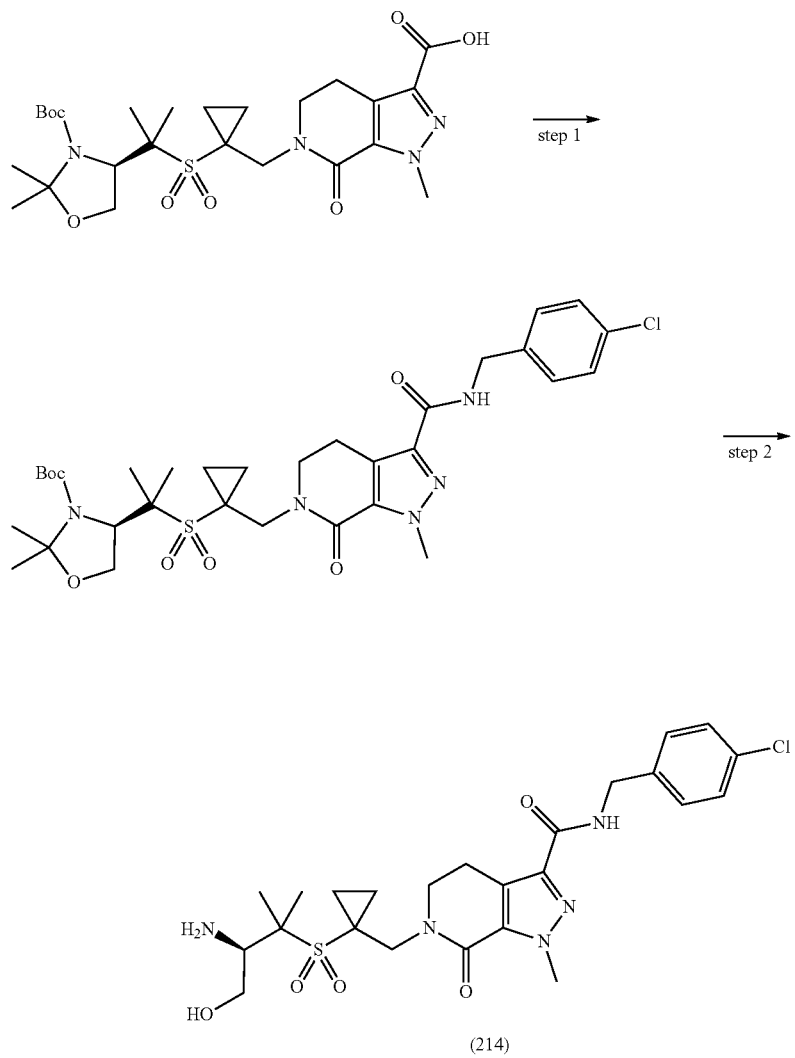

Step 1: tert-butyl (R)-4-(2-((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)propan-2-yl)-2,2-dimethyloxazolidine-3-carboxylate was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with (R)-6-((1-((2-(3-(tert-butoxycarbonyl)-2,2-dimethyloxazolidin-4-yl)propan-2-yl)sulfonyl)cyclopropyl)methyl)-1-methyl-7-oxo-4,5,6,7-tetrahydro-1H-pyrazolo[3,4-c]pyridine-3-carboxylic acid and 4-(aminomethyl)benzonitrile hydrochloride was replaced with (4-chlorophenyl)methanamine. MS (ESI): m/z 678.6 [M+H]$^+$.

Step 2: A suspension of (tert-butyl (R)-4-(2-((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)propan-2-yl)-2,2-dimethyloxazolidine-3-carboxylate (55 mg, 0.081 mmol, 1.0 equiv) in MeOH (1.5 mL) was cooled to 0° C. before it was treated with AcCl (150 μL, 2.110 mmol, 26.0 equiv) dropwise over a few minutes with efficient stirring. The resulting suspension was stirred at rt for 1 h before it was concentrated. The residue was suspended in EtOAc (2 mL), then the solid product was collected by filtration, rinsed with EtOAc (2×2 mL) and dried to give (R)-6-((1-((3-Amino-4-hydroxy-2-methylbutan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide hydrochloride (214). $^1$H NMR (500 MHz, DMSO-d$_6$) δ 8.85 (t, J=6.2 Hz, 1H), 8.04 (s, 3H), 7.37 (d, J=7.7 Hz, 2H), 7.31 (d, J=8.1 Hz, 2H), 5.52 (s, 1H), 4.37 (d, J=5.9 Hz, 2H), 4.10 (s, 3H), 4.09 (s, 2H), 3.88 (d, J=10.2 Hz, 1H), 3.70-3.58 (m, 3H), 2.98 (t, J=6.5 Hz, 2H), 1.58 (s, 3H), 1.54 (s, 3H), 1.40 (s, 2H), 1.12 (s, 2H). MS (ESI): m/z 538.5 [M+H]$^+$.

Example 215

((1-((3-((4-Chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-D-valine (215)

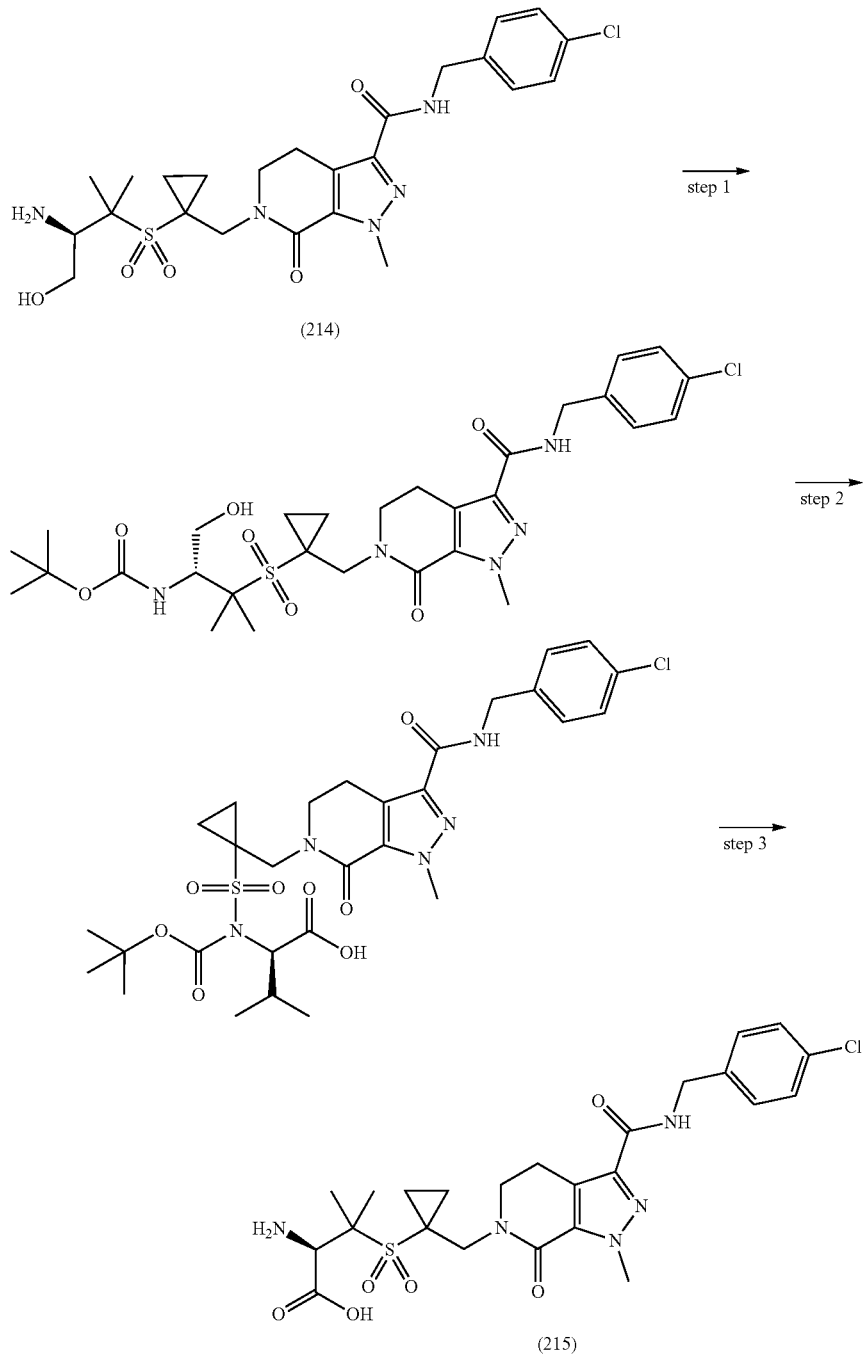

Step 1: A solution of (R)-6-(((1-((3-amino-4-hydroxy-2-methylbutan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide (214) (42 mg, 0.073 mmol, 1.0 equiv) and DIEA (0.128 mL, 0.731 mmol, 10.0 equiv) in $CH_2Cl_2$ (1.5 mL) was treated with $Boc_2O$ (0.026 mL, 0.110 mmol, 1.5 equiv) was stirred at rt overnight, then it was dry loaded onto $SiO_2$ and purified by column chromatography ($SiO_2$, 0-100% EtOAc/heptane) to give tert-butyl (R)-(3-(((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-1-hydroxy-3-methylbutan-2-yl)carbamate. $^1$H NMR (500 MHz, $CDCl_3$) δ 7.34-7.28 (m, 4H), 7.15 (d, J=11.9 Hz, 1H), 5.59 (s, 1H), 4.56 (d, J=6.0 Hz, 2H), 4.22

(d, J=14.3 Hz, 1H), 4.13 (s, 3H), 4.10 (d, J=14.2 Hz, 1H), 3.99-3.87 (m, 3H), 3.68 (h, J=6.2, 5.8 Hz, 2H), 3.18 (q, J=7.6, 7.2 Hz, 2H), 2.55 (s, 1H), 1.64 (d, J=3.7 Hz, 6H), 1.45 (s, 9H), 1.34-1.27 (m, 2H), 1.13-1.02 (m, 2H). MS (ESI): m/z 538.5 [M+H]$^+$.

Step 2: To a solution of tert-butyl (R)-(3-((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-1-hydroxy-3-methylbutan-2-yl)carbamate (38 mg, 0.0595 mmol, 1.0 equiv), NMO (86 mg, 0.731 mmol, 12.3 equiv) and water (0.013 mL, 0.731 mmol, 12.3 equiv) in MeCN (1 mL) was added TPAP (2.57 mg, 7.31 μmol, 0.123 equiv). The resulting solution was stirred at rt for 1 h before it was quenched with i-PrOH (0.1 mL), diluted with water (5 mL) and acidified with saturated KHSO$_4$. The mixture was extracted with EtOAc (5×3 mL), then the combined organic extracts were washed twice with brine, dried with MgSO$_4$, filtered and concentrated. The residue was dry loaded onto SiO$_2$ and purified by column chromatography [SiO$_2$, 0-100% (3:1 EtOAc-EtOH+1% AcOH)/heptane] to give (tert-butoxycarbonyl)((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-D-valine. MS (ESI): m/z 652.6 [M+H]$^+$.

Step 3: A solution of (tert-butoxycarbonyl)((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-D-valine (16 mg, 0.0245 mmol, 1.0 equiv) in TFA (1 mL) was stirred at rt for 30 min before it was concentrated. The residue was dissolved in 1:1 MeOH-DMSO (1.6 mL), filtered and purified by RP-HPLC to give ((1-((3-((4-Chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-D-valine (215) trifluoroacetate. $^1$H NMR (500 MHz, DMSO-d$_6$) δ 8.85 (t, J=6.3 Hz, 1H), 8.32 (s, 2H), 7.40-7.34 (m, 2H), 7.31 (d, J=8.5 Hz, 2H), 4.37 (d, J=6.3 Hz, 2H), 4.25 (s, 1H), 4.14 (d, J=14.7 Hz, 1H), 4.10 (s, 3H), 4.04 (d, J=14.7 Hz, 1H), 3.62 (t, J=6.8 Hz, 2H), 2.99 (t, J=6.8 Hz, 2H), 1.64 (s, 3H), 1.62 (s, 3H), 1.43 (q, J=8.3, 6.5 Hz, 2H), 1.16 (td, J=11.0, 6.3 Hz, 2H). MS (ESI): m/z 552.1 [M+H]$^+$.

Example 216

N-(4-Cyanobenzyl)-6-((1-(cyclopropylsulfonyl)cyclopropyl)methyl)-1-(2-hydroxyethyl)-7-oxo-4,5,6,7-tetrahydro-1H-pyrazolo[3,4-c]pyridine-3-carboxamide (216)

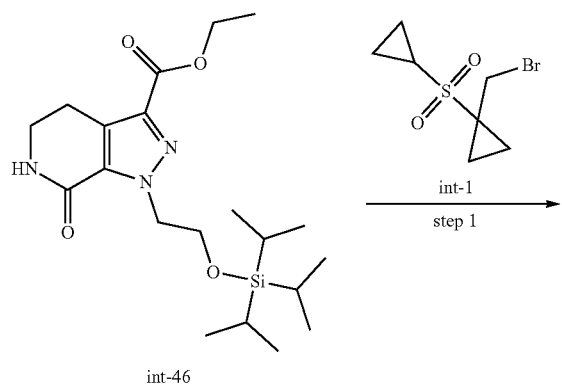

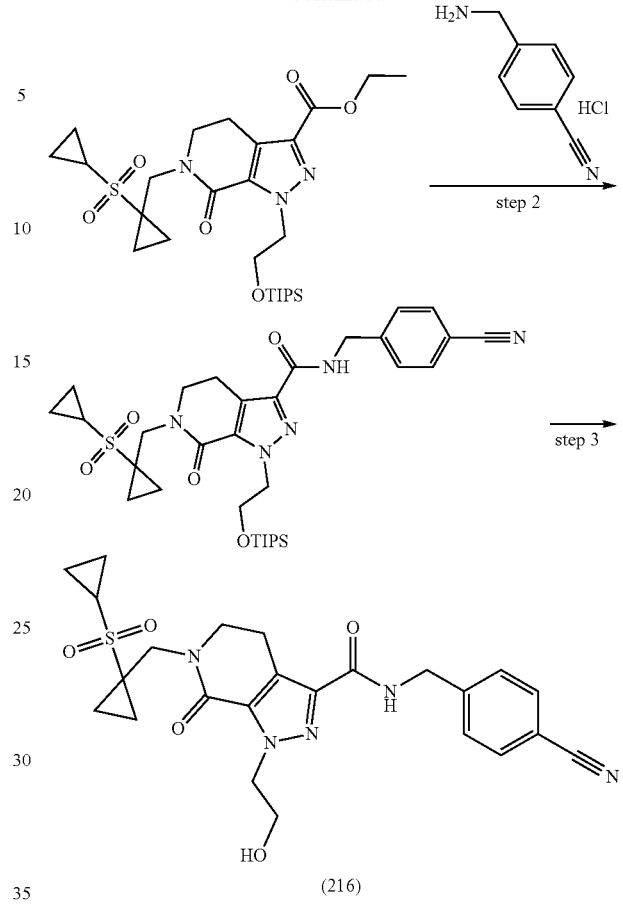

Step 1: Ethyl 6-((1-(cyclopropylsulfonyl)cyclopropyl)methyl)-7-oxo-1-(2-((triisopropylsilyl)oxy)ethyl)-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 7-oxo-1-(2-((triisopropylsilyl)oxy)ethyl)-4,5,6,7-tetrahydro-1H-pyrazolo[3,4-c]pyridine-3-carboxylate (int-46). $^1$H NMR (400 MHz, CDCl$_3$) δ 4.86-4.76 (m, 2H), 4.42 (m, 2H), 4.10-4.02 (m, 4H), 3.76-3.70 (m, 2H), 3.13 (m, 2H), 2.72-2.60 (m, 1H), 1.53-1.49 (m, 2H), 1.40 (m, 3H), 1.27-1.24 (m, 2H), 1.10-1.06 (m, 4H), 0.99-0.90 (m, 21H). MS (ESI): m/z 568.1 [M+H]$^+$.

Step 2: N-(4-Cyanobenzyl)-6-((1-(cyclopropylsulfonyl)cyclopropyl)methyl)-7-oxo-1-(2-((triisopropylsilyl)oxy)ethyl)-4,5,6,7-tetrahydro-1H-pyrazolo[3,4-c]pyridine-3-carboxamide was obtained using the method described in Example 1, except ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6) was replaced with ethyl 6-((1-(cyclopropylsulfonyl)cyclopropyl)methyl)-7-oxo-1-(2-((triisopropylsilyl)oxy)ethyl)-4,5,6,7-tetrahydro-1H-pyrazolo[3,4-c]pyridine-3-carboxylate. $^1$H NMR (400 MHz, CDCl$_3$) δ 7.64 (d, J=8.4 Hz, 2H), 7.45 (d, J=8.4 Hz, 2H), 7.31 (m, 1H), 4.72 (m, 2H), 4.67 (d, J=6.4 Hz, 2H), 4.07 (s, 2H), 4.06 (m, 2H), 3.74 (m, 2H), 3.21 (m, 2H), 2.70 (m, 1H), 1.52 (m, 2H), 1.25 (m, 2H), 1.06 (m, 21H). MS (ESI): m/z 654.3 [M+H]$^+$.

Step 3: To a solution of N-(4-cyanobenzyl)-6-((1-(cyclopropylsulfonyl)cyclopropyl)methyl)-7-oxo-1-(2-((triisopropylsilyl)oxy)ethyl)-4,5,6,7-tetrahydro-1H-pyrazolo[3,4-c]pyridine-3-carboxamide (140 mg, 0.21 mmol, 1.0 equiv) in THF (2 mL) was added TBAF (1.0 M in THF, 1.1 mL, 1.1 mmol, 5.0 equiv) at 25° C. The reaction mixture was stirred at 25° C. for 2 h before it was diluted with EtOAc (10 mL) and concentrated in vacuo. The residue was purified by RP-HPLC to give N-(4-cyanobenzyl)-6-((1-(cyclopropylsulfonyl)cyclopropyl)methyl)-1-(2-hydroxyethyl)-7-oxo-4,5,6,7-tetrahydro-1H-pyrazolo[3,4-c]pyridine-3-carboxamide (216). ¹H NMR (400 MHz, CDCl₃) δ 7.65 (d, J=8.0 Hz, 2H), 7.46 (d, J=8.4 Hz, 2H), 7.32 (m, 1H), 4.73 (m, 2H), 4.66 (d, J=6.4 Hz, 2H), 4.08 (s, 2H), 4.02 (m, 2H), 3.78 (m, 2H), 3.31 (m, 1H), 3.23 (m, 2H), 2.82 (m, 1H), 1.54 (m, 2H), 1.25 (m, 2H), 1.10 (m, 2H), 1.05 (m, 2H). MS (ESI): m/z 498.1 [M+H]⁺.

Compounds in the Table 15 below were prepared following procedures analogous to those described for Compound (216) in Example 216.

TABLE 15

| Example/ Compound Number | Compound Structure and Name | Physical Data MS (m/z), ¹H NMR |
|---|---|---|
| 217 | 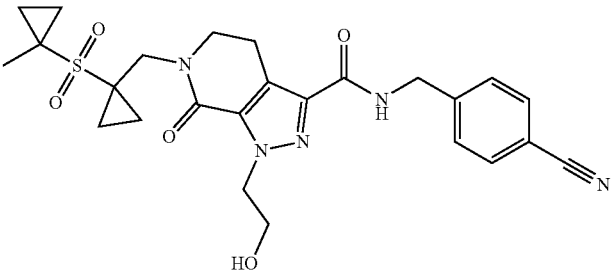<br>N-(4-Cyanobenzyl)-1-(2-hydroxyethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide | MS (ESI): m/z 512.0 [M + H]⁺. ¹H NMR (400 MHz, MeOH-d₄) δ 7.71 (d, J = 8.4 Hz, 2H), 7.54 (d, J = 8.8 Hz, 2H), 4.73 (m, 2H), 4.62 (s, 3H), 4.14 (s, 2H), 3.96 (m, 2H), 3.73-3.72 (m, 2H), 3.13 (t, J = 6.8 Hz, 2H), 1.62 (s, 3H), 1.44-1.42 (m, 2H), 1.43-1.40 (m, 2H), 1.15-1.13 (m, 2H), 0.95-0.93 (m, 2H). |
| 218 | 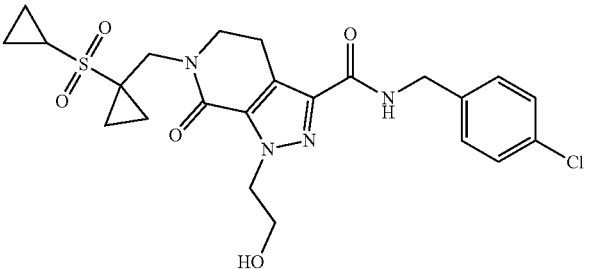<br>N-(4-Chlorobenzyl)-6-((1-(cyclopropylsulfonyl)cyclopropyl)methyl)-1-(2-hydroxyethyl)-7-oxo-4,5,6,7-tetrahydro-1H-pyrazolo[3,4-c]pyridine-3-carboxamide | MS (ESI): m/z 507.0 [M + H]⁺. ¹H NMR (400 MHz, DMSO-d₆) δ 8.85-8.82 (m, 1H), 7.38-7.30 (m, 4H), 4.87-4.84 (m, 1H), 4.58-4.55 (m, 2H), 4.38 (d, J = 6.4 Hz, 2H), 4.03 (s, 2H), 3.77-3.75 (m, 2H), 3.68-3.64 (m, 2H), 3.01-2.94 (m, 3H), 1.27-1.25 (m, 2H), 1.09-1.08 (m, 2H), 1.02-1.00 (m, 4H). |
| 219 | 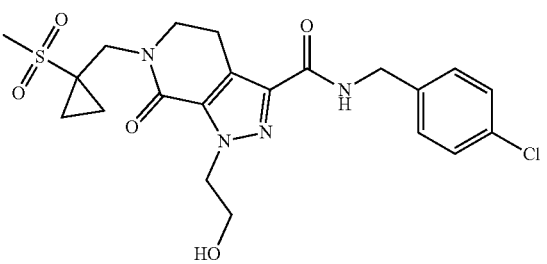<br>N-(4-Chlorobenzyl)-1-(2-hydroxyethyl)-6-((1-(methylsulfonyl)cyclopropyl)methyl)-7-oxo-4,5,6,7-tetrahydro-1H-pyrazolo[3,4-c]pyridine-3-carboxamide | MS (ESI): m/z 481.1 [M + H]⁺. ¹H NMR (400 MHz, DMSO-d₆) δ 8.85-8.82 (m, 1H), 7.38-7.30 (m, 4H), 4.87-4.85 (m, 1H), 4.57-4.54 (m, 2H), 4.38 (d, J = 6.0 Hz, 2H), 3.97 (s, 2H), 3.78-3.75 (m, 2H), 3.67-3.63 (m, 2H), 3.11 (s, 3H), 3.00-2.97 (m, 2H), 1.29-1.26 (m, 2H), 1.10-1.07 (m, 2H). |

TABLE 15-continued

| Example/ Compound Number | Compound Structure and Name | Physical Data MS (m/z), ¹H NMR |
|---|---|---|
| 220 | N-(4-Cyanobenzyl)-6-((1-((1-hydroxy-2-methylpropan-2-yl)sulfonyl)cyclopropyl)methyl)-1-(2-hydroxyethyl)-7-oxo-4,5,6,7-tetrahydro-1H-pyrazolo[3,4-c]pyridine-3-carboxamide | MS (ESI): m/z 530.1 [M + H]⁺. ¹H NMR (400 MHz, CDCl₃) δ 7.65 (m, 2H), 7.46 (m, 2H), 7.30 (m, 1H), 4.72 (m, 2H), 4.66 (d, J = 6.4 Hz, 2H), 4.17 (s, 2H), 4.01 (m, 2H), 3.85 (s, 2H), 3.75 (m, 2H), 3.22 (m, 2H), 1.61 (m, 2H), 1.50 (s, 6H), 1.08 (m, 2H). |
| 221 | N-(4-chlorobenzyl)-6-((1-((1-hydroxy-2-methylpropan-2-yl)sulfonyl)cyclopropyl)methyl)-1-(2-hydroxyethyl)-7-oxo-4,5,6,7-tetrahydro-1H-pyrazolo[3,4-c]pyridine-3-carboxamide | MS (ESI): m/z 539.3 [M + H]⁺. ¹H NMR (400 MHz, CDCl₃) δ 7.33 (m, 4H), 7.17 (m, 1H), 4.70 (m, 2H), 4.57 (d, J = 6.4 Hz, 2H), 3.99 (m, 2H), 3.85 (s, 2H), 3.74 (m, 2H), 3.23 (m, 2H), 1.61 (m, 2H), 1.50 (s, 6H), 1.12 (m, 2H). |

Example 222

N-(4-Chlorobenzyl)-1-(2-(2-hydroxyethoxy)ethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide (222)

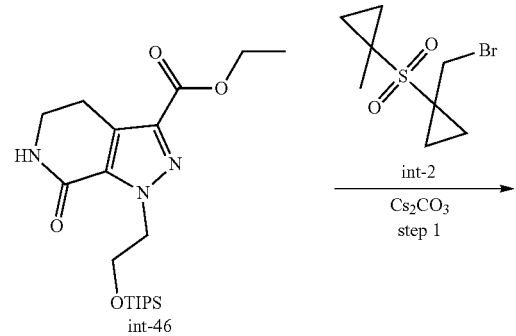

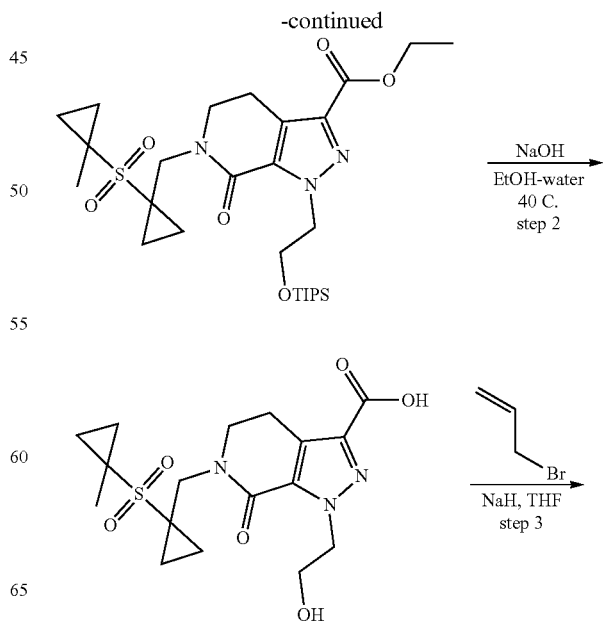

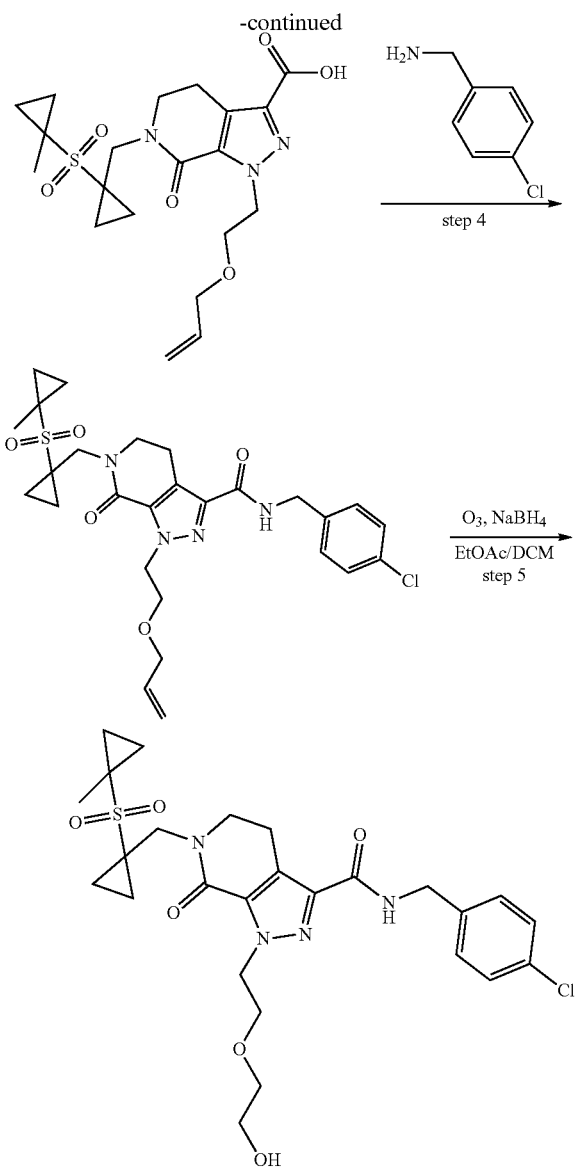

Step 1: Ethyl 6-((1-((1-methylcyclopropyl)sulfonyl)cyclopropyl)methyl)-7-oxo-1-(2-((triisopropylsilyl)oxy)ethyl)-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 7-oxo-1-(2-((triisopropylsilyl)oxy)ethyl)-4,5,6,7-tetrahydro-1H-pyrazolo[3,4-c]pyridine-3-carboxylate (int-46). and 1-(bromomethyl)-1-(cyclopropylsulfonyl)cyclopropane (int-1) was replaced with 1-(bromomethyl)-1-((1-methylcyclopropyl)sulfonyl)cyclopropane (int-2). TLC R$_f$=0.6 (50% EtOAc/petroleum ether). MS (ESI): m/z 582.4 [M+H]$^+$.

Step 2: 1-(2-Hydroxyethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylic acid was obtained using the method for the synthesis of intermediate (int-14), except the reaction was at 40° C. and except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-((1-methylcyclopropyl)sulfonyl)cyclopropyl)methyl)-7-oxo-1-(2-((triisopropylsilyl)oxy)ethyl)-4,5,6,7-tetrahydro-1H-pyrazolo[3,4-c]pyridine-3-carboxylate. TLC R$_f$=0.4 (50% EtOAc/petroleum ether). $^1$H NMR (400 MHz, DMSO-d$_6$) δ 4.84 (br s, 1H), 4.57 (m, 2H), 4.04 (s, 2H), 3.74 (m, 2H), 3.63 (m, 2H), 2.97 (m, 2H), 1.54 (s, 3H), 1.30-1.22 (m, 4H), 1.07-1.02 (m, 2H), 0.95-0.90 (m, 2H).

Step 3: 1-(2-(Allyloxy)ethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylic acid was obtained using the method described in step 1 of Example 87, except ethyl 6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxylate was replaced with 1-(2-Hydroxyethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylic acid. MS (ESI): m/z 438.3 [M+H]$^+$.

Step 4: 1-(2-(Allyloxy)ethyl)-N-(4-chlorobenzyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 1-(2-(Allyloxy)ethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylic acid and 4-(aminomethyl)benzonitrile hydrochloride was replaced with (4-chlorophenyl)methanamine. MS (ESI): m/z 561.4 [M+H]$^+$.

Step 5: N-(4-Chlorobenzyl)-1-(2-(2-hydroxyethoxy)ethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide (222) was obtained using the method described in step 2 in the synthesis of intermediate (int-29), except ethyl 1-(4-methoxybenzyl)-6-((1-((2-methylbut-3-en-2-yl)sulfonyl)cyclopropyl)methyl)-7-oxo-4,5,6,7-tetrahydro-1H-pyrazolo[3,4-c]pyridine-3-carboxylate was replaced with 1-(2-(Allyloxy)ethyl)-N-(4-chlorobenzyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide. $^1$H NMR (400 MHz, CDCl$_3$) δ 7.37-7.27 (m, 5H), 4.75 (t, J=5.4 Hz, 2H), 4.56 (d, J=6.2 Hz, 2H), 4.12 (s, 2H), 3.89 (t, J=5.2 Hz, 2H), 3.70 (t, J=6.8 Hz, 2H), 3.67-3.61 (m, 2H), 3.61-3.55 (m, 2H), 3.19 (t, J=6.8 Hz, 2H), 1.61 (s, 3H), 1.55-1.50 (m, 2H), 1.50-1.44 (m, 2H), 1.05-0.99 (m, 2H), 0.91-0.83 (m, 2H). MS (ESI): m/z 565.1 [M+H]$^+$.

Example 223

1-(2-(2-aminoethoxy)ethyl)-N-(4-chlorobenzyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide (223)

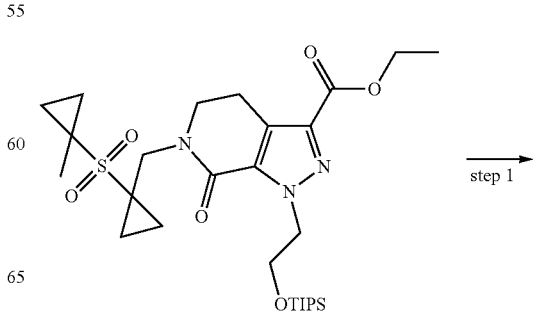

367 -continued

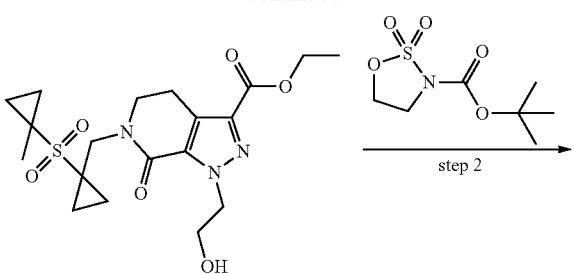

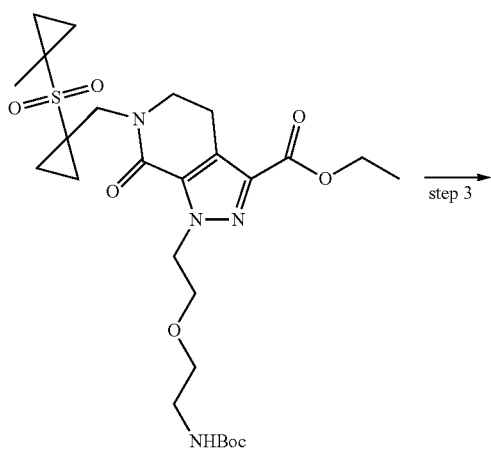

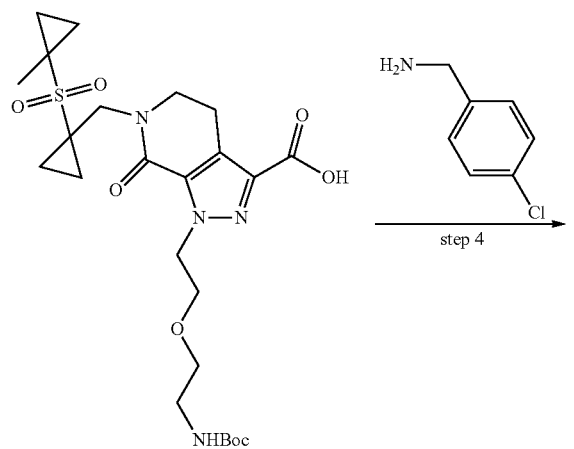

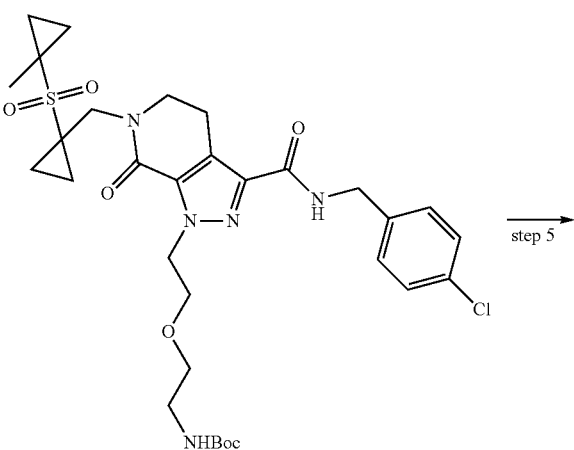

368 -continued

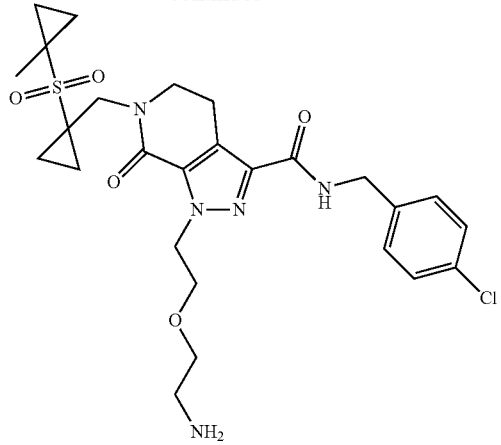

(223)

Step 1: Ethyl 1-(2-hydroxyethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylate was obtained using the method described in step 5 of Example 105, except 4-((4-(1-methyl-6-((1-((2-methyl-1-((triisopropylsilyl)oxy)propan-2-yl)sulfonyl)cyclopropyl)methyl)-7-oxo-4,5,6,7-tetrahydro-1H-pyrazolo[3,4-c]pyridin-3-yl)-1H-1,2,3-triazol-1-yl)methyl)benzonitrile was replaced with ethyl 6-((1-((1-methylcyclopropyl)sulfonyl)cyclopropyl)methyl)-7-oxo-1-(2-((triisopropylsilyl)oxy)ethyl)-4,5,6,7-tetrahydro-1H-pyrazolo[3,4-c]pyridine-3-carboxylate. TLC R$_f$=0.3 (50% EtOAc/petroleum ether). MS (ESI): m/z 426.3 [M+H]$^+$.

Step 2: Ethyl 1-(2-(2-((tert-butoxycarbonyl)amino)ethoxy)ethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylate was obtained using the procedure described in the synthesis of (int-11), except ethyl 1-methyl-7-oxo-4,5,6,7-tetrahydro-1H-pyrazolo[3,4-c]pyridine-3-carboxylate (int-10) was replaced with ethyl 1-(2-hydroxyethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylate. and 1-(bromomethyl)-1-(cyclopropylsulfonyl)cyclopropane (int-1) was replaced with tert-butyl 1,2,3-oxathiazolidine-3-carboxylate 2,2-dioxide. MS (ESI): m/z 469.4 [M-Boc+H]$^+$.

Step 3: 1-(2-(2-((tert-Butoxycarbonyl)amino)ethoxy)ethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 1-(2-(2-((tert-butoxycarbonyl)amino)ethoxy)ethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylate. MS (ESI): m/z 441.4 [M-Boc+H]$^+$.

Step 4: tert-Butyl (2-(2-(3-((4-chlorobenzyl)carbamoyl)-6-((1-((1-methylcyclopropyl)sulfonyl)cyclopropyl)methyl)-7-oxo-4,5,6,7-tetrahydro-1H-pyrazolo[3,4-c]pyridin-1-yl)ethoxy)ethyl)carbamate was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 1-(2-(2-((tert-Butoxycarbonyl)amino)ethoxy)ethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylic acid and 4-(aminomethyl)benzonitrile hydrochloride was replaced with (4-chlorophenyl)methanamine. MS (ESI): m/z 564.1 [M-Boc+H]⁺.

Step 5: 1-(2-(2-Aminoethoxy)ethyl)-N-(4-chlorobenzyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide (223) was obtained using the method described in step 3 of Example 215, except (tert-butoxycarbonyl)((1-((3-((4-chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-D-valine was replaced with tert-Butyl (2-(2-(3-((4-chlorobenzyl)carbamoyl)-6-((1-((1-methylcyclopropyl)sulfonyl)cyclopropyl)methyl)-7-oxo-4,5,6,7-tetrahydro-1H-pyrazolo[3,4-c]pyridin-1-yl)ethoxy)ethyl)carbamate. ¹H NMR (400 MHz, CDCl₃) δ 7.41 (brt, J=6.2 Hz, 1H), 7.36-7.22 (m, 4H), 4.75 (t, J=5.4 Hz, 2H), 4.58 (d, J=6.2 Hz, 2H), 4.14 (s, 2H), 3.86 (t, J=5.4 Hz, 2H), 3.71 (t, J=6.8 Hz, 2H), 3.47 (t, J=5.4 Hz, 2H), 3.20 (t, J=6.8 Hz, 2H), 2.80 (t, J=5.2 Hz, 2H), 1.63 (s, 3H), 1.58-1.45 (m, 4H), 1.08-1.00 (m, 2H), 0.92-0.85 (m, 2H). MS (ESI): m/z 564.2 [M+H]⁺.

Example 224

N-(4-Cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide (224)

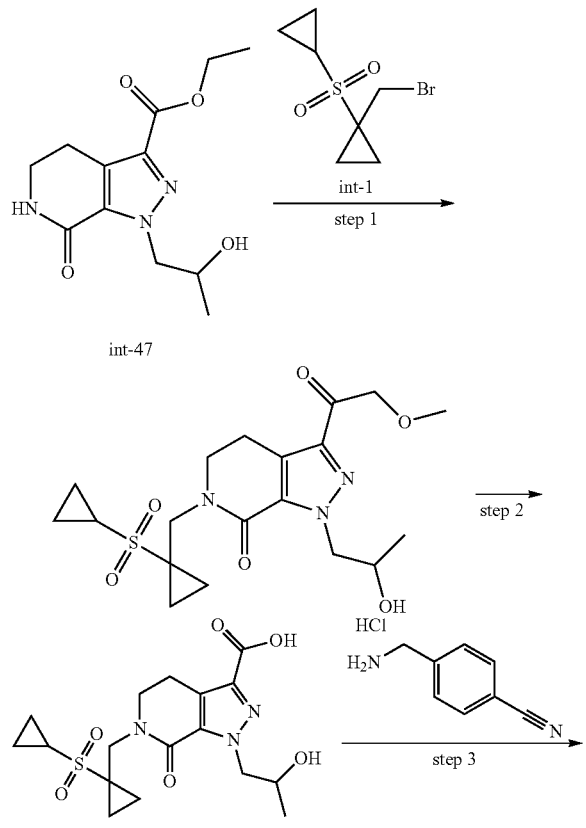

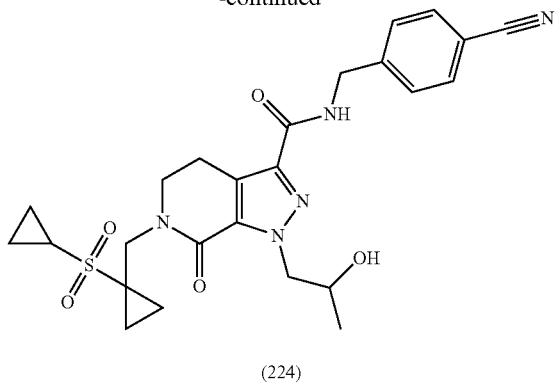

(224)

Step 1: Ethyl 6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-(2-hydroxypropyl)-7-oxo-4,5,6,7-tetrahydro-1H-pyrazolo[3,4-c]pyridine-3-carboxylate (int-47). ¹H NMR (400 MHz, CDCl₃) δ 4.70-4.61 (m, 2H), 4.44-4.39 (m, 2H), 4.26-4.20 (m, 1H), 4.12-4.00 (m, 2H), 3.80-3.77 (m, 2H), 3.17-3.14 (m, 2H), 2.72-2.70 (m, 1H), 1.54-1.51 (m, 2H), 1.42-1.38 (m, 3H), 1.27-1.24 (m, 5H), 1.06-1.03 (m, 4H). MS (ESI): m/z 426.1 [M+H]⁺.

Step 2: 6-((1-(Cyclopropylsulfonyl)cyclopropyl)methyl)-1-(2-hydroxypropyl)-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxylate. MS (ESI): m/z 398.1 [M+H]⁺.

Step 3: N-(4-Cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide (224) was obtained using the method described in step 1 of Example 26, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-(Cyclopropylsulfonyl)cyclopropyl)methyl)-1-(2-hydroxypropyl)-7-oxo-4,5,6,7-tetrahydro-1H-pyrazolo[3,4-c]pyridine-3-carboxylic acid and hydrazine was replaced with 4-(aminomethyl)benzonitrile hydrochloride. MS (ESI): m/z 512.2 [M+H]⁺.

Example 225 and Example 226

(R)- or(S)—N-(4-Cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide (225)

and (R)- or(S)—N-(4-Cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide (226)

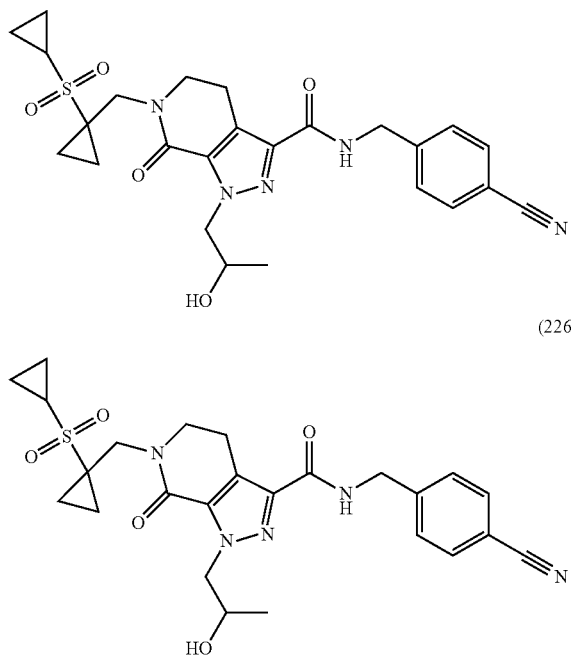

(R)- or (S)—N-(4-Cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide (225) and (R)- or (S)—N-(4-Cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide (226) were obtained by chiral SFC separation of N-(4-cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide.

Unless otherwise indicated, examples indicate relative stereochemistry. SFC: CHIRALPAK AD-3, 5-40% i-PrOH (0.05% Et$_2$NH), 3 mL/min (R)- or (S)—N-(4-cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide (225). $^1$H NMR (400 MHz, CDCl$_3$) δ 7.64 (d, J=8.4 Hz, 2H), 7.46 (d, J=8.0 Hz, 2H), 4.68-4.65 (m, 2H), 4.63-4.62 (m, 1H), 4.53-4.51 (m, 1H), 4.20 (s, 1H), 4.15-4.01 (m, 2H), 3.79-3.76 (m, 2H), 3.35-3.34 (m, 1H), 3.25-3.18 (m, 2H), 2.81-2.75 (m, 1H), 1.54-1.51 (m, 2H), 1.27-1.23 (m, 5H), 1.13-1.04 (m, 2H), 1.04-1.00 (m, 2H). MS (ESI): m/z 512.3 [M+H]$^+$. SFC: Rt=1.965 min, 100% ee (R)- or (S)—N-(4-cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide (226). $^1$H NMR (400 MHz, CDCl$_3$) δ 7.64 (d, J=8.4 Hz, 2H), 7.45 (d, J=8.0 Hz, 2H), 7.30-7.29 (m, 1H), 4.67-4.65 (m, 2H), 4.63-4.62 (m, 1H), 4.53-4.51 (m, 1H), 4.20 (s, 1H), 4.15-4.01 (m, 2H), 3.79-3.76 (m, 2H), 3.35-3.34 (m, 1H), 3.25-3.18 (m, 2H), 2.81-2.75 (m, 1H), 1.54-1.51 (m, 2H), 1.27-1.23 (m, 5H), 1.13-1.04 (m, 2H), 1.04-1.00 (m, 2H). MS (ESI): m/z 512.3 [M+H]$^+$. SFC: Rt=2.140 min, 98% ee

Example 227

N-(4-cyanobenzyl)-6-((1-(cyclopropylsulfonyl)cyclopropyl)methyl)-7-oxo-1-(2-oxobutyl)-4,5,6,7-tetrahydro-1H-pyrazolo[3,4-c]pyridine-3-carboxamide (227)

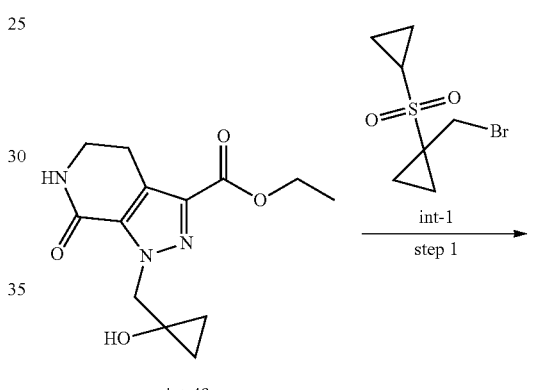

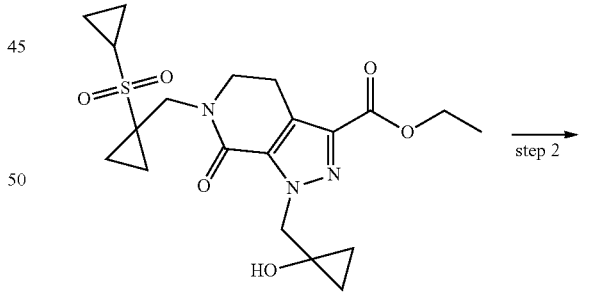

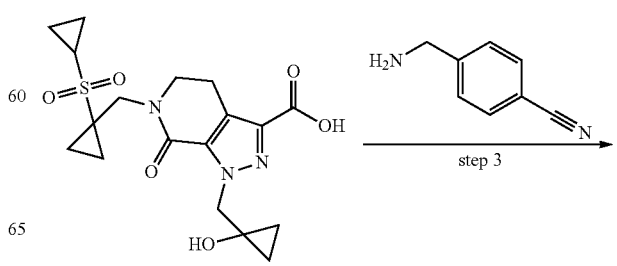

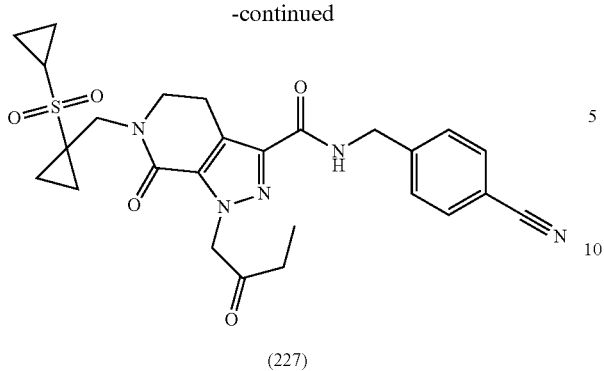

(227)

Step 1: Ethyl 6-((1-(cyclopropylsulfonyl)cyclopropyl)methyl)-1-((1-hydroxycyclopropyl)methyl)-7-oxo-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced ethyl 1-((1-hydroxycyclopropyl)methyl)-7-oxo-4,5,6,7-tetrahydro-1H-pyrazolo[3,4-c]pyridine-3-carboxylate (int-49). $^1$H NMR (400 MHz, CDCl$_3$) δ 4.77 (s, 2H), 4.41 (m, 2H), 4.08 (s, 2H), 3.88 (s, 2H), 3.83-3.75 (m, 2H), 3.16 (m, 2H), 2.74 (tt, J=4.8, 8.0 Hz, 1H), 2.65 (m, 1H), 1.76-1.70 (m, 1H), 1.56-1.49 (m, 2H), 1.40 (m, 3H), 1.31-1.18 (m, 6H), 1.16-1.01 (m, 7H), 0.87-0.72 (m, 4H). MS (ESI): m/z 438.0 [M+H]$^+$.

Step 2: 6-((1-(Cyclopropylsulfonyl)cyclopropyl)methyl)-1-((1-hydroxycyclopropyl)methyl)-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-(cyclopropylsulfonyl)cyclopropyl)methyl)-1-((1-hydroxycyclopropyl)methyl)-7-oxo-4,5,6,7-tetrahydro-1H-pyrazolo[3,4-c]pyridine-3-carboxylate. MS (ESI): m/z 410.2 [M+H]$^+$.

Step 3: N-(4-Cyanobenzyl)-6-((1-(cyclopropylsulfonyl)cyclopropyl)methyl)-7-oxo-1-(2-oxobutyl)-4,5,6,7-tetrahydro-1H-pyrazolo[3,4-c]pyridine-3-carboxamide (227) was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-(cyclopropylsulfonyl)cyclopropyl)methyl)-1-((1-hydroxycyclopropyl)methyl)-7-oxo-4,5,6,7-tetrahydro-1H-pyrazolo[3,4-c]pyridine-3-carboxylic acid. H NMR (400 MHz, CDCl$_3$) δ 7.64 (d, J=8.0 Hz, 2H), 7.45 (d, J=8.0 Hz, 2H), 7.24 (m, 1H), 5.34 (s, 2H), 4.65 (d, J=6.0 Hz, 2H), 4.03 (s, 2H), 3.79 (t, J=6.8 Hz, 2H), 3.24 (t, J=6.8 Hz, 2H), 2.73-2.62 (m, 1H), 2.52 (q, J=7.2 Hz, 2H), 1.53-1.47 (m, 2H), 1.27-1.18 (m, 2H), 1.12 (t, J=7.2 Hz, 3H), 1.09-0.99 (m, 4H). MS (ESI): m/z 524.3 [M+H]$^+$.

Example 228

N-(4-Cyanobenzyl)-6-((1-(cyclopropylsulfonyl)cyclopropyl)methyl)-1-((1-hydroxycyclopropyl)methyl)-7-oxo-4,5,6,7-tetrahydro-1H-pyrazolo[3,4-c]pyridine-3-carboxamide (228)

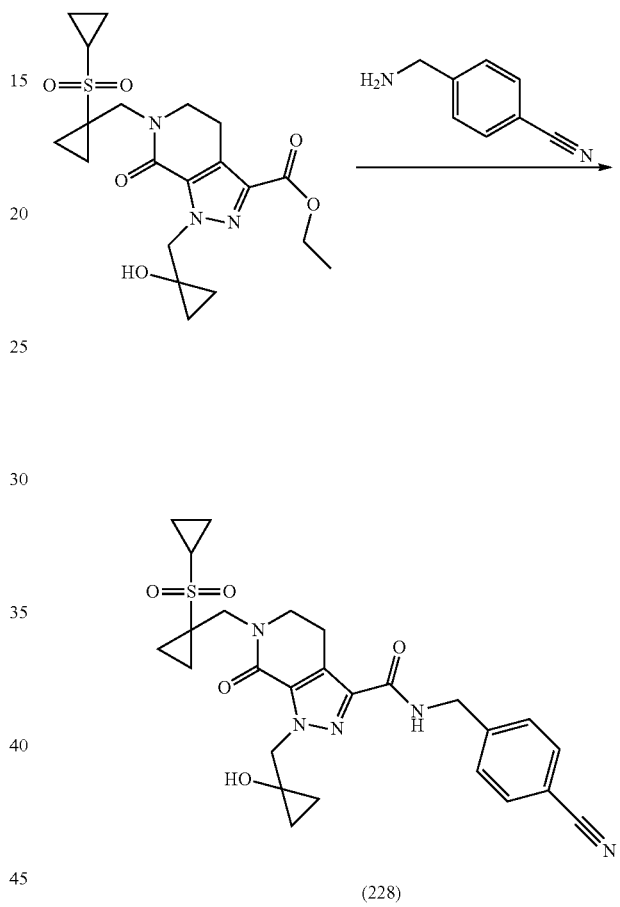

(228)

N-(4-Cyanobenzyl)-6-((1-(cyclopropylsulfonyl)cyclopropyl)methyl)-1-((1-hydroxycyclopropyl)methyl)-7-oxo-4,5,6,7-tetrahydro-1H-pyrazolo[3,4-c]pyridine-3-carboxamide (228) was obtained using the method described in Example 1, except ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6) was replaced with ethyl 6-((1-(cyclopropylsulfonyl)cyclopropyl)methyl)-1-((1-hydroxycyclopropyl)methyl)-7-oxo-4,5,6,7-tetrahydro-1H-pyrazolo[3,4-c]pyridine-3-carboxylate. $^1$H NMR (400 MHz, CDCl$_3$) δ 7.65 (d, J=8.2 Hz, 2H), 7.46 (d, J=8.2 Hz, 2H), 7.27 (m, 1H), 4.70 (s, 2H), 4.67 (m, 2H), 4.09 (s, 2H), 3.79 (m, 2H), 3.24 (m, 2H), 2.85-2.75 (m, 1H), 1.55-1.50 (m, 2H), 1.29-1.20 (m, 2H), 1.12-1.06 (m, 2H), 1.06-1.01 (m, 2H), 0.88-0.81 (m, 2H), 0.81-0.74 (m, 2H). MS (ESI): m/z 524.2 [M+H]$^+$.

Example 229

N-(4-Chlorobenzyl)-6-((1-(cyclopropylsulfonyl)cyclopropyl)methyl)-1-(2-hydroxy-2-methylpropyl)-7-oxo-4,5,6,7-tetrahydro-1H-pyrazolo[3,4-c]pyridine-3-carboxamide (229)

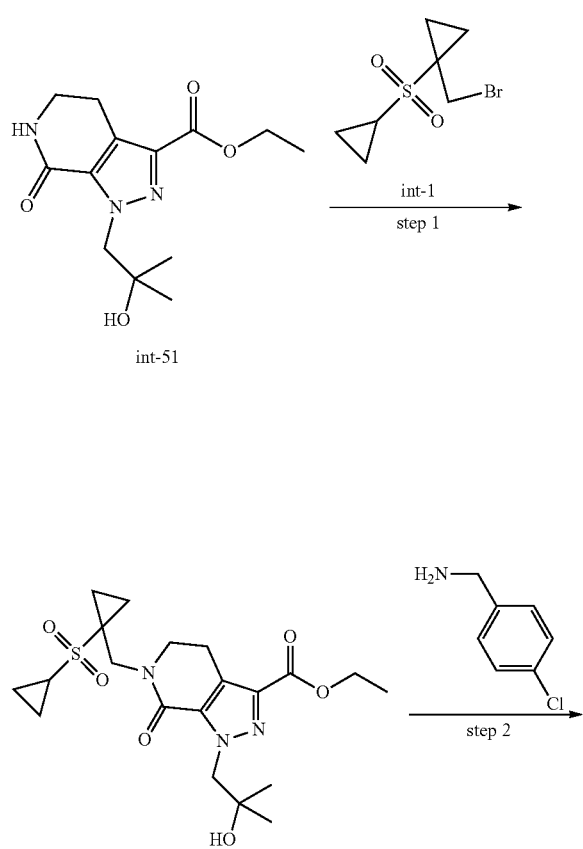

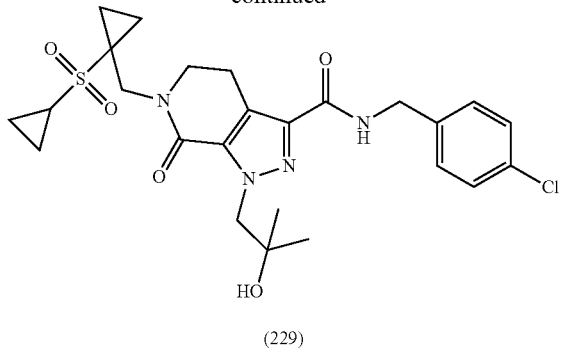

Step 1: Ethyl 6-((1-(cyclopropylsulfonyl)cyclopropyl)methyl)-1-(2-hydroxy-2-methylpropyl)-7-oxo-4,5,6,7-tetrahydro-1H-pyrazolo[3,4-c]pyridine-3-carboxylate was obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-(2-hydroxy-2-methylpropyl)-7-oxo-4,5,6,7-tetrahydro-1H-pyrazolo[3,4-c]pyridine-3-carboxylate (int-51). MS (ESI): m/z 440.1 [M+H]$^+$.

Step 2: N-(4-Chlorobenzyl)-6-((1-(cyclopropylsulfonyl)cyclopropyl)methyl)-1-(2-hydroxy-2-methylpropyl)-7-oxo-4,5,6,7-tetrahydro-1H-pyrazolo[3,4-c]pyridine-3-carboxamide (229) was obtained using the method described in Example 1, except ethyl 6-((1-(cyclopropylsulfonyl)cyclopropyl)methyl)-1-methyl-7-oxo-6,7-dihydro-1H-pyrazolo[3,4-c]pyridine-3-carboxylate (int-6) was replaced with ethyl 6-((1-(cyclopropylsulfonyl)cyclopropyl)methyl)-1-(2-hydroxy-2-methylpropyl)-7-oxo-4,5,6,7-tetrahydro-1H-pyrazolo[3,4-c]pyridine-3-carboxylate and 4-(aminomethyl)benzonitrile hydrochloride was replaced with (4-chlorophenyl)methanamine. $^1$H NMR (400 MHz, CDCl$_3$) δ 7.33-7.28 (m, 4H), 7.16-7.13 (m, 1H), 4.58-4.54 (m, 4H), 4.07 (s, 2H), 3.87 (s, 1H), 3.79-3.75 (m, 2H), 3.25-3.22 (m, 2H), 2.74-2.69 (m, 1H), 1.52-1.49 (m, 2H), 1.25-1.17 (m, 8H), 1.10-1.02 (m, 4H). MS (ESI): m/z 535.2 [M+H]$^+$.

Compounds in the Table 16 below were prepared following procedures analogous to those described for Compound (229) in Example 229.

TABLE 16

| Example/Compound Number | Compound Structure and Name | Physical Data MS (m/z), $^1$H NMR |
|---|---|---|
| 230 | N-(4-Cyanobenzyl)-6-((1-(cyclopropylsulfonyl)cyclopropyl)methyl)-1-(2-hydroxy-2-methylpropyl)-7-oxo-4,5,6,7-tetrahydro-1H-pyrazolo[3,4-c]pyridine-3-carboxamide | MS (ESI): m/z 526.3 [M + H]$^+$. $^1$H NMR (400 MHz, CDCl$_3$) δ 7.64-7.63 (m, 2H), 7.44 (d, J = 8.0 Hz, 2H), 7.29-7.21 (m, 1H), 4.66 (d, J = 6.4 Hz, 2H), 4.55 (s, 2H), 4.07 (s, 2H), 3.85 (s, 1H), 3.79-3.75 (m, 2H), 3.24-3.21 (m, 2H), 2.77-2.70 (m, 1H), 1.54-1.50 (m, 2H), 1.25-1.21 (m, 8H), 1.10-1.02 (m, 4H). |

TABLE 16-continued

| Example/ Compound Number | Compound Structure and Name | Physical Data MS (m/z), ¹H NMR |
|---|---|---|
| 231 | 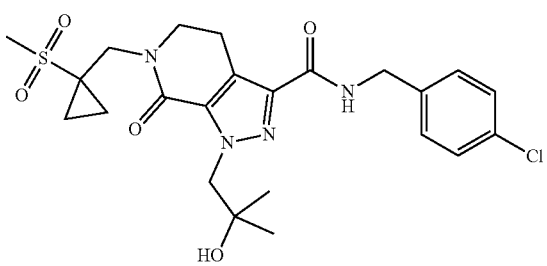<br>N-(4-Chlorobenzyl)-1-(2-hydroxy-2-methylpropyl)-6-((1-(methylsulfonyl)cyclopropyl)methyl)-7-oxo-4,5,6,7-tetrahydro-1H-pyrazolo[3,4-c]pyridine-3-carboxamide | MS (ESI): m/z 509.1 [M + H]⁺. ¹H NMR (400 MHz, DMSO-$d_6$) δ 8.81 (t, J = 6.2 Hz, 1H), 7.45-7.27 (m, 4H), 4.62 (s, 1H), 4.54 (s, 2H), 4.41 (m, 2H), 3.99 (s, 2H), 3.68 (m, 2H), 3.11 (s, 3H), 3.00 (br t, J = 6.8 Hz, 2H), 1.31-1.25 (m, 2H), 1.14-1.02 (m, 8H). |
| 232 | 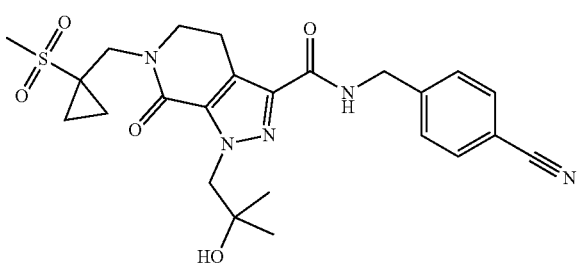<br>N-(4-Cyanobenzyl)-1-(2-hydroxy-2-methylpropyl)-6-((1-(methylsulfonyl)cyclopropyl)methyl)-7-oxo-4,5,6,7-tetrahydro-1H-pyrazolo[3,4-c]pyridine-3-carboxamide | MS (ESI): m/z 500.0 [M + H]⁺. ¹H NMR (400 MHz, DMSO-$d_6$) δ 8.91 (t, J = 6.2 Hz, 1H), 7.80 (d, J = 8.4 Hz, 2H), 7.50 (d, J = 8.0 Hz, 2H), 4.64 (br s, 1H), 4.55 (s, 2H), 4.50 (d, J = 6.0 Hz, 2H), 3.99 (s, 2H), 3.68 (t, J = 6.8 Hz, 2H), 3.11 (s, 3H), 3.04-2.94 (m, 2H), 1.34-1.22 (m, 2H), 1.17-1.01 (m, 8H). |
| 233 | 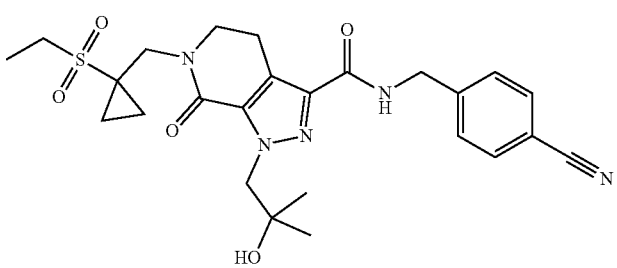<br>N-(4-Cyanobenzyl)-6-((1-(ethylsulfonyl)cyclopropyl)methyl)-1-(2-hydroxy-2-methylpropyl)-7-oxo-4,5,6,7-tetrahydro-1H-pyrazolo[3,4-c]pyridine-3-carboxamide | MS (ESI): m/z 514.4 [M + H]⁺. ¹H NMR (400 MHz, CDCl₃) δ 7.65-7.63 (m, 2H), 7.44 (d, J = 8.8 Hz, 2H), 4.66 (d, J = 6.0 Hz, 2 H), 4.55 (s, 2H), 3.96 (s, 2H), 3.81 (s, 1H), 3.77-3.75 (m, 2H), 3.28-3.20 (m, 4H), 1.54-1.53 (m, 2H), 1.40 (t, 3H), 1.22 (s, 6H), 1.05-1.01 (m, 2H). |
| 234 | 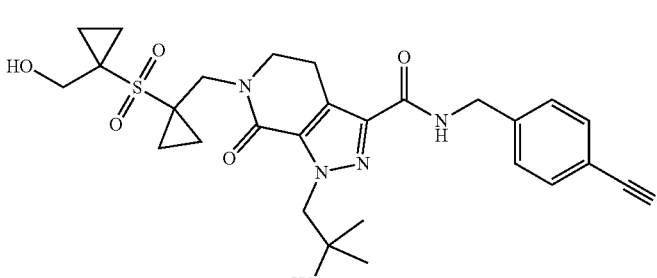<br>N-(4-Cyanobenzyl)-1-(2-hydroxy-2-methylpropyl)-6-((1-((1-(hydroxymethyl)cyclopropyl)sulfonyl)cyclopropyl)methyl)--7-oxo-4,5,6,7-tetrahydro-1H-pyrazolo[3,4-c]pyridine-3-carboxamide | MS (ESI): m/z 556.3 [M + H]⁺. ¹H NMR (400 MHz, CDCl₃) δ 7.65 (d, J = 8.0 Hz, 2H), 7.45 (d, J = 8.4 Hz, 2H), 4.67 (d, J = 6.4 Hz, 2H), 4.55 (s, 2H), 4.15 (s, 1H), 4.19-4.12 (m, 1H), 3.94 (s, 2H), 3.71 (m, 2H), 3.62 (br s, 1H), 3.22 (m, 2H), 2.89 (br s, 1H), 1.63-1.59 (m, 2H), 1.55-1.53 (m, 2H), 1.23 (s, 6H), 1.16-1.10 (m, 2H), 1.07-1.00 (m, 2H). |

TABLE 16-continued

| Example/Compound Number | Compound Structure and Name | Physical Data MS (m/z), $^1$H NMR |
|---|---|---|
| 235 | 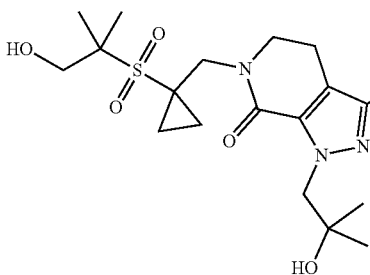<br>N-(4-Cyanobenzyl)-6-((1-(((1-hydroxy-2-methylpropan-2-yl)sulfonyl)cyclopropyl)methyl)-1-(2-hydroxy-2-methylpropyl)-7-oxo-4,5,6,7-tetrahydro-1H-pyrazolo[3,4-c]pyridine-3-carboxamide | MS (ESI): m/z 558.3 [M + H]$^+$. $^1$H NMR (400 MHz, CDCl$_3$) δ 7.66 (d, J = 8.4 Hz, 2H), 7.47 (d, J = 8.4 Hz, 2H), 7.31-7.30 (m, 1H), 4.68 (d, J = 6.4 Hz, 2H), 4.55 (s, 2H), 4.19 (s, 2H), 3.87 (s, 2H), 3.78-3.74 (m, 2H), 3.25-3.22 (m, 2H), 3.05 (br s, 1H), 1.62 (m, 2H), 1.52 (s, 6H), 1.24 (s, 6H), 1.10-1.06 (m, 2H). |

Example 236

N-(4-Cyanobenzyl)-6-((1-(cyclopropylsulfonyl)cyclopropyl)methyl)-1-(3-hydroxypropyl)-7-oxo-4,5,6,7-tetrahydro-1H-pyrazolo[3,4-c]pyridine-3-carboxamide (236)

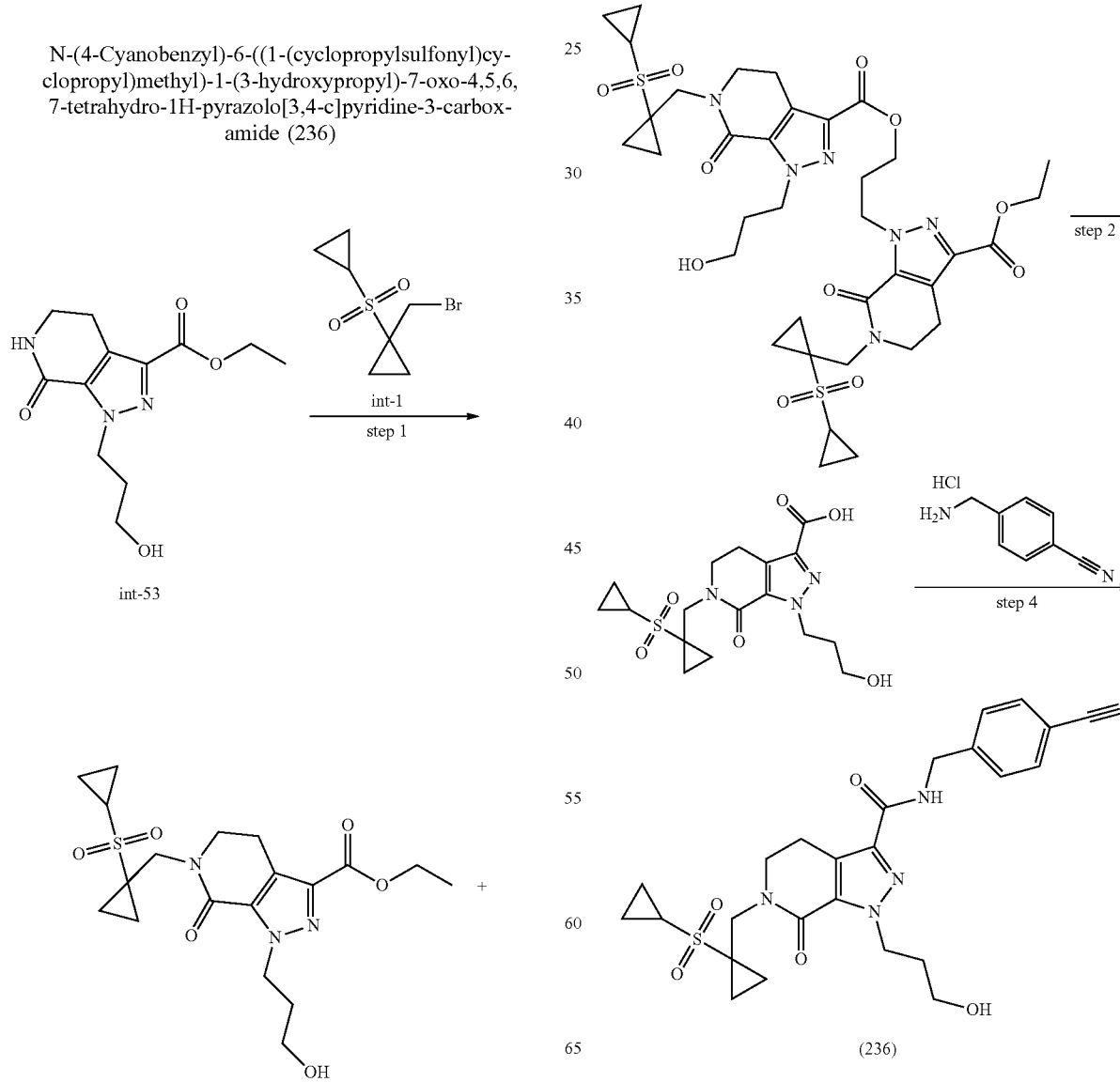

Step 1: Ethyl 6-((1-cyclopropylsulfonyl)cyclopropyl)methyl)-1-(3-hydroxypropy)-7-oxo-4,5,6,7-tetrahydro-1H-pyrazolo[3,4-c]pyridine-3-carboxylate (monomer) and 3-(6-((1-(cyclopropylsulfonyl)cyclopropyl)methyl)-3-(ethoxycarbonyl)-7-oxo-4,5,6,7-tetrahydro-1H-pyrazolo[3,4-c]pyridin-1-yl)propyl 6-((1-(cyclopropylsulfonyl)cyclopropyl)methyl)-1-(3-hydroxypropyl)-7-oxo-4,5,6,7-tetrahydro-1H-pyrazolo[3,4-c]pyridine-3-carboxylate (dimer) were obtained using the procedure for intermediate (int-6), except ethyl 1-methyl-7-oxo-6,7-dihydro-1H-pyrazolo[3,4-c]pyridine-3-carboxylate (int-5) was replaced ethyl 1-(3-hydroxypropyl)-7-oxo-4,5,6,7-tetrahydro-1H-pyrazolo[3,4-c]pyridine-3-carboxylate (int-53) Ethyl 6-((1-(cyclopropylsulfonyl)cyclopropyl)methyl)-1-(3-hydroxypropyl)-7-oxo-4,5,6,7-tetrahydro-1H-pyrazolo[3,4-c]pyridine-3-carboxylate (monomer). MS (ESI): m/z 426.1 [M+H]$^+$. 3-(6-((1-(cyclopropylsulfonyl)cyclopropyl)methyl)-3-(ethoxycarbonyl)-7-oxo-4,5,6,7-tetrahydro-1H-pyrazolo[3,4-c]pyridin-1-yl)propyl 6-((1-(cyclopropylsulfonyl)cyclopropyl)methyl)-1-(3-hydroxypropyl)-7-oxo-4,5,6,7-tetrahydro-1H-pyrazolo[3,4-c]pyridine-3-carboxylate (dimer). MS (ESI): m/z 805.2 [M+H]$^+$.

Step 2: 6-((1-(Cyclopropylsulfonyl)cyclopropyl)methyl)-1-(3-hydroxypropyl)-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 6-((1-(cyclopropylsulfonyl)cyclopropyl)methyl)-1-(3-hydroxypropyl)-7-oxo-4,5,6,7-tetrahydro-1H-pyrazolo[3,4-c]pyridine-3-carboxylate (monomer) or 3-(6-((1-(cyclopropylsulfonyl)cyclopropyl)methyl)-3-(ethoxycarbonyl)-7-oxo-4,5,6,7-tetrahydro-1H-pyrazolo[3,4-c]pyridin-1-yl)propyl 6-((1-(cyclopropylsulfonyl)cyclopropyl)methyl)-1-(3-hydroxypropyl)-7-oxo-4,5,6,7-tetrahydro-1H-pyrazolo[3,4-c]pyridine-3-carboxylate (dimer). MS (ESI): m/z 398.1 [M+H]$^+$.

Step 3: N-(4-Cyanobenzyl)-6-((1-(cyclopropylsulfonyl)cyclopropyl)methyl)-1-(3-hydroxypropyl)-7-oxo-4,5,6,7-tetrahydro-1H-pyrazolo[3,4-c]pyridine-3-carboxamide (236). was obtained using the method described in step 1 of Example 26, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 6-((1-(Cyclopropylsulfonyl)cyclopropyl)methyl)-1-(3-hydroxypropyl)-7-oxo-4,5,6,7-tetrahydro-1H-pyrazolo[3,4-c]pyridine-3-carboxylic acid and hydrazine was replaced with 4-(aminomethyl)benzonitrile hydrochloride. H NMR (400 MHz, CDCl$_3$) δ 7.66 (d, J=8.4 Hz, 2H), 7.48 (d, J=8.4 Hz, 2H), 7.32-7.30 (m, 1H), 4.73-4.67 (m, 4H), 4.10 (s, 2H), 3.80-3.77 (m, 2H), 3.51-3.43 (m, 3H), 3.25-3.22 (m, 2H), 2.90-2.87 (m, 1H), 2.10-2.08 (m, 2H), 1.55-1.54 (m, 2H), 1.26-1.24 (m, 2H), 1.12-1.10 (m, 2H), 1.06-1.04 (m, 2H). MS (ESI): m/z 512.2 [M+H]$^+$.

Example 237

N-(4-Cyanobenzyl)-1-(3-hydroxypropyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide (237)

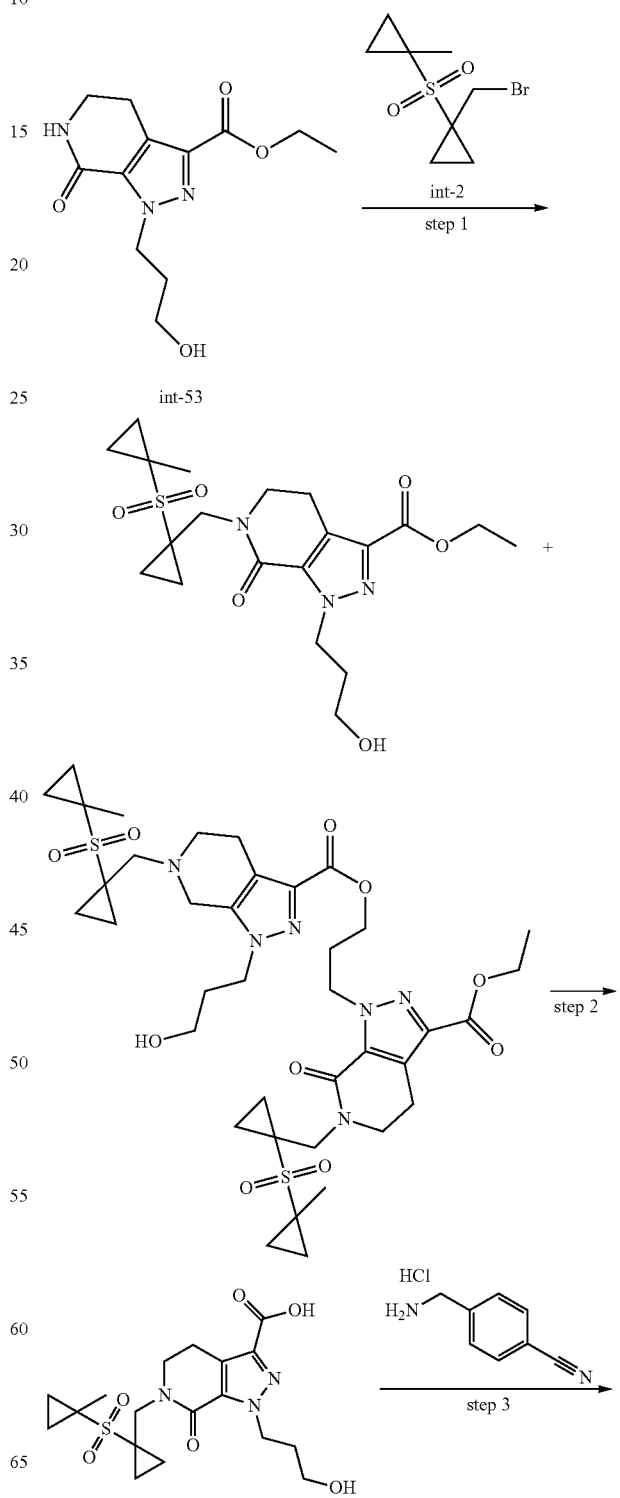

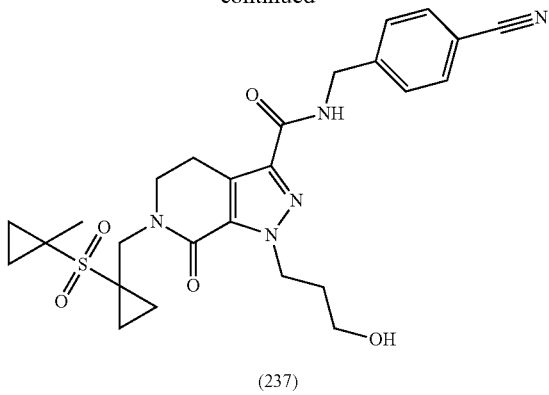

(237)

Step 1: Ethyl 1-(3-hydroxypropyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylate (monomer) and 3-(3-(Ethoxycarbonyl)-6-((1-((1-methylcyclopropyl)sulfonyl)cyclopropyl)methyl)-7-oxo-4,5,6,7-tetrahydro-1H-pyrazolo[3,4-c]pyridin-1-yl)propyl 1-(3-hydroxypropyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylate (dimer) were obtained using the procedure for intermediate (int-6), except ethyl 1-methyl-7-oxo-6,7-dihydro-1H-pyrazolo[3,4-c]pyridine-3-carboxylate (int-5) was replaced with ethyl 1-(3-hydroxypropyl)-7-oxo-4,5,6,7-tetrahydro-1H-pyrazolo[3,4-c]pyridine-3-carboxylate (int-53) and 1-(bromomethyl)-1-(cyclopropylsulfonyl)cyclopropane (int-1) was replaced with 1-(bromomethyl)-1-((1-methylcyclopropyl)sulfonyl)cyclopropane (int-2) Ethyl 1-(3-hydroxypropyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylate (monomer). MS (ESI): m/z 440.1 [M+H]+.

3-(3-(Ethoxycarbonyl)-6-((1-((1-methylcyclopropyl)sulfonyl)cyclopropyl)methyl)-7-oxo-4,5,6,7-tetrahydro-1H-pyrazolo[3,4-c]pyridin-1-yl)propyl 1-(3-hydroxypropyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylate (dimer). MS (ESI): m/z 833.3 [M+H]+.

Step 2: 1-(3-Hydroxypropyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with ethyl 1-(3-hydroxypropyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylate (monomer) or 3-(3-(ethoxycarbonyl)-6-((1-((1-methylcyclopropyl)sulfonyl)cyclopropyl)methyl)-7-oxo-4,5,6,7-tetrahydro-1H-pyrazolo[3,4-c]pyridin-1-yl)propyl 1-(3-hydroxypropyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylate (dimer). MS (ESI): m/z 412.1 [M+H]+.

Step 3: N-(4-Cyanobenzyl)-1-(3-hydroxypropyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide (237) was obtained using the method described in step 1 of Example 26, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with 1-(3-Hydroxypropyl)-6-((1-((1-methylcyclopropyl)sulfonyl)cyclopropyl)methyl)-7-oxo-4,5,6,7-tetrahydro-1H-pyrazolo[3,4-c]pyridine-3-carboxylic acid and hydrazine was replaced with 4-(aminomethyl)benzonitrile hydrochloride. $^1$H NMR (400 MHz, CDCl$_3$) δ 7.64 (d, J=8.0 Hz, 2H), 7.46 (d, J=8.4 Hz, 2H), 7.29 (m, 1H), 4.69-4.66 (m, 4H), 4.14 (s, 2H), 3.74-3.71 (m, 2H), 3.50-3.47 (m, 2H), 3.22-3.19 (m, 2H), 2.10-2.06 (m, 2H), 1.61 (s, 3H), 1.58-1.55 (m, 2H), 1.47-1.46 (m, 2H), 1.04-1.03 (m, 2H), 0.89-0.88 (m, 2H). MS (ESI): m/z 526.2 [M+H]+.

Example 238

1-(2-(2-Bromoethoxy)ethyl)-N-(4-cyanobenzyl)-6-((1-((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide (238)

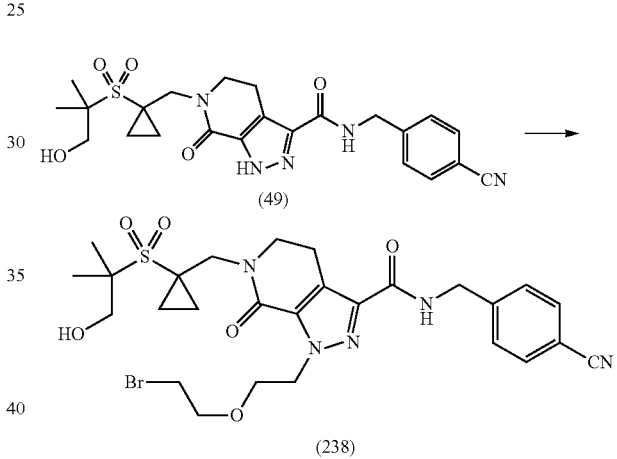

Step 1: A solution of N-(4-cyanobenzyl)-6-((1-((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide (49) (100 mg, 0.206 mmol, 1.0 equiv) and 1-bromo-2-(2-bromoethoxy)ethane (47.8 mg, 0.206 mmol, 1.0 equiv) in DMF (1 mL) was treated with Cs$_2$CO$_3$ (134 mg, 0.412 mmol, 2.0 equiv). After 2 h at rt, the reaction mixture was diluted with sat. aq. NH$_4$Cl and EtOAc, then the layers were separated. The aq. layer was extracted with EtOAc (3×5 mL) and the combined organic extracts were dried with Na$_2$SO$_4$, filtered, and concentrated to afford an oil. The residue was purified by column chromatography (SiO$_2$, 0-100%, EtOAc/heptane) to provide 1-(2-(2-bromoethoxy)ethyl)-N-(4-cyanobenzyl)-6-((1-((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide (238). $^1$H NMR (500 MHz, CDCl$_3$) δ 7.63 (d, J=7.9 Hz, 2H), 7.45 (d, J=7.9 Hz, 2H), 7.31 (d, J=6.1 Hz, 1H), 4.75 (t, J=5.3 Hz, 2H), 4.65 (d, J=5.7 Hz, 2H), 4.16 (s, 2H), 3.90 (t, J=5.3 Hz, 2H), 3.85 (d, J=6.5 Hz, 2H), 3.72 (dt, J=10.8, 6.3 Hz, 4H), 3.38 (t, J=5.9 Hz, 2H), 3.18 (t, J=6.8 Hz, 2H), 3.14 (d, J=6.5 Hz, 1H), 1.59 (d, J=2.4 Hz, 2H), 1.50 (s, 6H), 1.31-1.21 (m, 1H), 1.11-1.04 (m, 2H). MS (ESI): m/z 636.2 [M+H]+.

Example 239

Ethylene glycol macrocycle
N-(4-cyanobenzyl)carboxamide (939)

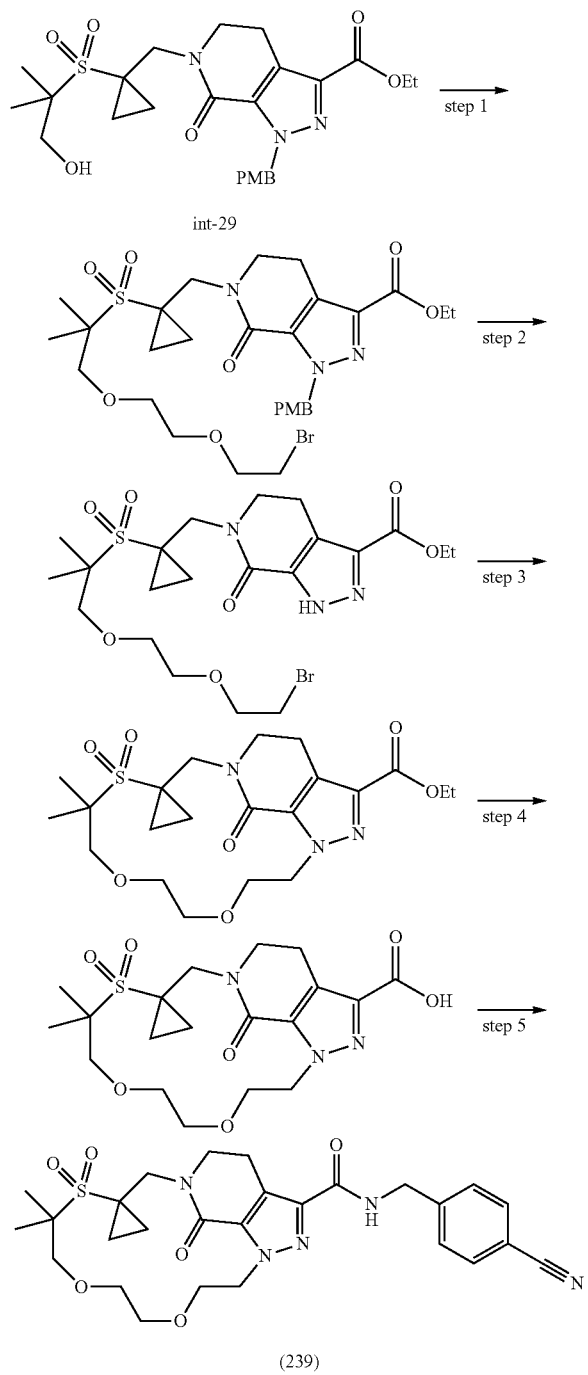

Step 1: Ethyl 6-((1-((1-hydroxy-2-methylpropan-2-yl)sulfonyl)cyclopropyl)methyl)-1-(4-methoxybenzyl)-7-oxo-4,5,6,7-tetrahydro-1H-pyrazolo[3,4-c]pyridine-3-carboxylate (int-29) (750 mg, 1.44 mmol, 1.0 equiv) and 1-bromo-2-(2-bromoethoxy)ethane (1.51 g, 6.50 mmol, 4.5 equiv) were dissolved in DMF (7.2 mL) and NaH (60% in mineral oil, 144 mg, 3.61 mmol, 2.5 equiv) was added at 23° C. (gas evolution). The mixture was sonicated for 20 min before being stirred for 20 min. The reaction mixture was diluted with saturated NH$_4$Cl and EtOAc, and then the aqueous phase was extracted with EtOAc (3×20 mL). The combined organic extracts were dried with MgSO$_4$, filtered, and concentrated. The residue was purified by column chromatography (SiO$_2$, 0-100% EtOAc/heptane) to afford ethyl 6-((1-((1-(2-(2-bromoethoxy)ethoxy)-2-methylpropan-2-yl)sulfonyl)cyclopropyl)methyl)-1-(4-methoxybenzyl)-7-oxo-4,5,6,7-tetrahydro-1H-pyrazolo[3,4-c]pyridine-3-carboxylate. $^1$H NMR (500 MHz, CDCl$_3$) δ 7.33 (d, J=8.7 Hz, 2H), 6.81 (d, J=8.8 Hz, 2H), 5.72 (s, 2H), 4.40 (q, J=7.1 Hz, 2H), 4.15 (s, 2H), 3.81 (t, J=6.1 Hz, 2H), 3.76 (s, 3H), 3.73-3.61 (m, 8H), 3.46 (t, J=6.0 Hz, 2H), 3.07 (t, J=6.9 Hz, 2H), 1.59 (d, J=1.3 Hz, 2H), 1.55 (t, J=3.6 Hz, 2H), 1.48 (s, 6H), 1.39 (t, J=7.1 Hz, 3H), 1.09-0.99 (m, 2H). MS (ESI): m/z 670.5 [M+H]$^+$.

Step 2: A solution of ethyl 6-((1-((1-(2-(2-bromoethoxy)ethoxy)-2-methylpropan-2-yl)sulfonyl)cyclopropyl)methyl)-1-(4-methoxybenzyl)-7-oxo-4,5,6,7-tetrahydro-1H-pyrazolo[3,4-c]pyridine-3-carboxylate (510 mg, 0.760 mmol, 1.0 equiv) in TFA (3.5 mL) was stirred at 30° C. for 3 h. The mixture was diluted with CH$_2$Cl$_2$ (5 mL) and water (5 mL) and basified to pH 10 with solid Na$_2$CO$_3$ (gas evolution). The aqueous layer was extracted with EtOAc (3×4 mL), and then the combined organic extracts were dried with MgSO$_4$, filtered, and concentrated to afford ethyl 6-((1-((1-(2-(2-bromoethoxy)ethoxy)-2-methylpropan-2-yl)sulfonyl)cyclopropyl)methyl)-7-oxo-4,5,6,7-tetrahydro-1H-pyrazolo[3,4-c]pyridine-3-carboxylate. $^1$H NMR (500 MHz, CDCl$_3$) δ 4.41 (q, J=7.1 Hz, 2H), 4.21 (s, 2H), 3.87-3.62 (m, 16H), 3.48 (t, J=6.0 Hz, 2H), 3.12 (t, J=6.9 Hz, 2H), 1.61-1.57 (m, 3H), 1.49 (s, 7H), 1.41 (t, J=7.1 Hz, 3H), 1.16-1.06 (m, 2H). MS (ESI): m/z 550.4 [M+H]$^+$.

Step 3: A mixture of ethyl 6-((1-((1-(2-(2-bromoethoxy)ethoxy)-2-methylpropan-2-yl)sulfonyl)cyclopropyl)methyl)-7-oxo-4,5,6,7-tetrahydro-1H-pyrazolo[3,4-c]pyridine-3-carboxylate (400 mg, 0.690 mmol, 1.0 equiv) and Cs$_2$CO$_3$ (743 mg, 2.281 mmol, 3.0 equiv) in DMF (100 mL) was stirred at rt for 16 h before it was diluted with EtOAc (100 mL) and H$_2$O (50 mL). The aqueous layer was extracted with EtOAc (3×50 mL) and the combined organic extracts were dried with Na$_2$SO$_4$, filtered, and concentrated. The resulting product was purified by column chromatography (SiO$_2$, 50-100% EtOAc/heptane) to afford the ethylene glycol macrocycle ethyl ester. $^1$H NMR (500 MHz, CDCl$_3$) δ 4.41 (q, J=7.1 Hz, 2H), 3.80 (s, 4H), 3.58 (d, J=4.5 Hz, 5H), 3.18 (s, 2H), 1.61 (s, 2H), 1.45 (s, 6H), 1.39 (t, J=7.1 Hz, 3H), 1.17 (s, 1H). MS (ESI): m/z 470.2 [M+H]$^+$.

Step. 4: Ethylene glycol macrocycle carboxylic acid was obtained using the method for the synthesis of intermediate (int-14), except ethyl 1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxylate (int-13) was replaced with the ethylene glycol macrocycle ethyl ester. MS (ESI): m/z 442.4 [M+H]$^+$.

Step 5: Ethylene glycol macrocycle N-(4-cyanobenzyl)carboxamide (239) was obtained using the method described in Example 3, except 6-((1-(cyclopropylsulfonyl)cyclopropyl)methyl)-1-methyl-7-oxo-4,5,6,7-tetrahydro-1H-pyrazolo[3,4-c]pyridine-3-carboxylic acid (int-11) was replaced with ethylene glycol macrocycle carboxylic acid. $^1$H NMR (500 MHz, DMSO-d$_6$) δ 8.91 (t, J=6.3 Hz, 1H), 7.81-7.76 (m, 2H), 7.52-7.47 (m, 2H), 4.47 (d, J=6.2 Hz, 2H), 3.71 (dd, J=13.9, 6.4 Hz, 4H), 3.54 (s, 6H), 3.01 (t, J=7.0 Hz, 2H), 1.41 (s, 2H), 1.32 (s, 6H), 1.21 (s, 2H). MS (ESI): m/z 556.5 [M+H]$^+$.

Example 240

Ethylene glycol macrocycle N-(4-chlorobenzyl)carboxamide (240)

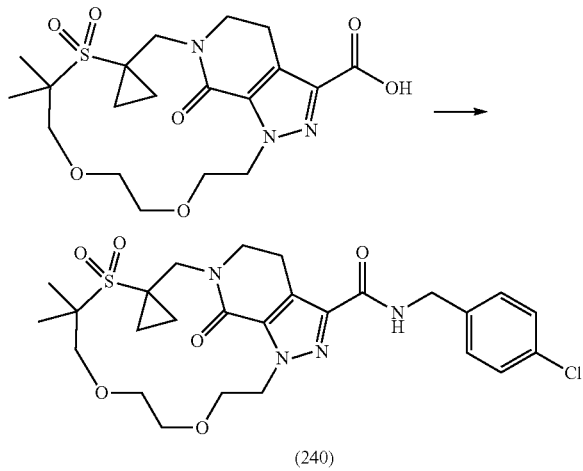

(240)

Ethylene glycol macrocycle N-(4-chlorobenzyl)carboxamide (240) was obtained using the procedure described in Example 240, except in step 5 4-(aminomethyl)benzonitrile was replaced with (4-chlorophenyl)methanamine. $^1$H NMR (500 MHz, DMSO-$d_6$) δ 8.82 (t, J=6.4 Hz, 1H), 7.37 (d, J=8.4 Hz, 2H), 7.33 (d, J=8.3 Hz, 2H), 4.38 (d, J=6.3 Hz, 2H), 3.76-3.64 (m, 4H), 3.53 (s, 6H), 3.37 (s, 4H), 3.00 (t, J=7.0 Hz, 2H), 1.40 (s, 2H), 1.31 (s, 6H), 1.22 (d, J=9.6 Hz, 3H). MS (ESI): m/z 565.5 [M+H]$^+$.

Example 241

Lactam macrocycle N-(4-cyanobenzyl)carboxamide (241)

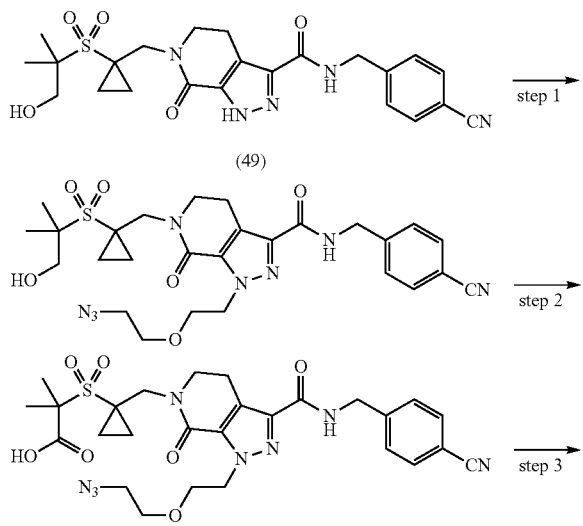

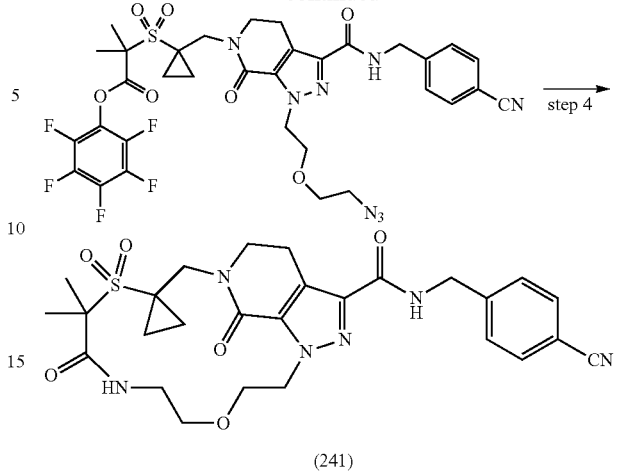

(241)

Step 1: A solution of N-(4-cyanobenzyl)-6-((1-(((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide (49) (100 mg, 0.206 mmol, 1.0 equiv) and 1-bromo-2-(2-bromoethoxy)ethane (47.8 mg, 0.206 mmol, 1.0 equiv) in DMF (500 μL) was treated with $Cs_2CO_3$ (134 mg, 0.412 mmol, 2.0 equiv) at rt. After 2 h, $NaN_3$ (26.8 mg, 0.412 mmol, 2.0 equiv) was added in one portion and the mixture was stirred at rt for 30 min, then at 40° C. for 12 h. Additional $NaN_3$ (26.8 mg, 0.412 mmol, 2.0 equiv) was added and the mixture was heated to 60° C. for 1 h before it was diluted with $H_2O$ (5 mL) and EtOAc (5 mL). The aqueous phase was extracted with EtOAc (3×5 mL) and the combined organic extracts were dried with $Na_2SO_4$, filtered, and concentrated. The residue was purified by column chromatography ($SiO_2$, 0-100%, EtOAc/heptane) to afford 1-(2-(2-azidoethoxy)ethyl)-N-(4-cyanobenzyl)-6-((1-((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide. MS (ESI): m/z 599.5 [M+H]$^+$.

Step 2: 1-(2-(2-azidoethoxy)ethyl)-N-(4-cyanobenzyl)-6-((1-(((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide (80 mg, 0.134 mmol, 1.0 equiv) and NMO monohydrate (181 mg, 1.34 mmol, 10 equiv) were dissolved in MeCN (700 μL) before adding TPAP (3.76 mg, 10.69 μmol, 0.08 equiv) at rt. After 2 h, additional TPAP (3.76 mg, 10.69 μmol, 0.08 equiv) was added. After 1 h of stirring, the reaction mixture was quenched with i-PrOH (100 μL) and concentrated. The residue was acidified to pH 3 with 2 M $NaHSO_4$ and extracted with $Et_2O$ (6×5 mL). The combined organic extracts were dried with $Na_2SO_4$, filtered, and concentrated to afford an oil containing a ~5:1 mixture of 2-((1-((1-(2-(2-azidoethoxy)ethyl)-3-((4-cyanobenzyl)carbamoyl)-7-oxo-1,4,5,7-tetrahydro-6H-pyrazolo[3,4-c]pyridin-6-yl)methyl)cyclopropyl)sulfonyl)-2-methylpropanoic acid and 1-(2-(2-azidoethoxy)ethyl)-N-(4-cyanobenzyl)-6-((1-(((2-methyl-1-oxopropan-2-yl)sulfonyl)cyclopropyl)methyl)-7-oxo-4,5,6,7-tetrahydro-1H-pyrazolo[3,4-c]pyridine-3-carboxamide.

Step 3: To a solution of the crude material from step 2, 2,3,4,5,6-pentafluorophenol (24.6 mg, 0.134 mmol, 1.0 equiv), and DMAP (1.6 mg, 0.013 mmol, 0.1 equiv) in $CH_2Cl_2$ (1 mL) was added EDC (38.4 mg, 0.200 mmol, 1.5 equiv) in one portion at rt. After 1 h, the reaction mixture was diluted with $H_2O$ (3 mL) and extracted with $CH_2Cl_2$ (3×5 mL). The combined organic extracts were dried with $MgSO_4$, filtered, and concentrated. The residue was purified by column chromatography ($SiO_2$, 0-100%, EtOAc/heptane) to afford perfluorophenyl 2-((1-((1-(2-(2-azidoethoxy)

ethyl)-3-((4-cyanobenzyl)carbamoyl)-7-oxo-1,4,5,7-tetrahydro-6H-pyrazolo[3,4-c]pyridin-6-yl)methyl)cyclopropyl)sulfonyl)-2-methylpropanoate. $^1$H NMR (500 MHz, CDCl$_3$) δ 7.70-7.56 (m, 2H), 7.45 (d, J=8.0 Hz, 2H), 7.34 (s, 1H), 4.75 (d, J=5.0 Hz, 2H), 4.64 (d, J=6.2 Hz, 2H), 4.15 (s, 2H), 3.88 (d, J=5.0 Hz, 2H), 3.71 (d, J=7.7 Hz, 2H), 3.66-3.56 (m, 2H), 3.28 (d, J=4.9 Hz, 2H), 3.18 (s, 2H), 1.91 (d, J=3.7 Hz, 6H), 1.64 (s, 2H), 1.19 (s, 2H). MS (ESI): m/z 779.6 [M+H]$^+$. In addition, the aldehyde was recovered during purification. $^1$H NMR (500 MHz, CDCl$_3$) δ 9.77 (d, J=3.3 Hz, 1H), 7.66-7.58 (m, 2H), 7.45 (d, J=7.9 Hz, 2H), 7.35 (s, 1H), 4.74 (q, J=4.7 Hz, 2H), 4.64 (t, J=4.6 Hz, 2H), 3.95 (d, J=3.4 Hz, 2H), 3.88 (d, J=4.9 Hz, 2H), 3.63 (dt, J=26.7, 5.8 Hz, 4H), 3.28 (t, J=4.6 Hz, 2H), 3.17 (d, J=6.6 Hz, 2H), 1.61 (d, J=3.7 Hz, 9H), 1.49 (s, 2H), 1.10 (s, 2H). MS (ESI): m/z 597.4 [M+H]$^+$.

Step 4: A solution of perfluorophenyl 2-((1-((1-(2-(2-azidoethoxy)ethyl)-3-((4-cyanobenzyl)carbamoyl)-7-oxo-1,4,5,7-tetrahydro-6H-pyrazolo[3,4-c]pyridin-6-yl)methyl)cyclopropyl)sulfonyl)-2-methylpropanoate (36 mg, 0.046 mmol, 1.0 equiv) and Ph$_3$P (36.4 mg, 0.139 mmol, 3.0 equiv) in toluene (10 mL) was heated to 110° C. for 4 h. The mixture was cooled and concentrated, then the residue was dissolved in 4:1 MeCN/H$_2$O (1 mL) and heated at 60° C. for 14 h. The mixture was concentrated and purified by prep-TLC [R$_f$=0.3, 70% (3:1 EtOAc-EtOH)/heptane]. The silica was stirred in 10% MeOH/DCM, filtered, and concentrated to afford semi-pure material. Further purification by RP-HPLC afforded Lactam macrocycle N-(4-cyanobenzyl)carboxamide (241). $^1$H NMR (500 MHz, DMSO-d$_6$) δ 8.94 (t, J=6.3 Hz, 1H), 7.85 (s, 1H), 7.81-7.75 (m, 2H), 7.52-7.44 (m, 2H), 4.47 (d, J=6.2 Hz, 2H), 3.75 (t, J=4.5 Hz, 2H), 3.62-3.58 (m, 6H), 3.24 (s, 2H), 2.96 (t, J=6.9 Hz, 2H), 1.95-1.70 (m, 6H), 1.24 (s, 2H), 0.99 (s, 2H). MS (ESI): m/z 569.5 [M+H]$^+$.

Example 242

Amine macrocycle N-(4-cyanobenzyl)carboxamide (242)

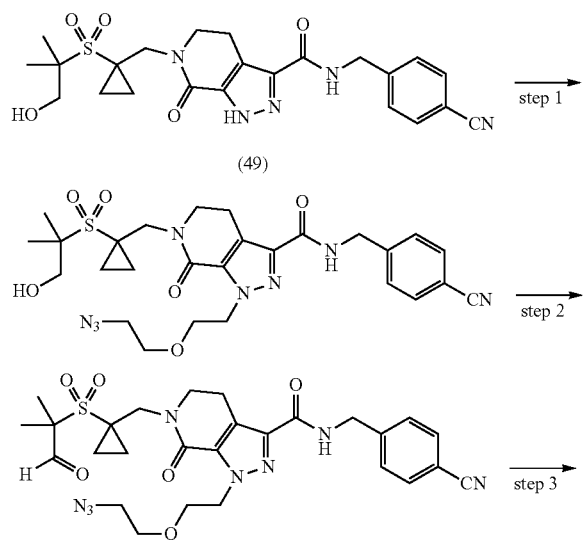

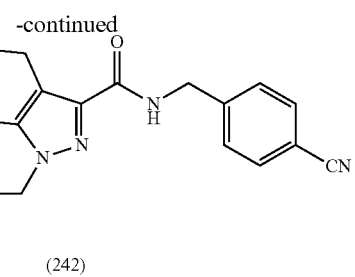

(242)

Step 1: A solution of N-(4-cyanobenzyl)-6-((1-((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide (49) (100 mg, 0.206 mmol, 1.0 equiv) and 1-bromo-2-(2-bromoethoxy)ethane (47.8 mg, 0.206 mmol, 1.0 equiv) in DMF (500 μL) was treated with Cs$_2$CO$_3$ (134 mg, 0.412 mmol, 2.0 equiv) at rt. After 2 h, NaN$_3$ (26.8 mg, 0.412 mmol, 2.0 equiv) was added in one portion and the mixture was stirred at rt for 30 min, then at 40° C. for 12 h. Additional NaN$_3$ (26.8 mg, 0.412 mmol, 2.0 equiv) was added and the mixture was heated to 60° C. for 1 h before it was diluted with H$_2$O (5 mL) and EtOAc (5 mL). The aqueous phase was extracted with EtOAc (3×5 mL) and the combined organic extracts were dried with Na$_2$SO$_4$, filtered, and concentrated. The residue was purified by column chromatography (SiO$_2$, 0-100%, EtOAc/heptane) to afford 1-(2-(2-azidoethoxy)ethyl)-N-(4-cyanobenzyl)-6-((1-((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide. MS (ESI): m/z 599.5 [M+H]$^+$.

Step 2: 1-(2-(2-azidoethoxy)ethyl)-N-(4-cyanobenzyl)-6-((1-((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide (80 mg, 0.134 mmol, 1.0 equiv) and NMO monohydrate (181 mg, 1.34 mmol, 10 equiv) were dissolved in MeCN (700 μL) before adding TPAP (3.76 mg, 10.69 μmol, 0.08 equiv) at rt. After 2 h, additional TPAP was added (3.76 mg, 10.69 μmol, 0.08 equiv) was added. After 1 h of stirring, the reaction mixture was quenched with i-PrOH (100 μL) and concentrated. The residue was acidified to pH 3 with 2 M NaHSO$_4$ and extracted with Et$_2$O (6×5 mL). The combined organic extracts were dried with Na$_2$SO$_4$, filtered, and concentrated to afford-5:1 mixture of 2-((1-((1-(2-(2-azidoethoxy)ethyl)-3-((4-cyanobenzyl)carbamoyl)-7-oxo-1,4,5,7-tetrahydro-6H-pyrazolo[3,4-c]pyridin-6-yl)methyl)cyclopropyl)sulfonyl)-2-methylpropanoic acid and 1-(2-(2-azidoethoxy)ethyl)-N-(4-cyanobenzyl)-6-((1-((2-methyl-1-oxopropan-2-yl)sulfonyl)cyclopropyl)methyl)-7-oxo-4,5,6,7-tetrahydro-1H-pyrazolo[3,4-c]pyridine-3-carboxamide.

Step 3: A solution of 1-(2-(2-azidoethoxy)ethyl)-N-(4-cyanobenzyl)-6-((1-((2-methyl-1-oxopropan-2-yl)sulfonyl)cyclopropyl)methyl)-7-oxo-4,5,6,7-tetrahydro-1H-pyrazolo[3,4-c]pyridine-3-carboxamide, obtained from step 3 in Example 241, (15 mg, 0.025 mmol, 1.0 equiv) and Ph$_3$P (19 mg, 0.075 mmol, 3.0 equiv) in toluene (3 mL) was heated to 110° C. for 16 h. The mixture was cooled to rt and NaBH$_4$ (2.8 mg, 0.075 mmol, 3.0 equiv) was added in one portion. After 10 min MeOH (100 μL) was added (gas evolution) before the mixture was diluted with H$_2$O (5 mL) and CH$_2$Cl$_2$ (5 mL). The aqueous phase was extracted with CH$_2$Cl$_2$ (3×5 mL) and the combined organic extracts were dried with MgSO$_4$, filtered, and concentrated. The crude material was purified by RP-HPLC to afford amine macrocycle N-(4-cyanobenzyl)carboxamide (242). $^1$H NMR (500 MHz, MeOH-d$_4$) δ 8.93 (t, J=5.2 Hz, 2H), 7.71 (d, J=8.0 Hz, 2H), 7.54 (d, J=8.0 Hz, 2H), 5.61 (br s, 2H), 4.63 (d, J=5.2 Hz, 2H), 3.71-3.87 (m, 6H), 3.42 (s, 2H), 3.14 (br s, 2H), 2.05 (br s, 2H), 1.24-1.77 (d, J=75.6 Hz, 4H). MS (ESI): m/z 555.7 [M+H]$^+$.

Example 243

N-(4-cyanobenzyl)-6-((1-(N-(6-(hydroxymethyl)pyridin-2-yl)sulfamoyl)cyclopropyl)methyl)-1-methyl-7-oxo-4,5,6,7-tetrahydro-1H-pyrazolo[3,4-c]pyridine-3-carboxamide (243)

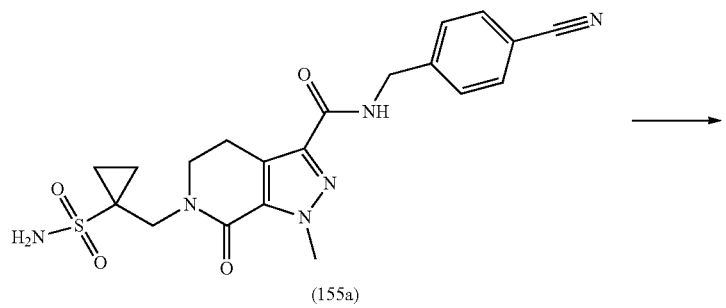

(155a)

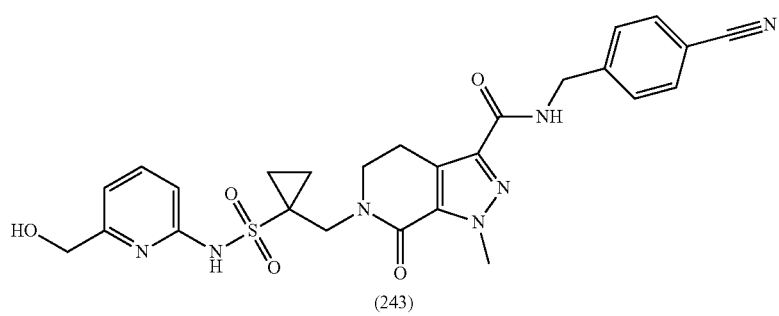

(243)

N-(4-cyanobenzyl)-6-((1-(N-(6-(hydroxymethyl)pyridin-2-yl)sulfamoyl)cyclopropyl)methyl)-1-methyl-7-oxo-4,5,6,7-tetrahydro-1H-pyrazolo[3,4-c]pyridine-3-carboxamide (243) was synthesized using the procedure provided for Example 155 (see also Wang et al, Tet. Lett., pp. 7-10, 53, 2012), except replacing 2-Bromopyridine with (6-bromo-2-pyridyl)methanol. The intermediate 155a was obtained using the method described in step 4 of Example 123, except methylamine was replaced with $NH_3$. 1H NMR (400 MHz, DMSO-d6) δ 10.91 (s, 1H), 8.93 (t, J=6.2 Hz, 1H), 8.40 (s, 1H), 8.31 (d, J=12.4 Hz, 2H), 7.83-7.76 (m, 2H), 7.48 (d, J=8.2 Hz, 2H), 4.47 (d, J=6.2 Hz, 2H), 4.10 (s, 3H), 3.96 (s, 2H), 3.63 (t, J=6.8 Hz, 2H), 3.17 (s, 1H), 2.89 (t, J=6.8 Hz, 2H), 1.47 (s, 2H), 1.24 (s, 2H), 1.16 (q, J=5.3 Hz, 2H). 19F NMR (376 MHz, DMSO-d6) δ −74.86. LCMS (ESI): m/z 550.2 [M+H]$^+$.

Example 244

6-((1-(N-(6-acetamidopyridin-2-yl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide (244)

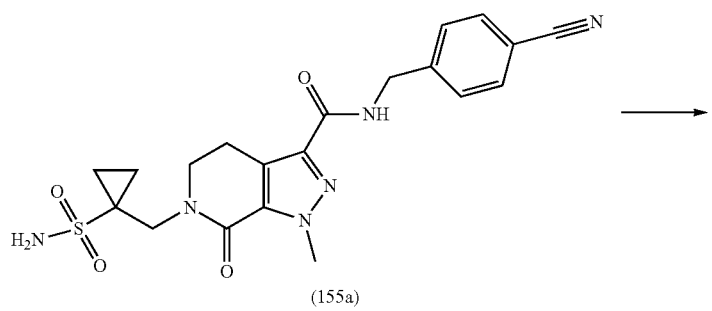

(155a)

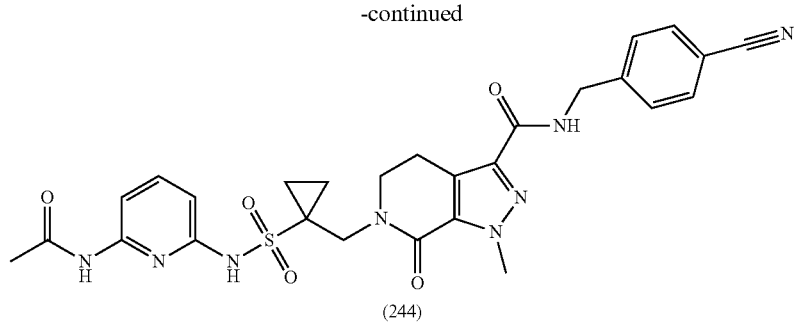

(244)

6-((1-(N-(6-acetamidopyridin-2-yl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide (244) was synthesized using the procedure provided for Example 155, except replacing 2-Bromopyridine with N-(6-aminopyridin-2-yl)acetamide. The intermediate 155a was obtained using the method described in step 4 of Example 123, except methylamine was replaced with $NH_3$. 1H NMR (400 MHz, DMSO-d6) δ 10.09 (d, J=15.8 Hz, 2H), 8.93 (t, J=6.3 Hz, 1H), 7.83-7.70 (m, 3H), 7.67 (t, J=7.9 Hz, 1H), 7.51-7.44 (m, 2H), 6.81 (d, J=8.0 Hz, 1H), 4.47 (d, J=6.2 Hz, 2H), 4.12 (s, 3H), 3.96 (s, 2H), 3.62 (t, J=6.8 Hz, 2H), 2.91 (t, J=6.8 Hz, 2H), 2.83 (t, J=6.8 Hz, OH), 2.11 (s, 3H), 1.49 (q, J=5.0 Hz, 2H), 1.13-1.05 (m, 2H). 19F NMR (376 MHz, DMSO-d6) δ-75.07. LCMS (ESI): m/z 577.2 [M+H]⁺.

Example 245

N-(4-cyanobenzyl)-1-methyl-7-oxo-6-((1-(N-(pyrazin-2-yl)sulfamoyl)cyclopropyl)methyl)-4,5,6,7-tetrahydro-1H-pyrazolo[3,4-c]pyridine-3-carboxamide (245)

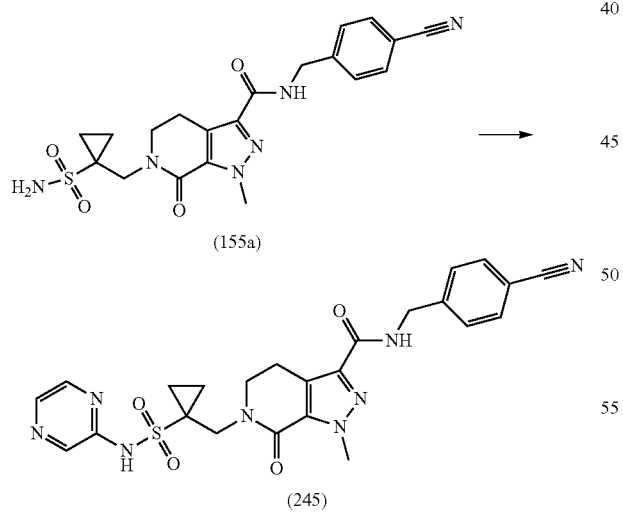

N-(4-cyanobenzyl)-1-methyl-7-oxo-6-((1-(N-(pyrazin-2-yl)sulfamoyl)cyclopropyl)methyl)-4,5,6,7-tetrahydro-1H-pyrazolo[3,4-c]pyridine-3-carboxamide (245) was synthesized using the procedure provided for Example 155, except replacing 2-Bromopyridine with 2-bromopyrazine. The intermediate (155a) was obtained using the method described in step 4 of Example 123, except methylamine was replaced with $NH_3$. 1H NMR (400 MHz, DMSO-d6) δ 10.91 (s, 1H), 8.93 (t, J=6.2 Hz, 1H), 8.40 (s, 1H), 8.31 (d, J=12.4 Hz, 2H), 7.83-7.76 (m, 2H), 7.48 (d, J=8.2 Hz, 2H), 4.47 (d, J=6.2 Hz, 2H), 4.10 (s, 3H), 3.96 (s, 2H), 3.63 (t, J=6.8 Hz, 2H), 3.17 (s, 1H), 2.89 (t, J=6.8 Hz, 2H), 1.47 (s, 2H), 1.24 (s, 2H), 1.16 (q, J=5.3 Hz, 2H). 19F NMR (376 MHz, DMSO-d6) δ −74.86. LCMS (ESI): m/z 521.2 [M+H]⁺.

Example 246

N-(4-cyanobenzyl)-1-methyl-7-oxo-6-((1-(N-phenylsulfamoyl)cyclopropyl)methyl)-4,5,6,7-tetrahydro-1H-pyrazolo[3,4-c]pyridine-3-carboxamide (246)

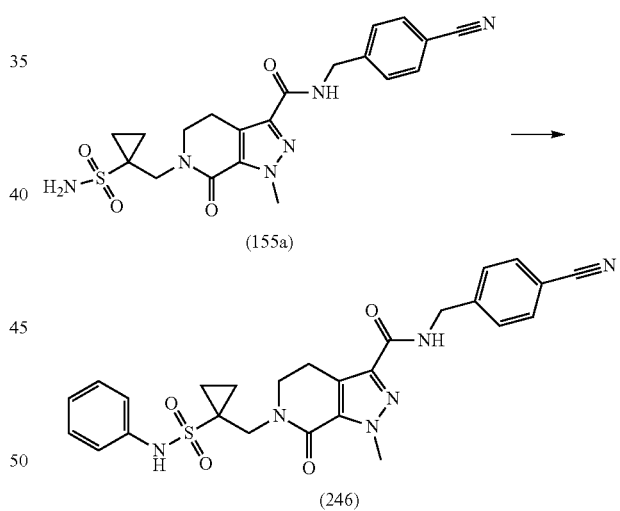

N-(4-cyanobenzyl)-1-methyl-7-oxo-6-((1-(N-phenylsulfamoyl)cyclopropyl)methyl)-4,5,6,7-tetrahydro-1H-pyrazolo[3,4-c]pyridine-3-carboxamide (246) was synthesized using the procedure provided for Example 155, except replacing 2-Bromopyridine with bromobenzene. The intermediate (155a) was obtained using the method described in step 4 of Example 123, except methylamine was replaced with $NH_3$. 1H NMR (400 MHz, DMSO-d6) δ 9.73 (s, 2H), 8.94 (t, J=6.3 Hz, 2H), 8.08-7.69 (m, 3H), 7.48 (d, J=8.1 Hz, 2H), 7.42-7.18 (m, 4H), 7.13 (t, J=7.2 Hz, 1H), 4.47 (d, J=6.1 Hz, 3H), 4.11 (s, 3H), 3.91 (s, 2H), 3.61 (t, J=6.8 Hz, 4H), 2.94 (t, J=6.8 Hz, 2H), 1.14 (q, J=4.9, 4.5 Hz, 2H), 1.10-0.89 (m, 2H). 19F NMR (376 MHz, DMSO-d6) δ −74.76. LCMS (ESI): m/z 519.2 [M+H]⁺.

Example 247

N-(4-cyanobenzyl)-6-((1-(N-(3-fluoropyridin-2-yl)sulfamoyl)cyclopropyl)methyl)-1-methyl-7-oxo-4,5,6,7-tetrahydro-1H-pyrazolo[3,4-c]pyridine-3-carboxamide (247)

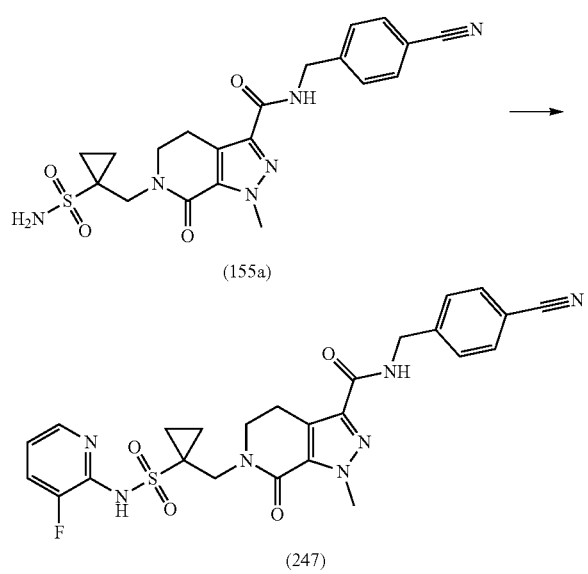

N-(4-cyanobenzyl)-6-((1-(N-(3-fluoropyridin-2-yl)sulfamoyl)cyclopropyl)methyl)-1-methyl-7-oxo-4,5,6,7-tetrahydro-1H-pyrazolo[3,4-c]pyridine-3-carboxamide (247) was synthesized using the procedure provided for Example 155, except replacing 2-Bromopyridine with 3-fluoropyridin-2-amine. The intermediate (155a) was obtained using the method described in step 4 of Example 123, except methylamine was replaced with NH$_3$. 1H NMR (400 MHz, DMSO-d6) δ 8.93 (t, J=6.3 Hz, 1H), 7.76 (dd, J=27.1, 8.7 Hz, 3H), 7.48 (d, J=8.0 Hz, 2H), 4.47 (d, J=6.2 Hz, 3H), 4.12 (s, 3H), 4.04 (s, 2H), 3.69 (t, J=6.8 Hz, 2H), 2.93 (t, J=6.8 Hz, 2H), 1.42 (s, 2H), 1.13 (s, 2H). 19F NMR (376 MHz, DMSO-d6) δ −75.17. LCMS (ESI): m/z 538.2 [M+H]$^+$.

Example 248

N-(4-cyanobenzyl)-6-((1-(N-(2-cyanophenyl)sulfamoyl)cyclopropyl)methyl)-1-methyl-7-oxo-4,5,6,7-tetrahydro-1H-pyrazolo[3,4-c]pyridine-3-carboxamide (248)

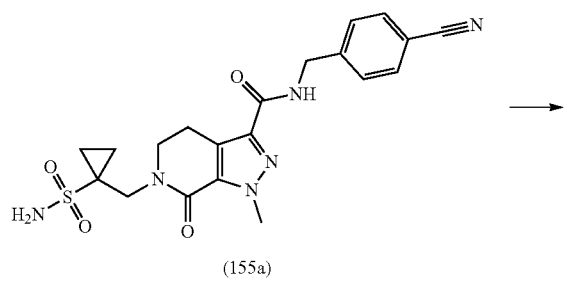

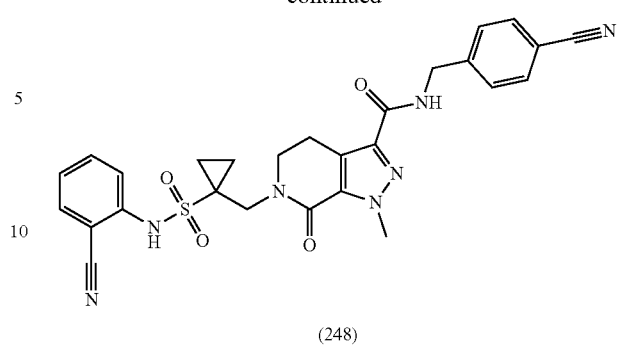

N-(4-cyanobenzyl)-6-((1-(N-(2-cyanophenyl)sulfamoyl)cyclopropyl)methyl)-1-methyl-7-oxo-4,5,6,7-tetrahydro-1H-pyrazolo[3,4-c]pyridine-3-carboxamide (248) was synthesized using the procedure provided for Example 155, except replacing 2-Bromopyridine with bromobenzene. The intermediate (155a) was obtained using the method described in step 4 of Example 123, except methylamine was replaced with NH$_3$. 1H NMR (400 MHz, Methanol-d4) δ 8.16 (dd, J=7.5, 1.8 Hz, 1H), 7.82-7.61 (m, 2H), 7.61-7.41 (m, 2H), 4.62 (s, 2H), 4.26-4.14 (m, 1H), 4.13-4.02 (m, 3H), 3.87 (t, J=6.8 Hz, 2H), 3.11 (q, J=7.1 Hz, 2H), 1.54 (s, 2H), 1.31 (s, 2H), 1.27-1.10 (m, 2H). 19F NMR (376 MHz, Methanol-d4) δ−77.96. LCMS (ESI): m/z 545.2 [M+H]$^+$.

Examples 249-251

N-(4-chloro-3-fluorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide

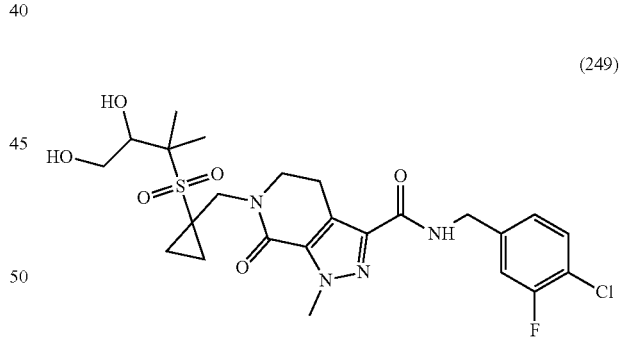

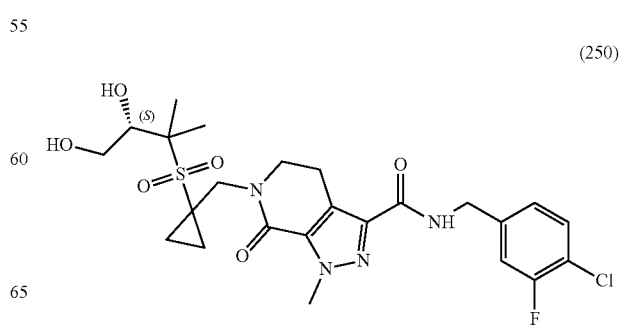

(251)

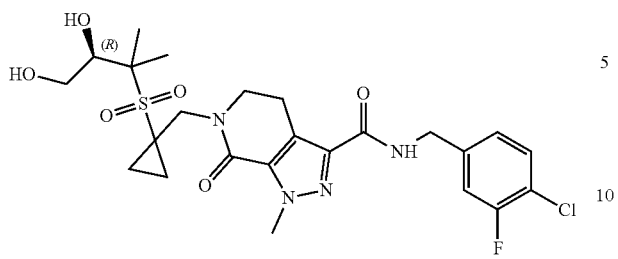

N-(4-chloro-3-fluorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (249) was synthesized using the procedure provided for Example 189 except replacing (4-chlorophenyl)methanamine with (4-chlorophenyl)-methanamine with (4-chloro-3-fluorophenyl)-methanamine. The enantiomers (250, 251) were obtained by chiral SFC separation in a manner like that described in Example 190 and 191. N-(4-chloro-3-fluorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (249): 1H NMR (400 MHz, DMSO-d6) δ 8.93 (t, J=6.3 Hz, 1H), 7.54 (t, J=8.0 Hz, 1H), 7.31 (dd, J=10.4, 2.0 Hz, 1H), 7.16 (dd, J=8.3, 1.9 Hz, 1H), 4.39 (d, J=6.2 Hz, 2H), 4.19-4.03 (m, 5H), 3.86 (dd, J=7.1, 3.4 Hz, 1H), 3.70-3.53 (m, 3H), 3.36 (dd, J=11.4, 7.1 Hz, 1H), 2.98 (t, J=6.8 Hz, 2H), 2.48 (s, 5H), 1.50-1.24 (m, 8H), 1.07-0.96 (m, 2H), 0.96-0.92 (m, 1H). 19F NMR (376 MHz, DMSO-d6) δ −75.61 (d, J=83.6 Hz), -116.87--117.83 (m). LCMS (ESI): m/z 557.2 [M+H]+.

(R)—N-(4-chloro-3-fluorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (250): 1H NMR (400 MHz, DMSO-d6) δ 8.93 (t, J=6.3 Hz, 1H), 7.54 (t, J=8.0 Hz, 1H), 7.31 (dd, J=10.4, 2.0 Hz, 1H), 7.16 (dd, J=8.3, 1.9 Hz, 1H), 4.39 (d, J=6.2 Hz, 2H), 4.19-4.03 (m, 5H), 3.86 (dd, J=7.1, 3.4 Hz, 1H), 3.70-3.53 (m, 3H), 3.36 (dd, J=11.4, 7.1 Hz, 1H), 2.98 (t, J=6.8 Hz, 2H), 2.48 (s, 5H), 1.50-1.24 (m, 8H), 1.07-0.96 (m, 2H), 0.96-0.92 (m, 1H). 19F NMR (376 MHz, DMSO-d6) δ −75.61 (d, J=83.6 Hz), -116.87--117.83 (m). LCMS (ESI): m/z 557.2 [M+H]+. SFC: Rt=4.87 min, 99% ee.

(S)—N-(4-chloro-3-fluorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (251). 1H NMR (400 MHz, DMSO-d6) δ 8.93 (t, J=6.3 Hz, 1H), 7.54 (t, J=8.0 Hz, 1H), 7.31 (dd, J=10.4, 2.0 Hz, 1H), 7.16 (dd, J=8.3, 1.9 Hz, 1H), 4.39 (d, J=6.2 Hz, 2H), 4.19-4.03 (m, 5H), 3.86 (dd, J=7.1, 3.4 Hz, 1H), 3.70-3.53 (m, 3H), 3.36 (dd, J=11.4, 7.1 Hz, 1H), 2.98 (t, J=6.8 Hz, 2H), 2.48 (s, 5H), 1.50-1.24 (m, 8H), 1.07-0.96 (m, 2H), 0.96-0.92 (m, 1H). 19F NMR (376 MHz, DMSO-d6) δ −75.61 (d, J=83.6 Hz), -116.87--117.83 (m). LCMS (ESI): m/z 557.2 [M+H]+. SFC: Rt=6.47 min, 99% ee.

Example 252

N-(4-cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (252)

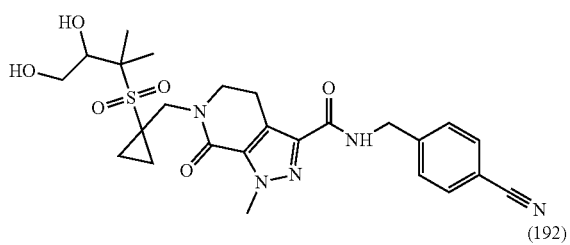
(192)

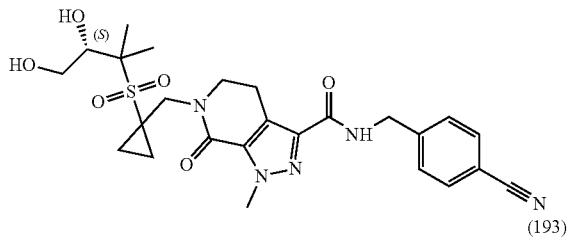
(193)

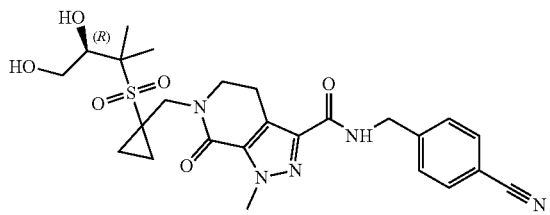

N-(4-cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (252) was synthesized using the procedure provided for Example 189, except replacing (4-chlorophenyl)methanamine with 4-(aminomethyl)benzonitrile. The enantiomers (192) and (193) were obtained by chiral SFC separation in a manner similar to that described in Example 190 and 191.

N-(4-cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (252): 1H NMR (400 MHz, DMSO-d6) 8.98 (t, J=6.3 Hz, 1H), 7.83-7.76 (s, 2H), 7.51-7.44 (m, 2H), 4.47 (d, J=6.3 Hz, 2H), 4.19-4.00 (m, 5H), 3.86 (dd, J=7.1, 3.4 Hz, 1H), 3.70-3.53 (m, 3H), 3.36 (dd, J=11.4, 7.1 Hz, 1H), 2.97 (t, J=6.8 Hz, 2H), 1.42 (s, 3H), 1.31 (d, J=18.3 Hz, 5H), 1.08-0.92 (m, 2H). 19F NMR (376 MHz, DMSO-d6) δ −75.33, −83.92, −84.58. LCMS (ESI): m/z 530.1 [M+H]+.

(S)—N-(4-cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide (192): 19F NMR (376 MHz, DMSO-d6) δ −75.33, −83.92, −84.58.

(R)—N-(4-cyanobenzyl)-6-((1-((3,4-dihydroxy-2-methylbutan-2-yl)sulfonyl)cyclopropyl)methyl)-1-methyl-7- oxo-4,5,6,7-tetrahydro-1H-pyrazolo[3,4-c]pyridine-3-carboxamide (193): 19F NMR (376 MHz, DMSO-d6) δ −75.33, −83.92, −84.58.

Example 262

N-(4-cyanobenzyl)-1-methyl-7-oxo-6-((1-sulfamoylcyclopropyl)methyl)-4,5,6,7-tetrahydro-1H-pyrazolo[3,4-c]pyridine-3-carboxamide

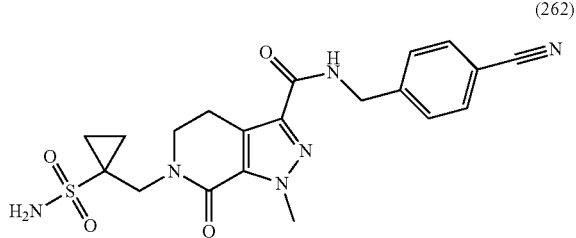 [SMILES: Cn1nc(C(=O)NCc2ccc(C#N)cc2)c2c1C(=O)N(CC1(S(N)(=O)=O)CC1)CC2]

(262)

N-(4-cyanobenzyl)-1-methyl-7-oxo-6-((1-sulfamoylcyclopropyl)methyl)-4,5,6,7-tetrahydro-1H-pyrazolo[3,4-c]pyridine-3-carboxamide (262) was synthesized using the procedure provided for Example 129 except replacing $NH_3$ with the corresponding amine. $^1$H NMR (400 MHz, DMSO-d6) δ 8.94 (t, J=6.3 Hz, 1H), 7.87-7.68 (m, 2H), 7.48 (d, J=8.2 Hz, 2H), 6.91 (s, 2H), 4.47 (d, J=6.2 Hz, 2H), 4.12 (s, 2H), 3.94 (s, 2H), 3.68 (t, J=6.8 Hz, 2H), 2.98 (t, J=6.8 Hz, 2H), 1.20 (dd, J=6.8, 4.5 Hz, 2H), 1.14-0.89 (m, 2H). LCMS (ESI): m/z 443.2 [M+H]$^+$.

The compounds of the present disclosure may also serve as an intermediate in the synthesis of other compounds within the scope of the present disclosure. As one example, reference is made to Example 155, where the present Example 262 serves as an intermediate (labeled 155a) to the final product, Example 155.

Bioactivity of the compounds of the invention was determined using the following methods.

CMV and HSV Polymerase Protein Production

Both human CMV DNA polymerase UL54 and human HSV DNA polymerase UL30 were produced as N-terminal MBP fusion of the full length, wild type recombinant proteins in order to enhance soluble expression in insect cell expression system. The proteins were expressed in sf9 insect cells via baculovirus transduction and cells were harvested after 48 hours. The soluble proteins were purified using the standard Ni-IMAC purification strategy via the N-terminal hexa-Histidine tag, followed by heparin affinity chromatography. Both of the final MBP fusion proteins were more than 90% pure and the yield of UL54 was up to 1.8 mg per liter culture while UL30 was up to 15 mg per liter culture. All purification steps were performed on ice, with buffers chilled on ice and FPLC fraction collectors set at 6° C. The final UL54 protein was concentrated and stored in buffer containing 35 mM Tris pH7.5, 375 mM NaCl, 42.5% Glycerol, and 1 mM TCEP at −20° C. UL30 protein was stored in buffer containing 20 mM HEPES, pH7.0, 420 mM NaCl, 20% glycerol, 6 mM Imidazole, and 0.8 mM DTT at −80° C.

CMV and HSV Polymerase Biochemical Assay

DNA polymerase activity was measured using a molecular beacon-based assay, as described in Ma et. al. 100 pM CMV polymerase or 625 pM HSV polymerase was added to a buffer containing 20 mM Tris, pH=7.5, 100 mM NaCl, 10 mM $MgCl_2$, 0.01% Tween-20, 0.5 mM EDTA, 10% Sucrose and 1 mM DTT. The inhibitor was pre-incubated with the polymerase for 30 minutes at room temperature. Reactions were initiated by the addition of a mixture containing 1.25 uM dATP, 1.25 uM dCTP, 1.25 uM dTTP, 1.25 uM dGTP, 200 nM Primer B (5'-GAC GGG AAG-3'5'-GAC GGG AAG-3') and 100 nM molecular beacon (5'-5,6-FAM-CCT CTC CGT GTC TTG TAC TTC CCG TCA GAG AGG-BHQ1-3'). For human CMV polymerase the reactions were incubated for 60 minutes at room temperature. For HSV polymerase the reactions were incubated for 20 minutes at room temperature. The reactions were then read on a Perkin-Elmer EnVision 2101 reader (fluorescence) using an excitation of 480 nm and emission of 535 nm. IC50s were determined using an internal Novartis software (Helios). References: Ma et. al. (2006). Real-time monitoring of DNA polymerase activity using molecular beacon. *Analytical Biochemistry*, 353 (1): 141-143

CMV Polymerase and HSV Polymerase Assay Protocols 100 pM CMV polymerase or 625 pM HSV polymerase was added to a buffer containing 20 mM Tris, pH=7.5, 100 mM NaCl, 10 mM MgCl2, 0.01% Tween-20, 0.5 mM EDTA, 10% Sucrose and 1 mM DTT. The inhibitor was pre-incubated with the polymerase for 30 minutes at room temperature. Reactions were initiated by the addition of a mixture containing 1.25 uM dATP, 1.25 uM dCTP, 1.25 uM dTTP, 1.25 uM dGTP, 200 nM Primer B (5'-GAC GGG AAG-3'5'-GAC GGG AAG-3') and 100 nM molecular beacon (5'-5,6-FAM-CCT CTC CGT GTC TTG TAC TTC CCG TCA GAG AGG-BHQ1-3'). For human CMV polymerase the reactions were incubated for 60 minutes at room temperature. For HSV polymerase the reactions were incubated for 20 minutes at room temperature. The reactions were then read on a Perkin-Elmer EnVision 2101 reader (fluorescence) using an excitation of 480 nm and emission of 535 nm.

Cellular Herpesvirus Replication Assays

Compound Dilutions:

For all viral assays, 10 mM DMSO stock compound solutions were serially diluted in DMSO at 3.16 fold dilutions in 96-well clear round bottom plates. Compounds were then diluted in assay media at 1:20 and subsequently 10 μL of these dilutions were added to cells for final compound concentrations ranging either from 0.0159 μM to 50 μM in 0.5% DMSO/assay media, or from 0.00318 to 10 μM in 0.5% DMSO/assay media.

CMV Luciferase Assay:

The assay uses a Luciferase-encoding HCMV. Luciferase is expressed under the control of a late viral gene (pp28) promoter in the AD169 strain, so that expression of the reporter is dependent on viral DNA replication. Compounds that affect any stage from viral entry to DNA replication result in a change in luciferase levels.

For compounds 1-242, viral replication in the presence or absence of compounds was measured by luciferase activity according to the following procedure: Neo-natal normal human dermal fibroblast cells (NN-NHDF, from ATCC cat #201-010) were seeded at 9,000 cells/well in 96-well white solid bottom plate at 80 uL/well in assay media: 2% FBS, 4 mM GlutaMax® (Invitrogen cat #35050) in DMEM/high glucose/no glutamine/no phenol red media (Invitrogen cat #31053). After 2 hrs at 37° C., 10 uL of compound diluted in assay media or 5% DMSO (final 0.5% DMSO/well) was added and the plates returned to 37° C. One hour later, 10 uL of virus diluted in assay media was added at a final Multiplicity of infection (MOI) of 1. Plates were incubated at 37° C. for 72 hrs. At 72 hours post-infection (hpi), plates were equilibrated to room temperature. After 25 min, 100 uL Renilla-Glo® Luciferase Assay Reagent (Promega cat #E2750) was added to each well and incubated for 10 min. Plates were covered to protect from light. Luminescence was measured on the PHERAstar FS®.

The following controls were included in the data analysis: No virus, no compound (0.5% DMSO)=IC (maximal inhibitory control); Virus, no compound (0.5% DMSO)=NC (neutral control). Data were analyzed using an internal Novartis software (Helios). The means of the controls (NC, IC) were used to normalize the results to a % scale using the formula:

% Control=100−(100*(Sample value−NC)/(IC−NC)).

For each compound, the software derived an $EC_{50}$ using a 4-parameter logistical model.

CMV Luciferase Assay of Compounds 243-262.

Compounds 243-262 were tested in a luminescence assay as follows.

ARPE-19 cells were maintained in growth medium (DMEM/F12 Glutamax+10 fetal bovine serum (FBS)+PenStrep) and, before reaching full confluence, were transferred to a centrifuge tube and spun for 5 minutes at 1000 rpm. The cells were resuspended in assay medium (DMEM/F12 Glutamax+2% FBS+PenStrep) and counted. Cell density was adjusted to one million cells per milliliter and infected with HCMV-Rluc virus (AD169 pp28-hRluc rUL131; MOI 0.6) in a 50 ml conical tube for 2 hours while shaking. After dilution of the infectious suspension ten-fold (to 100,000 cells per milliliter), 8000 cells are directly plated in 384-well plates pre-spotted with the compound to be tested. The cells were incubated for 72 hours at 37 degrees Celsius. Cells were then placed at room temperature and allowed to equilibrate for 20 minutes before addition of the Renilla-Glo (Promega) reagent. After a 10-minute incubation at room temperature, luminescence was measured on a microplate reader.

HSV-1 qPCR assay: The assay uses KOS strain of HSV-1 virus (ATCC cat #VR-1493). Viral replication in the presence or absence of compounds was measured by qPCR according to the following procedure: NN-NHDF cells were plated at 9,000 cells/well in 96-well white-wall clear bottom plates in 80 µL/well of assay media (same as CMV) and left at room temperature in laminar flow hood for 20 mins followed by incubation at 37° C. One hr later, 10 µL of diluted compound, or 10 µL of 5% DMSO as a control were added to each well (0.5% DMSO final). One hr later, virus was added at a final MOI of 0.01, in 10 uL/well assay media. Cells were then incubated at 37° C. After 24 hrs, medium was removed, cells were washed once with 100 µL DPBS (Invitrogen, cat #21-031-CV), and lysed using the prepGEM® tissue kit (ZyGEM, cat #PTI0500K), by addition of 100 µL of prepGEM® master mix (89 µL $H_2O$, 10 µL 10×prepGEM® Buffer, 1 µL prepGEM® enzyme per well) to each well. Plates were sealed with aluminum foil sealers, and lysed on a heat block at 75° C. for 15 min. Plates were then allowed to cool to room temperature with light shaking before proceeding to the qPCR setup.

VZV qPCR assay: The assay uses co-infection with VZV Ellen strain-infected MRC-5 cells (ATCC cat #VR-1367). Viral replication in the presence or absence of compounds was measured by qPCR according to the following procedure: 12,000 uninfected MRC-5 cells were mixed with VZV-infected MRC-5 cells at a ratio of 1 to 10 infected to uninfected cells, in 96-well white-wall clear bottom plates in 90 µL/well of assay media: 4% FBS in EMEM (ATCC cat #30-2003). After 1 hr at 37° C., 10 µL of diluted compound, or 10 µL of 5% DMSO as a control were added to each well (0.5% DMSO final). Cells were then incubated at 37° C. The chosen ratio of infected to uninfected cells gave approximately 3% VZV-positive cells at 6 hours post co-culturing, as detected by immunofluorescent staining of VZV Immediate Early 62 gene. After two days, medium was removed, cells were washed once with 100 µL DPBS and lysed using the prepGEM tissue kit as described above.

EBV qPCR assay: The assay uses the SNU-719 gastric carcinoma cell line which is latently infected with EBV. Upon reactivation with chemical reagents, EBV DNA copy number was measured by qPCR. Viral replication in the presence or absence of compounds was measured according to the following procedure: SNU-719 cells were plated at $2 \times 10^4$ cells/well in 96-well clear bottom plates, black in 80 µL/well of assay media: 2% FBS in RPMI 1640 (ATCC cat #30-2001). After 1 hr at 37° C., 10 µL of diluted compound, or 10 µL of 5% DMSO as a control, were added to each well (0.5% DMSO final). Lytic replication of the virus was then activated by addition of 10 µL of a mixture of 20 ng/ml tetradecanoyl phorbol acetate (TPA) and 3 mM sodium butyrate (NaB). At 18 hpi, media was removed, fresh assay media with compound or DMSO was added, and cells were returned to 37° C. After 72 hrs of lytic replication, media was removed, cells were washed with 100 µL DPBS and lysed using the prepGEM tissue kit as before.

qPCR Procedure and Data Analysis for HSV, VZV and EBV:

qPCR reactions were carried out in a total reaction volume of 20 µL, using the QuantiFast® Multiplex PCR kit (Qiagen cat #204656). Eighteen µL of qPCR master mix (10 µL of 2× QuantiFast® Multiplex PCR Master Mix, 1 µL of 20× Primer/Probe Mix specific to housekeeping gene, 1 µL of 20× Primer/Probe Mix specific to viral gene, 6 µL of $H_2O$) was distributed into each well of a 384 well plate. Two µL of cell lysate was added to each well. Each cell lysate was run in duplicate. Plates were sealed with a clear sealer, spun down, and qPCR reactions were performed in an ABI 7900HT instrument using the following conditions: 95° C. for 5 min, then 40 cycles: 95° C. for 30 sec.

Relative quantification was calculated with the $\Delta \Delta C_T$ Method, and then converted into percent inhibitions. Virus+ DMSO samples (without drug) were used to determine the calibrator. $EC_{50}$ values were calculated using XLFit Dose Response One Site Model 205. PCR primers and probes

| Primer/probe specificity | Sequence (5'-3') |
|---|---|
| HSV-1 qPCR: | |
| HSV-1 gpJ gene, forward primer | TAGTCGGTGGGCTGTGT (SEQ ID NO: 1) |
| HSV-1 gpJ gene, reverse primer | AACTGGGTCCATGTAGGGAT (SEQ ID NO: 2) |
| HSV-1 gpJ gene, probe | TGCTTGAGCTCCTGCGTCGTAC (SEQ ID NO: 3) |

-continued

| Primer/probe specificity | Sequence (5'-3') |
|---|---|
| VZV qPCR: | |
| VZV IE62 gene, forward primer | CCTCCGTATCGGGACTTCAA (SEQ ID NO: 4) |
| VZV IE62 gene, reverse primer | TGACCGTCCTCGCATACGTA (SEQ ID NO: 5) |
| VZV IE62 gene, probe | TTGGCGAAGAGCTAAC (SEQ ID NO: 6) |
| Housekeeping gene for HSV and VZV assays: | |
| Forward MT-ATP6 primer | ACACCCCTTATCCCCATACTAG (SEQ ID NO: 7) |
| Reverse MT-ATP6 primer | ATGGTTGATATTGCTAGGGTGG (SEQ ID NO: 8) |
| MT-ATP6 probe | ACCGCTAACATTACTGCAGGCCA (SEQ ID NO: 9) |
| EBV qPCR: | |
| EBV BNRF1 forward primer | CGGCCGTGATGGAGGCTATG (SEQ ID NO: 10) |
| EBV BNRF1 reverse primer | AGACAGAGGCCACCACGG (SEQ ID NO: 11) |
| EBV BNRF1 probe | TGACCTTTGGCTCGGCCTCCTGC (SEQ ID NO: 12) |
| Housekeeping gene for EBV assay: | |
| HuALB forward primer | GCTGTCATCTCTTGTGGGCTGT (SEQ ID NO: 13) |
| HuALB reverse primer | AAACTCATGGGAGCTGCTGGTT (SEQ ID NO: 14) |
| HuALB probe | CCTGTCATGCCCACACAAATCTCTCC (SEQ ID NO: 15) |

TABLE 17

Bioactivity Data

| Example No. | CMV-polymerase Biochemical $IC_{50}$ (uM) | CMV-Luc Cellular $EC_{50}$ (uM) | HSV-polymerase Biochemical $IC_{50}$ (uM) |
|---|---|---|---|
| 1 | 0.010 | 0.124 | 0.269 |
| 2 | 0.027 | 0.536 | 1.876 |
| 3 | 0.002 | 0.039 | 0.055 |
| 4 | 0.002 | 0.023 | 0.048 |
| 5 | 0.030 | 0.284 | 0.416 |
| 6 | 0.030 | 0.770 | 0.959 |
| 7 | 0.056 | 0.534 | 0.861 |
| 8 | 0.035 | 0.339 | 1.632 |
| 9 | 0.001 | 0.031 | 0.045 |
| 10 | 0.026 | 0.259 | 0.641 |
| 11 | 0.017 | 0.214 | 2.229 |
| 12 | 0.002 | 0.087 | 0.346 |
| 13 | 0.006 | 0.102 | 0.311 |
| 14 | 0.095 | 0.585 | 1.611 |
| 15 | 0.011 | 0.162 | 0.385 |
| 16 | 0.013 | 0.170 | 0.239 |
| 17 | 16.924 | >10 | >25 |
| 18 | 0.022 | 0.301 | 1.055 |
| 19 | 0.055 | >10 | 8.183 |
| 20 | 0.006 | 0.106 | 0.259 |
| 21 | 0.009 | 0.147 | 0.517 |
| 22 | 0.012 | 0.113 | 0.436 |
| 23 | 0.007 | 0.086 | 0.345 |
| 24 | 0.018 | 0.197 | 0.467 |
| 25 | 0.002 | 0.030 | 0.053 |
| 26 | 0.052 | 0.761 | 3.956 |
| 27 | 0.007 | 0.211 | nd |
| 28 | 0.001 | 0.024 | 0.029 |
| 29 | 0.001 | 0.080 | 0.086 |
| 30 | 0.940 | >10 | 6.238 |
| 31 | 0.012 | 0.101 | 0.293 |
| 32 | 0.003 | 0.041 | 0.161 |
| 33 | 1.185 | 9.935 | >25 |
| 34 | 0.001 | 0.010 | 0.010 |
| 35 | 0.003 | 0.038 | 0.141 |
| 36 | 0.005 | 0.571 | nd |
| 37 | 0.007 | 0.105 | nd |
| 38 | 0.014 | 0.607 | 0.784 |
| 39 | 0.025 | 0.376 | 0.625 |
| 41 | 9.770 | >10 | nd |
| 42 | 0.149 | 1.184 | 1.999 |
| 43 | 0.002 | 0.066 | 0.101 |
| 44 | 0.004 | 0.076 | 0.137 |
| 45 | 0.006 | 0.146 | 0.169 |
| 46 | 0.041 | 0.746 | 1.777 |
| 47 | 0.002 | 0.042 | 0.059 |
| 48 | 0.011 | 0.331 | 0.801 |
| 49 | 0.004 | 0.058 | 0.037 |
| 50 | 0.001 | 0.020 | 0.016 |
| 51 | 0.006 | 0.172 | 0.089 |
| 52 | 0.001 | 0.019 | 0.019 |
| 53 | 0.007 | 0.141 | 0.070 |
| 54 | 0.002 | 0.053 | 0.103 |
| 55 | 0.601 | >10 | >25 |
| 56 | 0.001 | 0.021 | 0.017 |
| 57 | 0.001 | 0.022 | 0.035 |

TABLE 17-continued

Bioactivity Data

| Example No. | CMV-polymerase Biochemical IC$_{50}$ (uM) | CMV-Luc Cellular EC$_{50}$ (uM) | HSV-polymerase Biochemical IC$_{50}$ (uM) |
|---|---|---|---|
| 58 | 0.001 | 0.025 | 0.024 |
| 59 | 0.001 | 0.033 | 0.023 |
| 60 | 0.002 | 0.062 | 0.045 |
| 61 | 0.006 | 0.145 | 0.075 |
| 62 | 0.004 | 0.136 | 0.139 |
| 63 | 0.006 | 0.220 | 0.100 |
| 64 | 0.004 | 0.106 | 0.060 |
| 65 | 0.002 | 0.050 | 0.052 |
| 66 | 0.002 | 0.088 | 0.050 |
| 67 | 0.002 | 0.082 | 0.048 |
| 68 | 0.001 | 0.115 | 0.021 |
| 69 | 0.001 | 0.057 | 0.040 |
| 70 | 0.003 | 0.061 | 0.037 |
| 71 | 0.001 | 0.095 | 0.033 |
| 72 | 0.002 | 0.083 | 0.051 |
| 73 | 0.002 | 0.053 | 0.040 |
| 74 | 0.003 | 0.148 | 0.065 |
| 75 | 0.007 | 0.047 | 0.133 |
| 76 | 0.010 | 0.084 | 0.123 |
| 77 | 0.012 | 0.115 | 0.142 |
| 78 | 0.026 | 0.112 | 0.206 |
| 80 | 0.006 | 0.036 | 0.067 |
| 81 | 0.003 | 0.042 | 0.046 |
| 82 | 0.002 | 0.029 | 0.082 |
| 83 | 0.001 | 0.133 | 0.071 |
| 84 | 0.004 | 0.051 | 0.045 |
| 85 | 0.003 | 0.050 | 0.049 |
| 86 | 0.018 | 0.145 | 0.159 |
| 87 | 0.001 | 0.044 | 0.032 |
| 88 | 0.002 | 0.036 | 0.039 |
| 90 | 0.007 | 0.058 | 0.097 |
| 91 | 0.005 | 0.076 | 0.069 |
| 92 | 0.001 | 0.012 | 0.030 |
| 93 | 0.001 | 0.005 | 0.025 |
| 94 | 0.009 | 0.022 | 0.054 |
| 95 | 0.002 | 0.011 | 0.025 |
| 96 | 0.001 | 0.026 | 0.020 |
| 97 | 0.001 | 0.008 | 0.023 |
| 98 | 0.001 | 0.008 | 0.026 |
| 99 | 0.004 | 0.014 | 0.063 |
| 100 | 0.004 | 0.013 | 0.060 |
| 101 | 0.001 | 0.009 | 0.032 |
| 102 | 0.005 | 0.026 | 0.042 |
| 103 | 0.009 | 0.041 | 0.117 |
| 104 | 0.003 | 0.021 | 0.108 |
| 105 | 0.001 | 0.042 | 0.032 |
| 107 | 0.872 | >10 | >25 |
| 108 | 0.001 | 0.032 | 0.047 |
| 109 | 0.003 | 0.078 | 0.076 |
| 110 | 0.005 | 0.218 | 0.166 |
| 111 | 0.005 | 0.159 | 0.148 |
| 112 | 0.002 | 0.064 | 0.089 |
| 113 | 0.003 | 0.036 | 0.038 |
| 115 | 0.003 | 0.059 | 0.071 |
| 116 | 0.002 | 0.039 | 0.048 |
| 117 | 0.004 | 0.035 | 0.059 |
| 118 | 0.019 | 0.327 | 0.412 |
| 119 | 0.004 | 0.156 | 0.153 |
| 120 | 0.003 | 0.151 | 0.091 |
| 121 | 0.008 | 0.156 | 0.671 |
| 122 | 0.007 | 0.298 | 0.324 |
| 123 | 0.009 | 0.157 | 0.196 |
| 124 | 0.006 | 0.156 | 0.121 |
| 125 | 0.003 | 0.196 | 0.136 |
| 126 | 0.004 | 0.118 | 0.084 |
| 127 | 0.004 | 0.122 | 0.067 |
| 128 | 0.005 | 0.094 | 0.137 |
| 129 | 0.016 | 0.247 | 0.213 |
| 130 | 0.007 | 0.163 | 0.122 |
| 131 | 0.016 | 0.223 | 0.162 |
| 132 | 0.020 | 0.289 | 0.451 |
| 133 | 0.020 | 0.097 | 0.258 |
| 134 | 0.031 | 0.443 | 0.282 |
| 135 | 0.062 | 0.536 | 1.086 |
| 136 | 0.018 | 0.199 | 0.243 |
| 137 | 0.044 | 0.636 | 0.691 |
| 138 | 0.021 | 0.127 | 0.326 |
| 139 | 0.008 | 0.533 | 0.143 |
| 140 | 0.011 | 0.418 | 0.147 |
| 141 | 0.013 | 0.051 | 0.192 |
| 142 | 0.018 | 0.066 | 0.268 |
| 143 | 0.019 | 0.138 | 0.344 |
| 144 | 0.004 | 0.044 | 0.067 |
| 145 | 0.014 | 0.303 | 0.237 |
| 146 | 0.003 | 0.061 | 0.074 |
| 147 | 0.030 | 0.604 | 0.644 |
| 148 | 0.015 | 0.139 | 0.155 |
| 149 | 0.012 | 0.166 | 0.161 |
| 150 | 0.006 | 0.067 | 0.081 |
| 151 | 0.008 | 0.064 | 0.118 |
| 152 | 0.030 | 0.834 | 0.827 |
| 153 | 0.020 | 0.305 | 0.292 |
| 154 | 0.002 | 0.083 | 0.038 |
| 155 | 0.002 | 0.057 | 0.078 |
| 156 | 0.003 | 0.100 | 0.062 |
| 157 | 0.002 | 0.058 | 0.046 |
| 158 | 0.003 | 0.037 | 0.058 |
| 159 | 0.013 | 0.298 | 0.423 |
| 160 | 0.006 | 0.118 | 0.301 |
| 161 | 0.002 | 0.061 | 0.040 |
| 162 | 0.001 | 0.030 | 0.018 |
| 163 | 0.002 | 0.067 | 0.036 |
| 164 | 0.006 | 0.157 | 0.185 |
| 165 | 0.001 | 0.136 | 0.014 |
| 166 | 0.001 | 0.088 | 0.012 |
| 167 | 0.004 | 0.517 | 0.104 |
| 168 | 0.004 | 0.072 | 0.097 |
| 169 | 0.014 | 0.201 | 0.238 |
| 170 | 0.004 | 0.124 | 0.122 |
| 171 | 0.003 | 0.104 | 0.078 |
| 172 | 0.005 | 0.069 | 0.063 |
| 173 | 0.003 | 0.074 | 0.062 |
| 174 | 0.006 | 0.212 | 0.092 |
| 175 | 0.003 | 0.026 | 0.027 |
| 176 | 0.002 | 0.052 | 0.039 |
| 177 | 0.004 | 0.168 | 0.122 |
| 178 | 0.240 | 9.723 | 8.059 |
| 179 | 0.002 | 0.049 | 0.061 |
| 181 | 0.004 | 0.077 | 0.069 |
| 182 | 0.002 | 0.050 | 0.046 |
| 183 | 0.005 | 0.220 | 0.065 |
| 184 | 0.004 | 0.165 | 0.052 |
| 185 | 0.004 | 0.275 | 0.059 |
| 186 | 0.008 | 0.090 | 0.037 |
| 187 | 0.013 | 0.071 | 0.086 |
| 188 | 0.022 | 0.160 | 0.108 |
| 190 | 0.001 | 0.019 | 0.020 |
| 191 | 0.001 | 0.005 | 0.011 |
| 192 | 0.001 | 0.035 | 0.030 |
| 193 | 0.001 | 0.022 | 0.011 |
| 194 | 0.001 | 0.050 | 0.020 |
| 195 | 0.001 | 0.053 | 0.023 |
| 196 | 0.001 | 0.019 | 0.019 |
| 197 | 0.001 | 0.020 | 0.019 |
| 198 | 0.001 | 0.018 | 0.023 |
| 199 | 0.001 | 0.019 | 0.028 |
| 200 | 0.001 | 0.005 | 0.014 |
| 201 | 0.001 | 0.006 | 0.015 |
| 202 | 0.002 | 0.030 | 0.030 |
| 203 | 0.002 | 0.019 | 0.038 |
| 204 | 0.003 | 0.011 | 0.037 |
| 205 | 0.002 | 0.009 | 0.029 |
| 206 | 0.021 | 0.071 | 0.074 |
| 207 | 0.023 | 0.050 | 0.088 |
| 208 | 0.001 | 0.051 | 0.022 |
| 209 | 0.001 | 0.010 | 0.016 |
| 211 | 0.009 | 0.028 | 0.077 |
| 212 | 0.003 | 0.007 | 0.039 |

TABLE 17-continued

Bioactivity Data

| Example No. | CMV-polymerase Biochemical IC$_{50}$ (uM) | CMV-Luc Cellular EC$_{50}$ (uM) | HSV-polymerase Biochemical IC$_{50}$ (uM) |
|---|---|---|---|
| 213 | 0.002 | 0.081 | 0.048 |
| 214 | 0.003 | 0.042 | 0.032 |
| 215 | 0.001 | 1.900 | 0.028 |
| 216 | 0.002 | 0.067 | 0.069 |
| 217 | 0.001 | 0.029 | 0.026 |
| 218 | 0.006 | 0.042 | 0.050 |
| 219 | 0.030 | 0.207 | 0.401 |
| 220 | 0.001 | 0.049 | 0.023 |
| 221 | 0.001 | 0.017 | 0.013 |
| 222 | 0.003 | 0.033 | 0.043 |
| 223 | 0.005 | 0.049 | 0.035 |
| 225 | 0.004 | 0.063 | 0.090 |
| 226 | 0.002 | 0.044 | 0.101 |
| 227 | 0.001 | 0.028 | 0.031 |
| 228 | 0.002 | 0.051 | 0.056 |
| 229 | 0.001 | 0.020 | 0.031 |
| 230 | 0.001 | 0.031 | 0.034 |
| 231 | 0.007 | 0.088 | 0.278 |
| 232 | 0.006 | 0.160 | 0.339 |
| 233 | 0.002 | 0.096 | 0.150 |
| 234 | 0.001 | 0.049 | 0.019 |
| 235 | 0.001 | 0.031 | 0.016 |
| 236 | 0.004 | 0.077 | 0.091 |
| 237 | 0.002 | 0.038 | 0.041 |
| 238 | 0.001 | 0.016 | 0.016 |
| 239 | 0.001 | 0.023 | 0.020 |
| 240 | 0.001 | 0.043 | 0.034 |
| 241 | 0.013 | 0.467 | 0.393 |
| 242 | 0.006 | 0.101 | 0.319 |

Note:
nd indicates not determined

TABLE 18

Cellular activity against various human herpesviruses (EC$_{50}$, μM)

| Example No. | CMV | HSV-1 | VZV | EBV |
|---|---|---|---|---|
| 3 | 0.039 | 0.033 | 0.011 | nd |
| 4 | 0.023 | 0.064 | 0.008 | nd |
| 92 | 0.012 | 0.03 | nd | nd |
| 175 | 0.026 | 0.058 | 0.034 | 0.008 |
| 176 | 0.052 | 0.095 | 0.074 | 0.014 |
| 193 | 0.026 | 0.058 | 0.034 | 0.008 |
| 198 | 0.022 | 0.05 | 0.039 | 0.004 |
| 199 | 0.018 | 0.03 | 0.127 | 0.011 |
| 200 | 0.005 | 0.016 | nd | nd |
| 201 | 0.006 | 0.018 | nd | nd |
| 216 | 0.067 | 0.112 | 0.109 | 0.028 |
| 217 | 0.029 | 0.036 | nd | nd |
| 221 | 0.017 | 0.01 | nd | nd |
| 234 | 0.049 | 0.083 | 0.115 | 0.011 |

Note:
nd indicates not determined

TABLE 19

Bioactivity Data

| Example No. | CMV-Luc Cellular EC$_{50}$ in ARPE-19 (nM) |
|---|---|
| 243 | 115.42 |
| 244 | 116.31 |
| 245 | 181.13 |
| 246 | 74.461 |
| 247 | 387.64 |
| 248 | 10000 |
| 249 | 8.244 |
| 250 | 26.72 |
| 251 | 9.83 |
| 252 | 21.86 |
| 253 | 386.03 |
| 254 | 1000 |
| 255 | 312.51 |
| 256 | 10000 |
| 257 | 357.64 |
| 258 | 687.79 |
| 259 | 713.61 |
| 260 | 277.87 |
| 261 | 2576 |
| 262 | 251.82 |

The invention claimed is:
1. A compound of Formula (I), or a pharmaceutically acceptable salt thereof,

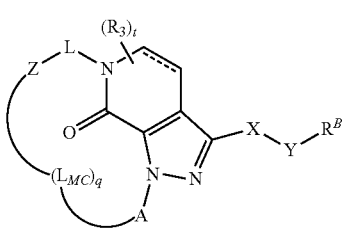

wherein:
X is

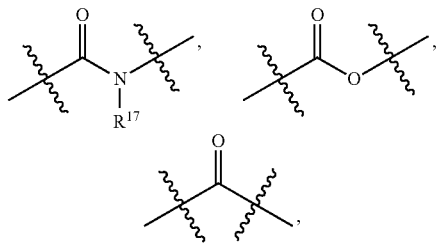

a 5-6 membered heteroaryl having 1 to 4 heteroatoms independently selected from N, O and S as ring members, or a saturated or partially saturated 5-6 membered heterocyclyl containing 1 to 4 ring members independently selected from N, NH, $NR^{17}$, O or S;
Y is a bond,

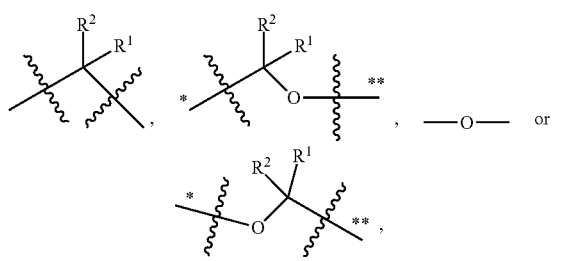

wherein the * of Y indicates the point of attachment to X and the ** of Y indicates the point of attachment to $R^B$;
q is 0;
$L_{MC}$ is absent, and Z is W, and A is $R^4$;

$R^B$ is phenyl, pyridinyl, thiophenyl, pyrimidinyl, or a 5-8 membered cycloalkyl, wherein $R^B$ is optionally substituted with 1 to 3 $R^5$ groups;
$R^1$ is selected from H, $C_1$-$C_3$alkyl and $C_1$-$C_3$alkyl substituted with 1 to 3 —OH groups;
$R^2$ is selected from H, $C_1$-$C_3$alkyl and $C_1$-$C_3$alkyl substituted with 1 to 3 —OH groups;
or $R^1$ and $R^2$ taken together with the carbon to which they are attached can form a 3-6 membered cycloalkyl ring;
t is 0, 1 or 2;
each $R^3$, when present, is a substituent on the ring to which -L-W is directly attached, wherein each $R^3$ is independently selected from halo, CN, $C_1$-$C_3$alkoxy, $C_1$-$C_3$alkyl, $C(=O)OR^{10}$, and $C(=O)NR^{13}R^{14}$;
$R^4$ is H, $C_1$-$C_3$alkyl, $C_3$-$C_6$cycloalkyl, —$(CH_2)_2O(CH_2)_2$Br or a $C_1$-$C_3$alkyl substituted with 1 to 2 groups independently selected from —OH, —$C(=O)R^{15}$ and $R^{10}$;
each $R^5$ is independently selected from halo, —CN, hydroxy, —$NR^{13}R^{14}$, $C_3$-$C_6$cycloalkyl, $C_1$-$C_3$alkoxy, $C_1$-$C_3$haloalkyl, and $C_1$-$C_3$alkyl optionally substituted with 1 to 3 $R^6$ groups, wherein when $R^B$ is substituted with two $R^5$ and each $R^5$ is a $C_1$-$C_3$alkyl optionally substituted with 1 to 3 $R^6$ groups, when directly attached to the same carbon atom, may be taken together with the carbon to which both are directly attached to form a 3-5 membered cycloalkyl ring optionally substituted with 1 to 3 $R^6$ groups;
each $R^6$ is independently selected at each occurrence from halo, hydroxy, CN, $C_1$-$C_3$alkoxy, $C_1$-$C_3$alkyl, and $C_3$-$C_5$cycloalkyl,
or two $R^6$ groups, taken together with a carbon atom to which both are directly attached may form a 3-5 membered cycloalkyl ring or a 4-6 membered heterocyclic ring containing O, N or S as a ring member and optionally substituted with 1 to 2 groups independently selected from oxo and $C_1$-$C_3$alkyl;
L is a $C_1$-$C_4$ straight chain or branched alkylene linker, or L can be a $C_1$-$C_4$ straight chain or branched alkylene linker or a bond when W is an optionally substituted ring;
W is H, —OH, —$OR^{10}$, —$C(=O)NR^{13}R^{14}$, —$C(=O)OR^{13}$, —$NR^{13}R^{14}$, —$NR^{13}C(=O)OR^{10}$, —$NR^{13}C(=O)R^{10}$, —$SO_2R^{10}$, —$SO_2NR^{13}R^{14}$, —$NR^{13}SO_2R^{10}$, —$P(=O)(OR^{13})_2$, —$S(=O)R^{10}$, —$S(=O)(=NR^{13})R^{10}$, —$CR^{11}R^{12}C(=O)NR^{13}R^{14}$, —$CR^{11}R^{12}C(=O)OR^{13}$, —$CR^{11}R^{12}NR^{13}R^{14}$, —$CR^{11}R^{12}NR^{13}C(=O)OR^{10}$, —$CR^{11}R^{12}NR^{13}C(=O)R^{10}$, —$CR^{11}R^{12}SO_2R^{10}$, —$CR^{11}R^{12}SO_2NR^{13}R^{14}$, —$CR^{11}R^{12}NR^{13}SO_2R^{10}$, —$CR^{11}R^{12}P(=O)(OR^{13})_2$, —$CR^{11}R^{12}S(=O)R^{10}$, —$CR^{11}R^{12}S(=O)(=NR^{13})R^{10}$, a 3-6 membered cycloalkyl, phenyl, a saturated or partially saturated 5-6-membered heterocyclyl containing one or two ring members independently selected from N, NH, NR$^{17}$, O or S, or a 5-membered heteroaryl having 1 to 4 heteroatoms selected from N, O and S as ring members that are optionally fused to phenyl, wherein the 3-6 membered cycloalkyl, phenyl, saturated or partially saturated 5-6-membered heterocyclyl and 5-membered heteroaryl of W are each optionally substituted with 1 to 3 groups independently selected from C$_1$-C$_3$alkyl, oxo, halo, C$_1$-C$_3$haloalkyl, —OH, —OR$^{10}$, —OC(=O) NR$^{13}$R$^{14}$, —SO$_2$R$^{10}$, —SO$_2$NR$^{14}$R$^{10}$, —SO$_2$ NR$^{13}$R$^{14}$, —SO$_2$N=CR$^{13}$NR$^{13}$R$^{14}$, —SO$_2$NR$^{13}$C (=O)R$^{10}$, —C(=O)NR$^{13}$SO$_2$R$^{10}$, —S(=O)R$^{10}$, —S(=O)(=NR$^{13}$)R$^{10}$, —NR$^{13}$SO$_2$NR$^{13}$R$^{14}$, —NR$^{13}$SO$_2$R$^{10}$, —NR$^{13}$R$^{14}$, —NR$^{13}$C(=O)R$^{13}$, —NR$^{13}$C(=O)OR$^{10}$, —C(=O)NR$^{13}$R$^{14}$, and —C(=O)OR$^{13}$;

R$^{10}$ is selected from C$_1$-C$_5$alkyl, C$_1$-C$_3$haloalkyl, 3-6 membered cycloalkyl, phenyl, 5-6 membered heteroaryl having 1 to 4 heteroatoms independently selected from N, O and S as ring members, and saturated or partially saturated 4-6 membered heterocyclyl containing 1 to 2 ring members independently selected from N, NH, NR$^{17}$, O or S, wherein each R$^{10}$ is optionally substituted with 1 to 5 groups independently selected from C$_1$-C$_4$alkyl, deuterium, C$_1$-C$_4$haloalkoxy, —OH, —CN, —OC(=O)R$^{14}$, -L$^3$OR$^{13}$, C$_1$-C$_2$haloalkyl, oxo, -halo, —C$_1$-C$_3$alkoxy, —OC(=O)NR$^{13}$R$^{14}$, —SO$_2$R$^{13}$, —SO$_2$NR$^{13}$R$^{14}$, —SO$_2$NR$^{13}$C(=O)R$^{13}$, —C(=O)NR$^{13}$SO$_2$R$^{13}$, —S(=O)R$^{13}$, —S(=O)(=NR$^{14}$)R$^{13}$, —NR$^{13}$SO$_2$NR$^{13}$R$^{14}$, —NR$^{13}$SO$_2$R$^{13}$, —NR$^{13}$R$^{14}$, —NRC(=O)R$^{13}$, —NR$^{14}$C(=O)OR$^{13}$, —C(=O) NR$^{13}$R$^{14}$, —C(=O)OR$^{13}$, (saturated or partially saturated 4-7-membered heterocyclyl containing 1 to 2 ring members independently selected from N, NH, NR$^{17}$, O or S), —C$_3$-C$_5$cycloalkyl, and (5-6 membered heteroaryl ring having 1 to 4 heteroatoms comprising 1-4 nitrogen atoms, 0 or 1 oxygen atoms, and 0 or 1 sulfur atoms as ring members), where the C$_1$-C$_4$alkyl, saturated or partially saturated 4-7-membered heterocyclyl, C$_3$-05cycloalkyl and 5-6 membered heteroaryl ring are each optionally further substituted with 1 to 3 groups independently selected from halo, C$_1$-C$_3$alkyl, C$_1$-C$_3$haloalkyl, —OR$^{13}$, —CN, and —NR$^{13}$R$^{14}$;

R$^{11}$ and R$^{12}$ are each independently selected from H and C$_1$-C$_4$alkyl;

each R$^{13}$ is independently selected from H, C$_1$-C$_4$alkyl, a saturated or partially saturated 4-7-membered heterocyclyl containing 1 to 2 ring members independently selected from N, NH, NR$^{17}$, O or S, and a C$_3$-C$_6$cycloalkyl, wherein the C$_1$-C$_4$alkyl, the saturated or partially saturated 4-7 membered heterocyclyl, and the C$_3$-C$_6$cycloalkyl are optionally substituted with 1 to 3 groups independently selected from C$_1$-C$_4$alkyl, halo, —OH, —NR$^{15}$R$^{16}$, —C(=O)OR$^{15}$, C$_1$-C$_2$alkoxy and C$_1$-C$_4$alkyl substituted with 1 to 2 hydroxy groups;

R$^{14}$ is selected from H, C$_1$-C$_4$alkyl and C$_3$-C$_6$cycloalkyl, wherein the C$_1$-C$_4$alkyl and C$_3$-C$_6$cycloalkyl are optionally substituted with 1 to 3 groups independently selected from C$_1$-C$_4$alkyl, halo, —OH, —NR$^{15}$R$^{16}$, C$_1$-C$_2$alkoxy and C$_1$-C$_4$alkyl substituted with 1 to 2 hydroxy groups;

or R$^{13}$ and R$^{14}$, taken together with a nitrogen atom to which both are directly attached, can form a 4-6 membered ring optionally containing an additional N, O or S as a ring member and optionally substituted with one to three groups selected from C$_1$-C$_2$alkyl, C$_1$-C$_2$alkoxy, oxo, and hydroxy;

R$^{15}$ and R$^{16}$ are each independently selected from H and C$_1$-C$_4$alkyl;

each R$^{17}$ is independently selected from H, C$_1$-C$_4$alkyl and C$_3$-C$_8$cycloalkyl, or R$^{17}$ is C$_1$-C$_4$alkyl which, together with a nitrogen atom to which it is directly attached and a nitrogen atom from the pyrazole ring, can form a 5-8 membered ring fused to the pyrazole ring;

L$^3$ is a bond or a straight chain or branched C$_1$-C$_3$alkylene;

and

'---' represents a single or double bond.

2. The compound of claim 1 having the structure of Formula (II), or a pharmaceutically acceptable salt thereof,

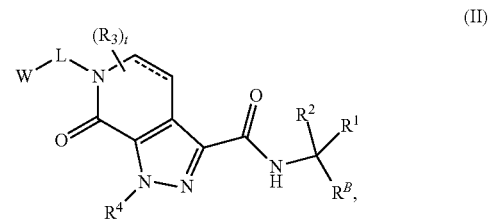

wherein W, L, R$^1$, R$^2$, R$^3$, R$^4$ and R$^B$ are as defined in claim 1.

3. The compound of claim 1, wherein:

R$^B$ is phenyl, pyridinyl, thiophenyl or a 5-8 membered cycloalkyl, wherein R$^B$ is optionally substituted with 1 to 3 R$^5$ groups;

R$^1$ is selected from H, C$_1$-C$_3$alkyl and a C$_1$-C$_3$alkyl substituted with 1 to 3 —OH groups;

R$^2$ is H;

each R$^3$, when present, is a substituent on the ring to which -L-W is directly attached, wherein each R$^3$ is independently selected from C$_1$-C$_3$alkyl;

each R$^5$ is independently selected from halo, —CN, C$_1$-C$_3$alkoxy and C$_1$-C$_3$alkyl;

W is a 3-6 membered cycloalkyl, wherein the 3-6 membered cycloalkyl is substituted with 1 to 3 groups independently selected from —SO$_2$R$^{10}$, —SO$_2$NR$^{14}$R$^{10}$, —SO$_2$NR$^{13}$R$^{14}$, and —SO$_2$N=CR$^{13}$NR$^{13}$R$^{14}$;

R$^{10}$ is selected from C$_1$-C$_5$alkyl, C$_1$-C$_3$haloalkyl, 3-6 membered cycloalkyl, 5-6 membered heteroaryl having 1 to 4 heteroatoms independently selected from N, O and S as ring members, and saturated or partially saturated 4-6 membered heterocyclyl containing 1 to 2 ring members independently selected from N, NH, NR$^{17}$, O or S, wherein each R$^{10}$ is optionally substituted with 1 to 5 groups independently selected from C$_1$-C$_4$alkyl, deuterium, C$_1$-C$_4$haloalkoxy, —OH, —CN, —OC(=O)R$^{14}$, -L$^3$OR$^{13}$, —NR$^{13}$R$^{14}$, —NR$^{14}$C(=O) R$^{13}$, —NR$^{14}$C(=O)OR$^{13}$, —C(=O)NR$^{13}$R$^{14}$, —C(=O)OR$^{13}$, (saturated or partially saturated 4-7-membered heterocyclyl containing 1 to 2 ring members independently selected from N, NH, NR$^{17}$, O or S) and —C$_3$-C$_5$cycloalkyl, where the C$_1$-C$_4$alkyl, saturated or partially saturated 4-7-membered heterocyclyl, and C$_3$-C$_5$cycloalkyl are each optionally further substituted with 1 to 3 groups independently selected from halo, —OR$^{13}$, and —NR$^{13}$R$^{14}$;

each R$^{13}$ is independently selected from H, C$_1$-C$_4$alkyl, a saturated or partially saturated 4-7-membered heterocyclyl containing 1 to 2 ring members independently selected from N, NH, NR$^{17}$, O or S, and a C$_3$-C$_6$cycloalkyl, wherein the C$_1$-C$_4$alkyl, saturated or partially saturated 4-7-membered heterocyclyl and C$_3$-C$_6$cycloalkyl are optionally substituted with 1 to 3 groups independently selected from C$_1$-C$_4$alkyl, halo, —OH, —NR$^{15}$R$^{16}$, —C(=O)OR$^{15}$, C$_1$-C$_2$alkoxy and C$_1$-C$_4$alkyl substituted with 1 to 2 hydroxy groups;

R$^{14}$ is selected from H and C$_1$-C$_4$alkyl;

wherein t, R$^4$, L, R$^{11}$, R$^{12}$, R$^{13}$, R$^{15}$, R$^{16}$, L$^3$, and '---' are as defined in claim 1.

4. The compound of claim 1, having the structure of Formula (IIIa), Formula (IIIb) or Formula (IIIc), or a pharmaceutically acceptable salt thereof:

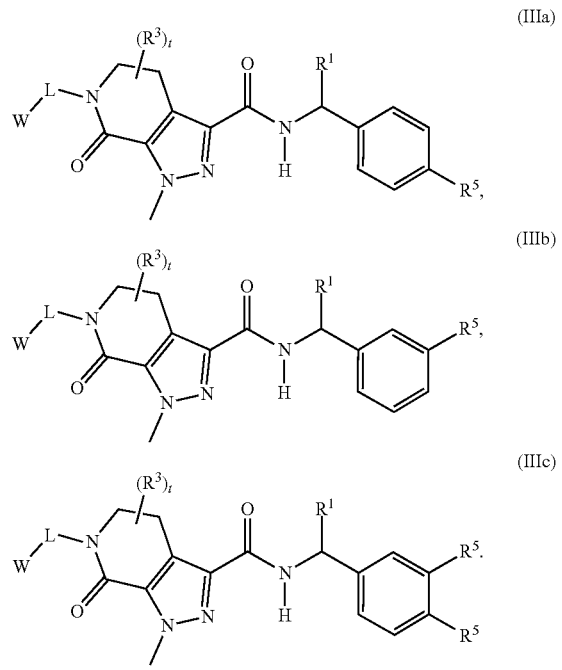

5. The compound of claim 1, wherein the moiety W-L- is selected from:

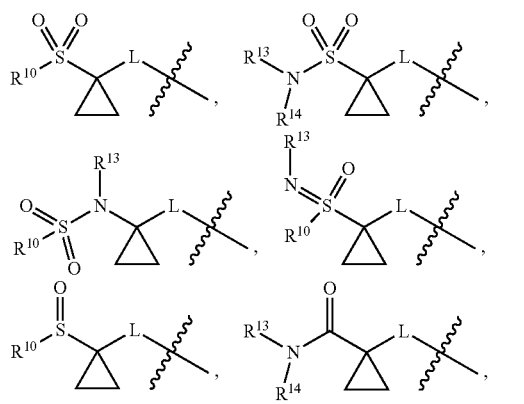

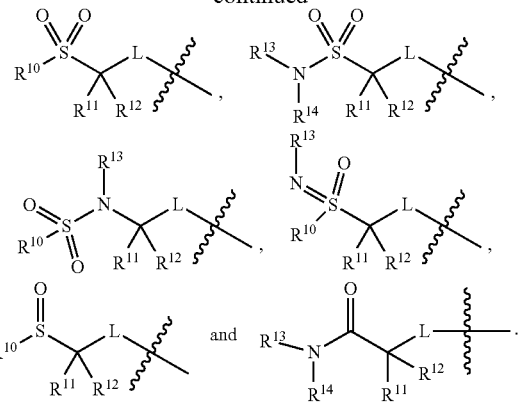

6. The compound of claim 1, having the structure of Formula (Va), or a pharmaceutically acceptable salt thereof:

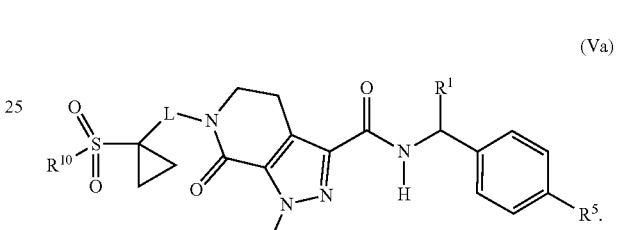

7. The compound of claim 1, or a pharmaceutically acceptable salt thereof, wherein:

R$^1$ is H, methyl or methyl substituted with one —OH group;

each R$^5$ is independently selected from Cl, F, and —CN;

L is a bond or CH$_2$ or CH$_2$CH$_2$;

and

R$^{10}$ is selected from methyl, ethyl, propyl, isopropyl, butyl, isobutyl, pentyl, cyclopropyl, cyclobutyl, pyridinyl, pyrazolyl, isoxazolyl, oxetanyl, tetrahydrofuranyl, tetrahydropyranyl, morpholinyl, piperidinyl, piperazinyl, pyrrolidinyl and azetidinyl, wherein each R$^{10}$ is optionally substituted with 1 to 4 groups independently selected from methyl, ethyl, deuterium, —OCH$_3$, —OH, —OCHF$_2$, —CN, —NH$_2$, —NHCH$_3$, —N(CH$_3$)$_2$, —NHR$^{13}$, —NHCH(=O), —NHC(=O)CH$_3$, —NHC(=O) OCH$_3$, —NHC(=O)CH$_2$NH$_2$, —NHC(=O)CH$_2$N (CH$_3$)$_2$, —NHC(=O)CH(CH$_3$)NH$_2$, —NHC(=O) C(CH$_3$)$_2$NH$_2$, —OCH$_2$CH$_2$OH, —OCH$_2$CH(CH$_3$) OH, —OCH$_2$CH(CH$_3$)$_2$OH, —OCH(F)CH$_2$OH, —OCF$_2$CH$_2$OH, —OCH$_2$CH$_2$NH$_2$, —OCH$_2$CH (CH$_3$)NH$_2$, —OCH$_2$C(CH$_3$)$_2$NH$_2$, —OCH$_2$C H$_2$NHCH$_3$, —OCH$_2$CH$_2$N(CH$_3$)$_2$, —OCH(F) CH$_2$NH$_2$, —OCF$_2$CH$_2$NH$_2$, —CH$_2$OCH$_2$CH$_2$NH$_2$, —CH$_2$CH$_2$OH, —CH$_2$OH, —CH$_2$NH$_2$, —O-azetidinyl, —C(=O)NH$_2$, —C(=O)NHCH$_3$, —OC (=O)CH$_3$, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6-azaspiro[3.3]heptanyl and 4,5-dihydroisoxazolyl, where the methyl, ethyl, cyclopropyl, azetidinyl, pyrrolidinyl, morpholinyl, 6-oxa-3-azabicyclo[3.1.1]heptanyl, 2-oxa-5-azabicyclo[2.2.1]heptanyl, 2-oxa-6- azaspiro[3.3]heptanyl and 4,5-dihydroisoxazolyl are each optionally further substituted with 1 to 3 groups independently selected from —F, —OH, —OCH$_3$, and —NH$_2$.
8. The compound of claim 1, or a pharmaceutically acceptable salt thereof, wherein R$^{10}$ is selected from:
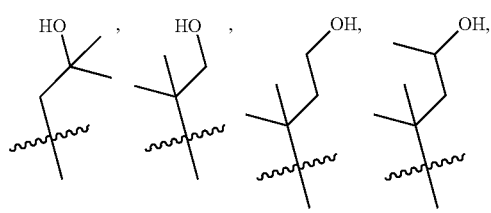
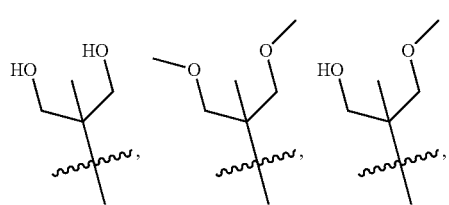
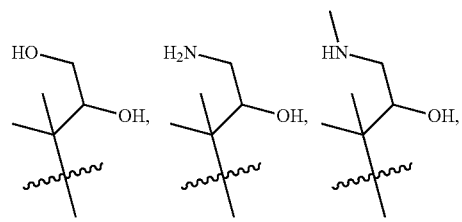
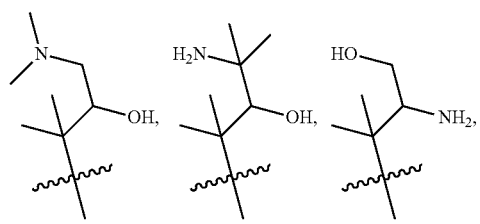
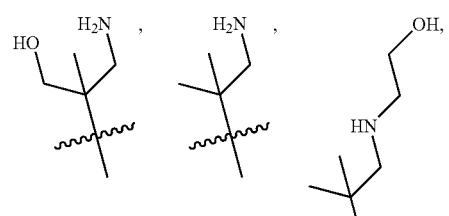
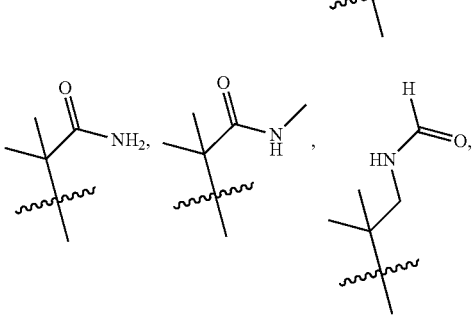
-continued
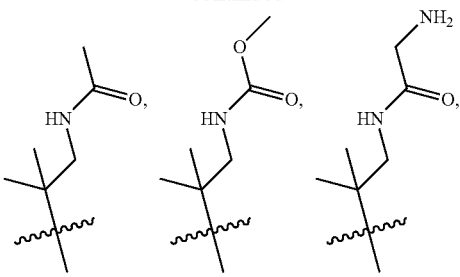
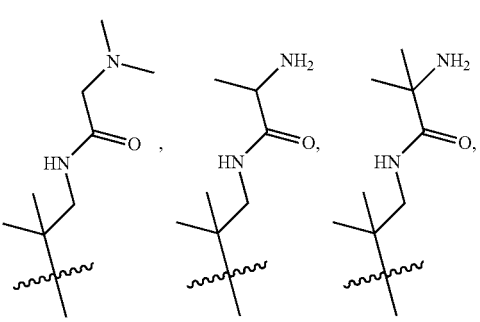
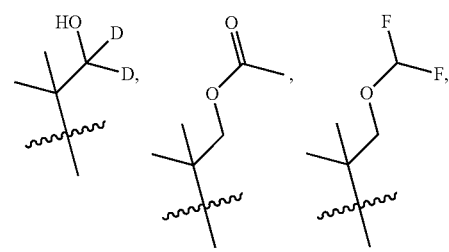
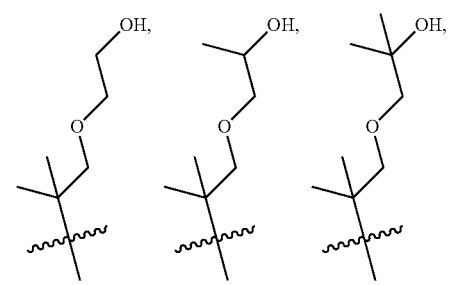
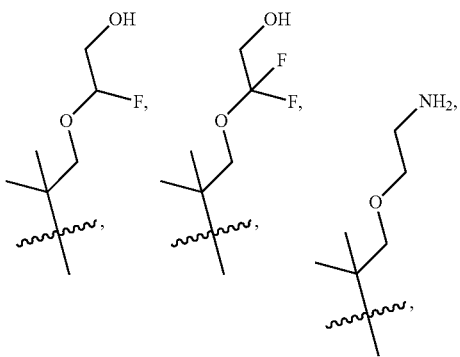

421
-continued
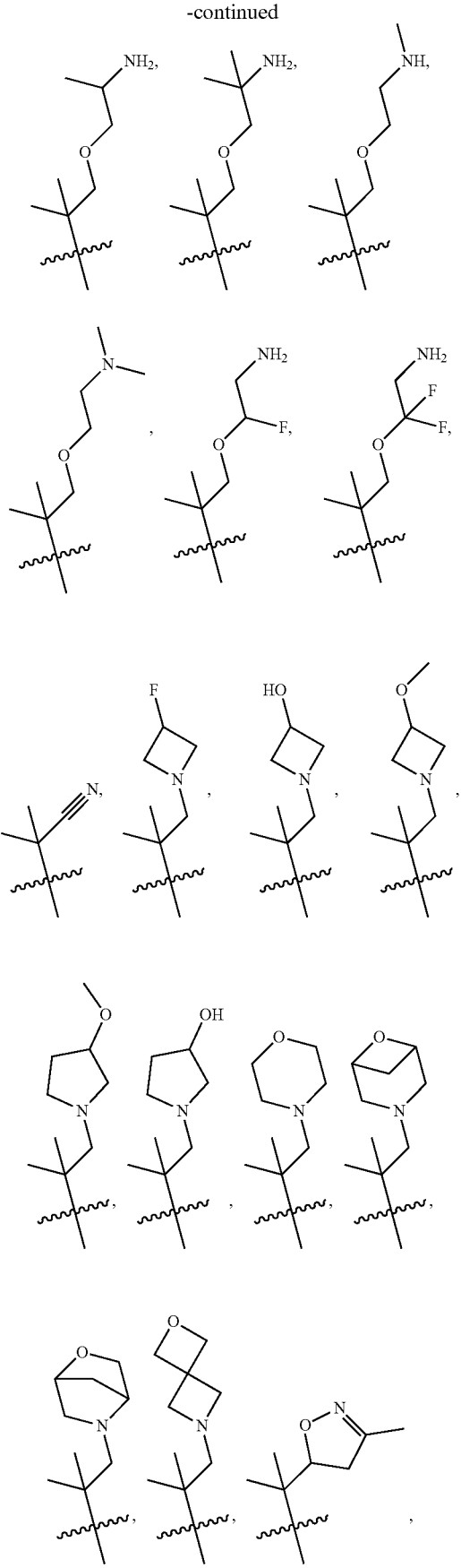
422
-continued
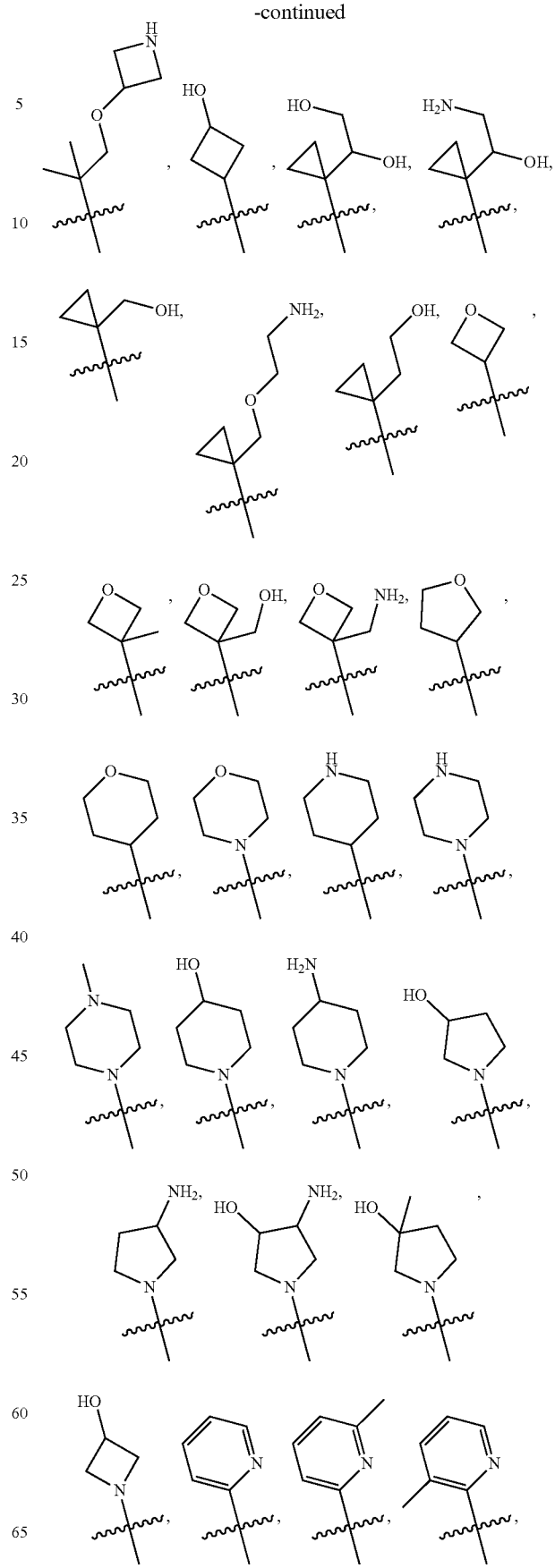

-continued

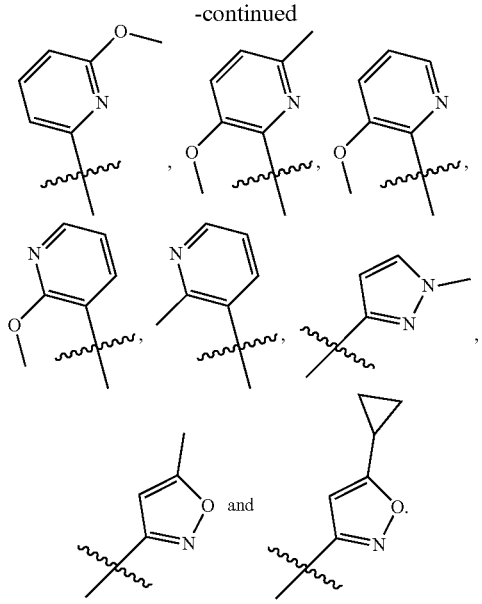

9. The compound of claim 1, or a pharmaceutically acceptable salt thereof, wherein R¹ is H.

10. The compound of claim 1, or a pharmaceutically acceptable salt thereof, wherein each R⁵ is independently selected from Cl, F, —CN, —OCH₃ and methyl.

11. The compound of claim 1, or a pharmaceutically acceptable salt thereof, wherein each R⁵ is independently selected from Cl and —CN.

12. The compound of claim 1, or a pharmaceutically acceptable salt thereof, wherein L is —CH₂— or —CH₂CH₂—.

13. The compound of claim 1, or a pharmaceutically acceptable salt thereof, wherein L is —CH₂—.

14. The compound of claim 1, or a pharmaceutically acceptable salt thereof, selected from:

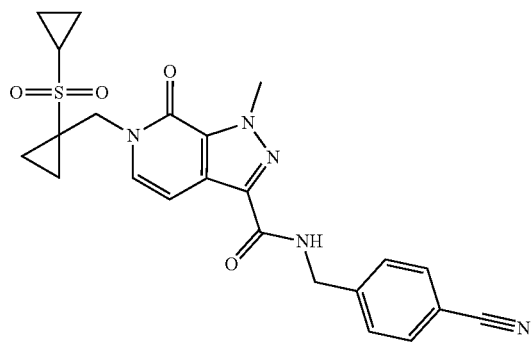 [SMILES: Cn1nc(C(=O)NCc2ccc(C#N)cc2)c2ccn(CC3(S(=O)(=O)C4CC4)CC3)c(=O)c21]

N-(4-Cyanobenzyl)-6-((1-(cyclopropylsulfonyl)cyclopropyl)methyl)-1-methyl-7-oxo-6,7-dihydro-1H-pyrazolo[3,4-c]pyridine-3-carboxamide;

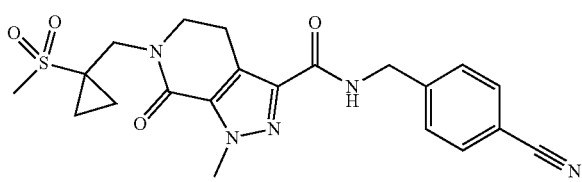 [SMILES: Cn1nc(C(=O)NCc2ccc(C#N)cc2)c2c1C(=O)N(CC1(S(C)(=O)=O)CC1)CC2]

N-(4-cyanobenzyl)-1-methyl-6-((1-(methylsulfonyl)cyclopropyl)methyl)-7-oxo-6,7-dihydro-1H-pyrazolo[3,4-c]pyridine-3-carboxamide;

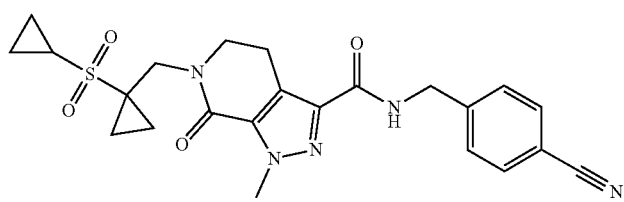 [SMILES: Cn1nc(C(=O)NCc2ccc(C#N)cc2)c2c1C(=O)N(CC1(S(=O)(=O)C3CC3)CC1)CC2]

N-(4-cyanobenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

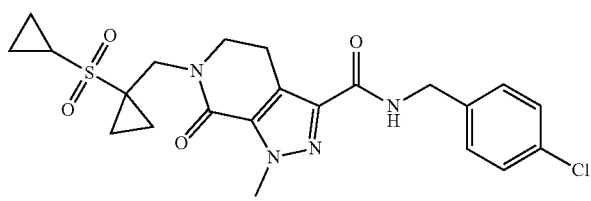

N-(4-Chlorobenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

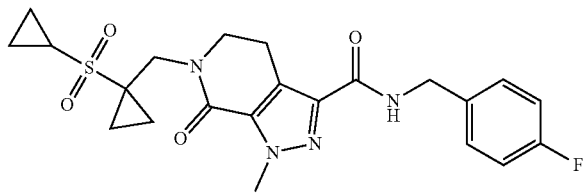 [SMILES: Cn1nc(C(=O)NCc2ccc(F)cc2)c2c1C(=O)N(CC1(S(=O)(=O)C3CC3)CC1)CC2]

6-((1-(Cyclopropylsulfonyl)cyclopropyl)methyl)-N-(4-fluorobenzyl)-1-methyl-7-oxo-4,5,6,7-tetrahydro-1H-pyrazolo[3,4-c]pyridine-3-carboxamide;

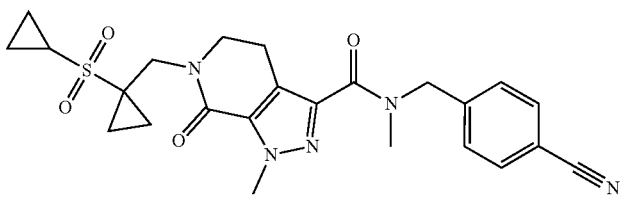 [SMILES: CN(Cc1ccc(C#N)cc1)C(=O)c1nn(C)c2c1CCN(CC1(S(=O)(=O)C3CC3)CC1)C2=O]

N-(4-Cyanobenzyl)-6-((1-(cyclopropylsulfonyl)cyclopropyl)methyl)-N,1-dimethyl-7-oxo-4,5,6,7-tetrahydro-1H-pyrazolo[3,4-c]pyridine-3-carboxamide;

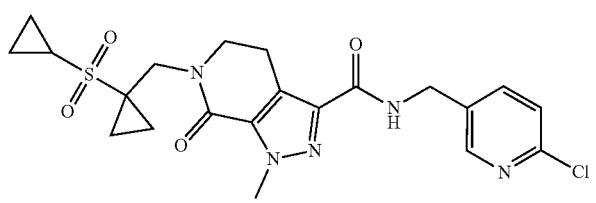 [SMILES: Cn1nc(C(=O)NCc2ccc(Cl)nc2)c2c1C(=O)N(CC1(S(=O)(=O)C3CC3)CC1)CC2]

N-((6-Chloropyridin-3-yl)methyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

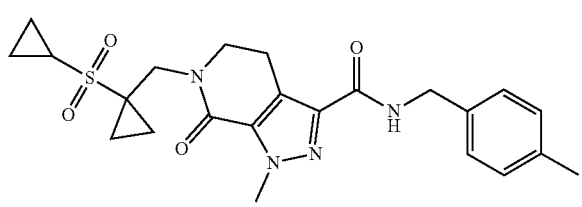 [SMILES: Cc1ccc(CNC(=O)c2nn(C)c3c2CCN(CC2(S(=O)(=O)C4CC4)CC2)C3=O)cc1]

6-(1-(Cyclopropylsulfonyl)cyclopropyl)methyl)-1-methyl-N-(4-methylbenzyl)-7-oxo-4,5,6,7-tetrahydro-1H-pyrazolo[3,4-c]pyridine-3-carboxamide;

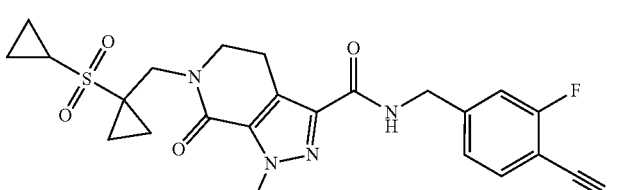

N-(4-Cyano-3-fluorobenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

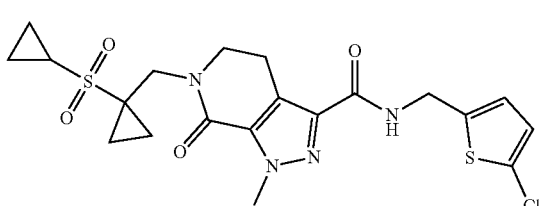

N-((5-Chlorothiophen-2-yl)methyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

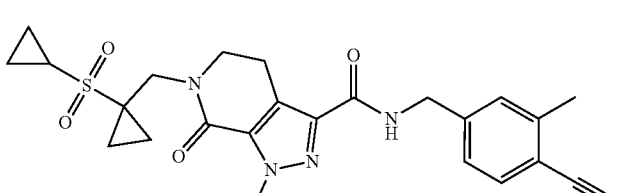

N-(4-Cyano-3-methylbenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

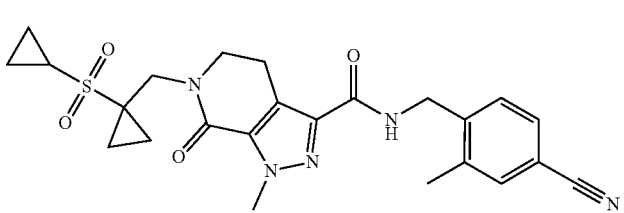 [SMILES: Cc1cc(C#N)ccc1CNC(=O)c1nn(C)c2c1CCN(CC1(S(=O)(=O)C3CC3)CC1)C2=O]

N-(4-Cyano-2-methylbenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

-continued

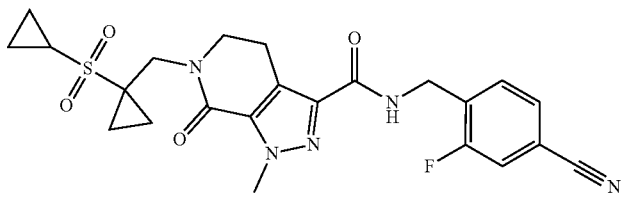 [SMILES: Cn1nc(C(=O)NCc2ccc(C#N)cc2F)c2c1C(=O)N(CC1(S(=O)(=O)C3CC3)CC1)CC2]

N-(4-Cyano-2-fluorobenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

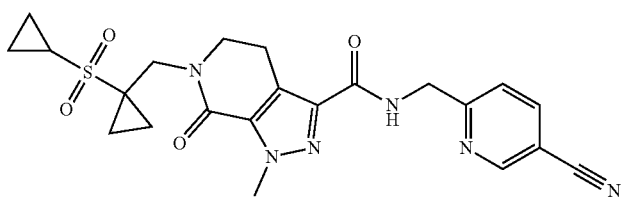 [SMILES: Cn1nc(C(=O)NCc2ccc(C#N)cn2)c2c1C(=O)N(CC1(S(=O)(=O)C3CC3)CC1)CC2]

N-((5-Cyanopyridin-2-yl)methyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

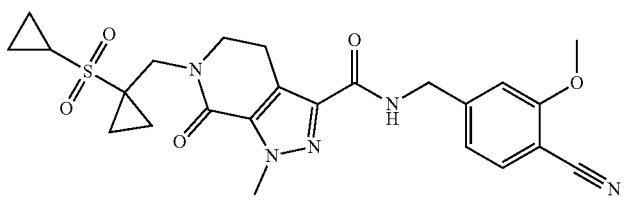 [SMILES: COc1cc(CNC(=O)c2nn(C)c3c2CCN(CC2(S(=O)(=O)C4CC4)CC2)C3=O)ccc1C#N]

N-(4-Cyano-3-methoxybenzyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

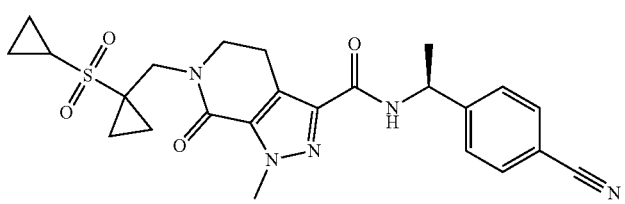 [SMILES: C[C@H](NC(=O)c1nn(C)c2c1CCN(CC1(S(=O)(=O)C3CC3)CC1)C2=O)c1ccc(C#N)cc1]

(S)-N-(1-(4-Cyanophenyl)ethyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

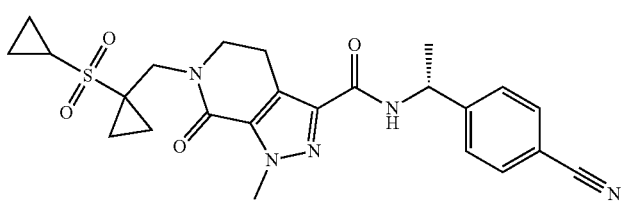 [SMILES: C[C@@H](NC(=O)c1nn(C)c2c1CCN(CC1(S(=O)(=O)C3CC3)CC1)C2=O)c1ccc(C#N)cc1]

(R)-N-(1-(4-Cyanophenyl)ethyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

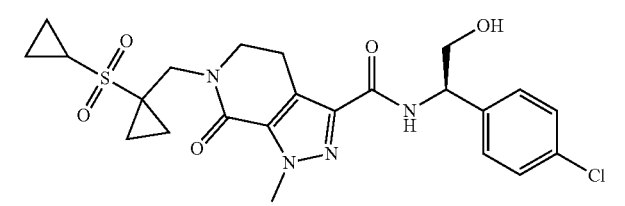 [SMILES: Cn1nc(C(=O)N[C@@H](CO)c2ccc(Cl)cc2)c2c1C(=O)N(CC1(S(=O)(=O)C3CC3)CC1)CC2]

(R)-N-(1-(4-Chlorophenyl)-2-hydroxyethyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

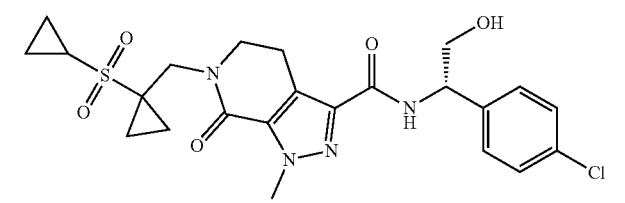 [SMILES: Cn1nc(C(=O)N[C@H](CO)c2ccc(Cl)cc2)c2c1C(=O)N(CC1(S(=O)(=O)C3CC3)CC1)CC2]

(S)-N-(1-(4-Chlorophenyl)-2-hydroxyethyl)-6-((1-(cyclopropylsulfonyl)cyclopropyl)methyl)-1-methyl-7-oxo-4,5,6,7-tetrahydro-1H-pyrazolo[3,4-c]pyridine-3-carboxamide;

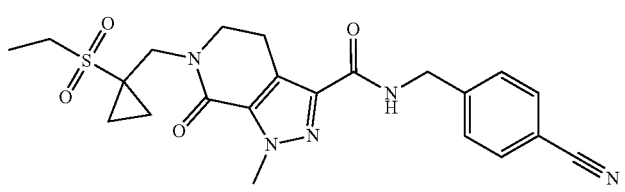 [SMILES: CCS(=O)(=O)C1(CN2CCc3c(C(=O)NCc4ccc(C#N)cc4)nn(C)c3C2=O)CC1]

N-(4-Cyanobenzyl)-6-((1-(ethylsulfonyl)cyclopropyl)methyl)-1-methyl-7-oxo-4,5,6,7-tetrahydro-1H-pyrazolo[3,4-c]pyridine-3-carboxamide;

-continued

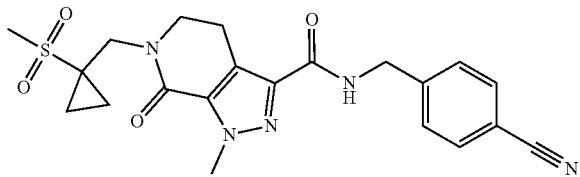 [SMILES: Cn1nc(C(=O)NCc2ccc(C#N)cc2)c2c1C(=O)N(CC1(S(C)(=O)=O)CC1)CC2]

N-(4-Cyanobenzyl)-1-methyl-6-((1-(methylsulfonyl)cyclopropyl)methyl)-7-oxo-4,5,6,7-tetrahydro-1H-pyrazolo[3,4-c]pyridine-3-carboxamide;

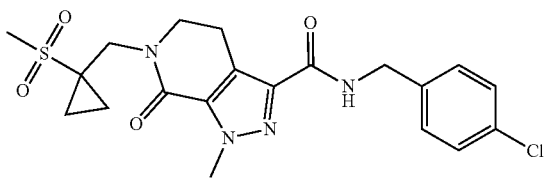 [SMILES: Cn1nc(C(=O)NCc2ccc(Cl)cc2)c2c1C(=O)N(CC1(S(C)(=O)=O)CC1)CC2]

N-(4-Chlorobenzyl)-1-methyl-6-((1-(methylsulfonyl)cyclopropyl)methyl)-7-oxo-4,5,6,7-tetrahydro-1H-pyrazolo[3,4-c]pyridine-3-carboxamide;

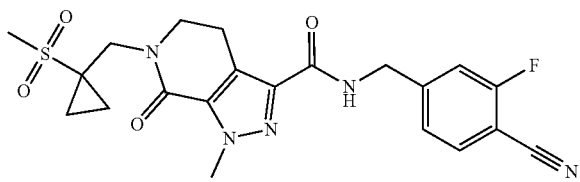 [SMILES: Cn1nc(C(=O)NCc2ccc(C#N)c(F)c2)c2c1C(=O)N(CC1(S(C)(=O)=O)CC1)CC2]

N-(4-Cyano-3-fluorobenzyl)-1-methyl-6-((1-(methylsulfonyl)cyclopropyl)methyl)-7-oxo-4,5,6,7-tetrahydro-1H-pyrazolo[3,4-c]pyridine-3-carboxamide;

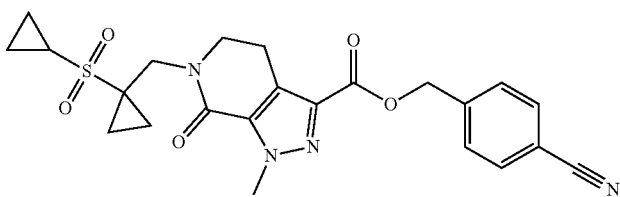 [SMILES: Cn1nc(C(=O)OCc2ccc(C#N)cc2)c2c1C(=O)N(CC1(S(=O)(=O)C3CC3)CC1)CC2]

4-Cyanobenzyl 6-((1-(cyclopropylsulfonyl)cyclopropyl)methyl)-1-methyl-7-oxo-4,5,6,7-tetrahydro-1H-pyrazolo[3,4-c]pyridine-3-carboxylate;

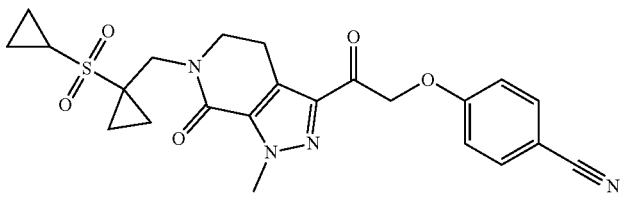 [SMILES: Cn1nc(C(=O)COc2ccc(C#N)cc2)c2c1C(=O)N(CC1(S(=O)(=O)C3CC3)CC1)CC2]

4-(2-(6-((1-(cyclopropylsulfonyl)cyclopropyl)methyl)-1-methyl-7-oxo-4,5,6,7-tetrahydro-1H-pyrazolo[3,4-c]pyridin-3-yl)-2-oxoethoxy)benzonitrile;

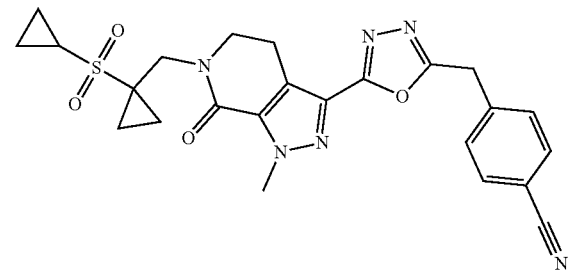 [SMILES: Cn1nc(-c2nnc(Cc3ccc(C#N)cc3)o2)c2c1C(=O)N(CC1(S(=O)(=O)C3CC3)CC1)CC2]

4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,3,4-oxadiazol-2-yl)methyl)benzonitrile;

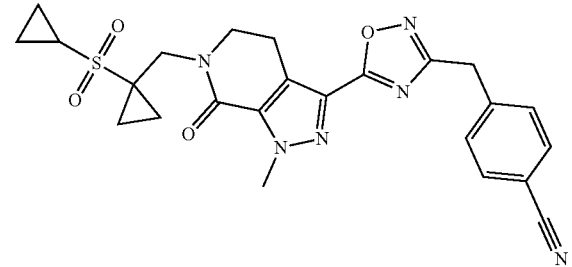 [SMILES: Cn1nc(-c2nc(Cc3ccc(C#N)cc3)no2)c2c1C(=O)N(CC1(S(=O)(=O)C3CC3)CC1)CC2]

4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,2,4-oxadiazol-3-yl)methyl)benzonitrile;

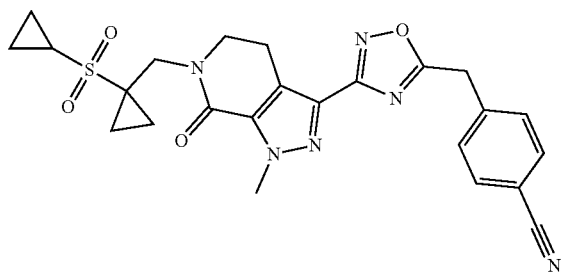 [SMILES: Cn1nc(-c2noc(Cc3ccc(C#N)cc3)n2)c2c1C(=O)N(CC1(S(=O)(=O)C3CC3)CC1)CC2]

4-((3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1,2,4-oxadiazol-5-yl)methyl)benzonitrile;

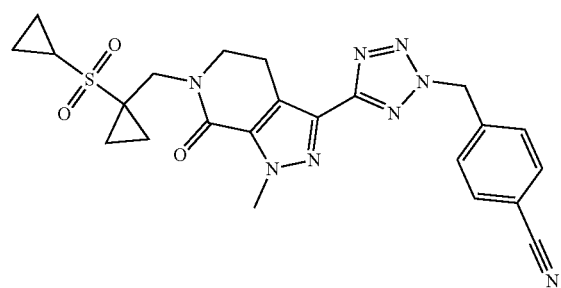 [SMILES: Cn1nc(-c2nnn(Cc3ccc(C#N)cc3)n2)c2c1C(=O)N(CC1(S(=O)(=O)C3CC3)CC1)CC2]

4-((5-(6-((1-(Cyclopropylsulfonyl)cyclopropyl)methyl)-1-methyl-7-oxo-4,5,6,7-tetrahydro-1H-pyrazolo[3,4-c]pyridin-3-yl)-2H-tetrazol-2-yl)methyl)benzonitrile;

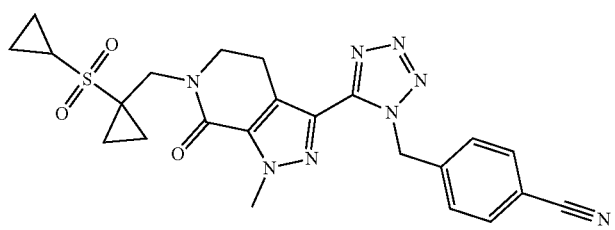 [SMILES: Cn1nc(-c2nnnn2Cc2ccc(C#N)cc2)c2c1C(=O)N(CC1(S(=O)(=O)C3CC3)CC1)CC2]

4-((5-(6-((1-(cyclopropylsulfonyl)cyclopropyl)methyl)-1-methyl-7-oxo-4,5,6,7-tetrahydro-1H-pyrazolo[3,4-c]pyridin-3-yl)-1H-tetrazol-1-yl)methyl)benzonitrile;

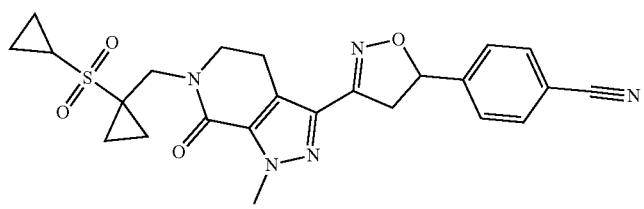 [SMILES: Cn1nc(C2=NOC(c3ccc(C#N)cc3)C2)c2c1C(=O)N(CC1(S(=O)(=O)C3CC3)CC1)CC2]

4-(3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile;

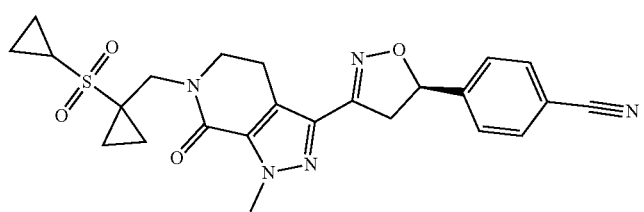 [SMILES: Cn1nc(C2=NO[C@@H](c3ccc(C#N)cc3)C2)c2c1C(=O)N(CC1(S(=O)(=O)C3CC3)CC1)CC2]

(R)-4-(3-(6-((1-(Cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile;

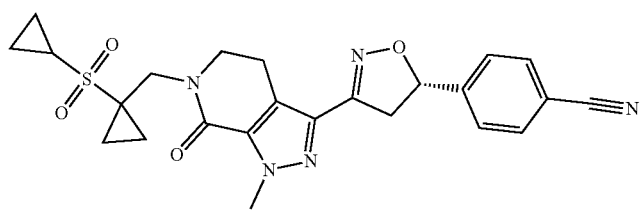 [SMILES: Cn1nc(C2=NO[C@H](c3ccc(C#N)cc3)C2)c2c1C(=O)N(CC1(S(=O)(=O)C3CC3)CC1)CC2]

(S)-4-(3-(6-((1-(cyclopropylsulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile;

-continued

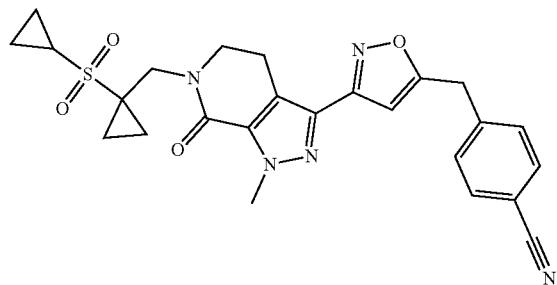 [SMILES: Cn1nc(-c2cc(Cc3ccc(C#N)cc3)on2)c2c1C(=O)N(CC1(S(=O)(=O)C3CC3)CC1)CC2]

4-((3-(6-((1-(Cyclopropylsulfonyl)cyclopropyl)methyl)-1-methyl-7-oxo-4,5,6,7-tetrahydro-1H-pyrazolo[3,4-c]pyridin-3-yl)isoxazol-5-yl)methyl)benzonitrile;

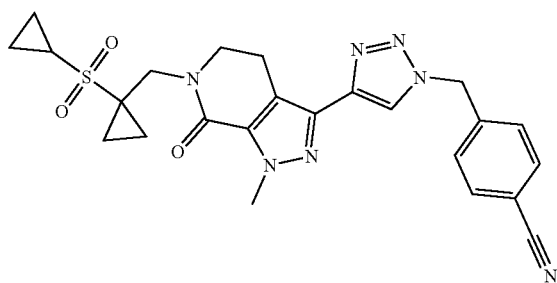 [SMILES: Cn1nc(-c2cn(Cc3ccc(C#N)cc3)nn2)c2c1C(=O)N(CC1(S(=O)(=O)C3CC3)CC1)CC2]

4-((4-(6-((1-(Cyclopropylsulfonyl)cyclopropyl)methyl)-1-methyl-7-oxo-4,5,6,7-tetrahydro-1H-pyrazolo[3,4-c]pyridin-3-yl)-1H-1,2,3-triazol-1-yl)methyl)benzonitrile;

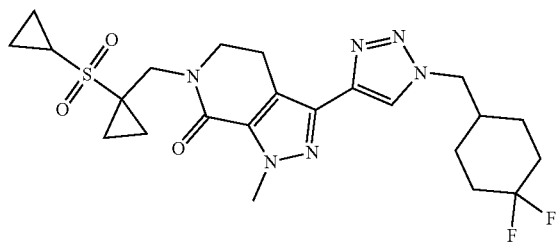 [SMILES: Cn1nc(-c2cn(CC3CCC(F)(F)CC3)nn2)c2c1C(=O)N(CC1(S(=O)(=O)C3CC3)CC1)CC2]

6-((1-(Cyclopropylsulfonyl)cyclopropyl)methyl)-3-(1-((4,4-difluorocyclohexyl)methyl)-1H-1,2,3-triazol-4-yl)-1-methyl-5,6-dihydro-1H-pyrazolo[3,4-c]pyridin-7(4H)-one;

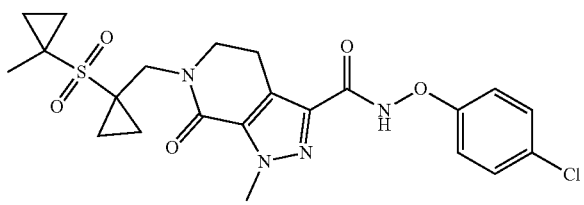 [SMILES: Cn1nc(C(=O)NOc2ccc(Cl)cc2)c2c1C(=O)N(CC1(S(=O)(=O)C3(C)CC3)CC1)CC2]

N-(4-Chlorophenoxy)-1-methyl-6-((1-((1-methylcyclopropyl)sulfonyl)cyclopropyl)methyl)-7-oxo-4,5,6,7-tetrahydro-1H-pyrazolo[3,4-c]pyridine-3-carboxamide;

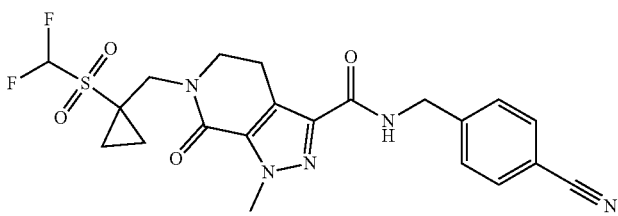 [SMILES: Cn1nc(C(=O)NCc2ccc(C#N)cc2)c2c1C(=O)N(CC1(S(=O)(=O)C(F)F)CC1)CC2]

N-(4-Cyanobenzyl)-6-((1-(((difluoromethyl)sulfonyl)cyclopropyl)methyl)-1-methyl-7-oxo-4,5,6,7-tetrahydro-1H-pyrazolo[3,4-c]pyridine-3-carboxamide;

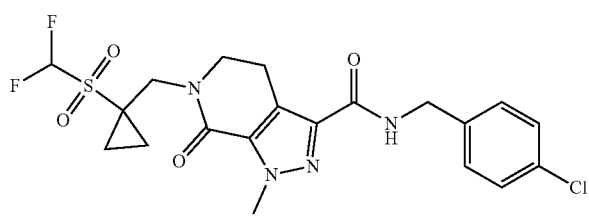 [SMILES: Cn1nc(C(=O)NCc2ccc(Cl)cc2)c2c1C(=O)N(CC1(S(=O)(=O)C(F)F)CC1)CC2]

N-(4-Chlorobenzyl)-6-((1-(((difluoromethyl)sulfonyl)cyclopropyl)methyl)-1-methyl-7-oxo-4,5,6,7-tetrahydro-1H-pyrazolo[3,4-c]pyridine-3-carboxamide;

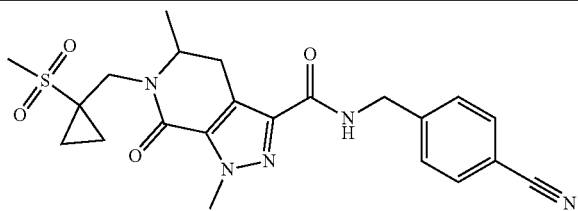 N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide;

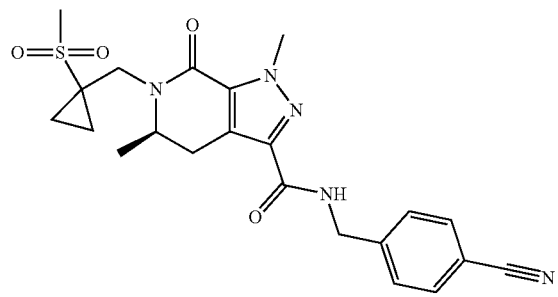 [SMILES: C[C@@H]1Cc2c(C(=O)NCc3ccc(C#N)cc3)nn(C)c2C(=O)N1CC1(S(C)(=O)=O)CC1] (R)-N-(4-cyanobenzyl)-1,5-dimethyl-6-((1-(methylsulfonyl)cyclopropyl)methyl)-7-oxo-4,5,6,7-tetrahydro-1H-pyrazolo[3,4-c]pyridine-3-carboxamide;

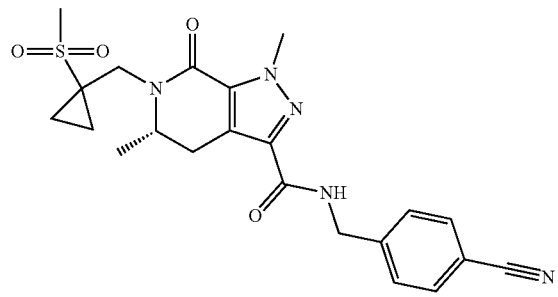 [SMILES: C[C@H]1Cc2c(C(=O)NCc3ccc(C#N)cc3)nn(C)c2C(=O)N1CC1(S(C)(=O)=O)CC1] (S)-N-(4-cyanobenzyl)-1,5-dimethyl-6-((1-(methylsulfonyl)cyclopropyl)methyl)-7-oxo 4,5,6,7-tetrahydro-1H-pyrazolo[3,4-c]pyridine-3-carboxamide;

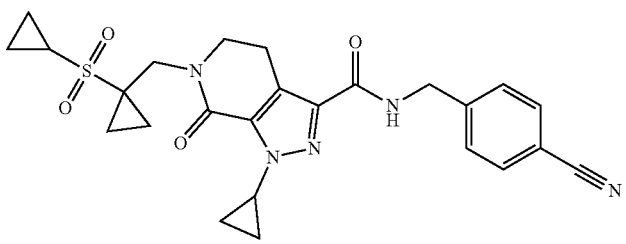 [SMILES: N#Cc1ccc(CNC(=O)c2nn(C3CC3)c3c2CCN(CC2(S(=O)(=O)C4CC4)CC2)C3=O)cc1] N-(4-Cyanobenzyl)-1-cyclopropyl-6-((1-(cyclopropylsulfonyl)cyclopropyl)methyl)-7-oxo-4,5,6,7-tetrahydro-1H-pyrazolo[3,4-c]pyridine-3-carboxamide;

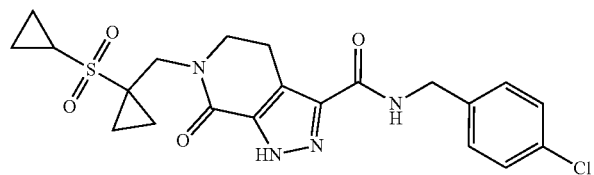 [SMILES: O=C(NCc1ccc(Cl)cc1)c1n[nH]c2c1CCN(CC1(S(=O)(=O)C3CC3)CC1)C2=O] N-(4-Chlorobenzyl)-6-((1-(cyclopropylsulfonyl)cyclopropyl)methyl)-7-oxo-4,5,6,7-tetrahydro-1H-pyrazolo[3,4-c]pyridine-3-carboxamide;

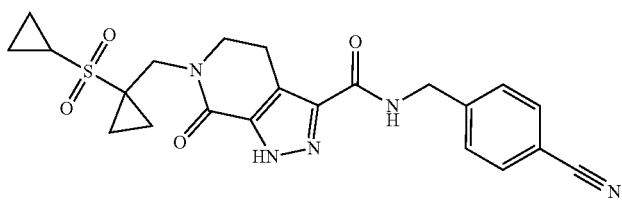 [SMILES: N#Cc1ccc(CNC(=O)c2n[nH]c3c2CCN(CC2(S(=O)(=O)C4CC4)CC2)C3=O)cc1] N-(4-Cyanobenzyl)-6-((1-(cyclopropylsulfonyl)cyclopropyl)methyl)-7-oxo-4,5,6,7-tetrahydro-1H-pyrazolo[3,4-c]pyridine-3-carboxamide;

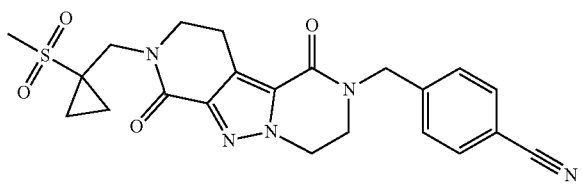 [SMILES: CS(=O)(=O)C1(CN2CCc3c(nn4c3C(=O)N(Cc3ccc(C#N)cc3)CC4)C2=O)CC1] 4-((8-((1-(Methylsulfonyl)cyclopropyl)methyl)-1,7-dioxo-3,4,7,8,9,10-hexahydropyrido[3',4':3,4]pyrazolo[1,5-a]pyrazin-2(1H)-yl)methyl)benzonitrile;

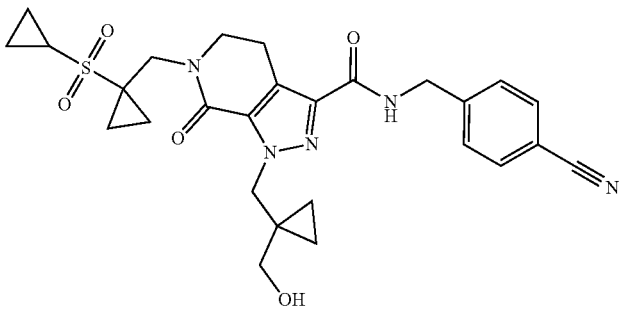 [SMILES: N#Cc1ccc(CNC(=O)c2nn(CC3(CO)CC3)c3c2CCN(CC2(S(=O)(=O)C4CC4)CC2)C3=O)cc1]

N-(4-Cyanobenzyl)-6-((1-(cyclopropylsulfonyl)cyclopropyl)methyl)-1-((1-(hydroxymethyl)cyclopropyl)methyl)-7-oxo-4,5,6,7-tetrahydro-1H-pyrazolo[3,4-c]pyridine-3-carboxamide;

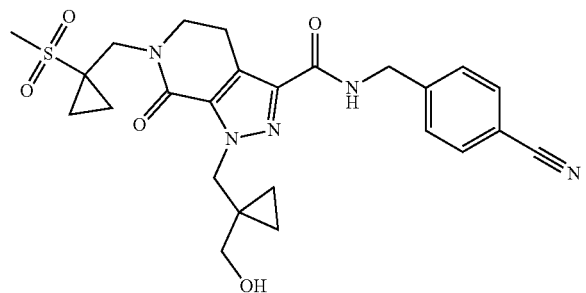 [SMILES: CS(=O)(=O)C1(CN2CCc3c(C(=O)NCc4ccc(C#N)cc4)nn(CC4(CO)CC4)c3C2=O)CC1]

N-(4-Cyanobenzyl)-1-((1-(hydroxymethyl)cyclopropyl)methyl)-6-((1-(methylsulfonyl)cyclopropyl)methyl)-7-oxo-4,5,6,7-tetrahydro-1H-pyrazolo[3,4-c]pyridine-3-carboxamide;

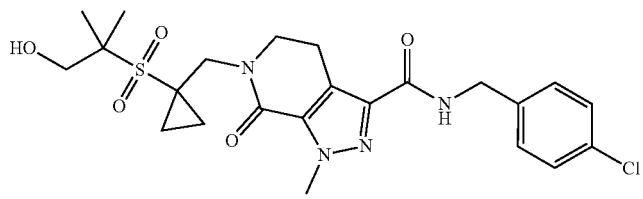 [SMILES: Cn1nc(C(=O)NCc2ccc(Cl)cc2)c2c1C(=O)N(CC1(S(=O)(=O)C(C)(C)CO)CC1)CC2]

N-(4-chlorobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

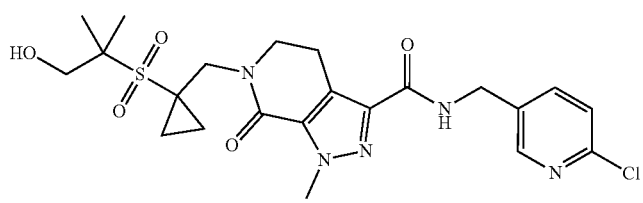 [SMILES: Cn1nc(C(=O)NCc2ccc(Cl)nc2)c2c1C(=O)N(CC1(S(=O)(=O)C(C)(C)CO)CC1)CC2]

N-((6-Chloropyridin-3-yl)methyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

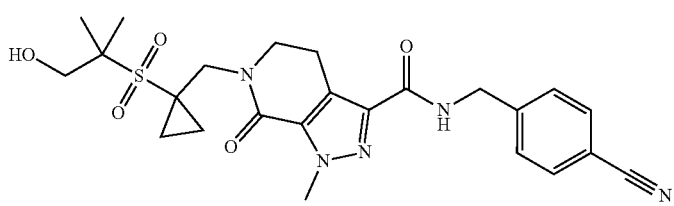 [SMILES: Cn1nc(C(=O)NCc2ccc(C#N)cc2)c2c1C(=O)N(CC1(S(=O)(=O)C(C)(C)CO)CC1)CC2]

N-(4-Cyanobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

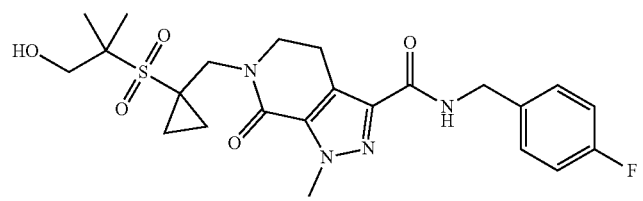 [SMILES: Cn1nc(C(=O)NCc2ccc(F)cc2)c2c1C(=O)N(CC1(S(=O)(=O)C(C)(C)CO)CC1)CC2]

N-(4-Fluorobenzyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

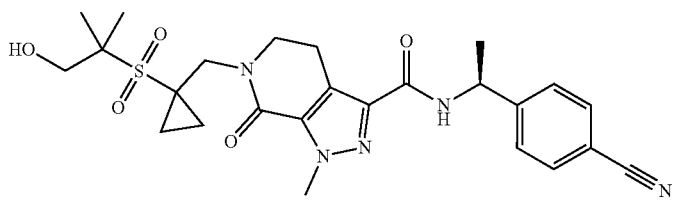 [SMILES: C[C@H](NC(=O)c1nn(C)c2c1CCN(CC1(S(=O)(=O)C(C)(C)CO)CC1)C2=O)c1ccc(C#N)cc1]

(S)-N-(1-(4-Cyanophenyl)ethyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

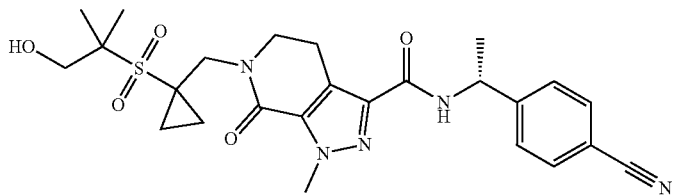 [SMILES: C[C@@H](NC(=O)c1nn(C)c2c1CCN(CC1(S(=O)(=O)C(C)(C)CO)CC1)C2=O)c1ccc(C#N)cc1]

(R)-N-(1-(4-Cyanophenyl)ethyl)-6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

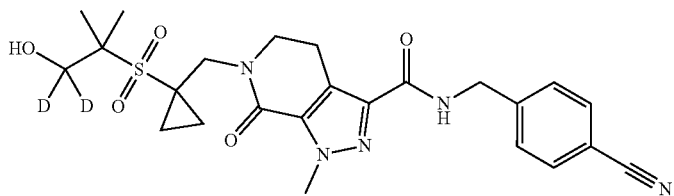 [SMILES: [2H]C([2H])(O)C(C)(C)S(=O)(=O)C1(CN2CCc3c(C(=O)NCc4ccc(C#N)cc4)nn(C)c3C2=O)CC1]

N-(4-Cyanobenzyl)-6-((1-((1-hydroxy-2-methylpropan-2-yl-1,1-d$_2$)sulfonyl)cyclopropyl)methyl)-1-methyl-7-oxo-4,5,6,7-tetrahydro-1H-pyrazolo[3,4-c]pyridine-3-carboxamide;

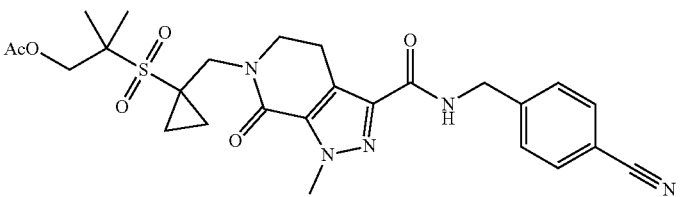 [SMILES: CC(=O)OCC(C)(C)S(=O)(=O)C1(CN2CCc3c(C(=O)NCc4ccc(C#N)cc4)nn(C)c3C2=O)CC1]

2-((1-((3-((4-Cyanobenzyl)carbamoyl)-1-methyl-7-oxo-4,5-dihydro-1H-pyrazolo[3,4-c]pyridin-6(7H)-yl)methyl)cyclopropyl)sulfonyl)-2-methylpropyl acetate;

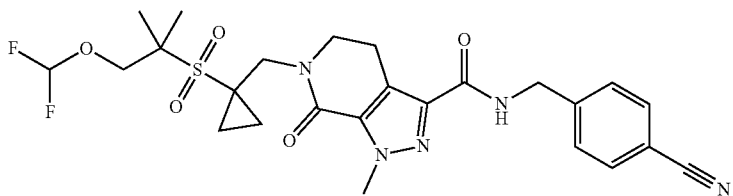 [SMILES: Cn1nc(C(=O)NCc2ccc(C#N)cc2)c2c1C(=O)N(CC1(S(=O)(=O)C(C)(C)COC(F)F)CC1)CC2]

N-(4-Cyanobenzyl)-6-((1-((1-(difluoromethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

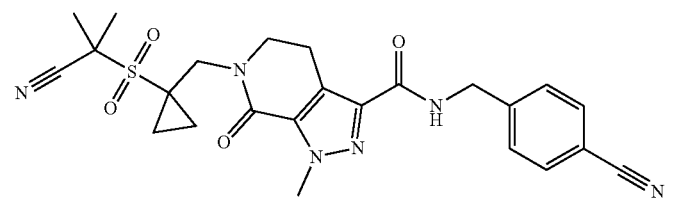 [SMILES: Cn1nc(C(=O)NCc2ccc(C#N)cc2)c2c1C(=O)N(CC1(S(=O)(=O)C(C)(C)C#N)CC1)CC2]

N-(4-Cyanobenzyl)-6-((1-((2-cyanopropan-2-yl)sulfonyl)cyclopropyl)methyl)-1-methyl-7-oxo-4,5,6,7-tetrahydro-1H-pyrazolo[3,4-c]pyridine-3-carboxamide;

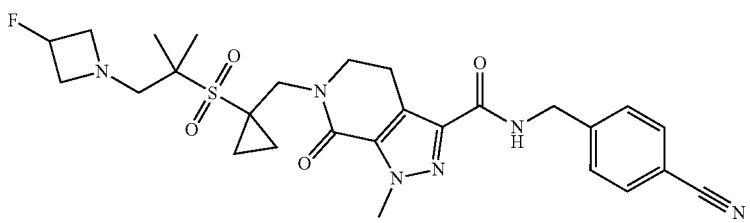 [SMILES: Cn1nc(C(=O)NCc2ccc(C#N)cc2)c2c1C(=O)N(CC1(S(=O)(=O)C(C)(C)CN3CC(F)C3)CC1)CC2]

N-(4-Cyanobenzyl)-6-((1-((1-(3-fluoroazetidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

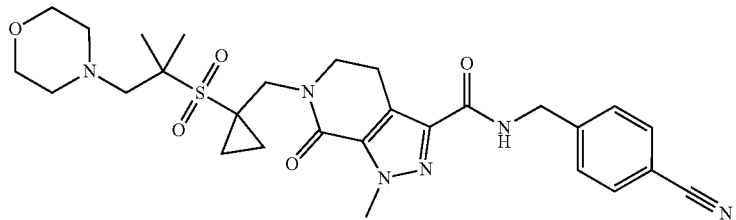 [SMILES: Cn1nc(C(=O)NCc2ccc(C#N)cc2)c2c1C(=O)N(CC1(S(=O)(=O)C(C)(C)CN3CCOCC3)CC1)CC2]
N-(4-Cyanobenzyl)-1-methyl-6-((1-((2-methyl-1-morpholinopropan-2-yl)sulfonyl)cyclopropyl)methyl)-7-oxo-4,5,6,7-tetrahydro-1H-pyrazolo[3,4-c]pyridine-3-carboxamide;

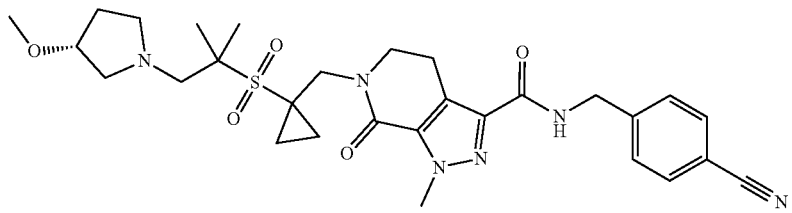 [SMILES: CO[C@@H]1CCN(CC(C)(C)S(=O)(=O)C2(CN3CCc4c(C(=O)NCc5ccc(C#N)cc5)nn(C)c4C3=O)CC2)C1]
(R)-N-(4-cyanobenzyl)-6-((1-((1-(3-methoxypyrrolidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

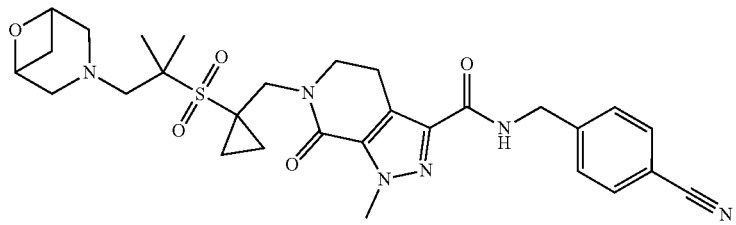 [SMILES: Cn1nc(C(=O)NCc2ccc(C#N)cc2)c2c1C(=O)N(CC1(S(=O)(=O)C(C)(C)CN3CC4CC(C3)O4)CC1)CC2]
6-((1-((1-(6-Oxa-3-azabicyclo[3.1.1]heptan-3-yl)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

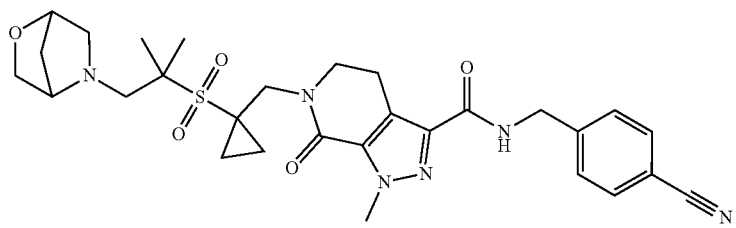 [SMILES: Cn1nc(C(=O)NCc2ccc(C#N)cc2)c2c1C(=O)N(CC1(S(=O)(=O)C(C)(C)CN3CC4CC3CO4)CC1)CC2]
6-((1-((1-(2-Oxa-5-azabicyclo[2.2.1]heptan-5-yl)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

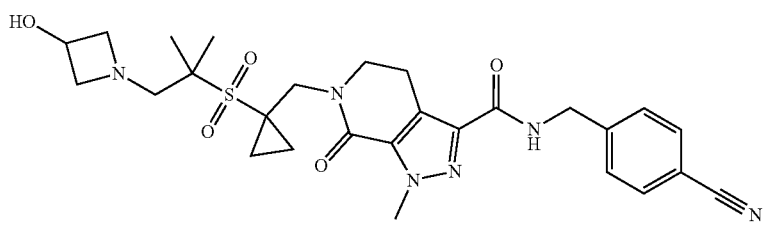 [SMILES: Cn1nc(C(=O)NCc2ccc(C#N)cc2)c2c1C(=O)N(CC1(S(=O)(=O)C(C)(C)CN3CC(O)C3)CC1)CC2]
N-(4-Cyanobenzyl)-6-((1-((1-(3-hydroxyazetidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

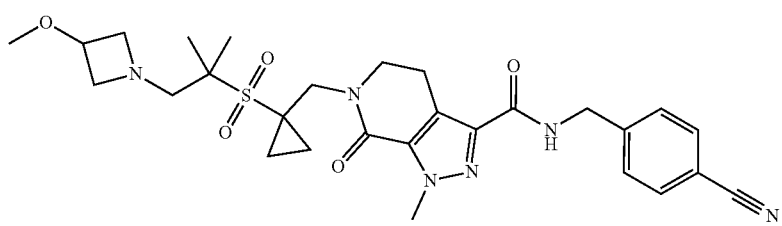 [SMILES: COC1CN(CC(C)(C)S(=O)(=O)C2(CN3CCc4c(C(=O)NCc5ccc(C#N)cc5)nn(C)c4C3=O)CC2)C1]
N-(4-Cyanobenzyl)-6-((1-((1-(3-methoxyazetidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

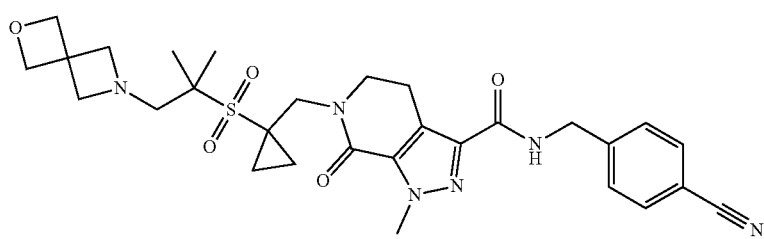 [SMILES: Cn1nc(C(=O)NCc2ccc(C#N)cc2)c2c1C(=O)N(CC1(S(=O)(=O)C(C)(C)CN3CC4(COC4)C3)CC1)CC2]
N-(4-Cyanobenzyl)-1-methyl-6-((1-((2-methyl-1-(2-oxa-6-azaspiro[3.3]heptan-6-yl)propan-2-yl)sulfonyl)cyclopropyl)methyl)-7-oxo-4,5,6,7-tetrahydro-1H-pyrazolo[3,4-c]pyridine-3-carboxamide;

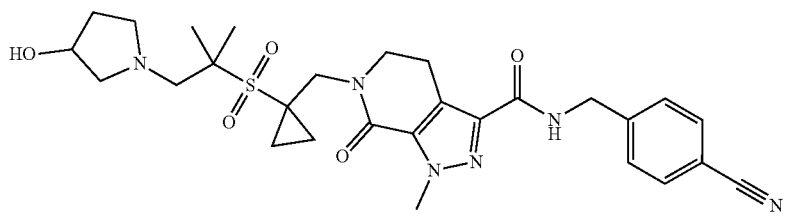 [SMILES: Cn1nc(C(=O)NCc2ccc(C#N)cc2)c2c1C(=O)N(CC1(S(=O)(=O)C(C)(C)CN3CCC(O)C3)CC1)CC2]

N-(4-Cyanobenzyl)-6-((1-((1-(3-hydroxypyrrolidin-1-yl)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

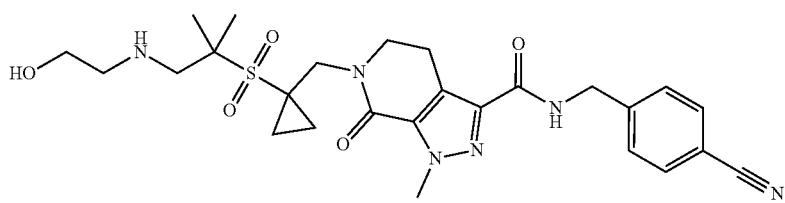 [SMILES: Cn1nc(C(=O)NCc2ccc(C#N)cc2)c2c1C(=O)N(CC1(S(=O)(=O)C(C)(C)CNCCO)CC1)CC2]

N-(4-Cyanobenzyl)-6-((1-((1-((2-hydroxyethyl)amino)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

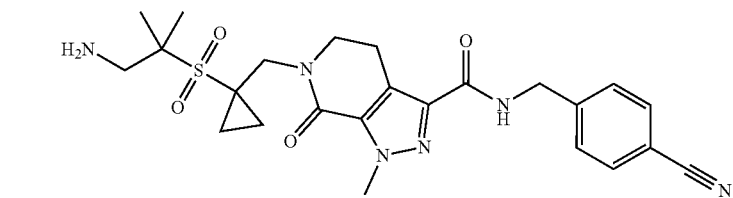 [SMILES: Cn1nc(C(=O)NCc2ccc(C#N)cc2)c2c1C(=O)N(CC1(S(=O)(=O)C(C)(C)CN)CC1)CC2]

6-((1-((1-Amino-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

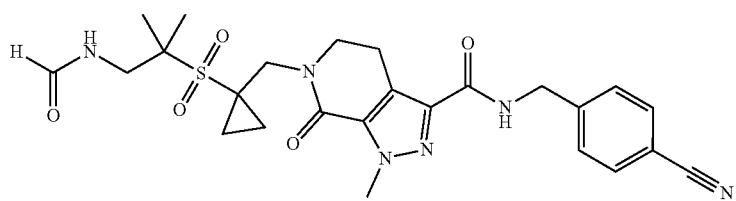 [SMILES: Cn1nc(C(=O)NCc2ccc(C#N)cc2)c2c1C(=O)N(CC1(S(=O)(=O)C(C)(C)CNC=O)CC1)CC2]

N-(4-Cyanobenzyl)-6-((1-((1-(1-formamido-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

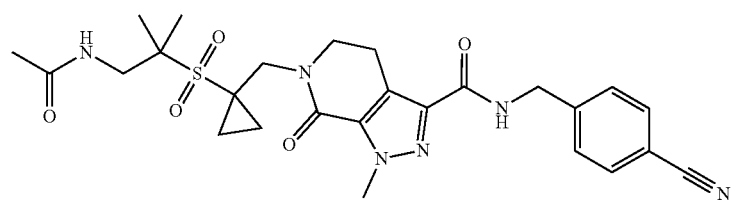 [SMILES: CC(=O)NCC(C)(C)S(=O)(=O)C1(CN2CCc3c(C(=O)NCc4ccc(C#N)cc4)nn(C)c3C2=O)CC1]

6-((1-((1-Acetamido-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

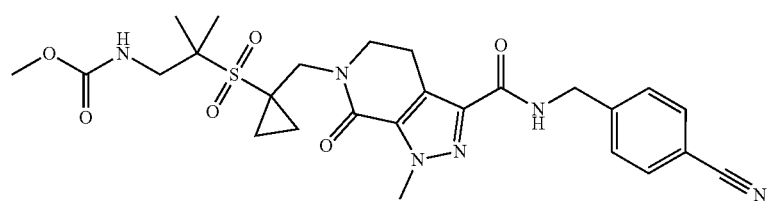 [SMILES: COC(=O)NCC(C)(C)S(=O)(=O)C1(CN2CCc3c(C(=O)NCc4ccc(C#N)cc4)nn(C)c3C2=O)CC1]

Methyl (2-((1-((3-((4-cyanobenzyl)carbamoyl)-1-methyl-7-oxo-1,4,5,7-tetrahydro-6H-pyrazolo[3,4-c]pyridin-6-yl)methyl)cyclopropyl)sulfonyl)-2-methylpropyl)carbamate;

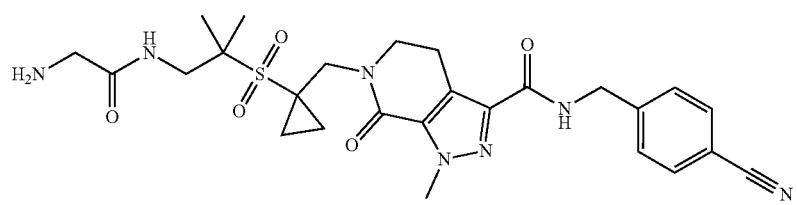 [SMILES: Cn1nc(C(=O)NCc2ccc(C#N)cc2)c2c1C(=O)N(CC1(S(=O)(=O)C(C)(C)CNC(=O)CN)CC1)CC2]

6-((1-((1-(2-Aminoacetamido)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

-continued

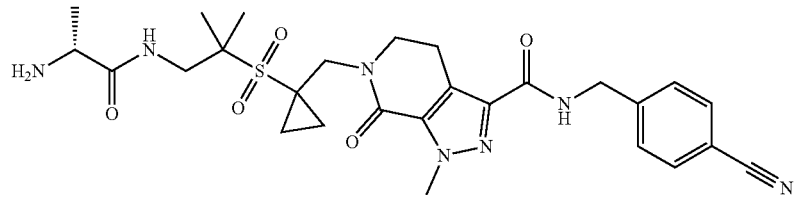 [SMILES: C[C@@H](N)C(=O)NCC(C)(C)S(=O)(=O)C1(CN2CCc3c(C(=O)NCc4ccc(C#N)cc4)nn(C)c3C2=O)CC1]
(R)-6-((1-(((1-(2-Aminopropanamido)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

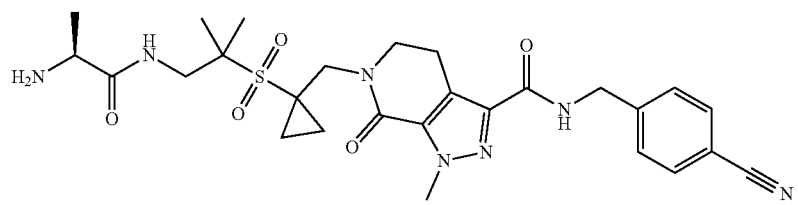 [SMILES: C[C@H](N)C(=O)NCC(C)(C)S(=O)(=O)C1(CN2CCc3c(C(=O)NCc4ccc(C#N)cc4)nn(C)c3C2=O)CC1]
(S)-6-((1-(((1-(2-Aminopropanamido)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

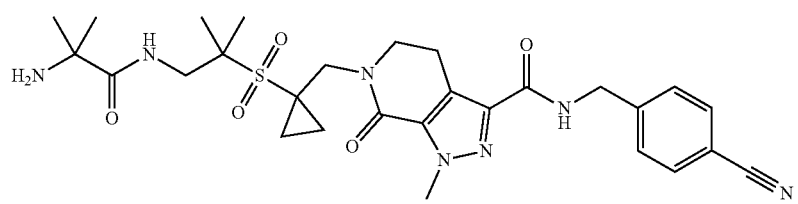 [SMILES: Cn1nc(C(=O)NCc2ccc(C#N)cc2)c2c1C(=O)N(CC1(S(=O)(=O)C(C)(C)CNC(=O)C(C)(C)N)CC1)CC2]
6-((1-(((1-(2-Amino-2-methylpropanamido)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

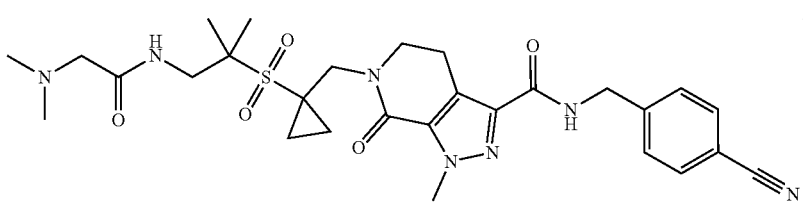 [SMILES: CN(C)CC(=O)NCC(C)(C)S(=O)(=O)C1(CN2CCc3c(C(=O)NCc4ccc(C#N)cc4)nn(C)c3C2=O)CC1]
N-(4-Cyanobenzyl)-6-((1-(((1-(2-(dimethylamino)acetamido)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

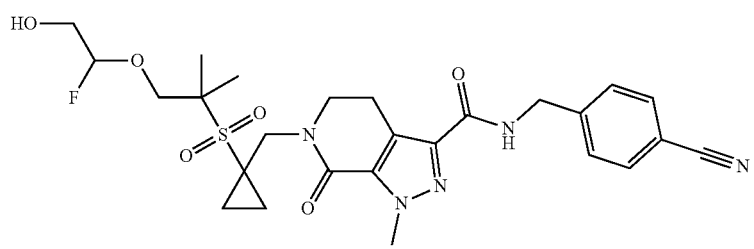 [SMILES: Cn1nc(C(=O)NCc2ccc(C#N)cc2)c2c1C(=O)N(CC1(S(=O)(=O)C(C)(C)COC(F)CO)CC1)CC2]
N-(4-Cyanobenzyl)-6-((1-(((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

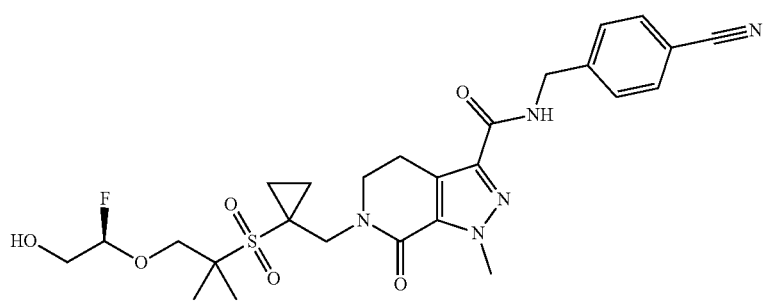 [SMILES: Cn1nc(C(=O)NCc2ccc(C#N)cc2)c2c1C(=O)N(CC1(S(=O)(=O)C(C)(C)CO[C@H](F)CO)CC1)CC2]
(R)-N-(4-Cyanobenzyl)-6-((1-(((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

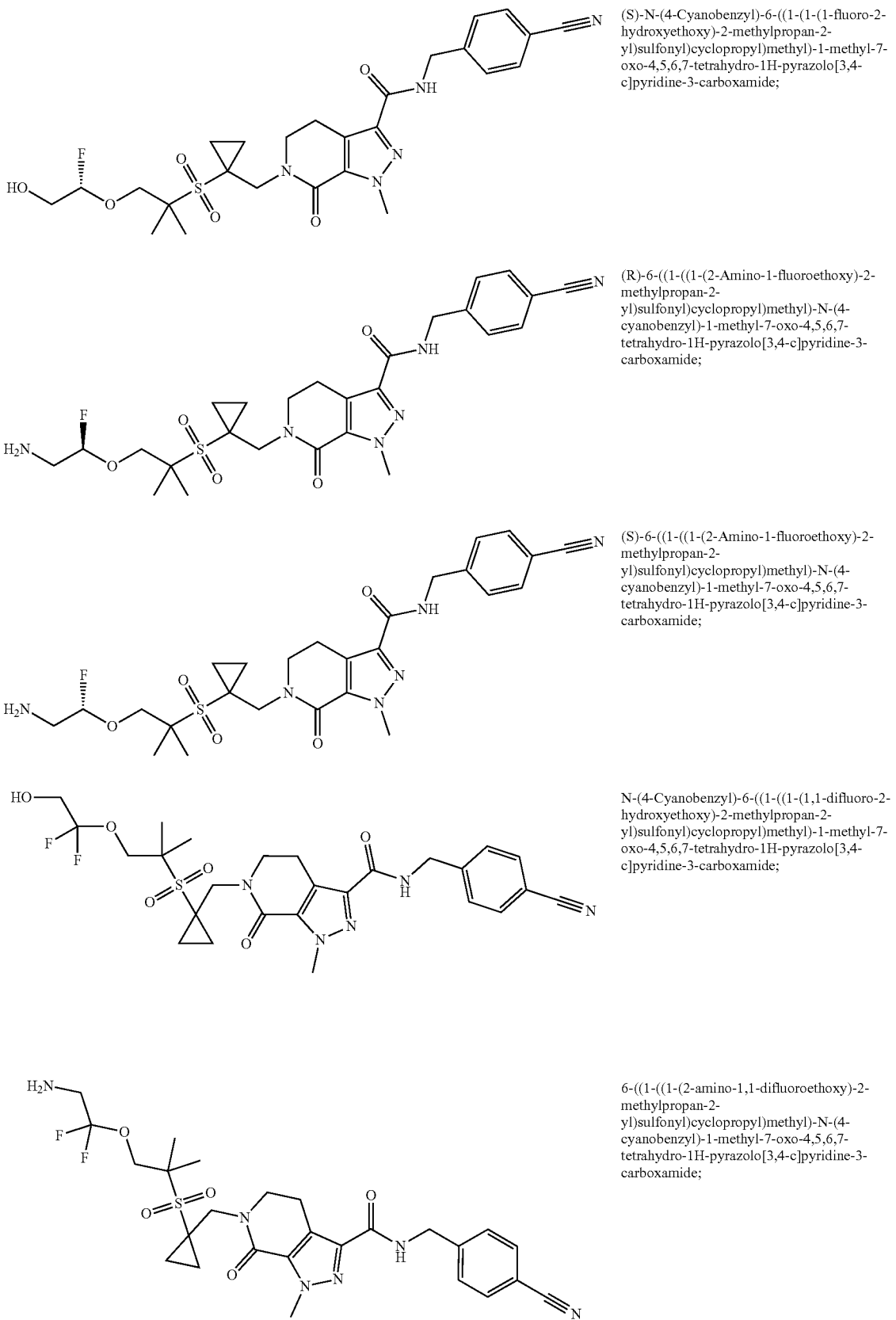

(S)-N-(4-Cyanobenzyl)-6-((1-(1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

(R)-6-((1-((1-(2-Amino-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

(S)-6-((1-((1-(2-Amino-1-fluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-Cyanobenzyl)-6-((1-((1-(1,1-difluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

6-((1-((1-(2-amino-1,1-difluoroethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

-continued

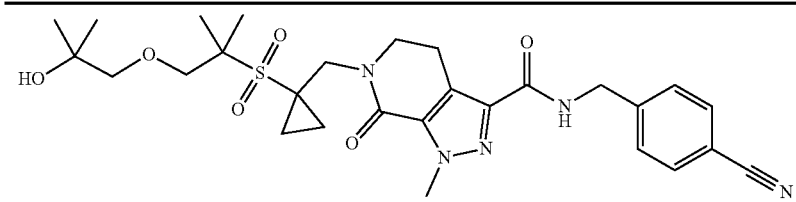
N-(4-Cyanobenzyl)-6-((1-((1-(2-hydroxy-2-methylpropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

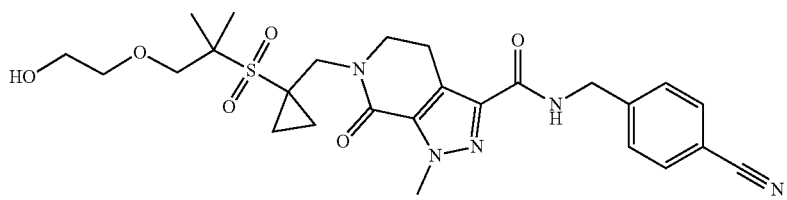 [SMILES: Cn1nc(C(=O)NCc2ccc(C#N)cc2)c2c1C(=O)N(CC1(S(=O)(=O)C(C)(C)COCCO)CC1)CC2]
N-(4-Cyanobenzyl)-6-((1-((1-(2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

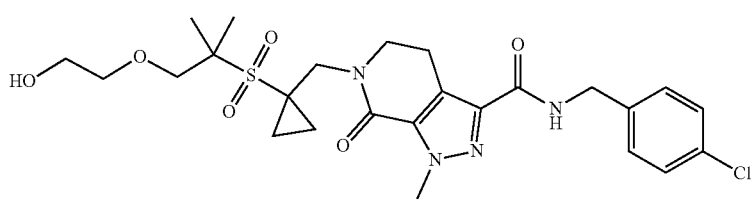 [SMILES: Cn1nc(C(=O)NCc2ccc(Cl)cc2)c2c1C(=O)N(CC1(S(=O)(=O)C(C)(C)COCCO)CC1)CC2]
N-(4-Chlorobenzyl)-6-((1-((1-(2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

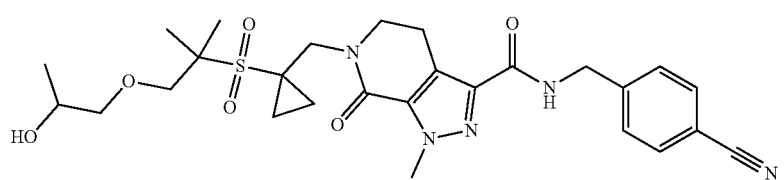 [SMILES: CC(O)COCC(C)(C)S(=O)(=O)C1(CN2CCc3c(C(=O)NCc4ccc(C#N)cc4)nn(C)c3C2=O)CC1]
N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

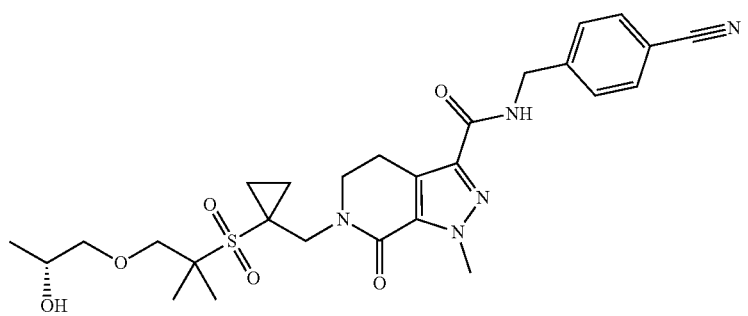 [SMILES: C[C@@H](O)COCC(C)(C)S(=O)(=O)C1(CN2CCc3c(C(=O)NCc4ccc(C#N)cc4)nn(C)c3C2=O)CC1]
(R)-N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

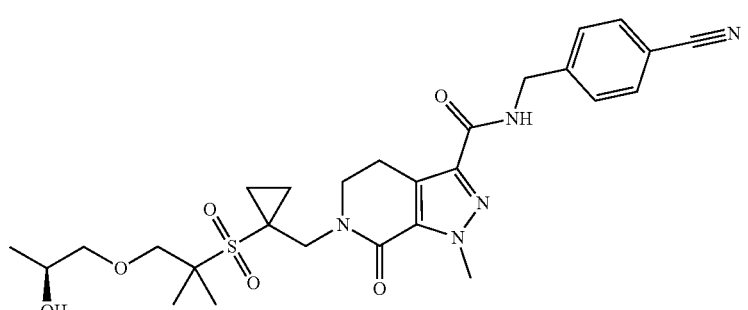
(S)-N-(4-Cyanobenzyl)-6-((1-((1-(2-hydroxypropoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

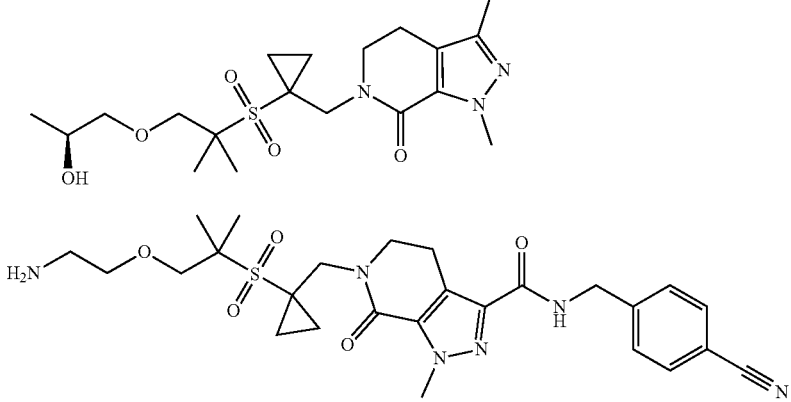
6-((1-((1-(2-Aminoethoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

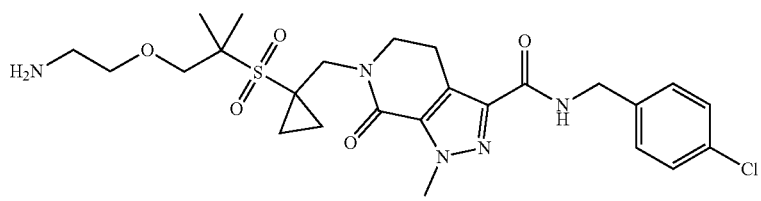 [SMILES: Cn1nc(C(=O)NCc2ccc(Cl)cc2)c2c1C(=O)N(CC1(S(=O)(=O)C(C)(C)COCCN)CC1)CC2]

6-((1-((1-(2-Aminoethoxy)-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

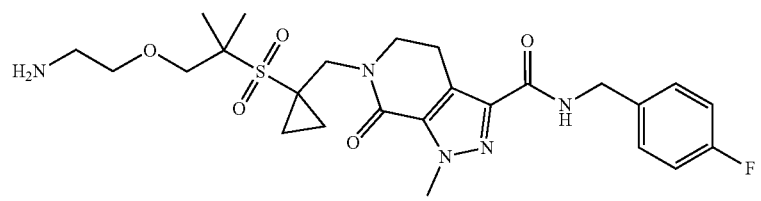 [SMILES: Cn1nc(C(=O)NCc2ccc(F)cc2)c2c1C(=O)N(CC1(S(=O)(=O)C(C)(C)COCCN)CC1)CC2]

6-((1-((1-(2-aminoethoxy)-2-methylpropan-2-yl)sulfonyl)cyclopropyl)methyl)-N-(4-fluorobenzyl)-1-methyl-7-oxo-4,5,6,7-tetrahydro-1H-pyrazolo[3,4-c]pyridine-3-carboxamide;

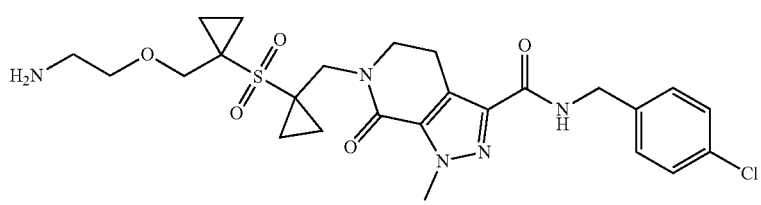 [SMILES: Cn1nc(C(=O)NCc2ccc(Cl)cc2)c2c1C(=O)N(CC1(S(=O)(=O)C3(COCCN)CC3)CC1)CC2]

6-((1-((1-((2-Aminoethoxy)methyl)cyclopropyl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

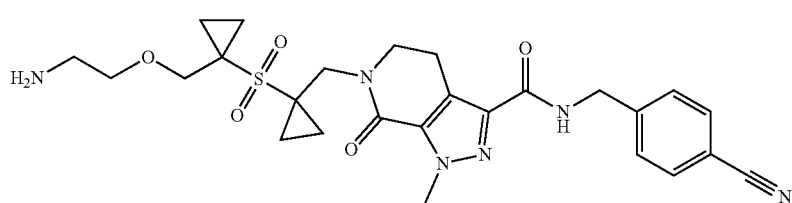 [SMILES: Cn1nc(C(=O)NCc2ccc(C#N)cc2)c2c1C(=O)N(CC1(S(=O)(=O)C3(COCCN)CC3)CC1)CC2]

6-((1-((1-((2-aminoethoxy)methyl)cyclopropyl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

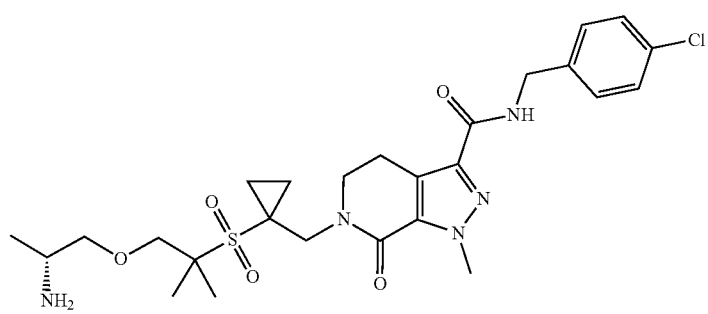 [SMILES: C[C@@H](N)COCC(C)(C)S(=O)(=O)C1(CN2CCc3c(C(=O)NCc4ccc(Cl)cc4)nn(C)c3C2=O)CC1]

(R)-6-((1-((1-(2-Aminopropoxy)-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

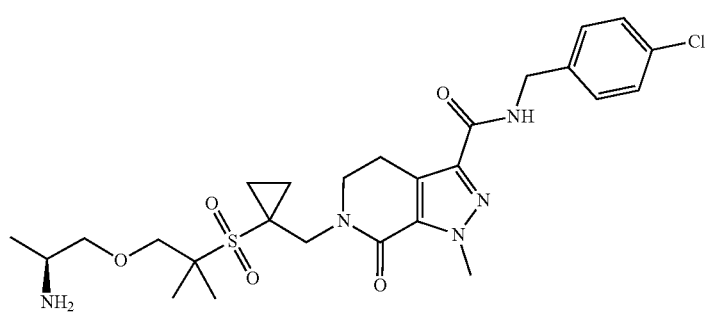 [SMILES: C[C@H](N)COCC(C)(C)S(=O)(=O)C1(CN2CCc3c(C(=O)NCc4ccc(Cl)cc4)nn(C)c3C2=O)CC1]

(S)-6-((1-((1-(2-Aminopropoxy)-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

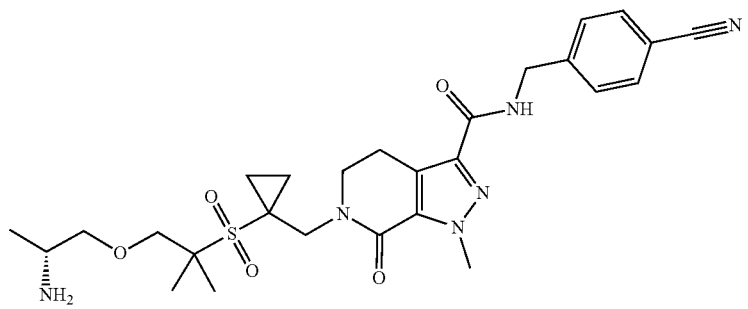 [SMILES: C[C@@H](N)COCC(C)(C)S(=O)(=O)C1(CN2CCc3c(C(=O)NCc4ccc(C#N)cc4)nn(C)c3C2=O)CC1]

(R)-6-((1-((1-(2-Aminopropoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

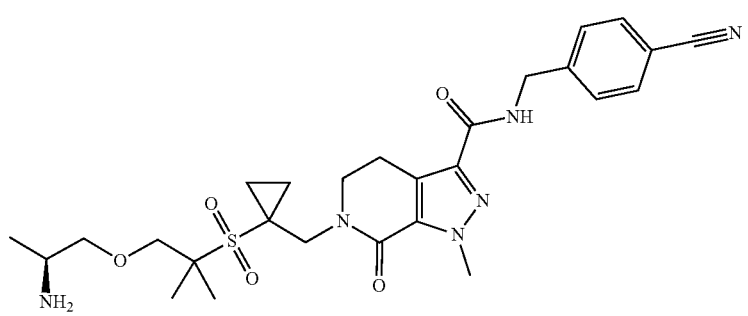 [SMILES: C[C@H](N)COCC(C)(C)S(=O)(=O)C1(CN2CCc3c(C(=O)NCc4ccc(C#N)cc4)nn(C)c3C2=O)CC1]

(S)-6-((1-((1-(2-Aminopropoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

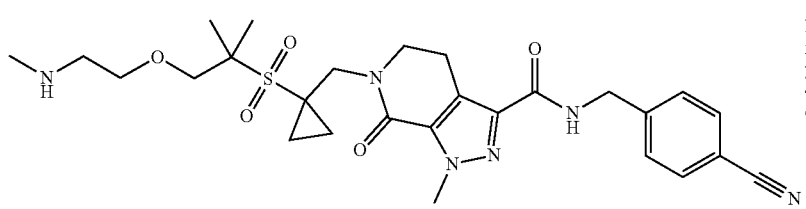 [SMILES: CNCCOCC(C)(C)S(=O)(=O)C1(CN2CCc3c(C(=O)NCc4ccc(C#N)cc4)nn(C)c3C2=O)CC1]

N-(4-Cyanobenzyl)-1-methyl-6-((1-((2-methyl-1-(2-(methylamino)ethoxy)propan-2-yl)sulfonyl)cyclopropyl)methyl)-7-oxo-4,5,6,7-tetrahydro-1H-pyrazolo[3,4-c]pyridine-3-carboxamide;

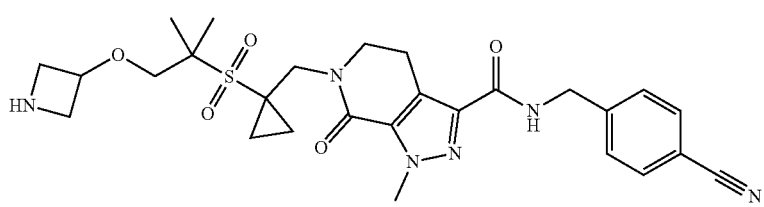 [SMILES: Cn1nc(C(=O)NCc2ccc(C#N)cc2)c2c1C(=O)N(CC1(S(=O)(=O)C(C)(C)COC3CNC3)CC1)CC2]

6-((1-((1-(Azetidin-3-yloxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

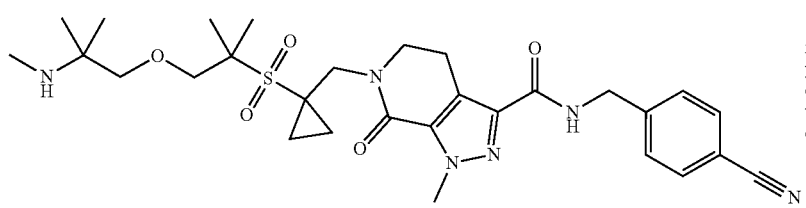 [SMILES: CNC(C)(C)COCC(C)(C)S(=O)(=O)C1(CN2CCc3c(C(=O)NCc4ccc(C#N)cc4)nn(C)c3C2=O)CC1]

6-((1-((1-(2-Amino-2-methylpropoxy)-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

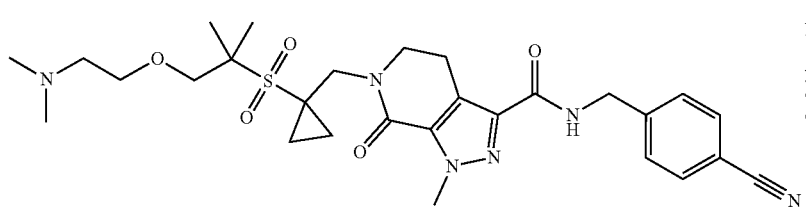

N-(4-Cyanobenzyl)-6-((1-((1-(2-(dimethylamino)ethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

-continued

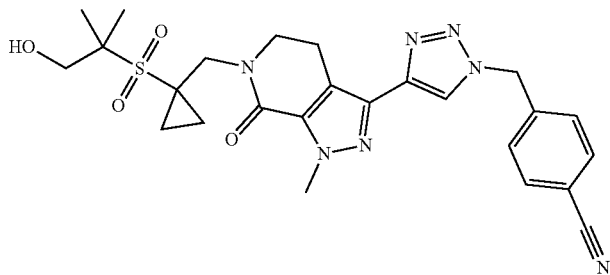 [SMILES: Cn1nc(-c2cn(Cc3ccc(C#N)cc3)nn2)c2c1C(=O)N(CC1(S(=O)(=O)C(C)(C)CO)CC1)CC2]

4-((4-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-1H-1,2,3-triazol-1-yl)methyl)benzonitrile;

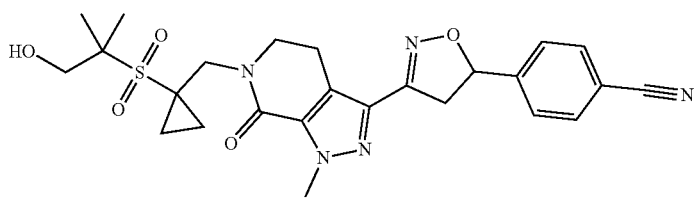 [SMILES: Cn1nc(C2=NOC(c3ccc(C#N)cc3)C2)c2c1C(=O)N(CC1(S(=O)(=O)C(C)(C)CO)CC1)CC2]

4-(3-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile;

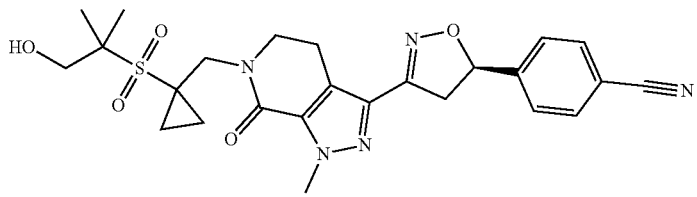 [SMILES: Cn1nc(C2=NO[C@@H](c3ccc(C#N)cc3)C2)c2c1C(=O)N(CC1(S(=O)(=O)C(C)(C)CO)CC1)CC2]

(R)-4-(3-(6-((1-((1-Hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile;

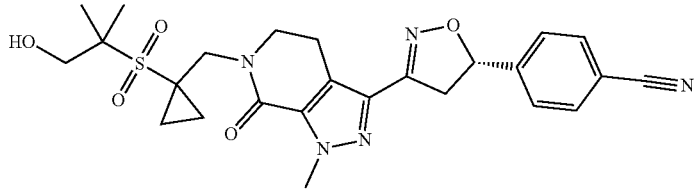 [SMILES: Cn1nc(C2=NO[C@H](c3ccc(C#N)cc3)C2)c2c1C(=O)N(CC1(S(=O)(=O)C(C)(C)CO)CC1)CC2]

(S)-4-(3-(6-((1-((1-hydroxy-2-methylpropan-2-yl)sulfonyl)cyclopropyl)methyl)-1-methyl-7-oxo-4,5,6,7-tetrahydro-1H-pyrazolo[3,4-c]pyridin-3-yl)-4,5-dihydroisoxazol-5-yl)benzonitrile;

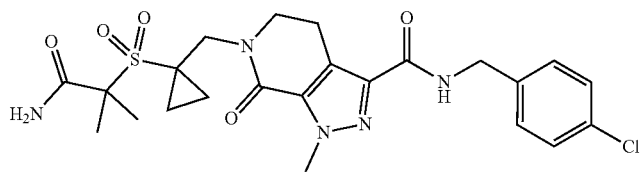 [SMILES: Cn1nc(C(=O)NCc2ccc(Cl)cc2)c2c1C(=O)N(CC1(S(=O)(=O)C(C)(C)C(N)=O)CC1)CC2]

6-((1-((1-Amino-2-methyl-1-oxopropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

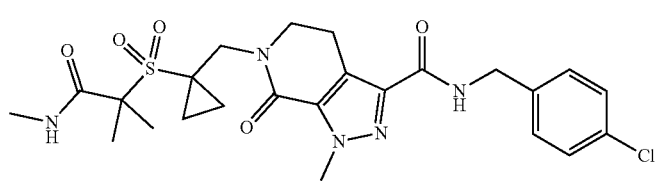 [SMILES: CNC(=O)C(C)(C)S(=O)(=O)C1(CN2CCc3c(C(=O)NCc4ccc(Cl)cc4)nn(C)c3C2=O)CC1]

N-(4-Chlorobenzyl)-1-methyl-6-((1-((2-methyl-1-(methylamino)-1-oxopropan-2-yl)sulfonyl)cyclopropyl)methyl)-7-oxo-4,5,6,7-tetrahydro-1H-pyrazolo[3,4-c]pyridine-3-carboxamide;

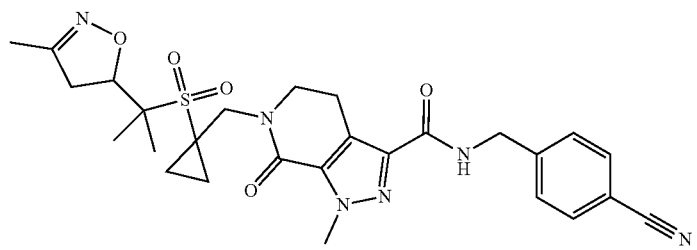 [SMILES: CC1=NOC(C(C)(C)S(=O)(=O)C2(CN3CCc4c(C(=O)NCc5ccc(C#N)cc5)nn(C)c4C3=O)CC2)C1]

N-(4-Cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide

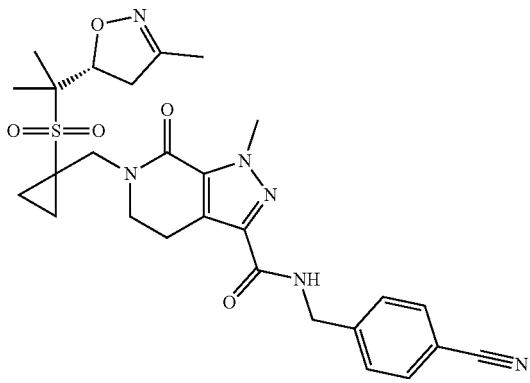 [SMILES: CC1=NO[C@@H](C(C)(C)S(=O)(=O)C2(CN3CCc4c(C(=O)NCc5ccc(C#N)cc5)nn(C)c4C3=O)CC2)C1]

(R)-N-(4-Cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide;

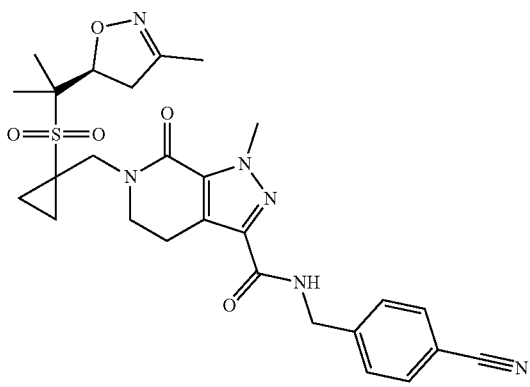 [SMILES: CC1=NO[C@H](C(C)(C)S(=O)(=O)C2(CN3CCc4c(C(=O)NCc5ccc(C#N)cc5)nn(C)c4C3=O)CC2)C1]

(S)-N-(4-Cyanobenzyl)-1-methyl-6-((1-((2-(3-methyl-4,5-dihydroisoxazol-5-yl)propan-2-yl)sulfonyl)cyclopropyl)methyl)-7-oxo-4,5,6,7-tetrahydro-1H-pyrazolo[3,4-c]pyridine-3-carboxamide;

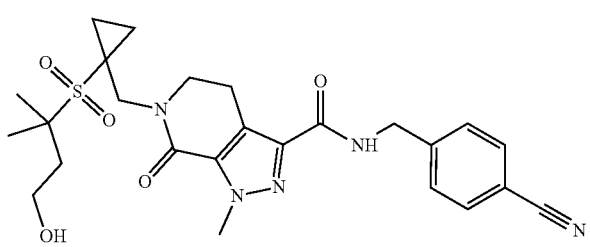 [SMILES: Cn1nc(C(=O)NCc2ccc(C#N)cc2)c2c1C(=O)N(CC1(S(=O)(=O)C(C)(C)CCO)CC1)CC2]

N-(4-Cyanobenzyl)-6-((1-((4-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

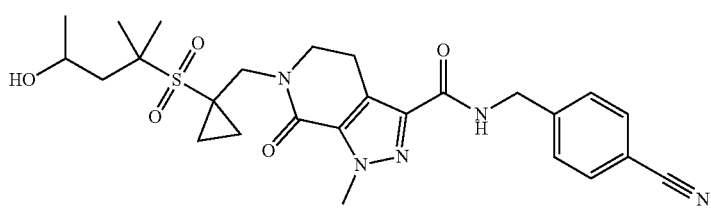 [SMILES: CC(O)CC(C)(C)S(=O)(=O)C1(CN2CCc3c(C(=O)NCc4ccc(C#N)cc4)nn(C)c3C2=O)CC1]

N-(4-cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide;

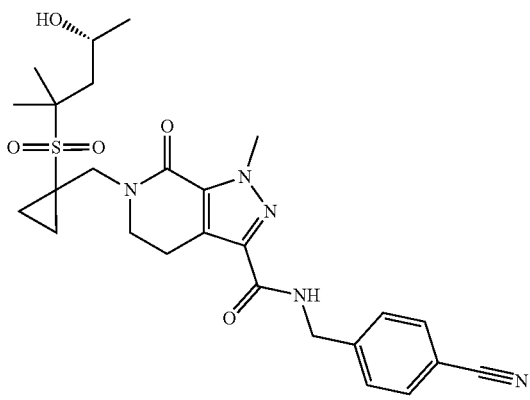 [SMILES: C[C@@H](O)CC(C)(C)S(=O)(=O)C1(CN2CCc3c(C(=O)NCc4ccc(C#N)cc4)nn(C)c3C2=O)CC1]

(R)-N-(4-Cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide;

-continued

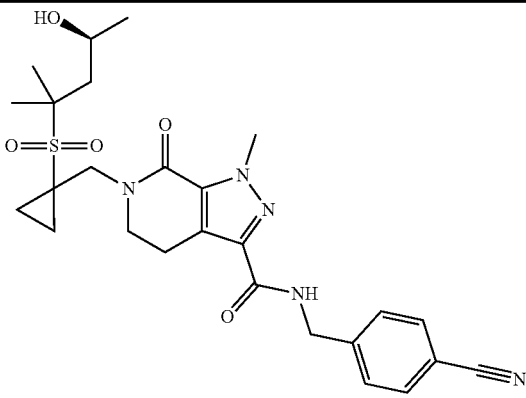
(S)-N-(4-Cyanobenzyl)-6-((1-((4-hydroxy-2-methylpentan-2-yl)sulfonyl)cyclopropyl)methyl)-1-methyl-7-oxo-4,5,6,7-tetrahydro-1H-pyrazolo[3,4-c]pyridine-3-carboxamide;

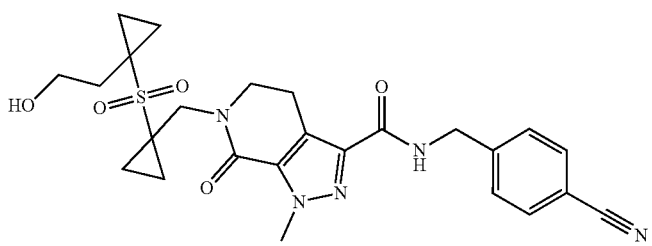 [SMILES: Cn1nc(C(=O)NCc2ccc(C#N)cc2)c2c1C(=O)N(CC1(S(=O)(=O)C3(CCO)CC3)CC1)CC2]
N-(4-Cyanobenzyl)-6-((1-((1-(2-hydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;

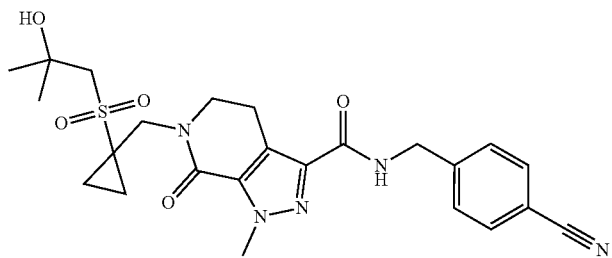 [SMILES: Cn1nc(C(=O)NCc2ccc(C#N)cc2)c2c1C(=O)N(CC1(S(=O)(=O)CC(C)(C)O)CC1)CC2]
N-(4-Cyanobenzyl)-6-((1-(((2-hydroxy-2-methylpropyl)sulfonyl)cyclopropyl)methyl)-1-methyl-7-oxo-4,5,6,7-tetrahydro-1H-pyrazolo[3,4-c]pyridine-3-carboxamide;

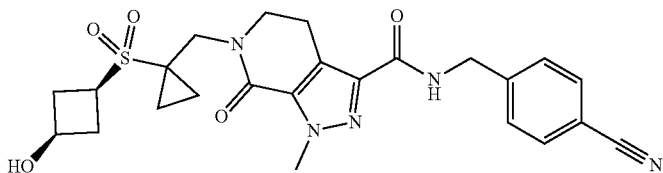 [SMILES: Cn1nc(C(=O)NCc2ccc(C#N)cc2)c2c1C(=O)N(CC1(S(=O)(=O)[C@H]3C[C@@H](O)C3)CC1)CC2]
N-(4-Cyanobenzyl)-6-((1-(((1s,3s)-3-hydroxycyclobutyl)sulfonyl)cyclopropyl)methyl)-1-methyl-7-oxo-4,5,6,7-tetrahydro-1H-pyrazolo[3,4-c]pyridine-3-carboxamide;

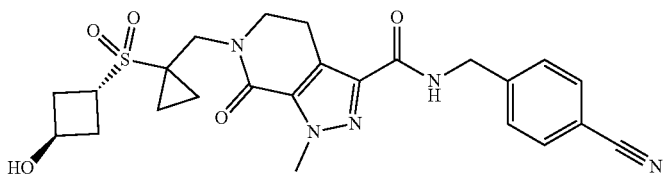 [SMILES: Cn1nc(C(=O)NCc2ccc(C#N)cc2)c2c1C(=O)N(CC1(S(=O)(=O)[C@H]3C[C@H](O)C3)CC1)CC2]
N-(4-Cyanobenzyl)-6-((1-(((1r,3r)-3-hydroxycyclobutyl)sulfonyl)cyclopropyl)methyl)-1-methyl-7-oxo-4,5,6,7-tetrahydro-1H-pyrazolo[3,4-c]pyridine-3-carboxamide;

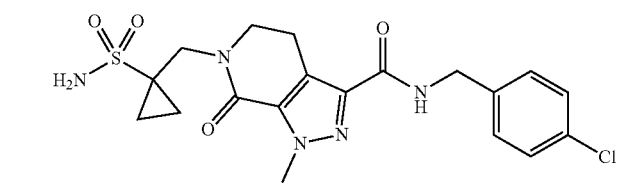 [SMILES: Cn1nc(C(=O)NCc2ccc(Cl)cc2)c2c1C(=O)N(CC1(S(N)(=O)=O)CC1)CC2]
N-(4-Chlorobenzyl)-1-methyl-7-oxo-6-((1-sulfamoylcyclopropyl)methyl)-4,5,6,7-tetrahydro-1H-pyrazolo[3,4-c]pyridine-3-carboxamide;

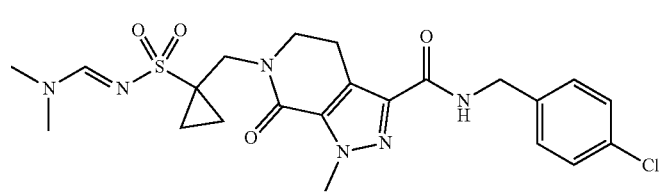 [SMILES: CN(C)/C=N/S(=O)(=O)C1(CN2CCc3c(C(=O)NCc4ccc(Cl)cc4)nn(C)c3C2=O)CC1]
(E)-N-(4-Chlorobenzyl)-6-((1-(N-((dimethylamino)methylene)sulfamoyl)cyclopropyl)methyl)-1-methyl-7-oxo-4,5,6,7-tetrahydro-1H-pyrazolo[3,4-c]pyridine-3-carboxamide;

-continued

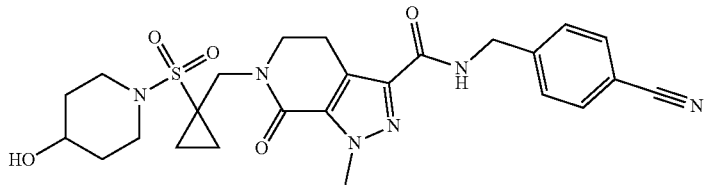 [SMILES: Cn1nc(C(=O)NCc2ccc(C#N)cc2)c2c1C(=O)N(CC1(S(=O)(=O)N3CCC(O)CC3)CC1)CC2]

N-(4-Cyanobenzyl)-1-methyl-6-((1-(N-methylsulfamoyl)cyclopropyl)methyl)-7-oxo-4,5,6,7-tetrahydro-1H-pyrazolo[3,4-c]pyridine-3-carboxamide;

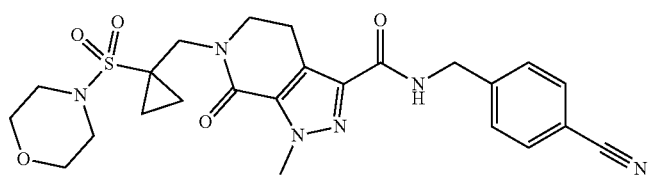 [SMILES: Cn1nc(C(=O)NCc2ccc(C#N)cc2)c2c1C(=O)N(CC1(S(=O)(=O)N3CCOCC3)CC1)CC2]

N-(4-Cyanobenzyl)-1-methyl-6-((1-(morpholinosulfonyl)cyclopropyl)methyl)-7-oxo-4,5,6,7-tetrahydro-1H-pyrazolo[3,4-c]pyridine-3-carboxamide;

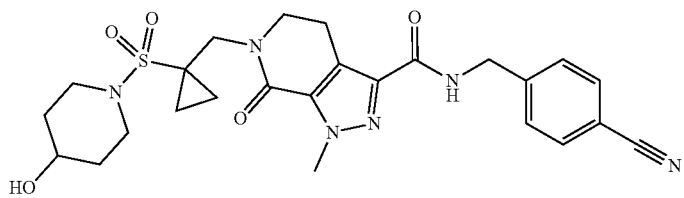 [SMILES: Cn1nc(C(=O)NCc2ccc(C#N)cc2)c2c1C(=O)N(CC1(S(=O)(=O)N3CCC(O)CC3)CC1)CC2]

N-(4-Cyanobenzyl)-6-((1-((4-hydroxypiperidin-1-yl)sulfonyl)cyclopropyl)methyl)-1-methyl-7-oxo-4,5,6,7-tetrahydro-1H-pyrazolo[3,4-c]pyridine-3-carboxamide;

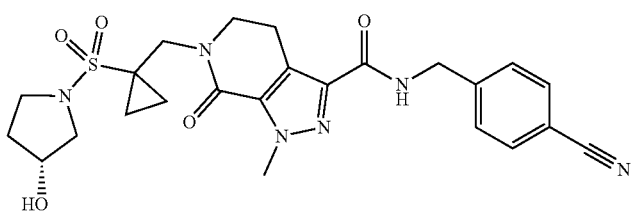 [SMILES: Cn1nc(C(=O)NCc2ccc(C#N)cc2)c2c1C(=O)N(CC1(S(=O)(=O)N3CC[C@@H](O)C3)CC1)CC2]

(R)-N-(4-Cyanobenzyl)-6-((1-((3-hydroxypyrrolidin-1-yl)sulfonyl)cyclopropyl)methyl)-1-methyl-7-oxo-4,5,6,7-tetrahydro-1H-pyrazolo[3,4-c]pyridine-3-carboxamide;

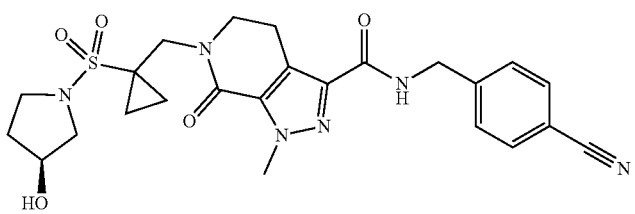 [SMILES: Cn1nc(C(=O)NCc2ccc(C#N)cc2)c2c1C(=O)N(CC1(S(=O)(=O)N3CC[C@H](O)C3)CC1)CC2]

(S)-N-(4-Cyanobenzyl)-6-((1-((3-hydroxypyrrolidin-1-yl)sulfonyl)cyclopropyl)methyl)-1-methyl-7-oxo-4,5,6,7-tetrahydro-1H-pyrazolo[3,4-c]pyridine-3-carboxamide;

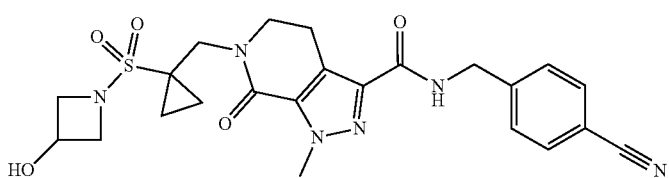 [SMILES: Cn1nc(C(=O)NCc2ccc(C#N)cc2)c2c1C(=O)N(CC1(S(=O)(=O)N3CC(O)C3)CC1)CC2]

N-(4-Cyanobenzyl)-6-((1-((3-hydroxyazetidin-1-yl)sulfonyl)cyclopropyl)methyl)-1-methyl-7-oxo-4,5,6,7-tetrahydro-1H-pyrazolo[3,4-c]pyridine-3-carboxamide;

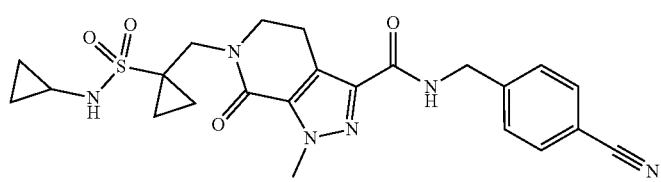 [SMILES: Cn1nc(C(=O)NCc2ccc(C#N)cc2)c2c1C(=O)N(CC1(S(=O)(=O)NC3CC3)CC1)CC2]

N-(4-cyanobenzyl)-6-((1-(N-cyclopropylsulfamoyl)cyclopropyl)methyl)-1-methyl-7-oxo-4,5,6,7-tetrahydro-1H-pyrazolo[3,4-c]pyridine-3-carboxamide;

-continued

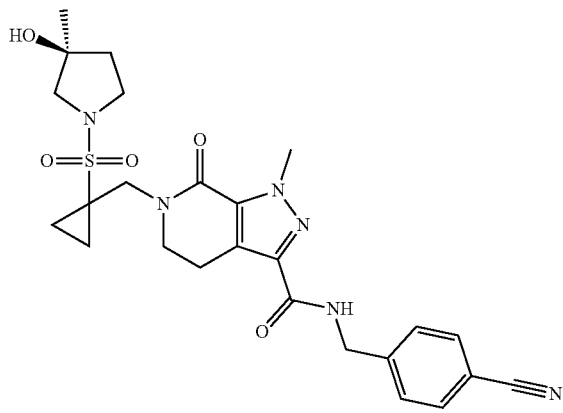 [SMILES: Cn1nc(C(=O)NCc2ccc(C#N)cc2)c2c1C(=O)N(CC1(S(=O)(=O)N3CC[C@](C)(O)C3)CC1)CC2]

(S)-N-(4-Cyanobenzyl)-6-((1-((3-hydroxy-3-methylpyrrolidin-1-yl)sulfonyl)cyclopropyl)methyl)-1-methyl-7-oxo-4,5,6,7-tetrahydro-1H-pyrazolo[3,4-c]pyridine-3-carboxamide;

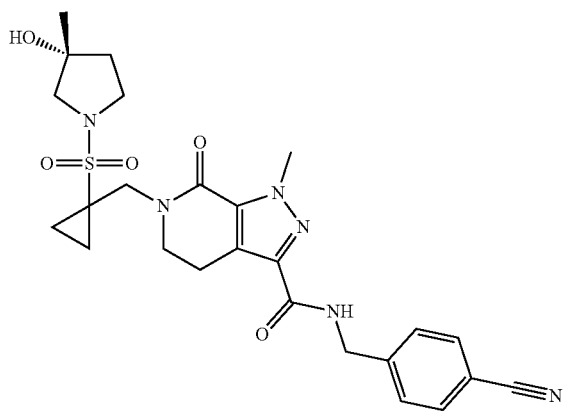 [SMILES: Cn1nc(C(=O)NCc2ccc(C#N)cc2)c2c1C(=O)N(CC1(S(=O)(=O)N3CC[C@@](C)(O)C3)CC1)CC2]

(R)-N-(4-Cyanobenzyl)-6-((1-((3-hydroxy-3-methylpyrrolidin-1-yl)sulfonyl)cyclopropyl)methyl)-1-methyl-7-oxo-4,5,6,7-tetrahydro-1H-pyrazolo[3,4-c]pyridine-3-carboxamide;

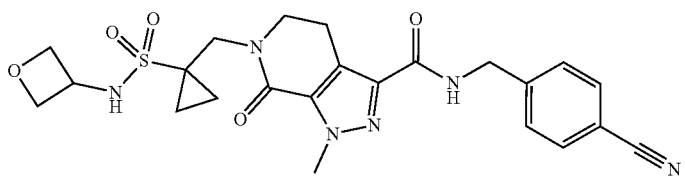 [SMILES: Cn1nc(C(=O)NCc2ccc(C#N)cc2)c2c1C(=O)N(CC1(S(=O)(=O)NC3COC3)CC1)CC2]

N-(4-Cyanobenzyl)-1-methyl-6-((1-(N-(oxetan-3-yl)sulfamoyl)cyclopropyl)methyl)-7-oxo-4,5,6,7-tetrahydro-1H-pyrazolo[3,4-c]pyridine-3-carboxamide;

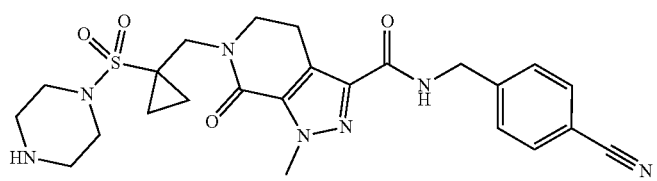 [SMILES: Cn1nc(C(=O)NCc2ccc(C#N)cc2)c2c1C(=O)N(CC1(S(=O)(=O)N3CCNCC3)CC1)CC2]

N-(4-Cyanobenzyl)-1-methyl-7-oxo-6-((1-(piperazin-1-ylsulfonyl)cyclopropyl)methyl)-4,5,6,7-tetrahydro-1H-pyrazolo[3,4-c]pyridine-3-carboxamide;

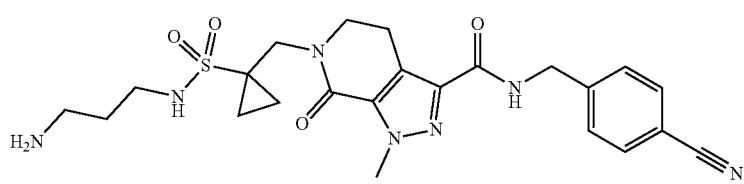 [SMILES: Cn1nc(C(=O)NCc2ccc(C#N)cc2)c2c1C(=O)N(CC1(S(=O)(=O)NCCCN)CC1)CC2]

6-((1-(N-(3-Aminopropyl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide;

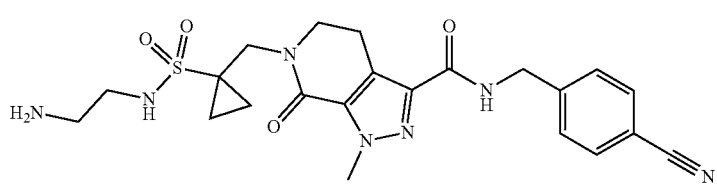 [SMILES: Cn1nc(C(=O)NCc2ccc(C#N)cc2)c2c1C(=O)N(CC1(S(=O)(=O)NCCN)CC1)CC2]

6-((1-(N-(2-Aminoethyl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide;

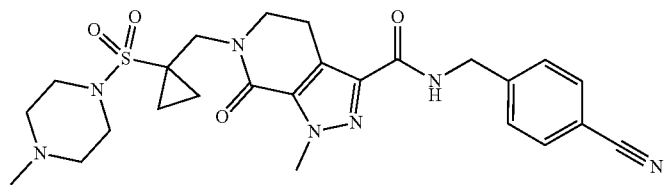 [SMILES: CN1CCN(S(=O)(=O)C2(CN3CCc4c(C(=O)NCc5ccc(C#N)cc5)nn(C)c4C3=O)CC2)CC1]

N-(4-Cyanobenzyl)-1-methyl-6-((1-((4-methylpiperazin-1-yl)sulfonyl)cyclopropyl)methyl)-7-oxo-4,5,6,7-tetrahydro-1H-pyrazolo[3,4-c]pyridine-3-carboxamide;

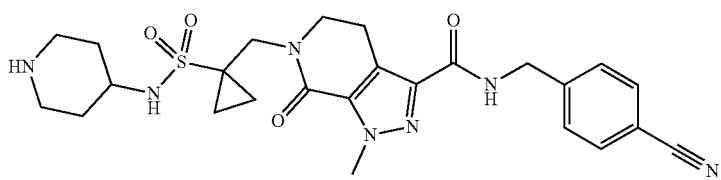 [SMILES: Cn1nc(C(=O)NCc2ccc(C#N)cc2)c2c1C(=O)N(CC1(S(=O)(=O)NC3CCNCC3)CC1)CC2]

N-(4-Cyanobenzyl)-1-methyl-7-oxo-6-((1-(N-(piperidin-4-yl)sulfamoyl)cyclopropyl)methyl)-4,5,6,7-tetrahydro-1H-pyrazolo[3,4-c]pyridine-3-carboxamide;

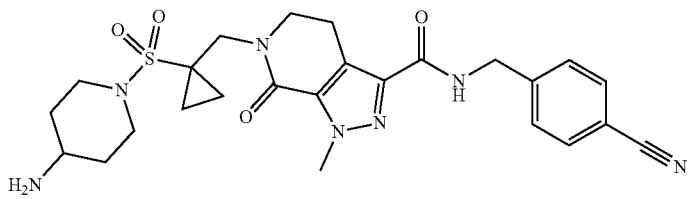 [SMILES: Cn1nc(C(=O)NCc2ccc(C#N)cc2)c2c1C(=O)N(CC1(S(=O)(=O)N3CCC(N)CC3)CC1)CC2]

6-((1-((4-Aminopiperidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

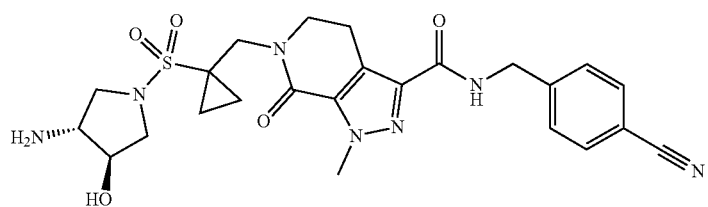 [SMILES: Cn1nc(C(=O)NCc2ccc(C#N)cc2)c2c1C(=O)N(CC1(S(=O)(=O)N3C[C@@H](N)[C@H](O)C3)CC1)CC2]

6-((1-(((3S,4R)-3-Amino-4-hydroxypyrrolidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

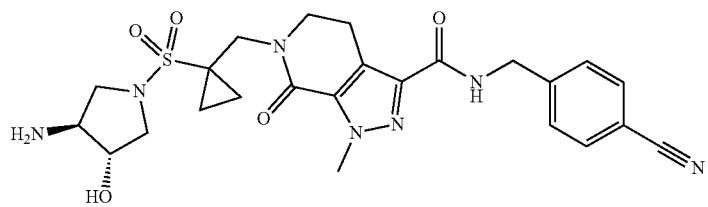 [SMILES: Cn1nc(C(=O)NCc2ccc(C#N)cc2)c2c1C(=O)N(CC1(S(=O)(=O)N3C[C@H](N)[C@@H](O)C3)CC1)CC2]

6-((1-(((3S,4S)-3-Amino-4-hydroxypyrrolidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

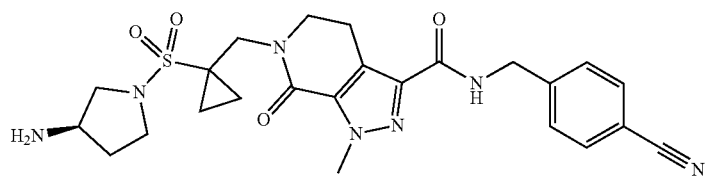 [SMILES: Cn1nc(C(=O)NCc2ccc(C#N)cc2)c2c1C(=O)N(CC1(S(=O)(=O)N3CC[C@@H](N)C3)CC1)CC2]

(R)-6-((1-((3-Aminopyrrolidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

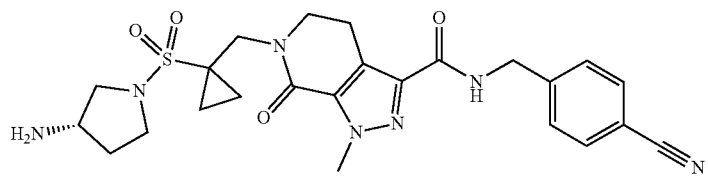 [SMILES: Cn1nc(C(=O)NCc2ccc(C#N)cc2)c2c1C(=O)N(CC1(S(=O)(=O)N3CC[C@H](N)C3)CC1)CC2]

(S)-6-((1-((3-Aminopyrrolidin-1-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

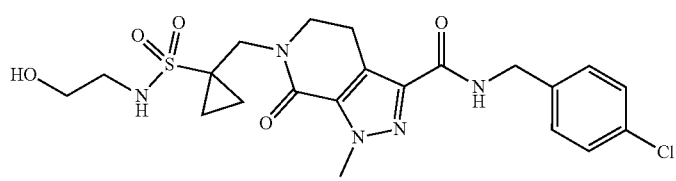 [SMILES: Cn1nc(C(=O)NCc2ccc(Cl)cc2)c2c1C(=O)N(CC1(S(=O)(=O)NCCO)CC1)CC2]

N-(4-Chlorobenzyl)-6-((1-(N-(2-hydroxyethyl)sulfamoyl)cyclopropyl)methyl)-1-methyl-7-oxo-4,5,6,7-tetrahydro-1H-pyrazolo[3,4-c]pyridine-3-carboxamide;

-continued

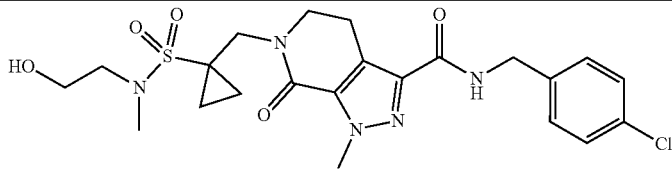
N-(4-Chlorobenzyl)-6-((1-(N-(2-hydroxyethyl)-N-methylsulfamoyl)cyclopropyl)methyl)-1-methyl-7-oxo-4,5,6,7-tetrahydro-1H-pyrazolo[3,4-c]pyridine-3-carboxamide;

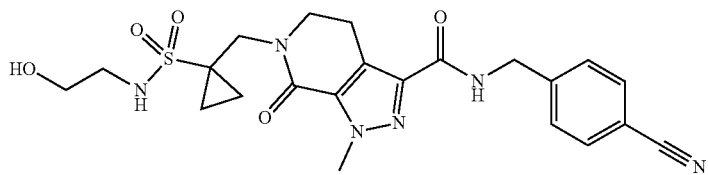 [SMILES: Cn1nc(C(=O)NCc2ccc(C#N)cc2)c2c1C(=O)N(CC1(S(=O)(=O)NCCO)CC1)CC2]
N-(4-Cyanobenzyl)-6-((1-(N-(2-hydroxyethyl)sulfamoyl)cyclopropyl)methyl)-1-methyl-7-oxo-4,5,6,7-tetrahydro-1H-pyrazolo[3,4-c]pyridine-3-carboxamide;

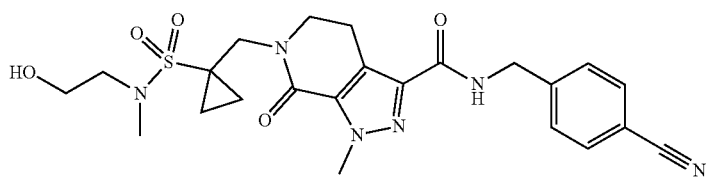
N-(4-Cyanobenzyl)-6-((1-(N-(2-hydroxyethyl)-N-methylsulfamoyl)cyclopropyl)methyl)-1-methyl-7-oxo-4,5,6,7-tetrahydro-1H-pyrazolo[3,4-c]pyridine-3-carboxamide;

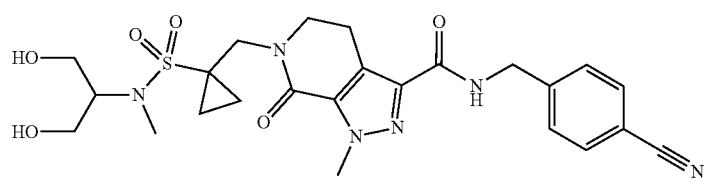 [SMILES: CN(C(CO)CO)S(=O)(=O)C1(CN2CCc3c(C(=O)NCc4ccc(C#N)cc4)nn(C)c3C2=O)CC1]
N-(4-Cyanobenzyl)-6-((1-(N-(1,3-dihydroxypropan-2-yl)-N-methylsulfamoyl)cyclopropyl)methyl)-1-methyl-7-oxo-4,5,6,7-tetrahydro-1H-pyrazolo[3,4-c]pyridine-3-carboxamide;

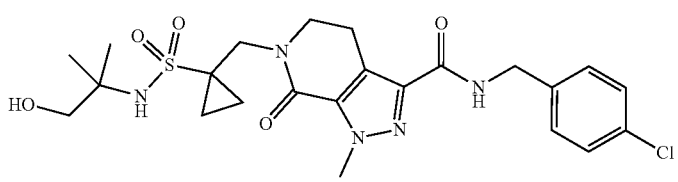 [SMILES: Cn1nc(C(=O)NCc2ccc(Cl)cc2)c2c1C(=O)N(CC1(S(=O)(=O)NC(C)(C)CO)CC1)CC2]
N-(4-Chlorobenzyl)-6-((1-(N-(1-hydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxamide;

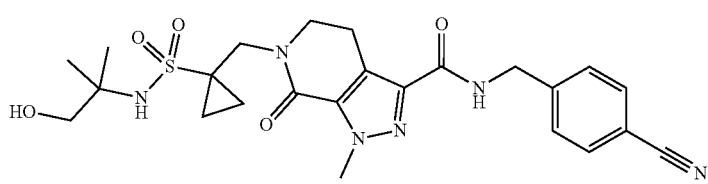 [SMILES: Cn1nc(C(=O)NCc2ccc(C#N)cc2)c2c1C(=O)N(CC1(S(=O)(=O)NC(C)(C)CO)CC1)CC2]
N-(4-Cyanobenzyl)-6-((1-(N-(1-hydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxamide;

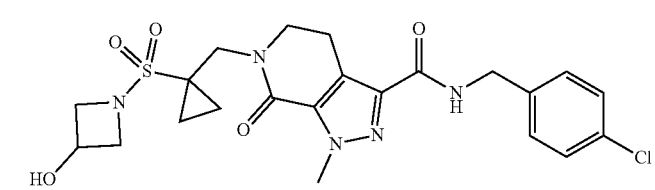 [SMILES: Cn1nc(C(=O)NCc2ccc(Cl)cc2)c2c1C(=O)N(CC1(S(=O)(=O)N3CC(O)C3)CC1)CC2]
N-(4-Chlorobenzyl)-6-((1-((3-hydroxyazetidin-1-yl)sulfonyl)cyclopropyl)methyl)-1-methyl-7-oxo-4,5,6,7-tetrahydro-1H-pyrazolo[3,4-c]pyridine-3-carboxamide;

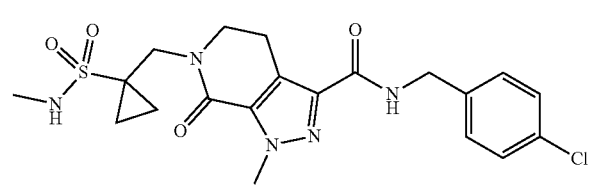 [SMILES: CNS(=O)(=O)C1(CN2CCc3c(C(=O)NCc4ccc(Cl)cc4)nn(C)c3C2=O)CC1]
N-(4-Chlorobenzyl)-1-methyl-6-((1-(N-methylsulfamoyl)cyclopropyl)methyl)-7-oxo-4,5,6,7-tetrahydro-1H-pyrazolo[3,4-c]pyridine-3-carboxamide;

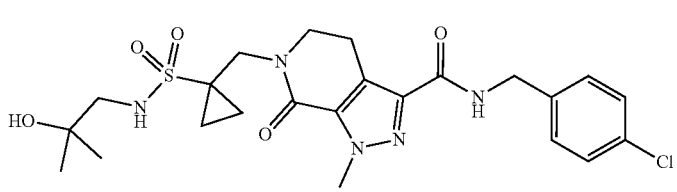 [SMILES: Cn1nc(C(=O)NCc2ccc(Cl)cc2)c2c1C(=O)N(CC1(S(=O)(=O)NCC(C)(C)O)CC1)CC2]
N-(4-Chlorobenzyl)-6-((1-(N-(2-hydroxy-2-methylpropyl)sulfamoyl)cyclopropyl)methyl)-1-methyl-7-oxo-4,5,6,7-tetrahydro-1H-pyrazolo[3,4-c]pyridine-3-carboxamide;

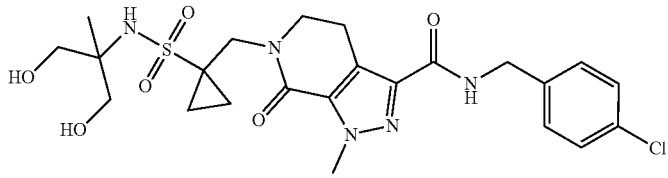 [SMILES: Cn1nc(C(=O)NCc2ccc(Cl)cc2)c2c1C(=O)N(CC1(S(=O)(=O)NC(C)(CO)CO)CC1)CC2]

N-(4-Chlorobenzyl)-6-((1-(N-(1,3-dihydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxamide;

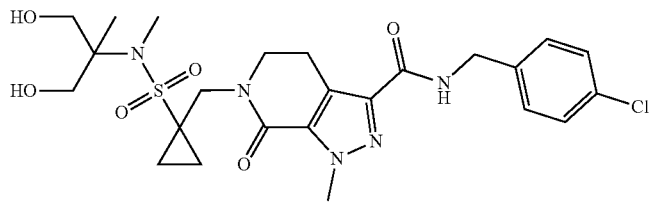 [SMILES: CN(C(C)(CO)CO)S(=O)(=O)C1(CN2CCc3c(C(=O)NCc4ccc(Cl)cc4)nn(C)c3C2=O)CC1]

N-(4-Chlorobenzyl)-6-((1-(N-(1,3-dihydroxy-2-methylpropan-2-yl)-N-methylsulfamoyl)cyclopropyl)methyl)-1-methyl-7-oxo-4,5,6,7-tetrahydro-1H-pyrazolo[3,4-c]pyridine-3-carboxamide;

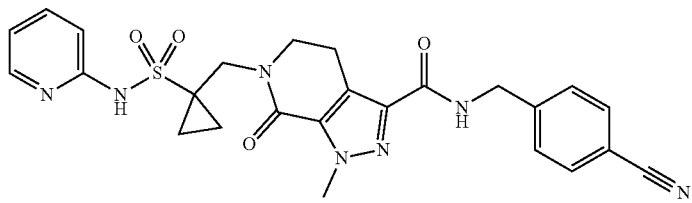 [SMILES: Cn1nc(C(=O)NCc2ccc(C#N)cc2)c2c1C(=O)N(CC1(S(=O)(=O)Nc3ccccn3)CC1)CC2]

N-(4-Cyanobenzyl)-1-methyl-7-oxo-6-((1-(N-(pyridin-2-yl)sulfamoyl)cyclopropyl)methyl)-4,5,6,7-tetrahydro-1H-pyrazolo[3,4-c]pyridine-3-carboxamide;

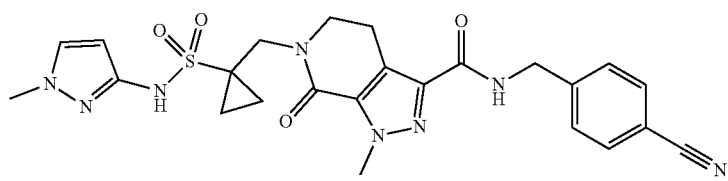 [SMILES: Cn1ccc(NS(=O)(=O)C2(CN3CCc4c(C(=O)NCc5ccc(C#N)cc5)nn(C)c4C3=O)CC2)n1]

N-(4-Cyanobenzyl)-1-methyl-6-((1-(N-(1-methyl-1H-pyrazol-3-yl)sulfamoyl)cyclopropyl)methyl)-7-oxo-4,5,6,7-tetrahydro-1H-pyrazolo[3,4-c]pyridine-3-carboxamide;

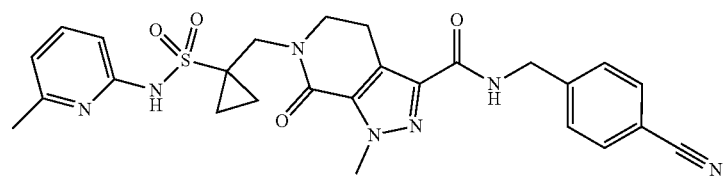 [SMILES: Cc1cccc(NS(=O)(=O)C2(CN3CCc4c(C(=O)NCc5ccc(C#N)cc5)nn(C)c4C3=O)CC2)n1]

N-(4-Cyanobenzyl)-1-methyl-6-((1-(N-(6-methylpyridin-2-yl)sulfamoyl)cyclopropyl)methyl)-7-oxo-4,5,6,7-tetrahydro-1H-pyrazolo[3,4-c]pyridine-3-carboxamide;

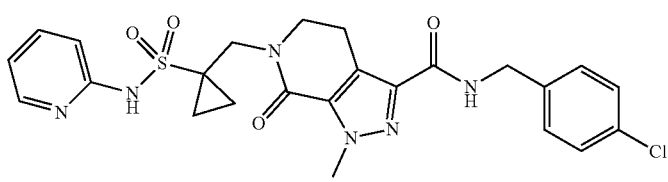 [SMILES: Cn1nc(C(=O)NCc2ccc(Cl)cc2)c2c1C(=O)N(CC1(S(=O)(=O)Nc3ccccn3)CC1)CC2]

N-(4-Chlorobenzyl)-1-methyl-7-oxo-6-((1-(N-(pyridin-2-yl)sulfamoyl)cyclopropyl)methyl)-4,5,6,7-tetrahydro-1H-pyrazolo[3,4-c]pyridine-3-carboxamide;

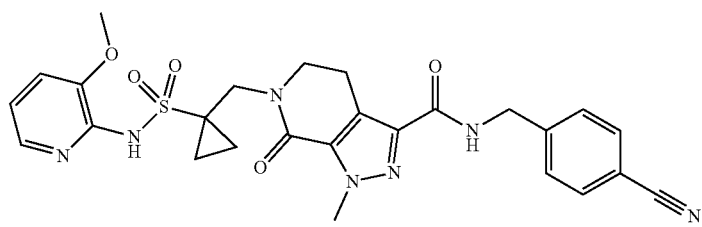 [SMILES: COc1cccnc1NS(=O)(=O)C1(CN2CCc3c(C(=O)NCc4ccc(C#N)cc4)nn(C)c3C2=O)CC1]

N-(4-Cyanobenzyl)-6-((1-(N-(3-methoxypyridin-2-yl)sulfamoyl)cyclopropyl)methyl)-1-methyl-7-oxo-4,5,6,7-tetrahydro-1H-pyrazolo[3,4-c]pyridine-3-carboxamide;

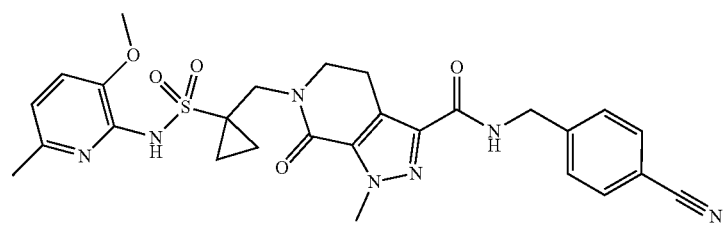 [SMILES: COc1ccc(C)nc1NS(=O)(=O)C1(CN2CCc3c(C(=O)NCc4ccc(C#N)cc4)nn(C)c3C2=O)CC1]

N-(4-Cyanobenzyl)-6-((1-(N-(3-methoxy-6-methylpyridin-2-yl)sulfamoyl)cyclopropyl)methyl)-1-methyl-7-oxo-4,5,6,7-tetrahydro-1H-pyrazolo[3,4-c]pyridine-3-carboxamide;

-continued

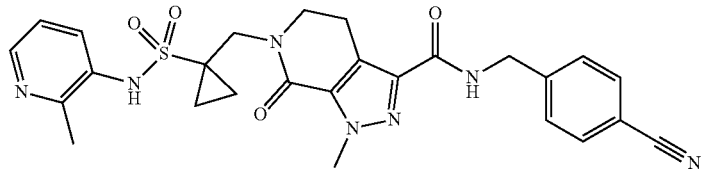 [SMILES: Cc1ncccc1NS(=O)(=O)C1(CN2CCc3c(C(=O)NCc4ccc(C#N)cc4)nn(C)c3C2=O)CC1]

N-(4-Cyanobenzyl)-1-methyl-6-((1-(N-(2-methylpyridin-3-yl)sulfamoyl)cyclopropyl)methyl)-7-oxo-4,5,6,7-tetrahydro-1H-pyrazolo[3,4-c]pyridine-3-carboxamide;

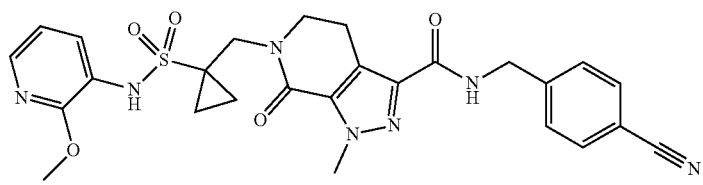 [SMILES: COc1ncccc1NS(=O)(=O)C1(CN2CCc3c(C(=O)NCc4ccc(C#N)cc4)nn(C)c3C2=O)CC1]

N-(4-Cyanobenzyl)-6-((1-(N-(2-methoxypyridin-3-yl)sulfamoyl)cyclopropyl)methyl)-1-methyl-7-oxo-4,5,6,7-tetrahydro-1H-pyrazolo[3,4-c]pyridine-3-carboxamide;

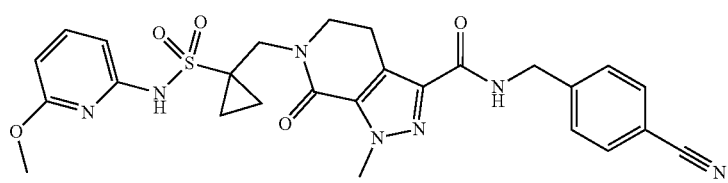 [SMILES: COc1cccc(NS(=O)(=O)C2(CN3CCc4c(C(=O)NCc5ccc(C#N)cc5)nn(C)c4C3=O)CC2)n1]

N-(4-Cyanobenzyl)-6-((1-(N-(6-methoxypyridin-2-yl)sulfamoyl)cyclopropyl)methyl)-1-methyl-7-oxo-4,5,6,7-tetrahydro-1H-pyrazolo[3,4-c]pyridine-3-carboxamide;

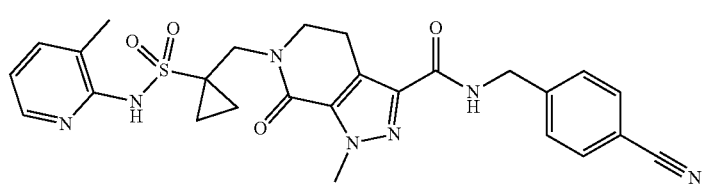 [SMILES: Cc1cccnc1NS(=O)(=O)C1(CN2CCc3c(C(=O)NCc4ccc(C#N)cc4)nn(C)c3C2=O)CC1]

N-(4-Cyanobenzyl)-1-methyl-6-((1-(N-(3-methylpyridin-2-yl)sulfamoyl)cyclopropyl)methyl)-7-oxo-4,5,6,7-tetrahydro-1H-pyrazolo[3,4-c]pyridine-3-carboxamide;

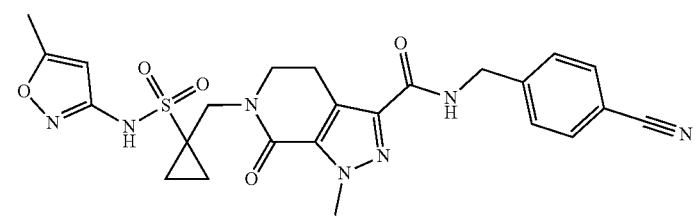 [SMILES: Cc1cc(NS(=O)(=O)C2(CN3CCc4c(C(=O)NCc5ccc(C#N)cc5)nn(C)c4C3=O)CC2)no1]

N-(4-Cyanobenzyl)-1-methyl-6-((1-(N-(5-methylisoxazol-3-yl)sulfamoyl)cyclopropyl)methyl)-7-oxo-4,5,6,7-tetrahydro-1H-pyrazolo[3,4-c]pyridine-3-carboxamide;

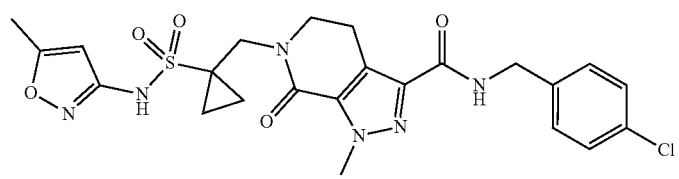 [SMILES: Cc1cc(NS(=O)(=O)C2(CN3CCc4c(C(=O)NCc5ccc(Cl)cc5)nn(C)c4C3=O)CC2)no1]

N-(4-Chlorobenzyl)-1-methyl-6-((1-(N-(5-methylisoxazol-3-yl)sulfamoyl)cyclopropyl)methyl)-7-oxo-4,5,6,7-tetrahydro-1H-pyrazolo[3,4-c]pyridine-3-carboxamide;

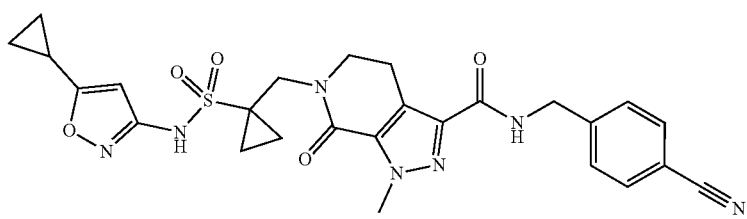 [SMILES: Cn1nc(C(=O)NCc2ccc(C#N)cc2)c2c1C(=O)N(CC1(S(=O)(=O)Nc3cc(C4CC4)on3)CC1)CC2]

N-(4-Cyanobenzyl)-6-((1-(N-(5-cyclopropylisoxazol-3-yl)sulfamoyl)cyclopropyl)methyl)-1-methyl-7-oxo-4,5,6,7-tetrahydro-1H-pyrazolo[3,4-c]pyridine-3-carboxamide;

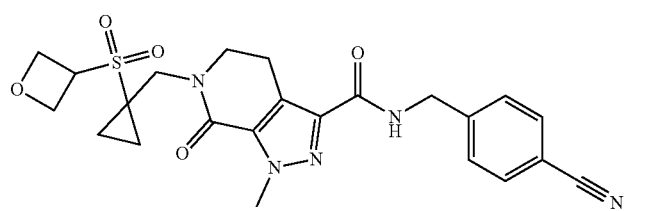 [SMILES: Cn1nc(C(=O)NCc2ccc(C#N)cc2)c2c1C(=O)N(CC1(S(=O)(=O)C3COC3)CC1)CC2]

N-(4-Cyanobenzyl)-1-methyl-6-((1-(oxetan-3-ylsulfonyl)cyclopropyl)methyl)-7-oxo-4,5,6,7-tetrahydro-1H-pyrazolo[3,4-c]pyridine-3-carboxamide;

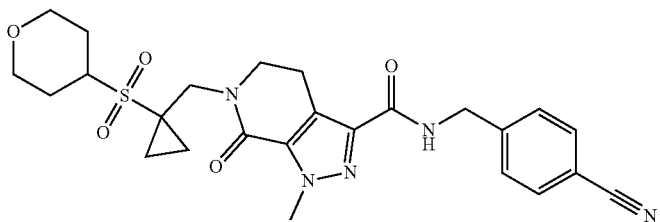 [SMILES: Cn1nc(C(=O)NCc2ccc(C#N)cc2)c2c1C(=O)N(CC1(S(=O)(=O)C3CCOCC3)CC1)CC2] N-(4-Cyanobenzyl)-1-methyl-7-oxo-6-((1-((tetrahydro-2H-pyran-4-yl)sulfonyl)cyclopropyl)methyl)-4,5,6,7-tetrahydro-1H-pyrazolo[3,4-c]pyridine-3-carboxamide;

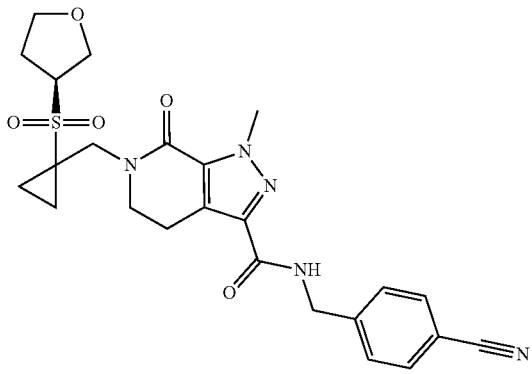 [SMILES: Cn1nc(C(=O)NCc2ccc(C#N)cc2)c2c1C(=O)N(CC1(S(=O)(=O)[C@H]3CCOC3)CC1)CC2] (S)-N-(4-Cyanobenzyl)-1-methyl-7-oxo-6-((1-((tetrahydrofuran-3-yl)sulfonyl)cyclopropyl)methyl)-4,5,6,7-tetrahydro-1H-pyrazolo[3,4-c]pyridine-3-carboxamide;

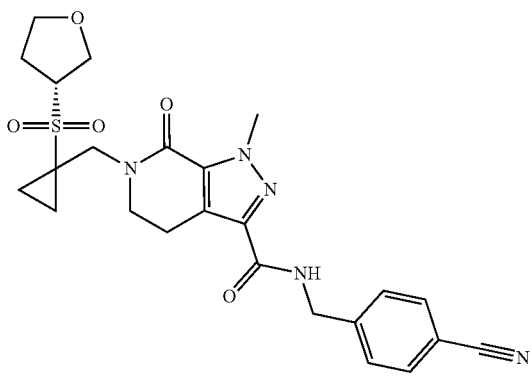 [SMILES: Cn1nc(C(=O)NCc2ccc(C#N)cc2)c2c1C(=O)N(CC1(S(=O)(=O)[C@@H]3CCOC3)CC1)CC2] (R)-N-(4-Cyanobenzyl)-1-methyl-7-oxo-6-((1-((tetrahydrofuran-3-yl)sulfonyl)cyclopropyl)methyl)-4,5,6,7-tetrahydro-1H-pyrazolo[3,4-c]pyridine-3-carboxamide;

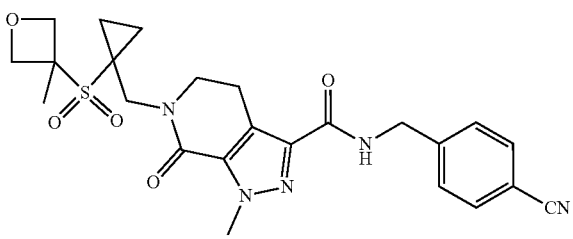 [SMILES: Cn1nc(C(=O)NCc2ccc(C#N)cc2)c2c1C(=O)N(CC1(S(=O)(=O)C3(C)COC3)CC1)CC2] N-(4-Cyanobenzyl)-1-methyl-6-((1-((3-methyloxetan-3-yl)sulfonyl)cyclopropyl)methyl)-7-oxo-4,5,6,7-tetrahydro-1H-pyrazolo[3,4-c]pyridine-3-carboxamide;

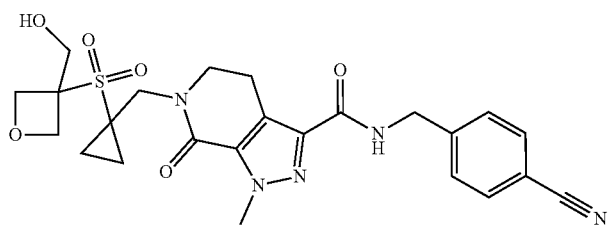 [SMILES: Cn1nc(C(=O)NCc2ccc(C#N)cc2)c2c1C(=O)N(CC1(S(=O)(=O)C3(CO)COC3)CC1)CC2] N-(4-Cyanobenzyl)-6-((1-((3-(hydroxymethyl)oxetan-3-yl)sulfonyl)cyclopropyl)methyl)-1-methyl-7-oxo-4,5,6,7-tetrahydro-1H-pyrazolo[3,4-c]pyridine-3-carboxamide;

-continued

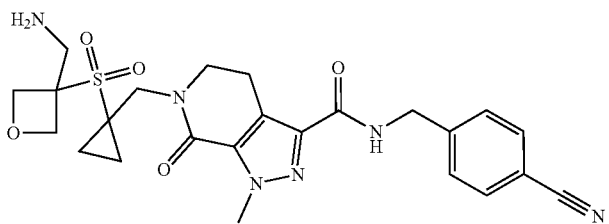
6-((1-((3-(Aminomethyl)oxetan-3-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

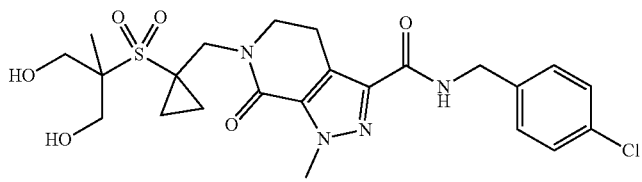 [SMILES: Cn1nc(C(=O)NCc2ccc(Cl)cc2)c2c1C(=O)N(CC1(S(=O)(=O)C(C)(CO)CO)CC1)CC2]
N-(4-chlorobenzyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

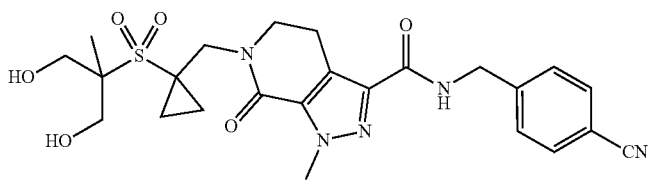 [SMILES: Cn1nc(C(=O)NCc2ccc(C#N)cc2)c2c1C(=O)N(CC1(S(=O)(=O)C(C)(CO)CO)CC1)CC2]
N-(4-cyanobenzyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

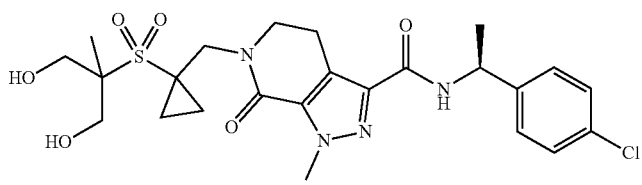 [SMILES: C[C@H](NC(=O)c1nn(C)c2c1CCN(CC1(S(=O)(=O)C(C)(CO)CO)CC1)C2=O)c1ccc(Cl)cc1]
(S)-N-(1-(4-Chlorophenyl)ethyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

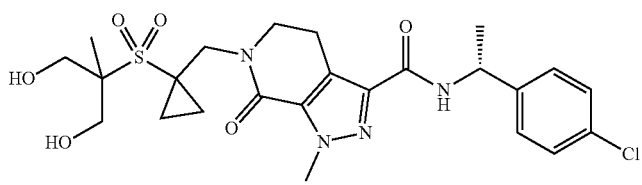 [SMILES: C[C@@H](NC(=O)c1nn(C)c2c1CCN(CC1(S(=O)(=O)C(C)(CO)CO)CC1)C2=O)c1ccc(Cl)cc1]
(R)-N-(1-(4-Chlorophenyl)ethyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

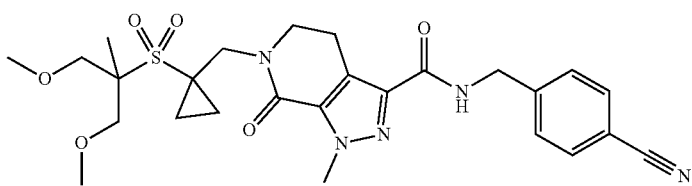 [SMILES: COCC(C)(COC)S(=O)(=O)C1(CN2CCc3c(C(=O)NCc4ccc(C#N)cc4)nn(C)c3C2=O)CC1]
N-(4-Cyanobenzyl)-6-((1-((1,3-dimethoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

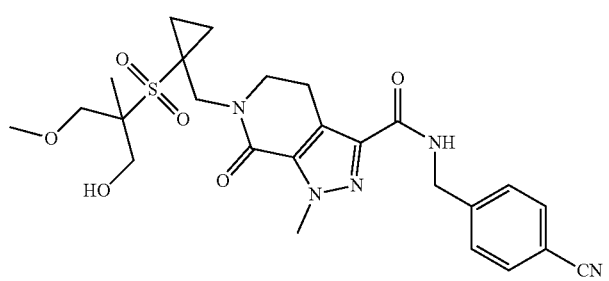 [SMILES: COCC(C)(CO)S(=O)(=O)C1(CN2CCc3c(C(=O)NCc4ccc(C#N)cc4)nn(C)c3C2=O)CC1]
N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

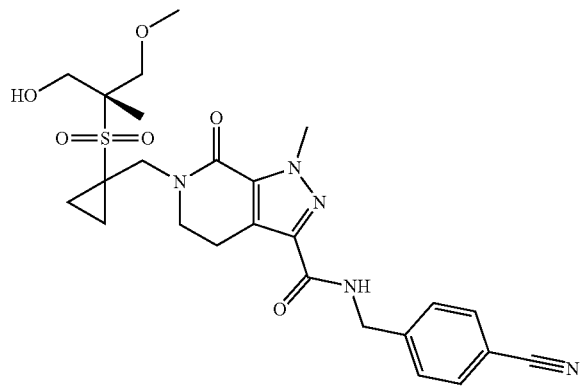 [SMILES: COC[C@@](C)(CO)S(=O)(=O)C1(CN2CCc3c(C(=O)NCc4ccc(C#N)cc4)nn(C)c3C2=O)CC1]

(R)-N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

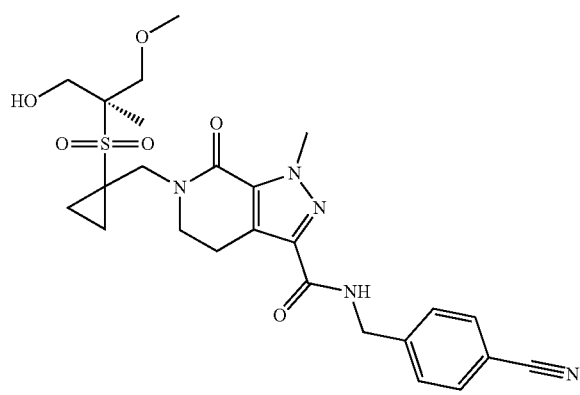 [SMILES: COC[C@](C)(CO)S(=O)(=O)C1(CN2CCc3c(C(=O)NCc4ccc(C#N)cc4)nn(C)c3C2=O)CC1]

(S)-N-(4-Cyanobenzyl)-6-((1-((1-hydroxy-3-methoxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

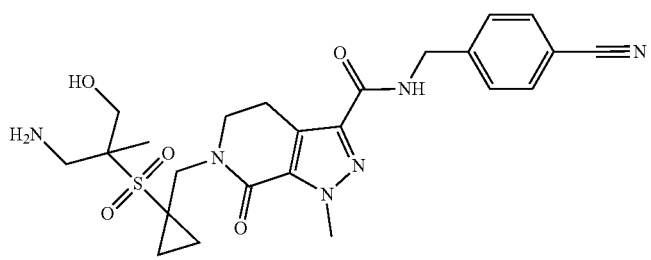 [SMILES: Cn1nc(C(=O)NCc2ccc(C#N)cc2)c2c1C(=O)N(CC1(S(=O)(=O)C(C)(CN)CO)CC1)CC2]

6-((1-((1-Amino-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

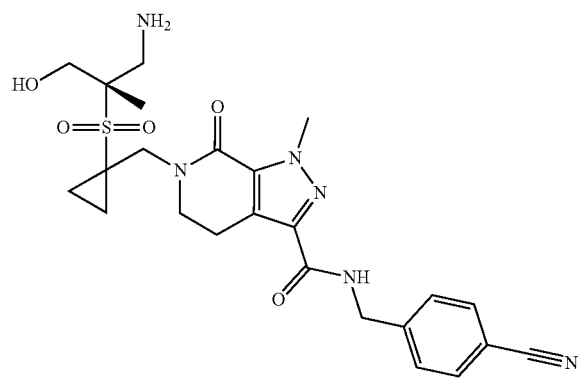 [SMILES: Cn1nc(C(=O)NCc2ccc(C#N)cc2)c2c1C(=O)N(CC1(S(=O)(=O)[C@@](C)(CN)CO)CC1)CC2]

(S)-6-((1-((1-Amino-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

-continued

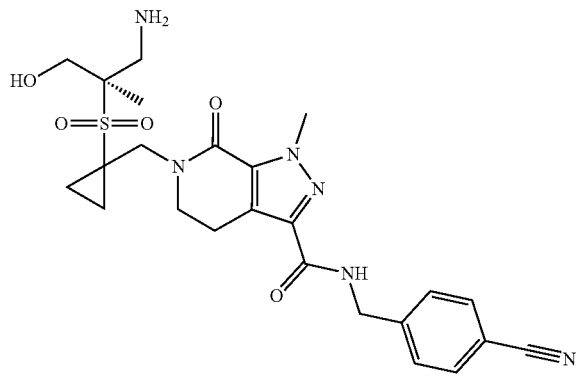 [SMILES: Cn1nc(C(=O)NCc2ccc(C#N)cc2)c2c1C(=O)N(CC1(S(=O)(=O)[C@](C)(CN)CO)CC1)CC2]

(R)-6-((1-((1-Amino-3-hydroxy-2-methylpropan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

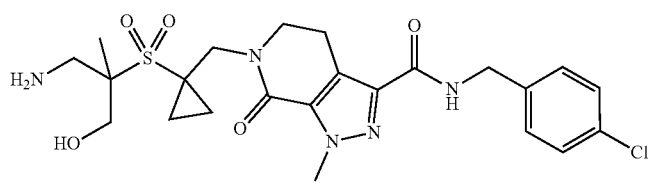 [SMILES: Cn1nc(C(=O)NCc2ccc(Cl)cc2)c2c1C(=O)N(CC1(S(=O)(=O)C(C)(CN)CO)CC1)CC2]

6-((1-((1-Amino-3-hydroxy-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

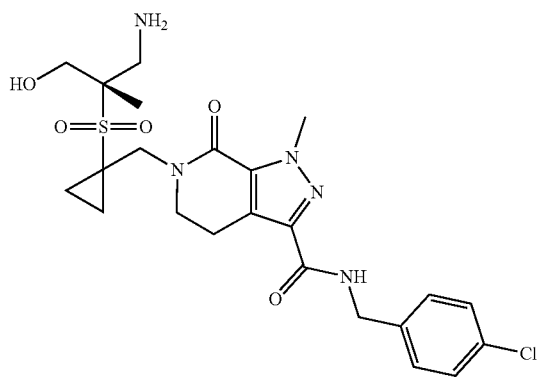 [SMILES: Cn1nc(C(=O)NCc2ccc(Cl)cc2)c2c1C(=O)N(CC1(S(=O)(=O)[C@@](C)(CN)CO)CC1)CC2]

(S)-6-((1-((1-Amino-3-hydroxy-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

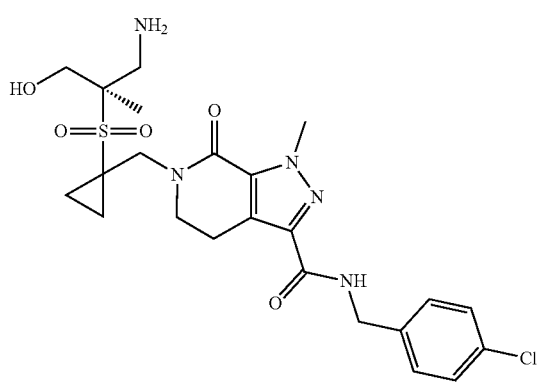 [SMILES: Cn1nc(C(=O)NCc2ccc(Cl)cc2)c2c1C(=O)N(CC1(S(=O)(=O)[C@](C)(CN)CO)CC1)CC2]

(R)-6-((1-((1-Amino-3-hydroxy-2-methylpropan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

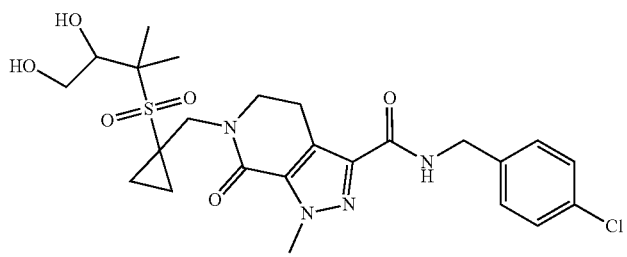 [SMILES: Cn1nc(C(=O)NCc2ccc(Cl)cc2)c2c1C(=O)N(CC1(S(=O)(=O)C(C)(C)C(O)CO)CC1)CC2]

N-(4-chlorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

-continued

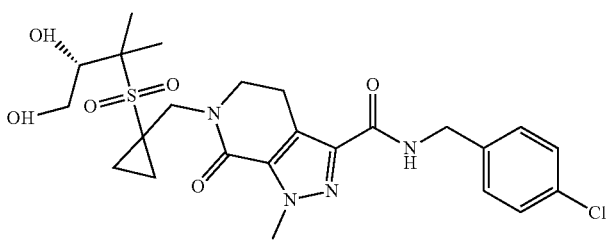 [SMILES: Cn1nc(C(=O)NCc2ccc(Cl)cc2)c2c1C(=O)N(CC1(S(=O)(=O)C(C)(C)[C@@H](O)CO)CC1)CC2]

(S)-N-(4-Chlorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

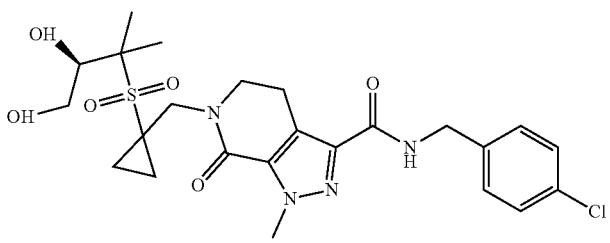 [SMILES: Cn1nc(C(=O)NCc2ccc(Cl)cc2)c2c1C(=O)N(CC1(S(=O)(=O)C(C)(C)[C@H](O)CO)CC1)CC2]

(R)-N-(4-Chlorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

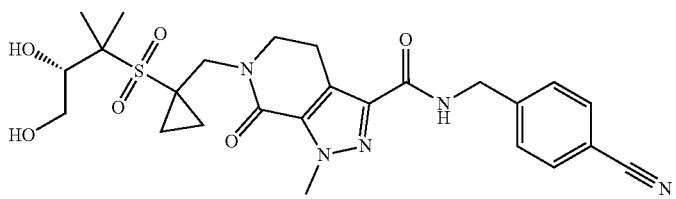 [SMILES: Cn1nc(C(=O)NCc2ccc(C#N)cc2)c2c1C(=O)N(CC1(S(=O)(=O)C(C)(C)[C@@H](O)CO)CC1)CC2]

(S)-N-(4-Cyanobenzyl)-6-((1-(3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

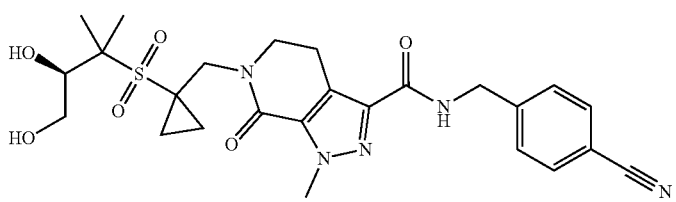 [SMILES: Cn1nc(C(=O)NCc2ccc(C#N)cc2)c2c1C(=O)N(CC1(S(=O)(=O)C(C)(C)[C@H](O)CO)CC1)CC2]

(R)-N-(4-Cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

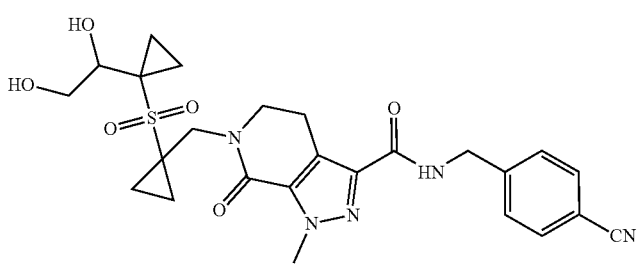 [SMILES: Cn1nc(C(=O)NCc2ccc(C#N)cc2)c2c1C(=O)N(CC1(S(=O)(=O)C3(C(O)CO)CC3)CC1)CC2]

N-(4-Cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;

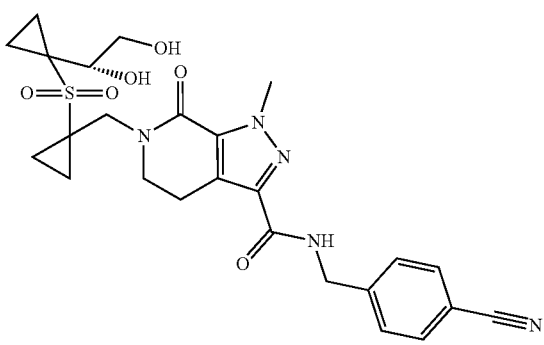 [SMILES: Cn1nc(C(=O)NCc2ccc(C#N)cc2)c2c1C(=O)N(CC1(S(=O)(=O)C3([C@@H](O)CO)CC3)CC1)CC2]

(S)-N-(4-Cyanobenzyl)-6-((1-(1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;

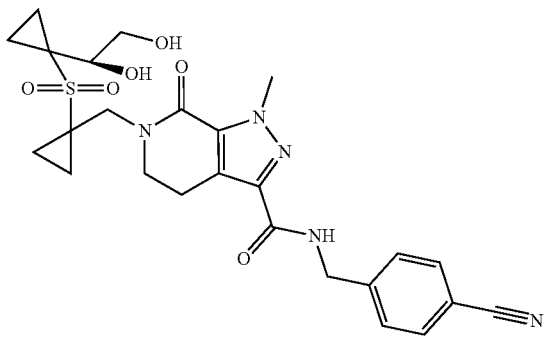 [SMILES: Cn1nc(C(=O)NCc2ccc(C#N)cc2)c2c1C(=O)N(CC1(S(=O)(=O)C3([C@H](O)CO)CC3)CC1)CC2]

(R)-N-(4-Cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;

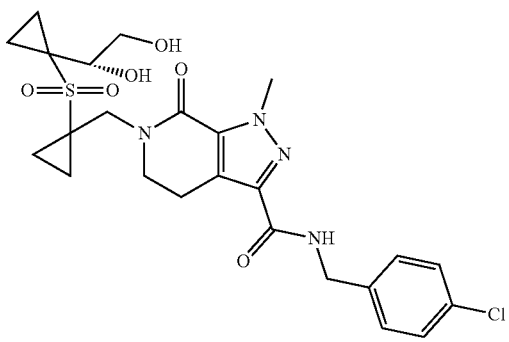 [SMILES: Cn1nc(C(=O)NCc2ccc(Cl)cc2)c2c1C(=O)N(CC1(S(=O)(=O)C3([C@@H](O)CO)CC3)CC1)CC2]

(S)-N-(4-Chlorobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;

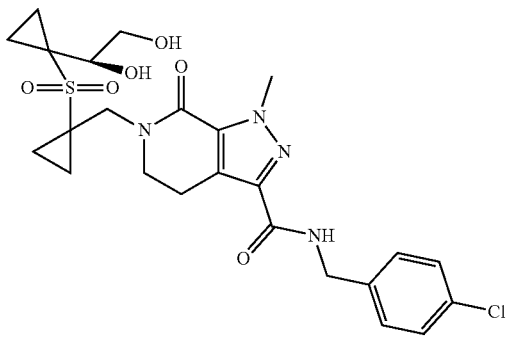 [SMILES: Cn1nc(C(=O)NCc2ccc(Cl)cc2)c2c1C(=O)N(CC1(S(=O)(=O)C3([C@H](O)CO)CC3)CC1)CC2]

(R)-N-(4-Chlorobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;

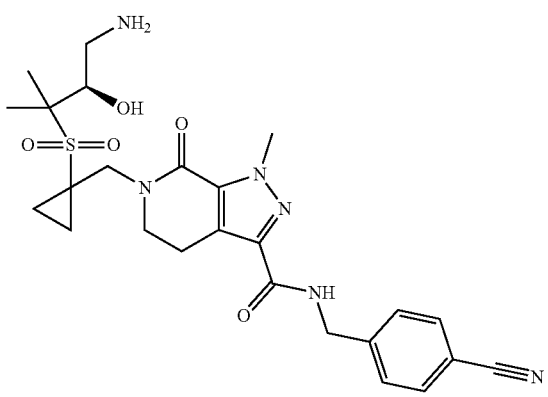 [SMILES: Cn1nc(C(=O)NCc2ccc(C#N)cc2)c2c1C(=O)N(CC1(S(=O)(=O)C(C)(C)[C@H](O)CN)CC1)CC2]

(R)-6-((1-((4-Amino-3-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

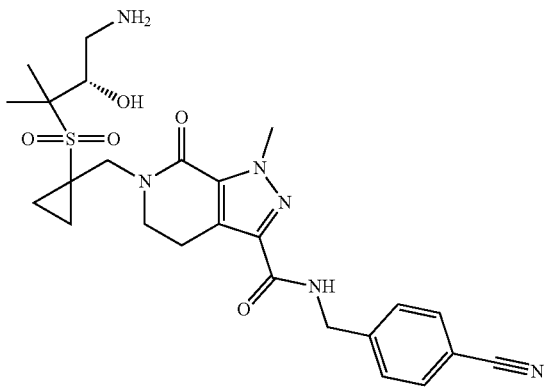 [SMILES: Cn1nc(C(=O)NCc2ccc(C#N)cc2)c2c1C(=O)N(CC1(S(=O)(=O)C(C)(C)[C@@H](O)CN)CC1)CC2]

(S)-6-((1-((4-Amino-3-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

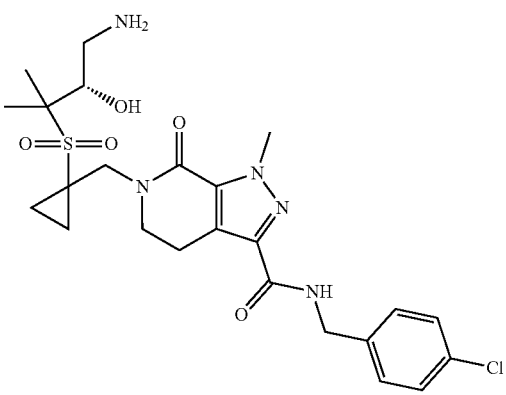 [SMILES: Cn1nc(C(=O)NCc2ccc(Cl)cc2)c2c1C(=O)N(CC1(S(=O)(=O)C(C)(C)[C@@H](O)CN)CC1)CC2]

(S)-6-((1-((4-Amino-3-hydroxy-2-methylbutan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

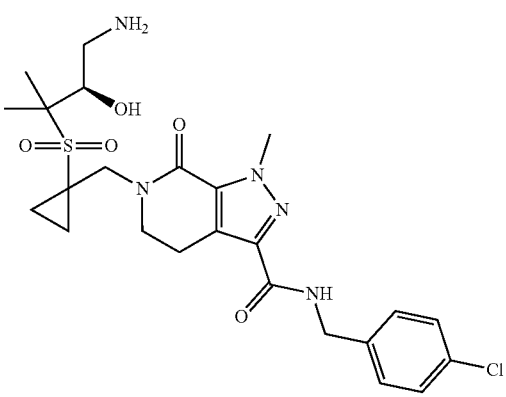 [SMILES: Cn1nc(C(=O)NCc2ccc(Cl)cc2)c2c1C(=O)N(CC1(S(=O)(=O)C(C)(C)[C@H](O)CN)CC1)CC2]

(R)-6-((1-((4-Amino-3-hydroxy-2-methylbutan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

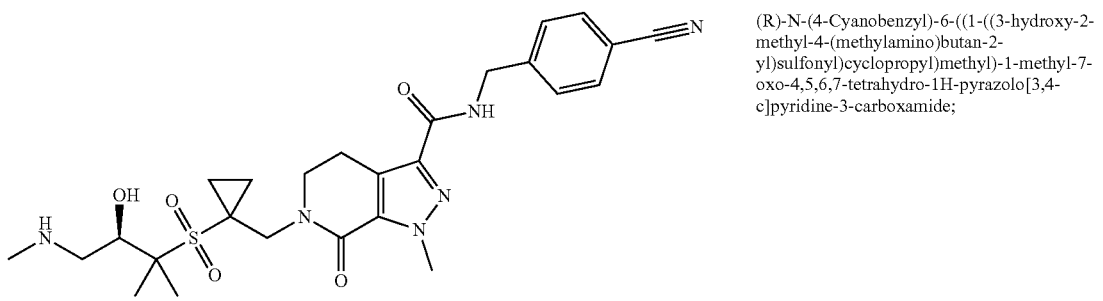

(R)-N-(4-Cyanobenzyl)-6-((1-((3-hydroxy-2-methyl-4-(methylamino)butan-2-yl)sulfonyl)cyclopropyl)methyl)-1-methyl-7-oxo-4,5,6,7-tetrahydro-1H-pyrazolo[3,4-c]pyridine-3-carboxamide;

-continued

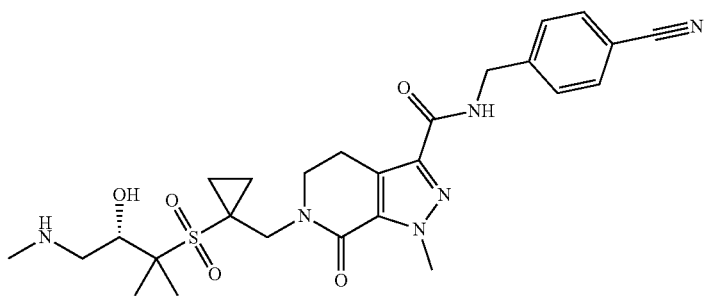 [SMILES: CNC[C@H](O)C(C)(C)S(=O)(=O)C1(CN2CCc3c(C(=O)NCc4ccc(C#N)cc4)nn(C)c3C2=O)CC1]
(S)-N-(4-Cyanobenzyl)-6-((1-((3-hydroxy-2-methyl-4-(methylamino)butan-2-yl)sulfonyl)cyclopropyl)methyl)-1-methyl-7-oxo-4,5,6,7-tetrahydro-1H-pyrazolo[3,4-c]pyridine-3-carboxamide;

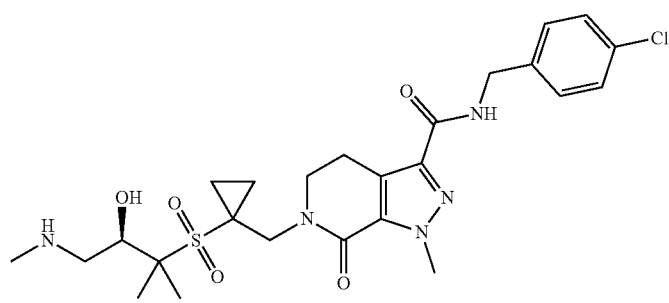 [SMILES: CNC[C@@H](O)C(C)(C)S(=O)(=O)C1(CN2CCc3c(C(=O)NCc4ccc(Cl)cc4)nn(C)c3C2=O)CC1]
(R)-N-(4-Chlorobenzyl)-6-((1-((3-hydroxy-2-methyl-4-(methylamino)butan-2-yl)sulfonyl)cyclopropyl)methyl)-1-methyl-7-oxo-4,5,6,7-tetrahydro-1H-pyrazolo[3,4-c]pyridine-3-carboxamide;

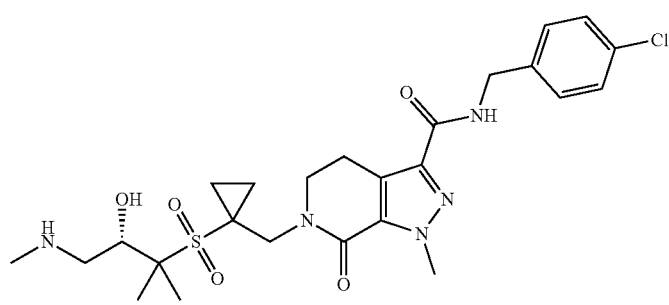 [SMILES: CNC[C@H](O)C(C)(C)S(=O)(=O)C1(CN2CCc3c(C(=O)NCc4ccc(Cl)cc4)nn(C)c3C2=O)CC1]
(S)-N-(4-Chlorobenzyl)-6-((1-((3-hydroxy-2-methyl-4-(methylamino)butan-2-yl)sulfonyl)cyclopropyl)methyl)-1-methyl-7-oxo-4,5,6,7-tetrahydro-1H-pyrazolo[3,4-c]pyridine-3-carboxamide;

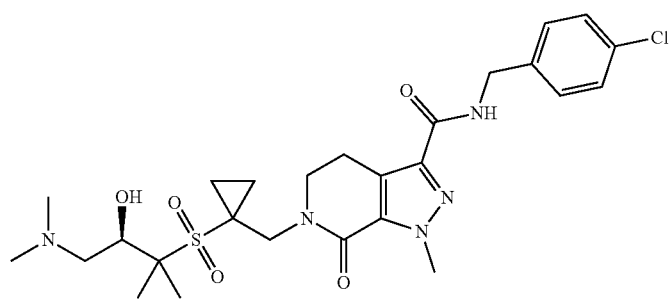 [SMILES: CN(C)C[C@@H](O)C(C)(C)S(=O)(=O)C1(CN2CCc3c(C(=O)NCc4ccc(Cl)cc4)nn(C)c3C2=O)CC1]
(R)-N-(4-Chlorobenzyl)-6-((1-((4-(dimethylamino)-3-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

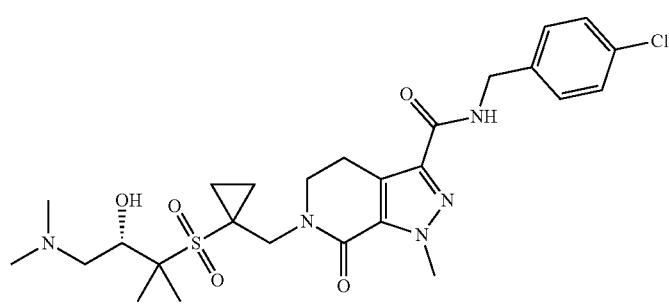 [SMILES: CN(C)C[C@H](O)C(C)(C)S(=O)(=O)C1(CN2CCc3c(C(=O)NCc4ccc(Cl)cc4)nn(C)c3C2=O)CC1]
(S)-N-(4-Chlorobenzyl)-6-((1-((4-(dimethylamino)-3-hydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

-continued

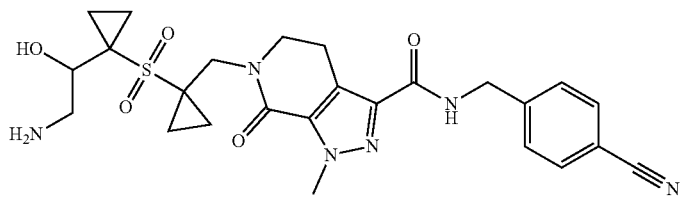 [SMILES: Cn1nc(C(=O)NCc2ccc(C#N)cc2)c2c1C(=O)N(CC1(S(=O)(=O)C3(C(O)CN)CC3)CC1)CC2]
6-((1-((1-(2-Amino-1-hydroxyethyl)cyclopropyl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

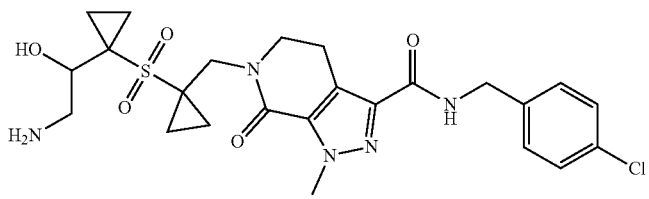 [SMILES: Cn1nc(C(=O)NCc2ccc(Cl)cc2)c2c1C(=O)N(CC1(S(=O)(=O)C3(C(O)CN)CC3)CC1)CC2]
6-((1-((1-(2-Amino-1-hydroxyethyl)cyclopropyl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide;

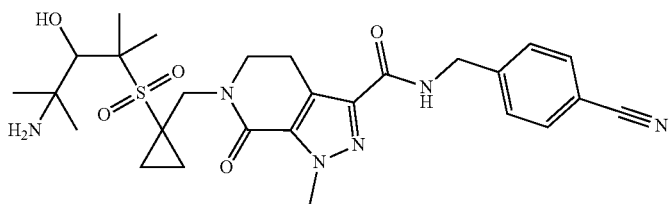 [SMILES: Cn1nc(C(=O)NCc2ccc(C#N)cc2)c2c1C(=O)N(CC1(S(=O)(=O)C(C)(C)C(O)C(C)(C)N)CC1)CC2]
6-((1-((4-amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

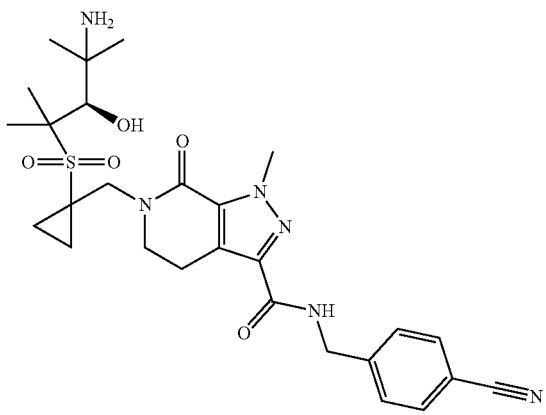 [SMILES: Cn1nc(C(=O)NCc2ccc(C#N)cc2)c2c1C(=O)N(CC1(S(=O)(=O)C(C)(C)[C@H](O)C(C)(C)N)CC1)CC2]
(R)-6-((1-((4-Amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

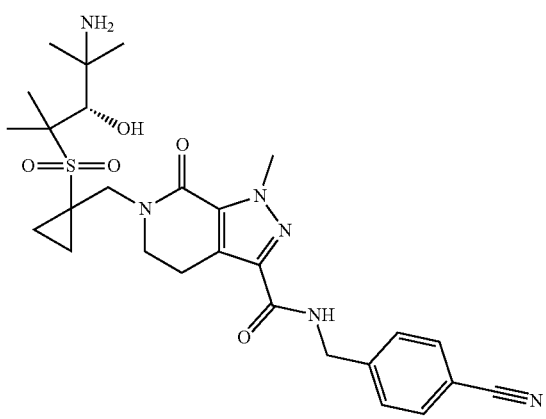 [SMILES: Cn1nc(C(=O)NCc2ccc(C#N)cc2)c2c1C(=O)N(CC1(S(=O)(=O)C(C)(C)[C@@H](O)C(C)(C)N)CC1)CC2]
(S)-6-((1-((4-Amino-3-hydroxy-2,4-dimethylpentan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

-continued

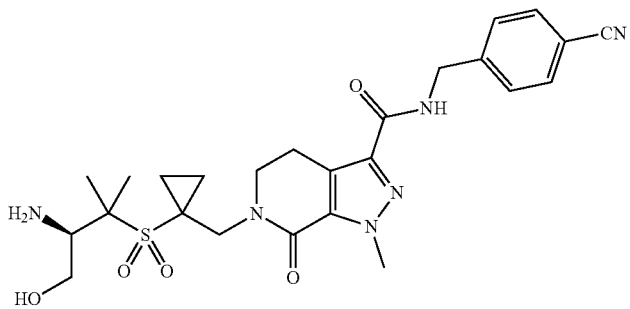 [SMILES: Cn1nc(C(=O)NCc2ccc(C#N)cc2)c2c1C(=O)N(CC1(S(=O)(=O)C(C)(C)[C@H](N)CO)CC1)CC2]

(R)-6-((1-((3-amino-4-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

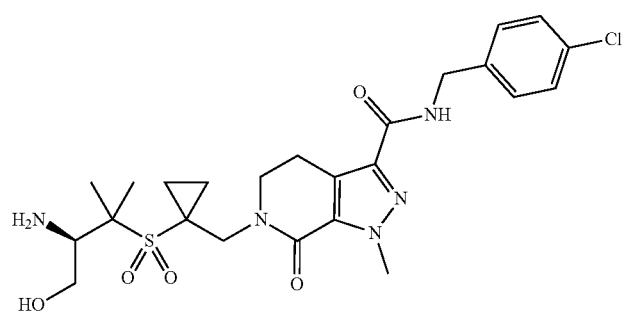 [SMILES: Cn1nc(C(=O)NCc2ccc(Cl)cc2)c2c1C(=O)N(CC1(S(=O)(=O)C(C)(C)[C@H](N)CO)CC1)CC2]

(R)-6-((1-((3-Amino-4-hydroxy-2-methylbutan-2-yl)sulfonyl)cyclopropyl)methyl)-N-(4-chlorobenzyl)-1-methyl-7-oxo-4,5,6,7-tetrahydro-1H-pyrazolo[3,4-c]pyridine-3-carboxamide hydrochloride;

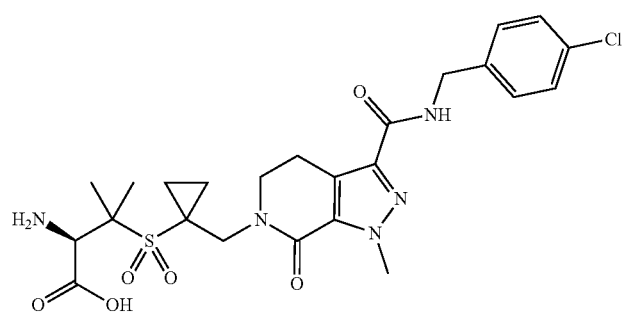 [SMILES: Cn1nc(C(=O)NCc2ccc(Cl)cc2)c2c1C(=O)N(CC1(S(=O)(=O)C(C)(C)[C@H](N)C(=O)O)CC1)CC2]

((1-((3-((4-Chlorobenzyl)carbamoyl)-1-methyl-7-oxo-1,4,5,7-tetrahydro-6H-pyrazolo[3,4-c]pyridin-6-yl)methyl)cyclopropyl)sulfonyl)-D-valine;

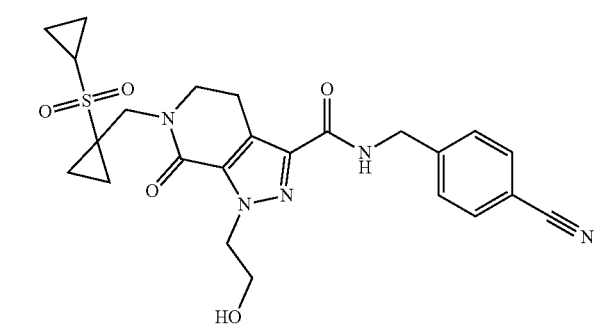 [SMILES: N#Cc1ccc(CNC(=O)c2nn(CCO)c3c2CCN(CC2(S(=O)(=O)C4CC4)CC2)C3=O)cc1]

N-(4-Cyanobenzyl)-6-((1-(cyclopropylsulfonyl)cyclopropyl)methyl)-1-(2-hydroxyethyl)-7-oxo-4,5,6,7-tetrahydro-1H-pyrazolo[3,4-c]pyridine-3-carboxamide;

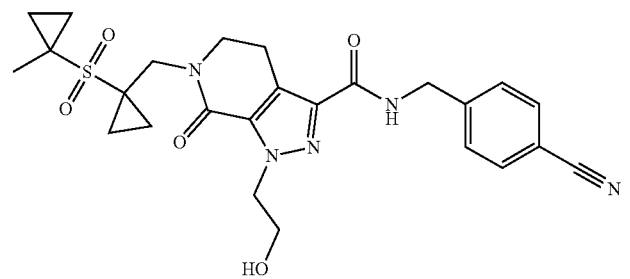 [SMILES: CC1(S(=O)(=O)C2(CN3CCc4c(C(=O)NCc5ccc(C#N)cc5)nn(CCO)c4C3=O)CC2)CC1]

N-(4-Cyanobenzyl)-1-(2-hydroxyethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide;

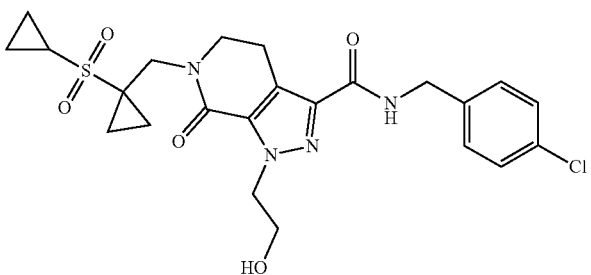 [SMILES: O=C(NCc1ccc(Cl)cc1)c1nn(CCO)c2c1CCN(CC1(S(=O)(=O)C3CC3)CC1)C2=O]

N-(4-Chlorobenzyl)-6-((1-(cyclopropylsulfonyl)cyclopropyl)methyl)-1-(2-hydroxyethyl)-7-oxo-4,5,6,7-tetrahydro-1H-pyrazolo[3,4-c]pyridine-3-carboxamide;

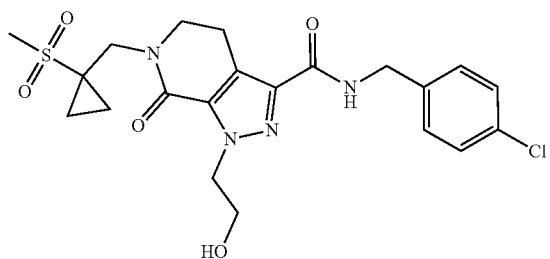 [SMILES: CS(=O)(=O)C1(CN2CCc3c(C(=O)NCc4ccc(Cl)cc4)nn(CCO)c3C2=O)CC1]

N-(4-Chlorobenzyl)-1-(2-hydroxyethyl)-6-((1-(methylsulfonyl)cyclopropyl)methyl)-7-oxo-4,5,6,7-tetrahydro-1H-pyrazolo[3,4-c]pyridine-3-carboxamide;

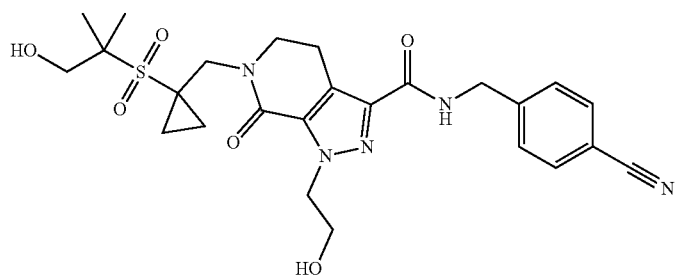 [SMILES: CC(C)(CO)S(=O)(=O)C1(CN2CCc3c(C(=O)NCc4ccc(C#N)cc4)nn(CCO)c3C2=O)CC1]

N-(4-Cyanobenzyl)-6-((1-(((1-hydroxy-2-methylpropan-2-yl)sulfonyl)cyclopropyl)methyl)-1-(2-hydroxyethyl)-7-oxo-4,5,6,7-tetrahydro-1H-pyrazolo[3,4-c]pyridine-3-carboxamide;

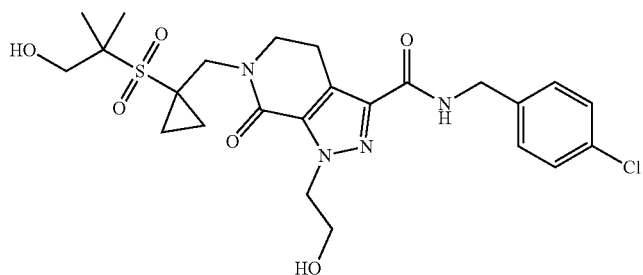 [SMILES: CC(C)(CO)S(=O)(=O)C1(CN2CCc3c(C(=O)NCc4ccc(Cl)cc4)nn(CCO)c3C2=O)CC1]

N-(4-chlorobenzyl)-6-((1-(((1-hydroxy-2-methylpropan-2-yl)sulfonyl)cyclopropyl)methyl)-1-(2-hydroxyethyl)-7-oxo-4,5,6,7-tetrahydro-1H-pyrazolo[3,4-c]pyridine-3-carboxamide;

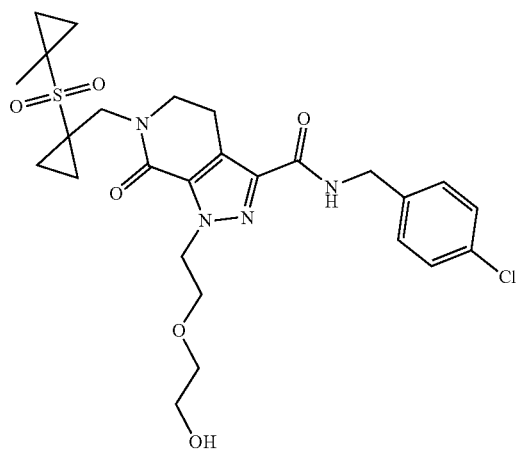 [SMILES: CC1(S(=O)(=O)C2(CN3CCc4c(C(=O)NCc5ccc(Cl)cc5)nn(CCOCCO)c4C3=O)CC2)CC1]

N-(4-Chlorobenzyl)-1-(2-(2-hydroxyethoxy)ethyl)-6-((1-(((1-methylcyclopropyl)sulfonyl)cyclopropyl)methyl)-7-oxo-4,5,6,7-tetrahydro-1H-pyrazolo[3,4-c]pyridine-3-carboxamide;

-continued

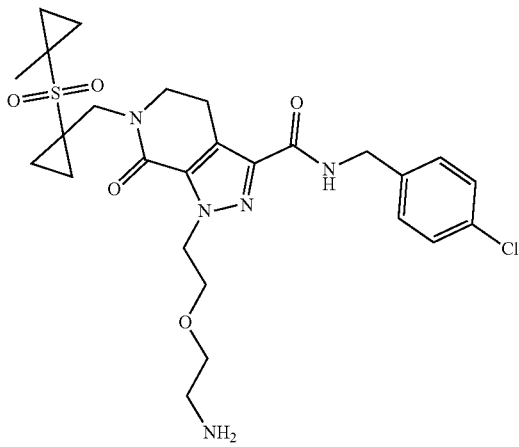 [SMILES: CC1(S(=O)(=O)C2(CN3CCc4c(C(=O)NCc5ccc(Cl)cc5)nn(CCOCCN)c4C3=O)CC2)CC1]

1-(2-(2-aminoethoxy)ethyl)-N-(4-chlorobenzyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide;

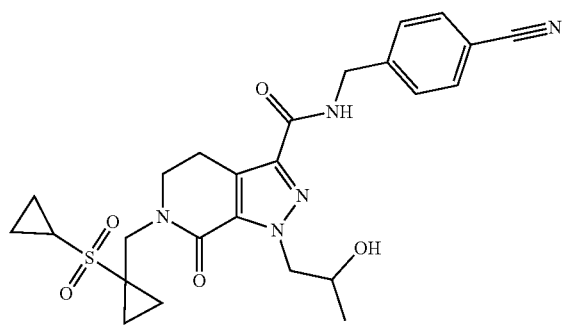 [SMILES: CC(O)Cn1nc(C(=O)NCc2ccc(C#N)cc2)c2c1C(=O)N(CC1(S(=O)(=O)C3CC3)CC1)CC2]

N-(4-Cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide;

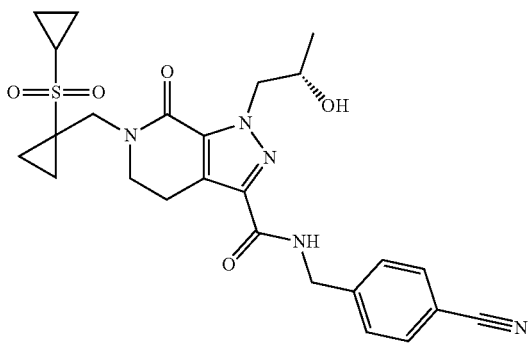 [SMILES: C[C@H](O)Cn1nc(C(=O)NCc2ccc(C#N)cc2)c2c1C(=O)N(CC1(S(=O)(=O)C3CC3)CC1)CC2]

(S)-N-(4-Cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide;

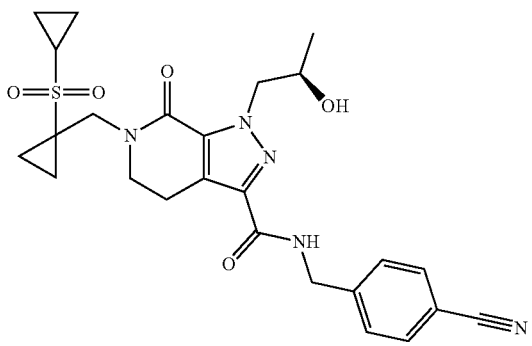 [SMILES: C[C@@H](O)Cn1nc(C(=O)NCc2ccc(C#N)cc2)c2c1C(=O)N(CC1(S(=O)(=O)C3CC3)CC1)CC2]

(R)-N-(4-Cyanobenzyl)-6-((1-(cyclopropylsulfonyl)cyclopropyl)methyl)-1-(2-hydroxypropyl)-7-oxo-4,5,6,7-tetrahydro-1H-pyrazolo[3,4-c]pyridine-3-carboxamide;

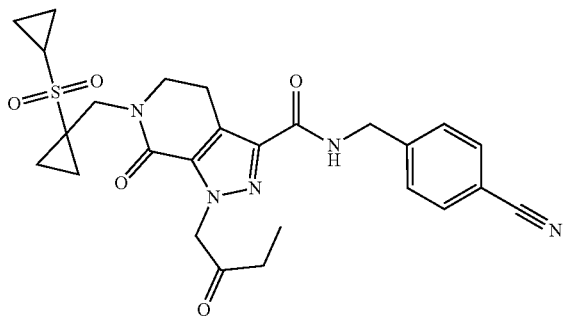 [SMILES: CCC(=O)Cn1nc(C(=O)NCc2ccc(C#N)cc2)c2c1C(=O)N(CC1(S(=O)(=O)C3CC3)CC1)CC2]

N-(4-Cyanobenzyl)-6-((1-(cyclopropylsulfonyl)cyclopropyl)methyl)-7-oxo-1-(2-oxobutyl)-4,5,6,7-tetrahydro-1H-pyrazolo[3,4-c]pyridine-3-carboxamide;

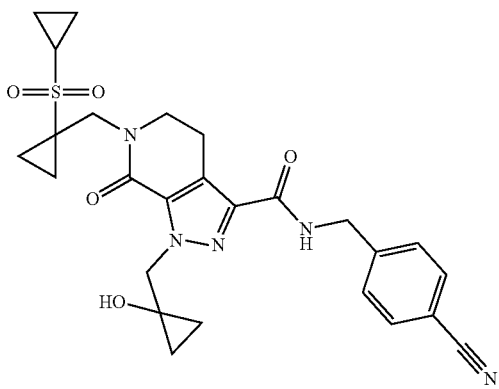 [SMILES: N#Cc1ccc(CNC(=O)c2nn(CC3(O)CC3)c3c2CCN(CC2(S(=O)(=O)C4CC4)CC2)C3=O)cc1]

N-(4-Cyanobenzyl)-6-((1-(cyclopropylsulfonyl)cyclopropyl)methyl)-1-((1-hydroxycyclopropyl)methyl)-7-oxo-4,5,6,7-tetrahydro-1H-pyrazolo[3,4-c]pyridine-3-carboxamide;

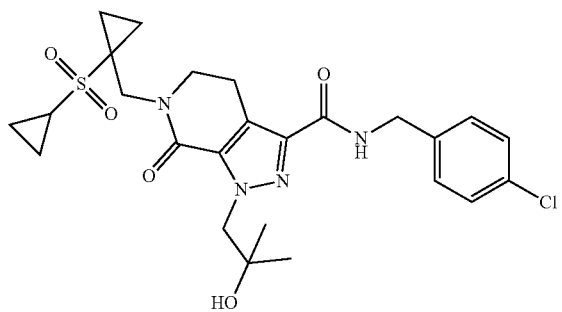 [SMILES: CC(C)(O)Cn1nc(C(=O)NCc2ccc(Cl)cc2)c2c1C(=O)N(CC1(S(=O)(=O)C3CC3)CC1)CC2]

N-(4-Chlorobenzyl)-6-((1-(cyclopropylsulfonyl)cyclopropyl)methyl)-1-(2-hydroxy-2-methylpropyl)-7-oxo-4,5,6,7-tetrahydro-1H-pyrazolo[3,4-c]pyridine-3-carboxamide;

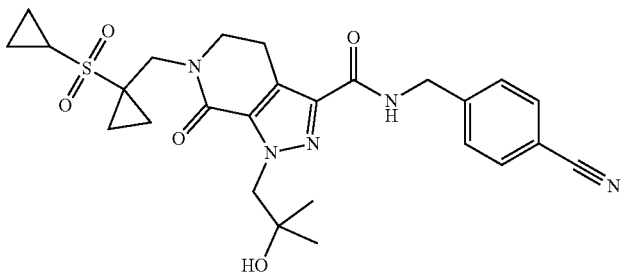 [SMILES: CC(C)(O)Cn1nc(C(=O)NCc2ccc(C#N)cc2)c2c1C(=O)N(CC1(S(=O)(=O)C3CC3)CC1)CC2]

N-(4-Cyanobenzyl)-6-((1-(cyclopropylsulfonyl)cyclopropyl)methyl)-1-(2-hydroxy-2-methylpropyl)-7-oxo-4,5,6,7-tetrahydro-1H-pyrazolo[3,4-c]pyridine-3-carboxamide;

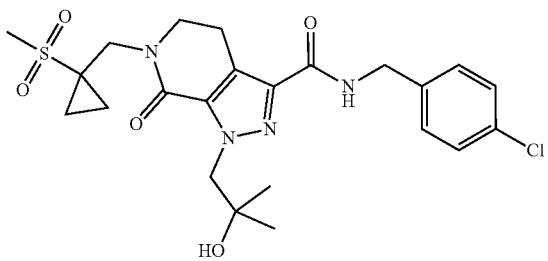 [SMILES: CC(C)(O)Cn1nc(C(=O)NCc2ccc(Cl)cc2)c2c1C(=O)N(CC1(S(C)(=O)=O)CC1)CC2]

N-(4-Chlorobenzyl)-1-(2-hydroxy-2-methylpropyl)-6-((1-(methylsulfonyl)cyclopropyl)methyl)-7-oxo-4,5,6,7-tetrahydro-1H-pyrazolo[3,4-c]pyridine-3-carboxamide;

-continued

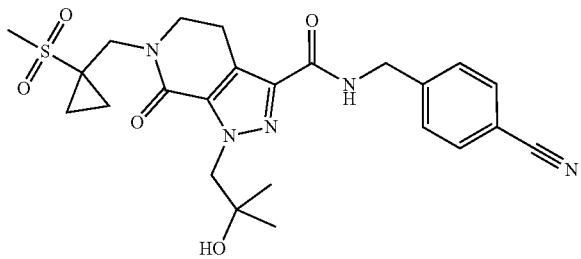 [SMILES: CC(C)(O)Cn1nc(C(=O)NCc2ccc(C#N)cc2)c2c1C(=O)N(CC1(S(C)(=O)=O)CC1)CC2]

N-(4-Cyanobenzyl)-1-(2-hydroxy-2-methylpropyl)-6-((1-(methylsulfonyl)cyclopropyl)methyl)-7-oxo-4,5,6,7-tetrahydro-1H-pyrazolo[3,4-c]pyridine-3-carboxamide;

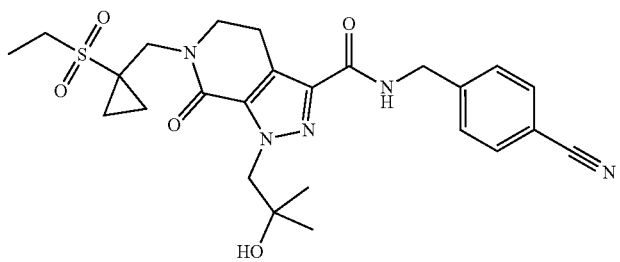 [SMILES: CCS(=O)(=O)C1(CN2CCc3c(C(=O)NCc4ccc(C#N)cc4)nn(CC(C)(C)O)c3C2=O)CC1]

N-(4-Cyanobenzyl)-6-((1-(ethylsulfonyl)cyclopropyl)methyl)-1-(2-hydroxy-2-methylpropyl)-7-oxo-4,5,6,7-tetrahydro-1H-pyrazolo[3,4-c]pyridine-3-carboxamide;

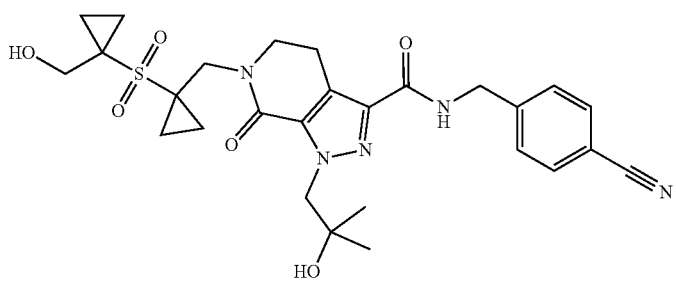 [SMILES: CC(C)(O)Cn1nc(C(=O)NCc2ccc(C#N)cc2)c2c1C(=O)N(CC1(S(=O)(=O)C3(CO)CC3)CC1)CC2]

N-(4-Cyanobenzyl)-1-(2-hydroxy-2-methylpropyl)-6-((1-((1-(hydroxymethyl)cyclopropyl)sulfonyl)cyclopropyl)methyl)-7-oxo-4,5,6,7-tetrahydro-1H-pyrazolo[3,4-c]pyridine-3-carboxamide;

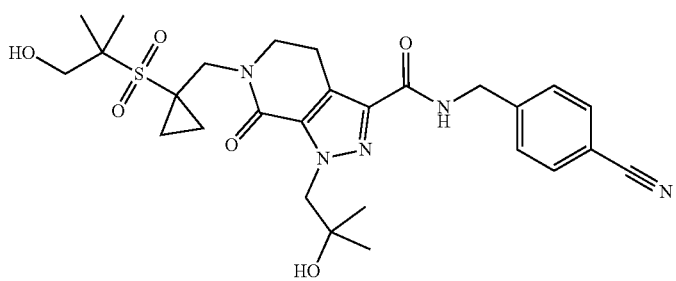 [SMILES: CC(C)(O)Cn1nc(C(=O)NCc2ccc(C#N)cc2)c2c1C(=O)N(CC1(S(=O)(=O)C(C)(C)CO)CC1)CC2]

N-(4-Cyanobenzyl)-6-((1-((1-hydroxy-2-methylpropan-2-yl)sulfonyl)cyclopropyl)methyl)-1-(2-hydroxy-2-methylpropyl)-7-oxo-4,5,6,7-tetrahydro-1H-pyrazolo[3,4-c]pyridine-3-carboxamide;

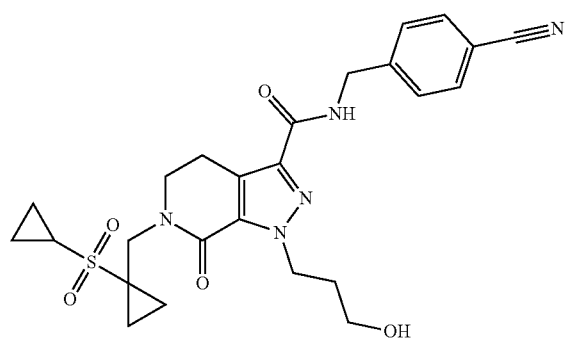 [SMILES: N#Cc1ccc(CNC(=O)c2nn(CCCO)c3c2CCN(CC2(S(=O)(=O)C4CC4)CC2)C3=O)cc1]

N-(4-Cyanobenzyl)-6-((1-(cyclopropylsulfonyl)cyclopropyl)methyl)-1-(3-hydroxypropyl)-7-oxo-4,5,6,7-tetrahydro-1H-pyrazolo[3,4-c]pyridine-3-carboxamide; and -continued

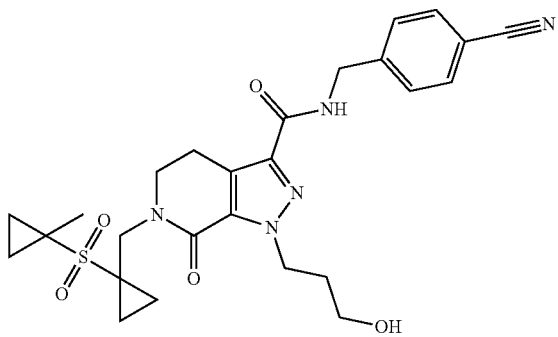 [SMILES: CC1(S(=O)(=O)C2(CN3CCc4c(C(=O)NCc5ccc(C#N)cc5)nn(CCCO)c4C3=O)CC2)CC1]

N-(4-Cyanobenzyl)-1-(3-hydroxypropyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide.

15. The compound of claim 1, or a pharmaceutically acceptable salt thereof, selected from:

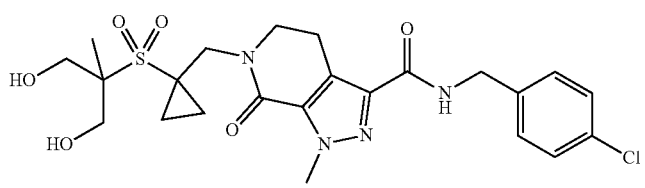 [SMILES: Cn1nc(C(=O)NCc2ccc(Cl)cc2)c2c1C(=O)N(CC1(S(=O)(=O)C(C)(CO)CO)CC1)CC2]

N-(4-chlorobenzyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

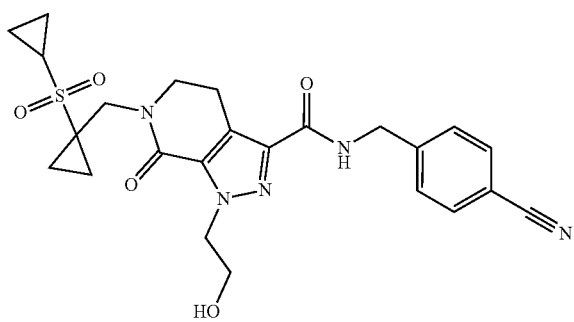 [SMILES: N#Cc1ccc(CNC(=O)c2nn(CCO)c3c2CCN(CC2(S(=O)(=O)C4CC4)CC2)C3=O)cc1]

N-(4-Cyanobenzyl)-6-((1-(cyclopropylsulfonyl)cyclopropyl)methyl)-1-(2-hydroxyethyl)-7-oxo-4,5,6,7-tetrahydro-1H-pyrazolo[3,4-c]pyridine-3-carboxamide;

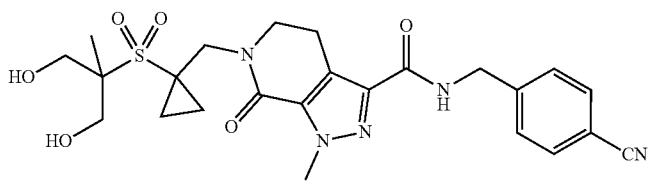 [SMILES: Cn1nc(C(=O)NCc2ccc(C#N)cc2)c2c1C(=O)N(CC1(S(=O)(=O)C(C)(CO)CO)CC1)CC2]

N-(4-cyanobenzyl)-6-((1-((1,3-dihydroxy-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;

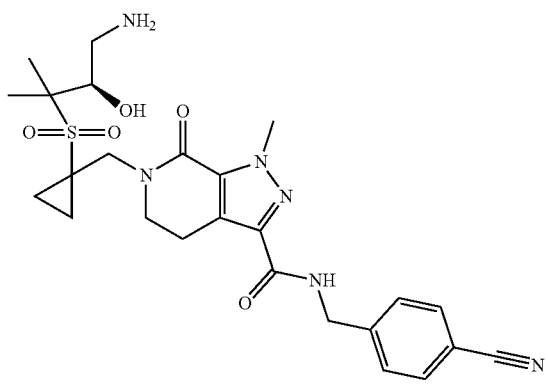 [SMILES: Cn1nc(C(=O)NCc2ccc(C#N)cc2)c2c1C(=O)N(CC1(S(=O)(=O)C(C)(C)[C@H](O)CN)CC1)CC2]

(R)-6-((1-((4-Amino-3-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

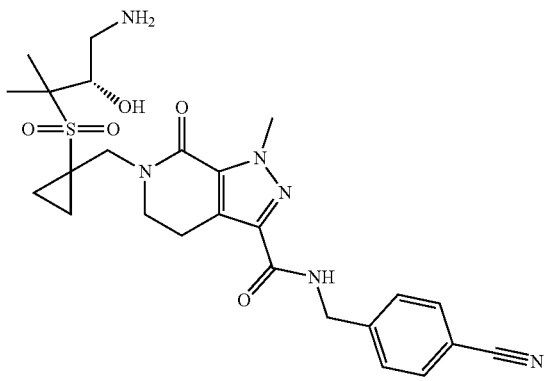 [SMILES: Cn1nc(C(=O)NCc2ccc(C#N)cc2)c2c1C(=O)N(CC1(S(=O)(=O)C(C)(C)[C@@H](O)CN)CC1)CC2]

(S)-6-((1-((4-Amino-3-hydroxy-2-methylbutan-2-yl)sulfonyl)cyclopropyl)methyl)-N-(4-cyanobenzyl)-1-methyl-7-oxo-4,5,6,7-tetrahydro-1H-pyrazolo[3,4-c]pyridine-3-carboxamide;

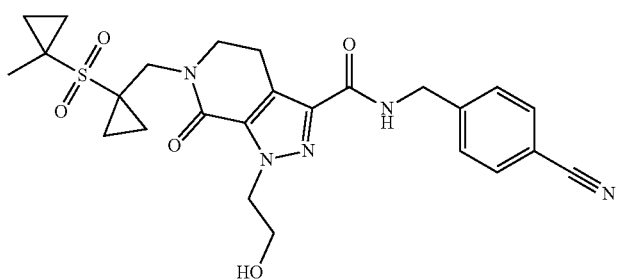 [SMILES: CC1(S(=O)(=O)C2(CN3CCc4c(C(=O)NCc5ccc(C#N)cc5)nn(CCO)c4C3=O)CC2)CC1]

N-(4-Cyanobenzyl)-1-(2-hydroxyethyl)-6-((1-((1-methylcyclopropyl)sulfonyl)cyclopropyl)methyl)-7-oxo-4,5,6,7-tetrahydro-1H-pyrazolo[3,4-c]pyridine-3-carboxamide;

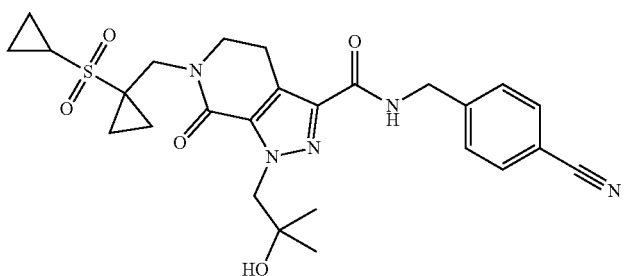 [SMILES: CC(C)(O)Cn1nc(C(=O)NCc2ccc(C#N)cc2)c2c1C(=O)N(CC1(S(=O)(=O)C3CC3)CC1)CC2]

N-(4-Cyanobenzyl)-6-((1-(cyclopropylsulfonyl)cyclopropyl)methyl)-1-(2-hydroxy-2-methylpropyl)-7-oxo-4,5,6,7-tetrahydro-1H-pyrazolo[3,4-c]pyridine-3-carboxamide;

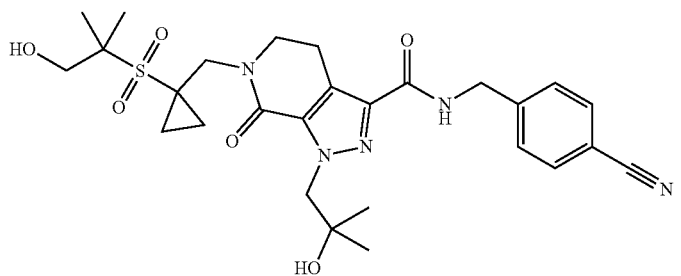 [SMILES: CC(C)(O)Cn1nc(C(=O)NCc2ccc(C#N)cc2)c2c1C(=O)N(CC1(S(=O)(=O)C(C)(C)CO)CC1)CC2]

N-(4-Cyanobenzyl)-6-((1-((1-hydroxy-2-methylpropan-2-yl)sulfonyl)cyclopropyl)methyl)-1-(2-hydroxy-2-methylpropyl)-7-oxo-4,5,6,7-tetrahydro-1H-pyrazolo[3,4-c]pyridine-3-carboxamide;

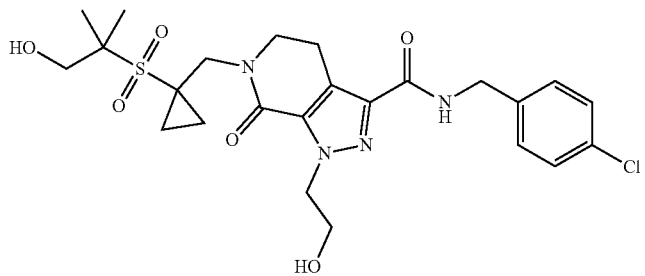 [SMILES: CC(C)(CO)S(=O)(=O)C1(CN2CCc3c(C(=O)NCc4ccc(Cl)cc4)nn(CCO)c3C2=O)CC1]

N-(4-chlorobenzyl)-6-((1-((1-hydroxy-2-methylpropan-2-yl)sulfonyl)cyclopropyl)methyl)-1-(2-hydroxyethyl)-7-oxo-4,5,6,7-tetrahydro-1H-pyrazolo[3,4-c]pyridine-3-carboxamide;

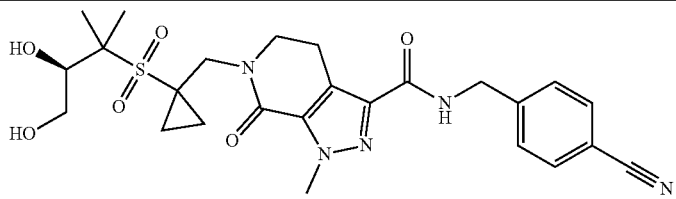

(R)-N-(4-Cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

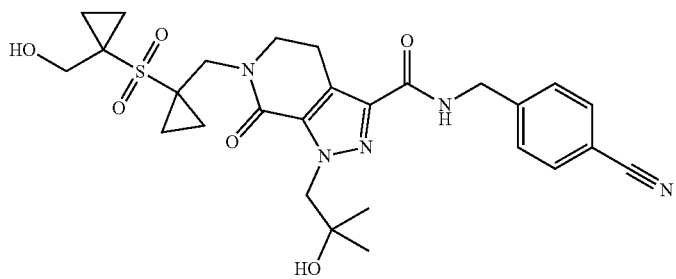 [SMILES: CC(C)(O)Cn1nc(C(=O)NCc2ccc(C#N)cc2)c2c1C(=O)N(CC1(S(=O)(=O)C3(CO)CC3)CC1)CC2]

N-(4-Cyanobenzyl)-1-(2-hydroxy-2-methylpropyl)-6-((1-((1-(hydroxymethyl)cyclopropyl)sulfonyl)cyclopropyl)methyl)-7-oxo-4,5,6,7-tetrahydro-1H-pyrazolo[3,4-c]pyridine-3-carboxamide; and

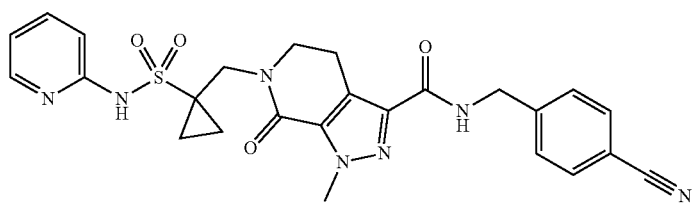 [SMILES: Cn1nc(C(=O)NCc2ccc(C#N)cc2)c2c1C(=O)N(CC1(S(=O)(=O)Nc3ccccn3)CC1)CC2]

N-(4-Cyanobenzyl)-1-methyl-7-oxo-6-((1-(N-(pyridin-2-yl)sulfamoyl)cyclopropyl)methyl)-4,5,6,7-tetrahydro-1H-pyrazolo[3,4-c]pyridine-3-carboxamide.

16. A pharmaceutical composition, comprising a compound of claim 1, and at least one pharmaceutically acceptable carrier.

17. A method of treating a herpes virus infection, comprising administering to a patient having a herpesvirus infection a compound of claim 1 or a pharmaceutical composition comprising a compound of claim 1.

18. The method of claim 17, wherein the herpesvirus is selected from cytomegalovirus (CMV), Epstein-Barr virus (EBV), Varicella zoster virus (VZV), herpes simplex virus including HSV-1 and HSV-2, herpesvirus 6, human herpesvirus 7, and Kaposi's sarcoma-associated herpesvirus.

19. The method of claim 17, comprising treating a disorder which is induced, exacerbated, or accelerated by the herpes virus infection, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), celiac disease and type 1 diabetes.

20. The method of claim 17, comprising treating atherosclerosis (AS), wherein AS is induced, exacerbated, or accelerated by the herpes virus infection.

21. The compound of claim 1, which is:

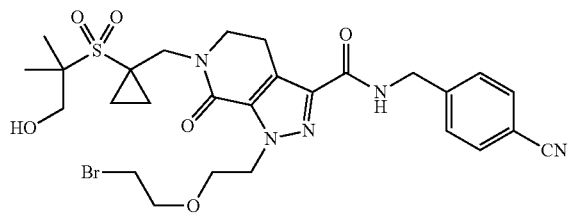 [SMILES: CC(C)(CO)S(=O)(=O)C1(CN2CCc3c(C(=O)NCc4ccc(C#N)cc4)nn(CCOCCBr)c3C2=O)CC1]

1-(2-(2-Bromoethoxy)ethyl)-N-(4-cyanobenzyl)-6-((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide, or a pharmaceutically acceptable salt thereof.

22. The compound of claim 1, or a pharmaceutically acceptable salt thereof, wherein $R^4$ is $C_2$-$C_3$ alkyl substituted with 1 to 2 groups independently selected from —OH and $R^{10}$.

23. The compound of claim 1, or a pharmaceutically acceptable salt thereof, wherein $R^4$ is substituted with —OH, and optionally substituted with methyl.

24. The compound of claim 1, or a pharmaceutically acceptable salt thereof, wherein W is substituted with $SO_2R^{10}$.

25. The compound of claim 1, or a pharmaceutically acceptable salt thereof, wherein $R^{10}$ is $C_1$-$C_4$ alkyl substituted with 1-3 groups selected from $C_1$-$C_4$ alkyl and —OH.

26. The compound of Formula (Va) of claim 6, or pharmaceutically acceptable salt thereof, wherein $R^5$ is halo, and $R^{10}$ is $C_1$-$C_5$ alkyl substituted with two —OH.

27. The compound of Formula (Va) of claim 6, or pharmaceutically acceptable salt thereof, wherein $R^5$ is —CN, and $R^{10}$ is $C_1$-$C_5$ alkyl substituted with two —OH.

28. The compound of claim 1, having the structure of Formula (Vc),

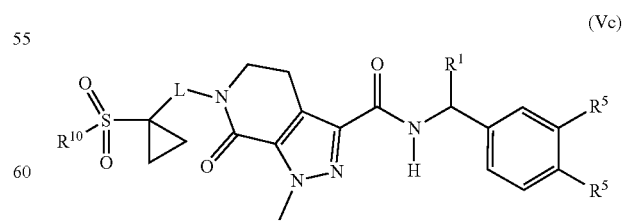

(Vc)

or a pharmaceutically acceptable salt thereof.

29. The compound of Formula (Vc) of claim 28, or the pharmaceutically acceptable salt thereof, wherein each $R^5$ is halo, and $R^{10}$ is $C_1$-$C_5$ alkyl substituted with two —OH.

30. A compound of claim 1, having the structure of Formula (VIII), or a pharmaceutically acceptable salt thereof, (VIII)

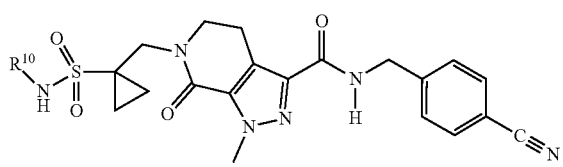

wherein $R^{10}$ is selected from:
phenyl, unsubstituted or substituted with one —CN;
6-membered heteroaryl having 1-2 heteroatoms, each heteroatom being N, unsubstituted or substituted with one group selected from -halo, —OH, and —NHC(=O)$R^{13}$, wherein $R^{13}$ is $C_1$-$C_4$ alkyl; and
$C_1$-$C_5$ alkyl substituted with one —C(=O)$NR^{13}R^{14}$ or 2 or 3 —OH, wherein $R^{13}$ is H or $C_1$-$C_4$ alkyl, and $R^{14}$ is H or $C_1$-$C_4$ alkyl.

31. The compound of claim 30, or a pharmaceutically acceptable salt thereof, wherein $R^{10}$ is unsubstituted 6-membered heteroaryl having 1-2 heteroatoms, each heteroatom being N.

32. The compound of claim 1, or a pharmaceutically acceptable salt thereof, wherein the compound is selected from:

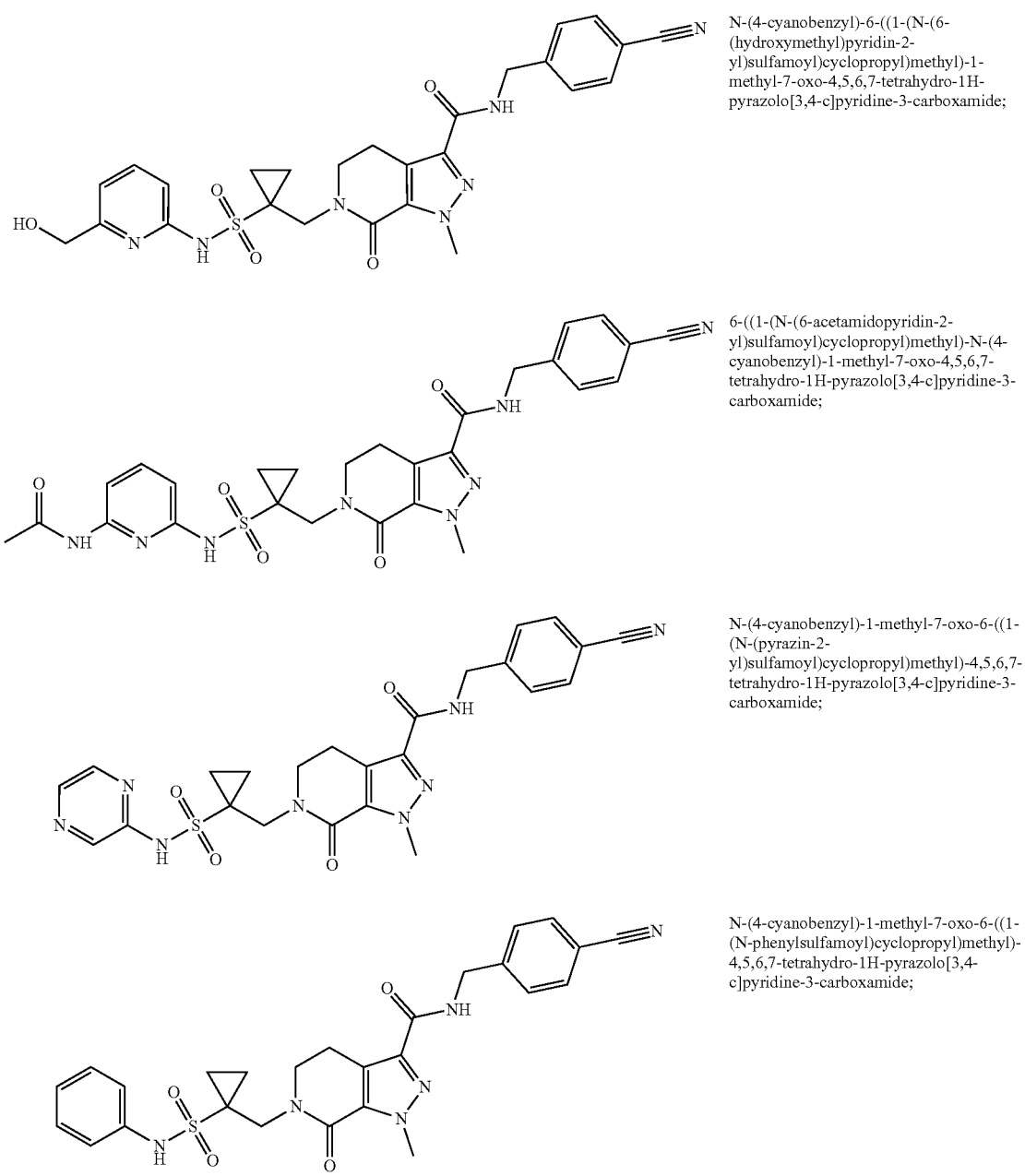

N-(4-cyanobenzyl)-6-((1-(N-(6-(hydroxymethyl)pyridin-2-yl)sulfamoyl)cyclopropyl)methyl)-1-methyl-7-oxo-4,5,6,7-tetrahydro-1H-pyrazolo[3,4-c]pyridine-3-carboxamide;

6-((1-(N-(6-acetamidopyridin-2-yl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide;

N-(4-cyanobenzyl)-1-methyl-7-oxo-6-((1-(N-(pyrazin-2-yl)sulfamoyl)cyclopropyl)methyl)-4,5,6,7-tetrahydro-1H-pyrazolo[3,4-c]pyridine-3-carboxamide;

N-(4-cyanobenzyl)-1-methyl-7-oxo-6-((1-(N-phenylsulfamoyl)cyclopropyl)methyl)-4,5,6,7-tetrahydro-1H-pyrazolo[3,4-c]pyridine-3-carboxamide;

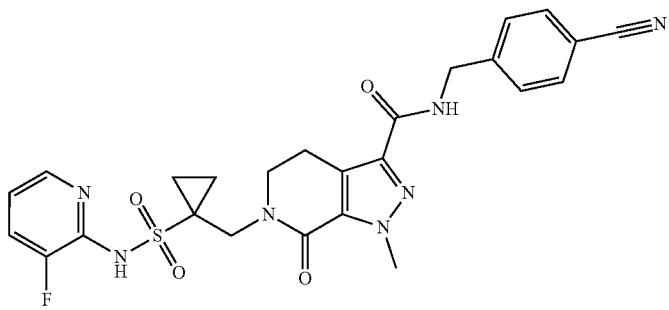 [SMILES: Cn1nc(C(=O)NCc2ccc(C#N)cc2)c2c1C(=O)N(CC1(S(=O)(=O)Nc3ncccc3F)CC1)CC2]

N-(4-cyanobenzyl)-6-((1-(N-(3-fluoropyridin-2-yl)sulfamoyl)cyclopropyl)methyl)-1-methyl-7-oxo-4,5,6,7-tetrahydro-1H-pyrazolo[3,4-c]pyridine-3-carboxamide;

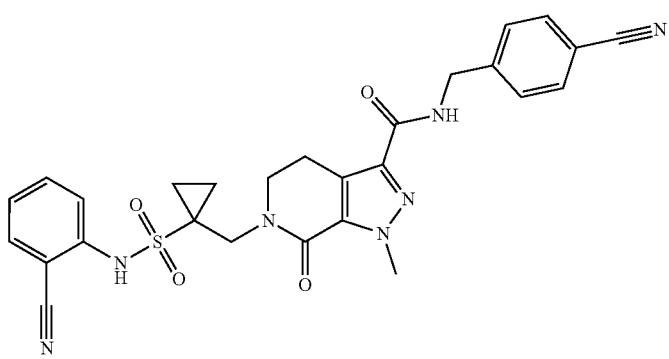 [SMILES: Cn1nc(C(=O)NCc2ccc(C#N)cc2)c2c1C(=O)N(CC1(S(=O)(=O)Nc3ccccc3C#N)CC1)CC2]

N-(4-cyanobenzyl)-6-((1-(N-(2-cyanophenyl)sulfamoyl)cyclopropyl)methyl)-1-methyl-7-oxo-4,5,6,7-tetrahydro-1H-pyrazolo[3,4-c]pyridine-3-carboxamide;

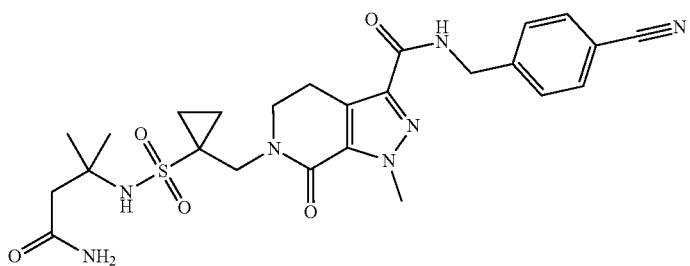 [SMILES: Cn1nc(C(=O)NCc2ccc(C#N)cc2)c2c1C(=O)N(CC1(S(=O)(=O)NC(C)(C)CC(N)=O)CC1)CC2]

6-((1-(N-(4-amino-2-methyl-4-oxobutan-2-yl)sulfamoyl)cyclopropyl)methyl)-N-(4-cyanobenzyl)-1-methyl-7-oxo-4,5,6,7-tetrahydro-1H-pyrazolo[3,4-c]pyridine-3-carboxamide;

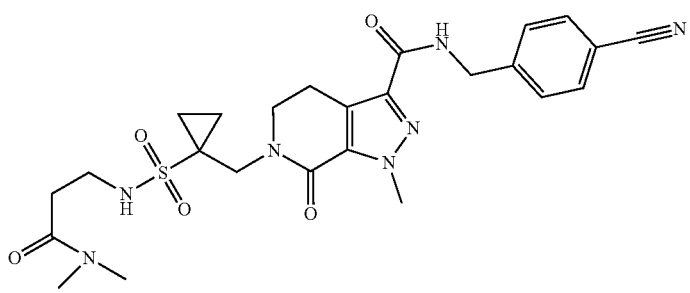 [SMILES: CN(C)C(=O)CCNS(=O)(=O)C1(CN2CCc3c(C(=O)NCc4ccc(C#N)cc4)nn(C)c3C2=O)CC1]

N-(4-cyanobenzyl)-6-((1-(N-(3-(dimethylamino)-3-oxopropyl)sulfamoyl)cyclopropyl)methyl)-1-methyl-7-oxo-4,5,6,7-tetrahydro-1H-pyrazolo[3,4-c]pyridine-3-carboxamide;

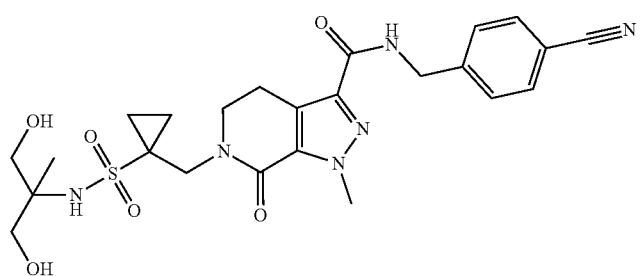 [SMILES: Cn1nc(C(=O)NCc2ccc(C#N)cc2)c2c1C(=O)N(CC1(S(=O)(=O)NC(C)(CO)CO)CC1)CC2]

N-(4-cyanobenzyl)-6-((1-(N-(1,3-dihydroxy-2-methylpropan-2-yl)sulfamoyl)cyclopropyl)methyl)-1-methyl-7-oxo-4,5,6,7-tetrahydro-1H-pyrazolo[3,4-c]pyridine-3-carboxamide; and

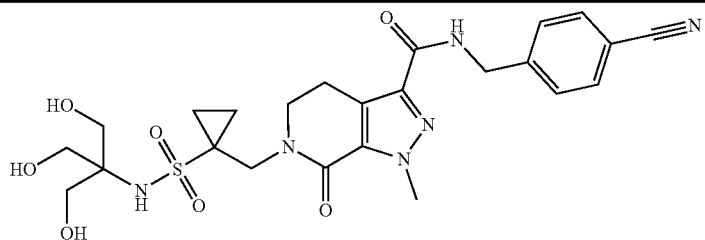

N-(4-cyanobenzyl)-6-((1-(N-(1,3-dihydroxy-2-(hydroxymethyl)propan-2-yl)sulfamoyl)cyclopropyl)methyl)-1-methyl-7-oxo-4,5,6,7-tetrahydro-1H-pyrazolo[3,4-c]pyridine-3-carboxamide.

33. A pharmaceutical composition, comprising a compound of claim 32, and at least one pharmaceutically acceptable carrier.

34. A method of treating a herpes virus infection, comprising administering to a patient having a herpesvirus infection a compound of claim 32 or a pharmaceutical composition comprising a compound of claim 32.

35. The method of claim 34, wherein the herpesvirus is selected from cytomegalovirus (CMV), Epstein-Barr virus (EBV), Varicella zoster virus (VZV), herpes simplex virus including HSV-1 and HSV-2, herpesvirus 6, human herpesvirus 7, and Kaposi's sarcoma-associated herpesvirus.

36. The method of claim 34, comprising treating a disorder which is induced, exacerbated, or accelerated by the herpes virus infection, wherein the disorder is selected from Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), atherosclerosis (AS), celiac disease and type 1 diabetes.

37. The compound of claim 7, or a pharmaceutically acceptable salt thereof, wherein the compound is selected from:

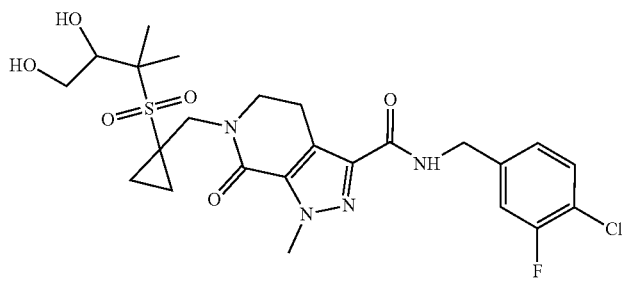 [SMILES: Cn1nc(C(=O)NCc2ccc(Cl)c(F)c2)c2c1C(=O)N(CC1(S(=O)(=O)C(C)(C)C(O)CO)CC1)CC2]

N-(4-chloro-3-fluorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

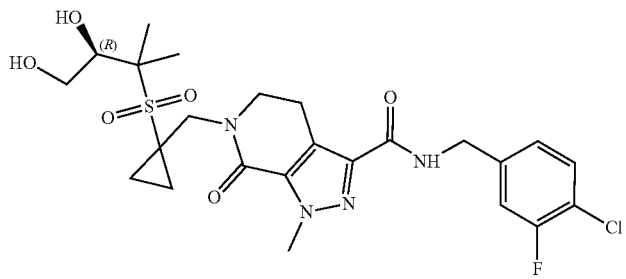

(R)-N-(4-chloro-3-fluorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

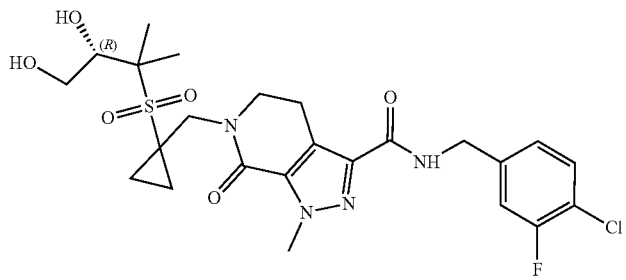

(S)-N-(4-chloro-3-fluorobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;

-continued

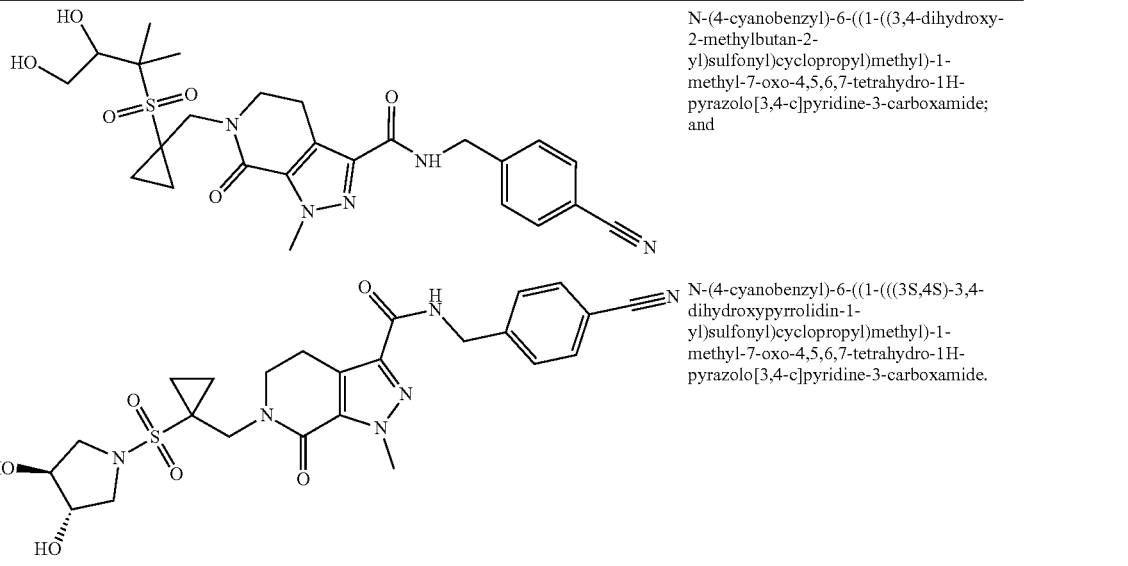

N-(4-cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide; and N-(4-cyanobenzyl)-6-((1-(((3S,4S)-3,4-dihydroxypyrrolidin-1-yl)sulfonyl)cyclopropyl)methyl)-1-methyl-7-oxo-4,5,6,7-tetrahydro-1H-pyrazolo[3,4-c]pyridine-3-carboxamide.

38. A compound selected from:

N-(4-cyanobenzyl)-1-methyl-7-oxo-6-((1-(N-(1-(pyridazin-3-yl)cyclopropyl)sulfamoyl)cyclopropyl)methyl)-4,5,6,7-tetrahydro-1H-pyrazolo[3,4-c]pyridine-3-carboxamide;

N-(4-cyanobenzyl)-1-methyl-7-oxo-6-((1-(N-(pyrimidin-2-ylmethyl)sulfamoyl)cyclopropyl)methyl)-4,5,6,7-tetrahydro-1H-pyrazolo[3,4-c]pyridine-3-carboxamide;

N-(4-cyanobenzyl)-1-methyl-7-oxo-6-((1-(N-(1-(pyrazin-2-yl)ethyl)sulfamoyl)cyclopropyl)methyl)-4,5,6,7-tetrahydro-1H-pyrazolo[3,4-c]pyridine-3-carboxamide;

-continued

| | |
|---|---|
| 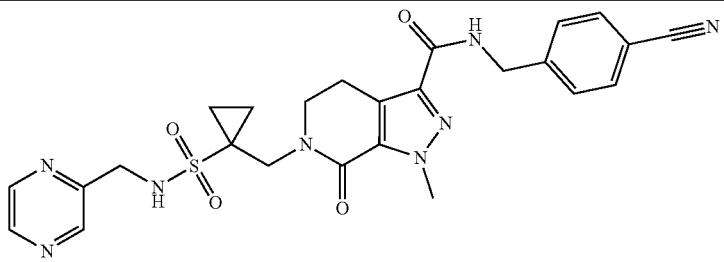 | N-(4-cyanobenzyl)-1-methyl-7-oxo-6-((1-(N-(pyrazin-2-ylmethyl)sulfamoyl)cyclopropyl)methyl)-4,5,6,7-tetrahydro-1H-pyrazolo[3,4-c]pyridine-3-carboxamide; |
| 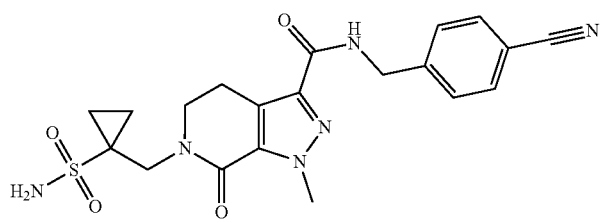 [SMILES: Cn1nc(C(=O)NCc2ccc(C#N)cc2)c2c1C(=O)N(CC1(S(N)(=O)=O)CC1)CC2] | N-(4-cyanobenzyl)-1-methyl-7-oxo-6-((1-sulfamoylcyclopropyl)methyl)-4,5,6,7-tetrahydro-1H-pyrazolo[3,4-c]pyridine-3-carboxamide, and |
|  | N-(4-Cyanobenzyl)-6-((1-(((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide. | or a pharmaceutically acceptable salt thereof.

* * * * *

UNITED STATES PATENT AND TRADEMARK OFFICE
CERTIFICATE OF CORRECTION

PATENT NO. : 11,667,613 B2
APPLICATION NO. : 17/030540
DATED : June 6, 2023
INVENTOR(S) : Zef Konst et al.

Page 1 of 2

It is certified that error appears in the above-identified patent and that said Letters Patent is hereby corrected as shown below:

In the Claims

In Claim 1, Column 413, Lines 20-28, please replace

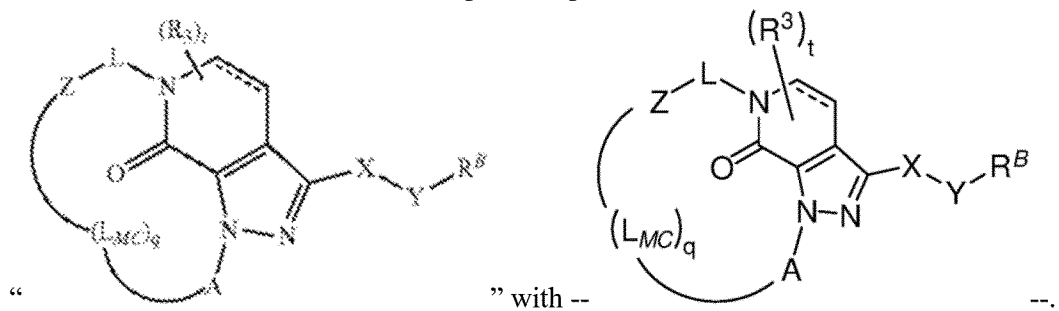
" with --  --.

In Claim 1, Column 414, Line 63, please replace "—$CR^{11}$ $R^{12}SO_2R^{10}$" with -- —$CR^{11}R^{12}SO_2R^{10}$--.

In Claim 1, Column 415, Line 33, please replace "—$NRC(=O)R^{13}$" with -- —$NR^{14}C(=O)R^{13}$--.

In Claim 1, Column 415, Line 42, please replace "$C_3$-05cycloalkyl" with --$C_3$-$C_5$cycloalkyl--.

In Claim 2, Column 416, Lines 21-28, please replace

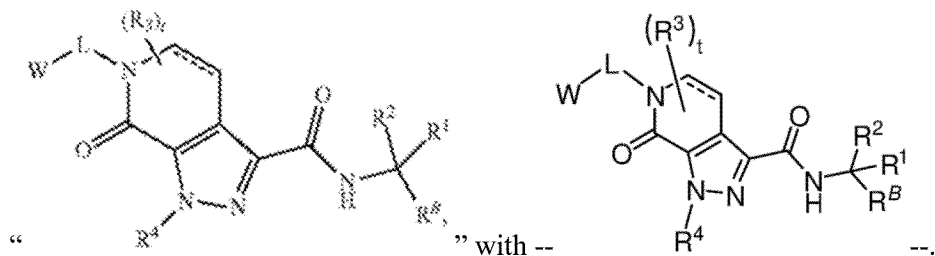
" with --  --.

Signed and Sealed this
Nineteenth Day of September, 2023

*Katherine Kelly Vidal*

Katherine Kelly Vidal
*Director of the United States Patent and Trademark Office*

CERTIFICATE OF CORRECTION (continued)
U.S. Pat. No. 11,667,613 B2

In Claim 8, Column 423, Lines 16-23, please replace

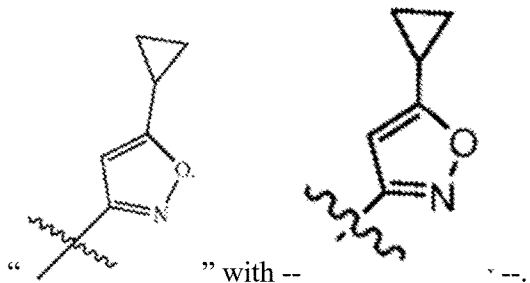

" with --    --.

In Claim 14, Column 426, please replace "6-(1-(Cyclopropylsulfonyl)cyclopropyl)methyl)-1-methyl-N-(4-methylbenzyl)-7-oxo-4,5,6,7-tetrahydro-1H-pyrazolo[3,4-c]pyridine-3-carboxamide;" with --6-((1-(Cyclopropylsulfonyl)cyclopropyl)methyl)-1-methyl-N-(4-methylbenzyl)-7-oxo-4,5,6,7-tetrahydro-1H-pyrazolo[3,4-c]pyridine-3-carboxamide;--.

In Claim 14, Column 448, please replace "(S)-N-(4-Cyanobenzyl)-6-((1-(1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;" with --(S)-N-(4-Cyanobenzyl)-6-((1-((1-(1-fluoro-2-hydroxyethoxy)-2-methylpropan-2-yl)sulfonyl)cyclopropyl)methyl)-1-methyl-7-oxo-4,5,6,7-tetrahydro-1H-pyrazolo[3,4-c]pyridine-3-carboxamide;--.

In Claim 14, Column 482, please replace "(S)-N-(4-Cyanobenzyl)-6-((1-(3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;" with --(S)-N-(4-Cyanobenzyl)-6-((1-((3,4-dihydroxy-2-methylbutan-2-yl)sulfonyl)cyclopropyl)methyl)-1-methyl-7-oxo-4,5,6,7-tetrahydro-1H-pyrazolo[3,4-c]pyridine-3-carboxamide;--.

In Claim 14, Column 482, please replace "(S)-N-(4-Cyanobenzyl)-6-((1-(1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;" with --(S)-N-(4-Cyanobenzyl)-6-((1-((1-(1,2-dihydroxyethyl)cyclopropyl)sulfonyl)cyclopropyl)methyl)-1-methyl-7-oxo-4,5,6,7-tetrahydro-1H-pyrazolo[3,4-c]pyridine-3-carboxamide;--.

In Claim 21, Column 505, Lines 64-67, please replace "1-(2-(2-Bromoethoxy)ethyl)-N-(4-cyanobenzyl)-6-((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide," with --1-(2-(2-Bromoethoxy)ethyl)-N-(4-cyanobenzyl)-6-((1-((1-hydroxy-2-methylpropan-2-yl)sulfonyl)cyclopropyl)methyl)-7-oxo-4,5,6,7-tetrahydro-1H-pyrazolo[3,4-c]pyridine-3-carboxamide,--.